United States Patent
Bissantz et al.

(10) Patent No.: US 10,385,022 B2
(45) Date of Patent: Aug. 20, 2019

(54) 3-AMINO-PYRIDINES AS GPBAR1 AGONISTS

(71) Applicant: HOFFMANN-LA ROCHE INC., Nutley, NJ (US)

(72) Inventors: Caterina Bissantz, Village-Neuf (FR); Henrietta Dehmlow, Loerrach (DE); Shawn David Erickson, Leonia, NJ (US); Prabha Saba Karnachi, Hillsborough, NJ (US); Kyungjin Kim, Livingston, NJ (US); Rainer E. Martin, Basel (CH); Patrizio Mattei, Riehen (CH); Ulrike Obst Sander, Reinach BL (CH); Sherrie Lynn Pietranico-Cole, Montclair, NJ (US); Hans Richter, Grenzach-Wyhlen (DE); Christoph Ullmer, Fischingen (DE)

(73) Assignee: HOFFMANN-LA ROCHE INC., Nutley, NJ (US)

(*) Notice: Subject to any disclaimer, the term of this patent is extended or adjusted under 35 U.S.C. 154(b) by 332 days.

(21) Appl. No.: 14/615,609

(22) Filed: Feb. 6, 2015

(65) Prior Publication Data
US 2015/0152058 A1   Jun. 4, 2015

Related U.S. Application Data

(62) Division of application No. 13/406,572, filed on Feb. 28, 2012, now Pat. No. 8,987,307.

(30) Foreign Application Priority Data

Mar. 3, 2011 (EP) .................................. 11156711

(51) Int. Cl.
| | | |
|---|---|---|
| *C07D 401/12* | (2006.01) | |
| *C07D 213/82* | (2006.01) | |
| *C07D 213/75* | (2006.01) | |
| *C07D 213/81* | (2006.01) | |
| *C07D 401/04* | (2006.01) | |
| *C07D 401/14* | (2006.01) | |
| *C07D 405/04* | (2006.01) | |
| *C07D 405/12* | (2006.01) | |
| *C07D 413/04* | (2006.01) | |
| *C07D 413/12* | (2006.01) | |
| *C07D 417/04* | (2006.01) | |
| *C07D 417/12* | (2006.01) | |
| *C07D 491/107* | (2006.01) | |

(52) U.S. Cl.
CPC .......... *C07D 213/75* (2013.01); *C07D 213/81* (2013.01); *C07D 213/82* (2013.01); *C07D 401/04* (2013.01); *C07D 401/12* (2013.01); *C07D 401/14* (2013.01); *C07D 405/04* (2013.01); *C07D 405/12* (2013.01); *C07D 413/04* (2013.01); *C07D 413/12* (2013.01); *C07D 417/04* (2013.01); *C07D 417/12* (2013.01); *C07D 491/107* (2013.01)

(58) Field of Classification Search
None
See application file for complete search history.

(56) References Cited

U.S. PATENT DOCUMENTS

| | | |
|---|---|---|
| 6,022,884 A | 2/2000 | Mantlo et al. |
| 6,297,375 B1 | 10/2001 | Bos et al. |
| 8,034,949 B2 | 10/2011 | Moritani et al. |
| 8,088,761 B2 | 1/2012 | Bavetsias et al. |
| 2010/0210660 A1 | 8/2010 | Kremoser et al. |

FOREIGN PATENT DOCUMENTS

| | | |
|---|---|---|
| WO | 2000/58293 | 10/2000 |
| WO | 2007/110237 | 10/2007 |
| WO | 2008/106692 | 9/2008 |
| WO | 2008/127399 | 10/2008 |
| WO | 2009/014637 | 1/2009 |

OTHER PUBLICATIONS

Keitel et al., "Hepatology" 50(3):861-870 ( 2009).
"International Search Report PCT/EP2012/053386—dated May 23, 2012".
Pelliceiari et al., "J. Med. Chem." 52(24):7958-7961 ( 2009).
Adrian et al., "Gut" 34:1219-1224 ( 1993).
Thomas et al., "Cell Metabolism." 10(3):167-177 ( 2009).
Watanabe et al., "Nature" 439:484-489 ( 2006).
Plaisancie et al., "J. Endocrin." 145(3):521-526 ( 1995).
Katsuma et al., "Biochem. Biophys. Res. Commun." 329(1):386-390 ( 2005).

*Primary Examiner* — Leslie A. Royds Draper

(57) ABSTRACT

This invention relates to novel 3-aminopyridines of the formula

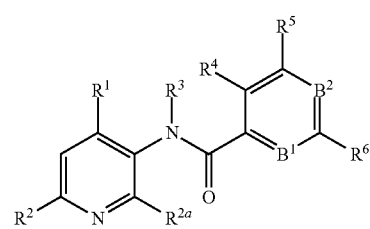

wherein $B^1$, $B^2$ and $R^1$ to $R^6$ are as defined in the description and in the claims, as well as pharmaceutically acceptable salts thereof. These compounds are GPBAR1 agonists and can be used as medicaments for the treatment of diseases such as type II diabetes.

15 Claims, No Drawings

3-AMINO-PYRIDINES AS GPBAR1 AGONISTS

PRIORITY TO RELATED APPLICATION(S)

This application claims priority to and is a divisional of pending U.S. patent application Ser. No. 13/406,572, filed Feb. 28, 2012, which in turn claims the benefit of European Patent Application No. 11156711.1, filed Mar. 3, 2011, which all are hereby incorporated by reference in their entireties.

FIELD OF THE INVENTION

The present invention relates to novel 3-amino pyridines having pharmaceutical activity, their manufacture, pharmaceutical compositions containing them and their potential use as medicaments.

In particular, the present invention relates to compounds of the formula

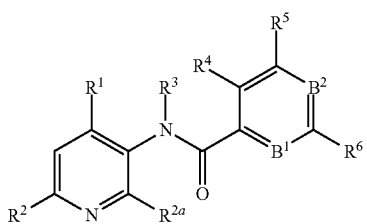

wherein $B^1$, $B^2$ and $R^1$ to $R^6$ are as described below, or to pharmaceutically acceptable salts thereof.

The compounds are modulators or ligands of the GPBAR1 receptor. More particularly, the compounds are potent GPBAR1 agonists and may therefore be useful for the treatment and prevention of metabolic and inflammatory diseases, in particular type II diabetes.

BACKGROUND OF THE INVENTION

Diabetes mellitus is an ever-increasing threat to human health. For example, in the United States current estimates maintain that about 16 million people suffer from diabetes mellitus. Type II diabetes also known as non-insulin-dependent diabetes mellitus accounts for approximately 90-95% of diabetes cases, killing about 193,000 U.S. residents each year. Type II diabetes is the seventh leading cause of all deaths. In Western societies, type II diabetes currently affects 6% of the adult population with world-wide frequency expected to grow by 6% per annum. Although there are certain inheritable traits that may predispose particular individuals to developing type II diabetes, the driving force behind the current increase in incidence of the disease is the increased sedentary life-style, diet, and obesity now prevalent in developed countries. About 80% of diabetics with type II diabetes are significantly overweight. Also, an increasing number of young people are developing the disease. Type II diabetes is now internationally recognized as one of the major threats to human health in the 21st century.

Type II diabetes manifests as inability to adequately regulate blood-glucose levels and may be characterized by a defect in insulin secretion or by insulin resistance. Namely, those who suffer from type II diabetes have too little insulin or cannot use insulin effectively. Insulin resistance refers to the inability of the body tissues to respond properly to endogenous insulin. Insulin resistance develops because of multiple factors, including genetics, obesity, increasing age, and having high blood sugar over long periods of time. Type II diabetes, sometimes called mature onset, can develop at any age, but most commonly becomes apparent during adulthood. However, the incidence of type II diabetes in children is rising. In diabetics glucose levels build up in the blood and urine causing excessive urination, thirst, hunger, and problems with fat and protein metabolism. If left untreated, diabetes mellitus may cause life-threatening complications, including blindness, kidney failure, and heart disease.

Type II diabetes is currently treated at several levels. A first level of therapy is through diet and/or exercise, either alone or in combination with therapeutic agents. Such agents may include insulin or pharmaceuticals that lower blood glucose levels. About 49% of individuals with Type II diabetes require oral medications, about 40% require insulin injections or a combination of insulin injections and oral medications, and 10% use diet and exercise alone.

Current therapies include: insulin secretagogues, such as sulphonylureas, which increase insulin production from pancreatic β-cells; glucose-lowering effectors, such as metformin which reduce glucose production from the liver; activators of the peroxisome proliferator-activated receptor γ (PPARγ), such as the thiazolidinediones, which enhance insulin action; and α-glucosidase inhibitors which interfere with gut glucose production. There are, however, deficiencies associated with currently available treatments. For example sulphonylureas and insulin injections can be associated with hypoglycemic episodes and weight gain. Furthermore, patients often lose responsiveness to sulphonylureas over time. Metformin and α-glucosidase inhibitors often lead to gastrointestinal problems and PPARγ agonists tend to cause increased weight gain and edema.

Bile acids (BA) are amphipathic molecules which are synthesized in the liver from cholesterol and stored in the gall bladder until secretion to the duodenum and intestine to play an important role in the solubilization and absorption of dietary fat and lipid-soluble vitamins. Approximately 99% of BA are absorbed again by passive diffusion and active transport in the terminal ileum and transported back to the liver via the portal vein (enterohepatic circulation). In the liver, BA decrease their own biosynthesis from cholesterol through the activation of the farnesoid X receptor alpha (FXRα) and small heterodimer partner (SHP), leading to the transcriptional repression of cholesterol 7α-hydroxylase, the rate-limiting step of BA biosynthesis from cholesterol.

GPBAR1, in the literature termed TGR5, M-BAR or BG37, was recently identified as a G-protein coupled receptor (GPCR) responsive to BA (Kawamata et al., *J. Biol. Chem.* 2003, 278, 9435-9440; Maruyama et al., *Biochem. Biophys. Res. Commun.* 2002, 298, 714-719). GPBAR1 is a G(alpha)s-coupled GPCR and stimulation by ligand binding causes activation of adenylyl cyclase which leads to the elevation of intracellular cAMP and subsequent activation of downstream signaling pathways. The human receptor shares 86, 90, 82, and 83% amino acid identity to bovine, rabbit, rat, and mouse receptor, respectively. GPBAR1 is abundantly expressed in the intestinal tract, monocytes and macrophages, lung, spleen, placenta, kidney, and stomach (Kawamata et al., *J. Biol. Chem.* 2003, 278, 9435-9440). BA induced receptor internalization, intracellular cAMP production and activation of extracellular signal-regulated kinase in GPBAR1-expressing HEK293 and CHO cells.

GPBAR1 was found to be abundantly expressed in monocytes/macrophages from humans and rabbits (Kawamata et al., *J. Biol. Chem.* 2003, 278, 9435-9440), and BA treatment suppressed LPS-induced cytokine production in rabbit alveolar macrophages and human THP-1 cells expressing GPBAR1. These data suggest that bile acids can suppress the macrophage function via activation of GPBAR1. In the liver functional GPBAR1 was found in the plasma membranes of Kupffer cells, mediating inhibition of LPS-induced cytokine expression (Keitel, *Biochem. Biophys. Res. Commun.* 2008, 372, 78-84), and of sinusoidal endothelial cells, where bile salts led to an increase in intracellular cAMP and to the activation and enhanced expression of the endothelial nitric oxide (NO) synthase (Keitel, *Hepatology* 2007, 45, 695-704). Furthermore, GPBAR1 has been detected in cholangiocytes of rat liver (Keitel, *Biochem. Biophys. Res. Commun.* 2008, 372, 78-84). Hydrophobic bile acids, such as taurolithocholic acid, increase cAMP in cholangiocytes suggesting that GPBAR1 may modulate ductal secretion and bile flow. Indeed, GPBAR1 staining colocalized with the cyclic adenosine monophosphate regulated chloride channel cystic fibrosis transmembrane conductance regulator (CFTR) and the apical sodium-dependent bile salt uptake transporter (ASBT). A functional coupling of GPBAR1 to chloride secretion and bile flow has been shown using GPBAR1 agonists (Keitel et al., *Hepatology* 2009, 50, 861-870; Pellicciari et al., *J. Med. Chem.* 2009, 52, 7958-7961). In summary, GPBAR1 agonists may trigger a protective as well as medicative mechanism in cholestatic livers.

GPBAR1 is expressed in intestinal enteroendocrine cell lines from human (NCI-H716) and murine (STC-1, GLUTag) origin (Maruyama et al., *Biochem. Biophys. Res. Commun.* 2002, 298, 714-719). Stimulation of GPBAR1 by BA stimulated cAMP production in NCI-H716 cells. Intracellular increases in cAMP suggested that BA may induce the secretion of glucagon-like peptide-1 (GLP-1). Indeed, activation of GPBAR1 by BA promoted GLP-1 secretion in STC-1 cells (Katsuma et al., *Biochem. Biophys. Res. Commun.* 2005, 329, 386-390). Receptor-specificity has been demonstrated by RNA interference experiments which revealed that reduced expression of GPBAR1 resulted in diminished secretion of GLP-1. There is compelling evidence that GPBAR1-mediated GLP-1 and PYY release from intestinal L-cells extends to in vivo. In the isolated vascularly perfused rat colon, BA have been shown to trigger GLP-1 secretion (Plaisancie et al., *J. Endocrin.* 1995, 145, 521-526). Using a combination of pharmacological and genetic gain- and loss-of-function studies in vivo, GPBAR1 signaling was shown to induce GLP-1 release, leading to improved liver and pancreatic function and enhanced glucose tolerance in obese mice (Thomas et al., *Cell Metabolism*, 2009, 10, 167-177). In humans, intracolonic administration of deoxycholate showed marked increases in plasma levels of GLP-1 and the co-secreted PYY (Adrian et al., *Gut* 1993, 34, 1219-1224).

GLP-1 is a peptide secreted from enteroendocrine L cells has been shown to stimulate insulin release in glucose dependent manner in humans (Kreymann et al., *Lancet* 1987, 2, 1300-1304) and studies in experimental animals demonstrated that this incretin hormone is necessary for normal glucose homeostasis. In addition, GLP-1 can exert several beneficial effects in diabetes and obesity, including 1) increased glucose disposal, 2) suppression in glucose production, 3) reduced gastric emptying, 4) reduction in food intake and 5) weight loss. More recently, much research has been focused on the use of GLP-1 in the treatment of conditions and disorders such as diabetes mellitus, stress, obesity, appetite control and satiety, Alzheimer's disease, inflammation, and diseases of the central nervous system (see, for example, Bojanowska et al., *Med. Sci. Monit.* 2005, 8, RA271-8; Perry et al., *Current Alzheimer Res.* 2005, 3, 377-385; and Meier et al., *Diabetes Metab. Res. Rev.* 2005, 2, 91-117). However, the use of a peptide in clinical treatment is limited due to difficult administration, and in vivo stability. Therefore, a small molecule that either mimics the effects of GLP-1 directly, or increases GLP-1 secretion, may be useful in treatment of the variety of conditions or disorders described above, namely diabetes mellitus.

PYY is co-secreted with GLP-1 from intestinal L-cells following a meal. A dipeptidyl peptidase-IV (DPP4) cleavage product of PYY is PYY[3-36] (Eberlein et al., *Peptides* 1989, 10, 797-803; Grandt et al., *Regul. Pept.* 1994, 51, 151-159). This fragment constitutes approximately 40% of total PYY-like immunoreactivity in human and canine intestinal extracts and about 36% of total plasma PYY immunoreactivity in a fasting state to slightly over 50% following a meal. PYY[3-36] is reportedly a selective ligand at the Y2 and Y5 receptors. Peripheral administration of PYY reportedly reduces gastric acid secretion, gastric motility, exocrine pancreatic secretion (Yoshinaga et al., *Am. J. Physiol.* 1992, 263, G695-701), gallbladder contraction and intestinal motility (Savage et al., *Gut* 1987, 28, 166-170). It has been demonstrated that intra-arcuate (IC) or intra-peritoneal (IP) injection of PYY3-36 reduced feeding in rats and, as a chronic treatment, reduced body weight gain. Intra-venous (IV) infusion (0.8 pmol/kg/min) for 90 min of PYY3-36 reduced food intake in obese and normal human subjects by 33% over 24 hours. These findings suggest that the PYY system may be a therapeutic target for the treatment of obesity (Bloom et. al., *Nature* 2002, 418, 650-654).

Furthermore, activation of GPBAR1 might be beneficial for the treatment of obesity and metabolic syndrome. Mice fed on a high fat diet (HFD) containing 0.5% cholic acid gained less weight than control mice on HFD alone independent of food intake (Watanabe et al., *Nature* 2006, 439, 484-489). These effects were independent of FXR-alpha, and are likely to result from the binding of BA to GPBAR1. The proposed GPBAR1-mediated mechanism is leading to the subsequent induction of the cAMP-dependent thyroid hormone activating enzyme type 2 (D2) which converts the inactive T3 into the active T4, resulting in the stimulation of the thyroid hormone receptor and promoting energy expenditure. Mice lacking the D2 gene were resistant to cholic acid-induced weight loss. In both rodents and humans, the most thermogenically important tissues (the brown adipose and skeletal muscle) are specifically targeted by this mechanism because they co-express D2 and GPBAR1. The BA-GPBAR1-cAMP-D2 signalling pathway is therefore a crucial mechanism for fine-tuning energy homeostasis that can be targeted to improve metabolic control.

It is therefore an object of the present invention to provide selective, directly acting GPBAR1 agonists. Such agonists are useful as therapeutically active substances, particularly in the treatment and/or prevention of diseases which are associated with the activation of GPBAR1.

The novel compounds of the present invention exceed the compounds known in the art, inasmuch as they are small molecules and they bind to and selectively activate GPBAR1 very efficiently. They are expected to have an enhanced therapeutic potential compared to the compounds already known in the art and can be used for the treatment of diabetes, obesity, metabolic syndrome, hypercholesterolemia, dyslipidemia and a wide range of acute and chronic inflammatory diseases.

SUMMARY OF THE INVENTION

The present invention relates to 3-aminopyridines of the formula

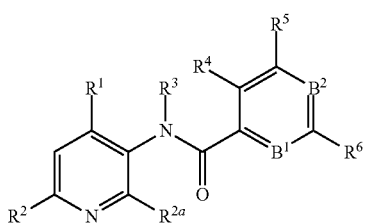

wherein $B^1$ is $CR^7$ or N;

$B^2$ is $CR^8$ or N;

$R^1$ is selected from the group consisting of phenyl, said phenyl being unsubstituted or substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy, cycloalkyl-oxy, cycloalkyl-$C_{1-7}$-alkoxy, cyano, cyano-$C_{1-7}$-alkoxy, carboxyl, carboxyl-$C_{1-7}$-alkyl, $C_{1-7}$-alkoxycarbonyl, hydroxy-$C_{1-7}$-alkyl, hydroxy-$C_{1-7}$-alkoxy, carboxyl-$C_{1-7}$-alkoxy, $C_{1-7}$-alkoxycarbonyl-$C_{1-7}$-alkoxy, amino, $C_{1-7}$-alkylamino, di-$C_{1-7}$-alkylamino, and phenyl-$C_{1-7}$-alkoxy, heterocyclyl-oxy and heterocyclyl-$C_{1-7}$-alkoxy, wherein heterocyclyl is unsubstituted or substituted by $C_{1-7}$-alkoxycarbonyl, heteroaryl, said heteroaryl being unsubstituted or substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy, cycloalkyl-oxy, and cycloalkyl-$C_{1-7}$-alkoxy, heterocyclyl-oxy and heterocyclyl-$C_{1-7}$-alkoxy, wherein heterocyclyl is unsubstituted or substituted by $C_{1-7}$-alkoxycarbonyl, 3,6-dihydro-2H-pyran-4-yl, and piperidinyl, said piperidinyl being substituted with one to four $C_{1-7}$-alkyl groups;

$R^2$ is selected from the group consisting of hydrogen, $C_{1-7}$-alkyl, halogen, halogen-$C_{1-7}$-alkyl, halogen-$C_{1-7}$-alkoxy, cyano, $C_{1-7}$-alkoxy, amino, $C_{1-7}$-alkylamino, di-$C_{1-7}$-alkylamino, aminocarbonyl, $C_{1-7}$-alkylaminocarbonyl, di-$C_{1-7}$-alkylaminocarbonyl, hydroxy-$C_{1-7}$-alkyl-($C_{1-7}$-alkyl)amino, $C_{1-7}$-alkoxy-$C_{1-7}$-alkyl-($C_{1-7}$-alkyl)amino, and heteroaryl;

$R^{2a}$ is selected from the group consisting of hydrogen, methyl and halogen;

$R^3$ is selected from the group consisting of $C_{1-7}$-alkyl, halogen-$C_{1-7}$-alkyl, hydroxy-$C_{1-7}$-alkyl, $C_{1-7}$-alkylcarbonyl-$C_{1-7}$-alkyl, carboxyl-$C_{1-7}$-alkyl, $C_{1-7}$-alkoxycarbonyl-$C_{1-7}$-alkyl, cyano-$C_{1-7}$-alkyl, aminocarbonyl-$C_{1-7}$-alkyl, $C_{1-7}$-alkylaminocarbonyl-$C_{1-7}$-alkyl, di-$C_{1-7}$-alkylaminocarbonyl-$C_{1-7}$-alkyl, $C_{1-7}$-alkylsulfonyl-$C_{1-7}$-alkyl, $C_{3-7}$-cycloalkyl, $C_{3-7}$-cycloalkyl-$C_{1-7}$-alkyl, unsubstituted heterocyclyl or heterocyclyl substituted with one or two groups selected from halogen, oxo, hydroxy and $C_{1-7}$-alkyl, heterocyclyl-$C_{1-7}$-alkyl, wherein heterocyclyl is unsubstituted or substituted with one or two groups selected from halogen, oxo and $C_{1-7}$-alkyl, heteroaryl-$C_{1-7}$-alkyl, wherein heteroaryl is unsubstituted or substituted with one or two groups selected from halogen, oxo and $C_{1-7}$-alkyl and phenyl-$C_{1-7}$-alkoxycarbonylamino-$C_{1-7}$-alkyl;

$R^4$ is selected from the group consisting of hydrogen, halogen, $C_{1-7}$-alkyl and $C_{1-7}$-alkoxy;

$R^5$ and $R^6$ are independently from each other selected from the group consisting of hydrogen, $C_{1-7}$-alkyl, $C_{1-7}$-cycloalkyl, halogen, halogen-$C_{1-7}$-alkyl, halogen-$C_{1-7}$-alkoxy, hydroxy, hydroxy-$C_{1-7}$-alkyl, $C_{1-7}$-alkoxy, cyano, carboxyl, $C_{1-7}$-alkoxycarbonyl, $C_{1-7}$-alkoxycarbonyl-$C_{1-7}$-alkyl, hydroxy-$C_{1-7}$-alkoxy, $C_{1-7}$-alkoxy-$C_{1-7}$-alkoxy, $C_{1-7}$-alkylsulfanyl, hydroxy-$C_{1-7}$-alkylsulfanyl, $C_{1-7}$-alkoxy-$C_{1-7}$-alkylsulfanyl, $C_{1-7}$-alkylsulfonyl, hydroxy-$C_{1-7}$-alkylsulfonyl, $C_{1-7}$-alkoxy-$C_{1-7}$-alkylsulfonyl, carboxyl-$C_{1-7}$-alkylsulfanyl, carboxyl-$C_{1-7}$-alkylsulfonyl, $C_{1-7}$-alkoxycarbonyl-$C_{1-7}$-alkylsulfanyl, $C_{1-7}$-alkoxycarbonyl-$C_{1-7}$-alkylsulfonyl, $C_{1-7}$-alkoxycarbonylamino-$C_{1-7}$-alkylsulfanyl, carboxyl-$C_{1-7}$-alkyl-aminocarbonyl-$C_{1-7}$-alkylsulfanyl, carboxyl-$C_{1-7}$-alkyl-aminocarbonyl-$C_{1-7}$-alkylsulfonyl, heterocyclylsulfanyl, wherein heterocyclyl is unsubstituted or substituted by $C_{1-7}$-alkoxycarbonyl, oxo, $C_{1-7}$-alkylsulfonyl or aminosulfonyl, heterocyclylsulfonyl, wherein heterocyclyl is unsubstituted or substituted by $C_{1-7}$-alkoxycarbonyl, oxo, $C_{1-7}$-alkylsulfonyl or aminosulfonyl, heterocyclyl-$C_{1-7}$-alkylsulfanyl, heterocyclyl-$C_{1-7}$-alkylsulfonyl, aminosulfonyl, $C_{1-7}$-alkylaminosulfonyl, di-($C_{1-7}$-alkyl)-aminosulfonyl, $C_{1-7}$-alkylsulfonylamino-$C_{1-7}$-alkylsulfanyl, $C_{1-7}$-alkylsulfonylamino-$C_{1-7}$-alkylsulfonyl, aminosulfonylamino-$C_{1-7}$-alkylsulfanyl, aminosulfonylamino-$C_{1-7}$-alkylsulfonyl, amino-$C_{1-7}$-alkylsulfanyl, amino-$C_{1-7}$-alkylsulfonyl, aminocarbonyl-$C_{1-7}$-alkyl, aminocarbonyl-$C_{1-7}$-alkylsulfonyl amino, $C_{1-7}$-alkylamino, di-($C_{1-7}$-alkyl)-amino, hydroxy-$C_{1-7}$-alkylamino, nitro, unsubstituted heterocyclyl and heterocyclyl substituted with one or two groups selected from the group consisting of halogen, oxo, $C_{1-7}$-alkyl and $C_{1-7}$-alkoxycarbonyl;

$R^7$ is hydrogen or halogen; and $R^8$ is selected from the group consisting of hydrogen, $C_{1-7}$-alkyl, halogen, halogen-$C_{1-7}$-alkyl and $C_{1-7}$-alkoxy;

or pharmaceutically acceptable salts thereof.

The invention is also concerned with processes for the manufacture of compounds of formula I.

The invention also relates to pharmaceutical compositions comprising a compound as described above and a pharmaceutically acceptable carrier and/or adjuvant.

A further aspect of the invention is the use of compounds of formula I as therapeutically active substances for the treatment of diseases which are associated with the modulation of GPBAR1 activity. The invention thus potentially relates to a method for the treatment of a disease associated with the modulation of GPBAR1 activity such as for example diabetes, particularly type II diabetes or gestational diabetes.

DETAILED DESCRIPTION OF THE INVENTION

Unless otherwise indicated, the following definitions are set forth to illustrate and define the meaning and scope of the various terms used to describe the invention.

The term "halogen" refers to fluoro, chloro, bromo and iodo, with fluoro, chloro and bromo being of particular interest. More particularly, halogen refers to fluoro and chloro.

The term "alkyl", alone or in combination with other groups, refers to a branched or straight-chain monovalent saturated aliphatic hydrocarbon radical of one to twenty carbon atoms, particularly one to sixteen carbon atoms, more particularly one to ten carbon atoms. The term "$C_{1-10}$-alkyl" refers to a branched or straight-chain monovalent saturated aliphatic hydrocarbon radical of one to ten carbon atoms, such as e.g., methyl, ethyl, n-propyl, isopropyl, n-butyl, sec-butyl, tert-butyl, pentyl, 1,1,3,3-tetramethyl-butyl and the like. Lower alkyl groups as described below are also preferred alkyl groups.

The term "lower alkyl" or "$C_{1-7}$-alkyl", alone or in combination, signifies a straight-chain or branched-chain alkyl group with 1 to 7 carbon atoms, in particular a straight or branched-chain alkyl group with 1 to 6 carbon atoms and more particularly a straight or branched-chain alkyl group with 1 to 4 carbon atoms. Examples of straight-chain and branched $C_{1-7}$ alkyl groups are methyl, ethyl, propyl, isopropyl, butyl, isobutyl, tert.-butyl, the isomeric pentyls, the isomeric hexyls and the isomeric heptyls, in particular methyl and ethyl.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl, more particularly cyclopropyl.

The term "lower cycloalkylalkyl" or "$C_{3-7}$-cycloalkyl-$C_{1-7}$-alkyl" refers to lower alkyl groups as defined above wherein at least one of the hydrogen atoms of the lower alkyl group is replaced by a cycloalkyl group. Among the lower cycloalkylalkyl groups of particular interest resides cyclopropylmethyl.

The term "cycloalkyl-oxy" or "$C_{3-7}$-cycloalkyl-oxy" refers to the group $R^c$—O—, wherein $R^c$ is cycloalkyl and the term "cycloalkyl" has the previously given significance. Examples of lower cycloalkyl-oxy groups are cyclopropyloxy or cyclobutyloxy.

The term "lower alkoxy" or "$C_{1-7}$-alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec-butoxy and tert-butoxy, in particular methoxy.

The term "lower cycloalkylalkoxy" or "$C_{3-7}$-cycloalkyl-$C_{1-7}$-alkoxy" refers to lower alkoxy groups as defined above wherein at least one of the hydrogen atoms of the lower alkyl group is replaced by a cycloalkyl group. Among the lower cycloalkylalkyl groups of particular interest resides cyclopropylmethyl.

The term "lower alkoxyalkyl" or "$C_{1-7}$-alkoxy-$C_{1-7}$-alkyl" refers to lower alkyl groups as defined above wherein at least one of the hydrogen atoms of the lower alkyl group is replaced by a lower alkoxy group. Among the lower alkoxyalkyl groups of particular interest are methoxymethyl and 2-methoxyethyl.

The term "lower alkoxyalkoxy" or "$C_{1-7}$-alkoxy-$C_{1-7}$-alkoxy" refers to lower alkoxy groups as defined above wherein at least one of the hydrogen atoms of the lower alkoxy group is replaced by a further lower alkoxy group. Among the lower alkoxyalkoxy groups of particular interest are 2-methoxyethoxy and 3-methoxypropoxy.

The term hydroxy means the group —OH.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Among the particular interesting lower hydroxyalkyl groups are hydroxymethyl or hydroxyethyl.

"Lower hydroxyalkoxy" or "hydroxy-$C_{1-7}$-alkoxy" refers to lower alkoxy groups as defined above wherein at least one of the hydrogen atoms of the lower alkoxy group is replaced by a hydroxy group. Among the particular interesting lower hydroxyalkyl groups are hydroxyethoxy or hydroxypropoxy.

The term "lower halogenalkyl" or "halogen-$C_{1-7}$-alkyl" refers to lower alkyl groups as defined above wherein at least one of the hydrogen atoms of the lower alkyl group is replaced by a halogen atom, particularly fluoro or chloro, most particularly fluoro. Among the lower halogenalkyl groups of particular interest are trifluoromethyl, difluoromethyl, trifluoroethyl, 2,2-difluoroethyl, fluoromethyl and chloromethyl, with trifluoromethyl or difluoromethyl being especially interesting.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, particularly fluoro or chloro, most particularly fluoro. Among the lower halogenalkoxy groups of particular interest are trifluoromethoxy, difluoromethoxy, fluoromethoxy and chloromethoxy, more particularly trifluoromethoxy.

The term "cyano" refers to the group —CN.

The term "lower cyanoalkyl" or "cyano-$C_{1-7}$-alkyl" refers to lower alkyl groups as defined above wherein at least one of the hydrogen atoms of the lower alkyl group is replaced by a cyano group. A cyanoalkyl group of particular interest is cyanomethyl. The term "lower cyanoalkoxy" or "cyano-$C_{1-7}$-alkoxy" refers to a lower alkoxy group as defined above wherein at least one of the hydrogen atoms of the lower alkoxy group is replaced by a cyano group.

The term "carboxyl" means the group —COOH.

The term "lower carboxylalkyl" or "carboxyl-$C_{1-7}$-alkyl" refers to lower alkyl groups as defined above wherein at least one of the hydrogen atoms of the lower alkyl group is replaced by a carboxyl group. Among the lower carboxylalkyl groups of particular interest are carboxylmethyl (—$CH_2$—COOH) and carboxyl ethyl (—$CH_2$—$CH_2$—COOH).

"Lower carboxylalkoxy" or "carboxyl-$C_{1-7}$-alkoxy" refers to a lower alkoxy group as defined above wherein at least one of the hydrogen atoms of the lower alkoxy group is replaced by a carboxyl group. Among the lower carboxylalkoxy groups of particular interest are carboxylmethoxy (—O—$CH_2$—COOH) and carboxylethoxy (—O—$CH_2$—$CH_2$—COOH).

The term "lower alkoxycarbonyl" or "$C_{1-7}$-alkoxycarbonyl" refers to the group —COOR, wherein R is lower alkyl and the term "lower alkyl" has the previously given significance. Lower alkoxycarbonyl groups of particular interest are methoxycarbonyl or ethoxycarbonyl.

The term "lower alkoxycarbonylalkyl" or "$C_{1-7}$-alkoxycarbonyl-$C_{1-7}$-alkyl" means a lower alkyl group as defined above wherein one of the hydrogen atoms of the lower alkyl group is replaced by $C_{1-7}$-alkoxycarbonyl. A lower alkoxycarbonylalkyl group of particular interest is —$CH_2$—COOCH$_3$.

The term "lower alkoxycarbonylalkoxy" or "$C_{1-7}$-alkoxycarbonyl-$C_{1-7}$-alkoxy" means a lower alkoxy group as defined above wherein one of the hydrogen atoms of the lower alkoxy group is replaced by $C_{1-7}$-alkoxycarbonyl. An example for a lower alkoxycarbonylalkoxy group is —O—CH$_2$—COOCH$_3$.

The term "lower alkylsulfanyl" or "$C_{1-7}$-alkylsulfanyl" means the group —S—R, wherein R is a lower alkyl group as defined above. A lower alkylsulfanyl group of particular interest is methylsulfanyl.

The term "lower hydroxyalkylsulfanyl" or "hydroxy-$C_{1-7}$-alkylsulfanyl" refers to lower alkylsulfanyl groups as defined above wherein at least one of the hydrogen atoms of the lower alkylsulfanyl group is replaced by a hydroxy group. Among the particular interesting lower hydroxyalkylsulfanyl groups are hydroxyethylsulfanyl.

The term "lower alkoxyalkylsulfanyl" or "$C_{1-7}$-alkoxy-$C_{1-7}$-alkylsulfanyl" refers to lower alkylsulfanyl groups as defined above wherein at least one of the hydrogen atoms of the lower alkylsulfanyl group is replaced by an alkoxy group. Among the particular interesting lower alkoxyalkylsulfanyl groups are methoxyethylsulfanyl.

The term "carboxylalkylsulfanyl" or "carboxyl-$C_{1-7}$-alkylsulfanyl" refers to lower alkylsulfanyl groups as defined above wherein at least one of the hydrogen atoms of the lower alkylsulfanyl group is replaced by a carboxyl group. Among the particular interesting lower carboxylalkylsulfanyl groups are —S—(CH$_2$)$_3$—COOH or —S—(CH$_2$)$_4$—COOH.

The term "lower alkoxycarbonylalkylsulfanyl" or "$C_{1-7}$-alkoxycarbonyl-$C_{1-7}$-alkylsulfanyl" refers to lower alkylsulfanyl groups as defined above wherein at least one of the hydrogen atoms of the lower alkylsulfanyl group is replaced by a lower alkoxycarbonyl group. Among the particular interesting lower alkoxycarbonyl-alkylsulfanyl groups is —S—(CH$_2$)$_2$—COOCH$_3$.

The term "lower alkoxycarbonylaminoalkylsulfanyl" or "$C_{1-7}$-alkoxycarbonylamino-$C_{1-7}$-alkylsulfanyl" refers to lower alkylsulfanyl groups as defined above wherein at least one of the hydrogen atoms of the lower alkylsulfanyl group is replaced by a lower alkoxycarbonylamino group. Among the particular interesting lower alkoxycarbonylamino-alkylsulfanyl groups is the group —S—(CH$_2$)$_2$—NH—COOC(CH$_3$)$_3$.

The term "lower carboxylalkyl-aminocarbonyl-alkylsulfanyl" or "carboxyl-$C_{1-7}$-alkyl-aminocarbonyl-$C_{1-7}$-alkylsulfanyl" refers to lower alkylsulfanyl groups as defined above wherein at least one of the hydrogen atoms of the lower alkylsulfanyl group is replaced by a lower carboxylalkyl-aminocarbonyl group. Among the particular interesting lower carboxylalkyl-aminocarbonyl-alkylsulfanyl groups is the group —S—(CH$_2$)$_4$—CO—NH—CH$_2$—COOH.

The term "aminosulfanyl" refers to the group —S—NH$_2$.

The term "lower aminoalkylsulfanyl" or "amino-$C_{1-7}$-alkylsulfanyl" refers to lower alkylsulfanyl groups as defined above wherein at least one of the hydrogen atoms of the lower alkylsulfanyl group is replaced by an amino group. Among the particular interesting lower aminoalkylsulfanyl groups is —S—(CH$_2$)$_2$—NH$_2$.

The term "lower alkylsulfonylamino-alkylsulfanyl" or "$C_{1-7}$-alkyl-sulfonylamino-$C_{1-7}$-alkylsulfanyl" refers to lower alkylsulfanyl groups as defined above wherein at least one of the hydrogen atoms of the lower alkylsulfanyl group is replaced by a lower alkylsulfonylamino group. Among the particular interesting lower alkylsulfonylamino-alkylsulfanyl groups is the group —S—(CH$_2$)$_2$—NH—SO$_2$—CH$_3$.

The term "lower aminosulfonylamino-alkylsulfanyl" or "aminosulfonylamino-$C_{1-7}$-alkylsulfanyl" refers to lower alkylsulfanyl groups as defined above wherein at least one of the hydrogen atoms of the lower alkylsulfanyl group is replaced by an aminosulfonylamino group. Among the particular interesting lower aminosulfonylamino-alkylsulfanyl groups is the group —S—(CH$_2$)$_2$—NH—SO$_2$—NH$_2$.

The term "lower heterocyclylalkylsulfanyl" or "heterocyclyl-$C_{1-7}$-alkylsulfanyl" refers to lower alkylsulfanyl groups as defined above wherein at least one of the hydrogen atoms of the lower alkylsulfanyl group is replaced by a heterocyclyl group as defined below. Among the particular interesting lower heterocyclylalkylsulfanyl groups is azetidinylethylsulfanyl.

The term "lower alkylsulfonyl" or "$C_{1-7}$-alkylsulfonyl" means the group —S(O)$_2$—R, wherein R is a lower alkyl group as defined above. A lower alkylsulfonyl group of particular interest is methylsulfonyl.

The term "lower alkylsulfonylalkyl" or "$C_{1-7}$-alkylsulfonyl-$C_{1-7}$-alkyl" means a lower alkyl group as defined above wherein one of the hydrogen atoms of the lower alkyl group is replaced by $C_{1-7}$-alkylsulfonyl. A preferred lower alkylsulfonylalkyl group is —(CH$_2$)$_2$—S(O)$_2$—CH$_3$.

The term "lower hydroxyalkylsulfonyl" or "hydroxy-$C_{1-7}$-alkylsulfonyl" refers to lower alkylsulfonyl groups as defined above wherein at least one of the hydrogen atoms of the lower alkylsulfonyl group is replaced by a hydroxy group. Among the particular interesting lower hydroxyalkylsulfonyl groups are hydroxyethylsulfonyl.

The term "lower alkoxyalkylsulfonyl" or "$C_{1-7}$-alkoxy-$C_{1-7}$-alkylsulfonyl" refers to lower alkylsulfonyl groups as defined above wherein at least one of the hydrogen atoms of the lower alkylsulfonyl group is replaced by an alkoxy group. Among the particular interesting lower alkoxyalkylsulfonyl groups is methoxyethylsulfonyl.

The term "carboxylalkylsulfonyl" or "carboxyl-$C_{1-7}$-alkylsulfonyl" refers to lower alkylsulfonyl groups as defined above wherein at least one of the hydrogen atoms of the lower alkylsulfonyl group is replaced by a carboxyl group. Among the particular interesting lower carboxylalkylsulfonyl groups are —S(O)$_2$—(CH$_2$)$_3$—COOH or —S(O)$_2$—(CH$_2$)$_4$—COOH.

The term "lower alkoxycarbonylalkylsulfonyl" or "$C_{1-7}$-alkoxycarbonyl-$C_{1-7}$-alkyl-sulfonyl" refers to lower alkylsulfonyl groups as defined above wherein at least one of the hydrogen atoms of the lower alkylsulfonyl group is replaced by a lower alkoxycarbonyl group. Among the particular interesting lower alkoxycarbonyl-alkylsulfonyl groups is —S(O)$_2$—(CH$_2$)$_2$—COOCH$_3$.

The term "lower aminocarbonyl-alkylsulfonyl" or "aminocarbonyl-$C_{1-7}$-alkylsulfonyl" refers to lower alkylsulfonyl groups as defined above wherein at least one of the hydrogen atoms of the lower alkylsulfonyl group is replaced by an aminocarbonyl group. Among the particular interesting lower aminocarbonyl-alkylsulfonyl groups is the group —S(O)$_2$—(CH$_2$)$_4$—CO—NH$_2$.

The term "lower alkylsulfonylamino-alkylsulfonyl" or "$C_{1-7}$-alkyl-sulfonylamino-$C_{1-7}$-alkylsulfonyl" refers to lower alkylsulfonyl groups as defined above wherein at least one of the hydrogen atoms of the lower alkylsulfonyl group is replaced by a lower alkylsulfonylamino group. Among the particular interesting lower alkylsulfonylamino-alkylsulfonyl groups is the group —SO$_2$—(CH$_2$)$_2$—NH—SO$_2$—CH$_3$.

The term "lower aminosulfonylamino-alkylsulfonyl" or "aminosulfonylamino-$C_{1-7}$-alkylsulfonyl" refers to lower alkylsulfonyl groups as defined above wherein at least one of the hydrogen atoms of the lower alkylsulfonyl group is replaced by an aminosulfonylamino group. Among the particular interesting lower aminosulfonylamino-alkylsulfonyl groups is the group —SO$_2$—(CH$_2$)$_2$—NH—SO$_2$—NH$_2$.

The term "lower heterocyclylalkylsulfonyl" or "heterocyclyl-C$_{1-7}$-alkylsulfonyl" refers to lower alkylsulfonyl groups as defined above wherein at least one of the hydrogen atoms of the lower alkylsulfonyl group is replaced by a heterocyclyl group as defined below. Among the particular interesting lower heterocyclylalkylsulfonyl groups is azetidinyl-ethylsulfonyl.

The term "lower carboxylalkyl-aminocarbonyl-alkylsulfonyl" or "carboxyl-C$_{1-7}$-alkyl-aminocarbonyl-C$_{1-7}$-alkylsulfonyl" refers to lower alkylsulfonyl groups as defined above wherein at least one of the hydrogen atoms of the lower alkylsulfonyl group is replaced by a lower carboxylalkyl-aminocarbonyl group. Among the particular interesting lower carboxylalkyl-aminocarbonyl-alkylsulfonyl groups is the group —S(O)$_2$—(CH$_2$)$_4$—CO—NH—CH$_2$—COOH.

The term "aminosulfonyl" means the group —S(O)$_2$—NH$_2$.

The term "lower alkylaminosulfonyl" or "C$_{1-7}$-alkylaminosulfonyl" defines the group —S(O)$_2$—NH—R, wherein R is lower alkyl and the term "lower alkyl" has the previously given meaning. An example of a lower alkylaminosulfonyl group is methylaminosulfonyl.

The term "di-lower alkylaminosulfonyl" or "di-C$_{1-7}$-alkylaminosulfonyl" defines the group —S(O)$_2$—NRR', wherein R and R$^1$ are lower alkyl groups as defined above. An example of a di-lower alkylaminosulfonyl group is dimethylaminosulfonyl.

The term "aminoalkylsulfonyl" or "amino-C$_{1-7}$-alkylsulfonyl" refers to lower alkylsulfonyl groups as defined above wherein at least one of the hydrogen atoms of the lower alkylsulfonyl group is replaced by an amino group. Among the particular interesting lower aminoalkylsulfonyl groups is —S(O)$_2$—(CH$_2$)$_2$—NH$_2$.

"Amino" refers to the group —NH$_2$. The term "C$_{1-7}$-alkylamino" means a group —NHR, wherein R is lower alkyl and the term "lower alkyl" has the previously given significance. The term "di-C$_{1-7}$-alkylamino" means a group —NRR', wherein R and R$^1$ are lower alkyl groups as defined above.

The term "C$_{1-7}$-alkoxy-C$_{1-7}$-alkyl-C$_{1-7}$-alkylamino" refers to a group —NRR", wherein R is a lower alkyl group as defined above and R" is a lower alkoxyalkyl group as defined herein.

The term "C$_{1-7}$-hydroxyalkyl-C$_{1-7}$-alkylamino" refers to a group —NRR", wherein R is a lower alkyl group as defined above and R" is a lower hydroxyalkyl group as defined herein.

The term "lower alkylcarbonyl" or "C$_{1-7}$-alkylcarbonyl" defines the group —CO—R, wherein R is lower alkyl and the term "lower alkyl" has the previously given meaning. A lower alkylcarbonyl group of particular interest is acetyl.

The term "lower alkylcarbonylalkyl" or "C$_{1-7}$-alkylcarbonyl-C$_{1-7}$-alkyl" refers to lower alkyl groups as defined above wherein at least one of the hydrogen atoms of the lower alkyl group is replaced by a lower alkylcarbonyl group.

The term "aminocarbonyl" refers to the group —CO—NH$_2$.

The term "lower aminocarbonylalkyl" or "aminocarbonyl-C$_{1-7}$-alkyl" means lower alkyl groups as defined above wherein one of the hydrogen atoms of the lower alkyl group is replaced by aminocarbonyl. A lower aminocarbonylalkyl group of particular interest is —CH$_2$—CONH$_2$.

The term "lower alkylaminocarbonyl" or "C$_{1-7}$-alkylaminocarbonyl" refers to a group —CONH—R$^{14}$, wherein R$^{14}$ is lower alkyl as defined herein before.

The term "lower alkylaminocarbonylalkyl" or "C$_{1-7}$-alkyl-aminocarbonyl-C$_{1-7}$-alkyl" means a lower alkyl group as defined above wherein one of the hydrogen atoms of the lower alkyl group is replaced by lower alkylaminocarbonyl. A typical lower alkylaminocarbonylalkyl group has for example the formula —CH$_2$—CONHR, wherein R is lower alkyl. The term "di-C$_{1-7}$-alkyl-aminocarbonyl-C$_{1-7}$-alkyl" refers to a lower alkyl group as defined above wherein one of the hydrogen atoms of the lower alkyl group is replaced by di-C$_{1-7}$-alkyl-aminocarbonyl group of the formula —CO—NRR', wherein R and R' are lower alkyl groups.

The term "di-C$_{1-7}$-alkyl-aminocarbonyl" refers to a group —CONR$^{14}$R$^{15}$, wherein R$^{14}$ and R$^{15}$ are lower alkyl as defined herein before.

The term "phenyloxy" refers to the group —O-Ph wherein Ph is phenyl.

The term "lower phenylalkyl" or "phenyl-C$_{1-7}$-alkyl" means lower alkyl groups as defined above wherein one of the hydrogen atoms of the lower alkyl group is replaced by an optionally substituted phenyl group. An example is benzyl.

The term "lower phenylalkoxy" or "phenyl-C$_{1-7}$-alkoxy" means a lower alkoxy group as defined above wherein one of the hydrogen atoms of the lower alkoxy group is replaced by an optionally substituted phenyl group. An example for a "phenyl-C$_{1-7}$-alkoxy" group is benzyloxy.

The term "lower phenylalkoxy-carbonylamino" or "phenyl-C$_{1-7}$-alkoxy-carbonylamino" means a group —NH—CO—OR$^V$, wherein R$^V$ is a lower phenylalkyl group as defined above. The term "lower phenylalkoxy-carbonylaminoalkyl" or "phenyl-C$_{1-7}$-alkoxy-carbonylamino-C$_{1-7}$-alkyl" means a lower alkyl group as defined above wherein one of the hydrogen atoms of the lower alkyl group is replaced by the group —NH—CO—OR$^V$.

The term "heterocyclyl" refers to a saturated or partly unsaturated 3-, 4-, 5-, 6- or 7-membered ring which can comprise one, two or three atoms selected from nitrogen, oxygen and/or sulphur. Examples of heterocyclyl rings include aziridinyl, azetidinyl, oxetanyl, piperidinyl, piperazinyl, azepanyl, pyrrolidinyl, pyrazolidinyl, imidazolinyl, imidazolidinyl, oxazolidinyl, isoxazolidinyl, morpholinyl, thiazolidinyl, isothiazolidinyl, thiadiazolylidinyl, dihydrofuryl, tetrahydrofuryl, dihydropyranyl, tetrahydropyranyl, thiomorpholinyl, 2-oxo-1,2-dihydropyridinyl and 1,1-dioxo-1λ6-thiomorpholinyl. The term "heterocyclyl" further refers to bicyclic groups comprising two 3- to 7-membered rings, in which one or both rings can contain one, two or three atoms selected from nitrogen, oxygen or sulphur and one of the carbon atoms is a member of both rings (a "spiro" group). An example for such a bicyclic heterocyclyl group is 2-oxa-6-aza-spiro[3.3]heptyl.

The term "heterocyclyl-oxy" refers to the group —O-Het wherein Het is a heterocyclyl group as defined above.

The term "lower heterocyclylalkyl" or "heterocyclyl-C$_{1-7}$-alkyl" refers to lower alkyl groups as defined above wherein at least one of the hydrogen atoms of the lower alkyl group is replaced by a heterocyclyl group as defined above.

The term "lower heterocyclylalkoxy" or "heterocyclyl-C$_{1-7}$-alkoxy" means a lower alkoxy group as defined above wherein one of the hydrogen atoms of the lower alkoxy group is replaced by a heterocyclyl group as defined above.

The term "heterocyclylsulfanyl" means the group —S—Het, wherein Het is a heterocyclyl group as defined above. Lower heterocyclylsulfanyl groups of particular interest are oxetan-3-yl-sulfanyl or azetidinyl-sulfanyl.

The term "heterocyclylsulfonyl" means the group —S(O)$_2$—Het, wherein Het is a heterocyclyl group as defined above. Lower heterocyclylsulfonyl groups of particular interest are oxetan-3-yl-sulfonyl, azetidinyl-sulfonyl or morpholinyl-sulfonyl.

The term "heteroaryl" in general refers to an aromatic 5- or 6-membered ring which comprises one, two or three atoms selected from nitrogen, oxygen and/or sulphur, such as pyridyl, pyrazinyl, pyrimidinyl, pyridazinyl, pyrrolyl, oxazolyl, oxadiazolyl, isoxazolyl, thiadiazolyl, tetrazolyl, pyrazolyl, imidazolyl, furyl, thiazolyl and thienyl. The term "heteroaryl" further refers to bicyclic aromatic groups comprising two 5- or 6-membered rings, in which one or both rings can contain one, two or three atoms selected from nitrogen, oxygen or sulphur, such as quinolinyl, isoquinolinyl, cinnolinyl, pyrazolo[1,5-a]pyridyl, imidazo[1,2-a]pyridyl, quinoxalinyl, benzothiazolyl, benzotriazolyl, indolyl and indazolyl. Most particularly, heteroaryl is pyridyl or pyrrolyl.

The term "lower heteroarylalkyl" or "heteroaryl-$C_{1-7}$-alkyl" refers to lower alkyl groups as defined above wherein at least one of the hydrogen atoms of the lower alkyl group is replaced by a heteroaryl group as defined above.

The term "nitro" refers to the group —NO$_2$.

The term "oxo" means that a C-atom of the heterocyclyl or heteroaryl ring is substituted by =O, thus meaning that the heterocyclyl or heteroaryl ring may contain one or more carbonyl (—CO—) groups.

Compounds of formula I can form pharmaceutically acceptable salts. The term "pharmaceutically acceptable salts" refers to those salts which retain the biological effectiveness and properties of the free bases or free acids, which are not biologically or otherwise undesirable. The salts are for example acid addition salts of compounds of formula I with physiologically compatible mineral acids, such as hydrochloric acid, sulfuric acid, sulfurous acid or phosphoric acid; or with organic acids, such as methanesulfonic acid, ethanesulfonic acid, p-toluenesulfonic acid, acetic acid, propionic acid, glycolic acid, pyruvic acid, oxylic acid, lactic acid, trifluoroacetic acid, citric acid, fumaric acid, maleic acid, malonic acid, tartaric acid, benzoic acid, cinnamic acid, mandelic acid, succinic acid or salicylic acid. In addition, pharmaceutically acceptable salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Pharmaceutically acceptable salts of compounds of formula I of particular interest are the hydrochloride salts.

The compounds of formula I can also be solvated, e.g., hydrated. The solvation can be effected in the course of the manufacturing process or can take place e.g. as a consequence of hygroscopic properties of an initially anhydrous compound of formula I (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

In detail, the present invention relates to compounds of the formula

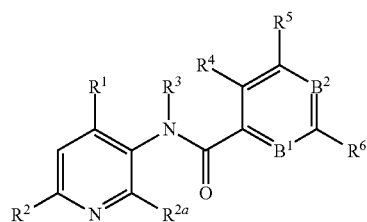

wherein
$B^1$ is $CR^7$ or N;
$B^2$ is $CR^8$ or N;
$R^1$ is selected from the group consisting of
  phenyl, said phenyl being unsubstituted or substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy, cycloalkyl-oxy, cycloalkyl-$C_{1-7}$-alkoxy, cyano, cyano-$C_{1-7}$-alkoxy, carboxyl, carboxyl-$C_{1-7}$-alkyl, $C_{1-7}$-alkoxycarbonyl, hydroxy-$C_{1-7}$-alkyl, hydroxy-$C_{1-7}$-alkoxy, $C_{1-7}$-alkoxy-$C_{1-7}$-alkyl, carboxyl-$C_{1-7}$-alkoxy, $C_{1-7}$-alkoxycarbonyl-$C_{1-7}$-alkoxy, amino, $C_{1-7}$-alkylamino, di-$C_{1-7}$-alkylamino, and phenyl-$C_{1-7}$-alkoxy,
  heterocyclyl-oxy and heterocyclyl-$C_{1-7}$-alkoxy, wherein heterocyclyl is unsubstituted or substituted by $C_{1-7}$-alkoxycarbonyl,
  heteroaryl, said heteroaryl being unsubstituted or substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy, cycloalkyl-oxy, and cycloalkyl-$C_{1-7}$-alkoxy,
  heterocyclyl-oxy and heterocyclyl-$C_{1-7}$-alkoxy, wherein heterocyclyl is unsubstituted or substituted by $C_{1-7}$-alkoxycarbonyl,
  3,6-dihydro-2H-pyran-4-yl, and
  piperidinyl, said piperidinyl being substituted with one to four $C_{1-7}$-alkyl groups;
$R^2$ is selected from the group consisting of hydrogen, $C_{1-7}$-alkyl, halogen, halogen-$C_{1-7}$-alkyl, halogen-$C_{1-7}$-alkoxy, cyano, $C_{1-7}$-alkoxy, amino, $C_{1-7}$-alkylamino, di-$C_{1-7}$-alkylamino, aminocarbonyl, $C_{1-7}$-alkylaminocarbonyl, di-$C_{1-7}$-alkylaminocarbonyl, hydroxy-$C_{1-7}$-alkyl-($C_{1-7}$-alkyl)amino, $C_{1-7}$-alkoxy-$C_{1-7}$-alkyl-($C_{1-7}$-alkyl)amino, and heteroaryl;
$R^{2a}$ is selected from the group consisting of hydrogen, methyl and halogen;
$R^3$ is selected from the group consisting of $C_{1-7}$-alkyl, halogen-$C_{1-7}$-alkyl, hydroxy-$C_{1-7}$-alkyl, $C_{1-7}$-alkylcarbonyl-$C_{1-7}$-alkyl, carboxyl-$C_{1-7}$-alkyl, $C_{1-7}$-alkoxycarbonyl-$C_{1-7}$-alkyl, cyano-$C_{1-7}$-alkyl, aminocarbonyl-$C_{1-7}$-alkyl, $C_{1-7}$-alkylaminocarbonyl-$C_{1-7}$-alkyl, di-$C_{1-7}$-alkylaminocarbonyl-$C_{1-7}$-alkyl, $C_{1-7}$-alkylsulfonyl-$C_{1-7}$-alkyl, $C_{3-7}$-cycloalkyl, unsubstituted heterocyclyl or heterocyclyl substituted with one or two groups selected from halogen, oxo, hydroxy and $C_{1-7}$-alkyl, heterocyclyl-$C_{1-7}$-alkyl, wherein heterocyclyl is unsubstituted or substituted with one or two groups selected from halogen, oxo and $C_{1-7}$-alkyl, heteroaryl-$C_{1-7}$-alkyl, wherein heteroaryl is unsubstituted or substituted with one or two groups selected from halogen, oxo and $C_{1-7}$-alkyl and phenyl-$C_{1-7}$-alkoxycarbonylamino-$C_{1-7}$-alkyl;

$R^4$ is selected from the group consisting of hydrogen, halogen, $C_{1-7}$-alkyl and $C_{1-7}$-alkoxy;

$R^5$ and $R^6$ are independently from each other selected from the group consisting of hydrogen, $C_{1-7}$-alkyl, $C_{1-7}$-cycloalkyl, halogen, halogen-$C_{1-7}$-alkyl, halogen-$C_{1-7}$-alkoxy, hydroxy, hydroxy-$C_{1-7}$-alkyl, $C_{1-7}$-alkoxy, cyano, carboxyl, $C_{1-7}$-alkoxycarbonyl, $C_{1-7}$-alkoxycarbonyl-$C_{1-7}$-alkyl, hydroxy-$C_{1-7}$-alkoxy, $C_{1-7}$-alkoxy-$C_{1-7}$-alkoxy, $C_{1-7}$-alkylsulfanyl, hydroxy-$C_{1-7}$-alkylsulfanyl, $C_{1-7}$-alkoxy-$C_{1-7}$-alkylsulfanyl, $C_{1-7}$-alkylsulfonyl, hydroxy-$C_{1-7}$-alkylsulfonyl, $C_{1-7}$-alkoxy-$C_{1-7}$-alkylsulfonyl, carboxyl-$C_{1-7}$-alkylsulfanyl, carboxyl-$C_{1-7}$-alkylsulfonyl, $C_{1-7}$-alkoxycarbonyl-$C_{1-7}$-alkylsulfanyl, $C_{1-7}$-alkoxycarbonyl-$C_{1-7}$-alkylsulfonyl, $C_{1-7}$-alkoxycarbonylamino-$C_{1-7}$-alkylsulfanyl, carboxyl-$C_{1-7}$-alkyl-aminocarbonyl-$C_{1-7}$-alkylsulfanyl, carboxyl-$C_{1-7}$-alkyl-aminocarbonyl-$C_{1-7}$-alkylsulfonyl, heterocyclylsulfanyl, wherein heterocyclyl is unsubstituted or substituted by $C_{1-7}$-alkoxycarbonyl, oxo, $C_{1-7}$-alkylsulfonyl or aminosulfonyl, heterocyclylsulfonyl, wherein heterocyclyl is unsubstituted or substituted by $C_{1-7}$-alkoxycarbonyl, oxo, $C_{1-7}$-alkylsulfonyl or aminosulfonyl, heterocyclyl-$C_{1-7}$-alkylsulfanyl, heterocyclyl-$C_{1-7}$-alkylsulfonyl, aminosulfonyl, $C_{1-7}$-alkylaminosulfonyl, di-($C_{1-7}$-alkyl)-aminosulfonyl, $C_{1-7}$-alkylsulfonylamino-$C_{1-7}$-alkylsulfanyl, $C_{1-7}$-alkylsulfonylamino-$C_{1-7}$-alkylsulfonyl, aminosulfonylamino-$C_{1-7}$-alkylsulfanyl, aminosulfonylamino-$C_{1-7}$-alkylsulfonyl, amino-$C_{1-7}$-alkylsulfanyl, amino-$C_{1-7}$-alkylsulfonyl, aminocarbonyl-$C_{1-7}$-alkyl, aminocarbonyl-$C_{1-7}$-alkylsulfonyl amino, $C_{1-7}$-alkylamino, di-($C_{1-7}$-alkyl)-amino, hydroxy-$C_{1-7}$-alkylamino, nitro, unsubstituted heterocyclyl and heterocyclyl substituted with one or two groups selected from the group consisting of halogen, oxo, $C_{1-7}$-alkyl and $C_{1-7}$-alkoxycarbonyl;

$R^7$ is hydrogen or halogen; and $R^8$ is selected from the group consisting of hydrogen, $C_{1-7}$-alkyl, halogen, halogen-$C_{1-7}$-alkyl and $C_{1-7}$-alkoxy;

or pharmaceutically acceptable salts thereof.

One group of compounds of formula I according to the invention are those, wherein $R^1$ is phenyl, said phenyl being unsubstituted or substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy, cycloalkyl-oxy, cycloalkyl-$C_{1-7}$-alkoxy, cyano, cyano-$C_{1-7}$-alkoxy, carboxyl, carboxyl-$C_{1-7}$-alkyl, $C_{1-7}$-alkoxycarbonyl, hydroxy-$C_{1-7}$-alkyl, hydroxy-$C_{1-7}$-alkoxy, $C_{1-7}$-alkoxy-$C_{1-7}$-alkyl, carboxyl-$C_{1-7}$-alkoxy, $C_{1-7}$-alkoxycarbonyl-$C_{1-7}$-alkoxy, amino, $C_{1-7}$-alkylamino, di-$C_{1-7}$-alkylamino, phenyl-$C_{1-7}$-alkoxy, heterocyclyl-oxy and heterocyclyl-$C_{1-7}$-alkoxy, wherein heterocyclyl is unsubstituted or substituted by $C_{1-7}$-alkoxycarbonyl.

In particular, $R^1$ is phenyl, said phenyl being substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy, cycloalkyl-oxy, cycloalkyl-$C_{1-7}$-alkoxy, cyano, cyano-$C_{1-7}$-alkoxy, carboxyl, carboxyl-$C_{1-7}$-alkyl, $C_{1-7}$-alkoxycarbonyl, hydroxy-$C_{1-7}$-alkyl, hydroxy-$C_{1-7}$-alkoxy, $C_{1-7}$-alkoxy-$C_{1-7}$-alkyl, carboxyl-$C_{1-7}$-alkoxy, $C_{1-7}$-alkoxycarbonyl-$C_{1-7}$-alkoxy, amino, $C_{1-7}$-alkylamino, di-$C_{1-7}$-alkylamino, phenyl-$C_{1-7}$-alkoxy, heterocyclyl-oxy and heterocyclyl-$C_{1-7}$-alkoxy, wherein heterocyclyl is unsubstituted or substituted by $C_{1-7}$-alkoxycarbonyl, more particularly being substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy, cycloalkyl-$C_{1-7}$-alkoxy, cyano, cyano-$C_{1-7}$-alkoxy, carboxyl, carboxyl-$C_{1-7}$-alkyl, $C_{1-7}$-alkoxycarbonyl, hydroxy-$C_{1-7}$-alkyl, hydroxy-$C_{1-7}$-alkoxy, $C_{1-7}$-alkoxy-$C_{1-7}$-alkyl, carboxyl-$C_{1-7}$-alkoxy, $C_{1-7}$-alkoxycarbonyl-$C_{1-7}$-alkoxy, amino, $C_{1-7}$-alkylamino, di-$C_{1-7}$-alkylamino and phenyl-$C_{1-7}$-alkoxy.

More particularly, the invention relates to compounds of formula I as shown above, wherein $R^1$ is phenyl, said phenyl being substituted with one, two or three groups selected from the group consisting of $C_{1-7}$-alkyl, halogen, and $C_{1-7}$-alkoxy.

Most particularly, the invention relates to compounds of formula I, wherein $R^1$ is selected from the group consisting of phenyl, 2-methyl-phenyl, 2-ethyl-phenyl, 2-fluoro-phenyl, 2-chloro-phenyl, 2-trifluoromethyl-phenyl, 2-methoxy-phenyl, 2-isopropoxy-phenyl, 2-trifluoromethoxy-phenyl, 2-aminophenyl, 2-cyano-phenyl, 2-cyclopropyloxy-phenyl, 2-cyclobutyloxy-phenyl, 2-benzyloxy-phenyl, 2-oxetan-3-yl-phenyl, 2-oxetan-3-ylmethoxy-phenyl, 2,3-dimethyl-phenyl, 2,3-dimethoxy-phenyl, 2,4-difluoro-phenyl, 2-fluoro-3-methoxy-phenyl, 2-fluoro-5-methoxy-phenyl, 2-fluoro-6-methoxy-phenyl, 4-fluoro-2-methoxy-phenyl, 4-fluoro-2-methyl-phenyl, 2,4-dimethyl-phenyl, 4-methoxy-2-methyl-phenyl, 4-chloro-2-methyl-phenyl, 5-chloro-2-methyl-phenyl, 5-fluoro-2-methyl-phenyl, 3-fluoro-2-methoxy-phenyl, 3-fluoro-2-methyl-phenyl, 2-fluoro-5-methyl-phenyl, 2-benzyloxy-4-fluoro-phenyl, 4-fluoro-2-methoxy-phenyl, 4-fluoro-2-hydroxy-phenyl, 2-cyanomethoxy-4-fluoro-phenyl, 4-fluoro-2-(2-hydroxyethoxy)-phenyl, 2-(cyano-methyl-methoxy)-4-fluoro-phenyl, 5-fluoro-2-methoxy-phenyl, 2,5-difluoro-phenyl, 2,6-difluoro-phenyl, 2-chloro-3-fluoro-phenyl, 2-methyl-5-methoxycarbonyl-phenyl, 2-methyl-5-carboxyl-phenyl, 2-methoxycarbonyl-methoxy-4-fluoro-phenyl, 5-chloro-4-fluoro-2-methoxy-phenyl, 3,5-difluoro-2-methoxy-phenyl, 2,6-difluoro-3-methoxyphenyl, 3,4-difluoro-2-methoxy-phenyl and 4,5-difluoro-2-methoxy-phenyl.

Furthermore, the invention relates to compounds of formula I as shown above, wherein $R^1$ is selected from the group consisting of heteroaryl, said heteroaryl being unsubstituted or substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy, cycloalkyl-oxy, cycloalkyl-$C_{1-7}$-alkoxy, heterocyclyl-oxy and heterocyclyl-$C_{1-7}$-alkoxy, wherein heterocyclyl is unsubstituted or substituted by $C_{1-7}$-alkoxycarbonyl, 3,6-dihydro-2H-pyran-4-yl, and
piperidinyl, said piperidinyl being substituted with one to four $C_{1-7}$-alkyl groups.

In particular, the invention relates to compounds of formula I as shown above, wherein $R^1$ is selected from the group consisting of heteroaryl, said heteroaryl being substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy and cycloalkyl-$C_{1-7}$-alkoxy, 3,6-dihydro-2H-pyran-4-yl, and piperidinyl, said piperidinyl being substituted with one to four $C_{1-7}$-alkyl groups.

More particularly, compounds of the present invention are those, wherein $R^1$ is pyridyl, said pyridyl being substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy, cycloalkyl-oxy, cycloalkyl-$C_{1-7}$-alkoxy, heterocyclyl-oxy and heterocyclyl-$C_{1-7}$-alkoxy, wherein heterocyclyl is unsubstituted or substituted by $C_{1-7}$-alkoxycarbonyl. More particularly, $R^1$ is pyridyl being substituted with one, two or three groups selected from the group consisting of $C_{1-7}$-alkyl, halogen, hydroxy, $C_{1-7}$-alkoxy, halogen-$C_{1-7}$-alkoxy and cycloalkyl-$C_{1-7}$-alkoxy. Even more particularly, $R^1$ is pyridyl substituted with $C_{1-7}$-alkoxy.

The invention also relates to compounds of formula I as shown above, wherein $R^1$ is pyridazinyl, said pyridazinyl being substituted with one or two groups selected from the group consisting of $C_{1-7}$-alkyl, halogen, hydroxy, $C_{1-7}$-alkoxy, halogen-$C_{1-7}$-alkyl, halogen-$C_{1-7}$-alkoxy and cycloalkyl-$C_{1-7}$-alkoxy. More particularly, $R^1$ is pyridazinyl being substituted with one or two $C_{1-7}$-alkoxy groups.

The invention further relates to compounds of formula I, wherein $R^1$ is 3,6-dihydro-2H-pyran-4-yl or piperidinyl, said piperidinyl being substituted with one to four $C_{1-7}$-alkyl groups.

Compounds of formula I according to the present invention are further those, wherein $R^2$ selected from the group consisting of hydrogen, $C_{1-7}$-alkyl, halogen, halogen-$C_{1-7}$-alkyl, halogen-$C_{1-7}$-alkoxy, cyano, $C_{1-7}$-alkoxy, amino, $C_{1-7}$-alkylamino, di-$C_{1-7}$-alkylamino, aminocarbonyl, $C_{1-7}$-alkylaminocarbonyl, di-$C_{1-7}$-alkylaminocarbonyl, hydroxy-$C_{1-7}$-alkyl-($C_{1-7}$-alkyl)amino, $C_{1-7}$-alkoxy-$C_{1-7}$-alkyl-($C_{1-7}$-alkyl)amino, and heteroaryl. More particularly, $R^2$ is hydrogen or halogen and even more particularly, $R^2$ is hydrogen. Most particularly, heteroaryl is pyrrolyl.

Compounds of formula I are further those, wherein $R^{2a}$ is selected from the group consisting of hydrogen, methyl and halogen. More particularly, $R^{2a}$ is hydrogen or halogen, and most particularly, $R^{2a}$ is hydrogen.

Compounds of formula I according to the invention are further those, wherein $R^3$ is selected from the group consisting of $C_{1-7}$-alkyl, halogen-$C_{1-7}$-alkyl, hydroxy-$C_{1-7}$-alkyl, $C_{1-7}$-alkoxy-$C_{1-7}$-alkyl, $C_{1-7}$-alkylcarbonyl-$C_{1-7}$-alkyl, carboxyl-$C_{1-7}$-alkyl, $C_{1-7}$-alkoxycarbonyl-$C_{1-7}$-alkyl, cyano-$C_{1-7}$-alkyl, aminocarbonyl-$C_{1-7}$-alkyl, $C_{1-7}$-alkylaminocarbonyl-$C_{1-7}$-alkyl, di-$C_{1-7}$-alkylaminocarbonyl-$C_{1-7}$-alkyl, $C_{1-7}$-alkylsulfonyl-$C_{1-7}$-alkyl, $C_{3-7}$-cycloalkyl, $C_{3-7}$-cycloalkyl-$C_{1-7}$-alkyl, unsubstituted heterocyclyl or heterocyclyl substituted with one or two groups selected from halogen, oxo, hydroxy and $C_{1-7}$-alkyl, heterocyclyl-$C_{1-7}$-alkyl, wherein heterocyclyl is unsubstituted or substituted with one or two groups selected from halogen, oxo and $C_{1-7}$-alkyl, heteroaryl-$C_{1-7}$-alkyl, wherein heteroaryl is unsubstituted or substituted with one or two groups selected from halogen, oxo and $C_{1-7}$-alkyl and phenyl-$C_{1-7}$-alkoxycarbonylamino-$C_{1-7}$-alkyl.

More particularly, $R^3$ is selected from the group consisting of $C_{1-7}$-alkyl, halogen-$C_{1-7}$-alkyl, aminocarbonyl-$C_{1-7}$-alkyl and $C_{1-7}$-alkylsulfonyl-$C_{1-7}$-alkyl. In particular, $R^3$ is methyl and even more particularly, $R^3$ is selected from halogen-$C_{1-7}$-alkyl, aminocarbonyl-$C_{1-7}$-alkyl and $C_{1-7}$-alkylsulfonyl-$C_{1-7}$-alkyl.

The present invention further relates to compounds of formula I, wherein $R^4$ is selected from the group consisting of hydrogen, halogen, $C_{1-7}$-alkyl and $C_{1-7}$-alkoxy. In particular, $R^4$ is hydrogen or halogen and more particularly, $R^4$ is hydrogen.

Compounds of formula I according to the invention are furthermore those, wherein $R^5$ and $R^6$ are independently from each other from each other selected from the group consisting of hydrogen, $C_{1-7}$-alkyl, $C_{1-7}$-cycloalkyl, halogen, halogen-$C_{1-7}$-alkyl, halogen-$C_{1-7}$-alkoxy, hydroxy, hydroxy-$C_{1-7}$-alkyl, $C_{1-7}$-alkoxy, cyano, carboxyl, $C_{1-7}$-alkoxycarbonyl, $C_{1-7}$-alkoxycarbonyl-$C_{17}$-alkyl, hydroxy-$C_{1-7}$-alkoxy, $C_{1-7}$-alkoxy-$C_{1-7}$-alkoxy, $C_{1-7}$-alkylsulfanyl, hydroxy-$C_{1-7}$-alkylsulfanyl, $C_{1-7}$-alkoxy-$C_{1-7}$-alkylsulfanyl, $C_{1-7}$-alkylsulfonyl, hydroxy-$C_{1-7}$-alkylsulfonyl, $C_{1-7}$-alkoxy-$C_{1-7}$-alkylsulfonyl, carboxyl-$C_{1-7}$-alkylsulfanyl, carboxyl-$C_{1-7}$-alkylsulfonyl, $C_{1-7}$-alkoxycarbonyl-$C_{1-7}$-alkylsulfanyl, $C_{1-7}$-alkoxycarbonyl-$C_{1-7}$-alkylsulfonyl, $C_{1-7}$-alkoxycarbonylamino-$C_{1-7}$-alkylsulfanyl, carboxyl-$C_{1-7}$-alkyl-aminocarbonyl-$C_{1-7}$-alkylsulfanyl, carboxyl-$C_{1-7}$-alkyl-aminocarbonyl-$C_{1-7}$-alkylsulfonyl, heterocyclylsulfanyl, wherein heterocyclyl is unsubstituted or substituted by $C_{1-7}$-alkoxycarbonyl, oxo, $C_{1-7}$-alkylsulfonyl or aminosulfonyl, heterocyclylsulfonyl, wherein heterocyclyl is unsubstituted or substituted by $C_{1-7}$-alkoxycarbonyl, oxo, $C_{1-7}$-alkylsulfonyl or aminosulfonyl, heterocyclyl-$C_{1-7}$-alkylsulfanyl, heterocyclyl-$C_{1-7}$-alkylsulfonyl, aminosulfonyl, $C_{1-7}$-alkylaminosulfonyl, di-($C_{1-7}$-alkyl)-aminosulfonyl, $C_{1-7}$-alkylsulfonylamino-$C_{1-7}$-alkylsulfanyl, $C_{1-7}$-alkylsulfonylamino-$C_{1-7}$-alkylsulfonyl, aminosulfonylamino-$C_{1-7}$-alkylsulfanyl, aminosulfonylamino-$C_{1-7}$-alkylsulfonyl, amino-$C_{1-7}$-alkylsulfanyl, amino-$C_{1-7}$-alkylsulfonyl, aminocarbonyl-$C_{1-7}$-alkyl, aminocarbonyl-$C_{1-7}$-alkylsulfonyl, amino, $C_{1-7}$-alkylamino, di-($C_{1-7}$-alkyl)-amino, hydroxy-$C_{1-7}$-alkylamino, nitro, unsubstituted heterocyclyl and heterocyclyl substituted with one or two groups selected from halogen, oxo, $C_{1-7}$-alkyl and $C_{1-7}$-alkoxycarbonyl.

In particular, $R^5$ and $R^6$ are independently from each other selected from the group consisting of hydrogen, $C_{1-7}$-alkyl, $C_{1-7}$-cycloalkyl, halogen, halogen-$C_{1-7}$-alkyl, halogen-$C_{1-7}$-alkoxy, hydroxy, hydroxy-$C_{1-7}$-alkyl, $C_{1-7}$-alkoxy, cyano, carboxyl, $C_{1-7}$-alkoxycarbonyl, $C_{1-7}$-alkylsulfanyl, hydroxy-$C_{1-7}$-alkylsulfanyl, $C_{1-7}$-alkoxy-$C_{1-7}$-alkylsulfanyl, $C_{1-7}$-alkylsulfonyl, hydroxy-$C_{1-7}$-alkylsulfonyl, $C_{1-7}$-alkoxy-$C_{1-7}$-alkylsulfonyl-aminosulfonyl, $C_{1-7}$-alkylaminosulfonyl, di-($C_{1-7}$-alkyl)-aminosulfonyl, amino, $C_{1-7}$-alkylamino, di-($C_{1-7}$-alkyl)-amino, nitro, unsubstituted heterocyclyl and heterocyclyl substituted with one or two groups selected from halogen, oxo and $C_{1-7}$-alkyl.

In an embodiment, $R^5$ and $R^6$ are independently from each other selected from the group consisting of hydrogen, $C_{1-7}$-alkyl, halogen, halogen-$C_{1-7}$-alkyl, halogen-$C_{1-7}$-alkoxy, hydroxy, hydroxy-$C_{1-7}$-alkyl, $C_{1-7}$-alkoxy, cyano, $C_{1-7}$- alkoxycarbonyl, $C_{1-7}$-alkylsulfonyl, di-($C_{1-7}$-alkyl)-aminosulfonyl, amino, nitro, heterocyclyl selected from morpholinyl or 2-oxo-pyrrolidinyl, and heterocyclylsulfonyl, wherein heterocyclyl is oxetanyl or morpholinyl. More particularly, $R^5$ and $R^6$ are independently from each other selected from the group consisting of hydrogen, $C_{1-7}$-alkyl, halogen, halogen-$C_{1-7}$-alkyl, halogen-$C_{1-7}$-alkoxy, hydroxy, hydroxy-$C_{1-7}$-alkyl, $C_{1-7}$-alkoxy, cyano, $C_{1-7}$-alkoxycarbonyl, $C_{1-7}$-alkylsulfonyl, di-($C_{1-7}$-alkyl)-aminosulfonyl, amino, nitro, and heterocyclyl selected from morpholinyl or 2-oxo-pyrrolidinyl. Even more particularly, $R^5$ and $R^6$ are independently from each other selected from the group consisting of halogen, halogen-$C_{1-7}$-alkyl, $C_{1-7}$-alkyl and $C_{1-7}$-alkylsulfonyl.

Compounds of formula I according to the invention are further those, wherein $B^1$ is $CR^1$ and $B^2$ is $CR^8$ and wherein $R^7$ is hydrogen or halogen and $R^8$ is selected from the group consisting of hydrogen, $C_{1-7}$-alkyl, halogen, halogen-$C_{1-7}$-alkyl and $C_{1-7}$-alkoxy.

Compounds of formula I according to the invention are also those, wherein $B^1$ is N and $B^2$ is $CR^8$ and wherein $R^7$ is hydrogen or halogen and $R^8$ is selected from the group consisting of hydrogen, $C_{1-7}$-alkyl, halogen, halogen-$C_{1-7}$-alkyl and $C_{1-7}$-alkoxy.

In addition, compounds of formula I according to the invention are also those, wherein $B^1$ is $CR^7$ and $B^2$ is N and wherein $R^7$ is hydrogen or halogen and $R^8$ is selected from the group consisting of hydrogen, $C_{1-7}$-alkyl, halogen, halogen-$C_{1-7}$-alkyl and $C_{1-7}$-alkoxy.

In particular, $R^7$ and $R^8$ are independently selected from hydrogen or halogen, more particularly $R^7$ and $R^8$ are hydrogen.

In a further aspect, the invention relates to compounds of formula I, wherein
$B^1$ is $CR^7$ or N;
$B^2$ is $CR^8$ or N;
$R^1$ is selected from the group consisting of
  phenyl, said phenyl being substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy, cycloalkyl-$C_{1-7}$-alkoxy, cyano, cyano-$C_{1-7}$-alkoxy, carboxyl, carboxyl-$C_{1-7}$-alkyl, $C_{1-7}$-alkoxycarbonyl, hydroxy-$C_{1-7}$-alkyl, hydroxy-$C_{1-7}$-alkoxy, $C_{1-7}$-alkoxy-$C_1$ carboxyl-$C_{1-7}$-alkoxy, $C_{1-7}$-alkoxycarbonyl-$C_{1-7}$-alkoxy, amino, $C_{1-7}$-alkylamino, di-$C_{1-7}$-alkylamino and phenyl-$C_{1-7}$-alkoxy,
  heteroaryl, said heteroaryl being substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy and cycloalkyl-$C_{1-7}$-alkoxy,
  3,6-dihydro-2H-pyran-4-yl, and
  piperidinyl, said piperidinyl being substituted with one to four $C_{1-7}$-alkyl groups;
$R^2$ is selected from the group consisting of hydrogen, $C_{1-7}$-alkyl,
  halogen, halogen-$C_{1-7}$-alkyl, halogen-$C_{1-7}$-alkoxy, cyano, $C_{1-7}$-alkoxy, amino, $C_{1-7}$-alkylamino, di-$C_{1-7}$-alkylamino, aminocarbonyl, $C_{1-7}$-alkylaminocarbonyl, di-$C_{1-7}$-alkylaminocarbonyl, hydroxy-$C_{1-7}$-alkyl-($C_{1-7}$-alkyl)amino, $C_{1-7}$-alkoxy-$C_{1-7}$-alkyl-($C_{1-7}$-alkyl)amino, and heteroaryl;
$R^{2a}$ is selected from the group consisting of hydrogen, methyl and halogen;
$R^3$ is selected from the group consisting of $C_{1-7}$-alkyl, halogen-$C_{1-7}$-alkyl, hydroxy-$C_{1-7}$-alkyl, $C_{1-7}$-alkoxy-$C_{1-7}$-alkyl, $C_{1-7}$-alkylcarbonyl-$C_{1-7}$-alkyl, carboxyl-$C_{1-7}$-alkyl, $C_{1-7}$-alkoxycarbonyl-$C_{1-7}$-alkyl, cyano-$C_{1-7}$-alkyl, aminocarbonyl-$C_{1-7}$-alkyl, $C_{1-7}$-alkylaminocarbonyl-$C_{1-7}$-alkyl, di-$C_{1-7}$-alkylamino carbonyl-$C_{1-7}$-alkyl, $C_{1-7}$-alkylsulfonyl-$C_{1-7}$-alkyl, $C_{3-7}$-cycloalkyl, $C_{3-7}$-cycloalkyl-$C_{1-7}$-alkyl,
  unsubstituted heterocyclyl or heterocyclyl substituted with one or two groups selected from halogen, oxo, hydroxy and $C_{1-7}$-alkyl,
  heterocyclyl-$C_{1-7}$-alkyl, wherein heterocyclyl is unsubstituted or substituted with one or two groups selected from halogen, oxo and $C_{1-7}$-alkyl,
  heteroaryl-$C_{1-7}$-alkyl, and
  phenyl-$C_{1-7}$-alkoxycarbonylamino-$C_{1-7}$-alkyl;
$R^4$ is selected from the group consisting of hydrogen, halogen, $C_{1-7}$-alkyl and $C_{1-7}$-alkoxy;
$R^5$ and $R^6$ are independently from each other selected from the group consisting of hydrogen, $C_{1-7}$-alkyl, $C_{1-7}$-cycloalkyl, halogen, halogen-$C_{1-7}$-alkyl, halogen-$C_{1-7}$-alkoxy, hydroxy, hydroxy-$C_{1-7}$-alkyl, $C_{1-7}$-alkoxy, cyano, carboxyl, $C_{1-7}$-alkoxycarbonyl, $C_{1-7}$-alkylsulfonyl, hydroxy-$C_{1-7}$-alkylsulfonyl, $C_{1-7}$-alkoxy-$C_{1-7}$-alkylsulfonyl, aminosulfonyl, $C_{1-7}$-alkylaminosulfonyl, di-($C_{1-7}$-alkyl)-aminosulfonyl,
  amino, $C_{1-7}$-alkylamino, di-($C_{1-7}$-alkyl)-amino, nitro, unsubstituted heterocyclyl and heterocyclyl substituted with one or two groups selected from halogen, oxo and $C_{1-7}$-alkyl;
$R^7$ is hydrogen or halogen; and
$R^8$ is selected from the group consisting of hydrogen, $C_{1-7}$-alkyl, halogen, halogen-$C_{1-7}$-alkyl and $C_{1-7}$-alkoxy;
or pharmaceutically acceptable salts thereof.

Particular compounds of formula I are the following:
N-methyl-N-(4-o-tolyl-pyridin-3-yl)-3,5-bis-trifluoromethyl-benzamide,
N-methyl-N-(4-o-tolyl-pyridin-3-yl)-3-trifluoromethyl-benzamide,
3-chloro-N-methyl-N-(4-o-tolyl-pyridin-3-yl)-benzamide,
2-fluoro-N-methyl-N-(4-o-tolyl-pyridin-3-yl)-5-trifluoromethyl-benzamide,
4-fluoro-N-methyl-N-(4-o-tolyl-pyridin-3-yl)-3-trifluoromethyl-benzamide,
3-fluoro-N-methyl-N-(4-o-tolyl-pyridin-3-yl)-5-trifluoromethyl-benzamide,
2-fluoro-N-methyl-N-(4-o-tolyl-pyridin-3-yl)-3-trifluoromethyl-benzamide,
3,5-dichloro-N-methyl-N-(4-o-tolyl-pyridin-3-yl)-benzamide,
3,5-difluoro-N-methyl-N-(4-o-tolyl-pyridin-3-yl)-benzamide,
3,4-dichloro-N-methyl-N-(4-o-tolyl-pyridin-3-yl)-benzamide,
3-chloro-4-fluoro-N-methyl-N-(4-o-tolyl-pyridin-3-yl)-benzamide,
N-(6-chloro-4-o-tolyl-pyridin-3-yl)-N-methyl-3,5-bis-trifluoromethyl-benzamide,
3,5-dichloro-N-(6-chloro-4-o-tolyl-pyridin-3-yl)-N-methyl-benzamide,
N-(6-methoxy-4-o-tolyl-pyridin-3-yl)-N-methyl-3,5-bis-trifluoromethyl-benzamide,
N-methyl-N-(6-methylamino-4-o-tolyl-pyridin-3-yl)-3,5-bis-trifluoromethyl-benzamide,
N-(6-amino-4-o-tolyl-pyridin-3-yl)-N-methyl-3,5-bis-trifluoromethyl-benzamide,
N-[6-(4-methanesulfonyl-piperazin-1yl)-4-o-tolyl-pyridin-3-yl]-N-methyl-3,5-bis-trifluoromethyl-benzamide,
N-{6-[(2-methoxy-ethyl)-methyl-amino]-4-o-tolyl-pyridin-3-yl}-N-methyl-3,5-bis-trifluoromethyl-benzamide, N-(6-cyano-4-o-tolyl-pyridin-3-yl)-N-methyl-3,5-bis-trifluoromethyl-benzamide,
N-methyl-N-(2-methyl-3,4,5,6-tetrahydro-2H-[1,4']bipyridinyl-3'-yl)-3,5-bis-trifluoromethyl-benzamide,
3,5-dichloro-N-methyl-N-(2-methyl-3,4,5,6-tetrahydro-2H-[1,4']bipyridinyl-3'-yl)-benzamide, hydrochloride salt,
N-[4-(4-fluoro-2-methoxy-phenyl-pyridin-3-yl]-3-methanesulfonyl-N-oxazol-2-ylmethyl-5-trifluoromethyl-benzamide,
N-[4-(4-fluoro-2-methyl-phenyl)-pyridin-3-yl]-N-methyl-3,5-bis-trifluoromethyl-benzamide,
3,5-dichloro-N-[4-(4-fluoro-2-methyl-phenyl)-pyridin-3-yl]-N-methyl-benzamide,
N-[4-(2-fluoro-phenyl)-pyridin-3-yl]-N-methyl-3,5-bis-trifluoromethyl-benzamide,
N-[4-(2,4-dimethyl-phenyl)-pyridin-3-yl]-N-methyl-3,5-bis-trifluoromethyl-benzamide,
N-[4-(4-methoxy-2-methyl-phenyl)-pyridin-3-yl]-N-methyl-3,5-bis-trifluoromethyl-benzamide,
N-methyl-3,5-bis-trifluoromethyl-N-[4-(2-trifluoromethyl-phenyl)-pyridin-3-yl]-benzamide,
N-[4-(2-methoxy-phenyl)-pyridin-3-yl]-N-methyl-3,5-bis-trifluoromethyl-benzamide,
N-[4-(4-chloro-2-methyl-phenyl)-pyridin-3-yl]-N-methyl-3,5-bis-trifluoromethyl-benzamide,
N-methyl-N-[4-(2-trifluoromethoxy-phenyl)-pyridin-3-yl]-3,5-bis-trifluoromethyl-benzamide,
N-(2-methoxy-[3,4']bipyridinyl-3'-yl)-N-methyl-3,5-bis-trifluoromethyl-benzamide,
N-methyl-N-(2-methyl-[3,4']bipyridinyl-3'-yl)-3,5-bis-trifluoromethyl-benzamide,
N-methyl-N-(3'-methyl-[4,4']bipyridinyl-3-yl)-3,5-bis-trifluoromethyl-benzamide,
N-[4-(2-isopropoxy-phenyl)-pyridin-3-yl]-N-methyl-3,5-bis-trifluoromethyl-benzamide,
N-[4-(2-cyano-phenyl)-pyridin-3-yl]-N-methyl-3,5-bis-trifluoromethyl-benzamide,
N-[4-(2,4-difluoro-phenyl)-pyridin-3-yl]-N-methyl-3,5-bis-trifluoromethyl-benzamide,
N-[4-(4-fluoro-2-methoxy-phenyl)-pyridin-3-yl]-N-methyl-3,5-bis-trifluoromethyl-benzamide,
N-[4-(4,5-difluoro-2-methoxy-phenyl)-pyridin-3-yl]-N-methyl-3,5-bis-trifluoromethyl-benzamide,
N-[4-(2,3-difluoro-phenyl)-pyridin-3-yl]-N-methyl-3,5-bis-trifluoromethyl-benzamide,
N-[4-(3-fluoro-2-methoxy-phenyl)-pyridin-3-yl]-N-methyl-3,5-bis-trifluoromethyl-benzamide,
N-[4-(2-fluoro-5-methyl-phenyl)-pyridin-3-yl]-N-methyl-3,5-bis-trifluoromethyl-benzamide,
N-[4-(2-benzyloxy-4-fluoro-phenyl)-pyridin-3-yl]-N-methyl-3,5-bis-trifluoromethyl-benzamide,
N-(5-fluoro-2-methoxy-[3,4']bipyridinyl-3'-yl)-N-methyl-3,5-bis-trifluoromethyl-benzamide,
N-(5-chloro-2-methoxy-[3,4']bipyridinyl-3'-yl)-N-methyl-3,5-bis-trifluoromethyl-benzamide,
N-(2-isopropoxy-[3,4']bipyridinyl-3'-yl)-N-methyl-3,5-bis-trifluoromethyl-benzamide,
N-(2-methoxy-6-methyl-[3,4']bipyridinyl-3'-yl)-N-methyl-3,5-bis-trifluoromethyl-benzamide,
N-[4-(4-fluoro-2-hydroxy-phenyl)-pyridin-3-yl]-N-methyl-3,5-bis-trifluoromethyl-benzamide,
(2-{3-[(3,5-bis-trifluoromethyl-benzoyl)-methyl-amino]-pyridin-4-yl}-5-fluoro-phenoxy)-acetic acid methyl ester,
N-(3'-chloro-T-methoxy-[4,4']bipyridinyl-3-yl)-N-methyl-3,5-bis-trifluoromethyl-benzamide,
N-[4-(2-cyanomethoxy-4-fluoro-phenyl)-pyridin-3-yl]-N-methyl-3,5-bis-trifluoromethyl-benzamide,
N-{4-[4-fluoro-2-(2-hydroxy-ethoxy)-phenyl]-pyridin-3-yl}-N-methyl-3,5-bis-trifluoromethyl-benzamide,
N-{4-[2-(cyano-methyl-methoxy)-4-fluoro-phenyl]-pyridin-3-yl}-N-methyl-3,5-bis-trifluoromethyl-benzamide,
N-[4-(3,6-dimethoxy-pyridazin-4-yl)-pyridin-3-yl]-N-methyl-3,5-bis-trifluoromethyl-benzamide,
N-(2-chloro-5-fluoro-[3,4']bipyridinyl-3'-yl)-N-methyl-3,5-bis-trifluoromethyl-benzamide,
N-(2'-chloro-3'-fluoro-[4,4']bipyridinyl-3-yl)-N-methyl-3,5-bis-trifluoromethyl-benzamide,
N-methyl-N-(3-methyl-[2,4']bipyridinyl-3'-yl)-3,5-bis-trifluoromethyl-benzamide,
N-[4-(5-fluoro-2-methoxy-phenyl)-pyridin-3-yl]-N-methyl-3,5-bis-trifluoromethyl-benzamide,
N-[4-(3,5-difluoro-2-methoxy-phenyl)-pyridin-3-yl]-N-methyl-3,5-bis-trifluoromethyl-benzamide,
N-[4-(3,4-difluoro-2-methoxy-phenyl)-pyridin-3-yl]-N-methyl-3,5-bis-trifluoromethyl-benzamide,
N-[4-(2,5-difluoro-phenyl)-pyridin-3-yl]-N-methyl-3,5-bis-trifluoromethyl-benzamide,
N-[4-(2-fluoro-3-methoxy-phenyl)-pyridin-3-yl]-N-methyl-3,5-bis-trifluoromethyl-benzamide,
N-[4-(2-fluoro-5-methoxy-phenyl)-pyridin-3-yl]-N-methyl-3,5-bis-trifluoromethyl-benzamide,
N-[4-(2,6-difluoro-phenyl)-pyridin-3-yl]-N-methyl-3,5-bis-trifluoromethyl-benzamide,
N-[4-(2-chloro-3-fluoro-phenyl)-pyridin-3-yl]-N-methyl-3,5-bis-trifluoromethyl-benzamide,
N-[4-(2-fluoro-6-methoxy-phenyl)-pyridin-3-yl]-N-methyl-3,5-bis-trifluoromethyl-benzamide,
N-[4-(2-chloro-4-fluoro-phenyl)-pyridin-3-yl]-N-methyl-3,5-bis-trifluoromethyl-benzamide,
N-(3-fluoro-[2,4']bipyridinyl-3'-yl)-N-methyl-3,5-bis-trifluoromethyl-benzamide,
N-(3'-methoxy-[4,4']bipyridinyl-3-yl)-N-methyl-3,5-bis-trifluoromethyl-benzamide,
N-(3'-fluoro-[4,4']bipyridinyl-3-yl)-N-methyl-3,5-bis-trifluoromethyl-benzamide,
N-(6-chloro-[2,4']bipyridinyl-3'-yl)-W-methyl-3,5-bis-trifluoromethyl-benzamide,
N-[6-chloro-4-(4-fluoro-2-methyl-phenyl)-pyridin-3-yl]-N-methyl-3,5-bis-trifluoromethyl-benzamide,
N-(3,6'-dichloro-[2,4']bipyridinyl-3'-yl)-N-methyl-3,5-bis-trifluoromethyl-benzamide,
3-bromo-N-[4-(2-chloro-phenyl)-pyridin-3-yl]-N-methyl-5-trifluoromethyl-benzamide,
N-[4-(2-chloro-phenyl)-pyridin-3-yl]-N-methyl-5-trifluoromethyl-isophthalamic acid methyl ester,
N-[4-(2-chloro-phenyl)-pyridin-3-yl]-3-hydroxymethyl-N-methyl-5-trifluoromethyl-benzamide,
N-[4-(2-chloro-phenyl)-pyridin-3-yl]-3-(1-hydroxy-1-methyl-ethyl)-N-methyl-5-trifluoromethyl-benzamide,
N-[4-(2-chloro-phenyl)-pyridin-3-yl]-N-methyl-3,5-bis-trifluoromethyl-benzamide,
N-[4-(2-chloro-phenyl)-pyridin-3-yl]-3-hydroxy-N-methyl-5-trifluoromethyl-benzamide,
4-bromo-N-[4-(2-chloro-phenyl)-pyridin-3-yl]-N-methyl-3-trifluoromethyl-benzamide,
N-[4-(2-chloro-phenyl)-pyridin-3-yl]-3-methoxy-N-methyl-5-trifluoromethyl-benzamide,
N-[4-(5-chloro-2-methyl-phenyl)-pyridin-3-yl]-N-methyl-3,5-bis-trifluoromethyl-benzamide,
3-{3-[(3,5-bis-trifluoromethyl-benzoyl)-methyl-amino]-pyridin-4-yl}-4-methyl-benzoic acid methyl ester,
3-{3-[(3,5-bis-trifluoromethyl-benzoyl)-methyl-amino]-pyridin-4-yl}-4-methyl-benzoic acid, N-[4-(2-chloro-phenyl)-pyridin-3-yl]-N-(2,2,2-trifluoro-ethyl)-3,5-bis-trifluoromethyl-benzamide,
N-[4-(2-chloro-phenyl)-pyridin-3-yl]-N-cyclopropylmethyl-3,5-bis-trifluoromethyl-benzamide,
N-(6,5'-dichloro-T-fluoro-[4,4']bipyridinyl-3-yl)-N-methyl-3,5-bis-trifluoromethyl-benzamide,
{(3,5-bis-trifluoromethyl-benzoyl)-[4-(2-chloro-phenyl)-pyridin-3-yl]-amino}-acetic acid methyl ester,
N-[4-(2-chloro-phenyl)-pyridin-3-yl]-N-(2-methoxy-ethyl)-3,5-bis-trifluoromethyl-benzamide,
N-methyl-N-(4-o-tolyl-pyridin-3-yl)-4-trifluoromethyl-benzamide,
4,N-dimethyl-N-(4-o-tolyl-pyridin-3-yl)-3-trifluoromethyl-benzamide,
4-methoxy-N-methyl-N-(4-o-tolyl-pyridin-3-yl)-3-trifluoromethyl-benzamide,
N-{4-[2-(2-hydroxy-ethyl)-phenyl]-pyridin-3-yl}-N-methyl-3,5-bis-trifluoromethyl-benzamide,
3-fluoro-N-methyl-N-(4-o-tolyl-pyridin-3-yl)-4-trifluoromethyl-benzamide,
4-chloro-N-methyl-N-(4-o-tolyl-pyridin-3-yl)-3-trifluoromethyl-benzamide,
3,5,N-trimethyl-N-(4-o-tolyl-pyridin-3-yl)-benzamide,
3-chloro-N-methyl-N-(4-o-tolyl-pyridin-3-yl)-4-trifluoromethyl-benzamide,
N-(6-methoxy-[2,4']bipyridinyl-3'-yl)-N-methyl-3,5-bis-trifluoromethyl-benzamide,
N-(6-methoxy-[3,4']bipyridinyl-3'-yl)-N-methyl-3,5-bis-trifluoromethyl-benzamide,
3-chloro-N-methyl-N-(4-o-tolyl-pyridin-3-yl)-5-trifluoromethoxy-benzamide,
N-methyl-N-(4-o-tolyl-pyridin-3-yl)-3,4-bis-trifluoromethyl-benzamide,
N-[4-(2-chloro-phenyl)-pyridin-3-yl]-N-methylcarbamoylmethyl-3,5-bis-trifluoromethyl-benzamide,
3-chloro-5-fluoro-N-methyl-N-(4-o-tolyl-pyridin-3-yl)-benzamide,
3,4,5-trifluoro-N-methyl-N-(4-o-tolyl-pyridin-3-yl)-benzamide,
N-[4-(2,3-dimethyl-phenyl)-pyridin-3-yl]-N-methyl-3,5-bis-trifluoromethyl-benzamide,
N-methyl-N-[2-(2,2,2-trifluoro-ethoxy)-[3,4']bipyridinyl-3'-yl]-3,5-bis-trifluoromethyl-benzamide,
N-(2-cyclopropylmethoxy-[3,4']bipyridinyl-3'-yl)-N-methyl-3,5-bis-trifluoromethyl-benzamide,
3,N-dimethyl-N-(4-o-tolyl-pyridin-3-yl)-5-trifluoromethyl-benzamide,
3-chloro-N-methyl-N-(4-o-tolyl-pyridin-3-yl)-5-trifluoromethyl-benzamide,
N-[4-(2-chloro-phenyl)-pyridin-3-yl]-N-(2-fluoro-ethyl)-3,5-bis-trifluoromethyl-benzamide,
N-[4-(3-chloro-2-fluoro-phenyl)-pyridin-3-yl]-N-methyl-3,5-bis-trifluoromethyl-benzamide,
N-[4-(2-chloro-phenyl)-pyridin-3-yl]-N-(2-methanesulfonyl-ethyl)-3,5-bis-trifluoromethyl-benzamide,
N-methyl-N-[6-(1H-pyrrol-2-yl)-4-o-tolyl-pyridin-3-yl]-3,5-bis-trifluoromethyl-benzamide,
3-methanesulfonyl-N-methyl-N-(4-o-tolyl-pyridin-3-yl)-5-trifluoromethyl-benzamide,
N-[4-(2-chloro-phenyl)-pyridin-3-yl]-N-(2-hydroxy-ethyl)-3,5-bis-trifluoromethyl-benzamide,
N-[4-(2-chloro-phenyl)-pyridin-3-yl]-N-(2,2-difluoro-ethyl)-3,5-bis-trifluoromethyl-benzamide,
N-carbamoylmethyl-N-[4-(2-chloro-phenyl)-pyridin-3-yl]-3,5-bis-trifluoromethyl-benzamide,
N-[4-(2-chloro-phenyl)-pyridin-3-yl]-N-dimethylcarbamoylmethyl-3,5-bis-trifluoromethyl-benzamide,
2-chloro-6,N-dimethyl-N-(4-o-tolyl-pyridin-3-yl)-isonicotinamide,
2,6-dichloro-N-methyl-N-(4-o-tolyl-pyridin-3-yl)-isonicotinamide,
4,6-dimethyl-pyridine-2-carboxylic acid methyl-(4-o-tolyl-pyridin-3-yl)-amide,
4-chloro-6-methyl-pyridine-2-carboxylic acid methyl-(4-o-tolyl-pyridin-3-yl)-amide,
4,6-dichloro-pyridine-2-carboxylic acid methyl-(4-o-tolyl-pyridin-3-yl)-amide,
N-[4-(2-chloro-phenyl)-pyridin-3-yl]-N-cyclopropyl-3,5-bis-trifluoromethyl-benzamide,
(2-{(3,5-bis-trifluoromethyl-benzoyl)-[4-(2-chloro-phenyl)-pyridin-3-yl]-amino}-ethyl)-carbamic acid benzyl ester,
N-[4-(2-chloro-phenyl)-pyridin-3-yl]-N-isopropyl-3,5-bis-trifluoromethyl-benzamide,
N-methyl-N-(6-methyl-4-o-tolyl-pyridin-3-yl)-3,5-bis-trifluoromethyl-benzamide,
3-dimethylsulfamoyl-N-methyl-N-(4-o-tolyl-pyridin-3-yl)-5-trifluoromethyl-benzamide,
3-fluoro-N-[4-(4-fluoro-2-methoxy-phenyl)-pyridin-3-yl]-N-methyl-5-trifluoromethyl-benzamide,
N-[4-(4,5-difluoro-2-methoxy-phenyl)-pyridin-3-yl]-3-fluoro-N-methyl-5-trifluoromethyl-benzamide,
N-methyl-N-(4-o-tolyl-pyridin-3-yl)-2,6-bis-trifluoromethyl-isonicotinamide,
N-[4-(4,5-difluoro-2-methoxy-phenyl)-pyridin-3-yl]-3-fluoro-N-(2,2,2-trifluoro-ethyl)-5-trifluoromethyl-benzamide,
3-dimethylsulfamoyl-N-[4-(4-fluoro-2-methoxy-phenyl)-pyridin-3-yl]-N-(2,2,2-trifluoro-ethyl)-5-trifluoromethyl-benzamide,
3-fluoro-N-[4-(4-fluoro-2-methoxy-phenyl)-pyridin-3-yl]-N-(2,2,2-trifluoro-ethyl)-5-trifluoromethyl-benzamide,
N-(2-methoxy-[3,4']bipyridinyl-3'-yl)-N-(2,2,2-trifluoro-ethyl)-3,5-bis-trifluoromethyl-benzamide,
N-[4-(4-fluoro-2-methoxy-phenyl)-pyridin-3-yl]-3-methanesulfonyl-N-(2,2,2-trifluoro-ethyl)-5-trifluoromethyl-benzamide,
N-[4-(4,5-difluoro-2-methoxy-phenyl)-pyridin-3-yl]-3-methanesulfonyl-N-methyl-5-trifluoromethyl-benzamide,
N-[4-(4-fluoro-2-methoxy-phenyl)-pyridin-3-yl]-3-methanesulfonyl-N-methyl-5-trifluoromethyl-benzamide,
N-[4-(4,5-difluoro-2-methoxy-phenyl)-pyridin-3-yl]-3-methanesulfonyl-N-(2,2,2-trifluoro-ethyl)-5-trifluoromethyl-benzamide,
N-[4-(4,5-difluoro-2-methoxy-phenyl)-pyridin-3-yl]-3-dimethylsulfamoyl-N-(2,2,2-trifluoro-ethyl)-5-trifluoromethyl-benzamide,
3-fluoro-N-(2-methoxy-[3,4']bipyridinyl-3'-yl)-N-(2,2,2-trifluoro-ethyl)-5-trifluoromethyl-benzamide,
3-methanesulfonyl-N-(2-methoxy-[3,4']bipyridinyl-3'-yl)-N-(2,2,2-trifluoro-ethyl)-5-trifluoromethyl-benzamide,
3-dimethylsulfamoyl-N-[4-(4-fluoro-2-methoxy-phenyl)-pyridin-3-yl]-N-methyl-5-trifluoromethyl-benzamide,
N-[4-(4,5-difluoro-2-methoxy-phenyl)-pyridin-3-yl]-N-methyl-2,6-bis-trifluoromethyl-isonicotinamide,
N-(2-methoxy-[3,4']bipyridinyl-3'-yl)-N-(2,2,2-trifluoro-ethyl)-2,6-bis-trifluoromethyl-isonicotinamide,
N-[4-(4,5-difluoro-2-methoxy-phenyl)-pyridin-3-yl]-N-(2,2,2-trifluoro-ethyl)-2,6-bis-trifluoromethyl-isonicotinamide,
N-[4-(4-fluoro-2-methoxy-phenyl)-pyridin-3-yl]-N-(2,2,2-trifluoro-ethyl)-2,6-bis-trifluoromethyl-isonicotinamide,
N-[4-(4-fluoro-2-methoxy-phenyl)-pyridin-3-yl]-N-methyl-2,6-bis-trifluoromethyl-isonicotinamide, 3-cyano-N-methyl-N-(4-o-tolyl-pyridin-3-yl)-5-trifluoromethyl-benzamide,
N-(4-o-tolyl-pyridin-3-yl)-N-(2,2,2-trifluoro-ethyl)-2,6-bis-trifluoromethyl-isonicotinamide,
N-[4-(2-fluoro-phenyl)-pyridin-3-yl]-N-(2,2,2-trifluoro-ethyl)-2,6-bis-trifluoromethyl-isonicotinamide,
N-methyl-3-morpholin-4-yl-N-(4-o-tolyl-pyridin-3-yl)-5-trifluoromethyl-benzamide,
N-(2,2-difluoro-ethyl)-N-[4-(4-fluoro-2-methoxy-phenyl)-pyridin-3-yl]-2,6-bis-trifluoromethyl-isonicotinamide,
N-(2,2-difluoro-ethyl)-N-[4-(4,5-difluoro-2-methoxy-phenyl)-pyridin-3-yl]-2,6-bis-trifluoromethyl-isonicotinamide,
N-(2,2-difluoro-ethyl)-N-[4-(2-fluoro-phenyl)-pyridin-3-yl]-2,6-bis-trifluoromethyl-isonicotinamide,
N-(2,2-difluoro-ethyl)-N-(2-methoxy-[3,4']bipyridinyl-3'-yl)-2,6-bis-trifluoromethyl-isonicotinamide,
N-(2,2-difluoro-ethyl)-N-(4-o-tolyl-pyridin-3-yl)-2,6-bis-trifluoromethyl-isonicotinamide,
N-[4-(4,5-difluoro-2-methoxy-phenyl)-pyridin-3-yl]-N-(2-methanesulfonyl-ethyl)-2,6-bis-trifluoromethyl-isonicotinamide,
N-[4-(2-fluoro-phenyl)-pyridin-3-yl]-N-(2-methanesulfonyl-ethyl)-2,6-bis-trifluoromethyl-isonicotinamide,
N-(2-methanesulfonyl-ethyl)-N-(2-methoxy-[3,4']bipyridinyl-3'-yl)-2,6-bis-trifluoromethyl-isonicotinamide,
N-cyanomethyl-N-(4-o-tolyl-pyridin-3-yl)-3,5-bis-trifluoromethyl-benzamide,
N-[4-(4-fluoro-2-methoxy-phenyl)-pyridin-3-yl]-N-(2-methanesulfonyl-ethyl)-2,6-bis-trifluoromethyl-isonicotinamide,
N-(2-methanesulfonyl-ethyl)-N-(4-o-tolyl-pyridin-3-yl)-2,6-bis-trifluoromethyl-isonicotinamide,
3-amino-N-methyl-N-(4-o-tolyl-pyridin-3-yl)-5-trifluoromethyl-benzamide,
N-(2-cyano-ethyl)-N-(4-o-tolyl-pyridin-3-yl)-3,5-bis-trifluoromethyl-benzamide,
N-[4-(3,6-dihydro-2H-pyran-4-yl)-pyridin-3-yl]-N-methyl-3,5-bis-trifluoromethyl-benzamide,
N-[4-(2,3-dimethoxy-phenyl)-pyridin-3-yl]-N-methyl-3,5-bis-trifluoromethyl-benzamide,
N-[4-(2-ethyl-phenyl)-pyridin-3-yl]-N-methyl-3,5-bis-trifluoromethyl-benzamide,
2-chloro-N-[4-(4-fluoro-2-methoxy-phenyl)-pyridin-3-yl]-N-methyl-6-trifluoromethyl-isonicotinamide,
3-dimethylsulfamoyl-N-(2-methoxy-[3,4']bipyridinyl-3'-yl)-N-(2,2,2-trifluoro-ethyl)-5-trifluoromethyl-benzamide,
2-chloro-N-methyl-N-(4-o-tolyl-pyridin-3-yl)-6-trifluoromethyl-isonicotinamide,
[[4-(4,5-difluoro-2-methoxy-phenyl)-pyridin-3-yl]-(3-methanesulfonyl-5-trifluoromethyl-benzoyl)-amino]-acetic acid methyl ester,
{(2,6-bis-trifluoromethyl-pyridine-4-carbonyl)-[4-(4,5-difluoro-2-methoxy-phenyl)-pyridin-3-yl]-amino}-acetic acid methyl ester,
N-(2-amino-2-oxoethyl)-N-(4-(4,5-difluoro-2-methoxyphenyl)pyridin-3-yl)-2,6-bis(trifluoromethyl)isonicotinamide,
N-[4-(2-cyanomethyl-phenyl)-pyridin-3-yl]-N-methyl-3,5-bis-trifluoromethyl-benzamide,
methyl 2-(N-(4-(4-fluoro-2-methoxyphenyl)pyridin-3-yl)-2,6-bis(trifluoromethyl)isonicotinamido)acetate,
N-carbamoylmethyl-N-[4-(4-fluoro-2-methoxy-phenyl)-pyridin-3-yl]-2,6-bis-trifluoromethyl-isonicotinamide,
methyl 2-(3-(N,N-dimethylsulfamoyl)-N-(2-methoxy-3,4'-bipyridin-3'-yl)-5-(trifluoromethyl)benzamido)acetate,
N-carbamoylmethyl-3-dimethylsulfamoyl-N-(2-methoxy-[3,4']bipyridinyl-3'-yl)-5-trifluoromethyl-benzamide,
[(3-methanesulfonyl-5-trifluoromethyl-benzoyl)-(2-methoxy-[3,4']bipyridinyl-3'-yl)-amino]-acetic acid methyl ester,
N-carbamoylmethyl-3-methanesulfonyl-N-(2-methoxy-[3,4']bipyridinyl-3'-yl)-5-trifluoromethyl-benzamide,
methyl 2-(N-(2-methoxy-3,4'-bipyridin-3'-yl)-2,6-bis(trifluoromethyl)isonicotinamido)acetate,
N-(2-amino-2-oxoethyl)-N-(2-methoxy-3,4'-bipyridin-3'-yl)-2,6-bis(trifluoromethyl)isonicotinamide,
N-methyl-3-nitro-N-(4-o-tolylpyridin-3-yl)-5-(trifluoromethyl)benzamide,
N-methyl-3-(2-oxo-pyrrolidin-1-yl)-N-(4-o-tolyl-pyridin-3-yl)-5-trifluoromethyl-benzamide,
[[4-(4-fluoro-2-methoxy-phenyl)-pyridin-3-yl]-(3-methanesulfonyl-5-trifluoromethyl-benzoyl)-amino]-acetic acid methyl ester,
N-carbamoylmethyl-N-[4-(4-fluoro-2-methoxy-phenyl)-pyridin-3-yl]-3-methanesulfonyl-5-trifluoromethyl-benzamide,
{(3,5-bis-trifluoromethyl-benzoyl)-[4-(4,5-difluoro-2-methoxy-phenyl)-pyridin-3-yl]-amino}-acetic acid methyl ester,
N-carbamoylmethyl-N-[4-(4,5-difluoro-2-methoxy-phenyl)-pyridin-3-yl]-3,5-bis-trifluoromethyl-benzamide,
4,6-bis-trifluoromethyl-pyridine-2-carboxylic acid methyl-(4-o-tolyl-pyridin-3-yl)-amide,
N-[4-(2-fluoro-phenyl)-pyridin-3-yl]-N-(2-methanesulfonyl-ethyl)-3,5-bis-trifluoromethyl-benzamide,
N-[4-(4-fluoro-2-methoxy-phenyl)-pyridin-3-yl]-N-(2-methanesulfonyl-ethyl)-3,5-bis-trifluoromethyl-benzamide,
N-(2-amino-2-oxoethyl)-N-(4-(4,5-difluoro-2-methoxyphenyl)pyridin-3-yl)-3-(methylsulfonyl)-5-(trifluoromethyl)benzamide,
2-methanesulfonyl-N-methyl-N-(4-o-tolyl-pyridin-3-yl)-6-trifluoromethyl-isonicotinamide,
methyl 2-(N-(4-(2-fluoro-6-methoxyphenyl)pyridin-3-yl)-2,6-bis(trifluoromethyl)isonicotinamido)acetate,
methyl 2-(N-(4-(2-fluorophenyl)pyridin-3-yl)-2,6-bis(trifluoromethyl)isonicotinamido)acetate,
N-carbamoylmethyl-N-[4-(2-fluoro-phenyl)-pyridin-3-yl]-2,6-bis-trifluoromethyl-isonicotinamide,
2-chloro-N-[4-(4-fluoro-2-methoxy-phenyl)-pyridin-3-yl]-6-methoxy-N-methyl-isonicotinamide,
N-carbamoylmethyl-N-[4-(2-fluoro-6-methoxy-phenyl)-pyridin-3-yl]-2,6-bis-trifluoromethyl-isonicotinamide,
N-oxetan-3-yl-N-(4-o-tolyl-pyridin-3-yl)-3,5-bis-trifluoromethyl-benzamide,
N-[6-chloro-4-(4-fluoro-2-methoxy-phenyl)-pyridin-3-yl]-3-methanesulfonyl-N-methyl-5-trifluoromethyl-benzamide,
N-[4-(4-fluoro-2-methoxy-phenyl)-6-methyl-pyridin-3-yl]-3-methanesulfonyl-N-methyl-5-trifluoromethyl-benzamide,
N-[4-(4-fluoro-2-methoxy-phenyl)-pyridin-3-yl]-N-(2-oxo-butyl)-2,6-bis-trifluoromethyl-isonicotinamide,
N-[4-(4-fluoro-2-methoxy-phenyl)-pyridin-3-yl]-3-methanesulfonyl-N-(2-oxo-butyl)-5-trifluoromethyl-benzamide,
N-[4-(2-fluoro-6-methoxy-phenyl)-pyridin-3-yl]-3-methanesulfonyl-N-methyl-5-trifluoromethyl-benzamide,
N-[4-(4-fluoro-2-methoxy-phenyl)-pyridin-3-yl]-2-methoxy-N-methyl-6-trifluoromethyl-isonicotinamide, N-[4-(4-fluoro-2-methoxy-phenyl)-pyridin-3-yl]-N-(3-methyl-oxetan-3-ylmethyl)-2,6-bis-trifluoromethyl-isonicotinamide,
N-methyl-3,5-bis-trifluoromethyl-N-[4-(1,3,5-trimethyl-1H-pyrazol-4-yl)-pyridin-3-yl]-benzamide,
N-[4-(2,4-dimethyl-thiazol-5-yl)-pyridin-3-yl]-N-methyl-3,5-bis-trifluoromethyl-benzamide,
N-[4-(3,5-dimethyl-isoxazol-4-yl)-pyridin-3-yl]-N-methyl-3,5-bis-trifluoromethyl-benzamide,
N-methyl-N-[4-(4-methyl-2H-pyrazol-3-yl)-pyridin-3-yl]-3,5-bis-trifluoromethyl-benzamide,
and
N-[2-chloro-4-(4-fluoro-2-methoxy-phenyl)-pyridin-3-yl]-3-methanesulfonyl-N-methyl-5-trifluoromethyl-benzamide,
or pharmaceutically acceptable salts thereof.

The invention further relates to
[[4-(2-fluoro-phenyl)-pyridin-3-yl]-(3-methanesulfonyl-5-trifluoromethyl-benzoyl)-amino]-acetic acid methyl ester,
N-[4-(2-fluoro-phenyl)-pyridin-3-yl]-3-methanesulfonyl-N-(2,2,2-trifluoro-ethyl)-5-trifluoromethyl-benzamide,
N-(2,2-difluoro-ethyl)-N-[4-(2-fluoro-phenyl)-pyridin-3-yl]-3-methanesulfonyl-5-trifluoromethyl-benzamide,
N-[4-(4-fluoro-2-methoxy-phenyl)-pyridin-3-yl]-3-(2-hydroxy-ethylsulfanyl)-N-methyl-5-trifluoromethyl-benzamide,
N-[4-(4-fluoro-2-methoxy-phenyl)-pyridin-3-yl]-3-(2-methoxy-ethanesulfonyl)-N-methyl-5-trifluoromethyl-benzamide,
N-[4-(4-fluoro-2-methoxy-phenyl)-pyridin-3-yl]-3-(2-hydroxy-ethanesulfonyl)-N-methyl-5-trifluoromethyl-benzamide,
N-carbamoylmethyl-N-[4-(2-fluoro-phenyl)-pyridin-3-yl]-3-methanesulfonyl-5-trifluoromethyl-benzamide,
N-(6-ethyl-4-o-tolyl-pyridin-3-yl)-N-methyl-3,5-bis-trifluoromethyl-benzamide,
N-[4-(4-fluoro-2-methoxy-phenyl)-pyridin-3-yl]-2-methanesulfonyl-N-methyl-6-trifluoromethyl-isonicotinamide,
N-[4-(2-amino-phenyl)-pyridin-3-yl]-N-methyl-3,5-bis-trifluoromethyl-benzamide,
N-[4-(2-fluoro-6-methoxy-phenyl)-pyridin-3-yl]-3-methanesulfonyl-N-(2,2,2-trifluoro-ethyl)-5-trifluoromethyl-benzamide,
3-(3-{[4-(4-fluoro-2-methoxy-phenyl)-pyridin-3-yl]-methyl-carbamoyl}-5-trifluoromethyl-benzenesulfonyl)-propionic acid methyl ester,
3-(3-{[4-(4-fluoro-2-methoxy-phenyl)-pyridin-3-yl]-methyl-carbamoyl}-5-trifluoromethyl-phenylsulfanyl)-propionic acid methyl ester,
N-[4-(4-fluoro-2-methoxy-phenyl)-pyridin-3-yl]-3-hydroxy-N-methyl-5-trifluoromethyl-benzamide,
3-chloro-N-[4-(4-fluoro-2-methoxy-phenyl)-pyridin-3-yl]-N-methyl-5-trifluoromethoxy-benzamide,
N-cyanomethyl-N-[4-(4-fluoro-2-methoxy-phenyl)-pyridin-3-yl]-3-methanesulfonyl-5-trifluoromethyl-benzamide,
N-[4-(2-fluoro-6-methoxy-phenyl)-pyridin-3-yl]-3-methanesulfonyl-N-(2-methoxy-ethyl)-5-trifluoromethyl-benzamide,
N-[4-(4-fluoro-2-methoxy-phenyl)-2-methyl-pyridin-3-yl]-3-methanesulfonyl-N-methyl-5-trifluoromethyl-benzamide,
N-[4-(4-fluoro-2-methoxy-phenyl)-pyridin-3-yl]-3-methanesulfonyl-N-(5-methyl-isoxazol-3-ylmethyl)-5-trifluoromethyl-benzamide,
N-[4-(4-fluoro-2-methoxy-phenyl)-pyridin-3-yl]-3-methanesulfonyl-N—[(R)-1-(tetrahydro-furan-2-yl)methyl]-5-trifluoromethyl-benzamide,
N-[4-(4-fluoro-2-methoxy-phenyl)-pyridin-3-yl]-3-methanesulfonyl-N—[(S)-1-(tetrahydro-furan-2-yl)methyl]-5-trifluoromethyl-benzamide,
[2-(3-{[4-(4-fluoro-2-methoxy-phenyl)-pyridin-3-yl]-methyl-carbamoyl}-5-trifluoromethyl-phenylsulfanyl)-ethyl]-carbamic acid tert-butyl ester,
N-[4-(4-fluoro-2-methoxy-phenyl)-pyridin-3-yl]-N-methyl-3-oxetan-3-yl-5-trifluoromethyl-benzamide,
N-[4-(4-fluoro-2-methoxy-phenyl)-pyridin-3-yl]-3-(2-methoxy-ethoxy)-N-methyl-5-trifluoromethyl-benzamide,
3-(2-amino-ethylsulfanyl)-N-[4-(4-fluoro-2-methoxy-phenyl)-pyridin-3-yl]-N-methyl-5-trifluoromethyl-benzamide,
3-chloro-5-cyclopropyl-N-[4-(4-fluoro-2-methoxy-phenyl)-pyridin-3-yl]-N-methyl-benzamide,
4-(3-{[4-(4-fluoro-2-methoxy-phenyl)-pyridin-3-yl]-methyl-carbamoyl}-5-trifluoromethyl-phenylsulfanyl)-butyric acid,
N-[4-(4-fluoro-2-methoxy-phenyl)-pyridin-3-yl]-3-(2-hydroxy-ethoxy)-N-methyl-5-trifluoromethyl-benzamide,
3-(2-amino-ethanesulfonyl)-N-[4-(4-fluoro-2-methoxy-phenyl)-pyridin-3-yl]-N-methyl-5-trifluoromethyl-benzamide,
N-[4-(2-cyclopropoxy-phenyl)-pyridin-3-yl]-3-methanesulfonyl-N-methyl-5-trifluoromethyl-benzamide,
5-(3-{[4-(4-fluoro-2-methoxy-phenyl)-pyridin-3-yl]-methyl-carbamoyl}-5-trifluoromethyl-phenylsulfanyl)-pentanoic acid,
N-[4-(2-fluoro-phenyl)-pyridin-3-yl]-N-(2-hydroxy-ethyl)-3-methanesulfonyl-5-trifluoromethyl-benzamide,
3-(3-{[4-(4-fluoro-2-methoxy-phenyl)-pyridin-3-yl]-methyl-carbamoyl}-5-trifluoromethyl-phenyl)-azetidine-1-carboxylic acid tert-butyl ester,
3-bromo-N-[4-(4-fluoro-2-methoxy-phenyl)-pyridin-3-yl]-N-methyl-5-trifluoromethoxy-benzamide,
4-(3-{[4-(4-fluoro-2-methoxy-phenyl)-pyridin-3-yl]-methyl-carbamoyl}-5-trifluoromethyl-benzenesulfonyl)-butyric acid,
5-(3-{[4-(4-fluoro-2-methoxy-phenyl)-pyridin-3-yl]-methyl-carbamoyl}-5-trifluoromethyl-benzenesulfonyl)-pentanoic acid,
3-(azetidine-1-sulfonyl)-N-[4-(4-fluoro-2-methoxy-phenyl)-pyridin-3-yl]-N-methyl-5-trifluoromethyl-benzamide,
N-[4-(4-fluoro-2-methoxy-phenyl)-pyridin-3-yl]-3-methanesulfonyl-N-(1-methyl-1H-imidazol-2-ylmethyl)-5-trifluoromethyl-benzamide,
N-[4-(4-fluoro-2-methoxy-phenyl)-pyridin-3-yl]-N-methyl-3-(oxetan-3-ylsulfanyl)-5-trifluoromethyl-benzamide,
N-[4-(4-fluoro-2-methoxy-phenyl)-pyridin-3-yl]-3-methanesulfonyl-N-methyl-5-trifluoromethoxy-benzamide,
N-[6-chloro-4-(5-fluoro-2-methyl-phenyl)-pyridin-3-yl]-3-methanesulfonyl-N-methyl-5-trifluoromethyl-benzamide,
3-(4-carbamoyl-butane-1-sulfonyl)-N-[4-(4-fluoro-2-methoxy-phenyl)-pyridin-3-yl]-N-methyl-5-trifluoromethyl-benzamide,
N-[4-(4-fluoro-2-methoxy-phenyl)-pyridin-3-yl]-N-methyl-3-(oxetane-3-sulfonyl)-5-trifluoromethyl-benzamide,
N-[4-(4-fluoro-2-methoxy-phenyl)-pyridin-3-yl]-N-methyl-3-(morpholine-4-sulfonyl)-5-trifluoromethyl-benzamide,
3-chloro-N-[4-(4-fluoro-2-methoxy-phenyl)-pyridin-3-yl]-5-methanesulfonyl-N-methyl-benzamide, N-[4-(2-benzyloxy-phenyl)-pyridin-3-yl]-3-methanesulfonyl-N-methyl-5-trifluoromethyl-benzamide,
3-(2-azetidin-1-yl-ethylsulfanyl)-N-[4-(4-fluoro-2-methoxy-phenyl)-pyridin-3-yl]-N-methyl-5-trifluoromethyl-benzamide,
3-cyclopropyl-N-[4-(4-fluoro-2-methoxy-phenyl)-pyridin-3-yl]-5-methanesulfonyl-N-methyl-benzamide,
N-[4-(4-fluoro-2-methoxyphenyl)pyridin-3-yl]-N-methyl-3-{[2-(sulfamoylamino)ethyl]sulfanyl}-5-(trifluoromethyl)benzamide,
N-[4-(4-fluoro-2-methoxy-phenyl)-pyridin-3-yl]-3-(2-methanesulfonylamino-ethylsulfanyl)-N-methyl-5-trifluoromethyl-benzamide,
3-methanesulfonyl-N-[4-(2-methoxy-phenyl)-pyridin-3-yl]-N-methyl-5-trifluoromethyl-benzamide,
N-[4-(5-fluoro-2-methyl-phenyl)-6-methyl-pyridin-3-yl]-3-methanesulfonyl-N-methyl-5-trifluoromethyl-benzamide,
3-(2-azctidin-1-yl-ethanesulfonyl)-N-[4-(4-fluoro-2-methoxy-phenyl)-pyridin-3-yl]-N-methyl-5-trifluoromethyl-benzamide,
3-(3-{[4-(4-fluoro-2-methoxy-phenyl)-pyridin-3-yl]-methyl-carbamoyl}-5-trifluoromethyl-phenyl)-propionic acid ethyl ester,
N-[4-(2-benzyloxy-4-fluoro-phenyl)-pyridin-3-yl]-3-methanesulfonyl-N-methyl-5-trifluoromethyl-benzamide,
3-(3-{[4-(4-fluoro-2-methoxy-phenyl)-pyridin-3-yl]-methyl-carbamoyl}-5-trifluoromethyl-phenylsulfanyl)-azetidine-1-carboxylic acid tert-butyl ester,
N-[4-(4-fluoro-2-methoxyphenyl)pyridin-3-yl]-N-methyl-3-{[2-(sulfamoylamino)ethyl]sulfonyl}-5-(trifluoromethyl)benzamide,
N-[4-(4-fluoro-2-methoxy-phenyl)-pyridin-3-yl]-3-(2-methanesulfonylamino-ethanesulfonyl)-N-methyl-5-trifluoromethyl-benzamide,
3-(2-hydroxy-ethylamino)-N-methyl-N-(4-o-tolyl-pyridin-3-yl)-5-trifluoromethyl-benzamide,
3-methanesulfonyl-N-methyl-N-{4-[2-(oxetan-3-yloxy)-phenyl]-pyridin-3-yl}-5-trifluoromethyl-benzamide,
N-[4-(4-fluoro-2-methoxy-phenyl)-pyridin-3-yl]-3-methanesulfonyl-N-(tetrahydro-furan-3-ylmethyl)-5-trifluoromethyl-benzamide,
3-methanesulfonyl-N-methyl-N-[4-(2-trifluoromethoxy-phenyl)-pyridin-3-yl]-5-trifluoromethyl-benzamide,
3-(azetidin-3-ylsulfanyl)-N-[4-(4-fluoro-2-methoxy-phenyl)-pyridin-3-yl]-N-methyl-5-trifluoromethyl-benzamide,
N-[4-(5-fluoro-2-methyl-phenyl)-pyridin-3-yl]-3-methanesulfonyl-N-methyl-5-trifluoromethyl-benzamide,
N-[4-(2-cyclobutoxy-phenyl)-pyridin-3-yl]-3-methanesulfonyl-N-methyl-5-trifluoromethyl-benzamide,
N-[4-(2-chloro-phenyl)-pyridin-3-yl]-3-methanesulfonyl-N-methyl-5-trifluoromethyl-benzamide,
3-methanesulfonyl-N-methyl-N-[2-(2,2,2-trifluoro-ethoxy)-[3,4']bipyridinyl-3'-yl]-5-trifluoromethyl-benzamide,
3-(azetidine-3-sulfonyl)-N-[4-(4-fluoro-2-methoxy-phenyl)-pyridin-3-yl]-N-methyl-5-trifluoromethyl-benzamide,
3-(2-carbamoyl-ethyl)-N-[4-(4-fluoro-2-methoxy-phenyl)-pyridin-3-yl]-N-methyl-5-trifluoromethyl-benzamide,
N-[4-(4-fluoro-2-methoxy-phenyl)-pyridin-3-yl]-3-(1-methanesulfonyl-azetidine-3-sulfonyl)-N-methyl-5-trifluoromethyl-benzamide,
N-[4-(4-fluoro-2-methoxy-phenyl)-pyridin-3-yl]-3-methanesulfonyl-N-(5-methyl-oxazol-2-ylmethyl)-5-trifluoromethyl-benzamide,
N-[4-(2,4-difluoro-5-methoxy-phenyl)-pyridin-3-yl]-3-methanesulfonyl-N-methyl-5-trifluoromethyl-benzamide,
N-[4-(2,6-difluoro-3-methoxy-phenyl)-pyridin-3-yl]-3-methanesulfonyl-N-methyl-5-trifluoromethyl-benzamide,
N-[4-(2-chloro-phenyl)-pyridin-3-yl]-N-cyanomethyl-3-methanesulfonyl-5-trifluoromethyl-benzamide,
N-[4-(2-chloro-phenyl)-pyridin-3-yl]-3-methanesulfonyl-N-(2,2,2-trifluoro-ethyl)-5-trifluoromethyl-benzamide,
N-[4-(2-chloro-phenyl)-pyridin-3-yl]-3-methanesulfonyl-N-(2-methanesulfonyl-ethyl)-5-trifluoromethyl-benzamide,
[[4-(2-chloro-phenyl)-pyridin-3-yl]-(3-methanesulfonyl-5-trifluoromethyl-benzoyl)-amino]-acetic acid methyl ester,
N-[4-(4-fluoro-2-methoxy-phenyl)-pyridin-3-yl]-3-methanesulfonyl-N—[(R)-1-(tetrahydro-pyran-2-yl)methyl]-5-trifluoromethyl-benzamide,
N-[4-(4-fluoro-2-methoxy-phenyl)-pyridin-3-yl]-3-methanesulfonyl-N—[(S)-1-(tetrahydro-pyran-2-yl)methyl]-5-trifluoromethyl-benzamide,
N-[4-(4-fluoro-2-methoxy-phenyl)-pyridin-3-yl]-N-methyl-3-(1-sulfamoyl-azetidine-3-sulfonyl)-5-trifluoromethyl-benzamide,
N-[4-(4-fluoro-2-methoxy-phenyl)-pyridin-3-yl]-3-methanesulfonyl-N-(4-methyl-oxazol-2-ylmethyl)-5-trifluoromethyl-benzamide,
N-[4-(2-chloro-phenyl)-pyridin-3-yl]-3-methanesulfonyl-N-oxazol-2-ylmethyl-5-trifluoromethyl-benzamide,
N-[4-(3-fluoro-2-methyl-phenyl)-pyridin-3-yl]-3-methanesulfonyl-N-methyl-5-trifluoromethyl-benzamide,
N-carbamoylmethyl-N-[4-(2-chloro-phenyl)-pyridin-3-yl]-3-methanesulfonyl-5-trifluoromethyl-benzamide,
N-carbamoylmethyl-N-[4-(5-fluoro-2-methoxy-phenyl)-pyridin-3-yl]-3-methanesulfonyl-5-trifluoromethyl-benzamide,
3-methanesulfonyl-N-(2,2,2-trifluoro-ethyl)-N-[4-(2-trifluoromethoxy-phenyl)-pyridin-3-yl]-5-trifluoromethyl-benzamide,
N-[4-(4-fluoro-2-methoxy-phenyl)-pyridin-3-yl]-3-methanesulfonyl-N—[(S)-1-(tetrahydro-pyran-3-yl)methyl]-5-trifluoromethyl-benzamide,
N-[4-(2-chloro-phenyl)-6-methyl-pyridin-3-yl]-3-methanesulfonyl-N-(2,2,2-trifluoro-ethyl)-5-trifluoromethyl-benzamide,
3-chloro-N-[4-(4-fluoro-2-methoxy-phenyl)-6-methyl-pyridin-3-yl]-5-methanesulfonyl-N-methyl-benzamide,
N-[4-(4-fluoro-2-methoxy-phenyl)-6-methyl-pyridin-3-yl]-N-methyl-3-(morpholine-4-sulfonyl)-5-trifluoromethyl-benzamide,
3-bromo-N-[4-(4-fluoro-2-methoxy-phenyl)-6-methyl-pyridin-3-yl]-N-methyl-5-trifluoromethyl-benzamide,
3-(1,1-dioxo-thiomorpholine-4-sulfonyl)-N-[4-(4-fluoro-2-methoxy-phenyl)-pyridin-3-yl]-N-methyl-5-trifluoromethyl-benzamide,
N-[4-(4-Fluoro-2-methoxy-phenyl)-pyridin-3-yl]-N-methyl-3-(2-oxa-6-aza-spiro[3.3]heptane-6-sulfonyl)-5-trifluoromethyl-benzamide
N-[4-(4-fluoro-2-methoxy-phenyl)-pyridin-3-yl]-3-methanesulfonyl-N-(2-methanesulfonyl-ethyl)-5-trifluoromethyl-benzamide,
N-[4-(4-fluoro-2-methoxy-phenyl)-6-methyl-pyridin-3-yl]-3-methanesulfonyl-N-(2,2,2-trifluoro-ethyl)-5-trifluoromethyl-benzamide,
3-methanesulfonyl-N-(2-methanesulfonyl-ethyl)-N-[4-(2-trifluoromethoxy-phenyl)-pyridin-3-yl]-5-trifluoromethyl-benzamide,
[[4-(5-fluoro-2-methoxy-phenyl)-pyridin-3-yl]-(3-methanesulfonyl-5-trifluoromethyl-benzoyl)-amino]-acetic acid methyl ester, N-[4-(4-fluoro-2-methoxy-phenyl)-6-methyl-pyridin-3-yl]-N-methyl-3-(oxetan-3-ylsulfanyl)-5-trifluoromethyl-benzamide, N-cyanomethyl-3-methanesulfonyl-N-[4-(2-trifluoromethoxy-phenyl)-pyridin-3-yl]-5-trifluoromethyl-benzamide, 5-(3-{[4-(4-fluoro-2-methoxy-phenyl)-6-methyl-pyridin-3-yl]-methyl-carbamoyl}-5-trifluoromethyl-phenylsulfanyl)-pentanoic acid, N-(2-chloro-[3,4']bipyridinyl-3'-yl)-3-methanesulfonyl-N-methyl-5-trifluoromethyl-benzamide, N-[4-(4-fluoro-2-methoxy-phenyl)-6-methyl-pyridin-3-yl]-N-methyl-3-(oxetane-3-sulfonyl)-5-trifluoromethyl-benzamide,

[5-(3-{[4-(4-fluoro-2-methoxy-phenyl)-6-methyl-pyridin-3-yl]-methyl-carbamoyl}-5-trifluoromethyl-phenylsulfanyl)-pentanoylamino]-acetic acid, 5-(3-{[4-(5-chloro-4-fluoro-2-methoxy-phenyl)-6-methyl-pyridin-3-yl]-methyl-carbamoyl}-5-trifluoromethyl-benzenesulfonyl)-pentanoic acid,

[5-(3-{[4-(4-fluoro-2-methoxy-phenyl)-6-methyl-pyridin-3-yl]-methyl-carbamoyl}-5-trifluoromethyl-benzenesulfonyl)-pentanoylamino]-acetic acid, 3-methanesulfonyl-N-methyl-N-{6-methyl-4-[2-(oxetan-3-yloxy)-phenyl]-pyridin-3-yl}-5-trifluoromethyl-benzamide, N-carbamoylmethyl-3-methanesulfonyl-N-[4-(2-trifluoromethoxy-phenyl)-pyridin-3-yl]-5-trifluoromethyl-benzamide, 3-{3'-[(3-methanesulfonyl-5-trifluoromethyl-benzoyl)-methyl-amino]-[3,4']bipyridinyl-2-yloxy}-azetidine-1-carboxylic acid tert-butyl ester, 3-methanesulfonyl-N-methyl-N-{6-methyl-4-[2-(oxetan-3-ylmethoxy)-phenyl]-pyridin-3-yl}-5-trifluoromethyl-benzamide, N-methyl-N-(4-phenyl-pyridin-3-yl)-3,5-bis-trifluoromethyl-benzamide, and 3-methanesulfonyl-N-methyl-N-(4-phenyl-pyridin-3-yl)-5-trifluoromethyl-benzamide, or pharmaceutically acceptable salts thereof.

More particularly, compounds of formula I of the present invention are the following:

N-(6-chloro-4-o-tolyl-pyridin-3-yl)-N-methyl-3,5-bis-trifluoromethyl-benzamide,

N-[4-(4-fluoro-2-methyl-phenyl)-pyridin-3-yl]-N-methyl-3,5-bis-trifluoromethyl-benzamide, N-[4-(2-methoxy-phenyl)-pyridin-3-yl]-N-methyl-3,5-bis-trifluoromethyl-benzamide, N-(2-methoxy-[3,4']bipyridinyl-3'-yl)-N-methyl-3,5-bis-trifluoromethyl-benzamide, N-[4-(4-fluoro-2-methoxy-phenyl)-pyridin-3-yl]-N-methyl-3,5-bis-trifluoromethyl-benzamide, N-[4-(4,5-difluoro-2-methoxy-phenyl)-pyridin-3-yl]-N-methyl-3,5-bis-trifluoromethyl-benzamide, N-[4-(3-fluoro-2-methoxy-phenyl)-pyridin-3-yl]-N-methyl-3,5-bis-trifluoromethyl-benzamide, N-[4-(2-fluoro-6-methoxy-phenyl)-pyridin-3-yl]-N-methyl-3,5-bis-trifluoromethyl-benzamide, 3-bromo-N-[4-(2-chloro-phenyl)-pyridin-3-yl]-N-methyl-5-trifluoromethyl-benzamide, N-[4-(2-chloro-phenyl)-pyridin-3-yl]-N-methyl-3,5-bis-trifluoromethyl-benzamide, 4-bromo-N-[4-(2-chloro-phenyl)-pyridin-3-yl]-N-methyl-3-trifluoromethyl-benzamide, N-[4-(5-chloro-2-methyl-phenyl)-pyridin-3-yl]-N-methyl-3,5-bis-trifluoromethyl-benzamide, 3-{3-[(3,5-bis-trifluoromethyl-benzoyl)-methyl-amino]-pyridin-4-yl}-4-methyl-benzoic acid methyl ester, N-[4-(2-chloro-phenyl)-pyridin-3-yl]-N-(2,2,2-trifluoroethyl)-3,5-bis-trifluoromethyl-benzamide, {(3,5-bis-trifluoromethyl-benzoyl)-[4-(2-chloro-phenyl)-pyridin-3-yl]-amino}-acetic acid methyl ester, N-(6-methoxy-[2,4']bipyridinyl-3'-yl)-N-methyl-3,5-bis-trifluoromethyl-benzamide, N-[4-(2-chloro-phenyl)-pyridin-3-yl]-N-(2-fluoro-ethyl)-3,5-bis-trifluoromethyl-benzamide, N-[4-(2-chloro-phenyl)-pyridin-3-yl]-N-(2-methanesulfonyl-ethyl)-3,5-bis-trifluoromethyl-benzamide, N-carbamoylmethyl-N-[4-(2-chloro-phenyl)-pyridin-3-yl]-3,5-bis-trifluoromethyl-benzamide, N-methyl-N-(4-o-tolyl-pyridin-3-yl)-2,6-bis-trifluoromethyl-isonicotinamide, N-[4-(4-fluoro-2-methoxy-phenyl)-pyridin-3-yl]-3-methanesulfonyl-N-methyl-5-trifluoromethyl-benzamide, N-[4-(4,5-difluoro-2-methoxy-phenyl)-pyridin-3-yl]-3-methanesulfonyl-N-(2,2,2-trifluoro-ethyl)-5-trifluoromethyl-benzamide, N-[4-(4-fluoro-2-methoxy-phenyl)-pyridin-3-yl]-N-methyl-2,6-bis-trifluoromethyl-isonicotinamide, N-[4-(2-fluoro-phenyl)-pyridin-3-yl]-N-(2,2,2-trifluoroethyl)-2,6-bis-trifluoromethyl-isonicotinamide, N-(2,2-difluoro-ethyl)-N-[4-(2-fluoro-phenyl)-pyridin-3-yl]-2,6-bis-trifluoromethyl-isonicotinamide, N-[4-(2-fluoro-phenyl)-pyridin-3-yl]-N-(2-methanesulfonyl-ethyl)-2,6-bis-trifluoromethyl-isonicotinamide, N-(2-amino-2-oxoethyl)-N-(4-(4,5-difluoro-2-methoxyphenyl)pyridin-3-yl)-2,6-bis(trifluoromethyl)isonicotinamide, N-carbamoylmethyl-N-[4-(4-fluoro-2-methoxy-phenyl)-pyridin-3-yl]-2,6-bis-trifluoromethyl-isonicotinamide, N-(2-amino-2-oxoethyl)-N-(2-methoxy-3,4'-bipyridin-3'-yl)-2,6-bis(trifluoromethyl)isonicotinamide, N-carbamoylmethyl-N-[4-(2-fluoro-phenyl)-pyridin-3-yl]-2,6-bis-trifluoromethyl-isonicotinamide, N-carbamoylmethyl-N-[4-(2-fluoro-6-methoxy-phenyl)-pyridin-3-yl]-2,6-bis-trifluoromethyl-isonicotinamide, N-[4-(2-fluoro-6-methoxy-phenyl)-pyridin-3-yl]-3-methanesulfonyl-N-methyl-5-trifluoromethyl-benzamide, and N-[4-(4-fluoro-2-methoxy-phenyl)-pyridin-3-yl]-2-methoxy-N-methyl-6-trifluoromethyl-isonicotinamide, N-[2-chloro-4-(4-fluoro-2-methoxy-phenyl)-pyridin-3-yl]-3-methanesulfonyl-N-methyl-5-trifluoromethyl-benzamide, 3-(2-amino-ethanesulfonyl)-N-[4-(4-fluoro-2-methoxy-phenyl)-pyridin-3-yl]-N-methyl-5-trifluoromethyl-benzamide, 4-(3-{[4-(4-fluoro-2-methoxy-phenyl)-pyridin-3-yl]-methyl-carbamoyl}-5-trifluoromethyl-benzenesulfonyl)-butyric acid, 5-(3-{[4-(4-fluoro-2-methoxy-phenyl)-pyridin-3-yl]-methyl-carbamoyl}-5-trifluoromethyl-benzenesulfonyl)-pentanoic acid, N-[4-(4-fluoro-2-methoxy-phenyl)-pyridin-3-yl]-N-methyl-3-(oxetane-3-sulfonyl)-5-trifluoromethyl-benzamide, N-[4-(4-fluoro-2-methoxy-phenyl)-pyridin-3-yl]-N-methyl-3-(morpholine-4-sulfonyl)-5-trifluoromethyl-benzamide, 3-chloro-N-[4-(4-fluoro-2-methoxy-phenyl)-pyridin-3-yl]-5-methanesulfonyl-N-methyl-benzamide, 3-methanesulfonyl-N-methyl-N-{4-[2-(oxctan-3-yloxy)-phenyl]-pyridin-3-yl}-5-trifluoromethyl-benzamide, N-carbamoylmethyl-N-[4-(5-fluoro-2-methoxy-phenyl)-pyridin-3-yl]-3-methanesulfonyl-5-trifluoromethyl-benzamide,
N-[4-(4-fluoro-2-methoxy-phenyl)-6-methyl-pyridin-3-yl]-3-methanesulfonyl-N-(2,2,2-trifluoro-ethyl)-5-trifluoromethyl-benzamide, and
3-methanesulfonyl-N-(2-methanesulfonyl-ethyl)-N-[4-(2-trifluoromethoxy-phenyl)-pyridin-3-yl]-5-trifluoromethyl-benzamide,
or pharmaceutically acceptable salts thereof.

Most particularly, compounds of formula I of the present invention are the following:
N-[4-(4-fluoro-2-methoxy-phenyl)-pyridin-3-yl]-N-methyl-3,5-bis-trifluoromethyl-benzamide,
N-[4-(2-fluoro-6-methoxy-phenyl)-pyridin-3-yl]-N-methyl-3,5-bis-trifluoromethyl-benzamide,
N-[4-(4-fluoro-2-methoxy-phenyl)-pyridin-3-yl]-3-methanesulfonyl-N-methyl-5-trifluoromethyl-benzamide,
N-[4-(4-fluoro-2-methoxy-phenyl)-pyridin-3-yl]-N-methyl-2,6-bis-trifluoromethyl-isonicotinamide,
N-carbamoylmethyl-N-[4-(4-fluoro-2-methoxy-phenyl)-pyridin-3-yl]-2,6-bis-trifluoromethyl-isonicotinamide,
N-carbamoylmethyl-N-[4-(2-fluoro-6-methoxy-phenyl)-pyridin-3-yl]-2,6-bis-trifluoromethyl-isonicotinamide,
N-[4-(2-fluoro-6-methoxy-phenyl)-pyridin-3-yl]-3-methanesulfonyl-N-methyl-5-trifluoromethyl-benzamide,
4-(3-{[4-(4-fluoro-2-methoxy-phenyl)-pyridin-3-yl]-methyl-carbamoyl}-5-trifluoromethyl-benzenesulfonyl)-butyric acid,
or pharmaceutically acceptable salts thereof.

The pharmaceutically acceptable salts of the compounds of formula I also individually constitute advantageous compounds of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises
a) reacting a compound of the formula II

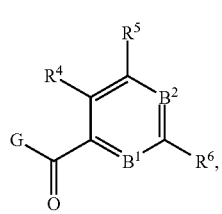

wherein G is —OH or —Cl, $B^1$, $B^2$ and $R^4$ to $R^6$ are as defined above, with an amine of the formula III

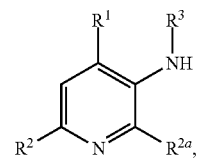

wherein $R^1$ to $R^3$ are as defined above, in the presence of a coupling reagent under basic conditions to obtain a compound of the formula I

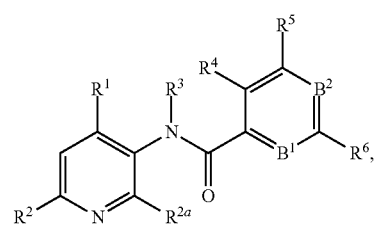

wherein $B^1$, $B^2$ and $R^1$ to $R^6$ are as defined above, and, if desired,
converting the compound obtained into a pharmaceutically acceptable salt, or, alternatively,
b) reacting a compound of the formula IV

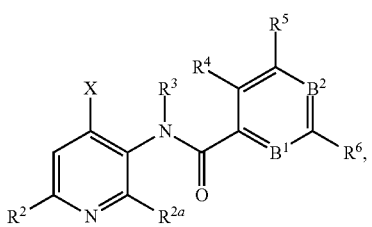

wherein $B^1$, $B^2$ and $R^2$ to $R^6$ are as defined above and X is selected from the group consisting of halogen, triflate and mesylate, with a boronic acid or ester of the formula V $R^1$—B(OR')$_2$      V, wherein $R^1$ is as defined above and $R^1$ is hydrogen or a pinacol or trimethylene glycol ester, in the presence of a palladium catalyst and a base to obtain a compound of the formula I

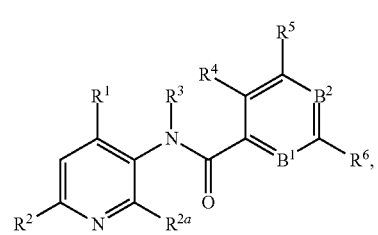

wherein $B^1$, $B^2$ and $R^1$ to $R^6$ are as defined above, and, if desired, converting the compound obtained into a pharmaceutically acceptable salt, or, alternatively, c) reacting a compound of the formula VI

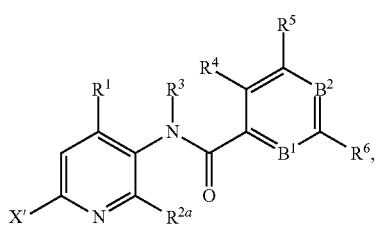

VI wherein $B^1$, $B^2$, $R^1$ and $R^3$ to $R^6$ are as defined above and X' means a halogen atom, with a boronic acid or ester of the formula V

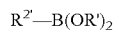

V, wherein $R^2$ is selected from $C_{1-7}$-alkyl, $C_{3-7}$-cycloalkyl, halogen-$C_{1-7}$-alkyl and heteroaryl and $R^1$ is hydrogen or a pinacol or trimethylene glycol ester, in the presence of a palladium catalyst and a base to obtain a compound of the formula I*

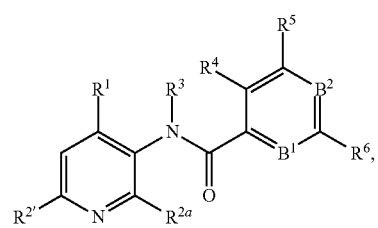

I* wherein $B^1$, $B^2$, $R^1$ and $R^3$ to $R^6$ are as defined above and $R^{2'}$ is selected from $C_{1-7}$-alkyl, $C_{3-7}$-cycloalkyl, halogen-$C_{1-7}$-alkyl and heteroaryl, and, if desired, converting the compound obtained into a pharmaceutically acceptable salt.

Appropriate coupling agents are for example N,N'-carbonyldiimidazole (CDI), N,N'-dicyclohexylcarbodiimide (DCC), N-(3-dimethylaminopropyl)-N'-ethyl-carbodiimide-hydrochloride (EDCI), O-(benzotriazol-1-yl)-N,N,N',N'-tetramethyluronium tetrafluoroborate (TBTU), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), 2-chloro-1-methylpyridinium iodide, 2-bromo-1-methylpyridinium iodide or benzotriazol-1-yloxytris(dimethylamino)phosphonium hexafluorophoshate (BOP). "Under basic conditions" means the presence of a base such as diisopropylethylamine, triethylamine, N-methylmorpholine or 4-(dimethylamino)-pyridine. The reaction is carried out in a suitable solvent such as for example N,N-dimethylformamide (DMF), dimethylacetamide (DMAc), dichloromethane or dioxane, at temperatures between 0° C. and ambient temperature.

A palladium catalyst means a catalyst suitable for a Suzuki coupling reaction such as dichloro[1,1'-bis(diphenylphosphino)-ferrocene]palladium(II) dichloromethane adduct, tetrakis(triphenylphosphine)palladium(0) or palladium(II) acetate with triphenylphosphine. The coupling is preferably carried out in the presence of a base such as sodium carbonate, sodium hydrogen carbonate, potassium fluoride, potassium carbonate or triethylamine in an appropriate solvent (e.g. dioxane, dimethoxyethane, water, toluene, N,N-dimethylformamide or mixtures thereof) at temperatures between room temperature and the boiling point of the solvent or solvent mixture.

The invention further relates to compounds of formula I as defined above obtainable according to a process as defined above.

In more detail, compounds of formula I according to the present invention can be prepared by the methods and procedures given below.

If one of the starting materials or compounds of formula I contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 4$^{th}$ Ed., 2006, Wiley N.Y.) can be introduced before the critical step applying methods well known in the art. Such protecting groups can be removed at a later stage of the synthesis using standard methods described in the literature.

A typical procedure for the preparation of compounds of formula I is illustrated in Scheme 1.

Compounds of general formula IA ($R^2=R^{2a}=H$), IB ($R^2=Cl$, $R^{2a}=H$) and IC($R^2=H$, $R^{2a}=Cl$) can be prepared for example as outlined in Scheme 1 by reacting commercially available pyridin-3-yl-carbamic acid tert-butyl esters 1 ($R^2=R^{2a}=H$, $R^2=H$, $R^{2a}=Cl$, or $R^2=Cl$, $R^{2a}=H$) with a suitable base such as tert-butyllithium in an appropriate solvent, such as tetrahydrofuran or diethyl ether, at temperatures between 0° C. and −75° C. and treating the generated lithium species with an iodinating agent such as iodine to give intermediate 2 (step a). Alternatively, intermediates 2 in which $R^2$ is chloro and $R^{2a}$ is hydrogen can be prepared by literature procedures (for example WO2008/127399 or J.-U. Peters et al., Bioorg. Med. Chem. Lett. 2010, 20, 3405-3408). Intermediates 2 in which $R^2$ is hydrogen and $R^{2a}$ is chloro are commercially available. Alkylation of intermediates 2 with $R^3X$, in which X is a suitable leaving group such as chlorine, bromine, iodine, $OSO_2$alkyl (e.g. mesylate (methanesulfonate), $OSO_2$fluoroalkyl (e.g. triflate (trifluoromethanesulfonate) or $OSO_2$aryl (e.g. tosylate (p-toluenesulfonate)), using a suitable base in an appropriate solvent (e.g. sodium hydride in DMF) at temperatures between 0° C. and the boiling temperature of the solvent, yields intermediates 3 (step b).

Removal of the Boc protective group applying methods known to those skilled in the art (e.g. using trifluoroacetic acid in dichloromethane at temperatures between 0° C. and room temperature) and as described for example in "Protective Groups in Organic Chemistry" by T. W. Greene and P. G. M. Wuts, 4$^{th}$ Ed., 2006, Wiley N.Y.), furnishes intermediates 4 (step c).

Scheme 1

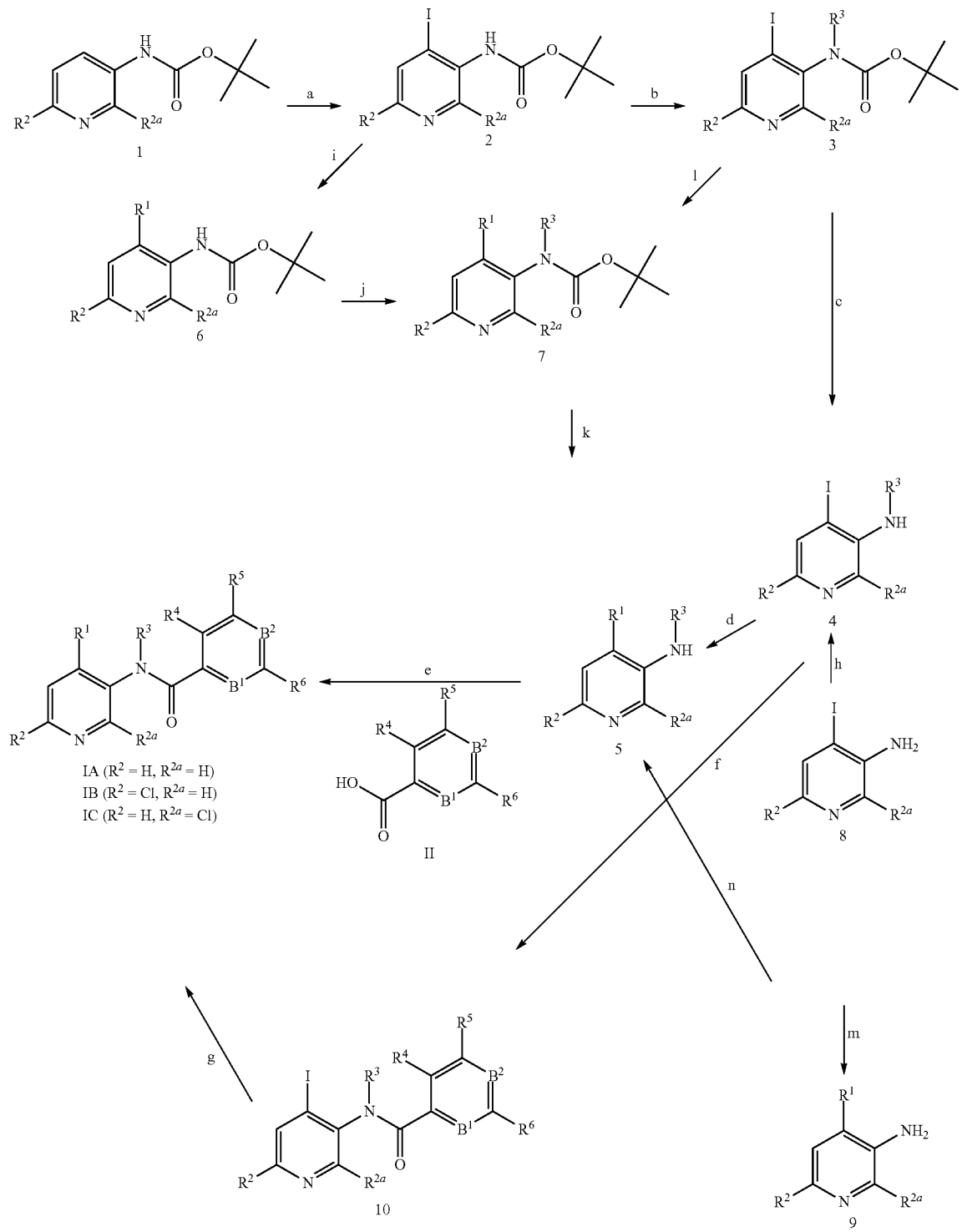

Reaction of intermediates 4 with (substituted) boronic acids R¹—B(OH)₂ or boronic esters R¹—B(OR')₂ (e.g. pinacol or trimethylene glycol ester, either commercially available or prepared using literature procedures as described for example in "Boronic Acids—Preparation and Applications in Organic Synthesis and Medicine" by Dennis G. Hall (ed.) 1$^{st}$ Ed., 2005, John Wiley & Sons, New York) using a suitable catalyst (e.g. dichloro[1,1'-bis(diphenylphosphino)-ferrocene]palladium(II) dichloromethane adduct, tetrakis (triphenylphosphine)palladium(0) or palladium(II) acetate with triphenylphosphine) in an appropriate solvent (e.g. dioxane, dimethoxyethane, water, toluene, N,N-dimethylformamide or mixtures thereof) and a suitable base (e.g. sodium carbonate, sodium hydrogen carbonate, potassium fluoride, potassium carbonate or triethylamine) at temperatures between room temperature and the boiling point of the solvent or solvent mixture yields intermediates 5 (step d). Suzuki reactions of this type are broadly described in literature (e.g. A. Suzuki, *Pure Appl. Chem.* 1991, 63, 419-422; A. Suzuki, N. Miyaura, Chem. Rev. 1995, 95, 2457-2483; A. Suzuki, *J. Organomet. Chem.* 1999, 576, 147-168; V. Polshettiwar et al., *Chem. Sus. Chem.* 2010, 3, 502-522) and are well known to those skilled in the art. Alternatively, aryl- or heteroaryl-trifluoroborates $R^1BF_3K$ can be used in the cross-coupling reaction applying a palladium catalyst such as, e.g. tetrakis(triphenylphosphine)palladium(0), palladium(II) acetate or dichloro[1,1'-bis(diphenylphosphino)ferrocene]-palladium(II) dichloromethane adduct in the presence of a suitable base such as cesium carbonate or potassium phosphate in solvents such as toluene, THF, dioxane, water or mixtures thereof, at temperatures between room temperature and the boiling point of the solvent or solvent mixture.

Intermediates 5 can be also synthesized by reacting intermediates 4 with (substituted) aryl- or heteroaryl tin reagents $R^1$—$SnR_3$ (R=e.g. Me or n-Bu; either commercially available or prepared according to literature procedures) in the presence of a suitable catalyst (e.g. tetrakis-(triphenylphosphine)palladium(0), benzylbis(triphenylphosphine)-palladium(II) chloride, bis(triphenylphosphine)palladium(II) dichloride or dichloro[1,1'-bis(diphenylphosphino)-ferrocene]palladium(II) dichloromethane adduct) in an appropriate solvent such as THF, dioxane, DMF (N,N-dimethylformamide) or HMPA (hexamethylphosphoramide) or mixtures thereof) at temperatures between room temperature and the boiling point of the solvent or solvent mixture, optionally in the presence of lithium chloride. Stille couplings of this type are broadly described in literature (e.g. J. K. Stille, *Angew. Chem. Int. Ed. Engl.* 1986, 25, 508-524; V. Farina et al., *J. Org. React.* 1998, 50, 1-652; T. N. Mitchell, *Synthesis* 1992, 9, 803-815) and well known to those skilled in the art.

Alternatively, intermediates 5 can be synthesized from reaction of intermediates 4 with (substituted) aryl- or heteroaryl zinc halides $R^1$—$ZnX$ (X=Cl, Br or I) (either commercially available or synthesized by methods described in literature) using a nickel (e.g. tetrakis(triphenylphosphine)nickel(0)) or palladium catalyst (e.g. tetrakis(triphenylphosphine) palladium(0)) in an appropriate solvent such as, e.g. THF or DMA in a temperature range between room temperature and boiling point of the solvent. Negishi couplings of this type are broadly described in literature (e.g. "Name Reactions for Homologations-Part I: Negishi cross-coupling reaction", Li, J. J., Corey, E. J., Eds.; Wiley & Sons, Hoboken, N.J., 2009, 70-99; "Metal-Catalyzed Cross-Coupling Reactions", Diederich, F.; Stang, P. J., Eds.; Wiley-VCH: Weinheim, Germany, 1998, 1-47; E. Erdik, *Tetrahedron* 1992, 48, 9577-9648; G. Organ, *Eur. J. Org. Chem.* 2010, 4343-4354) and well known to those skilled in the art.

Acylation of intermediates 5 with aryl- or heteroaryl carboxylic acids II (either commercially available or accessible by methods known in the art) furnishes target structures IA-IC (step e) Amide couplings of this type are widely described in the literature (e.g., Comprehensive Organic Transformations: A Guide to Functional Group Preparations, $2^{nd}$ Edition, Richard C. Larock, John Wiley & Sons, New York, N.Y. 1999) and can be accomplished by the usage of coupling reagents such as, e.g., N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) or 2-chloro- or 2-bromo-1-methylpyridinium iodide (Mukaiyama reagent) in a suitable solvent, e.g., N,N-dimethylformamide (DMF), dimethylacetamide (DMAc), dichloromethane or dioxane, optionally in the presence of a base (e.g., triethylamine, N,N-diisopropylethylamine (Huenig's base) or 4-(dimethylamino)pyridine). Alternatively, the aryl- or heteroaryl carboxylic acids II can be converted into their acid chlorides by treatment with, e.g., thionyl chloride, neat or optionally in a solvent such as dichloromethane and reaction of the acid chloride with intermediates 5 in an appropriate solvent such as dichloromethane or DMF (N,N-dimethylformamide) and a base, e.g. triethylamine, N,N-diisopropylethylamine (Huenig's base), pyridine, 4-(dimethylamino)pyridine or lithium bis(trimethylsilyl)amide at temperatures ranging from ambient temperature to the boiling point of the solvent or solvent mixture to furnish compounds of the general formula IA-IC.

Compounds of the general formula IA-IC can also be prepared by converting intermediates 4 into intermediates 10 (step f) by acylation with aryl- or heteroaryl carboxylic acids II (either commercially available or accessible by methods known in the art). Amide couplings of this type are widely described in the literature (e.g., Comprehensive Organic Transformations: A Guide to Functional Group Preparations, $2^{nd}$ Edition, Richard C. Larock, John Wiley & Sons, New York, N.Y. 1999) and can be accomplished by the usage of coupling reagents such as, e.g., N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) or 2-chloro- or 2-bromo-1-methylpyridinium iodide (Mukaiyama reagent) in a suitable solvent, e.g., N,N-dimethylformamide (DMF), dimethylacetamide (DMAc), dichloromethane or dioxane, optionally in the presence of a base (e.g., triethylamine, N,N-diisopropylethylamine (Huenig's base) or 4-(dimethylamino)pyridine). Alternatively, the aryl- or heteroaryl carboxylic acids II can be converted into their acid chlorides by treatment with, e.g., thionyl chloride, neat or optionally in a solvent such as dichloromethane and reaction of the acid chloride with intermediates 5 in an appropriate solvent such as dichloromethane or DMF (N,N-dimethylformamide) and a base, e.g. triethylamine, N,N-diisopropylethylamine (Huenig's base), pyridine, 4-(dimethylamino)pyridine or lithium bis(trimethylsilyl)amide at temperatures ranging from ambient temperature to the reflux temperature of the solvent or solvent mixture to furnish intermediates 10.

Reaction of intermediates 10 with (substituted) boronic acids $R^1$—$B(OH)_2$ or boronic esters $R^1$—$B(OR')_2$ (e.g. pinacol or trimethylene glycol ester, either commercially available or prepared using literature procedures as described for example in "Boronic Acids—Preparation and Applications in Organic Synthesis and Medicine" by Dennis G. Hall (ed.) $1^{st}$ Ed., 2005, John Wiley & Sons, New York) using a suitable catalyst (e.g. dichloro[1,1'-bis(diphenylphosphino)-ferrocene]palladium(II) dichloromethane adduct, tetrakis (triphenylphosphine)palladium(0) or palladium(II) acetate with triphenylphosphine) in an appropriate solvent (e.g. dioxane, dimethoxyethane, water, toluene, N,N-dimethylformamide or mixtures thereof) and a suitable base (e.g.

sodium carbonate, sodium hydrogen carbonate, potassium fluoride, potassium carbonate or triethylamine) at temperatures between room temperature and the boiling point of the solvent or solvent mixture yields compounds IA-IC (step g). Suzuki reactions of this type are broadly described in literature (e.g. A. Suzuki, *Pure Appl. Chem.* 1991, 63, 419-422; Chem. Rev. 1995, 95, 2457-2483; A. Suzuki, *J. Organomet. Chem.* 1999, 576, 147-168; V. Polshettiwar et al., *Chem. Sus. Chem.* 2010, 3, 502-522) and are well known to those skilled in the art. Alternatively, aryl- or heteroaryl-trifluoroborates $R^1BF_3K$ can be used in the cross-coupling reaction applying a palladium catalyst such as, e.g. tetrakis (triphenylphosphine)palladium(0), palladium(II) acetate or dichloro[1,1'-bis(diphenylphosphino)ferrocene]-palladium (II) dichloromethane adduct in the presence of a suitable base such as cesium carbonate or potassium phosphate in solvents such as toluene, THF, dioxane, water or mixtures thereof, at temperatures between room temperature and the boiling point of the solvent or solvent mixture.

Compounds IA-IC can be also synthesized by reacting intermediates 10 with (substituted) aryl- or heteroaryl tin reagents $R^1$—$SnR_3$ (R=e.g. Me or n-Bu; either commercially available or prepared according to literature procedures) in the presence of a suitable catalyst (e.g. tetrakis (triphenylphosphine)palladium(0), benzyl-bis (triphenylphosphine)palladium(II) chloride, bis (triphenylphosphine)palladium(II) dichloride or dichloro[1,1'-bis(diphenylphosphino)-ferrocene]palladium(II) dichloromethane adduct) in an appropriate solvent (e.g. THF, dioxane, DMF or HMPA or mixtures thereof) at temperatures between room temperature and the boiling point of the solvent or solvent mixture, optionally in the presence of lithium chloride. Stille couplings of this type are broadly described in literature (e.g. J. K. Stille, *Angew. Chem. Int. Ed. Engl.* 1986, 25, 508-524; V. Farina et al., *J. Org. React.* 1998, 50, 1-652; T. N. Mitchell, *Synthesis* 1992, 9, 803-815) and well known to those skilled in the art (step g).

Alternatively, compounds IA-IC can be synthesized from reaction of intermediates 10 with (substituted) aryl- or heteroaryl zinc halides $R^1$—ZnX (X=Cl, Br or I) (either commercially available or synthesized by methods described in literature) using a nickel (e.g. tetrakis(triphenylphosphine)nickel(0)) or palladium catalyst (e.g. tetrakis (triphenylphosphine)-palladium(0)) in an appropriate solvent such as, e.g. THF or DMA in a temperature range between room temperature and boiling point of the solvent. Negishi couplings of this type are broadly described in literature (e.g. "Name Reactions for Homologations-Part I: Negishi cross-coupling reaction", Li, J. J., Corey, E. J., Eds.; Wiley & Sons, Hoboken, N.J., 2009, 70-99; "Metal-Catalyzed Cross-Coupling Reactions", Diederich, F.; Stang, P. J., Eds.; Wiley-VCH: Weinheim, Germany, 1998, 1-47; E. Erdik, *Tetrahedron* 1992, 48, 9577-9648; G. Organ, *Eur. J. Org. Chem.* 2010, 4343-4354) and well known to those skilled in the art (step g).

Intermediates 4 in which $R^2$ is chlorine, $R^{2a}$ is hydrogen and $R^3$ is methyl can be prepared from commercially available (or prepared according to WO2006/018725) 6-chloro-4-iodo-pyridin-3-amine (8, $R^2$=Cl, $R^{2a}$=H), e.g. by reaction with trimethyl orthoformate in the presence of catalytic amounts of acid such as trifluoroacetic acid at elevated temperatures and reducing the in situ formed iminium species with a suitable reducing agent such as, e.g. lithium aluminum hydride in tetrahydrofuran at temperatures preferably between 0° C. and room temperature (step h).

Intermediates 4 in which $R^3$ is an $R^9CH_2$ or an $R^9R^{10}CH$ substituent can be also synthesized from commercially available 3-amino-4-iodopyridine (8, $R^2$=$R^{2a}$=H), for example via reductive alkylation (step h). Reductive alkylations (or sometimes called reductive aminations) are widely described in literature and are well known in the art. For example, the amine functionality in compound 8 can be reacted with (optionally substituted) aldehydes $R^9CHO$ or ketones $R^9C(O)R^{10}$ applying a reducing system such as, e.g. sodium borohydride, sodium triacetoxy-borohydride, sodium cyanoborohydride or di-n-butyltin dichloride with triphenyl-silane, in an appropriate solvent such as 1,2-dichloroethane or tetrahydrofuran to furnish intermediates 4 ($R^3$=$R^9CH_2$ and $R^9R^{10}CH$, respectively). Acetic acid may be used as catalyst for the reactions with ketones $R^9C(O)R^{10}$. Indium trichloride with triethylsilane in methanol might be used as well (step h). Intermediates 4 with $R^2$=$R^{2a}$=H and $R^3$=Me have also been described in literature: E. K. Yum, *Bull. Korean Chem. Soc.* 2002, 23, 535-536.

Intermediates 5 are accessible from intermediates 7 by removal of the Boc protective group applying methods known to those skilled in the art (e.g. using trifluoroacetic acid in dichloromethane at temperatures between 0° C. and room temperature) and as described for example in "Protective Groups in Organic Chemistry" by T. W. Greene and P. G. M. Wuts, $4^{th}$ Ed., 2006, Wiley N.Y. (step k).

Intermediates 7 can be synthesized for example from intermediates 3 (step 1) for example by reaction with (substituted) boronic acids $R^1$—$B(OH)_2$ or boronic esters $R^1$—$B(OR')_2$ (e.g. pinacol or trimethylene glycol ester, either commercially available or prepared using literature procedures as described for example in "Boronic Acids—Preparation and Applications in Organic Synthesis and Medicine" by Dennis G. Hall (cd.) $1^{st}$ Ed., 2005, John Wiley & Sons, New York) using a suitable catalyst (e.g. dichloro [1,1'-bis(diphenylphosphino)-ferrocene]palladium(II) dichloromethane adduct, tetrakis(triphenylphosphine)palladium(0) or palladium(II) acetate with triphenylphosphine) in an appropriate solvent (e.g. dioxane, dimethoxyethane, water, toluene, NN-dimethylformamide or mixtures thereof) and a suitable base (e.g. sodium carbonate, sodium hydrogen carbonate, potassium fluoride, potassium carbonate or triethylamine) at temperatures between room temperature and the boiling point of the solvent or solvent mixture. Suzuki reactions of this type are broadly described in literature (e.g. A. Suzuki, *Pure Appl. Chem.* 1991, 63, 419-422; A. Suzuki, N. Miyaura, *Chem. Rev.* 1995, 95, 2457-2483, A. Suzuki, *J. Organomet. Chem.* 1999, 576, 147-168; V. Polshettiwar et al., *Chem. Sus. Chem.* 2010, 3, 502-522) and are well known to those skilled in the art. Alternatively, aryl- or heteroaryl-trifluoro-borates $R^1BF_3K$ can be used in the cross-coupling reaction applying a palladium catalyst such as, e.g. tetrakis (triphenylphosphine)palladium (0), palladium (II) acetate or dichloro[1,1'-bis(diphenylphosphino)ferrocene]-palladium (II) dichloromethane adduct in the presence of a suitable base such as cesium carbonate or potassium phosphate in solvents such as toluene, THF, dioxane, water or mixtures thereof, at temperatures between room temperature and the boiling point of the solvent or solvent mixture.

Intermediates 7 can be also synthesized by reacting intermediates 3 with (substituted) aryl- or heteroaryl tin reagents $R^1$—$SnR_3$ (R=e.g. Me or n-Bu; either commercially available or prepared according to literature procedures) in the presence of a suitable catalyst (e.g. tetrakis-(triphenylphosphine)palladium(0), benzylbis(triphenylphosphine)-palladium(II) chloride, bis(triphenylphosphine)palladium(II) dichloride or dichloro[1,1'-bis(diphenylphosphino)-ferrocene]palladium(II) dichloromethane adduct) in an appropriate solvent (e.g. THF, dioxane, DMF or HMPA or mixtures thereof) at temperatures between room temperature and the boiling point of the solvent or solvent mixture, optionally in the presence of lithium chloride. Stille couplings of this type are broadly described in literature (e.g. J. K. Stille, *Angew. Chem. Int. Ed. Engl.* 1986, 25, 508-524; V. Farina, *J. Org. React.* 1998, 50, 1-652; T. N. Mitchell, *Synthesis* 1992, 9, 803-815) and well known to those skilled in the art (step 1).

Alternatively, intermediates 7 can be synthesized from reaction of intermediates 3 with (substituted) aryl- or heteroaryl zinc halides $R^1$—ZnX (X=Cl, Br or I) (either commercially available or synthesized by methods described in literature) using a nickel (e.g. tetrakis(tri-phenylphosphine) nickel (0)) or palladium catalyst (e.g. tetrakis(triphenylphosphine)palladium(0)) in an appropriate solvent such as, e.g. THF or DMA in a temperature range between room temperature and boiling point of the solvent. Negishi couplings of this type are broadly described in literature (e.g. "Name Reactions for Homologations-Part I: Negishi cross-coupling reaction", Li, J. J., Corey, E. J., Eds.; Wiley & Sons, Hoboken, N.J., 2009, 70-99; "Metal-Catalyzed Cross-Coupling Reactions", Diederich, F.; Stang, P. J., Eds.; Wiley-VCH: Weinheim, Germany, 1998, 1-47; E. Erdik, *Tetrahedron* 1992, 48, 9577-9648; G. Organ, *Eur. J. Org. Chem.* 2010, 4343) and well known to those skilled in the art (step 1).

Intermediates 7 can also be synthesized from intermediates 6 through alkylation using compounds of the type $R^3X$, in which X is a suitable leaving group such as chlorine, bromine, iodine, OSO$_2$alkyl (e.g. mesylate (methanesulfonate), OSO$_2$fluoroalkyl (e.g. triflate (trifluoromethanesulfonate) or OSO$_2$aryl (e.g. tosylate (p-toluenesulfonate)), using a suitable base in an appropriate solvent (e.g. sodium hydride in DMF) at temperatures between 0° C. and the boiling temperature of the solvent (step i).

Intermediates 6 in turn can be synthesized from intermediates 2 for example by reaction with (substituted) boronic acids $R^1$—B(OH)$_2$ or boronic esters $R^1$—B(OR')$_2$ (e.g. pinacol or trimethylene glycol ester, either commercially available or prepared using literature procedures as described for example in "Boronic Acids—Preparation and Applications in Organic Synthesis and Medicine" by Dennis G. Hall (ed.) 1$^{st}$ Ed., 2005, John Wiley & Sons, New York) using a suitable catalyst (e.g. dichloro[1,1'-bis(diphenylphosphino)-ferrocene]palladium(II) dichloro-methane adduct, tetrakis(triphenylphosphine)palladium(0) or palladium(II) acetate with triphenylphosphine) in an appropriate solvent (e.g. dioxane, dimethoxyethane, water, toluene, N,N-dimethylformamide or mixtures thereof) and a suitable base (e.g. sodium carbonate, sodium hydrogen carbonate, potassium fluoride, potassium carbonate or triethylamine) at temperatures between room temperature and the boiling point of the solvent or solvent mixture (step i). Suzuki reactions of this type are broadly described in literature (e.g. A. Suzuki, *Pure Appl. Chem.* 1991, 63, 419-422; A. Suzuki, N. Miyaura, *Chem. Rev.* 1979, 95, 2457-2483; A. Suzuki, *J. Organomet. Chem.* 1999, 576, 147-168; V. Polshettiwar et al., *Chem. Sus. Chem.* 2010, 3, 502-522) and are well known to those skilled in the art. Alternatively, aryl- or heteroaryl-trifluoroborates $R^1BF_3K$ can be used in the cross-coupling reaction applying a palladium catalyst such as, e.g. tetrakis(triphenylphosphine)palladium (0), palladium(II) acetate or dichloro[1,1'-bis(diphenyl-phosphino)ferrocene]-palladium(II) dichloromethane adduct in the presence of a suitable base such as cesium carbonate or potassium phosphate in solvents such as toluene, THF, dioxane, water or mixtures thereof, at temperatures between room temperature and the boiling point of the solvent or solvent mixture.

Intermediates 6 can be also synthesized by reacting intermediates 2 with (substituted) aryl- or heteroaryl tin reagents $R^1$—SnR$_3$ (R=e.g. Me or n-Bu; either commercially available or prepared according to literature procedures) in the presence of a suitable catalyst (e.g. tetrakis-(triphenylphosphine)palladium(0), benzylbis(triphenylphosphine)-palladium(II) chloride, bis(triphenylphosphine)palladium(II) dichloride or dichloro[1,1'-bis(diphenylphosphino)-ferrocene]palladium(II) dichloromethane adduct) in an appropriate solvent (e.g. THF, dioxane, DMF or HMPA or mixtures thereof) at temperatures between room temperature and the boiling point of the solvent or solvent mixture, optionally in the presence of lithium chloride. Stille couplings of this type are broadly described in literature (e.g. J. K. Stille, *Angew. Chem. Int. Ed. Engl.* 1986, 25, 508-524; V. Farina, *J. Org. React.* 1998, 50, 1-652; T. N. Mitchell, *Synthesis* 1992, 9, 803-815) and well known to those skilled in the art (step i).

Alternatively, intermediates 6 can be synthesized from reaction of intermediates 2 with (substituted) aryl- or heteroaryl zinc halides $R^1$—ZnX (X=Cl, Br or I) (either commercially available or synthesized by methods described in literature) using a nickel (e.g. tetrakis(triphenylphosphine) nickel(0)) or palladium catalyst (e.g. tetrakis(triphenylphosphine)palladium(0)) in an appropriate solvent such as, e.g. THF or DMA in a temperature range between room temperature and boiling point of the solvent. Negishi couplings of this type are broadly described in literature (e.g. "Name Reactions for Homologations-Part I: Negishi cross-coupling reaction", Li, J. J., Corey, E. J., Eds.; Wiley & Sons, Hoboken, N.J., 2009, 70-99; "Metal-Catalyzed Cross-Coupling Reactions", Diederich, F.; Stang, P. J., Eds.; Wiley-VCH: Weinheim, Germany, 1998, 1-47; E. Erdik, *Tetrahedron* 1992, 48, 9577-9648; G. Organ, *Eur. J. Org. Chem.* 2010, 4343-4354) and well known to those skilled in the art (step i).

Intermediates 5 are also accessible from intermediates 9 (step n) using reductive alkylations (or sometimes called reductive aminations) that are widely described in literature and are well known in the art. For example, intermediates 5 in which $R^3$ is a methyl group can be synthesized by reaction with trimethyl orthoformate in the presence of catalytic amounts of acid such as trifluoroacetic acid at elevated temperatures and reducing the in situ formed iminium species with a suitable reducing agent such as, e.g. lithium aluminum hydride in tetrahydrofuran at temperatures preferably between 0° C. and room temperature. Alternatively, for intermediates 5 wherein $R^3$ is a —CH$_2$—R$^9$ or —CHR$^9R^{10}$ substituent, the amine functionality in compounds 9 can be reacted with (optionally substituted) aldehydes R$^9$CHO or ketones R$^9$C(O)R$^{10}$ using a reducing system such as, e.g. sodium borohydride, sodium triacetoxyborohydride, sodium cyanoborohydride or di-n-butyltin dichloride with triphenylsilane, in an appropriate solvent such as 1,2-dichloroethane or tetrahydrofuran to furnish intermediates 5 (step n). Acetic acid may be used as catalyst for the reactions with ketones. Indium trichloride with triethylsilane in methanol might be used as well.

Intermediates 5 may be also synthesized from intermediates 9 by protection of the amine functionality in 9 with a suitable protective group such as, e.g. a Boc protective group using methods described in literature and known in the art, alkylating the resulting ten-butyl carbamate with $R^3X$, in which X is a suitable leaving group such as chlorine, bromine, iodine, OSO$_2$alkyl (e.g. mesylate (methanesulfonate), OSO$_2$fluoroalkyl (e.g. triflate (trifluoromethanesulfonate) or OSO$_2$aryl (e.g. tosylate (p-toluenesulfonate)) using a suitable base in an appropriate solvent (e.g. sodium hydride in DMF) at temperatures between 0° C. and the boiling temperature of the solvent and removing the Boc protective group by methods known to those skilled in the art (e.g. using trifluoroacetic acid in dichloromethane at temperatures between 0° C. and room temperature) and as described for example in "Protective Groups in Organic Chemistry" by T. W. Greene and P. G. M. Wuts, 4$^{th}$ Ed., 2006, Wiley N.Y.).

A number of intermediates 5 in which $R^2$ is chlorine, $R^{2a}$=hydrogen and $R^3$ is a methyl group have also been described in literature (e.g. WO2006/013050 or WO2005/002577).

Intermediates 9 can be synthesized from commercially available 3-amino-4-iodopyridines 8 ($R^2$=$R^{2a}$=H or $R^2$=Cl, $R^{2a}$=H) by reaction with (substituted) boronic acids $R^1$—B(OH)$_2$ or boronic esters $R^1$—B(OR')$_2$ (e.g. pinacol or trimethylene glycol ester, either commercially available or prepared using literature procedures as described for example in "Boronic Acids—Preparation and Applications in Organic Synthesis and Medicine" by Dennis G. Hall (ed.) 1$^{st}$ Ed., 2005, John Wiley & Sons, New York) using a suitable catalyst (e.g. dichloro[1,1'-bis(diphenylphosphino)-ferrocene]palladium(II) dichloromethane adduct, tetrakis (triphenylphosphine)palladium(0) or palladium(II) acetate with triphenylphosphine) in an appropriate solvent (e.g. dioxane, dimethoxyethane, water, toluene, N,N-dimethylformamide or mixtures thereof) and a suitable base (e.g. sodium carbonate, sodium hydrogen carbonate, potassium fluoride, potassium carbonate or triethylamine) at temperatures between room temperature and the boiling point of the solvent or solvent mixture (step m). Suzuki reactions of this type are broadly described in literature (e.g. A. Suzuki, *Pure Appl. Chem.* 1991, 63, 419-422; A. Suzuki, N. Miyaura, *Chem. Rev.* 1995, 95, 2457-2483; A. Suzuki, *Organomet. Chem.* 1999, 576, 147-168; V. Polshettiwar et al., *Chem. Sus. Chem.* 2010, 3, 502-522) and are well known to those skilled in the art. Alternatively, aryl- or heteroaryl-trifluoroborates $R^1BF_3K$ can be used in the cross-coupling reaction applying a palladium catalyst such as, e.g. tetrakis(triphenylphosphine)palladium(0), palladium(II) acetate or dichloro[1,1'-bis(diphenylphosphino)ferrocene]-palladium(II) dichloromethane adduct in the presence of a suitable base such as cesium carbonate or potassium phosphate in solvents such as toluene, THF, dioxane, water or mixtures thereof, at temperatures between room temperature and the boiling point of the solvent or solvent mixture.

Alternatively, intermediates 9 can be reacted with (substituted) aryl- or heteroaryl tin reagents $R^1$—SnR$_3$ (R=e.g. Me or n-Bu; either commercially available or prepared according to literature procedures) in the presence of a suitable catalyst (e.g. tetrakis-(triphenylphosphine) palladium(0), benzylbis(triphenylphosphine)-palladium(II) chloride, bis(triphenylphosphine) palladium(II) dichloride or dichloro[1,1'-bis(diphenylphosphino)-ferrocene]palladium (II) dichloromethane adduct) in an appropriate solvent (e.g. THF, dioxane, DMF or HMTP or mixtures thereof) at temperatures between room temperature and the boiling point of the solvent or solvent mixture, optionally in the presence of lithium chloride to furnish intermediates 5 (step n). Stille couplings of this type are broadly described in literature (e.g. J. K. Stille, *Angew. Chem. Int. Ed. Engl.* 1986, 25, 508-524; V. Farina, *J. Org. React.* 1998, 50, 1-652; T. N. Mitchell, *Synthesis* 1992, 9, 803-815) and well known to those skilled in the art.

Intermediates 5 can be also synthesized from reaction of intermediates 9 with (substituted) aryl- or heteroaryl zinc halides $R^1$—ZnX (X=Cl, Br or I) (either commercially available or synthesized by methods described in literature) using a nickel (e.g. tetrakis(triphenyl-phosphine)nickel(0)) or palladium catalyst (e.g. tetrakis(triphenylphosphine)palladium(0)) in an appropriate solvent such as, e.g. THF or DMA in a temperature range between room temperature and boiling point of the solvent. Negishi couplings of this type are broadly described in literature (e.g. "Name Reactions for Homologations-Part I: Negishi cross-coupling reaction", Li, J. J., Corey, E. J., Eds.; Wiley & Sons, Hoboken, N.J., 2009, 70-99; "Metal-Catalyzed Cross-Coupling Reactions", Diederich, F.; Stang, P. J., Eds.; Wiley-VCH: Weinheim, Germany, 1998, 1-47; E. Erdik, *Tetrahedron* 1992, 48, 9577-9648; G. Organ, *Eur. J. Org. Chem.* 2010, 4343-4354) and well known to those skilled in the art (step n).

Compounds of the general formula IA' in which $R^2$=$R^{2a}$=H and $R^3$ is a methyl group can also be prepared as outlined in Scheme 2. Commercially available 3-amino-4-bromopyridine 11 is converted into intermediate 12 through reductive alkylation, e.g. by reacting 11 with trimethyl orthoformate in the presence of catalytic amounts of acid such as trifluoroacetic acid at elevated temperatures and reducing the in situ formed iminium species with a suitable reducing agent such as, e.g. lithium aluminum hydride in tetrahydrofuran at temperatures preferably between 0° C. and room temperature (step a).

Scheme 2

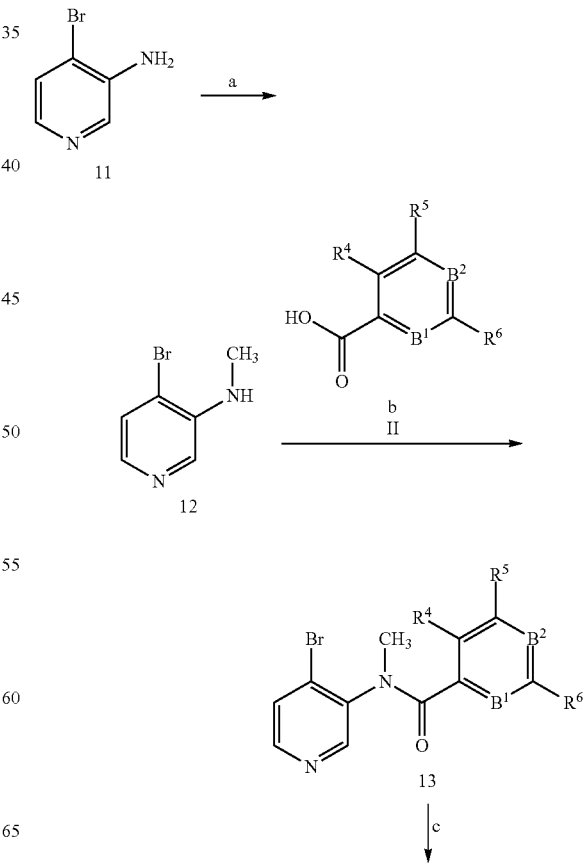

-continued

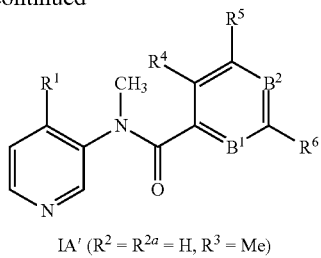

IA' (R² = R²ᵃ = H, R³ = Me)

Acylation of intermediate 12 with aryl- or heteroaryl carboxylic acids II (either commercially available or accessible by methods described in references or by methods known in the art) gives intermediates 13 (step b) Amide couplings of this type are widely described in the literature (e.g., Comprehensive Organic Transformations: A Guide to Functional Group Preparations, $2^{nd}$ Edition, Richard C. Larock, John Wiley & Sons, New York, N.Y. 1999) and can be accomplished by the usage of coupling reagents such as, e.g., N,N'-carbonyldiimidazole (CDI), N,N'-dicyclohexyl-carbodiimide (DCC), 1-(3-dimethylaminopropyl)-3-ethyl-carbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyl-uronium tetrafluoroborate (TBTU) or 2-chloro- or 2-bromo-1-methylpyridinium iodide (Mukaiyama reagent) in a suitable solvent, e.g., N,N-dimethyl-formamide (DMF), dimethylacetamide (DMAc), dichloromethane or dioxane, optionally in the presence of a base (e.g., triethylamine, N,N-diisopropylethylamine (Huenig's base) or 4-(dimethylamino)pyridine). Alternatively, the aryl- or heteroaryl carboxylic acids II can be converted into their acid chlorides by treatment with, e.g., thionyl chloride, neat or optionally in a solvent such as dichloromethane. Reaction of the acid chloride with amines 12 in an appropriate solvent such as dichloromethane or DMF (N,N-dimethylformamide) and a base, e.g. triethylamine, N,N-diisopropylethylamine (Huenig's base), pyridine, 4-(dimethylamino)pyridine or lithium bis(trimethylsilyl)amide at temperatures ranging from ambient temperature to the reflux temperature of the solvent or solvent mixture yields intermediates 13.

Reaction of intermediates 13 with (substituted) boronic acids $R^1$—$B(OH)_2$ or boronic esters $R^1$—$B(OR')_2$ (e.g. pinacol or trimethylene glycol ester, either commercially available or prepared using literature procedures as described for example in "Boronic Acids—Preparation and Applications in Organic Synthesis and Medicine" by Dennis G. Hall (ed.) $1^{st}$ Ed., 2005, John Wiley & Sons, New York) using a suitable catalyst (e.g. dichloro[1,1'-bis(diphenylphosphino)-ferrocene]palladium(II) dichloromethane adduct, tetrakis (triphenylphosphine)palladium(0) or palladium (II) acetate with triphenylphosphine) in an appropriate solvent (e.g. dioxane, dimethoxyethane, water, toluene, N,N-dimethyl-formamide or mixtures thereof) and a suitable base (e.g. sodium carbonate, sodium hydrogen carbonate, potassium fluoride, potassium carbonate or triethylamine) at temperatures between room temperature and the boiling point of the solvent or solvent mixture yields compounds IA' ($R^2$=$R^{2a}$=H, $R^3$=Me; step c). Suzuki reactions of this type are broadly described in literature (e.g. A. Suzuki, *Pure Appl. Chem.* 1991, 63, 419-422; A. Suzuki, N. Miyaura, *Chem. Rev.* 1979, 95, 2457-2483; A. Suzuki, *J. Organomet. Chem.* 1999, 576, 147-168; V. Polshettiwar et al., *Chem. Sus. Chem.* 2010, 3, 502-522) and are well known to those skilled in the art. Alternatively, aryl- or heteroaryl-trifluoroborates $R^1BF_3K$ can be used in the cross-coupling reaction applying a palladium catalyst such as, e.g. tetrakis-(triphenylphosphine)palladium(0), palladium(II) acetate or dichloro[1,1'-bis(diphenyl-phosphino)ferrocene]palladium(II) dichloromethane adduct in the presence of a suitable base such as cesium carbonate or potassium phosphate in solvents such as toluene, THF, dioxane, water or mixtures thereof, at temperatures between room temperature and the boiling point of the solvent or solvent mixture.

Compounds IA' ($R^2$=$R^{2a}$=H, $R^3$=Me) can be also synthesized by reacting intermediates 13 with (substituted) aryl- or heteroaryl tin reagents $R^1$—$SnR_3$ (R=e.g. Me or n-Bu; either commercially available or prepared according to literature procedures) in the presence of a suitable catalyst (e.g. tetrakis(triphenylphosphine)palladium(0), benzylbis (triphenyl-phosphine)palladium(II) chloride, bis(triphenyl-phosphine)palladium(II) dichloride or dichloro[1,1'-bis(diphenylphosphino)ferrocene]palladium(II) dichloromethane adduct) in an appropriate solvent (e.g. THF, dioxane, DMF or HMPA or mixtures thereof) at temperatures between room temperature and the boiling point of the solvent or solvent mixture, optionally in the presence of lithium chloride. Stille couplings of this type are broadly described in literature (e.g. J. K. Stille, *Angew. Chem. Int. Ed. Engl.* 1986, 25, 508-524; V. Farina, *J. Org. React.* 1998, 50, 1-652; T. N. Mitchell, *Synthesis* 1992, 9, 803-815) and well known to those skilled in the art (step c).

Alternatively, compounds IA' ($R^2$=$R^{2a}$=H, $R^3$=Me) can be synthesized from reaction of intermediates 13 with (substituted) aryl- or heteroaryl zinc halides $R^1$—ZnX (X=Cl, Br or I) (either commercially available or synthesized by methods described in literature) using a nickel (e.g. tetrakis (triphenylphosphine)nickel(0)) or palladium catalyst (e.g. tetrakis(triphenyl-phosphine)palladium(0)) in an appropriate solvent such as, e.g. THF or DMA in a temperature range between room temperature and boiling point of the solvent. Negishi couplings of this type are broadly described in literature (e.g. "Name Reactions for Homologations-Part I: Negishi cross-coupling reaction", Li, J. J., Corey, E. J., Eds.; Wiley & Sons, Hoboken, N.J., 2009, 70-99; "Metal-Catalyzed Cross-Coupling Reactions", Diederich, F.; Stang, P. J., Eds.; Wiley-VCH: Weinheim, Germany, 1998, 1-47; E. Erdik. *Tetrahedron* 1992, 48, 9577-9648; G. Organ, *Eur. J. Org. Chem.* 2010, 4343-4354) and well known to those skilled in the art (step c).

Compounds of the general formula ID ($R^2$=$R^{11}$=O, $R^{2a}$=H) may be prepared according to Scheme 3. For example, commercially available 2-chloro-5-nitropyridine 14 may be treated with sodium alkoxide (either commercially available or prepared by methods known in the art) in a manner described in the literature (R. H. Pager et al., *Aust. J. Chem.* 2003, 56, 913-916; Y. Nishikawa et al., *J. Med. Chem.* 1989, 32, 583-593) to give 2-alkoxy-5-nitropyridines 15 (step a). Intermediates 15 in which $R^{11}$ is a phenyl group have been described in the literature (e.g. WO 1999/24404; WO 2008/025539).

The nitro group in intermediates 15 may then be reduced to the amino group by one of numerous known methods such as tin(II) chloride in a solvent such as ethanol or hydrogenation catalyzed by a transition metal such as palladium or platinum in a solvent such as ethyl acetate or ethanol to give intermediates 16 (step b). Carbamoylation of the aniline in intermediates 16 can be carried out by conventional methods described in the literature, for example, WO 2009/119700, to give intermediates 17 (step c). Reaction of intermediates 17 with a suitable base such as, e.g. tert-butyllithium in an appropriate solvent, such as tetrahydrofuran or diethyl ether, at temperatures between 0° C. and 75° C. and treating the generated lithium species with an iodinating agent such as iodine gives intermediates 18 (step d).
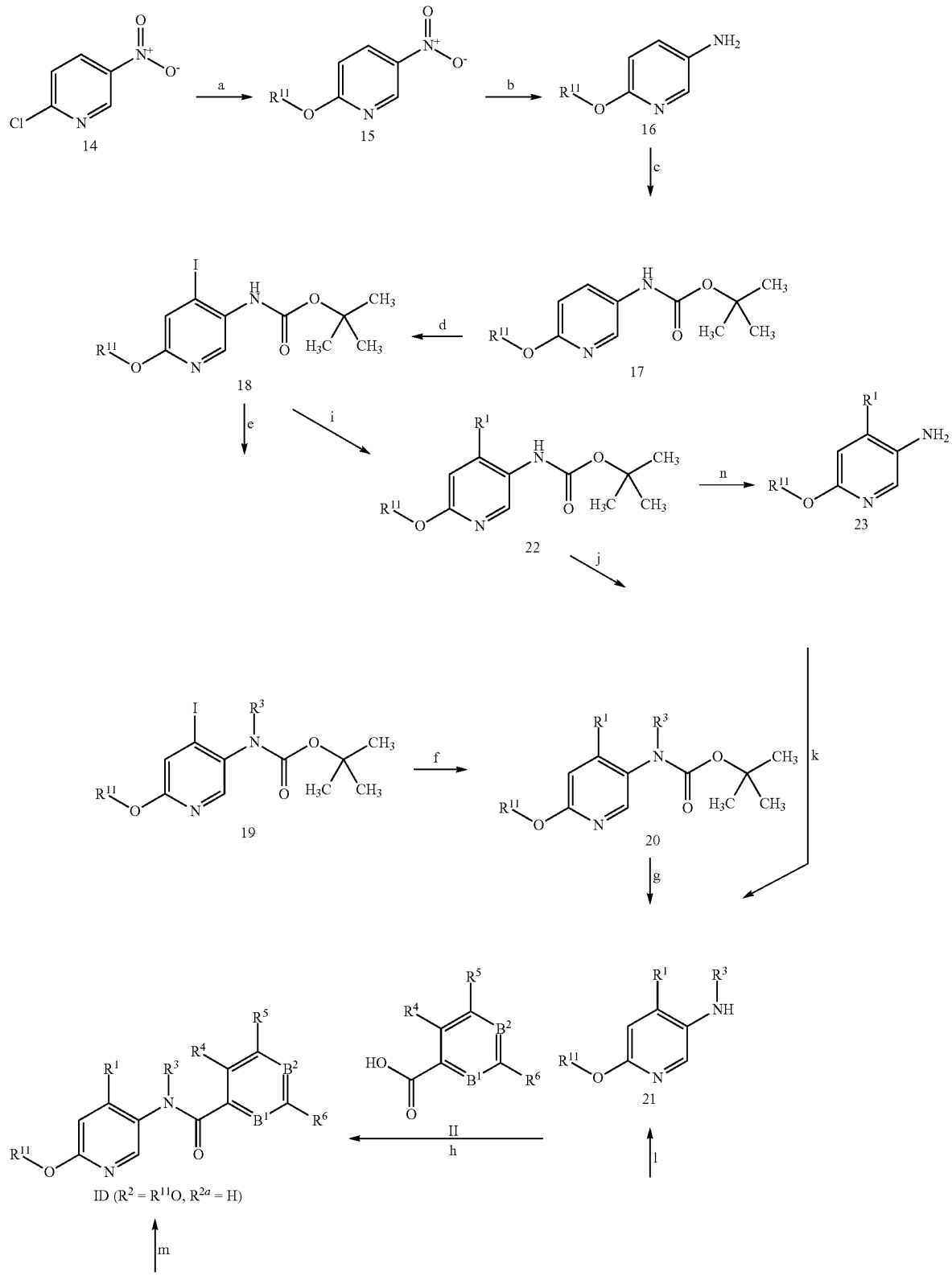
Scheme 3

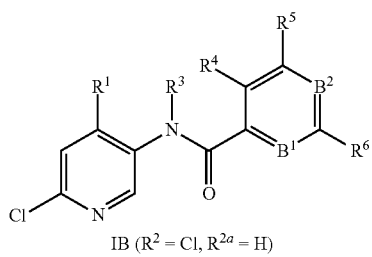

IB ($R^2$ = Cl, $R^{2a}$ = H)

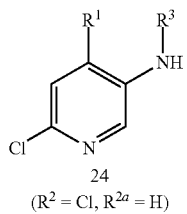

24
($R^2$ = Cl, $R^{2a}$ = H)

Alkylation of intermediates 18 with $R^3X$, in which X is a suitable leaving group such as chlorine, bromine, iodine, $OSO_2$alkyl (e.g. mesylate (methanesulfonate), $OSO_2$fluoroalkyl (e.g. triflate (trifluoromethanesulfonate) or $OSO_2$aryl (e.g. tosylate (p-toluenesulfonate)), using a suitable base in an appropriate solvent (e.g. sodium hydride in DMF) at temperatures between 0° C. and the boiling temperature of the solvent, yields intermediates 19 (step e).

Reaction of intermediates 19 with (substituted) boronic acids $R^1$—$B(OH)_2$ or boronic esters $R^1$—$B(OR')_2$ (e.g. pinacol or trimethylene glycol ester, either commercially available or prepared using literature procedures as described for example in "Boronic Acids—Preparation and Applications in Organic Synthesis and Medicine" by Dennis G. Hall (ed.) $1^{st}$ Ed., 2005, John Wiley & Sons, New York) using a suitable catalyst (e.g. dichloro[1,1-bis(diphenylphosphino)-ferrocene]palladium (II) dichloromethane adduct, tetrakis (triphenylphosphine)palladium(0) or palladium (II) acetate with triphenylphosphine) in an appropriate solvent (e.g. dioxane, dimethoxyethane, water, toluene, N,N-dimethylformamide or mixtures thereof) and a suitable base (e.g. sodium carbonate, sodium hydrogen carbonate, potassium fluoride, potassium carbonate or triethylamine) at temperatures between room temperature and the boiling point of the solvent or solvent mixture yields intermediates 20 (step f). Suzuki reactions of this type are broadly described in literature (e.g. A. Suzuki, Pure Appl. Chem. 1991, 63, 419-422; A. Suzuki, N. Miyaura, Chem. Rev. 1979, 95, 2457; A. Suzuki, J. Organomet. Chem. 1999, 576, 147-168; V. Polshettiwar, Chem. Sus. Chem. 2010, 3, 502-522) and are well known to those skilled in the art. Alternatively, aryl- or heteroaryl-trifluoroborates $R^1BF_3K$ can be used in the cross-coupling reaction applying a palladium catalyst such as, e.g. tetrakis(triphenylphosphine)palladium(0), palladium(II) acetate or dichloro[1,1'-bis(diphenylphosphino)ferrocene]-palladium(II) dichloromethane adduct in the presence of a suitable base such as cesium carbonate or potassium phosphate in solvents such as toluene, THF, dioxane, water or mixtures thereof, at temperatures between room temperature and the boiling point of the solvent or solvent mixture.

Intermediates 20 can be also synthesized by reacting intermediates 19 with (substituted) aryl- or heteroaryl tin reagents $R^1$—$SnR_3$ (R=e.g. Me or n-Bu; either commercially available or prepared according to literature procedures) in the presence of a suitable catalyst (e.g. tetrakis-(triphenylphosphine)palladium(0), benzylbis(triphenylphosphine)-palladium(II) chloride, bis(triphenylphosphine)palladium(II) dichloride or dichloro[1,1'-bis(diphenylphosphino)-ferrocene]palladium(II) dichloromethane adduct) in an appropriate solvent (e.g. THF, dioxane, DMF or HMTP or mixtures thereof) at temperatures between room temperature and the boiling point of the solvent or solvent mixture, optionally in the presence of lithium chloride. Stille couplings of this type are broadly described in literature (e.g. J. K. Stille, Angew. Chem. Int. Ed. Engl. 1986, 25, 508-524; V. Farina et al., J. Org. React. 1998, 50, 1-652; T. N. Mitchell, Synthesis 1992, 9, 803-815) and well known to those skilled in the art.

Alternatively, intermediates 20 can be synthesized from reaction of intermediates 19 with (substituted) aryl- or heteroaryl zinc halides $R^1$—ZnX (X=Cl, Br or I) (either commercially available or synthesized by methods described in literature) using a nickel (e.g. tetrakis-(triphenylphosphine)nickel(0)) or palladium catalyst (e.g. tetrakis (triphenyl-phosphine)palladium(0)) in an appropriate solvent such as, e.g. THF or DMA in a temperature range between room temperature and boiling point of the solvent. Negishi couplings of this type are broadly described in literature (e.g. "Name Reactions for Homologations-Part I: Negishi cross-coupling reaction", Li, J. J., Corey, E. J., Eds.; Wiley & Sons, Hoboken, N.J., 2009, 70-99; "Metal-Catalyzed Cross-Coupling Reactions", Dicdcrich, F.; Stang, P. J., Eds.; Wiley-VCH: Wcinhcim, Germany, 1998, 1-47; E. Erdik, Tetrahedron 1992, 48, 9577-9648; G. Organ, Eur. J. Org. Chem. 2010, 4343-4354) and well known to those skilled in the art.

Intermediates 20 may also be prepared by converting intermediates 18 into intermediates 22 by cross-coupling reactions (step i) and alkylation of intermediates 22 with compounds of the type $R^3X$ (step 0 using the conditions as outlined before.

Intermediates 20 are then converted into intermediates 21 by removal of the Boc protective group applying methods known to those skilled in the art (e.g. using trifluoroacetic acid in dichloromethane at temperatures between 0° C. and room temperature) and as described for example in "Protective Groups in Organic Chemistry" by T. W. Greene and P. G. M. Wuts, $4^{th}$ Ed., 2006, Wiley N.Y. (step g).

Acylation of intermediates 21 with aryl- or heteroaryl carboxylic acids II (either commercially available or accessible by methods known in the art) furnishes target structures ID (step h). Amide couplings of this type are widely described in the literature (e.g., Comprehensive Organic Transformations: A Guide to Functional Group Preparations, $2^{nd}$ Edition, Richard C. Larock, John Wiley & Sons, New York, N.Y. 1999) and can be accomplished by the usage of coupling reagents such as, e.g., N,N'-carbonyldiimidazole (CDI), N,N'-dicyclohexyl-carbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluoro-phosphate (HATU), 1-hydroxy-1,2,3-benzotriazole (HOBT), O-benzotriazol-1-yl-N,N,N',N'-tetramethyluronium tetrafluoroborate (TBTU) or 2-chloro- or 2-bromo-1-methylpyridinium iodide (Mukaiyama reagent) in a suitable solvent, e.g., N,N-dimethylformamide (DMF), dimethylacetamide (DMAc), dichloromethane or dioxane, optionally in the presence of a base (e.g., triethylamine, N,N-diisopropylethylamine (Huenig's base) or 4-(dimethylamino)pyridine). Alternatively, the aryl- or heteroaryl carboxylic acids II can be converted into their acid chlorides by treatment with, e.g., thionyl chloride, neat or optionally in a solvent such as dichloromethane and reaction of the acid chloride with intermediates 5 in an appropriate solvent such as dichloromethane or DMF (N,N-dimethylformamide) and a base, e.g. triethylamine, N,N-diisopropylethylamine (Huenig's base), pyridine, 4-(dimethylamino)pyridine or lithium bis (trimethylsilyl)amide at temperatures ranging from ambient temperature to the reflux temperature of the solvent or solvent mixture to furnish compounds of the general formula ID.

Intermediates 21 may also be prepared from intermediates 23 by reductive alkylations (or sometimes called reductive aminations) which are widely described in literature and well known in the art. For example, intermediates 21 in which $R^3$ is a methyl group may be prepared, e.g. by reaction of intermediates 23 with trimethyl orthoformate in the presence of catalytic amounts of acid such as trifluoroacetic acid at elevated temperatures and reducing the in situ formed iminium species with a suitable reducing agent such as, e.g. lithium aluminum hydride in tetrahydrofuran at temperatures preferably between 0° C. and room temperature (step k). Intermediates 21 in which $R^3$ is a $R^9CH_2$ or a $R^9R^{10}CH$ substituent can be also synthesized from intermediates 23 by reaction with (optionally substituted) aldehydes $R^9CHO$ and ketones $R^9C(O)R^{10}$, respectively, applying a reducing system such as, e.g. sodium borohydride, sodium triacetoxyborohydride, sodium cyanoborohydride or di-n-butyltin dichloride with triphenylsilane, in an appropriate solvent such as 1,2-dichloroethane or tetrahydrofuran ($R^3$=$R^9CH_2$ and $R^9R^{10}CH$, respectively; step k). Acetic acid may be used as catalyst for the reactions with ketones $R^9C(O)R^{10}$. Indium trichloride with triethylsilane in methanol might be used as well.

Intermediates 23 can be synthesized from intermediates 22 by removal of the Boc protective group applying methods known to those skilled in the art (e.g. using trifluoroacetic acid in dichloromethane at temperatures between 0° C. and room temperature) and as described for example in "Protective Groups in Organic Chemistry" by T. W. Greene and P. G. M. Wuts, 4$^{th}$ Ed., 2006, Wiley N.Y. (step n).

Furthermore, intermediates 21 can be prepared from intermediates 24 (prepared as described for intermediate 5 under Scheme 1) by reaction of intermediates 24 with alcohols $R^{11}OH$ in the presence of an appropriate base such as sodium or potassium hydroxide, in a suitable solvent such as, e.g. DMF or DMSO (step l). In order to enhance the rate of conversion heating might be applied, whereby conventional heating or microwave-assisted heating might be employed using a suitable microwave irradiation apparatus. Furthermore, the reaction can be conducted without a solvent using the alcohol $R^{11}OH$ as reactant and reagent.

Alternatively, compounds ID can be prepared by reacting compounds IB with an alcohol $R^{11}OH$ in the presence of an appropriate catalyst such as, e.g. tris(dibenzylideneacetone)-dipalladium(0) (optionally with a ligand such as, e.g. (R)-(+)-2,2'-bis(di-p-tolylphosphino)-1,1'-binaphthyl) and a base such as, e.g. potassium tert-butoxide or sodium hydride in a suitable solvent such as, e.g. dioxane or toluene (step m).

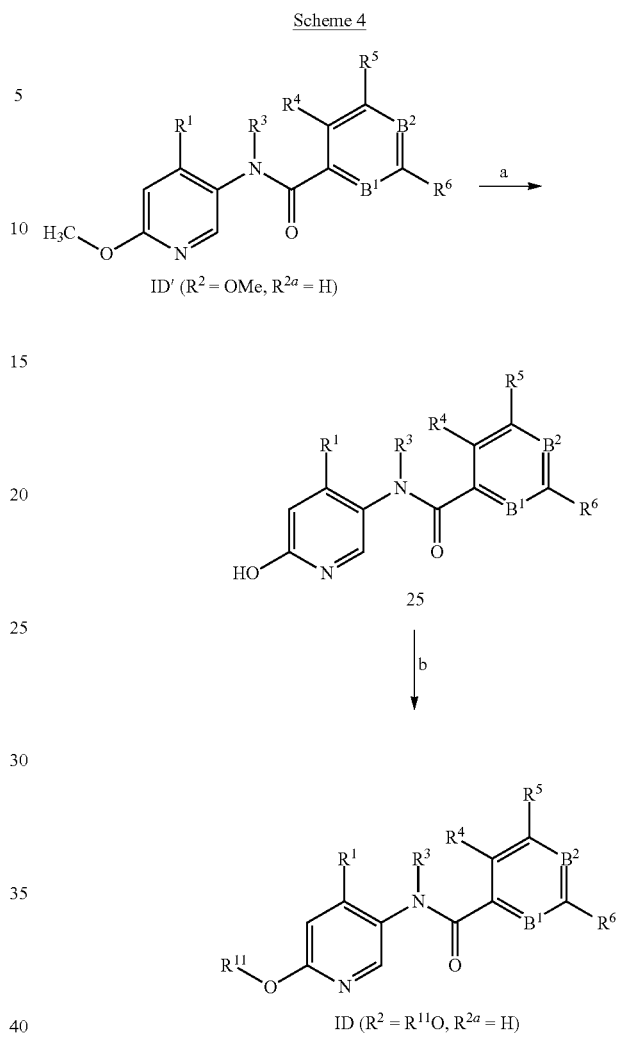

Scheme 4

Compounds of the general formula ID in which $R^2$ is $R^{11}O$, $R^{2a}$ is H and $R^{11}$ is an alkyl group can alternatively be prepared according to Scheme 4 from compounds ID' in which $R^2$ is a methoxy group (prepared by the methods described under Scheme 3). The 6-methoxypyridine compounds can be converted into the 6-hydroxypyridine intermediates 25 for example by treating with a strong aqueous acid such as HCl or HBr with or without heating in a polar solvent such as methanol (step a). Alternatively, compounds ID' ($R^2$=OMe) can be treated with iodo-trimethyl-silane in a suitable solvent such as, e.g. dichloromethane at temperatures between room temperature and the boiling point of the solvent to give intermediates 25. The 6-hydroxypyridine intermediates 25 may then be alkylated selectively on oxygen by methods described in literature (T. Ross-Kelly, *J. Am. Chem. Soc.* 1988, 110, 6471-6480; WO2005/115977) to give compounds ID. For example, reaction of intermediates 25 with alkyl halides such as benzyl bromide or n-propyl bromide in a solvent such as benzene or chloroform in the presence of silver salts such as silver carbonate gives the corresponding 6-alkoxy derivatives ID ($R^2$=$R^{11}O$, $R^{2a}$=H, $R^{11}$=alkyl; step b).

Scheme 5
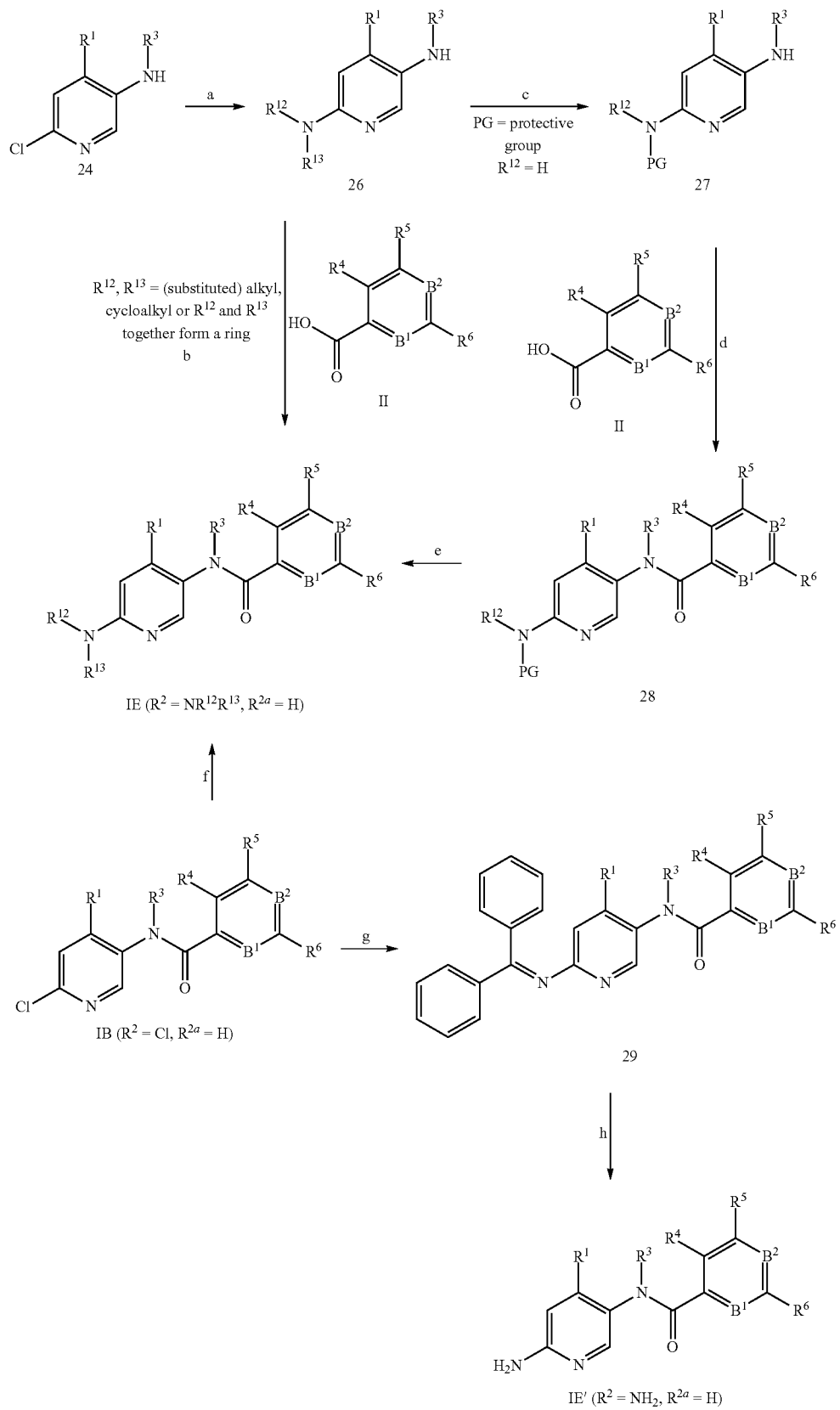

Compounds of general formula IE in which $R^2$ is an amino substituent $NR12R^{13}$ ($R^{12}$ (substituted) alkyl or cycloalkyl, $R^{2a}$ is hydrogen and $R^{13}$=H, (substituted) alkyl or cycloalkyl, or $R^{12}$ and $R^{13}$ together form a ring) may be prepared as described in Scheme 5.

The 6-chloro substituent in intermediates 24 (prepared as described for intermediate 5 in Scheme 1) may be directly converted to an amino group $NR^{12}R^{13}$ by a reaction commonly referred to as the Hartwig-Buchwald aryl amination. This reaction (step a) couples an aryl moiety with variously substituted and functionalized amines. It can be carried out under a variety of conditions employing a transition metal catalyst, e.g. palladium acetate or tris(dibenzylidene-acetone)dipalladium(0), a ligand such as (9,9-dimethyl-9H-xanthene-4,5-diyl)bis(diphenyl-phosphine) or triphenyl-phosphine, a base such as sodium tert-butoxide and a solvent such as toluene or dioxane (*Org. Synth., Coll.* 2004, 10, 423; J. F. Hartwig et al., *J. Am. Chem. Soc.* 1994, 116, 5969-5970; WO 2009/158431) to give intermediates 26. In order to enhance the rate of conversion heating might be applied, whereby conventional heating or microwave-assisted heating might be employed using a suitable microwave irradiation apparatus.

Intermediates 26 in which $R^{12}$ and $R^{13}$≠hydrogen then may be acylated directly with aryl and heteroaryl carboxylic acids II (step b) to give compounds of general formula IE ($R^{12}$≠H, $R^{13}$≠H). Amide couplings of this type are widely described in the literature (e.g., Comprehensive Organic Transformations: A Guide to Functional Group Preparations, $2^{nd}$ Edition, Richard C. Larock, John Wiley & Sons, New York, N.Y. 1999) and can be accomplished by the usage of coupling reagents such as, e.g., N,N'-carbonyldiimidazole (CDI), N,N'-dicyclohexyl-carbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluoro-phosphate (HATU), 1-hydroxy-1,2,3-benzotriazole (HOBT), O-benzotriazol-1-yl-N,N,N',N'-tetramethyluronium tetrafluoroborate (TBTU) or 2-chloro- or 2-bromo-1-methylpyridinium iodide (Mukaiyama reagent) in a suitable solvent, e.g., N,N-dimethylformamide (DMF), dimethylacetamide (DMAc), dichloromethane or dioxane, optionally in the presence of a base (e.g., triethylamine, N,N-diisopropylethylamine (Huenig's base) or 4-(dimethylamino)pyridine). Alternatively, the aryl- or heteroaryl carboxylic acids II can be converted into their acid chlorides by treatment with, e.g., thionyl chloride, neat or optionally in a solvent such as dichloromethane and reaction of the acid chloride with intermediates 26 in an appropriate solvent such as dichloromethane or DMF (N,N-dimethylformamide) and a base, e.g. triethylamine, N,N-diisopropylethylamine (Huenig's base), pyridine, 4-(dimethylamino)pyridine or lithium bis(trimethylsilyl)amide at temperatures ranging from ambient temperature to the reflux temperature of the solvent or solvent mixture to furnish compounds of the general formula IE.

For compounds in which $R^{12}$≠H and $R^{13}$=H, the secondary 6-amino group of intermediates 26 may be protected with a suitable protecting group to give intermediates 27 (step c) using methods well known to those skilled in the art and as described in the chemical literature, e.g. "Protective Groups in Organic Chemistry" by T. W. Greene and P. G. M. Wuts, $4^{th}$ Ed., 2006, Wiley N.Y.

The 3-amino group in intermediates 27 is then acylated with aryl- or heteroaryl carboxylic acids II using the conditions described above to give intermediates 28 (step d). Deprotection of the 6-amino group using methods well-known to those skilled in the art and as described for example in "Protective Groups in Organic Chemistry" by T. W. Greene and P. G. M. Wuts, $4^{th}$ Ed., 2006, Wiley N.Y. furnishes compounds IE ($R^{13}$=H, step e). Compounds of general formula IE in which $R^2$ signifies an amino substituent $NR^{12}R^{13}$ ($R^{12}$=(substituted) alkyl or cycloalkyl and $R^{13}$=H, (substituted) alkyl or cycloalkyl or $R^{12}$ and $R^{13}$ together form a ring) may be also prepared from compounds IB and amines of the type $HNR^{12}R^{13}$ (step f) by using for example a Hartwig-Buchwald amination reaction as described above under step a.

In order to facilitate an aryl amination, intermediates 24 and compounds IB may be first converted to the corresponding 6-iodo or 6-bromo pyridines. These trans-halogenation reactions are widely described in literature and known in the art. For example, conversion of 6-chloropyridyl intermediates to 6-iodopyridyl intermediates may be carried out by heating 6-chloropyridyl intermediates with hydriodic acid and an excess of iodide from a source such as sodium iodide in a polar solvent such as acetonitrile (e.g. U. Luening et al., *Eur. J. Org. Chem.* 2009, 14, 2328-2341). Alternatively, the 6-chloro intermediates may be reacted with sodium iodide and chloro-trimethyl-silane in a suitable solvent such as, e.g. propanenitrile (e.g. J. Clayden et al., *J. Am. Chem. Soc.* 2009, 131, 5331-5343) or with acetyl chloride or acetic anhydride and sodium iodide in, e.g. acetonitrile (e.g. M. G. Banwell, A. C. Bissember, *J. Org. Chem.* 2009, 74, 4893-4895) to furnish the 6-iodo compounds.

The 6-bromo intermediates may be produced by analogous methods, for example by reacting the 6-chloro intermediates with bromo-trimethyl-silane in a suitable solvent such as, e.g. propanenitrile (e.g. M. V. Patel et al., *J. Med. Chem.* 2006, 49, 7450-7465). Alternatively, phosphorus(V) oxybromide (e.g. J. W. Streef et al., *J. Heterocycl. Chem.* 1985, 22, 985-991) or hydrobromic acid in acetic acid (e.g. Md. K. Nazeeruddin et al., *Inorg. Chem.* 2006, 45, 4642-4653) may be used. The transformation can be carried out at temperatures ranging from room temperature up to the boiling point of the solvent. Microwave heating may also be applied.

Compounds of general formula IE' in which $R^2$ signifies a primary amino substituent $—NH_2$ may be prepared by converting the 6-chloro substituent in compounds IB to a benzhydrylidene amine ("imine") by treatment of compounds IB with commercially available benzophenone imine applying Hartwig-Buchwald amination conditions as described above under step a, to give intermediates 29 (step g). Cleavage of the imine group for example using an acid such as, e.g. aqueous HCl or by catalytic hydrogenation, treatment with hydroxylamine hydrochloride or a catalytic amount of HCl in wet THF provides compounds IE' in which $R^2$ is a primary amino group ($NH_2$, step h).

Scheme 6

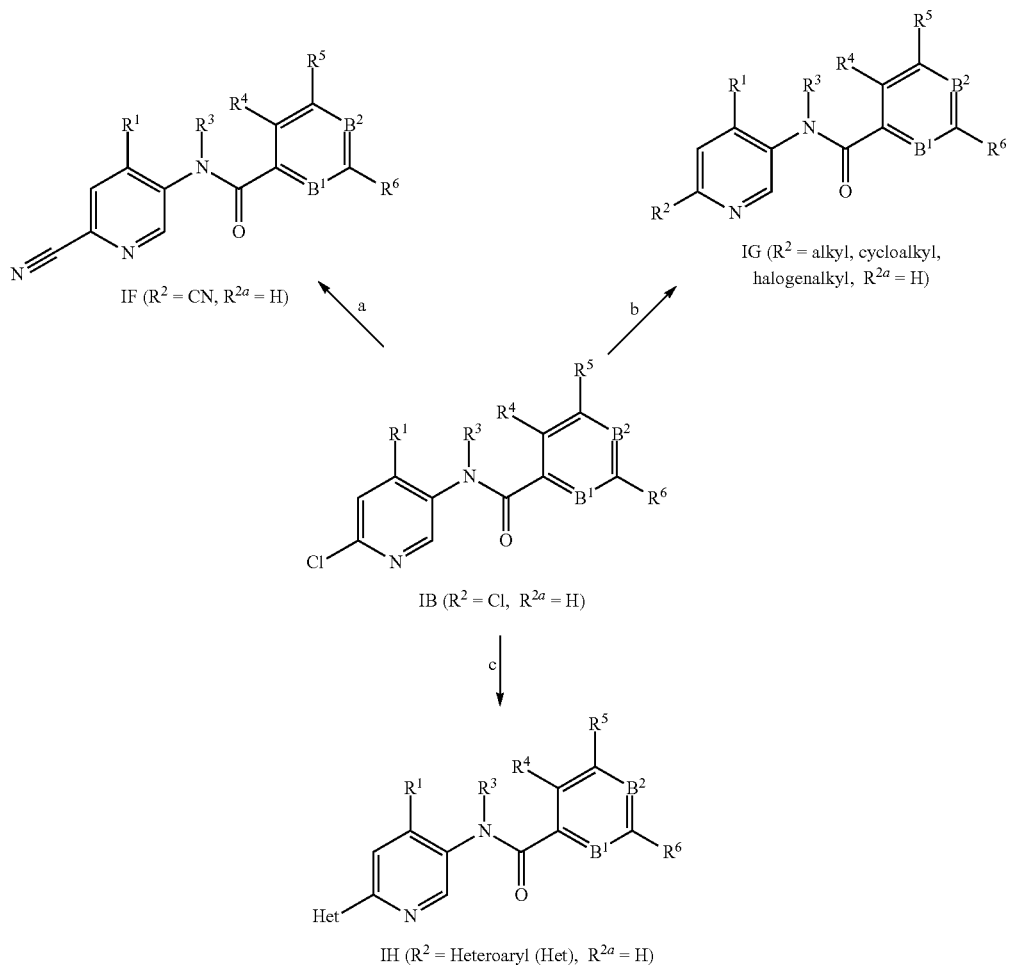

Compounds of the general formulas IF to 1-H can be prepared for example as outlined in Scheme 6 by the methods and procedures given below.

Compounds of the general formula IF in which $R^2$ is a cyano group and $R^{2a}$ is hydrogen can be prepared for example by reaction of compounds IB with a suitable source of cyanide such as zinc cyanide in a solvent such as, e.g. DMF or dioxane at elevated temperatures up to the boiling point of the solvent with or without using a substoichiometric amount of a transition metal catalyst such as e.g. tetrakis (triphenylphosphine)palladium(0). Alternatively, cyanide may be introduced using superstoichiometric amounts of copper(I)cyanide in a polar solvent such as DMF or dioxane and a suitable catalyst such as tris(dibenzylideneacetone) dipalladium(0) and 1,1'-bis(diphenyl-phosphino)ferrocene as ligand (step a). The use of microwave irradiation may facilitate the reaction.

Compounds of the general formula IG in which $R^2$ signifies an alkyl (e.g. a methyl, ethyl, propyl, isopropyl, isobutyl) or a cycloalkyl (e.g. a cyclopropyl) group and $R^{2a}$ is hydrogen can be prepared for example from compounds IB. For example, reaction of compounds IB with (substituted) boronic acids $R^2$—B(OH)$_2$ or boronic esters $R^2$—B(OR')$_2$ (e.g. pinacol or trimethylene glycol ester, either commercially available or prepared using literature procedures as described for example in "Boronic Acids—Preparation and Applications in Organic Synthesis and Medicine" by Dennis G. Hall (ed.) 1$^{st}$ Ed., 2005, John Wiley & Sons, New York) using a suitable catalyst (e.g. dichloro[1,1'-bis (diphenylphosphino)-ferrocene]palladium(II) dichloromethane adduct, tetrakis(triphenylphosphine)palladium(0) or palladium(II) acetate with triphenylphosphine) in an appropriate solvent (e.g. dioxane, dimethoxyethane, water, toluene, N,N-dimethylformamide or mixtures thereof) and a suitable base (e.g. sodium carbonate, sodium hydrogen carbonate, potassium fluoride, potassium carbonate or triethylamine) at temperatures between room temperature and the boiling point of the solvent or solvent mixture yields compounds I G (step b). Suzuki reactions of this type are broadly described in literature (e.g. A. Suzuki, *Pure Appl. Chem.* 1991, 63, 419-422; A. Suzuki, N. Miyaura, *Chem. Rev.* 1995, 95, 2457-2483; A. Suzuki, *J. Organomet. Chem.* 1999, 576, 147-168; V. Polshettiwar, *Chem. Sus. Chem.* 2010, 3, 502) and are well known to those skilled in the art. Compounds IG can be also synthesized by reacting compounds IB with (substituted) alkyl tin reagents $R^2$—SnR$_3$ (R=e.g. Me or n-Bu; either commercially available or prepared according to literature procedures) in the presence of a suitable catalyst (e.g. tetrakis-(triphenylphosphine)palladium(0), benzylbis(triphenylphosphine)-palladium(II) chloride, bis(triphenylphosphine)palladium(II) dichloride or dichloro[1,1'-bis(diphenylphosphino)-ferrocene]palladium (II) dichloromethane adduct) in an appropriate solvent (e.g. THF, dioxane, DMF or HMPA or mixtures thereof) at temperatures between room temperature and the boiling point of the solvent or solvent mixture, optionally in the presence of lithium chloride. Stille couplings of this type are broadly described in literature (e.g. J. K. Stille, *Angew. Chem. Int. Ed. Engl.* 1986, 25, 508-524; V. Farina et al., *J. Org. React.* 1998, 50, 1-652; T. N. Mitchell, *Synthesis* 1992, 9, 803-815) and well known to those skilled in the art (step b). Alternatively, compounds IF can be synthesized from reaction of compounds IB with (substituted) alkyl zinc halides $R^2$—ZnX (X=Cl, Br or I) (either commercially available or synthesized by methods described in literature) using a nickel (e.g. tetrakis(triphenylphosphine)nickel(0)) or palladium catalyst (e.g. tetrakis(triphenylphosphine)palladium(0)) in an appropriate solvent such as, e.g. THF or DMA in a temperature range between room temperature and boiling point of the solvent. Negishi couplings of this type are broadly described in literature (e.g. "Name Reactions for Homologations-Part I: Negishi cross-coupling reaction", Li, J. J., Corey, E. J., Eds.; Wiley & Sons, Hoboken, N.J., 2009, 70-99; "Metal-Catalyzed Cross-Coupling Reactions", Diederich, F.; Stang, P. J., Eds.; Wiley-VCH: Weinheim, Germany, 1998, 1-47; E. Erdik, *Tetrahedron* 1992, 48, 9577-9648; G. Organ, *Eur. J. Org. Chem.* 2010, 23, 4343-4354) and well known to those skilled in the art (step b).

Alternatively, Grignard reactions, treating compounds IB with organomagnesium compounds of the type $R^2$—MgX (X=Cl or Br) in an appropriate solvent such as, e.g. tetrahydrofuran or NMP may be used to prepare compounds IG. Reactions of this type have also been described in literature (e.g. F. Lamaty et al., *Synthetic Commun.* 2009, 39, 1583-1591).

Furthermore, compounds IB can be reacted with commercially available aluminum compounds of the type ($R^2$)$_3$Al ($R^2$=Me, Et, iso-butyl) using an appropriate catalyst such, as e.g. tetrakis(triphenylphosphine)palladium(0), bis(triphenylphosphine)palladium(II) dichloride or tris(dibenzylideneacetone)dipalladium(0) in the presence of triphenylphosphine, in a suitable solvent such as, e.g. dimethoxyethane, dioxane, toluene, hexane, DMF or mixtures thereof at temperatures ranging from room temperature to the boiling point of the solvent or solvent mixtures, to furnish compounds IG. Reactions of this type have also been described in literature (e.g. A. Cappelli et al., *ChemMedChem* 2010, 5, 739-748; M. J. Bamford et al., *Bioorg. Med. Chem. Lett.* 2005, 15, 3407-3411). In order to enhance the rate of conversion microwave-assisted heating might be applied.

Alternatively, compounds IG in which $R^2$ signifies a trifluoromethyl group can be synthesized from compounds IB by reaction with sodium trifluoroacetate in the presence of copper(I)iodide in an appropriate solvent like 1-methyl-2-pyrrolidone (e.g. R. D. Chambers et al., *J. Chem. Soc., Perkin Trans.* 1, 1988, 4, 921-926) or using (trifluoromethyl)trimethylsilane, copper(I)iodide with or without potassium fluoride in NMP as described in literature (e.g. R. C. Lemoine et al., *Bioorg. Med. Chem. Lett.* 2010, 20, 704-708; M. Schlosser et al., *Eur. J. Org. Chem.* 2003, 8, 1559-1568).

Furthermore, a cyclopropyl substituent can be introduced for example through palladium-catalyzed (e.g. tetrakis(triphenylphosphine)palladium(0)) reaction of compounds IB with a pre-formed complex of 9-borabicyclo[3.3.1]nonane and propargylbromide in the presence of an appropriate base like, e.g. sodium hydroxide in an appropriate solvent like tetrahydrofuran in analogy to published procedures (J. A. Soderquist et al., *Tetrahedron Lett.* 2000, 41, 4251-4255). Furthermore, compounds IG in which $R^2$ is a methyl or a trifluoromethyl group, respectively, may also be prepared from commercially available 4-chloro- or 4-bromo-6-methyl-pyridine-3-ylamine and 4-chloro- or 4-bromo-6-trifluoromethyl-pyridine-3-ylamine, respectively, as starting materials, applying the same synthetic methodology as described for compound 8 in Scheme 1.

Compounds of the general formula IH in which $R^2$ signifies a heteroaryl (Het) substituent and $R^{2a}$ is hydrogen can be prepared for example from compounds IB by reaction with (substituted) boronic acids Het-B(OH)$_2$ or boronic esters Het-B(OR')$_2$ (e.g. pinacol or trimethylene glycol ester, either commercially available or prepared using literature procedures as described for example in "Boronic Acids—Preparation and Applications in Organic Synthesis and Medicine" by Dennis G. Hall (ed.) 1$^{st}$ Ed., 2005, John Wiley & Sons, New York) using a suitable catalyst (e.g. dichloro [1,1'-bis(diphenylphosphino)-ferrocene]palladium (II) dichloromethane adduct, tetrakis(triphenylphosphine)palladium (0) or palladium (II) acetate with triphenylphosphine) in an appropriate solvent (e.g. dioxane, dimethoxyethane, water, toluene, N,N-dimethylformamide or mixtures thereof) and a suitable base (e.g. sodium carbonate, sodium hydrogen carbonate, potassium fluoride, potassium carbonate or triethylamine) at temperatures between room temperature and the boiling point of the solvent or solvent mixture (step c). Suzuki reactions of this type are broadly described in literature (e.g. A. Suzuki, *Pure Appl. Chem.* 1991, 63, 419-422; A. Suzuki, N. Miyaura, *Chem. Rev.* 1995, 95, 2457-2483; A. Suzuki, *J. Organomet. Chem.* 1999, 576, 147-168; V. Polshettiwar, *Chem. Sus. Chem.* 2010, 3, 502-522) and are well known to those skilled in the art. Alternatively, aryl- or heteroaryl-trifluoroborates $R^1BF_3K$ can be used in the cross-coupling reaction applying a palladium catalyst such as, e.g. tetrakis(triphenylphosphine) palladium (0), palladium(II) acetate or dichloro[1,1'-bis(diphenylphosphino)ferrocene]-palladium (II) dichloromethane adduct in the presence of a suitable base such as cesium carbonate or potassium phosphate in solvents such as toluene, THF, dioxane, water or mixtures thereof, at temperatures between room temperature and the boiling point of the solvent or solvent mixture.

Compounds IH can be also synthesized by reacting compounds IB with (substituted) heteroaryl tin reagents Het-SnR$_3$ (R=e.g. Me or n-Bu; either commercially available or prepared according to literature procedures) in the presence of a suitable catalyst (e.g. tetrakis-(triphenylphosphine)palladium (0), benzylbis(triphenylphosphine)-palladium (11) chloride, bis(triphenylphosphine)palladium (11) dichloride or dichloro[1,1'-bis(diphenylphosphino)-ferrocene]palladium(II) dichloromethane adduct) in an appropriate solvent (e.g. THF, dioxane, DMF or HMPA or mixtures thereof) at temperatures between room temperature and the boiling point of the solvent or solvent mixture, optionally in the presence of lithium chloride. Stille couplings of this type are broadly described in literature (e.g. J. K. Stille, *Angew. Chem. Int. Ed. Engl.* 1986, 25, 508-524; V. Farina et al., *J. Org. React.* 1998, 50, 1-652; T. N. Mitchell, *Synthesis* 1992, 9, 803-815) and well known to those skilled in the art.

Alternatively, compounds IH can be synthesized from reaction of compounds IB with (substituted) heteroaryl zinc halides Het-ZnX (X=Cl, Br or I) (either commercially available or synthesized by methods described in literature) using a nickel (e.g. tetrakis(triphenyl-phosphine)nickel(0)) or palladium catalyst (e.g. tetrakis(triphenylphosphine)palladium(0)) in an appropriate solvent such as, e.g. THF or DMA in a temperature range between room temperature and boiling point of the solvent. Negishi couplings of this type are broadly described in literature (e.g. "Name Reactions for Homologations-Part I: Negishi cross-coupling reaction", Li, J. J., Corey, E. J., Eds.; Wiley & Sons, Hoboken, N.J., 2009, 70-99; "Metal-Catalyzed Cross-Coupling Reactions", Diederich, F.; Stang, P. J., Eds.; Wiley-VCH: Weinheim, Germany, 1998, 1-47; E. Erdik, Tetrahedron 1992, 48, 9577-9648; G. Organ, Eur. J. Org. Chem. 2010, 4343-4354) and well known to those skilled in the art.

In some cases, the conversion of compounds IB into the corresponding 6-iodo or 6-bromo pyridines may facilitate an aryl alkylation. These trans-halogenation reactions are widely described in literature and known in the art. For example, conversion of compounds IB into their 6-iodopyridyl analogues may be carried out by heating compounds IB with hydriodic acid and an excess of iodide from a source such as sodium iodide in a polar solvent such as acetonitrile (e.g. F. Eggers, U. Luening, Eur. J. Org. Chem. 2009, 14, 2328-2341). Alternatively, compounds IB may be reacted with sodium iodide and chloro-trimethyl-silane in a suitable solvent such as, e.g. propanenitrile (e.g. J. Clayden et al., J. Am. Chem. Soc. 2009, 131, 5331-5343) or with acetyl chloride or acetic anhydride and sodium iodide in, e.g. acetonitrile (e.g. A. C. Bissember, M. G. Banwell, J. Org. Chem. 2009, 74, 4893-4895) to furnish the 6-iodo compounds. The 6-bromo intermediates may be produced by analogous methods, for example by reacting compounds IB with bromotrimethylsilane in a suitable solvent such as, e.g. propanenitrile (e.g. M. V. Patel et al., J. Med. Chem. 2006, 49, 7450-7465). Alternatively, phosphorus(V) oxybromide (e.g. J. W. Streef et al., J. Heterocycl. Chem. 1985, 22, 985-991) or hydrobromic acid in acetic acid (e.g. Md. K. Nazeeruddin, S. Fantacci, M. Graetzel et al., Inorg. Chem. 2006, 45, 4642-4653) may be used. The transformation can be carried out at temperatures ranging from room temperature up to the boiling point of the solvent. Microwave heating may also be applied.

Scheme 7

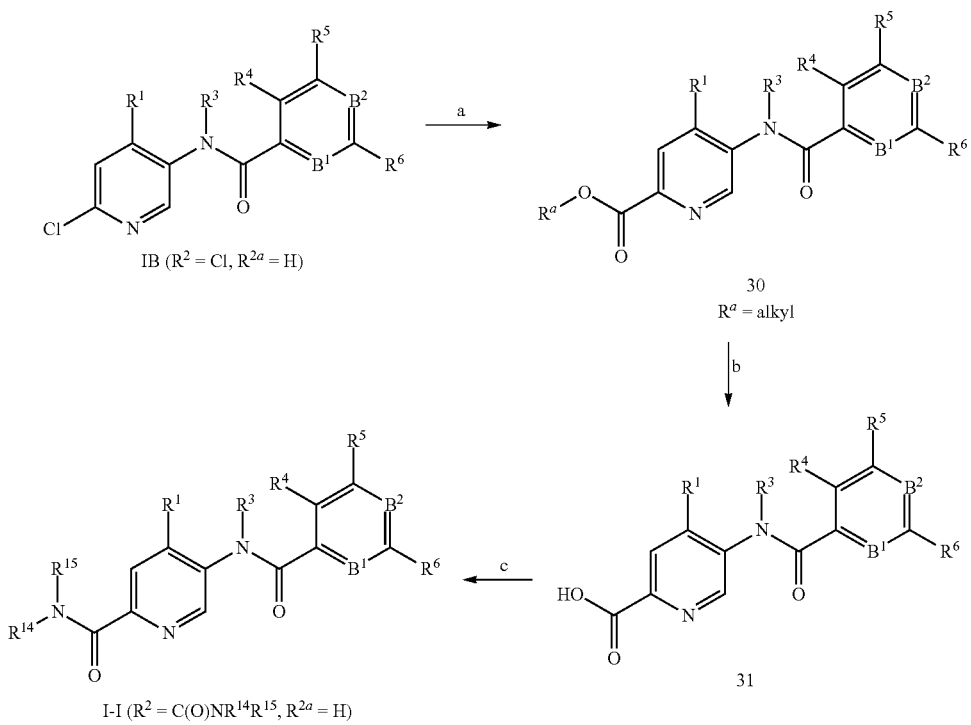

Compounds of the general formula I-I ($R^2$=C(O) $NR^{14}R^{15}$ with $R^{14}$ and $R^{15}$ independently from each other being hydrogen or $C_{1-7}$-alkyl) can be prepared as outlined in Scheme 7.

Intermediates 30 can be prepared for example by transition metal-catalyzed alkoxycarbonylation, reacting compounds IB with carbon monoxide using a suitable transition metal catalyst, for example, [1,1'-bis(diphenylphosphino) ferrocene]dichloropalladium(II) in a solvent such as methanol or ethanol, to give the alkyl ester intermediates 30 (step a). Supra-atmospheric pressures, e.g. 10 atm, of CO gas may facilitate the reaction. Under such pressures, the reaction is best run in a reaction vessel and using equipment designed to withstand high pressures. The reaction can be carried out in the presence of a base such as, e.g. tertiary amines, for example, triethylamine. Intermediates 31 are accessible by cleavage of the ester functionality in intermediates 30 under basic (e.g. methyl or ethyl esters with lithium or sodium hydroxide in polar solvents such as, e.g. methanol, water or tetrahydrofuran or mixtures of said solvents) or under acidic conditions (e.g. a tert-butyl ester using trifluoroacetic acid with or without a solvent (e.g. dichloromethane), concentrated hydrochloric acid in tetrahydrofuran or formic acid in an appropriate solvent such as alcohols like, e.g. isopropanol). Reaction of intermediates 31 with amines of the type $HNR^{14}R^{15}$ gives compounds I-I. Amide coupling of this type are widely described in the literature (e.g., Comprehensive Organic Transformations: A Guide to Functional Group Preparations, 2$^{nd}$ Edition, Richard C. Larock, John Wiley & Sons, New York, N.Y. 1999) and can be accomplished by the usage of coupling reagents such as, e.g., N,N'-carbonyldiimidazole (CDI), N,N'-dicyclohexylcarbodiimide (DCC), 1-(3-dimethyl-aminopropyl)-3-ethylcarbodiimide hydrochloride (EDCI), 1-[bis(d imethylamino)methylene]-1H-1,2,3-triazolo[4,5-h]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) or 2-chloro- or 2-bromo-1-methylpyridinium iodide (Mukaiyama reagent) in a suitable solvent, e.g., N,N-dimethylformamide (DMF), dimethylacetamide (DMAc), dichloromethane or dioxane, optionally in the presence of a base (e.g., triethylamine, N,N-diisopropylethylamine (Huenig's base) or 4-(dimethylamino)pyridine). Alternatively, the acid functionality in intermediates 31 can be converted into the acid chloride by treatment with, e.g., thionyl chloride, neat or optionally in a solvent such as dichloromethane and reaction of the acid chloride with amines of the type HNR$^{14}$R$^{15}$ in an appropriate solvent such as dichloromethane or DMF (N,N-dimethylformamide) and a base, e.g. triethylamine, N,N-diisopropylethylamine (Huenig's base), pyridine, 4-(dimethylamino)pyridine or lithium bis(trimethylsilyl)amide at temperatures ranging from ambient temperature to the reflux temperature of the solvent or solvent mixture furnishes compounds of the general formula I-I.

Compounds of the general formula I-I (R$^2$=C(O)NR$^{14}$R$^{15}$ with R$^{14}$ and R$^{15}$ independently from each other being hydrogen or C$_{1-7}$-alkyl, R$^{2a}$=H) can also be prepared as outlined in Scheme 8 from intermediate 32.

Alkylation of (6-chloro-4-iodo-pyridin-3-yl)-carbamic acid tert-butyl ester 32 (prepared according to published procedures, e.g. J.-U. Peters et al., Bioorg. Med. Chem. Lett. 2010, 20, 3405-3408; WO 2008/127399) with R$^3$X, in which X is a suitable leaving group such as chlorine, bromine, iodine, OSO$_2$alkyl (e.g. mesylate (methanesulfonate), OSO$_2$fluoroalkyl (e.g. triflate (trifluoromethane-sulfonate) or OSO$_2$aryl (e.g. tosylate (p-toluenesulfonate)), using a suitable base in an appropriate solvent (e.g. sodium hydride in DMF) at temperatures between 0° C. and the boiling temperature of the solvent, yields intermediates 33 (step a).

Scheme 8

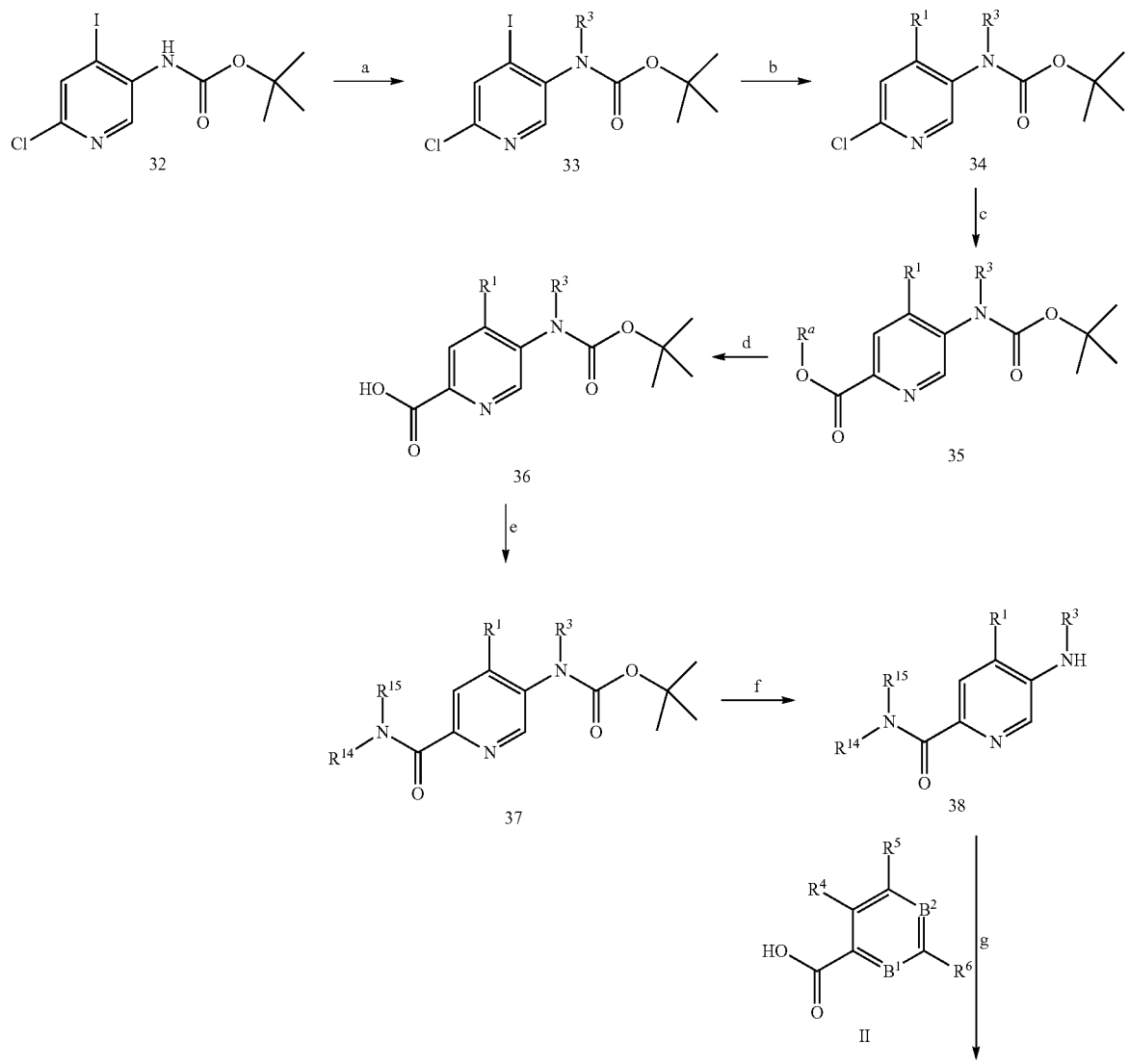

-continued

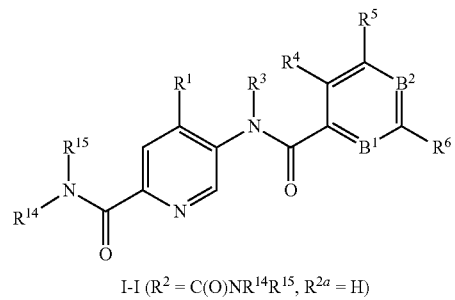

I-I ($R^2$ = C(O)N$R^{14}R^{15}$, $R^{2a}$ = H)

Reaction of intermediates 33 with (substituted) boronic acids $R^1$—B(OH)$_2$ or boronic esters $R^1$—B(OR')$_2$ (e.g. pinacol or trimethylene glycol ester, either commercially available or prepared using literature procedures as described for example in "Boronic Acids—Preparation and Applications in Organic Synthesis and Medicine" by Dennis G. Hall (ed.) 1$^{st}$ Ed., 2005, John Wiley & Sons, New York) using a suitable catalyst (e.g. dichloro[1,1'-bis(diphenylphosphino)-ferrocene]palladium (II) dichloromethane adduct, tetrakis (triphenylphosphine)palladium(0) or palladium (II) acetate with triphenylphosphine) in an appropriate solvent (e.g. dioxane, dimethoxyethane, water, toluene, N,N-dimethylformamide or mixtures thereof) and a suitable base (e.g. sodium carbonate, sodium hydrogen carbonate, potassium fluoride, potassium carbonate or triethylamine) at temperatures between room temperature and the boiling point of the solvent or solvent mixture yields intermediates 34 (step b). Suzuki reactions of this type are broadly described in literature (e.g. A. Suzuki, Pure Appl. Chem. 1991, 63, 419-422; A. Suzuki, N. Miyaura, Chem. Rev. 1995, 95, 2457-2483; A. Suzuki, J. Organomet. Chem. 1999, 576, 147-168; V. Polshettiwar et al., Chem. Sus. Chem. 2010, 3, 502-522) and are well known to those skilled in the art. Alternatively, aryl- or heteroaryl-trifluoroborates $R^1BF_3K$ can be used in the cross-coupling reaction applying a palladium catalyst such as, e.g. tetrakis(triphenyl-phosphine)palladium(0), palladium(II) acetate or dichloro[1,1'-bis(diphenylphosphino)-ferrocene]-palladium(II) dichloromethane adduct in the presence of a suitable base such as cesium carbonate or potassium phosphate in solvents such as toluene, THF, dioxane, water or mixtures thereof, at temperatures between room temperature and the boiling point of the solvent or solvent mixture.

Intermediates 34 can be also synthesized by reacting intermediates 33 with (substituted) aryl- or heteroaryl tin reagents $R^1$—SnR$_3$ (R=e.g. Mc or n-Bu; either commercially available or prepared according to literature procedures) in the presence of a suitable catalyst (e.g. tetrakis-(triphenylphosphine)palladium (0), benzylbis (triphenylphosphine)-palladium (II) chloride, bis (triphenylphosphine)palladium (II) dichloride or dichloro[1,1'-bis(diphenylphosphino)-ferrocene]palladium (II) dichloromethane adduct) in an appropriate solvent (e.g. THF, dioxane, DMF or HMPA or mixtures thereof) at temperatures between room temperature and the boiling point of the solvent or solvent mixture, optionally in the presence of lithium chloride (step b). Stille couplings of this type are broadly described in literature (e.g. J. K. Stille, Angew. Chem. Int. Ed. Engl. 1986, 25, 508-524; V. Farina et al., J. Org. React. 1998, 50, 1-652; T. N. Mitchell, Synthesis 1992, 9, 803-815) and well known to those skilled in the art.

Alternatively, intermediates 34 can be synthesized from reaction of intermediates 33 with (substituted) aryl- or heteroaryl zinc halides $R^1$—ZnX (X=Cl, Br or I) (either commercially available or synthesized by methods described in literature) using a nickel (e.g. tetrakis(triphenylphosphine)nickel(0)) or palladium catalyst (e.g. tetrakis (triphenyl-phosphine)palladium(0)) in an appropriate solvent such as, e.g. THF or DMA in a temperature range between room temperature and boiling point of the solvent (step b). Negishi couplings of this type are broadly described in literature (e.g. "Name Reactions for Homologations-Part I: Negishi cross-coupling reaction", Li, J. J., Corey, E. J., Eds.; Wiley & Sons, Hoboken, N.J., 2009, 70-99; "Metal-Catalyzed Cross-Coupling Reactions", Diederich, F.; Stang, P. J., Eds.; Wiley-VCH: Weinheim, Germany, 1998, 1-47; E. Erdik, Tetrahedron 1992, 48, 9577-9648; G. Organ, Eur. J. Org. Chem. 2010, 4343-4354) and well known to those skilled in the art.

Transition metal-catalyzed alkoxycarbonylation of intermediates 34 (step c), using carbon monoxide and a suitable transition metal catalyst, for example, [1,1'-bis(diphenylphosphino) ferrocene]dichloropalladium (II) in a solvent such as methanol or ethanol, gives the alkyl ester intermediates 35. Supra-atmospheric pressures, e.g. 10 atm, of CO gas may facilitate the reaction. Under such pressures, the reaction is best run in a reaction vessel and using equipment designed to withstand high pressures. The reaction can be carried out in the presence of a base such as, e.g. tertiary amines, for example, triethylamine.

The ester functionality in intermediates 35 is cleaved under basic (e.g. methyl or ethyl esters with lithium or sodium hydroxide in polar solvents such as, e.g. methanol, water or tetrahydrofuran or mixtures of said solvents) or under acidic conditions (e.g. a tert-butyl ester using trifluoroacetic acid with or without a solvent (e.g. dichloromethane), concentrated hydrochloric acid in tetrahydrofuran or formic acid in an appropriate solvent such as alcohols like, e.g. isopropanol) to furnish intermediates 36 (step d).

Reaction of intermediates 36 with amines of the type HN$R^{14}R^{15}$ gives intermediates 38 (step e). Amide coupling of this type are widely described in the literature (e.g., Comprehensive Organic Transformations: A Guide to Functional Group Preparations, 2$^{nd}$ Edition, Richard C. Larock, John Wiley & Sons, New York, N.Y. 1999) and can be accomplished by the usage of coupling reagents such as, e.g., N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino) methylene]-1H-1,2,3-triazolo[4,5-b]pyridinium-3-oxide hexafluoro-phosphate (HATU), 1-hydroxy-1,2,3-benzotriazole (HOBT), O-benzotriazol-1-yl-N,N,N',N'-tetramethyluronium tetrafluoroborate (TBTU) or 2-chloro- or 2-bromo- 1-methylpyridinium iodide (Mukaiyama reagent) in a suitable solvent, e.g., N,N-dimethylformamide (DMF), dimethylacetamide (DMAc), dichloromethane or dioxane, optionally in the presence of a base (e.g., triethylamine, N,N-diisopropylethylamine (Huenig's base) or 4-(dimethylamino)pyridine). Alternatively, the acid functionality in intermediates 36 can be converted into the acid chloride by treatment with, e.g., thionyl chloride, neat or optionally in a solvent such as dichloromethane and reaction of the acid chloride with amines of the type $HNR^{16}R^{17}$ in an appropriate solvent such as dichloromethane or DMF (N,N-dimethylformamide) and a base, e.g. triethylamine, N,N-diisopropylethylamine (Huenig's base), pyridine, 4-(dimethylamino)pyridine or lithium bis(trimethylsilyl)amide at temperatures ranging from ambient temperature to the reflux temperature of the solvent or solvent mixture furnishes intermediates 37. Removal of the Boc protective group in intermediates 37 applying methods known to those skilled in the art (e.g. using trifluoroacetic acid in dichloromethane at temperatures between 0° C. and room temperature) and as described for example in "Protective Groups in Organic Chemistry" by T. W. Greene and P. G. M. Wuts, 4$^{th}$ Ed., 2006, Wiley N.Y.) furnishes intermediates 38 (step f).

Acylation of intermediates 38 with aryl- or heteroaryl carboxylic acids II (either commercially available or accessible by methods known in the art) furnishes target structures I-I (step g). Amide couplings of this type are widely described in the literature (e.g., Comprehensive Organic Transformations: A Guide to Functional Group Preparations, 2 Edition, Richard C. Larock, John Wiley & Sons, New York, N.Y. 1999) and can be accomplished by the usage of coupling reagents such as, e.g., N,N'-carbonyldiimidazole (CDI), N,N'-dicyclohexyl-carbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) or 2-chloro- or 2-bromo-1-methylpyridinium iodide (Mukaiyama reagent) in a suitable solvent, e.g., N,N-dimethyl-formamide (DMF), dimethylacetamide (DMAc), dichloromethane or dioxane, optionally in the presence of a base (e.g., triethylamine, N,N-diisopropylethylamine (Huenig's base) or 4-(dimethylamino)pyridine). Alternatively, the aryl- or heteroaryl carboxylic acids II can be converted into their acid chlorides by treatment with, e.g., thionyl chloride, neat or optionally in a solvent such as dichloromethane and reaction of the acid chloride with intermediates 38 in an appropriate solvent such as dichloromethane or DMF (N,N-dimethylformamide) and a base, e.g. triethylamine, N,N-diisopropylethylamine (Huenig's base), pyridine, 4-(dimethylamino)pyridine or lithium bis(trimethylsilyl)amide at temperatures ranging from ambient temperature to the reflux temperature of the solvent or solvent mixture to furnish compounds of the general formula I-I.

Compounds of the general formula IJ in which $R^1$ is (alkyl-substituted) piperidinyl and $R^2$ and $R^{2a}$ signify hydrogen may be prepared according to Scheme 9.

Reacting commercially available 3-nitro-4-chloropyridine 39 with an excess of an optionally substituted piperidine with or without solvent at elevated temperatures, for example 150° C., gives rise to direct displacement of the 4-chloro substituent to give intermediates 40 (step a). Reactions of this general type are well-described in literature (WO 2008/106692; WO 2007/072017; C. Temple, Jr. et al., J. Med. Chem. 1983, 26, 91-95). If a solvent is used then a polar solvent such as DMF, NMP or ethanol is preferable. Microwave irradiation may facilitate the displacement of the 4-chloro substituent by the piperidine.

The resulting 3-nitro-4-piperidinopyridine intermediates 40 can then be reduced to 3-amino-4-piperidinopyridine intermediates 41 using a variety of reducing agents well-known to those skilled in the art of chemical synthesis, for example, tin (II) chloride or a catalytic amount of palladium on carbon under an atmosphere of hydrogen gas (step b).

Scheme 9

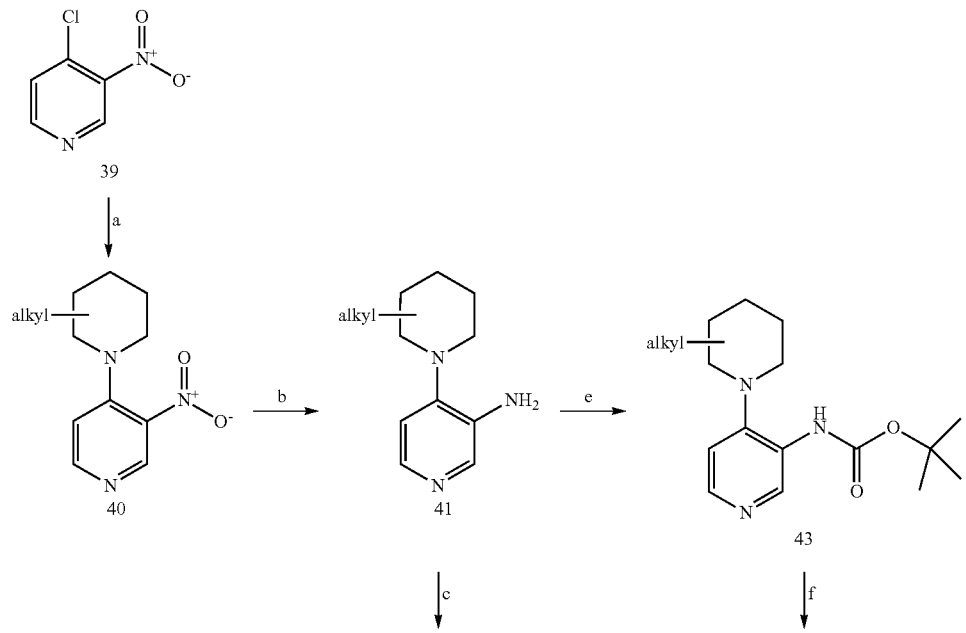

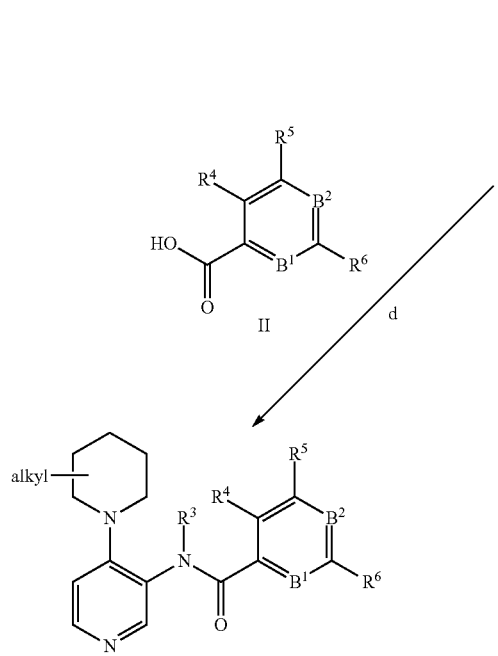

IJ ($R^1$ = (alkyl-substituted) piperidinyl; $R^2$ = $R^{2a}$ = H)

Intermediates 41 are transformed into intermediates 42 using reductive alkylations (or sometimes called reductive aminations) that are widely described in literature and are well known in the art (step c). For example, intermediates 42 in which $R^3$ is a methyl group can be synthesized by reaction with trimethyl orthoformate in the presence of catalytic amounts of acid such as trifluoroacetic acid at elevated temperatures and reducing the in situ formed iminium species with a suitable reducing agent such as, e.g. lithium aluminum hydride in tetrahydrofuran at temperatures preferably between 0° C. and room temperature. Alternatively, for intermediates 42 wherein $R^3$ is a —$CH_2$—$R^9$ or —$CHR^9R^{10}$ substituent, the amine functionality in compounds 41 can be reacted with (optionally substituted) aldehydes $R^9CHO$ or ketones $R^9C(O)R^{10}$ using a reducing system such as, e.g. sodium borohydride, sodium triacetoxyborohydride, sodium cyanoborohydride or di-n-butyltin dichloride with triphenylsilane, in an appropriate solvent such as 1,2-dichloroethane or tetrahydrofuran to furnish intermediates 42 (step n). Acetic acid may be used as catalyst for the reactions with ketones. Indium trichloride with triethylsilane in methanol might be used as well.

Intermediates 42 may be also synthesized from intermediates 41 by protection of the amine functionality in 41 with a suitable protective group such as, e.g. a Boc protective group using methods described in literature and known in the art (step e), alkylating the resulting tert-butyl carbamate 43 with $R^3X$, in which X is a suitable leaving group such as chlorine, bromine, iodine, $OSO_2$alkyl (e.g. mesylate (methanesulfonate), OSO2fluoroalkyl (e.g. triflate (trifluoromethanesulfonate) or $OSO_2$aryl (e.g. tosylate (p-toluenesulfonate)) using a suitable base in an appropriate solvent (e.g. sodium hydride in DMF) at temperatures between 0° C. and the boiling temperature of the solvent (step f) and removing the Boc protective group from intermediates 44 by methods known to those skilled in the art (e.g. using trifluoroacetic acid in dichloromethane at temperatures between 0° C. and room temperature) and as described for example in "Protective Groups in Organic Chemistry" by T. W. Greene and P. G. M. Wuts, $4^{th}$ Ed., 2006, Wiley N.Y., step g).

The 3-amino intermediates 42 may then be converted to compounds of general formula IJ by acylation with aryl- or heteroaryl carboxylic acids II (either commercially available or accessible by methods known in the art; step d) Amide couplings of this type are widely described in the literature (e.g., Comprehensive Organic Transformations: A Guide to Functional Group Preparations, $2^{nd}$ Edition, Richard C. Larock, John Wiley & Sons, New York, N.Y. 1999) and can be accomplished by the usage of coupling reagents such as, e.g., N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) or 2-chloro- or 2-bromo-1-methylpyridinium iodide (Mukaiyama reagent) in a suitable solvent, e.g., N,N-dimethylformamide (DMF), dimethylacetamide (DMAc), dichloromethane or dioxane, optionally in the presence of a base (e.g., triethylamine, N,N-diisopropylethylamine (Huenig's base) or 4-(dimethylamino)pyridine). Alternatively, the aryl- or heteroaryl carboxylic acids II can be converted into their acid chlorides by treatment with, e.g., thionyl chloride, neat or optionally in a solvent such as dichloromethane and reaction of the acid chloride with intermediates 42 in an appropriate solvent such as dichloromethane or DMF (N,N-dimethyl-formamide) and a base, e.g. triethylamine, N,N-diisopropylethylamine (Huenig's base), pyridine, 4-(dimethylamino)pyridine or lithium bis(trimethylsilyl)amide at temperatures ranging from ambient temperature to the reflux temperature of the solvent or solvent mixture to furnish compounds of the general formula IJ. The sequence of synthetic steps can be changed as required and as outlined in Scheme 1.

Scheme 10

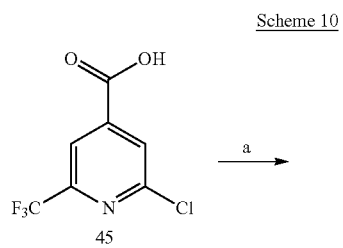

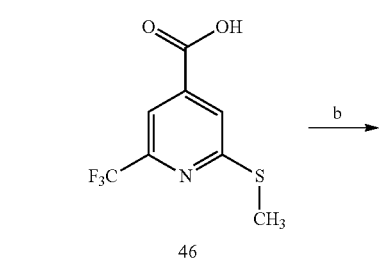

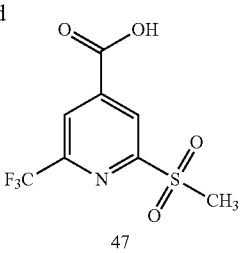

Aryl- or heteroaryl carboxylic acids II that are not commercially available they can be prepared by methods described in literature and known to those skilled in the art. For example, the pyridine carboxylic acid 47 can be prepared according to Scheme 10.

2-Chloro-6-(trifluoromethyl)isonicotinic acid 45 (prepared according to M. Schlosser et al., *Eur. J. Org. Chem.* 2004, 18, 3793-3798) can be reacted with sodium thiomethoxide in an appropriate solvent such as tetrahydrofuran at elevated temperatures such as 70° C. to give intermediate 46 (step a). Oxidation of the sulfur in intermediates 46 using an oxidizing agent such as, Oxone® in an appropriate solvent or solvent system such as water and methanol furnishes compound 47 (step b).

Another example for the synthesis of an arylcarboxylic acid II is shown in Scheme 11.

Scheme 11

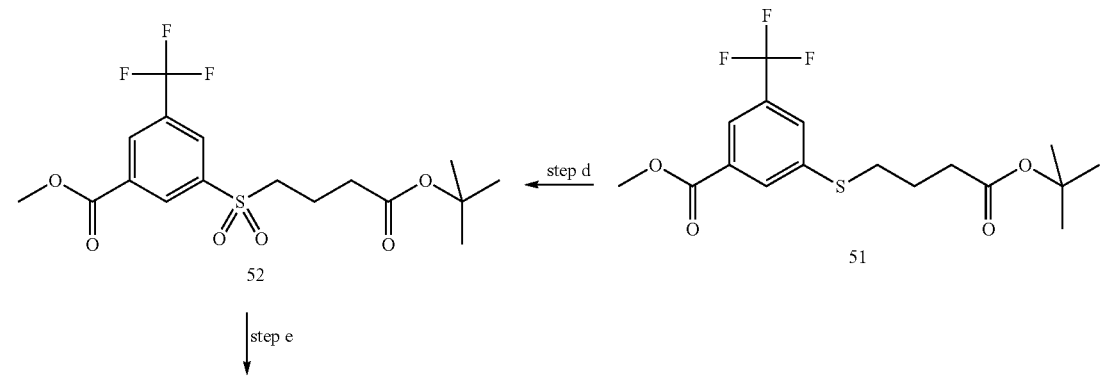

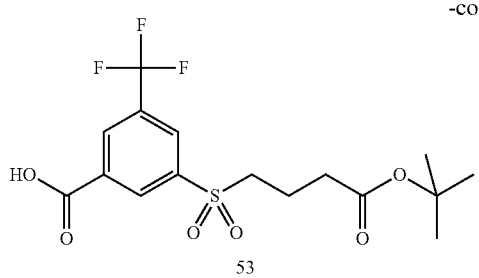

53

Cross-coupling of commercially available 3-bromo-5-trifluoromethyl-benzoic acid methyl ester 48 with 2-(trimethylsilyl)ethanethiol using a suitable catalytic system such as tris(di-benzylideneacetone)dipalladium(0)/Xantphos in the presence of a base such as diisopropyl-ethylamine in a suitable solvent such as dioxane, preferably at elevated temperatures, yields the thioether intermediate 49 (step a). Cleavage of the trimethylsilylethyl group in 49 with, e.g. tetrabutylammonium fluoride in tetrahydrofuran gives thiol 50 (step b). Reactions of this type have been described in the literature, for example in WO2008055847. Alkylation of the thiol group in 50 with commercially available 4-bromobutyric acid tert-butyl ester using an appropriate base and solvent such as, e.g. triethyl- or diisopropylethyl-amine in acetonitrile or N,N-dimethylformamide, furnishes intermediate 51 (step c). Oxidation of the sulfur atom with oxidizing agents such as Oxone® in suitable solvents such as methanol or water or mixture of said solvents affords the arylsulfonyl compound 52 (step d). Cleavage of the methyl ester group using for example lithium or sodium hydroxide as base in an appropriate solvent or solvent mixture such as dioxane and water furnishes acid intermediate 53 (step e).

Yet another example for the synthesis of an aryl carboxylic acid II is shown in Scheme 12.

Scheme 12

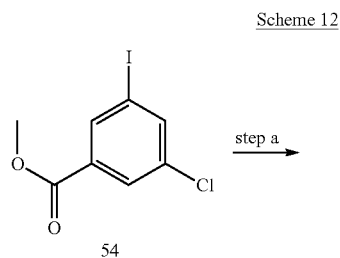

The iodine in commercially available methyl 3-chloro-5-iodobenzoate 54 can be exchanged for a methylsulfone group to give intermediate 55 (step a). Reactions of this type have been described in the literature (e.g. W. Zhu, D. Ma *J. Org. Chem.* 2005, 70(7), 2696-2700). For example, reaction of 54 with sodium methanesulfinate in the presence of a metal catalyst such as copper(I)iodide, L-proline and a base such as sodium hydroxide in an appropriate solvent such as DMSO gives intermediate 55. Heating may be applied to facilitate the reaction. The chloro group in intermediate 55 can be converted into a cyclopropyl group using for example cyclopropylzine(II) bromide in the presence of a suitable catalyst system such as PEPPSI-IPr ([1,3-bis(2,6-diisopropylphenyl)imidazol-2-ylidene](3-chloropyridyl)palladium(II) dichloride) with 1,3-dimethyl-2-imidazolidinone in a solvent such as tetrahydrofuran, preferably at higher temperatures up to the boiling point of the solvent to give intermediate 56. Pd-catalyzed reactions of that type using cyclopropylzine bromide have been described in the literature (e.g. WO2008154271; WO2010011316). Under the applied reaction conditions cleavage of the methyl ester may occur to give directly intermediates 56. If no ester cleavage occurs under the applied reaction conditions, the ester group can be cleaved by methods known in the art and as described for example in "Protective Groups in Organic Chemistry" by T. W. Greene and P. G. M. Wuts, 4$^{th}$ Ed., 2006, Wiley N.Y.) to give compounds 56 (step b).

Scheme 13

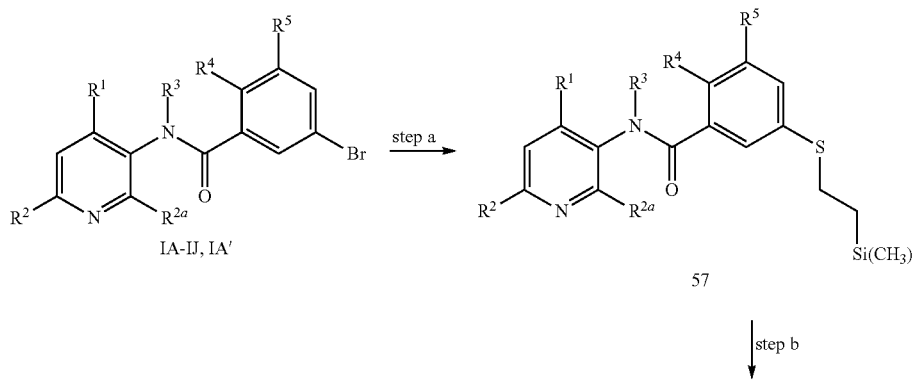

step b

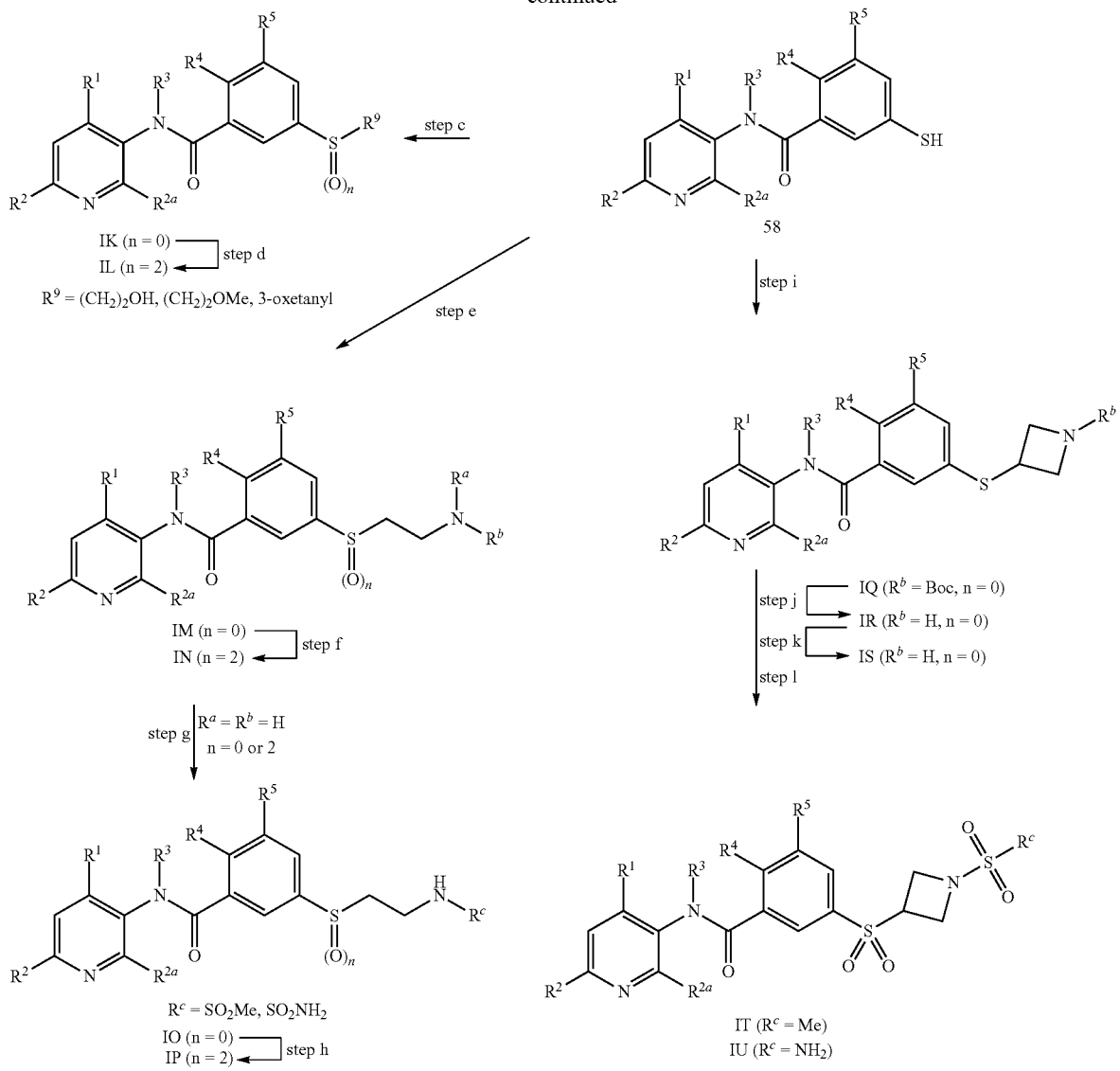

Compounds of the general formula IK-IU ($B^1$=$B^2$=CH) can be prepared for example according to Scheme 13 from compounds IA-IJ and IA' in which $B^1$=$B^2$=CH and $R^5$ or $R^6$ is bromine. Cross-coupling of IA-IJ and IA' ($B^1$=$B^2$=CH) with 2-(trimethylsilyl)ethanethiol using a suitable catalytic system such as, e.g. tris(dibenzylideneacetone)dipalladium(0)/Xantphos in the presence of a base such as, e.g. diisopropylethylamine in a suitable solvent such as, e.g. dioxane, preferably at elevated temperatures, yields the thioether intermediate 57 (step a). Cleavage of the trimethylsilylethyl group in 57 with, e.g. tetrabutylammonium fluoride in tetrahydrofuran gives thiol 58 (step b).

Alkylation of the thiol group in 58 with commercially available compounds $R^9$-LG in which $R^9$ is a methoxyethyl or hydroxyethyl or 3-oxetanyl substituent and LG signifies a suitable leaving group such as, e.g. bromo (or another leaving group such as, e.g. chloro, iodo or $OSO_2$alkyl, $OSO_2$fluoroalkyl, $OSO_2$aryl) using an appropriate base and solvent such as, e.g. triethyl- or diisopropylethyl-amine in acetonitrile or N,N-dimethylformamide, furnishes compounds IK (step c). The sulfur atom in compounds IK can be oxidized by methods known in the art, e.g. using an oxidizing agent such as Oxone® in suitable solvents such as, e.g. methanol or water or mixture of said solvents to afford compounds IL (step d).

The thiol group in intermediates 58 can also be alkylated with amines of the type LG-$(CH_2)_2$$NR^aR^b$ in which LG signifies a suitable leaving group such as, e.g. bromo (or another leaving group such as, e.g. chloro, iodo or $OSO_2$alkyl, $OSO_2$fluoroalkyl, $OSO_2$aryl) and one of Ra and $R^b$ is hydrogen while the other is alkyl or a protective group such as, e.g. tert-butoxycarbonyl, or $R^a$ and $R^b$ together form a four-(e.g. azetidine) to six-membered ring (e.g. morpholine), in an appropriate solvent such as, e.g. N,N-dimethylformamide or acetonitrile and a suitable base such as, e.g. diisopropylethyl-amine or cesium carbonate to give compounds IM (step e). The sulfur atom in compounds IM can be oxidized by methods known in the art and as described above to furnish compounds IN (step f). Compounds IM or IN in which $R^a$=$R^b$=H (prepared for example from intermediates 58 and compounds LG-$(CH_2)_2$$NR^aR^b$ in which LG is a leaving group as defined before and $R^a$ or $R^b$ is a protective group such as e.g. a tert-butoxycarbonyl group while the other substituent is hydrogen and subsequent cleavage of the protective group using methods known in the art) can be reacted with sulfonylchlorides (e.g. methanesulfonyl chloride) or sulfamoyl chlorides to give compounds IO and IP, respectively (step h). Compounds IO (prepared from compounds IM) may be oxidized using methods described above to give compounds IP (step h).

Compounds IQ-IU can also be synthesized from intermediate 58. Alkylation of the thiol group in 58 with tert-butyl 3-iodoazetidine-1-carboxylate using a suitable base and solvent such as diisopropylethylamine in acetonitrile gives compounds IQ. Heating may be applied to facilitate the conversion (step i). The tert-butoxycarbonyl group is removed using methods described in literature (e.g. with trifluoroacetic acid in dichlorormethane, step j) and the sulfur in the resulting compounds IR is oxidized by methods known in the art, e.g. using an oxidizing agent such as Oxone® in suitable solvents such as methanol or water or mixture of said solvents to afford compounds IS (step k). The secondary azetidine nitrogen can be acylated using literature procedures with sulfonylchlorides (e.g. methanesulfonyl chloride) or sulfamoyl chlorides to give compounds IT and IU, respectively (step l).

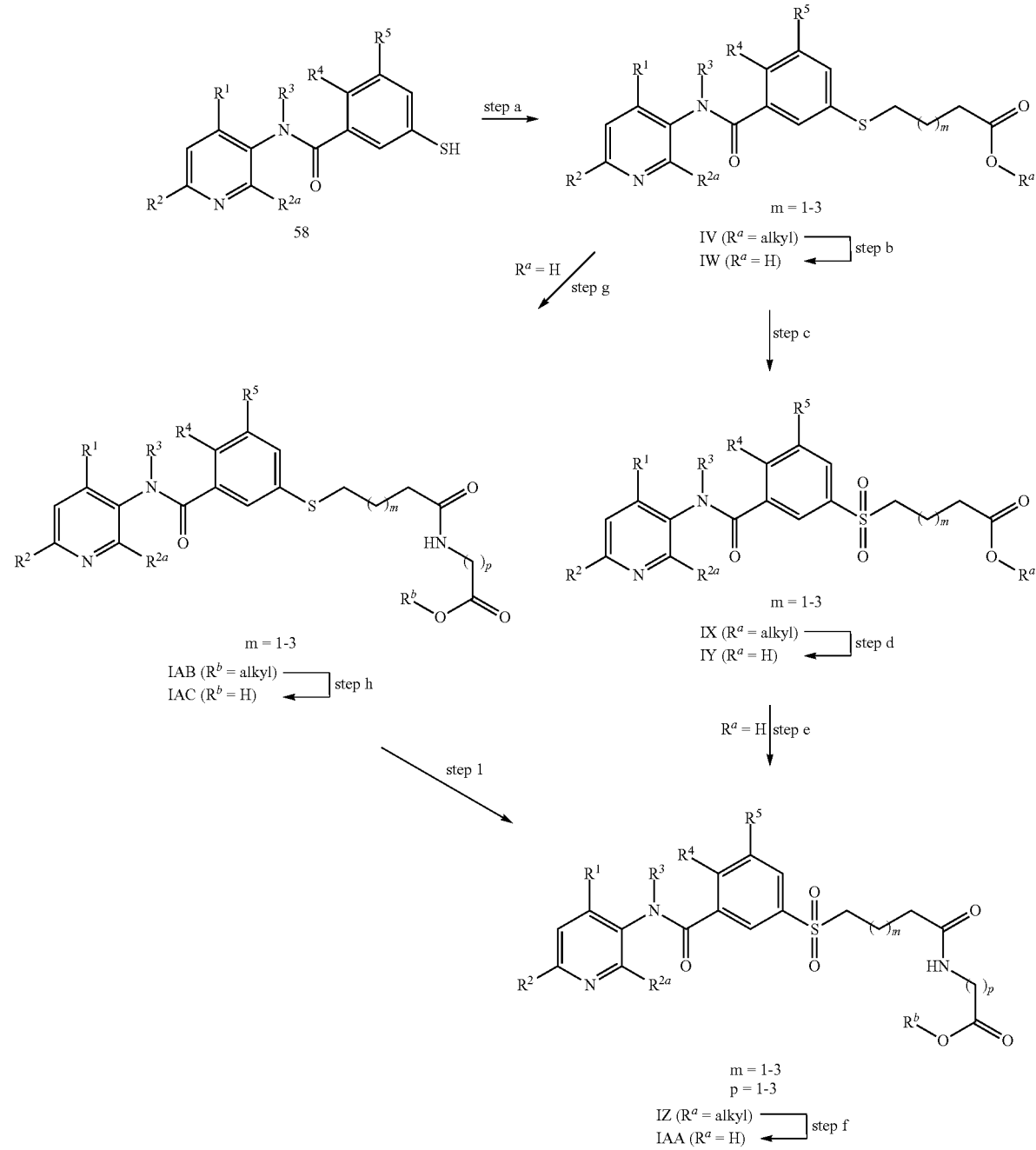

Scheme 14

Compounds of the general formula IV-IAC ($B^1=B^2=CH$) can be synthesized for example according to Scheme 14.

The thiol group of intermediates 58 (prepared as described under Scheme 13) can be alkylated with compounds of the type LG-$(CH_2)_{3-6}$COOR$^a$ in which LG is a leaving group as defined before and R$^a$ is hydrogen or an alkyl group using the methods outlined before to yield compounds IV and IW, respectively (step a). Compounds IW can alternatively be synthesized by cleavage of the ester group in compounds IV by methods known in the art (e.g. a tert-butyl group under acidic conditions such as trifluoroacetic acid in dichloromethane or formic acid in isopropanol) and as described for example in "Protective Groups in Organic Chemistry" by T. W. Greene and P. G. M. Wuts, 4$^{th}$ Ed., 2006, Wiley N.Y) (step b).

The sulfur atom in compounds IV and IW can be oxidized by methods described in the literature, e.g. using an oxidizing agent such as Oxone® in suitable solvents such as, e.g. methanol or water or mixture of said solvents to give the sulfone compounds IX and IY (step c). Compounds IY can alternatively be synthesized by cleavage of the ester group in compounds IX by methods outlined above (step d).

Compounds IY can be further converted into compounds IZ (step e) by reaction of IY with α- or β-amino acid esters (R$^b$=alkyl) which are either commercially available or accessible by methods known in the art (step e). Amide couplings of this type are widely described in the literature (e.g., Comprehensive Organic Transformations: A Guide to Functional Group Preparations, 2$^{nd}$ Edition, Richard C. Larock, John Wiley & Sons, New York, N.Y. 1999) and can be accomplished by the usage of coupling reagents such as, e.g., N,N'-carbonyl-diimidazole (CDI), N,N'-dicyclohexyl-carbodiimide (DCC), 1-(3-dimethylaminopropyl)-3-ethyl-carbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) or 2-chloro- or 2-bromo-1-methylpyridinium iodide (Mukaiyama reagent) in a suitable solvent, e.g., N,N-dimethylformamide (DMF), dimethylacetamide (DMAc), dichloromethane or dioxane, optionally in the presence of a base (e.g., triethylamine, N,N-diisopropylethylamine (Huenig's base) or 4-(dimethylamino)pyridine). Alternatively, the carboxylic acid group in compounds IY can be converted into the acid chloride by treatment with, e.g., thionyl chloride, neat or optionally in a solvent such as dichloromethane and the acid chloride is reacted with α- or β-amino acid esters (R$^b$=alkyl) in an appropriate solvent such as dichloromethane or DMF (N,N-dimethyl-formamide) and a base, e.g. triethylamine, N,N-diisopropylethylamine, pyridine, 4-(dimethylamino)pyridine or lithium bis(trimethylsilyl)amide at temperatures ranging from ambient temperature to the reflux temperature of the solvent or solvent mixture to furnish compounds of the general formula IZ.

Cleavage of the ester group in compounds IZ by methods known in the art and as described before furnishes the compounds IAA (step f).

Alternatively, compounds IZ and IAA can be prepared from compounds IAB and IAC, respectively, applying the methods described before (step i). Compounds IAB can be synthesized from compounds IW by amide coupling with α- or β-amino acid esters (R$^b$=alkyl) using the methods described above. Ester cleavage in compounds IAB using the methods outlined before furnishes compounds IAC (step h).

Compounds of the general formula IAD-IAI ($B^1=B^2=CH$) can be prepared for example according to Scheme 15 from compounds IA-IJ and IA' in which $B^1=B^2=CH$ and $R^5$ or $R^6$ is bromine.

For example, compounds of the general formula IAD and IAE in which $R^6$ signifies a 3-oxetanyl and a tert-butoxy-carbonyl-substituted 3-azetidinyl substituent, respectively can be synthesized by first converting the bromo into a boronic acid group (for example via reaction of the bromo compound with n-butyllithium in the presence of triisopropyl borate preferably at low temperatures (e.g. −75° C.) and hydrolysis of the resulting boron ester with, e.g. acetic acid in water) and reacting the boronic acid intermediate with 3-iodo-oxetane or 3-iodo-azetidine-1-carboxylic acid tert-butyl ester using a suitable catalyst system such as, e.g. nickel(II) iodide and (1R,2R)-2-aminocyclohexanol in the presence of a base such as sodium hexamethyldisilazane in a suitable solvent such as, e.g. 2-propanol. Heating or microwave irradiation may facilitate the reaction (step a).

Compounds IAF in which $R^6$ signifies a hydroxyethoxy or methoxyethoxy group can be prepared by first converting the bromo into a hydroxyl group (e.g. via conversion of the bromine into a boronic acid group as described above and in situ oxidation of the boronic acid group using, e.g. hydrogen peroxide in acetic acid and water) and alkylating the phenolic hydroxy group with bromo-ethanol or bromo-2-methoxyethane using a suitable base such as, e.g. diisopropylethylamine or potassium carbonate in an appropriate solvent such as, e.g. acetonitrile. Heating or microwave irradiation may facilitate the reaction (step b).

Scheme 15

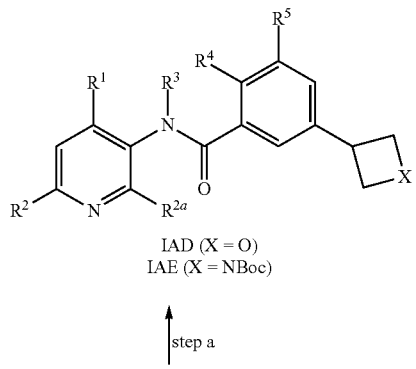

IAD (X = O)
IAE (X = NBoc)

↑ step a

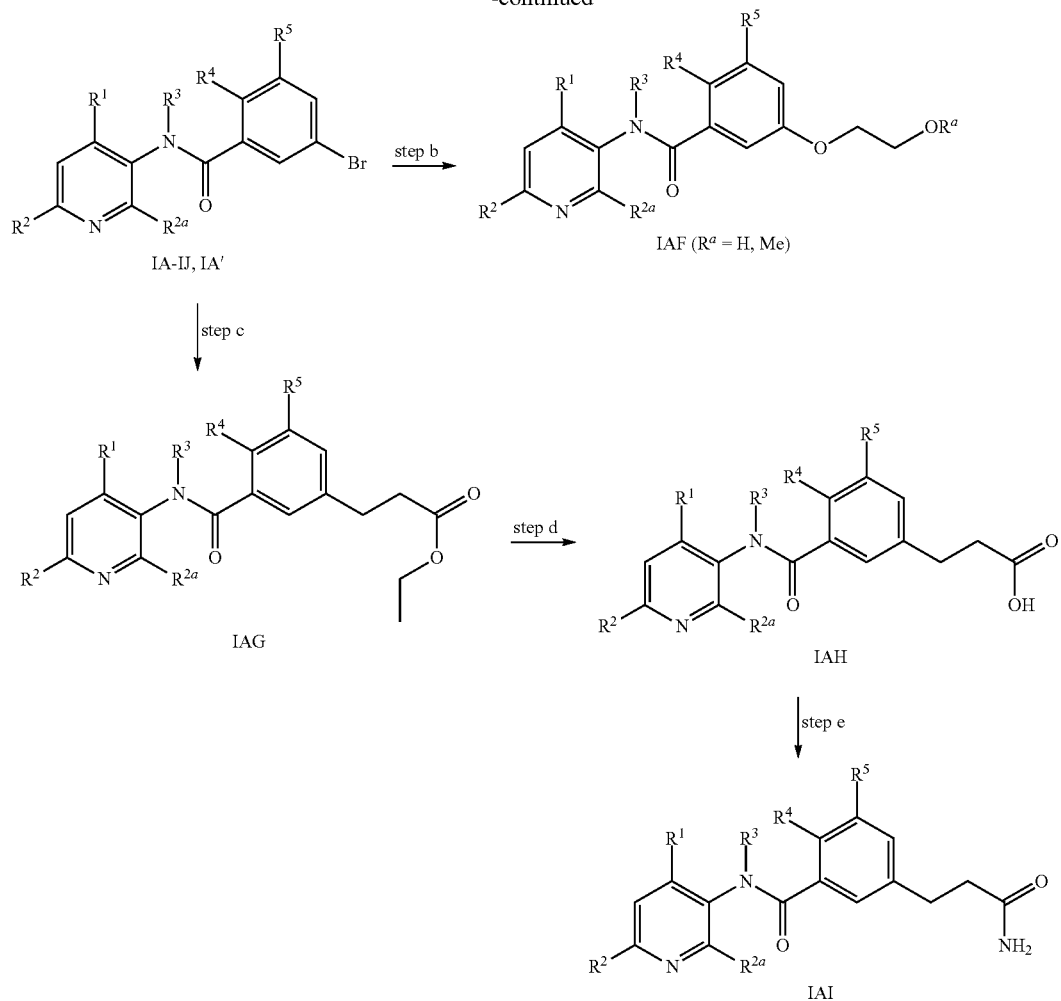

Compounds IAG can prepared for example by reacting the bromo derivatives of compounds IA-IJ and IA' with 3,3-diethoxyprop-1-ene preferably at elevated temperatures applying a suitable catalyst system such as, e.g. palladium (II) acetate with n-tributylamine in the presence of tetrabutylammonium chloride and using a suitable solvent such as, e.g. N,N-dimethylformamide (step c). The ester group in compounds IAG can be cleaved by methods known in the art and as described for example in "Protective Groups in Organic Chemistry" by T. W. Greene and P. G. M. Wuts, $4^{th}$ Ed., 2006, Wiley N.Y.) to give compounds IAH (step d). The acid functionality in compounds IAH can then be converted into an amide function by methods described in literature such as, e.g. activating the acid group with 1-ethyl-3-(3-dimethylaminopropyl) carbodiimide and 1-hydroxy-7-azabenzotriazole in the presence of a base such as, e.g. diisopropylethylamine in a suitable solvent such as N,N-dimethylformamide and treating the activated ester with an ammonia source such as, e.g. ammonium chloride in the repsence of a base such as, e.g. diisopropylethylamine to furnish compounds IAI (step e).

If desired or required, functional groups present in I (such as —$CO_2$alkyl, —$CO_2H$, halogens such as chlorine, bromine or iodine, amino groups, cyano groups) may be derivatized to other functional groups using typical standard procedures known to those skilled in the art (e.g. reduction of —$CO_2$alkyl to —$CH_2OH$ with $LiAlH_4$ or $NaBH_4$ and the like, hydrolysis of —$CO_2$alkyl to $CO_2H$ and subsequent optional conversion to an amide, acylation or reductive amination of amino groups, conversion of halogens such as chlorine, bromine or iodine to $CO_2$alkyl or alkyl and the like).

If compounds IA to IAI contain stereogenic centers, compounds of the general formula I can be obtained as mixtures of enantiomers or diastereomers, which can be separated by methods well known in the art, e.g. (chiral) HPLC or crystallization. Racemic compounds can e.g. be separated into their antipodes via diastereomeric salts by crystallization with optically pure acids or by separation of the antipodes by specific chromatographic methods using either a chiral adsorbent or a chiral eluant.

If one of the starting materials or compounds of formula (I) contains one or more functional groups which are not stable or are reactive under the reaction conditions of one or more reaction steps, appropriate protecting groups (as described, e.g. in "Protective Groups in Organic Chemistry" by T. W. Greene and P. G. M. Wuts, $4^{th}$ Ed., 2006, Wiley N.Y.) can be introduced before the critical step applying methods well known in the art. Such protecting groups can be removed at a later stage of the synthesis using standard methods described in the literature.

As described herein before, the compounds of formula I of the present invention can be used as medicaments for the treatment of diseases which are associated with the modulation of GPBAR1 activity.

As compounds of formula I of the invention are agonists of the GPBAR1 receptor, the compounds will be useful for lowering glucose, lipids, and insulin resistance in diabetic patients and in non-diabetic patients who have impaired glucose tolerance or who are in a pre-diabetic condition. The compounds of formula I are further useful to ameliorate hyperinsulinemia, which often occurs in diabetic or pre-diabetic patients, by modulating the swings in the level of serum glucose that often occurs in these patients. The compounds of formula I are also useful in reducing the risks associated with metabolic syndrome, in reducing the risk of developing atherosclerosis or delaying the onset of atherosclerosis, and reducing the risk of angina, claudication, heart attack, stroke, and coronary artery disease. By keeping hyperglycemia under control, the compounds are useful to delay or for preventing vascular restenosis and diabetic retinopathy.

The compounds of formula I of the present invention are useful in improving or restoring β-cell function, so that they may be useful in treating type 1 diabetes or in delaying or preventing a patient with type 2 diabetes from needing insulin therapy. The compounds may be useful for reducing appetite and body weight in obese subjects and may therefore be useful in reducing the risk of co-morbidities associated with obesity such as hypertension, atherosclerosis, diabetes, and dyslipidemia. By elevating the levels of active GLP-1 in vivo, the compounds are useful in treating neurological disorders such as Alzheimer's disease, multiple sclerosis, and schizophrenia.

Thus, the expression "diseases which are associated with the modulation of GPBAR1 activity" means diseases such as metabolic, cardiovascular, and inflammatory diseases, particularly for the treatment of diabetes, particularly type 2 diabetes or gestational diabetes, impaired fasting glucose, impaired glucose tolerance, insulin resistance, hyperglycemia, obesity, metabolic syndrome, ischemia, myocardial infarction, retinopathy, vascular restenosis, hypercholesterolemia, hypertriglyceridemia, dyslipidemia or hyperlipidemia, lipid disorders such as low HDL cholesterol or high LDL cholesterol, high blood pressure, angina pectoris, coronary artery disease, atherosclerosis, cardiac hypertrophy, rheumatoid arthritis, asthma, chronic obstructive pulmonary disease (COPD), psoriasis, ulcerative colitis, crohn's disease, disorders associated with parenteral nutrition especially during small bowel syndrome, irritable bowel syndrome (IBS), allergy diseases, particularly disorders associated with the liver and the kidneys, e.g. including renal disorders, kidney disorders, e.g. diabetic nephropathy, acute kidney injury, acute renal disease, kidney fibrosis, liver disorders, e.g. hepatitis, liver failure, acute/chronic hepatitis, acute/chronic interstitial/glomerulonephritis, granulomatous diseases, fatty liver (e.g. non-alcoholic fatty liver disease, NAFLD), liver fibrosis (e.g. non-alcoholic steatohepatitis, NASH), primary sclerosing cholangitis (PSC), liver cirrhosis, primary biliary cirrhosis (PBC), liver colestasis, kidney fibrosis, anorexia nervosa, bulimia nervosa and neurological disorders such as Alzheimer's disease, multiple sclerosis, schizophrenia and impaired cognition.

In a particular aspect, the expression 'diseases which are associated with the modulation of GPBAR1 activity' relates to diabetes, particularly type II diabetes, impaired fasting glucose, impaired glucose tolerance, hyperglycemia, metabolic syndrome, obesity, hypercholesterolemia and dyslipidemia.

The invention also relates to pharmaceutical compositions comprising a compound as defined above and a pharmaceutically acceptable carrier and/or adjuvant. More specifically, the invention relates to pharmaceutical compositions useful for the treatment of diseases which are associated with the modulation of GPBAR1 activity.

Further, the invention relates to compounds of formula I as defined above for use as therapeutically active substances, particularly as therapeutically active substances for the treatment of diseases which are associated with the modulation of GPBAR1 activity. In particular, the invention relates to compounds of formula I for use in the treatment of diabetes, particularly type 2 diabetes or gestational diabetes, impaired fasting glucose, impaired glucose tolerance, insulin resistance, hyperglycemia, obesity, metabolic syndrome, ischemia, myocardial infarction, retinopathy, vascular restenosis, hypercholesterolemia, hypertriglyceridemia, dyslipidemia or hyperlipidemia, lipid disorders such as low HDL cholesterol or high LDL cholesterol, high blood pressure, angina pectoris, coronary artery disease, atherosclerosis, cardiac hypertrophy, rheumatoid arthritis, asthma, chronic obstructive pulmonary disease (COPD), psoriasis, ulcerative colitis, crohn's disease, disorders associated with parenteral nutrition especially during small bowel syndrome, irritable bowel syndrome (IBS), allergy diseases, particularly disorders associated with the liver and the kidneys, e.g. including renal disorders, kidney disorders, e.g. diabetic nephropathy, acute kidney injury, acute renal disease, kidney fibrosis, liver disorders, e.g. hepatitis, liver failure, acute/chronic hepatitis, acute/chronic interstitial/glomerulonephritis, granulomatous diseases, fatty liver (e.g. non-alcoholic fatty liver disease, NAFLD), liver fibrosis (e.g. non-alcoholic steatohepatitis, NASH), primary sclerosing cholangitis (PSC), liver cirrhosis, primary biliary cirrhosis (PBC), liver colestasis, kidney fibrosis, anorexia nervosa, bulimia nervosa and neurological disorders such as Alzheimer's disease, multiple sclerosis, schizophrenia and impaired cognition. More particularly, the invention relates to compounds of formula I for use in the treatment of diabetes, particularly type II diabetes, impaired fasting glucose, impaired glucose tolerance, hyperglycemia, metabolic syndrome, obesity, hypercholesterolemia and dyslipidemia, most particularly for use in diabetes, preferably type II diabetes, or hyperglycemia.

In another aspect, the invention relates to a method for the treatment of diseases which are associated with the modulation of GPBAR1 activity, which method comprises administering a therapeutically active amount of a compound of formula I to a human being or animal. In particular, the invention relates to a method for the treatment of diabetes, particularly type II diabetes, impaired fasting glucose, impaired glucose tolerance, hyperglycemia, metabolic syndrome, obesity, hypercholesterolemia and dyslipidemia, more particularly for the treatment of diabetes, preferably type II diabetes, or hyperglycemia.

The invention further relates to the use of compounds of formula I as defined above for the treatment of diseases which are associated with the modulation of GPBAR1 activity.

In addition, the invention relates to the use of compounds of formula I as defined above for the preparation of medicaments for the treatment of diseases which are associated with the modulation of GPBAR1 activity. In particular, the invention relates to the use of compounds of formula I as defined above for the preparation of medicaments for the treatment of diabetes, particularly type II diabetes, impaired fasting glucose, impaired glucose tolerance, hyperglycemia, metabolic syndrome, obesity, hypercholesterolemia and dyslipidemia, more particularly for the preparation of medicaments for the treatment of diabetes, preferably type II diabetes, or hyperglycemia.

Also contemplated herein is a combination therapy using one or more compounds of formula I or compositions of the present invention, or a pharmaceutically acceptable salts thereof, in combination with one or more other pharmaceutically active compounds independently selected from the group consisting of the following:

(a) human peroxisome proliferator activated receptor (PPAR) gamma agonists (e.g., thiazolidinediones and glitazones, e.g., rosiglitazone, troglitazone, pioglitazone, englitazone, balaglitazone, and netoglitazone), (b) biguanides such as metformin, metformin hydrochloride, buformin and phenformin, (c) dipeptidyl peptidase IV (DPP-4) inhibitors, such as sitagliptin, sitagliptin phosphate, saxagliptin, vildagliptin, alogliptin, carmegliptin, gosogliptin, dutogliptin and linagliptin, (d) incretins such as glucagon-like peptide-1 (GLP-1) receptor agonists (e.g., exenatide, liraglutide), GLP-1(7-36) amide and its analogs, GLP-1(7-37) and its analogs, lixisenatide, taspoglutide, albiglutide, BRX-0585 (Pfizer/Biorexis) and CJC-1134-PC (Exendin-4:PC-DAC™) or glucose-dependent insulinotropic peptide (GIP), (e) insulin or insulin analogs such as LysPro insulin or inhaled formulations comprising insulin, (f) sulfonylureas such as tolazamide, chlorpropamide, glipizide, glimepiride, glyburide, glibenclamide, tolbutamide, acetohexamide or glypizide, (g) α-glucosidase inhibitors such as miglitol, acarbose, epalrestat, or voglibose, (h) cholesterol biosynthesis inhibitors such as HMG CoA reductase inhibitors, e.g., lovastatin, simvastatin, pravastatin, fluvastatin, atorvastatin, cerivastatin, itavastin, nisvastatin and rivastatin, or squalene epoxidase inhibitors, e.g., terbinafine, (i) plasma HDL-raising agents such as CETP inhibitors e.g., anacetrapib, torcetrapib and dalcetrapib, or PPAR alpha agonists, e.g., gemfibronzil, clofibrate, fenofibrate and bezafibrate, (j) PPAR dual alpha/gamma agonists such as muraglitazar, naveglitazar, aleglitazar, tesaglitazar, peliglitazar, farglitazar and JT-501, (k) bile acid sequestrants, e.g., anion exchange resins, or quaternary amines (e.g., cholestyramine or colestipol)), or ileal bile acid transporter inhibitors (BATi);

(l) nicotinyl alcohol, nicotinic acid, niacinamide or salts thereof, (m) cholesterol absorption inhibitors such as ezetimibe or acyl-Coenzyme A:cholesterol O-acyl transferase (ACAT) inhibitors such as avasimibe, (n) selective estrogen receptor modulators such as raloxifene or tamoxifen) or LXR alpha or beta agonists, antagonists or partial agonists (e.g., 22(R)-hydroxycholesterol, 24(S)-hydroxycholesterol, T0901317 or GW3965);

(o) microsomal triglyceride transfer protein (MTP) inhibitors, alpha2-antagonists and imidazolines (e.g., midaglizole, isaglidole, deriglidole, idazoxan, efaroxan, fluparoxan), (p) insulin secretagogues such as linogliride, nateglinide, repaglinide, mitiglinide calcium hydrate or meglitinide);

(q) SGLT-2 inhibitors (e.g., dapagliflozin, sergliflozin, canagliflozin and tofogliflozin, (s) glucokinase activators such as the compounds disclosed in e.g., WO00/58293 A1;

(t) protein tyrosine phosphatase-1B (PTP-1B) inhibitors, (u) glucagon receptor antagonists, (v) anti-obesity agents such as fenfluramine, dexfenfluramine, phentiramine, sibutramine, orlistat, neuropeptide Y1 or Y5 antagonists, neuropeptide Y2 agonists, MC4R (melanocortin 4 receptor) agonists, cannabinoid receptor 1 (CB-1) antagonists/inverse agonists, and β3 adrenergic receptor agonists (e.g., GW-320659), nerve growth factor agonist (e.g., axokine), growth hormone agonists (e.g., AOD-9604), 5-HT (serotonin) reuptake/transporter inhibitors (e.g., Prozac), DA (dopamine) reuptake inhibitors (e.g., Buproprion), 5-HT, NA and DA reuptake blockers, steroidal plant extracts (e.g., P57), CCK-A (cholecystokinin-A) agonists, GHSR1a (growth hormone secretagogue receptor) antagonist/inverse agonists, ghrelin antibody, MCH1R (melanin concentrating hormone 1R) antagonists (e.g., SNAP 7941), MCH2R (melanin concentrating hormone 2R) agonist/antagonists, H3 (histamine receptor 3) inverse agonists or antagonists, H1 (histamine 1 receptor) agonists, FAS (Fatty acid synthase) inhibitors, ACC-2 (acetyl-CoA carboxylase-1) inhibitors, DGAT-2 (diacylglycerol acyltransferase 2) inhibitors, DGAT-1 (diacylglycerol acyltransferase 1) inhibitors, CRF (corticotropin releasing factor) agonists, Galanin antagonists, UCP-1 (uncoupling protein-1), 2 or 3 activators, leptin or a leptin derivatives, opioid antagonists, orexin antagonists, BRS3 agonists, GLP-1 (glucagon-like peptide-1) agonists, IL-6 agonists, a-MSH agonists, AgRP antagonists, BRS3 (bombesin receptor subtype 3) agonists, 5-HT1B agonists, POMC antagonists, CNTF (ciliary neurotrophic factor or CNTF derivative), NN2211, topiramate, glucocorticoid antagonist, Exendin-4 agonists, 5-HT$_{2C}$ (serotonin receptor 2C) agonists (e.g., Lorcaserin), PDE (phosphodiesterase) inhibitors, fatty acid transporter inhibitors, dicarboxylate transporter inhibitors, glucose transporter inhibitors, (w) anti-inflammatory agents such as cyclooxygenase-2 (COX-2) inhibitors (e.g., rofecoxib and celecoxib); glucocorticoids, azulfidine, thrombin inhibitors (e.g., heparin, argatroban, melagatran, dabigatran) and platelet aggregation inhibitors (e.g., glycoprotein IIb/IIIa fibrinogen receptor antagonists or aspirin), and ursodeoxycholic acid (UDCA) and norursodeoxycholic acid (norUDCA) and (y) antihypertensives such as beta blockers (e.g., angiotensin II receptor antagonists such as losartan, eprosartan, irbesartan, tasosartan, telmisartan or valsartan; angiotensin converting enzyme inhibitors such as enalapril, captopril, cilazapril, ramapril, zofenopril, lisinopril and fosinopril; calcium channel blockers such as nifedipine and diltiazam and endothelian antagonists.

Such other pharmaceutically active compounds may be administered in an amount commonly used therefore, contemporaneously or sequentially with a compound of the formula I or a pharmaceutically acceptable salt thereof. In the treatment of patients who have type 2 diabetes, insulin resistance, obesity, metabolic syndrome, neurological disorders, and co-morbidities that accompany these diseases, more than one pharmaceutically active compound is commonly administered. The compounds of formula I of this invention may generally be administered to a patient who is already taking one or more other drugs for these conditions. When a compound of formula I is used contemporaneously with one or more other pharmaceutically active compounds, a pharmaceutical composition in an unit dosage form containing such other pharmaceutically active compounds and the compound of the formula I is preferred. Thus, the invention also relates to a pharmaceutical composition containing a compound of formula I in combination with one or more other pharmaceutically active compounds as defined above. When used in combination with one or more other active ingredients, the compound of formula I of the present invention and the other pharmaceutically active compounds may be used in lower doses than when each is used singly. These kinds of pharmaceutical compositions are also included in the invention.

However, the combination therapy also includes therapies in which the compound of formula I and one or more other pharmaceutically active compounds are administered in different dosage forms, but with overlapping schedules. The invention thus also relates to a method for the treatment a of diseases which are associated with the modulation of GPBAR1 activity, which method comprises administering a therapeutically active amount of a compound of formula I in combination with one or more other pharmaceutically active compounds to a human being or animal.

The following test was carried out in order to determine the activity of the compounds of formula I:

The cDNA of the human GPBAR1 receptor (Genbank: NM_170699 with the exception of a silent C:G mutation at position 339 from the start codon) was amplified by polymerase chain reaction (PCR) from human cDNA and inserted into pCineo (Promega) by standard methods (Current Protocols in Molecular Biology, Wiley Press, ed. Ausubel et al.). The final clone was verified by DNA sequence analysis. The plasmid was transfected into CHO cells deficient in dihydrofolate reductase activity (CHO-dhfr-) using Lipofectamine plus (Invitrogen). Clones were isolated in limited dilution conditions and identified by activities in the cAMP assay using lithocholic acid as agonist. A clonal cell line displaying the greatest activity in cAMP increases was selected and identified as giving consistently good responses for up to at least 20 passages.

cAMP Assay

CHO-dhfr(minus) cells expressing human GPBAR1 receptors are seeded 17-24 hours prior to the experiment 50.000 cells per well in a black 96 well plate with flat clear bottom (Corning Costar #3904) in DMEM (Invitrogen No. 31331), lx HT supplement, with 10% fetal calf serum and incubated at 5% $CO_2$ and 37° C. in a humidified incubator. The growth medium was exchanged with Krebs Ringer Bicarbonate buffer with 1 mM IBMX and incubated at 30° C. for 30 min Compounds were added to a final assay volume of 100 µl and incubated for 30 min at 30° C. The assay was stopped by the addition of 50 µl lysis reagent (Tris, NaCl, 1.5% Triton X100, 2.5% NP40, 10% $NaN_3$) and 50 detection solutions (20 µM mAb Alexa700-cAMP 1:1, and 48 µM Ruthenium-2-AHA-cAMP) and shaked for 2 h at room temperature. The time-resolved energy transfer is measured by a TRF reader (Evotec Technologies GmbH, Hamburg Germany), equipped with a ND:YAG laser as excitation source. The plate is measured twice with the excitation at 355 nm and at the emission with a delay of 100 ns and a gate of 100 ns, total exposure time 10 s at 730 (bandwidth 30 nm) or 645 nm (bandwidth 75 nm), respectively. The measured signal at 730 nm has to be corrected for the ruthenium background, the direct excitation of Alexa and the buffer control. The FRET signal is calculated as follows: FRET=T730−Alexa730−P(T645−B645) with P=Ru730−B730/Ru645−B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 µM to 0.13 nM cAMP.

$EC_{50}$ values were determined using Activity Base analysis (ID Business Solution, Limited). The $EC_{50}$ values for a wide range of bile acids generated from this assay were in agreement with the values published in the scientific literature. Specificity for GPBAR1 was tested in non-transfected CHO cells in the same assay as above.

The compounds according to formula I have an activity in the above assay ($EC_{50}$) preferably of 0.5 nM to 10 µM, more preferably of 0.5 nM to 1 µM and most preferably of 0.5 nM to 100 nM. For example, the following compounds showed the following human $EC_{50}$ values in the functional cAMP assay described above:

| Example | human $EC_{50}$ [µM] |
| --- | --- |
| 1 | 0.022 |
| 2 | 0.727 |
| 3 | 0.902 |
| 4 | 0.247 |
| 5 | 0.112 |
| 6 | 0.091 |
| 7 | 1.051 |
| 8 | 0.075 |
| 9 | 1.227 |
| 10 | 0.238 |
| 11 | 0.406 |
| 12 | 0.349 |
| 13 | 0.58 |
| 14 | 0.395 |
| 15 | 0.323 |
| 16 | 0.184 |
| 17 | 0.336 |
| 18 | 0.85 |
| 19 | 0.34 |
| 20 | 0.143 |
| 21 | 0.388 |
| 22 | 0.035 |
| 23 | 0.038 |
| 24 | 0.146 |
| 25 | 0.014 |
| 26 | 0.686 |
| 27 | 1.048 |
| 28 | 0.863 |
| 29 | 0.011 |
| 30 | 1.618 |
| 31 | 0.029 |
| 32 | 0.009 |
| 33 | 0.349 |
| 34 | 0.502 |
| 35 | 0.163 |
| 36 | 0.362 |
| 37 | 0.04 |
| 38 | 0.011 |
| 39 | 0.038 |
| 40 | 0.107 |
| 41 | 0.09 |
| 42 | 0.119 |
| 43 | 2.054 |
| 44 | 0.03 |
| 45 | 0.302 |
| 46 | 0.924 |
| 47 | 0.068 |
| 48 | 0.307 |
| 49 | 0.629 |
| 50 | 0.678 |
| 51 | 0.06 |
| 52 | 0.463 |
| 53 | 1.098 |
| 54 | 1.966 |
| 55 | 0.435 |
| 56 | 0.43 |
| 57 | 0.351 |
| 58 | 0.026 |
| 59 | 0.19 |

| Example | human EC$_{50}$ [μM] |
|---|---|
| 60 | 0.114 |
| 61 | 0.072 |
| 62 | 0.337 |
| 63 | 0.023 |
| 64 | 0.014 |
| 65 | 0.102 |
| 66 | 0.008 |
| 67 | 0.056 |
| 68 | 0.801 |
| 69 | 0.377 |
| 70 | 0.485 |
| 71 | 1.535 |
| 72 | 0.593 |
| 73 | 1.834 |
| 74 | 0.034 |
| 75 | 0.452 |
| 76 | 1.964 |
| 77 | 0.715 |
| 78 | 0.021 |
| 79 | 1.381 |
| 80 | 0.299 |
| 81 | 0.228 |
| 82 | 0.234 |
| 83 | 0.376 |
| 84 | 2.017 |
| 85 | 0.2 |
| 86 | 0.267 |
| 87 | 1.332 |
| 88 | 0.066 |
| 89 | 0.008 |
| 90 | 2.74 |
| 91 | 0.152 |
| 92 | 0.236 |
| 93 | 2.264 |
| 94 | 2.159 |
| 95 | 0.092 |
| 96 | 0.127 |
| 97 | 0.721 |
| 98 | 0.109 |
| 99 | 2.937 |
| 100 | 0.207 |
| 101 | 0.298 |
| 102 | 0.144 |
| 103 | 0.329 |
| 104 | 1.641 |
| 105 | 0.485 |
| 106 | 0.043 |
| 107 | 0.038 |
| 108 | 0.07 |
| 109 | 0.022 |
| 110 | 0.152 |
| 111 | 0.256 |
| 112 | 0.237 |
| 113 | 2.012 |
| 114 | 0.03 |
| 115 | 0.066 |
| 116 | 0.088 |
| 117 | 0.052 |
| 118 | 2.471 |
| 119 | 0.61 |
| 120 | 0.17 |
| 121 | 1.92 |
| 122 | 2.433 |
| 123 | 0.473 |
| 124 | 1.976 |
| 125 | 1.488 |
| 126 | 0.62 |
| 127 | 0.075 |
| 128 | 0.029 |
| 129 | 0.076 |
| 130 | 0.166 |
| 131 | 0.019 |
| 132 | 1.332 |
| 133 | 0.039 |
| 134 | 0.912 |
| 135 | 0.091 |
| 136 | 0.247 |
| 137 | 0.166 |
| 138 | 0.042 |
| 139 | 0.606 |
| 140 | 0.124 |
| 141 | 1.663 |
| 142 | 0.396 |
| 143 | 0.012 |
| 144 | 0.022 |
| 145 | 0.03 |
| 146 | 0.069 |
| 147 | 0.018 |
| 148 | 0.006 |
| 149 | 0.242 |
| 150 | 0.09 |
| 151 | 0.047 |
| 152 | 0.558 |
| 153 | 0.019 |
| 154 | 0.039 |
| 155 | 0.038 |
| 156 | 0.036 |
| 157 | 0.088 |
| 158 | 0.21 |
| 159 | 0.326 |
| 160 | 0.281 |
| 161 | 0.029 |
| 162 | 0.101 |
| 163 | 0.099 |
| 164 | 1.695 |
| 165 | 0.153 |
| 166 | 1.783 |
| 167 | 2.723 |
| 168 | 0.041 |
| 169 | 0.026 |
| 170 | 0.118 |
| 171 | 0.056 |
| 172 | 0.632 |
| 173 | 0.053 |
| 174 | 0.054 |
| 175 | 0.571 |
| 176 | 0.014 |
| 177 | 0.036 |
| 178 | 0.049 |
| 179 | 0.4 |
| 180 | 0.197 |
| 181 | 2.952 |
| 182 | 0.027 |
| 183 | 0.206 |
| 184 | 0.015 |
| 185 | 2.405 |
| 186 | 0.055 |
| 187 | 0.478 |
| 188 | 0.07 |
| 189 | 0.047 |
| 190 | 0.089 |
| 191 | 0.111 |
| 192 | 0.105 |
| 193 | 0.456 |
| 194 | 0.258 |
| 195 | 0.013 |
| 196 | 0.023 |
| 197 | 0.105 |
| 198 | 0.092 |
| 199 | 0.033 |
| 200 | 1.202 |
| 201 | 0.267 |
| 202 | 0.157 |
| 203 | 0.054 |
| 204 | 0.619 |
| 205 | 0.017 |
| 206 | 0.023 |
| 207 | 0.318 |
| 208 | 2.955 |
| 209 | 1.47 |
| 210 | 0.241 |
| 211 | 0.959 |

-continued

| Example | human EC$_{50}$ [μM] |
|---|---|
| 212 | 0.075 |
| 213 | 0.253 |
| 214 | 0.265 |
| 215 | 0.216 |
| 216 | 0.038 |
| 217 | 0.031 |
| 218 | 0.073 |
| 219 | 3.03 |
| 220 | 1.98 |
| 221 | 0.059 |
| 222 | 0.183 |
| 223 | 0.046 |
| 224 | 0.046 |
| 225 | 0.241 |
| 226 | 0.958 |
| 227 | 0.093 |
| 228 | 0.057 |
| 229 | 0.027 |
| 230 | 0.073 |
| 231 | 3.5 |
| 232 | 0.335 |
| 233 | 0.054 |
| 234 | 0.405 |
| 235 | 0.085 |
| 236 | 0.886 |
| 237 | 0.34 |
| 238 | 0.023 |
| 239 | 0.508 |
| 240 | 1.148 |
| 241 | 0.105 |
| 242 | 0.011 |
| 243 | 0.61 |
| 244 | 1.15 |
| 245 | 0.933 |
| 246 | 0.168 |
| 247 | 0.413 |
| 248 | 0.323 |
| 249 | 0.019 |
| 250 | 2.963 |
| 251 | 0.03 |
| 252 | 0.17 |
| 253 | 3.042 |
| 254 | 0.054 |
| 255 | 0.053 |
| 256 | 0.02 |
| 257 | 0.079 |
| 258 | 1.864 |
| 259 | 0.134 |
| 260 | 0.153 |
| 261 | 0.19 |
| 262 | 0.231 |
| 263 | 0.017 |
| 264 | 2.411 |
| 265 | 0.121 |
| 266 | 0.177 |
| 267 | 3.46 |
| 268 | 0.768 |
| 269 | 0.094 |
| 270 | 0.133 |
| 271 | 3.126 |
| 272 | 0.064 |
| 273 | 1.496 |
| 274 | 0.034 |
| 275 | 1.228 |
| 276 | 0.162 |
| 277 | 0.008 |
| 278 | 0.107 |
| 279 | 0.077 |
| 280 | 0.268 |
| 281 | 0.574 |
| 282 | 0.069 |
| 283 | 2.202 |
| 284 | 0.353 |
| 285 | 2.900 |
| 286 | 0.379 |
| 287 | 0.539 |

-continued

| Example | human EC$_{50}$ [μM] |
|---|---|
| 288 | 1.479 |
| 289 | 0.275 |
| 290 | 1.739 |
| 291 | 2.842 |
| 292 | 0.088 |
| 293 | 2.463 |
| 294 | 0.042 |
| 295 | 0.445 |
| 296 | 1.335 |
| 297 | 0.521 |
| 298 | 0.788 |
| 299 | 0.952 |
| 300 | 0.831 |
| 301 | 0.219 |
| 302 | >10 |
| 303 | 0.018 |
| 304 | 0.015 |
| 305 | 0.005 |
| 306 | 0.19 |
| 307 | 0.3 |
| 308 | 0.936 |
| 309 | 0.273 |
| 310 | 0.041 |
| 311 | 0.081 |
| 312 | 2.417 |
| 313 | 1.225 |
| 314 | 0.115 |
| 315 | 0.451 |
| 316 | 0.926 |
| 317 | 0.418 |
| 318 | 1.111 |
| 319 | 3.336 |
| 320 | 2.722 |
| 321 | 1.885 |
| 322 | 0.011 |
| 323 | 0.104 |

The compounds of formula I and their pharmaceutically acceptable salts can be used as medicaments, e.g., in the form of pharmaceutical preparations for enteral, parenteral or topical administration. They can be administered, for example, perorally, e.g., in the form of tablets, coated tablets, dragées, hard and soft gelatine capsules, solutions, emulsions or suspensions, rectally, e.g., in the form of suppositories, parenterally, e.g., in the form of injection solutions or suspensions or infusion solutions, or topically, e.g., in the form of ointments, creams or oils. Oral administration is preferred.

The production of the pharmaceutical preparations can be effected in a manner which will be familiar to any person skilled in the art by bringing the described compounds of formula I and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g., in 1 to 3 dosage units.

The pharmaceutical preparations conveniently contain about 1-500 mg, preferably 1-100 mg, of a compound of formula I.

The following examples serve to illustrate the present invention in more detail. They are, however, not intended to limit its scope in any manner.

EXAMPLES

Abbreviations:

AcOH=acetic acid, CAS RN=chemical abstracts registration number, CO=carbon monoxide, CuCl=copper (I) chloride, DMAP=4-dimethylaminopyridine, DME=dimethoxyethane, DMF=N,N-dimethylformamide, DIPEA=N,N-diisopropylethylamine, dppf=1,1 bis(diphenylphosphino)ferrocene, EI=electron impact, ESI=electrospray ionization, EtOAc=ethyl acetate, h=hour, $H_2O$=water, HATU=1-[bis(dimethylamino)methylene]-1H-1,2,3-triazolo[4,5-b]pyridinium-3-oxide hexafluorophosphate, HCl=hydrogen chloride, HPLC=high performance liquid chromatography, iPrMgCl=isopropylmagnesium chloride, ISP=ion spray positive (mode), ISN=ion spray negative (mode), min=minutes, $K_2CO_3$=potassium carbonate, $LiAlH_4$ or LAH=lithium aluminium hydride, LiHMDS=lithium bis(trimethylsilyl)amide, LiOH=lithium hydroxide, $MgSO_4$=magnesium sulfate, MPLC=medium performance liquid chromatography, MS=mass spectrum, NaH=sodium hydride, nBuLi=n-butyllithium, $NaHCO_3$=sodium hydrogen carbonate, NaOH=sodium hydroxide, $Na_2CO_3$=sodium carbonate, $Na_2SO_4$=sodium sulfate, $Na_2S_2O_3$=sodium thiosulfate, $NEt_3$=triethylamine, $NH_4Cl$=ammonium chloride, KOH=potassium hydroxide, P=protecting group, Pd—C=palladium on activated carbon, $PdCl_2$(dppf)-$CH_2Cl_2$=1,1'-bis(diphenylphosphino)ferrocene-palladium(II)dichloride dichloromethane complex, $Pd(OAc)_2$=palladium(II) acetate, $Pd(PPh_3)_4$=tetrakis(triphenylphosphine)palladium(0), R=any group, rt=room temperature, S-PHOS=2-dicyclohexylphosphino-2',6'-dimethoxybiphenyl, TFA=trifluroacetic acid, THF=tetrahydrofuran, TMEDA=N,N,N',N'-tetramethylethylenediamine, $ZnCl_2$=zinc chloride, X=halogen.

Example 1

N-Methyl-N-(4-o-tolyl-pyridin-3-yl)-3,5-bis-trifluoromethyl-benzamide

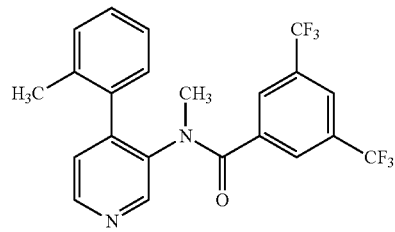 [SMILES: Cc1ccccc1-c1ccncc1N(C)C(=O)c1cc(C(F)(F)F)cc(C(F)(F)F)c1]

3,5-Bis-trifluoromethylbenzoyl chloride (36 mg, 0.13 mmol, CAS RN 1271-19-8) was added to a solution of methyl-(4-o-tolyl-pyridin-3-yl)-amine (20 mg, 0.10 mmol) and DIPEA (40 µL, 0.23 mmol) in $CH_2Cl_2$ (1 mL) The reaction mixture was stirred overnight and then loaded directly onto a silica gel column and eluted with 50% EtOAc in n-hexane to yield the desired product as a waxy solid (23 mg, 41%). MS (ESI): m/z=439.0 [M+H]

Intermediates a) Methyl-(4-o-tolyl-pyridin-3-yl)-amine

N-Boc-4-o-tolyl-pyridin-3-ylamine (45 mg, 0.158 mmol) in THF (0.5 mL) under argon was treated with LAH in THF (1.0M, 0.20 mL, 0.2 mmol). The reaction mixture was then heated to reflux for 6 hours. After cooling, $Na_2SO_4 \times 10\ H_2O$ was carefully added and the reaction mixture was stirred for 1 h after which a colorless solid formed. The solid was removed by filtration and all volatiles were evaporated to yield the desired compound as a solid (29 mg, 93%).

b) N-Boc-4-o-tolyl-pyridin-3-ylamine

Di-tert-butyldicarbonate (655 mg, 3.0 mmol, CAS RN 24424-99-5) was added to a solution of 4-o-tolyl-pyridin-3-ylamine (500 mg, 2.7 mmol), DMAP (66 mg, 0.54 mmol) and DIPEA (05.7 mL, 3.3 mmol) in $CH_2Cl_2$ (14 mL). The reaction mixture was stirred for 16 hours at room temperature. After evaporating the reaction mixture to dryness, the desired product was isolated by flash chromatography on silica gel (33-50% EtOAc in n-hexane) as a waxy solid (360 mg, 42%).

c) 4-o-Tolyl-pyridin-3-ylamine

Zinc dust (3.0 g, 46 mmol) was added to 3-nitro-4-o-tolyl-pyridine (1.35 g, 6.3 mmol) in acetic acid (32 mL). The reaction mixture was heated to 70° C. for 90 min. After cooling to room temperature, solids were removed from the reaction mixture by filtration. Evaporation of volatiles in vacuo gave a solid that was triturated with toluene. Removal of solids by filtration followed by evaporation of volatiles in vacuo gave a heavy oil. The product 4-o-tolyl-pyridin-3-ylamine was isolated by flash chromatography on silica gel eluting with EtOAc to 5% $CH_3OH$ in EtOAc (1.0 g, 86%).

d) 3-Nitro-4-o-tolyl-pyridine

Triphenylphosphine (2.10 g, 1.89 mmol) and potassium carbonate (7.80 g, 56.7 mmol) were added to a slurry of 4-chloro-3-nitropyridine (3.00 g, 18.9 mmol, CAS RN 13091-23-1) and 2-tolylboronic acid (2.83 g, 20.8 mmol, CAS RN 16419-60-6) in dioxane stirring under an argon atmosphere. The reaction mixture was heated to 120° C. for 16 hours and then cooled to room temperature. The solids were removed by filtration through celite and all volatiles were removed in vacuo resulting in a dark colored heavy oil. The product was isolated as a heavy oil by flash chromatography on silica gel (25-33% EtOAc in n-hexane) (1.75 g, 43%).

Example 2

N-Methyl-N-(4-o-tolyl-pyridin-3-yl)-3-trifluoromethyl-benzamide

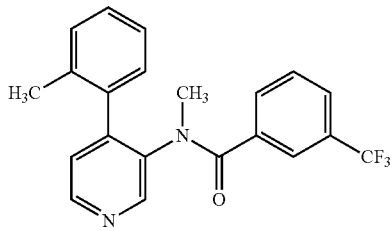 [SMILES: Cc1ccccc1-c1ccncc1N(C)C(=O)c1cccc(C(F)(F)F)c1]

3-Trifluoromethylbenzoyl chloride (30 mg, 0.14 mmol, CAS RN 2251-65-2) was added to a solution of methyl-(4-o-tolyl-pyridin-3-yl)-amine (20 mg, 0.10 mmol, example 1, intermediate a) and DIPEA (30 μL, 0.17 mmol) in CH$_2$Cl$_2$ (1 mL) The reaction mixture was stirred overnight and then loaded directly onto a silica gel column and eluted with 50% EtOAc in n-hexane to yield the desired product as a waxy solid (17 mg, 46%). MS (ESI): m/z=371.0 [M+H]$^+$.

Example 3

N-Methyl-N-(4-o-tolyl-pyridin-3-yl)-3-chloro-benzamide

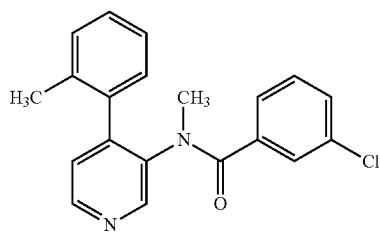 [SMILES: Cc1ccccc1-c1ccncc1N(C)C(=O)c1cccc(Cl)c1]

3-Chlorobenzoyl chloride (30 mg, 0.17 mmol, CAS RN 618-46-2) was added to a solution of methyl-(4-o-tolyl-pyridin-3-yl)-amine (20 mg, 0.10 mmol, example 1, intermediate a) and DIPEA (30 μL, 0.17 mmol) in CH$_2$Cl$_2$ (1 mL) The reaction mixture was stirred overnight and then loaded directly onto a silica gel column and eluted with 50% EtOAc in n-hexane to yield the title product as a waxy solid (12 mg, 36%). MS (ESI): m/z=337.0 [M+H]$^+$.

Example 4

2-Fluoro-N-methyl-N-(4-o-tolyl-pyridin-3-yl)-5-trifluoromethyl-benzamide

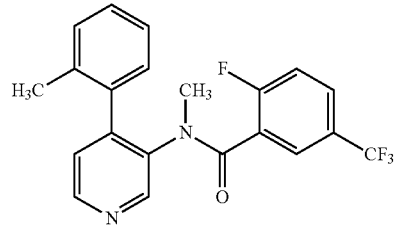 [SMILES: Cc1ccccc1-c1ccncc1N(C)C(=O)c1cc(C(F)(F)F)ccc1F]

2-Fluoro-5-trifluoromethylbenzoyl chloride (80 mg, 0.35 mmol, CAS RN 207981-46-2) was added to a solution of methyl-(4-o-tolyl-pyridin-3-yl)-amine (35 mg, 0.18 mmol, example 1, intermediate a) and DIPEA (92 μL, 0.53 mmol) in CH$_2$Cl$_2$ (1 mL) The reaction mixture was stirred overnight and then loaded directly onto a silica gel column and eluted with 50% EtOAc in n-hexane to yield the desired product as a waxy solid (36 mg, 53%). MS (ESI): m/z=389.0 [M+H]$^+$.

Example 5

4-Fluoro-N-methyl-N-(4-o-tolyl-pyridin-3-yl)-5-trifluoromethyl-benzamide

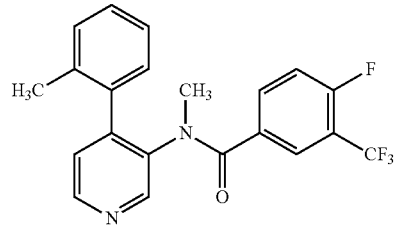 [SMILES: Cc1ccccc1-c1ccncc1N(C)C(=O)c1ccc(F)c(C(F)(F)F)c1]

4-Fluoro-5-trifluoromethylbenzoyl chloride (80 mg, 0.35 mmol, CAS RN 67515-56-4) was added to a solution of methyl-(4-o-tolyl-pyridin-3-yl)-amine (35 mg, 0.18 mmol, example 1, intermediate a) and DIPEA (92 μL, 0.53 mmol) in CH$_2$Cl$_2$ (1 mL) The reaction mixture was stirred overnight and then loaded directly onto a silica gel column and eluted with 50% EtOAc in n-hexane to yield the desired product as a waxy solid (33 mg, 48%) MS (ESI): m/z=388.9 [M+H]$^+$.

Example 6

3-Fluoro-N-methyl-N-(4-o-tolyl-pyridin-3-yl)-5 fluoro methyl-benzamide

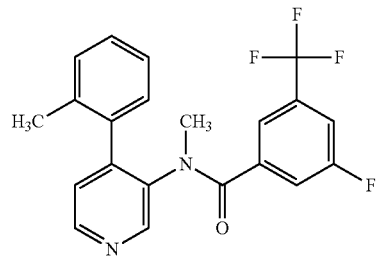 [SMILES: Cc1ccccc1-c1ccncc1N(C)C(=O)c1cc(F)cc(C(F)(F)F)c1]

3-Fluoro-5-trifluoromethylbenzoyl chloride (92 mg, 0.41 mmol, CAS RN 171243-30-4) was added to a solution of methyl-(4-o-tolyl-pyridin-3-yl)-amine (40 mg, 0.20 mmol, example 1, intermediate a) and DIPEA (70 μL, 0.40 mmol)

in THF (1 mL). After 2 h, an additional 25 µL of acyl chloride was added. The reaction mixture was stirred overnight, filtered and all volatiles removed. The resulting oil was purified by flash chromatography on silica gel eluting with 33-50% EtOAc in n-hexane to yield the product as a waxy solid (45 mg, 57%). MS (ESI): m/z=470.0 [M+H]⁺.

Example 7

2-Fluoro-N-methyl-N-(4-o-tolyl-pyridin-3-yl)-3-trifluoromethyl-benzamide

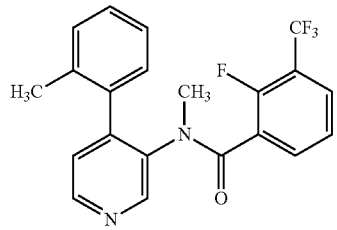 [SMILES: Cc1ccccc1-c1ccncc1N(C)C(=O)c1cccc(C(F)(F)F)c1F]

2-Fluoro-3-trifluoromethylbenzoyl chloride (92 mg, 0.41 mmol, CAS RN 208173-19-7) was added to a solution of methyl-(4-o-tolyl-pyridin-3-yl)-amine (40 mg, 0.20 mmol, example 1, intermediate a) and DIPEA (70 µL, 0.40 mmol) in THF (1 mL) The reaction mixture was stirred overnight, filtered and all volatiles removed. The resulting oil was purified by flash chromatography on silica gel eluting with 33-50% EtOAc in n-hexane to yield the product as a waxy solid (65 mg, 83%). MS (ESI): m/z=470.0 [M+H]⁺.

Example 8

3,5-Dichloro-N-methyl-N-(4-o-tolyl-pyridin-3-yl)-benzamide

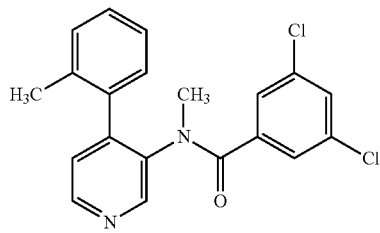 [SMILES: Cc1ccccc1-c1ccncc1N(C)C(=O)c1cc(Cl)cc(Cl)c1]

3,5-Dichlorobenzoyl chloride (85 mg, 0.40 mmol, CAS RN 2905-62-6) was added to a solution of methyl-(4-o-tolyl-pyridin-3-yl)-amine (40 mg, 0.20 mmol, example 1, intermediate a) and DIPEA (70 µL, 0.40 mmol) in THF (1 mL) The reaction mixture was stirred overnight, filtered and all volatiles removed. The resulting oil was purified by flash chromatography on silica gel eluting with 33-50% EtOAc in n-hexane to yield the product as a waxy solid (65 mg, 87%). MS (ESI): m/z=470.0 [M+H]⁺.

Example 9

3,5-Difluoro-N-methyl-N-(4-o-tolyl-pyridin-3-yl)-benzamide

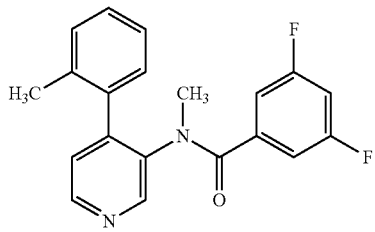 [SMILES: Cc1ccccc1-c1ccncc1N(C)C(=O)c1cc(F)cc(F)c1]

3,5-Difluorobenzoyl chloride (50 mg, 0.28 mmol, CAS RN 129714-97-2) was added to a solution of methyl-(4-o-tolyl-pyridin-3-yl)-amine (45 mg, 0.23 mmol, example 1, intermediate a) and DIPEA (79 µL, 0.45 mmol) in CH₂Cl₂ (1 mL) The reaction mixture was stirred overnight and then loaded directly onto a silica gel column and eluted with 50% EtOAc in n-hexane to yield the desired compound as a waxy solid (26 mg, 34%). MS (ESI): m/z=339.1 [M+H]⁺.

Example 10

3,4-Dichloro-N-methyl-N-(4-o-tolyl-pyridin-3-yl)-benzamide

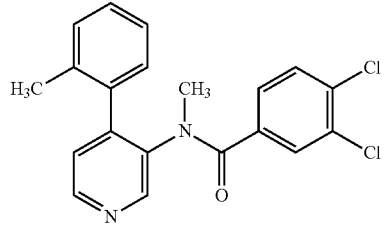 [SMILES: Cc1ccccc1-c1ccncc1N(C)C(=O)c1ccc(Cl)c(Cl)c1]

3,4-Dichlorobenzoyl chloride (60 mg, 0.29 mmol, CAS RN 2905-60-4) was added to a solution of methyl-(4-o-tolyl-pyridin-3-yl)-amine (45 mg, 0.23 mmol, example 1, intermediate a) and DIPEA (79 µL, 0.45 mmol) in CH₂Cl₂ (1 mL) The reaction mixture was stirred overnight and then loaded directly onto a silica gel column and eluted with 50% EtOAc in n-hexane to yield the product as a waxy solid (18 mg, 21%). MS (ESI): m/z=371.0 [M+H]⁺.

Example 11

3-Chloro-4-fluoro-N-methyl-N-(4-o-tolyl-pyridin-3-yl)-benzamide

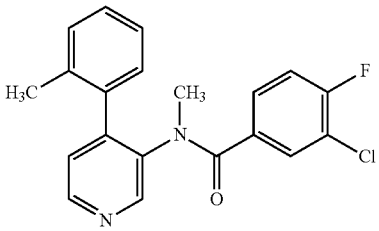

3-Chloro-4-fluorobenzoyl chloride (60 mg, 0.31 mmol, CAS RN 65055-17-6) was added to a solution of methyl-(4-o-tolyl-pyridin-3-yl)-amine (45 mg, 0.23 mmol, example 1, intermediate a) and DIPEA (79 µL, 0.45 mmol) in CH$_2$Cl$_2$ (1 mL) The reaction mixture was stirred overnight and then loaded directly onto a silica gel column and eluted with 50% EtOAc in n-hexane to yield the product as a waxy solid (23 mg, 29%). MS (ESI): m/z=355.0 [M+H]$^+$.

Example 12

N-(6-Chloro-4-o-tolyl-pyridin-3-yl)-N-methyl-3,5-bis-trifluoromethyl-benzamide

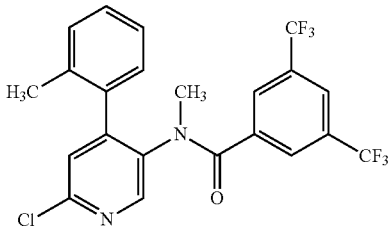 [SMILES: Cc1ccccc1-c1cc(Cl)ncc1N(C)C(=O)c1cc(C(F)(F)F)cc(C(F)(F)F)c1]

3,5-Bis-trifluoromethylbenzoyl chloride (76 mg, 0.28 mmol, CAS RN 1271-19-8) was added to a solution of 6-chloro-N-methyl-4-o-tolylpyridin-3-amine (30 mg, 0.13 mmol, prepared as described in WO2005/002577) and DIPEA (50 µL, 0.29 mmol) in THF (1.5 mL) The reaction mixture was stirred overnight, filtered and all volatiles removed in vacuo. The desired product was isolated by flash chromatography on silica gel (25% EtOAc in n-hexane) as a waxy solid (48 mg, 79%). MS (ESI): m/z=472.9 [M+H]$^+$.

Example 13

3,5-Dichloro-N-(6-chloro-4-o-tolyl-pyridin-3-yl)-N-methyl-benzamide

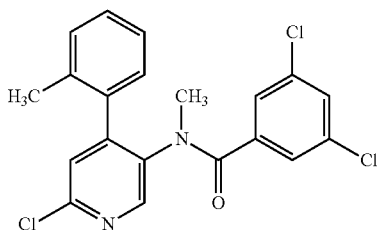 [SMILES: Cc1ccccc1-c1cc(Cl)ncc1N(C)C(=O)c1cc(Cl)cc(Cl)c1]

3,5-Dichlorobenzoyl chloride (635 mg, 3.03 mmol, CAS RN 2905-62-6) was added to a solution of 6-chloro-N-methyl-4-o-tolylpyridin-3-amine (470 mg, 2.02 mmol, prepared as described in WO2005/002577) and DIPEA (705 µL, 4.04 mmol) in CH$_2$Cl$_2$ (15 mL) The reaction mixture was stirred for 1 h after which the reaction mixture was loaded directly onto a silica gel column. The title compound was isolated by flash chromatography (25% EtOAc in n-hexane) as a foamy oil (641 mg, 78%). MS (ESI): m/z=404.9 [M+H]$^+$.

Example 14

N-(6-Methoxy-4-o-tolyl-pyridin-3-yl)-N-methyl-3,5-bis-trifluoromethyl-benzamide

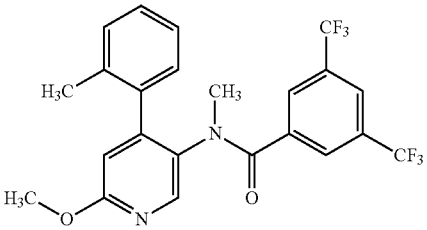

3,5-Bis-trifluoromethylbenzoyl chloride (126 µL, 0.69 mmol, CAS RN 1271-19-8) was added to a solution of 6-methoxy-N-methyl-4-o-tolylpyridin-3-amine (105 mg, 0.46 mmol) and DIPEA (240 µL, 1.38 mmol) in CH$_2$Cl$_2$ and stirred for 2 h. The reaction mixture was then loaded directly onto a silica gel column Elution with 20% EtOAc in n-hexane gave the title product as a colorless foam (161 mg, 76%). MS (ESI): m/z=469.0 [M+H]$^+$.

Intermediate

6-Methoxy-N-methyl-4-o-tolylpyridin-3-amine

6-Chloro-N-methyl-4-o-tolylpyridin-3-amine (150 mg, 0.645 mmol, prepared as described in WO2005/002577) in a 10% NaOH solution in CH$_3$OH (300 mg NaOH in 3 mL CH$_3$OH) was heated to 160° C. for 3 hours. After cooling, the reaction mixture was neutralized with 6M aqueous HCl and extracted three times with EtOAc. The combined organic layers were washed with brine and dried over MgSO$_4$. Filtration followed by removal of volatiles in vacuo gave a gummy oil. The desired compound was isolated by flash chromatography on silica gel (20% EtOAc in n-hexane) as a white waxy solid (115 mg, 78%).

Example 15

N-Methyl-N-(6-methylamino-4-o-tolyl-pyridin-3-yl)-3,5-bis-trifluoromethyl-benzamide

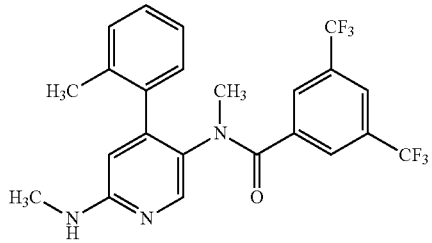

N-Methyl-N-(4-o-tolyl-6-(2,2,2-trifluoro-N-methylacetamido)pyridin-3-yl)-3,5-bis (trifluoromethyl)benzamide (70 mg, 0.12 mmol) was stirred in CH$_3$OH (1.5 mL) with potassium carbonate (75 mg, 0.54 mmol) for 1 h. The reaction mixture was then filtered and all volatiles removed under reduced pressure. The residue was dissolved in EtOAc and washed twice with water and twice with brine. The aqueous phases were back-extracted twice with EtOAc and washed with brine. The combined organic layers were dried over Na$_2$SO$_4$. Filtration followed by removal of volatiles under reduced pressure gave a waxy residue. N-Methyl-N-(6-methylamino-4-o-tolyl-pyridin-3-yl)-3,5-bis-trifluoromethyl-benzamide was isolated from this residue by flash chromatography on silica gel (50-67% EtOAc in n-hexane) as a white foam (40 mg, 69%). MS (ESI): m/z=468.0 [M+H]$^+$.

Intermediates a) N-Methyl-N-(4-o-tolyl-6-(2,2,2-trifluoro-N-methylacetamido)pyridin-3-yl)-3,5-bis(trifluoromethyl)benzamide 2,2,2-Trifluoro-N-methyl-N-(5-(methylamino)-4-o-tolylpyridin-2-yl)acetamide (46 mg, 0.14 mmol) and DIPEA (61 μL, 0.35 mmol) in THF (1.5 mL) were treated with 3,5-bis-trifluoromethylbenzoyl chloride (51 μL, 0.28 mmol, CAS RN 1271-19-8). 3,5-Bis-trifluorobenzoyl chloride (25 μL, 0.14 mmol, CAS RN 1271-19-8) was added again at 90 min. and 4 hours. The reaction mixture was stirred for 60 hours and then evaporated to dryness. From the resulting residue, the product N-methyl-N-(4-o-tolyl-6-(2,2,2-trifluoro-N-methylacetamido)pyridin-3-yl)-3,5-bis(trifluoromethyl)benzamide was isolated by flash chromatography on silica gel (33-50% EtOAc in n-hexane) as a foam (70 mg, 87% over two steps). The compound was used in the next step without further purification.

b) 2,2,2-Trifluoro-N-methyl-N-(5-(methylamino)-4-o-tolylpyridin-2-yl)acetamide

A solution of N2,N5-dimethyl-4-o-tolylpyridine-2,5-diamine and DIPEA (94 μL, 0.54 mmol) in CH$_2$Cl$_2$ was treated with trifluoroacetic anhydride (55 μL, 0.39 mmol, CAS RN 407-25-0). After stirring for 90 min, the reaction mixture was loaded directly onto a silica gel column Flash chromatography (33-50% EtOAc in n-hexane) gave the desired compound as a white gummy solid (46 mg, 45% from 6-chloropyridine starting material) which was pure enough to be used in the next step.

c) N2,N5-dimethyl-4-o-tolylpyridine-2,5-diamine

To a solution of 6-chloro-N-methyl-4-o-tolylpyridin-3-amine (74 mg, 0.318 mmol, prepared as described in WO2005/002577), palladium(II) acetate (7 mg, 0.031 mmol, CAS RN 3375-31-3) and (R)-(+)-2,2'-bis(diphenylphosphino)-1,1'-binaphthyl (60 mg, 0.96 mmol, CAS RN 76189-55-4) in toluene (2.5 mL) was added sodium tert-butoxide (92 mg, 0.96 mmol). After stirring for 5 min, methylamine (2.0 M solution in THF, 400 μL, 0.80 mmol, CAS RN 74-89-5) was added and the reaction mixture was heated by microwave irradiation to 150° C. for 30 min. The reaction mixture was applied directly to a silica gel column. Flash chromatography (33-50% EtOAc in n-hexane) gave the product, as a light brown oil which was used in the next step without further purification.

Example 16

N-(6-Amino-4-o-tolyl-pyridin-3-yl)-N-methyl-3 fluoro methyl-benzamide

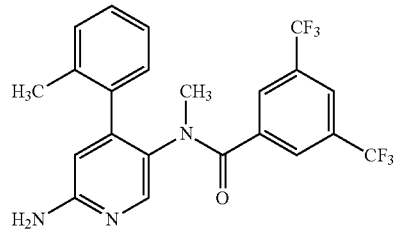 [SMILES: Cc1ccccc1-c1cc(N)ncc1N(C)C(=O)c1cc(C(F)(F)F)cc(C(F)(F)F)c1]

N-(6-Iodo-4-o-tolylpyridin-3-yl)-N-methyl-3,5-bis(trifluoromethyl)benzamide (60 mg, 0.11 mmol), sodium tert-butoxide (31 mg, 0.32 mmol), palladium acetate (2.4 mg, 0.011 mmol, CAS RN 3375-31-3) and BINAP (19.9 mg; 0.032 mmol, CAS RN 76189-55-4) were dissolved in toluene (4 mL) and stirred under an argon atmosphere for 10 min Benzophenone imine (38 mg, 0.21 mmol, CAS RN 1013-88-3) was added and the reaction mixture was sealed and heated to 150° C. by microwave irradiation for 30 minutes. The reaction mixture was cooled, unsealed and 200 μL of 1M aqueous HCl was added. After stirring for 1 h, the reaction mixture was neutralized with saturated aqueous NaHCO$_3$ solution and extracted three times with EtOAc. The combined organic layers were washed with brine and dried over MgSO$_4$. Filtration followed by removal of volatiles under reduced pressure afforded a brown solid. Column chromatography on silica gel (50% EtOAc in n-hexane) afforded the title compound as a yellow solid (17 mg, 35%). MS (ESI): m/z=453.9 [M+H]$^+$.

Intermediate

N-(6-Iodo-4-o-tolylpyridin-3-yl)-N-methyl-3,5-bis (trifluoromethyl)benzamide

To N-(6-chloro-4-o-tolylpyridin-3-yl)-N-methyl-3,5-bis(trifluoromethyl)benzamide (460 mg, 0.97 mmol, example 12) in acetone (3 mL) was added sodium iodide (1.17 g, 7.8 mmol) and hydriodic acid (170 μL, 1.07 mmol). The reaction mixture was heated to reflux for 4 hours. Acetone was evaporated and acetonitrile (3 mL) was added and the reaction mixture heated again to reflux. After 16 hours, the reaction mixture was carefully neutralized with saturated aqueous NaHCO$_3$ solution and extracted three times with EtOAc. The combined organic layers were washed with brine and dried over MgSO$_4$. Filtration and removal of volatiles under reduced pressure afforded a brown solid. The desired compound was isolated by flash chromatography on silica gel (50% EtOAc in n-hexane) as an amber oil (324 mg, 59%).

Example 17

N-[6-(4-Methanesulfonyl-piperazin-1-yl)-4-o-tolyl-pyridin-3-yl]-N-methyl-3,5-bis-trifluoromethyl-benzamide

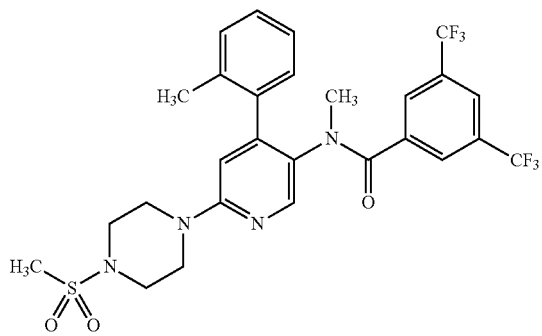 [SMILES: Cc1ccccc1-c1cc(N2CCN(S(C)(=O)=O)CC2)ncc1N(C)C(=O)c1cc(C(F)(F)F)cc(C(F)(F)F)c1]

A solution of N-methyl-6-(4-(methylsulfonyl)piperazin-1-yl)-4-o-tolylpyridin-3-amine (37 mg, 0.10 mmol) and DIPEA (50 μL, 0.29 mmol) in CH$_2$Cl$_2$ was treated with 3,5-bis-trifluoromethylbenzoyl chloride (43 mg, 0.15 mmol, CAS RN 1271-19-8). After stirring for 1 h, the reaction mixture was loaded directly onto a silica gel column. Elution with 50% EtOAc in n-hexane afforded the title compound as a yellow solid (48 mg, 80%). MS (ESI): m/z=601.0 [M+H]$^+$.

Intermediate

N-Methyl-6-(4-(methylsulfonyl)piperazin-1-yl)-4-o-tolylpyridin-3-amine

6-Chloro-N-methyl-4-o-tolylpyridin-3-amine (58 mg, 0.25 mmol, prepared as described in WO2005/002577), sodium tert-butoxide (72 mg, 0.75 mmol), palladium acetate (5.6 mg, 0.025 mmol, CAS RN 3375-31-3) and BINAP (47 mg, 0.075 mmol, CAS RN 76189-55-4) were dissolved in toluene (3 mL) and stirred under an argon atmosphere for 10 minutes. 1-(Methylsulfonyl)piperazine (82 mg, 0.5 mmol, CAS RN 55276-43-2) was added and the reaction mixture was sealed and heated to 150° C. under microwave irradiation for 30 min. The reaction mixture was loaded directly onto a silica gel column (elute with EtOAc) to yield the desired compound (39 mg, 43%) as a brown oil which was used in the next step without further purification.

Example 18

N-{6-[(2-Methoxy-ethyl)-methyl-amino]-4-o-tolyl-pyridin-3-yl}-N-methyl-3,5-bis-trifluoro methyl-benzamide

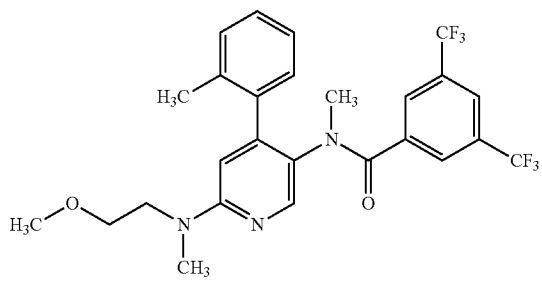 [SMILES: COCCN(C)c1cc(-c2ccccc2C)c(N(C)C(=O)c2cc(C(F)(F)F)cc(C(F)(F)F)c2)cn1]

A solution of N2-(2-methoxyethyl)-N2,N5-dimethyl-4-o-tolylpyridine-2,5-diamine (32 mg, 0.11 mmol) and DIPEA (43 μL, 0.25 mmol) in CH$_2$Cl$_2$ (1 mL) was treated with 3,5-bis-trifluoromethylbenzoyl chloride (46 mg, 0.17 mmol, CAS RN 1271-19-8). After stirring for 1 h, the reaction mixture was loaded directly onto a silica gel column. Elution with 25% EtOAc in n-hexane afforded the title compound as a yellow solid (19 mg, 33%). MS (ESI): m/z=526.2 [M+H]$^+$.

Intermediate

N2-(2-Methoxyethyl)-N2,N5-dimethyl-4-o-tolylpyridine-2,5-diamine

6-Chloro-N-methyl-4-o-tolylpyridin-3-amine (60 mg, 0.26 mmol, prepared as described in WO2005/002577), sodium tert-butoxide (74 mg, 0.77 mmol), palladium acetate (5.8 mg, 0.026 mmol, CAS RN 3375-31-3) and BINAP (48 mg, 0.077 mmol, CAS RN 76189-55-4) were dissolved in toluene (3 mL) and stirred under an argon atmosphere for 10 minutes. N-(2-Methoxyethyl)methylamine (46 mg, 0.52 mmol, CAS RN 38256-93-8) was added and the reaction mixture was sealed and heated to 150° C. under microwave irradiation for 30 min. The reaction mixture was columned directed on silica gel (EtOAc) to yield the product as a light brown oil (36 mg, 49%). This material was used in the next step without further purification.

Example 19

N-(6-Cyano-4-o-tolyl-pyridin-3-yl)-N-methyl-3,5-bis-trifluoromethyl-benzamide

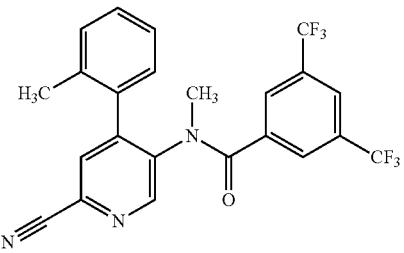 [SMILES: Cc1ccccc1-c1cc(C#N)ncc1N(C)C(=O)c1cc(C(F)(F)F)cc(C(F)(F)F)c1]

A stirring solution of N-(6-chloro-4-o-tolylpyridin-3-yl)-N-methyl-3,5-bis(trifluoromethyl)benzamide (100 mg, 0.21 mmol, example 12), tetrakis-triphenylphosphine palladium (0) (24 mg, 0.020 mmol, CAS RN 14221-01-3) and zinc cyanide (31 mg, 0.26 mmol, CAS RN 557-21-1) in DMF (1.5 mL) was heated to 100° C. for 30 min, 120° C. for 30 min and 150° C. for 30 min by microwave irradiation. After cooling, the reaction mixture was diluted with water and extracted three times with EtOAc. The combined organic layers were washed three times with water and once with brine and dried over Na$_2$SO$_4$. Filtration followed by removal of volatiles under reduced pressure gave crude product. The title compound was isolated by flash chromatography (25% EtOAc in n-hexane) as a viscous oil (7.5 mg, 8%). MS (ESI): m/z=463.9 [M+H]$^+$.

Example 20

N-Methyl-N-(2-methyl-3,4,5,6-tetrahydro-2H-[1,4']bipyridinyl-3'-yl)-3,5-bis-trifluoromethyl-benzamide

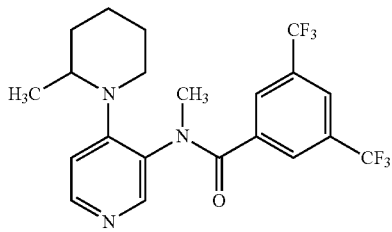 [SMILES: CC1CCCCN1c1ccncc1N(C)C(=O)c1cc(C(F)(F)F)cc(C(F)(F)F)c1]

Methyl-(2-methyl-3,4,5,6-tetrahydro-2H-[1,4']bipyridinyl-3'-yl)-amine trifluoroacetic acid salt was dissolved in CH$_2$Cl$_2$ (2 mL) and treated with DIPEA (100 μL, 0.59 mmol) and 3,5-bis-trifluoromethylbenzoyl chloride (76 mg, 0.28 mmol, CAS RN 1271-19-8). The reaction mixture was loaded directly on a silica gel column and the title product (23 mg, 26% over two steps) was isolated by elution with 66% EtOAc in n-hexane. MS (ESI): m/z=445.9 [M+H]$^+$.

Intermediates a) Methyl-(2-methyl-3,4,5,6-tetrahydro-2H-[1,4']bipyridinyl-3'-yl)-amine trifluoroacetic acid salt Methyl-(2-methyl-3,4,5,6-tetrahydro-2H-[1,4']bipyridinyl-3'-yl)-carbamic acid tert-butyl ester (60 mg, 0.20 mmol) was stirred in a solution of TFA (300 μL) and CH$_2$Cl$_2$ (2 mL) for 1 h after which all volatiles were removed under reduced pressure. The resulting compound was pure enough to be used directly in the next step without further purification.

b) Methyl-(2-methyl-3,4,5,6-tetrahydro-2H-[1,4']bipyridinyl-3'-yl)-carbamic acid tert-butyl ester (2-Methyl-3,4,5,6-tetrahydro-2H-[1,4']bipyridinyl-3'-yl)-carbamic acid tert-butyl ester was dissolved in THF (5 mL) and stirred under argon. NaH (24 mg, 0.98 mmol) was added and after 10 min, iodomethane (61 μL, 0.98 mmol) was added. After stirring for 3 hours, NaH (12 mg, 0.49 mmol) and iodomethane (30 μL, 0.49 mmol) were added again. After 1 h, the reaction mixture was poured into saturated, aqueous NH$_4$Cl solution and extracted three times with EtOAc. The combined organic phases were dried over MgSO$_4$. Filtration followed by removal of volatiles gave crude product. Column chromatography on silica gel (50% EtOAc in n-hexane) gave the desired compound (159 mg, 59% over two steps) that was used in the next step without further purification.

c) (2-Methyl-3,4,5,6-tetrahydro-2H-[1,4']bipyridinyl-3'-yl)-carbamic acid tert-butyl ester Di-tert-butyl dicarbonate (233 mg, 1.07 mmol, CAS RN 24424-99-5) was added to a stirring solution of 2-methyl-3,4,5,6-tetrahydro-2H-[1,4']bipyridinyl-3'-ylamine (170 mg, 0.89 mmol) and DMAP (33 mg, 0.27 mmol) in CH$_2$Cl$_2$ (5 mL) After 16 hours, the reaction mixture was poured into saturated, aqueous NH$_4$Cl solution and extracted three times with CH$_2$Cl$_2$. The combined organic phases were dried over MgSO$_4$. Filtration followed by removal of volatiles gave the desired product as a foam which was pure enough to be used in the next step without further purification.

d) 2-Methyl-3,4,5,6-tetrahydro-2H-[1,4']bipyridinyl-3'-ylamine

2-Methyl-3'-nitro-3,4,5,6-tetrahydro-2H-[1,4']bipyridinyl (650 mg, 2.94 mmol) and 10% palladium on carbon (156 mg, 0.15 mmol) in EtOH were stirred under 1 atmosphere of hydrogen gas for 16 hours. Filtration followed by removal of volatiles under reduced pressure gave the title compound (200 mg, 36%) which was used in the next step without further purification.

e) 2-Methyl-3'-nitro-3,4,5,6-tetrahydro-2H-[1,4']bipyridine

2-Methylpiperidine (938 mg, 9.5 mmol, CAS RN 109-05-7) and 3-chloro-4-nitropyridine (750 mg, 4.73 mmol, CAS RN 13194-60-0) were heated at 90° C. for 1 h. Direct column chromatography of the cooled reaction mixture gave the product as a yellow solid (655 mg, 63%). This material was pure enough to be used in the next step without further purification.

Example 21

3,5-Dichloro-N-methyl-N-(2-methyl-3,4,5,6-tetrahydro-2H-[1,4']bipyridinyl-3'-yl)-benzamide hydrochloride salt

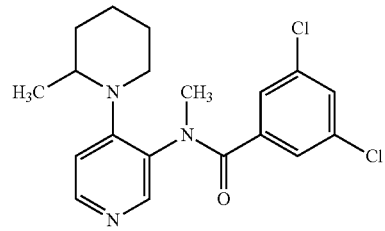 [SMILES: CC1CCCCN1c1ccncc1N(C)C(=O)c1cc(Cl)cc(Cl)c1]

Methyl-(2-methyl-3,4,5,6-tetrahydro-2H-[1,4']bipyridinyl-3'-yl)-carbamic acid tert-butyl ester (60 mg, 0.20 mmol, example 20, intermediate b) was stirred in a solution of TFA (300 μL) and CH$_2$Cl$_2$ (2 mL) for 1 h after which all volatiles were removed under reduced pressure to give crude methyl-(2-methyl-3,4,5,6-tetrahydro-2H-[1,4']bipyridinyl-3'-yl)-amine TFA salt. The crude TFA salt was dissolved in CH$_2$Cl$_2$ (2 mL) and treated with DIPEA (100 μL, 590 mmol) and 3,5-dichlorobenzoyl chloride (54 mg, 0.26 mmol, CAS RN 2905-62-6). The reaction mixture was loaded directly on a silica gel column and elution with 66% EtOAc in n-hexane gave the title product (12 mg, 16%). MS (ESI): m/z=378.0 [M+H]$^+$.

Example 22

N-[4-(4-Fluoro-2-methoxy-phenyl)-pyridin-3-yl]-3-methanesulfonyl-N-oxazol-2-ylmethyl-5-trifluoromethyl-benzamide

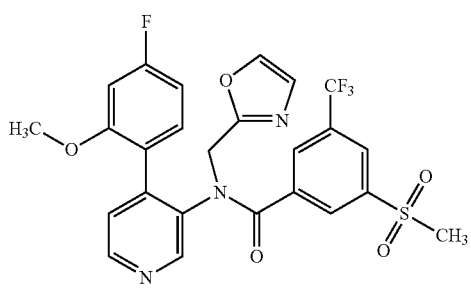

The title compound was prepared in analogy to example 90, from [4-(4-fluoro-2-methoxy-phenyl)-pyridin-3-yl]-oxazol-2-ylmethyl-amine and 3-methanesulfonyl-5-trifluoromethyl-benzoic acid (example 144, intermediate a) after a reaction time of 72 hours. The compound was purified by silica gel chromatography on a 20 g column using a MPLC system (CombiFlash Companion, Isco Inc.) eluting with a gradient of n-heptane: EtOAc (100:0 to 0:100). The product-containing fractions were pooled and evaporated. The remaining red solid was purified by preparative HPLC (Gemini NX) with a gradient of methanol:water containing 0.05% formic acid (80:20 to 98:2). Colorless foam (41%). MS (ESI): m/z=550.105 [M+H]$^+$.

Intermediates a) [4-(4-Fluoro-2-methoxy-phenyl)-pyridin-3-yl]-oxazol-2-ylmethyl-amine The title compound was prepared in analogy to example 85, intermediate a, from [4-(4-fluoro-2-methoxy-phenyl)-pyridin-3-yl]-oxazol-2-ylmethyl-carbamic acid tert-butyl ester. The compound was purified by silica gel chromatography on a 20 g column using a MPLC system (CombiFlash Companion, Isco Inc.) eluting with a gradient of n-heptane: EtOAc (100:0 to 0:100). Colorless solid (86%). MS (ESI): m/z=300.115 [M+H]$^+$.

b) [4-(4-Fluoro-2-methoxy-phenyl)-pyridin-3-yl]-oxazol-2-ylmethyl-carbamic acid tert-butyl ester The title compound was prepared in analogy to example 72, from (4-iodo-pyridin-3-yl)-oxazol-2-ylmethyl-carbamic acid tert-butyl ester and 4-fluoro-2-methoxyphenyl-boronic acid (CAS RN 179899-07-1) and using a gradient of n-heptane:EtOAc (100:0 to 0:100) for the chromatographic purification. Colorless solid (70%). MS (ESI): m/z=400.167 [M+H]$^+$.

c) (4-Iodo-pyridin-3-yl)-oxazol-2-ylmethyl-carbamic acid tert-butyl ester

The title compound was prepared in analogy to example 85, intermediate c, from (4-iodo-pyridin-3-yl)-carbamic acid tert-butyl ester (example 85, intermediate d) and 2-chloromethyl-oxazole (CAS RN 185246-17-7). Light yellow oil (93%). MS (ESI): m/z=402.031 [M+H]$^+$.

Example 23

N-[4-(4-Fluoro-2-methyl-phenyl)-pyridin-3-yl]-N-methyl-3,5-bis-trifluoromethyl-benzamide

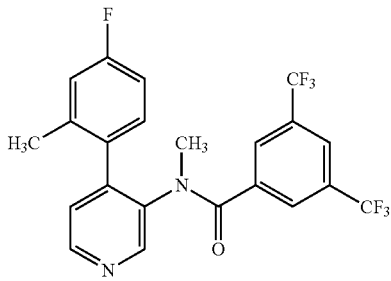 [SMILES: Cc1cc(F)ccc1-c1ccncc1N(C)C(=O)c1cc(C(F)(F)F)cc(C(F)(F)F)c1]

To a solution of 4-(4-fluoro-2-methylphenyl)-N-methyl-pyridin-3-amine (47 mg, 0.22 mmol) and DIPEA (57 µL, 0.33 mmol) was added 3,5-bis(trifluoromethyl)benzoyl chloride (78 mg, 0.28 mmol, CAS RN 1271-19-8) in CH$_2$Cl$_2$ (2 mL). After stirring for 16 hours, the reaction mixture was loaded directly onto a silica gel column and elution with EtOAc gave the title compound as a waxy oil which solidified upon standing (56 mg, 56%). MS (ESI): m/z=457.0 [M+H]$^+$.

Intermediates a) 4-(4-Fluoro-2-methylphenyl)-N-methylpyridin-3-amine

To a stirring solution of tert-butyl 4-(4-fluoro-2-methylphenyl)pyridin-3-ylcarbamate (230 mg, 0.76 mmol) in THF (5 mL) under argon was added NaH (23.9 mg, 1 mmol). After 15 min iodomethane (62 µL, 1 mmol) was added and the reaction mixture was stirred for 1 h. The reaction mixture was poured into saturated aqueous NH$_4$Cl solution and extracted three times with EtOAc. The combined organic phases were washed with brine and dried over MgSO$_4$. Filtration followed by removal of volatiles under reduced pressure gave the N-methylated product [4-(4-fluoro-2-methyl-phenyl)-pyridin-3-yl]-methyl-carbamic acid tert-butyl ester as a light brown oil. This oil was treated with 4M HCl in dioxane for 1 h. Removal of volatiles gave an oily solid which was suspended in CH$_2$Cl$_2$ and washed with 1M aqueous K$_2$CO$_3$ solution. The aqueous phase was extracted twice more with CH$_2$Cl$_2$ and the combined organic phases were dried over MgSO$_4$. Filtration followed by removal of volatiles gave the desired product (113 mg, 69%) which was pure enough for the next step without further purification.

b) Tert-butyl 4-(4-fluoro-2-methylphenyl)pyridin-3-ylcarbamate

DMAP (130 mg, 1.07 mmol) was added to a solution of 4-(4-fluoro-2-methylphenyl)pyridin-3-amine (720 mg, 3.56 mmol) and di-tert-butyl dicarbonate (1.01 g, 4.63 mmol, CAS RN 24424-99-5) in CH$_2$Cl$_2$ (20 mL). The reaction mixture was stirred for 16 hours at room temperature. All volatiles were then removed under reduced pressure and the title compound was isolated by chromatography on silica gel (50% EtOAc in n-hexane) as a colorless solid (268 mg, 25%) which was pure enough for the next step without further purification.

c) 4-(4-Fluoro-2-methylphenyl)pyridin-3-amine

Zinc dust (4.37 g, 66.7 mmol) was added in three portions over 15 min to 4-(4-fluoro-2-methylphenyl)-3-nitropyridine (3.1 g, 13.3 mmol) in acetic acid (30 mL) The reaction mixture was then heated to 70° C. for two hours. After cooling to room temperature, the reaction mixture was filtered through Celite and all volatiles were removed under reduced pressure. The resulting oil was suspended in EtOAc and washed with saturated aqueous NaHCO₃ solution and brine. The organic phase was dried over MgSO₄ and filtered. Evaporation of volatiles under reduced pressure gave the crude product which was purified by flash chromatography (EtOAc) to yield the desired compound (890 mg, 33%). The material was used in the next step without further purification.

d) 4-(4-Fluoro-2-methylphenyl)-3-nitropyridine

A solution of 4-chloro-3-nitropyridine (2.4 g, 15.1 mmol, CAS RN 13091-23-1), 4-fluoro-2-methylphenylboronic acid (2.8 g, 18.2 mmol, CAS RN 139911-29-8), potassium carbonate (6.28 g, 45.4 mmol) and palladium tetrakis-triphenylphosphine (794 mg, 0.76 mmol, CAS RN 14221-01-3) in dioxane (75 mL) was heated to reflux for 16 hours. After cooling to room temperature, the reaction mixture was filtered through Celite and all volatiles were removed under reduced pressure. Column chromatography on silica gel (20-33% EtOAc in n-hexane) afforded 4-(4-fluoro-2-methylphenyl)-3-nitropyridine as a yellow crystalline solid (3.2 g, 90%) which was used in the next step without further purification.

Example 24

3,5-Dichloro-N-[4-(4-fluoro-2-methyl-phenyl)-pyridin-3-yl]-N-methyl-benzamide

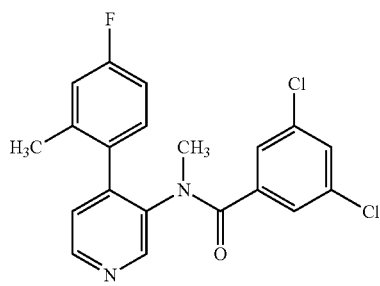 [SMILES: Cc1cc(F)ccc1-c1ccncc1N(C)C(=O)c1cc(Cl)cc(Cl)c1]

To a solution of 4-(4-fluoro-2-methylphenyl)-N-methyl-pyridin-3-amine (60 mg, 0.28 mmol, example 23, intermediate a) and DIPEA (97 µL, 0.56 mmol) was added 3,5-dichlorobenzoyl chloride (87 mg, 0.42 mmol, CAS RN 2905-62-6) in CH₂Cl₂ (2 mL) After stirring for 16 hours, the reaction mixture was loaded directly onto a silica gel column and elution with EtOAc gave the title compound (43 mg, 40%). MS (ESI): m/z=388.9 [M+H]⁺.

Example 25

N-[4-(2-Fluoro-phenyl)-pyridin-3-yl]-N-methyl-3,5-bis-trifluoromethyl-benzamide

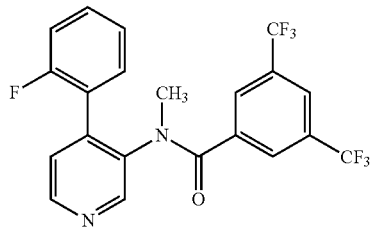 [SMILES: CN(C(=O)c1cc(C(F)(F)F)cc(C(F)(F)F)c1)c1cnccc1-c1ccccc1F]

A solution of N-(4-bromo-pyridin-3-yl)-N-methyl-3,5-bis-trifluoromethyl-benzamide (120 mg, 0.281 mmol), 2-fluorophenylboronic acid (472 mg, 0.337 mmol, CAS RN 1993-03-9) and K₂CO₃ (155 mg, 1.124 mmol) in a mixture of water:ethanol:toluene (10 mL; 0.5:1:3) was thoroughly degassed for 30 min at 25° C. under an atmosphere of argon in a sealed tube. Pd(PPh₃)₄ (32.5 mg, 0.0281 mmol, CAS RN 14221-01-3) was then added to the mixture, and continued degassing for another 15 min. The reaction mixture was heated to 90-100° C. for 14 hours. After the completion of reaction, the mixture was filtered though a bed of celite and the residue washed with EtOAc. The combined filtrates were evaporated in vacuo and the resultant residue was diluted with EtOAc. The organic layer washed with brine, dried over anhydrous Na₂SO₄, filtered and concentrated in vacuo. The crude residue thus obtained was purified by preparative HPLC to afford the desired compound as an off-white solid (69%). MS (ESI): m/z=443.2 [M+H]⁺.

Intermediates a) N-(4-Bromo-pyridin-3-yl)-N-methyl-3,5-bis-trifluoromethyl-benzamide To a solution of (4-bromo-pyridin-3-yl)-methyl-amine (1 g, 5.376 mmol) in THF (8 mL) was added LiHMDS (1M solution in THF, 10.7 mL, 10.7 mmol, CAS RN 4039-32-1) dropwise at −78° C., and stirred for 15 minutes before 3,5-bis-trifluoromethyl-benzoyl chloride (1.5 mL, 8.06 mmol, CAS RN 785-56-8) was added to the reaction mixture. After stirring at −78° C. for 1 h the reaction mixture was quenched with saturated aqueous NH₄Cl solution (10 mL) and diluted with EtOAc (40 mL) The combined organic layers were washed with brine (15 mL), dried over anhydrous Na₂SO₄, filtered, and evaporated off in vacuo. The residue was purified by column chromatography over silica gel (15% EtOAc in n-hexane) to afford the title compound. Pale yellow solid (985 mg, 43%). MS (ESI): m/z=427.2 [M+H]⁺.

b) (4-Bromo-pyridin-3-yl)-methyl-amine

A mixture of 4-bromo-pyridin-3-ylamine (2 g, 11.56 mmol, CAS RN 239137-39-4) in trimethyl orthoformate (19 mL, 173.4 mmol, CAS RN 149-73-5) and a catalytic amount of TFA (1 drop) was heated to reflux for 2 hours. Volatiles were removed in vacuo, the resultant dark brown material was dissolved in THF (40 mL), treated portionwise with LiAlH₄ (440 mg, 11.56 mmol) at 0° C. and then left stirring at 0° C. for 30 minutes. The reaction mixture was quenched with saturated aqueous NH₄Cl solution (15 mL), filtered through a bed of celite, and the residue further washed with EtOAc (30 mL). The combined organic layers were washed with brine, dried over anhydrous Na₂SO₄, filtered, and evaporated off in vacuo. The residue was purified by column chromatography over alumina (10% EtOAc in n-hexane) to afford the title compound. Light yellow oil (875 mg, 40%). MS (ESI): m/z=187.2 [M+H]⁺.

Example 26

N-[4-(2,4-Dimethyl-phenyl)-pyridin-3-yl]-N-methyl-3,5-bis-trifluoromethyl-benzamide

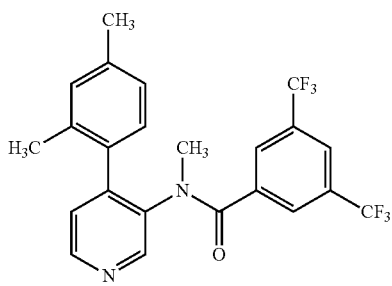 [SMILES: Cc1ccc(-c2ccncc2N(C)C(=O)c2cc(C(F)(F)F)cc(C(F)(F)F)c2)c(C)c1]

The title compound was prepared in analogy to example 25, from N-(4-bromo-pyridin-3-yl)-N-methyl-3,5-bis-trifluoromethyl-benzamide (example 25, intermediate a) and 2,4-dimethylbenzeneboronic acid (CAS RN 55499-44-0). Colorless solid (52%). MS (ESI): m/z=453.4 [M+H]⁺.

Example 27

N-[4-(4-Methoxy-2-methyl-phenyl)-pyridin-3-yl]-N-methyl-3,5-bis-trifluoromethyl-benzamide

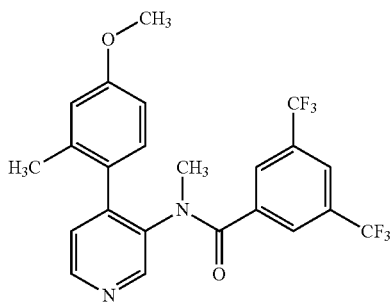 [SMILES: COc1ccc(-c2ccncc2N(C)C(=O)c2cc(C(F)(F)F)cc(C(F)(F)F)c2)c(C)c1]

The title compound was prepared in analogy to example 25, from N-(4-bromo-pyridin-3-yl)-N-methyl-3,5-bis-trifluoromethyl-benzamide (example 25, intermediate a) and 4-methoxy-2-methylphenylboronic acid (CAS RN 208399-66-0). Pale yellow sticky solid (67%). MS (ESI): m/z=469.2 [M+H]⁺.

Example 28

N-Methyl-3,5-bis-trifluoromethyl-N-[4-(2-trifluoromethyl-phenyl)-pyridin-3-yl]-benzamide

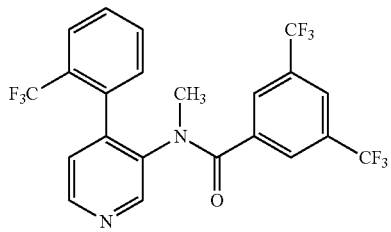 [SMILES: CN(C(=O)c1cc(C(F)(F)F)cc(C(F)(F)F)c1)c1cnccc1-c1ccccc1C(F)(F)F]

The title compound was prepared in analogy to example 25, from N-(4-bromo-pyridin-3-yl)-N-methyl-3,5-bis-trifluoromethyl-benzamide (example 25, intermediate a) and 2-trifluoromethylphenylboronic acid (CAS RN 1423-27-4). Off-white solid (60%). MS (ESI): m/z=493.4 [M+H]⁺.

Example 29

N-[4-(2-Methoxy-phenyl)-pyridin-3-yl]-N-methyl-3,5-bis-trifluoromethyl-benzamide

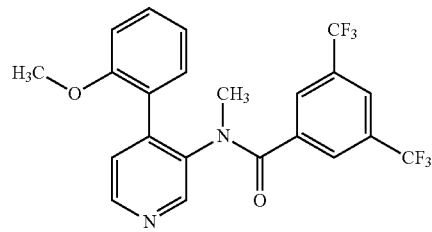 [SMILES: COc1ccccc1-c1ccncc1N(C)C(=O)c1cc(C(F)(F)F)cc(C(F)(F)F)c1]

The title compound was prepared in analogy to example 25, from N-(4-bromo-pyridin-3-yl)-N-methyl-3,5-bis-trifluoromethyl-benzamide (example 25, intermediate a) and 2-methoxyphenylboronic acid (CAS RN 5720-06-9). Off-white solid (45%). MS (ESI): m/z=455.4 [M+H]⁺.

Example 30

N-[4-(4-Chloro-2-methyl-phenyl)-pyridin-3-yl]-N-methyl-3,5-bis-trifluoromethyl-benzamide

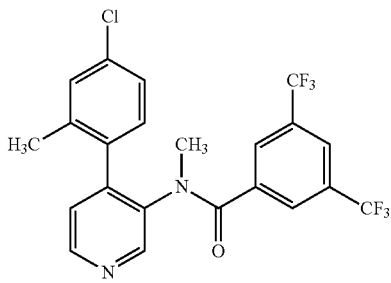 [SMILES: Cc1cc(Cl)ccc1-c1ccncc1N(C)C(=O)c1cc(C(F)(F)F)cc(C(F)(F)F)c1]

The title compound was prepared in analogy to example 25, from N-(4-bromo-pyridin-3-yl)-N-methyl-3,5-bis-trifluoromethyl-benzamide (example 25, intermediate a) and 4-chloro-2-methylphenylboronic acid (CAS RN 209919-30-2). Off-white solid (27%). MS (ESI): m/z=472.8 [M+H]$^+$.

Example 31

N-Methyl-N-[4-(2-trifluoromethoxy-phenyl)-pyridin-3-yl]-3,5-bis-trifluoromethyl-benzamide

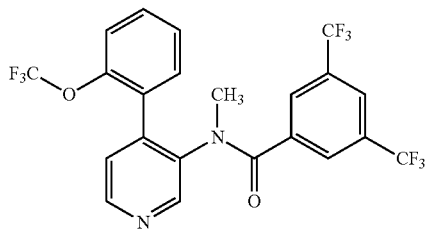 [SMILES: CN(C(=O)c1cc(C(F)(F)F)cc(C(F)(F)F)c1)c1cnccc1-c1ccccc1OC(F)(F)F]

The title compound was prepared in analogy to example 25, from N-(4-bromo-pyridin-3-yl)-N-methyl-3,5-bis-trifluoromethyl-benzamide (example 25, intermediate a) and 2-(trifluormethoxy)phenylboronic acid (CAS RN 175676-65-0). Off-white solid (34%). MS (ESI): m/z=509.4 [M+H]$^+$.

Example 32

N-(2-Methoxy-[3,4']bipyridinyl-3'-yl)-N-methyl-3,5-bis-trifluoromethyl-benzamide

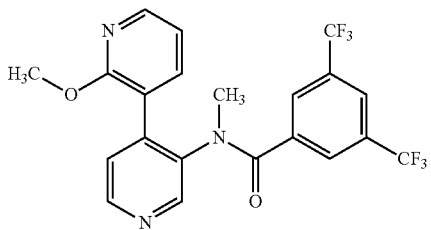 [SMILES: COc1ncccc1-c1ccncc1N(C)C(=O)c1cc(C(F)(F)F)cc(C(F)(F)F)c1]

The title compound was prepared in analogy to example 25, from N-(4-bromo-pyridin-3-yl)-N-methyl-3,5-bis-trifluoromethyl-benzamide (example 25, intermediate a) and 2-methoxy-3-pyridinyl boronic acid (CAS RN 163105-90-6) and using DMF as reaction solvent. Colorless solid (23%). MS (ESI): m/z=455.8 [M+H]$^+$.

Example 33

N-Methyl-N-(2-methyl-[3,4']bipyridinyl-3'-yl)-3,5-bis-trifluoromethyl-benzamide

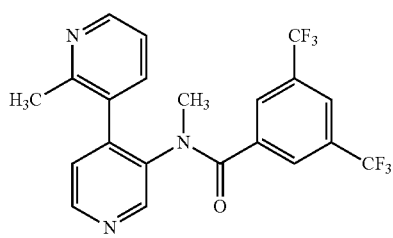

The title compound was prepared in analogy to example 25, from N-(4-bromo-pyridin-3-yl)-N-methyl-3,5-bis-trifluoromethyl-benzamide (example 25, intermediate a) and 2-methylpyridine-3-boronic acid (CAS RN 899436-71-6) and using DMF as solvent for the reaction. Yellow sticky liquid (11%). MS (ESI): m/z=439.8 [M+H]$^+$.

Example 34

N-Methyl-N-(3'-methyl-[4,4']bipyridinyl-3-yl)-3,5-bis-trifluoromethyl-benzamide

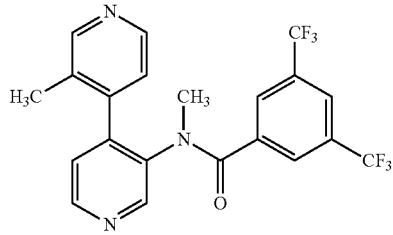 [SMILES: Cc1cnccc1-c1ccncc1N(C)C(=O)c1cc(C(F)(F)F)cc(C(F)(F)F)c1]

The title compound was prepared in analogy to example 25, from N-(4-bromo-pyridin-3-yl)-N-methyl-3,5-bis-trifluoromethyl-benzamide (example 25, intermediate a) and 3-methylpyridine-4-boronic acid (CAS RN 894808-72-1) and using DMF as solvent for the reaction. Colorless solid (13%). MS (ESI): m/z=440.2 [M+H]$^+$.

Example 35

N-[4-(2-Isopropoxy-phenyl)-pyridin-3-yl]-N-methyl-3,5-bis-trifluoromethyl-benzamide

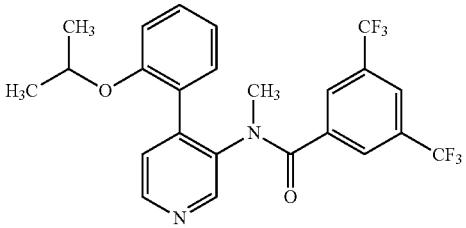 [SMILES: CC(C)Oc1ccccc1-c1ccncc1N(C)C(=O)c1cc(C(F)(F)F)cc(C(F)(F)F)c1]

The title compound was prepared in analogy to example 25, from N-(4-bromo-pyridin-3-yl)-N-methyl-3,5-bis-trifluoromethyl-benzamide (example 25, intermediate a) and 2-isopropoxyphenylboronic acid (CAS RN 138008-97-6). Black solid (25%). MS (ESI): m/z=483.0 [M+H]$^+$.

Example 36

N-[4-(2-Cyano-phenyl)-pyridin-3-yl]-N-methyl-3,5-bis-trifluoromethyl-benzamide

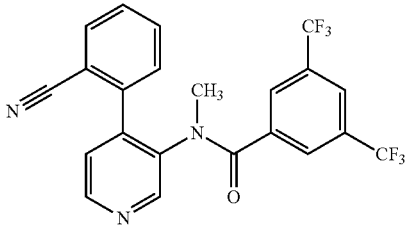 [SMILES: CN(C(=O)c1cc(C(F)(F)F)cc(C(F)(F)F)c1)c1cnccc1-c1ccccc1C#N]

The title compound was prepared in analogy to example 25, from N-(4-iodo-pyridin-3-yl)-N-methyl-3,5-bis-trifluoromethyl-benzamide and 2-cyanophenylboronic acid (CAS RN 138642-62-3) and using DMF as solvent for the reaction. Off-white solid (21%). MS (ESI): m/z=450.0 [M+H]$^+$.

Intermediates a) N-(4-Iodo-pyridin-3-yl)-N-methyl-3,5-bis-trifluoromethyl-benzamide The title compound was prepared in analogy to example 25, intermediate a, from (4-iodo-pyridin-3-yl)-methyl-amine and 3,5-bis-trifluoromethyl-benzoyl chloride (CAS RN 785-56-8). Pale yellow liquid (15%). MS (ESI): m/z=475 [M+H]$^+$.

b) (4-Iodo-pyridin-3-yl)-methyl-amine

The title compound was prepared in analogy to example 25, intermediate b, from 4-iodo-pyridin-3-ylamine. Brown oil (22%) which was pure enough to be used in the next step.

c) 4-Iodo-pyridin-3-ylamine

A solution of N-(4-iodo-pyridin-3-yl)-2,2-dimethyl-propionamide (6 g, 19.73 mmol) in aqueous 3M HCl (50 mL) was heated to 100° C. for 18 hours. After the completion of reaction, the reaction mass was washed with EtOAc. Under cooling the pH of the aqueous layer was adjusted to pH 9 using solid Na$_2$CO$_3$ and the aqueous layer was extracted with EtOAc. The combined organic layers were washed with brine, dried over anhydrous Na$_2$SO$_4$, filtered, and concentrated in vacuo to afford 4-iodo-pyridin-3-ylamine (3.2 g crude, 73%) as a brown sticky solid that was used in the next step without further purification.

d) N-(4-Iodo-pyridin-3-yl)-2,2-dimethyl-propionamide

To a solution of 2,2-dimethyl-N-pyridin-3-yl-propionamide (7 g, 39.32 mmol) in THF (50 mL) was added TMEDA (20 mL, CAS RN 110-18-9) at 25° C. The mixture was cooled to −70° C., n-butyllithium was added (66 mL, 1.6M solution in n-hexane, CAS RN 109-72-8) within a period of 30 min under an atmosphere of argon. The reaction mixture was allowed to stir at −15° C. for 1 h, followed by another 1 h at 0° C. The reaction mixture was re-cooled to −70° C., then a solution of iodine (29.2 g, 115.1 mmoL) in THF (120 mL) was added slowly during 1 h, and the resultant mixture was allowed to stir at 25° C. for 16 h. Water and saturated aqueous Na$_2$S$_2$O$_3$ solution was added to the mixture, and then extracted with EtOAc. The combined organic layers were washed with brine, dried over anhydrous Na$_2$SO$_4$, filtered and concentrated in vacuo to afford the crude residue which was purified by column chromatography over silica gel (40% EtOAc in n-hexane) to give the title compound. Pale yellow solid (800 mg, 37%). MS (ESI): m/z=305.4 [M+H]$^+$.

e) 2,2-Dimethyl-N-pyridin-3-yl-propionamide

To a solution of pyridin-3-ylamine (20 g, 212.49 mmol, CAS RN 462-08-8) in a mixture of THF:Et$_2$O (175 mL; 2.5:1 v/v) was added slowly a solution of pivaloyl chloride (26 mL, 212.5 mmol, CAS RN 3282-30-2) in THF (50 mL) and Et$_3$N (44 mL, 318.7 mmol) at 0° C. and left stirring at that temperature for 1 h. After the completion of reaction, the reaction mixture was filtered, and the filtrate was evaporated in vacuo. The crude filter cake was washed with n-hexane to yield the title compound. Colorless crystalline solid (32 g, 85%). MS (ESI): m/z=179.4 [M+H]$^+$.

Example 37

N-[4-(2,4-Difluoro-phenyl)-pyridin-3-yl]-N-methyl-3,5-bis-trifluoromethyl-benzamide

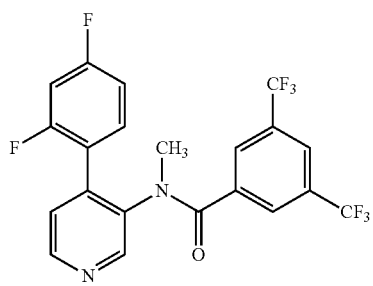 [SMILES: CN(C(=O)c1cc(C(F)(F)F)cc(C(F)(F)F)c1)c1cnccc1-c1ccc(F)cc1F]

The title compound was prepared in analogy to example 25, from N-(4-bromo-pyridin-3-yl)-N-methyl-3,5-bis-trifluoromethyl-benzamide (example 25, intermediate a) and 2,4-difluorophenylboronic acid (CAS RN 144025-03-6) and using DMF as reaction solvent. Off-white solid (60%). MS (ESI): m/z=461.0 [M+H]$^+$.

Example 38

N-[4-(4-Fluoro-2-methoxy-phenyl)-pyridin-3-yl]-N-methyl-3,5-bis-trifluoromethyl-benzamide

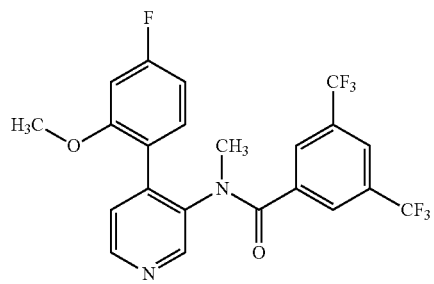 [SMILES: COc1cc(F)ccc1-c1ccncc1N(C)C(=O)c1cc(C(F)(F)F)cc(C(F)(F)F)c1]

The title compound was prepared in analogy to example 25, from N-(4-bromo-pyridin-3-yl)-N-methyl-3,5-bis-trifluoromethyl-benzamide (example 25, intermediate a) and 4-fluoro-2-methoxyphenylboronic acid (CAS RN 179899-07-1) and using DMF as reaction solvent. Off-white solid (38%). MS (ESI): m/z=473.4 [M+H]$^+$.

Example 39

N-[4-(4,5-Difluoro-2-methoxy-phenyl)-pyridin-3-yl]-N-methyl-3,5-bis-trifluoromethyl-benzamide

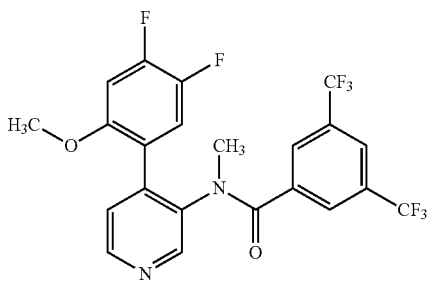 [SMILES: COc1cc(F)c(F)cc1-c1ccncc1N(C)C(=O)c1cc(C(F)(F)F)cc(C(F)(F)F)c1]

The title compound was prepared in analogy to example 25, from N-(4-bromo-pyridin-3-yl)-N-methyl-3,5-bis-trifluoromethyl-benzamide (example 25, intermediate a) and 4,5-difluoro-2-methoxy phenylboronic acid (CAS RN 870777-32-5) and using DMF as reaction solvent. Off-white solid (27%). MS (ESI): m/z=491.4 [M+H]$^+$.

Example 40

N-[4-(2,3-Difluoro-phenyl)-pyridin-3-yl]-N-methyl-3,5-bis-trifluoromethyl-benzamide

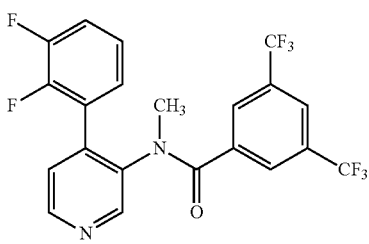 [SMILES: CN(C(=O)c1cc(C(F)(F)F)cc(C(F)(F)F)c1)c1cnccc1-c1cccc(F)c1F]

The title compound was prepared in analogy to example 25, from N-(4-bromo-pyridin-3-yl)-N-methyl-3,5-bis-trifluoromethyl-benzamide (example 25, intermediate a) and 2,3-difluorophenylboronic acid (CAS RN 121219-16-7) and using DMF as reaction solvent. Off-white solid (14%). MS (ESI): m/z=461.2 [M+H]$^+$.

Example 41

N-[4-(3-Fluoro-2-methoxy-phenyl)-pyridin-3-yl]-N-methyl-3,5-bis-trifluoromethyl-benzamide

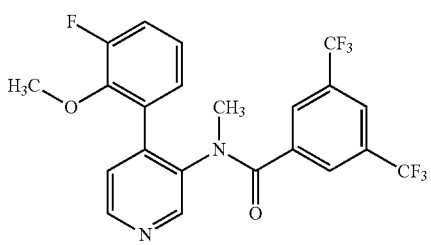 [SMILES: COc1c(F)cccc1-c1ccncc1N(C)C(=O)c1cc(C(F)(F)F)cc(C(F)(F)F)c1]

The title compound was prepared in analogy to example 25, from N-(4-bromo-pyridin-3-yl)-N-methyl-3,5-bis-trifluoromethyl-benzamide (example 25, intermediate a) and 3-fluoro-2-methoxyphenylboronic acid (CAS RN 762287-59-2) and using DMF as reaction solvent. Off-white solid (27%). MS (ESI): m/z=473.2 [M+H]$^+$.

Example 42

N-[4-(2-Fluoro-5-methyl-phenyl)-pyridin-3-yl]-N-methyl-3,5-bis-trifluoromethyl-benzamide

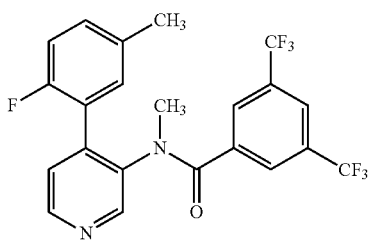 [SMILES: Cc1ccc(F)c(-c2ccncc2N(C)C(=O)c2cc(C(F)(F)F)cc(C(F)(F)F)c2)c1]

The title compound was prepared in analogy to example 25, from N-(4-bromo-pyridin-3-yl)-N-methyl-3,5-bis-trifluoromethyl-benzamide (example 25, intermediate a) and 2-fluoro-5-methylphenylboronic acid (CAS RN 166328-16-1) and using DMF as reaction solvent. Pale yellow solid (26%). MS (ESI): m/z=457.2 [M+H]$^+$.

Example 43

N-[4-(2-Benzyloxy-4-fluoro-phenyl)-pyridin-3-yl]-N-methyl-3,5-bis-trifluoromethyl-benzamide

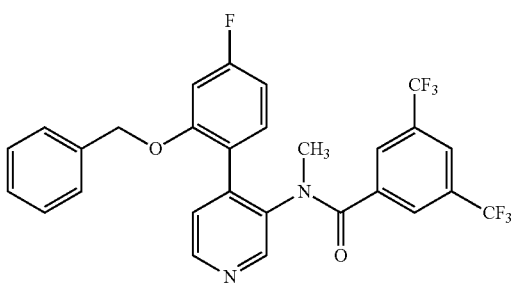 [SMILES: CN(C(=O)c1cc(C(F)(F)F)cc(C(F)(F)F)c1)c1cnccc1-c1ccc(F)cc1OCc1ccccc1]

The title compound was prepared in analogy to example 25, from N-(4-bromo-pyridin-3-yl)-N-methyl-3,5-bis-trifluoromethyl-benzamide (example 25, intermediate a) and 2-benzyloxy-4-fluorophenylboronic acid (CAS RN 848779-87-3) and using DMF as reaction solvent. Off-white solid (29%). MS (ESI): m/z=549.0 [M+H]$^+$.

Example 44

N-(5-Fluoro-2-methoxy-[3,4']bipyridinyl-3'-yl)-N-methyl-3,5-bis-trifluoromethyl-benzamide

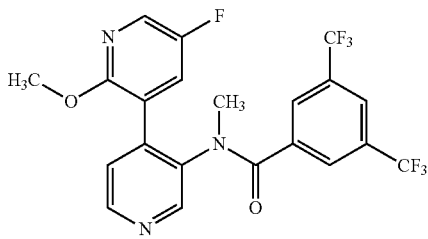 [SMILES: COc1ncc(Cl)cc1-c1ccncc1N(C)C(=O)c1cc(C(F)(F)F)cc(C(F)(F)F)c1]

The title compound was prepared in analogy to example 25, from N-(4-bromo-pyridin-3-yl)-N-methyl-3,5-bis-trifluoromethyl-benzamide (example 25, intermediate a) and 5-fluoro-2-methoxypyridine-3-boronic acid (CAS RN 957120-32-0) and using DMF as reaction solvent. Off-white solid (27%). MS (ESI): m/z=474.1 [M+H]$^+$.

Example 45

N-(5-Chloro-2-methoxy-[3,4']bipyridinyl-3'-yl)-N-methyl-3,5-bis-trifluoromethyl-benzamide

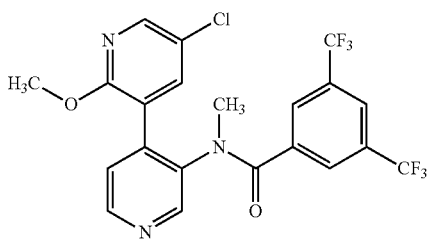

The title compound was prepared in analogy to example 25, from N-(4-bromo-pyridin-3-yl)-N-methyl-3,5-bis-trifluoromethyl-benzamide (example 25, intermediate a) and 5-chloro-2-methoxypyridine-3-boronic acid (CAS RN 943153-22-8) and using DMF as reaction solvent. Off-white solid (28%). MS (ESI): m/z=490.0 [M+H]$^+$.

Example 46

N-(2-Isopropoxy-[3,4']bipyridinyl-3'-yl)-N-methyl-3,5-bis-trifluoromethyl-benzamide

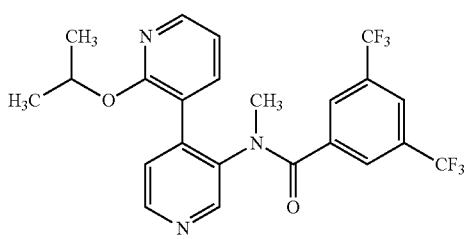

The title compound was prepared in analogy to example 25, from N-(4-bromo-pyridin-3-yl)-N-methyl-3,5-bis-trifluoromethyl-benzamide (example 25, intermediate a) and 2-isopropoxypyridine-3-boronic acid pinacol ester (CAS RN 848243-25-4) and using DMF as reaction solvent. Off-white solid (13%). MS (ESI): m/z=483.8 [M+H]$^+$.

Example 47

N-(2-Methoxy-6-methyl-[3,4']bipyridinyl-3'-yl)-N-methyl-3,5-bis-trifluoromethyl-benzamide

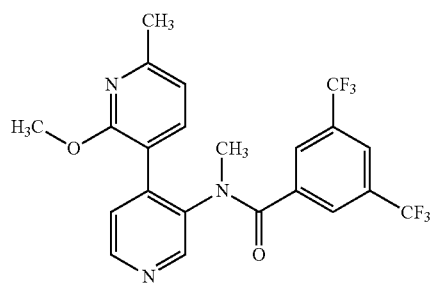 [SMILES: COc1nc(C)ccc1-c1ccncc1N(C)C(=O)c1cc(C(F)(F)F)cc(C(F)(F)F)c1]

The title compound was prepared in analogy to example 25, from N-(4-bromo-pyridin-3-yl)-N-methyl-3,5-bis-trifluoromethyl-benzamide (example 25, intermediate a) and 2-methoxy-6-methylpyridine-3-boronic acid (CAS RN 1000802-75-4) and using DMF as reaction solvent. Off-white solid (42%). MS (ESI): m/z=469.8 [M+H]$^+$.

Example 48

N-[4-(4-Fluoro-2-hydroxy-phenyl)-pyridin-3-yl]-N-methyl-3,5-bis-trifluoromethyl-benzamide

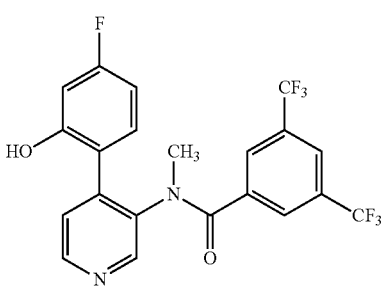 [SMILES: CN(C(=O)c1cc(C(F)(F)F)cc(C(F)(F)F)c1)c1cnccc1-c1ccc(F)cc1O]

A solution of N-[4-(2-benzyloxy-4-fluoro-phenyl)-pyridin-3-yl]-N-methyl-3,5-bis-trifluoromethyl-benzamide (65 mg, 0.118 mmol, example 43) in MeOH (10 mL) was purged with argon for 20 minutes before 10% Pd—C (10 mg) was added. The resulting reaction mixture was hydrogenated under balloon pressure hydrogen at 25° C. for 16 hours. The reaction mixture was filtered through a bed of celite and the residue was further washed with EtOAc. The combined filtrate was concentrated in vacuo, and the crude material thus obtained was purified by column chromatography over silica gel (25-35% EtOAc in n-hexane) to give 45 mg of the desired compound. Off-white solid (60%). MS (ESI): m/z=459.0 [M+H]$^+$.

Example 49

(2-{3-[(3,5-Bis-trifluoromethyl-benzoyl)-methyl-amino]-pyridin-4-yl}-5-fluoro-phenoxy)-acetic acid methyl ester

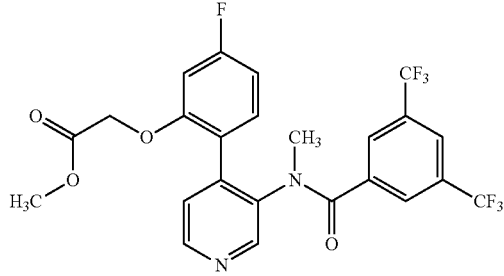

To a solution of N-[4-(4-fluoro-2-hydroxy-phenyl)-pyridin-3-yl]-N-methyl-3,5-bis-trifluoromethyl-benzamide (150 mg, 0.327 mmol, example 48) in DMF (5 mL) was added K$_2$CO$_3$ (90 mg, 0.654 mmol) and methyl chloroacetate (0.06 mL, 0.654 mmol, CAS RN 96-34-4) at 25° C. and the resulting mixture was heated to 70° C. for 16 hours. The mixture was diluted with EtOAc (25 mL), washed with brine (10 mL), dried over anhydrous Na$_2$SO$_4$, filtered and evaporated in vacuo. The crude material thus obtained was purified by column chromatography over silica gel (30% EtOAc in n-hexane) to give 100 mg of the title compound. Pale yellow solid (58%). MS (ESI): m/z=531.0 [M+H]$^+$.

Example 50

N-(3'-Chloro-2'-methoxy-[4,4']bipyridinyl-3-yl)-N-methyl-3,5-bis-trifluoromethyl-benzamide

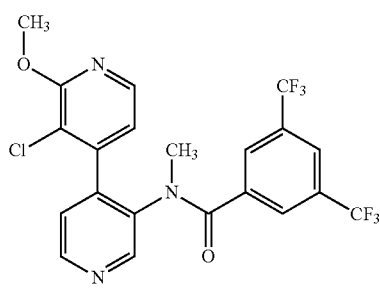 [SMILES: COc1nccc(-c2ccncc2N(C)C(=O)c2cc(C(F)(F)F)cc(C(F)(F)F)c2)c1Cl]

The title compound was prepared in analogy to example 25, from N-(4-bromo-pyridin-3-yl)-N-methyl-3,5-trifluoromethyl-benzamide (example 25, intermediate a) and 3-chloro-2-methoxypyridine-4-boronic acid (CAS RN 957060-88-7) and using DMF as solvent. Pale yellow sticky solid (11%). MS (ESI): m/z=489.9 [M+H]$^+$.

Example 51

N-[4-(2-Cyano methoxy-4-fluoro-phenyl)-pyridin-3-yl]-N-methyl-3,5-bis-trifluoromethyl-benzamide

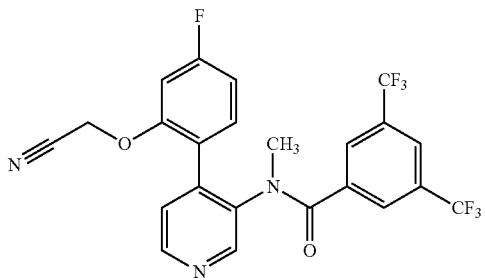 [SMILES: CN(C(=O)c1cc(C(F)(F)F)cc(C(F)(F)F)c1)c1cnccc1-c1ccc(F)cc1OCC#N]

The title compound was prepared in analogy to example 49, from N-[4-(4-fluoro-2-hydroxy-phenyl)-pyridin-3-yl]-N-methyl-3,5-bis-trifluoromethyl-benzamide (example 48) and bromoacetonitrile (CAS RN 590-17-0). Yellow solid (32%). MS (ESI): m/z=497.8 [M+H]$^+$.

Example 52

N-{4-[4-Fluoro-2-(2-hydroxy-ethoxy)-phenyl]-pyridin-3-yl}-N-methyl-3,5-bis-trifluoromethyl-benzamide

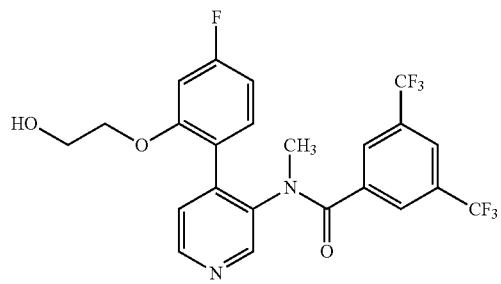 [SMILES: CN(C(=O)c1cc(C(F)(F)F)cc(C(F)(F)F)c1)c1cnccc1-c1ccc(F)cc1OCCO]

The title compound was prepared in analogy to example 49, from N-[4-(4-fluoro-2-hydroxy-phenyl)-pyridin-3-yl]-N-methyl-3,5-bis-trifluoromethyl-benzamide (example 48) and 2-chloroethanol (CAS RN 107-07-3). Off-white solid (62%). MS (ESI): m/z=502.9 [M+H]$^+$.

Example 53

N-{4-[2-(Cyano-methyl-methoxy)-4-fluoro-phenyl]-pyridin-3-yl}-N-methyl-3,5-bis-trifluoromethyl-benzamide

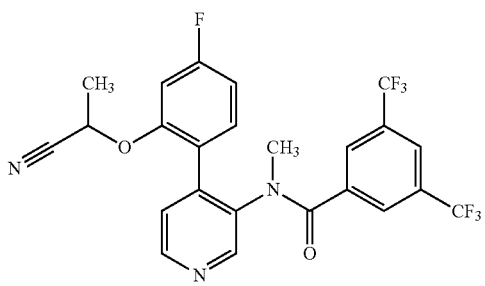

The title compound was prepared in analogy to example 49, from N-[4-(4-fluoro-2-hydroxy-phenyl)-pyridin-3-yl]-N-methyl-3,5-bis-trifluoromethyl-benzamide (example 48) and 2-bromopropionitrile (CAS RN 19481-82-4). Off-white solid (74%). MS (ESI): m/z=512.0 [M+H]⁺.

Example 54

N-[4-(3,6-Dimethoxy-pyridazin-4-yl)-pyridin-3-yl]-N-methyl-3,5-bis-trifluoromethyl-benzamide

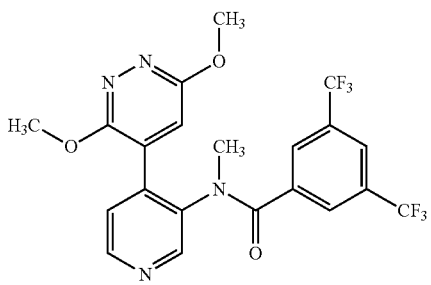 [SMILES: COc1cc(-c2ccncc2N(C)C(=O)c2cc(C(F)(F)F)cc(C(F)(F)F)c2)c(OC)nn1]

A solution of N-(4-bromo-pyridin-3-yl)-N-methyl-3,5-bis-trifluoromethyl-benzamide (example 25, intermediate a) (200 mg, 0.468 mmol), 3,6-dimethoxylpyridazine-4-boronic acid (129 mg, 0.702 mmol, CAS RN 1015480-87-1) and K₂CO₃ (194 mg, 1.404 mmol) in DMF (6 mL) in a sealed tube was degassed with argon for 30 minutes. To this mixture were added S-PHOS (96 mg, 0.234 mmol, CAS RN 657408-07-6) and Pd(PPh₃)₄ (44 mg, 0.046 mmol), degassed for another 15 minutes, and heated to 90° C. for 1 h in microwave. Work up and purification as described in example 25 yielded 15 mg of the title compound. Off-white solid (7%). MS (ESI): m/z=487.0 [M+H]⁺.

Example 55

N-(2-Chloro-5-fluoro-[3,4']bipyridinyl-3'-yl)-N-methyl-3,5-bis-trifluoromethyl-benzamide

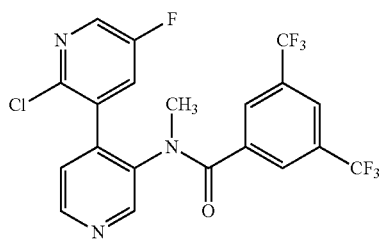 [SMILES: CN(C(=O)c1cc(C(F)(F)F)cc(C(F)(F)F)c1)c1cnccc1-c1cc(F)cnc1Cl]

To a solution of (2-chloro-5-fluoro-[3,4']bipyridinyl-3'-yl)-methyl-amine (80 mg, 0.34 mmol) in CH₂Cl₂ (10 mL) were added Et₃N (0.187 mL, 1.35 mmol) and 3,5-bis(trifluoromethyl)-benzoyl chloride (0.061 mL, 0.34 mmol, CAS RN 1271-19-8) at 25° C. and the resulting reaction mixture was stirred for 4 hours at 25° C. The mixture was diluted with CH₂Cl₂ (20 mL), the organic layer was washed with saturated aqueous NaHCO₃ solution (2×20 mL) and brine (25 mL), dried over Na₂SO₄, filtered and concentrated under vacuum to afford the crude product which was purified using preparative HPLC. Off-white solid (22 mg, 14%). MS (ESI): m/z=478.4 [M+H]⁺.

Intermediate (2-Chloro-5-fluoro-[3,4']bipyridinyl-3'-yl)-methyl-amine

To a solution of 2-chloro-5-fluoro-3-iodo-pyridine (100 mg, 0.388 mmol, CAS RN 884494-33-1) in THF (3 mL) was added iPrMgCl (2M solution in THF, 0.194 mL, 0.388 mmol, CAS RN 1068-55-9) at −20° C., and the mixture was stirred at this temperature for 1 hour. To this mixture was added a freshly prepared ZnCl₂ solution (1M solution in THF; 1.55 mL, 1.55 mmol) at −20° C. The reaction mixture was allowed to stir at 25° C. for 1.5 hours to give the corresponding zinc reagent. A solution of (4-iodo-pyridin-3-yl)-methyl-amine (91 mg, 0.388 mmol, example 36, intermediate b) in THF (2 mL) and Pd(PPh₃)₄ (22.44 mg, 0.019 mmol) were then added to this solution, and the reaction mixture was refluxed for 2 hours. The mixture was poured into 10% NaHCO₃ solution (15 mL), and extracted with EtOAc (2×15 mL) The combined organic layers were washed with brine (30 mL), dried over Na₂SO₄, filtered, and evaporated in vacuo to afford the desired compound (72 mg, 78%) as a brown sticky solid which was used in the next step without further purification. MS (ESI): m/z=238.1 [M+H]⁺.

Example 56

N-(2'-Chloro-3'-fluoro-[4,4']bipyridinyl-3-yl)-N-methyl-3,5-bis-trifluoromethyl-benzamide

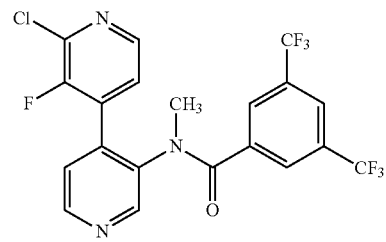 [SMILES: CN(C(=O)c1cc(C(F)(F)F)cc(C(F)(F)F)c1)c1cnccc1-c1ccnc(Cl)c1F]

The title compound was prepared in analogy to example 55, from (2'-chloro-3'-fluoro-[4,4']bipyridinyl-3-yl)-methyl-amine and 3,5-bis(trifluoromethyl)benzoyl chloride (CAS RN 1271-19-8) and using preparative HPLC for the chromatographic purification. Off-white solid (12%). MS (ESI): m/z=478.0 [M+H]⁺.

Intermediate (2'-Chloro-3'-fluoro-[4,4']bipyridinyl-3-yl)-methyl-amine

The title compound was prepared in analogy to example 55, intermediate, from 2-chloro-3-fluoro-4-iodo-pyridine (CAS RN 148639-07-0) and (4-iodo-pyridin-3-yl)-methyl-amine (example 36, intermediate b). Brown sticky solid (86%). MS (ESI): m/z=238.0 [M+H]⁺.

Example 57

N-Methyl-N-(3-methyl-[2,4']bipyridinyl-3'-yl)-3,5-bis-trifluoromethyl-benzamide

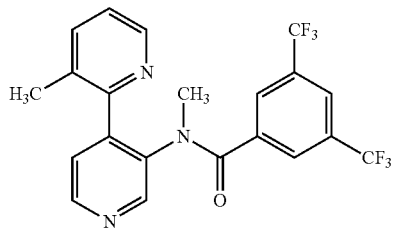 [SMILES: Cc1cccnc1-c1ccncc1N(C)C(=O)c1cc(C(F)(F)F)cc(C(F)(F)F)c1]

The title compound was prepared in analogy to example 55, from methyl-(3-methyl-[2,4']bipyridinyl-3'-yl)-amine and 3,5-bis(trifluoromethyl)benzoyl chloride (CAS RN 1271-19-8) and using preparative HPLC for the chromatographic purification. Off-white solid (20%). MS (ESI): m/z=440.4 [M+H]$^+$.

Intermediate

Methyl-(3-methyl-[2,4']bipyridinyl-3'-yl)-amine

The title compound was prepared in analogy to example 55, intermediate, from 3-methyl-2-pyridylzine bromide (CAS RN 308795-91-7) and (4-iodo-pyridin-3-yl)-methylamine (example 36, intermediate b). Light yellow sticky solid (93%). MS (ESI): m/z=200.3 [M+H]$^+$.

Example 58

N-[4-(5-Fluoro-2-methoxy-phenyl)-pyridin-3-yl]-N-methyl-3,5-bis-trifluoromethyl-benzamide

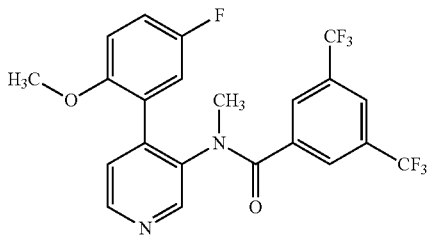 [SMILES: COc1ccc(F)cc1-c1ccncc1N(C)C(=O)c1cc(C(F)(F)F)cc(C(F)(F)F)c1]

To a solution of N-(4-bromo-pyridin-3-yl)-N-methyl-3,5-bis-trifluoromethyl-benzamide (100 mg, 0.23 mmol, example 25, intermediate a) and 5-fluoro-2-methoxybenzeneboronic acid (CAS RN 179897-94-0) (59.7 mg, 0.35 mmol) in dry DMF (3 mL) was added potassium carbonate (129.4 mg, 0.94 mmol) at 25° C. in a sealed tube and the reaction mixture was purged with argon for 10 min. Then Pd(PPh$_3$)$_4$ (27.05 mg, 0.023 mmol) was added and again purged with argon for 15 min. The reaction mixture was heated at 100° C. for 16 hours. The reaction mass was cooled to 25° C., filtered through a bed of celite and washed with EtOAc. The solvent was evaporated and the residue was dissolved in EtOAc and washed with water. The organic layer was washed with brine, dried over Na$_2$SO$_4$ and evaporated. The resulting crude product was purified by preparative HPLC. Off-white solid (55 mg, 50%). MS (ESI): m/z=473.2 [M+H]$^+$.

Example 59

N-[4-(3,5-Difluoro-2-methoxy-phenyl)-pyridin-3-yl]-N-methyl-3,5-bis-trifluoromethyl-benzamide

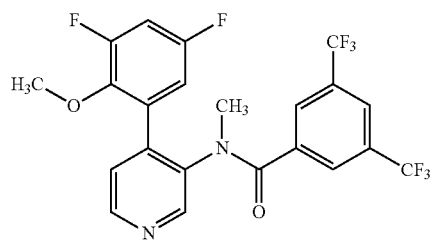

The title compound was prepared in analogy to example 58, from N-(4-bromo-pyridin-3-yl)-N-methyl-3,5-bis-trifluoromethyl-benzamide (example 25, intermediate a) and 2-methoxy-3,5-difluorophenylboronic acid (CAS RN 737000-76-9) and using preparative HPLC for the chromatographic purification. Off-white solid (49%). MS (ESI): m/z=491.1 [M+H]$^+$.

Example 60

N-[4-(3,4-Difluoro-2-methoxy-phenyl)-pyridin-3-yl]-N-methyl-3,5-bis-trifluoromethyl-benzamide

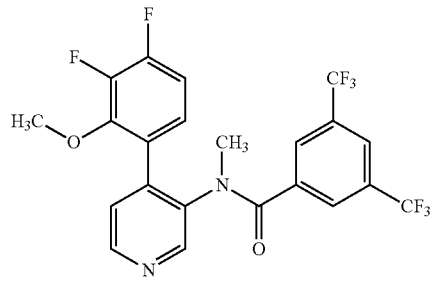

The title compound was prepared in analogy to example 58, from N-(4-bromo-pyridin-3-yl)-N-methyl-3,5-bis-trifluoromethyl-benzamide (example 25, intermediate a) and 2-methoxy-3,4-difluorophenylboronic acid (CAS RN 905583-06-4) and using preparative HPLC for the chromatographic purification. Off-white solid (49%). MS (ESI): m/z=491.1 [M+H]$^+$.

Example 61

N-[4-(2,5-Difluoro-phenyl)-pyridin-3-yl]-N-methyl-3,5-bis-trifluoromethyl-benzamide

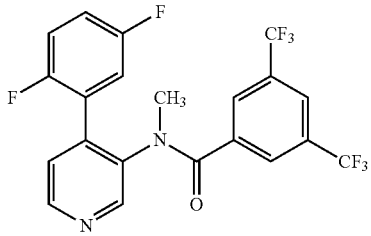 [SMILES: CN(C(=O)c1cc(C(F)(F)F)cc(C(F)(F)F)c1)c1cnccc1-c1cc(F)ccc1F]

The title compound was prepared in analogy to example 58, from N-(4-bromo-pyridin-3-yl)-N-methyl-3,5-bis-trifluoromethyl-benzamide (example 25, intermediate a) and 2,5-difluorophenyl-boronic acid (CAS RN 193353-34-3) and using preparative HPLC for the chromatographic purification. Off-white solid (36%). MS (ESI): m/z=461.2 [M+H]$^+$.

Example 62

N-[4-(2-Fluoro-3-methoxy-phenyl)-pyridin-3-yl]-N-methyl-3,5-bis-trifluoromethyl-benzamide

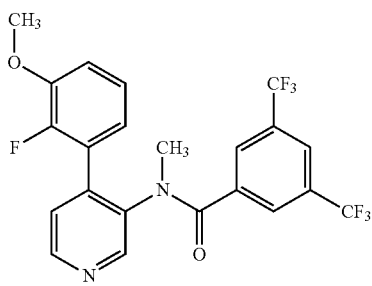 [SMILES: COc1cccc(-c2ccncc2N(C)C(=O)c2cc(C(F)(F)F)cc(C(F)(F)F)c2)c1F]

The title compound was prepared in analogy to example 58, from N-(4-bromo-pyridin-3-yl)-N-methyl-3,5-bis-trifluoromethyl-benzamide (example 25, intermediate a) and 2-fluoro-3-methoxy-phenylboronic acid (CAS RN 352303-67-4) and using preparative HPLC for the chromatographic purification. Off-white solid (42%). MS (ESI): m/z=472.8 [M+H]$^+$.

Example 63

N-[4-(2-Fluoro-5-methoxy-phenyl)-pyridin-3-yl]-N-methyl-3,5-bis-trifluoromethyl-benzamide

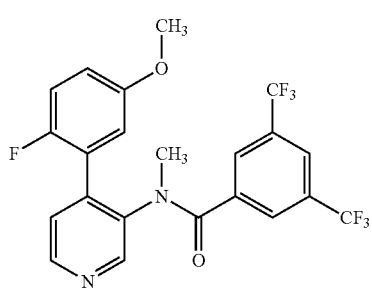 [SMILES: COc1ccc(F)c(-c2ccncc2N(C)C(=O)c2cc(C(F)(F)F)cc(C(F)(F)F)c2)c1]

The title compound was prepared in analogy to example 58, from N-(4-bromo-pyridin-3-yl)-N-methyl-3,5-bis-trifluoromethyl-benzamide (example 25, intermediate a) and 2-fluoro-5-methoxy-phenylboronic acid (CAS RN 406482-19-7) and using preparative HPLC for the chromatographic purification. Off-white solid (45%). MS (ESI): m/z=473.2 [M+H]$^+$.

Example 64

N-[4-(2,6-Difluoro-phenyl)-pyridin-3-yl]-N-methyl-3,5-bis-trifluoromethyl-benzamide

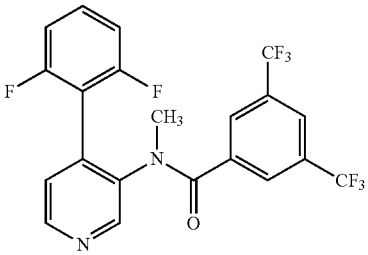 [SMILES: CN(C(=O)c1cc(C(F)(F)F)cc(C(F)(F)F)c1)c1cnccc1-c1c(F)cccc1F]

The title compound was prepared in analogy to example 58, from N-(4-bromo-pyridin-3-yl)-N-methyl-3,5-bis-trifluoromethyl-benzamide (example 25, intermediate a) and 2,6-difluorophenyl-boronic acid (CAS RN 162101-25-9) and using preparative HPLC for the chromatographic purification. Off-white solid (16%). MS (ESI): m/z=461.2 [M+H]$^+$.

Example 65

N-[4-(2-Chloro-3-fluoro-phenyl)-pyridin-3-yl]-N-methyl-3,5-bis-trifluoromethyl-benzamide

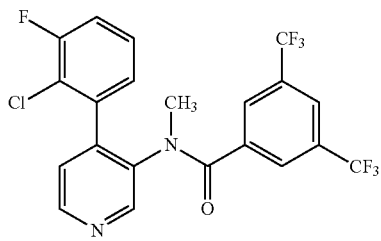 [SMILES: CN(C(=O)c1cc(C(F)(F)F)cc(C(F)(F)F)c1)c1cnccc1-c1cccc(F)c1Cl]

The title compound was prepared in analogy to example 58, from N-(4-bromo-pyridin-3-yl)-N-methyl-3,5-bis-trifluoromethyl-benzamide (example 25, intermediate a) and 2-chloro-3-fluoro-benzeneboronic acid (CAS RN 871329-52-1) and using preparative HPLC for the chromatographic purification. Off-white sticky solid (36%). MS (ESI): m/z=477.2 [M+H]$^+$.

Example 66

N-[4-(2-Fluoro-6-methoxy-phenyl)-pyridin-3-yl]-N-methyl-3,5-bis-trifluoromethyl-benzamide

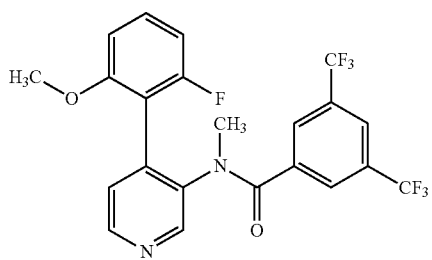 [SMILES: COc1cccc(F)c1-c1ccncc1N(C)C(=O)c1cc(C(F)(F)F)cc(C(F)(F)F)c1]

The title compound was prepared in analogy to example 58, from N-(4-bromo-pyridin-3-yl)-N-methyl-3,5-bis-trifluoromethyl-benzamide (example 25, intermediate a) and 2-fluoro-6-methoxy-phenylboronic acid (CAS RN 78495-63-3) and using preparative HPLC for the chromatographic purification. Off-white solid (36%). MS (ESI): m/z=473.2 [M+H]$^+$.

Example 67

N-[4-(2-Chloro-4-fluoro-phenyl)-pyridin-3-yl]-N-methyl-3,5-bis-trifluoromethyl-benzamide

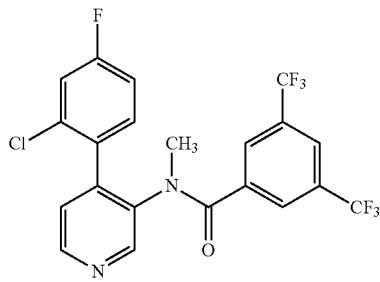 [SMILES: CN(C(=O)c1cc(C(F)(F)F)cc(C(F)(F)F)c1)c1cnccc1-c1ccc(F)cc1Cl]

The title compound was prepared in analogy to example 58, from N-(4-bromo-pyridin-3-yl)-N-methyl-3,5-bis-trifluoromethyl-benzamide (example 25, intermediate a) and 2-chloro-4-fluorophenyl-boronic acid (CAS RN 313545-72-1) and using preparative HPLC for the chromatographic purification. Brown sticky solid (33%). MS (ESI): m/z=476.8 [M+H]$^+$.

Example 68

N-(3-Fluoro-[2,4']bipyridinyl-3'-yl)-N-methyl-3,5-bis-trifluoromethyl-benzamide

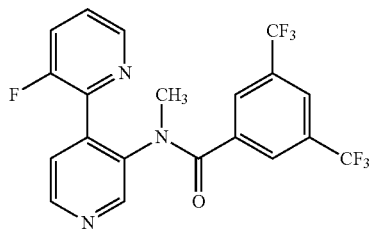 [SMILES: CN(C(=O)c1cc(C(F)(F)F)cc(C(F)(F)F)c1)c1cnccc1-c1ncccc1F]

The title compound was prepared in analogy to example 55, from (3-fluoro-[2,4']bipyridinyl-3'-yl)-methyl-amine and 3,5-bis(trifluoromethyl)benzoyl chloride (CAS RN 1271-19-8) and using preparative HPLC for the chromatographic purification. Brown Solid (13%). MS (ESI): m/z=444.4 [M+H]$^+$.

Intermediate (3-Fluoro-[2,4']bipyridinyl-3'-yl)-methyl-amine

To a solution of compound (4-bromo-pyridin-3-yl)-methyl-amine (50 mg, 0.267 mmol, example 25, intermediate b) and 3-fluoro pyridine-2-boronic acid pinacol ester (Milestone Pharmtech LLC) (89.4 mg 0.4 mmol) dissolved in dry DMF (3 mL) in a sealed tube was added cesium carbonate (348.4 mg, 1.07 mmol) and the reaction mixture was purged with argon for 10 min. Then Pd(OAc)$_2$ (9.38 mg, 0.013 mmol), dppf (1.48 mg, 0.0026 mmol) and CuCl (26.46 mg, 0.27 mmol) were added to the reaction mixture and again purged with nitrogen for 15 min. The reaction mixture was heated at 100° C. for 16 hours. The reaction mixture was cooled to 25° C., filtered through a bed of celite and washed with EtOAc. The organic layer was washed with water, dried over sodium sulphate and evaporated to yield the desired compound as a light yellow solid (50 mg, 92%) which was used in next step without further purification. MS (ESI): m/z=204.2 [M+H]$^+$.

Example 69

N-(3'-Methoxy-[4,4']bipyridinyl-3-yl)-N-methyl-3,5-bis-trifluoromethyl-benzamide

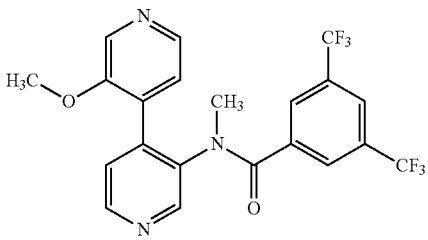

The title compound was prepared in analogy to example 55, from (3'-methoxy-[4,4']bipyridinyl-3-yl)-methyl-amine and 3,5-bis(trifluoromethyl)benzoyl chloride (CAS RN 1271-19-8) and using preparative HPLC for the chromatographic purification. Off-white solid (24%). MS (ESI): m/z=456.2 [M+H]$^+$.

Intermediate (3'-Methoxy-[4,4']bipyridinyl-3-yl)-methyl-amine

To a solution of (4-bromo-pyridin-3-yl)-methyl-amine (50 mg, 0.267 mmol, example 25, intermediate b) and 3-methoxypyridine-4-boronic acid (CAS RN 1008506-24-8) (61.35 mg, 0.4 mmol) in dry DMF (3 mL) in a sealed tube was added potassium carbonate (2.14 mmol) and the reaction mixture was purged with argon for 10 min. Then, Pd(PPh$_3$)$_4$ (30.89 mg, 0.03 mmol) was added and again purged with nitrogen for 15 min. The reaction mixture was heated at 100° C. for 16 hours. After cooling to room temperature the reaction mixture was filtered through a bed of celite and the filter cake washed with EtOAc. The solvent was evaporated, the residue was dissolved in EtOAc and washed with water. The organic layer was dried over sodium sulphate and evaporated to get compound that was used in next step without further purification. Brown solid (55 mg, 95%). MS (ESI): m/z=216.2 [M+H]$^+$.

Example 70

N-(3'-Fluoro-[4,4']bipyridinyl-3-yl)-N-methyl-3,5-bis-trifluoromethyl-benzamide

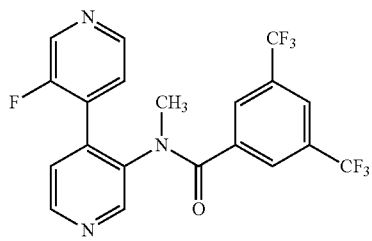 [SMILES: CN(C(=O)c1cc(C(F)(F)F)cc(C(F)(F)F)c1)c1cnccc1-c1ccncc1F]

The title compound was prepared in analogy to example 55, from (3'-fluoro-[4,4']bipyridinyl-3-yl)-methyl-amine and 3,5-bis(trifluoromethyl)benzoyl chloride (CAS RN 1271-19-8) and using preparative HPLC for the chromatographic purification. Off-white solid (5%). MS (ESI): m/z=444.4 [M+H]$^+$.

Intermediate (3'-Fluoro-[4,4']bipyridinyl-3-yl)-methyl-amine

The title compound was prepared in analogy to example 69, intermediate, from (4-bromo-pyridin-3-yl)-methyl-amine (example 25, intermediate b) and 3-fluoropyridine-4-boronic acid (CAS RN 458532-97-3). Brown solid (92%). MS (ESI): m/z=204.2 [M+H]$^+$.

Example 71

N-(6-Chloro-[2,4']bipyridinyl-3'-yl)-N-methyl-3,5-bis-trifluoromethyl-benzamide

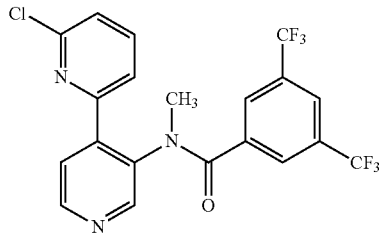 [SMILES: CN(C(=O)c1cc(C(F)(F)F)cc(C(F)(F)F)c1)c1cnccc1-c1cccc(Cl)n1]

The title compound was prepared in analogy to example 55, from (6-chloro-[2,4']bipyridinyl-3'-yl)-methyl-amine and 3,5-bis(trifluoromethyl)benzoyl chloride (CAS RN 1271-19-8) and using preparative HPLC for the purification. Off-white sticky solid (20%). MS (ESI): m/z=460.2 [M+H]$^+$.

Intermediate (6-Chloro-[2,4']bipyridinyl-3'-yl)-methyl-amine

The title compound was prepared in analogy to example 68, intermediate, from (4-bromo-pyridin-3-yl)-methyl-amine (example 25, intermediate b) and 6-chloropyridine-2-boronic acid (CAS RN 652148-90-8). Brown sticky solid (90%). MS (ESI): m/z=220.0 [M+H]$^+$.

Example 72

N-[6-Chloro-4-(4-fluoro-2-methyl-phenyl)-pyridin-3-yl]-N-methyl-3,5-bis-trifluoromethyl-benzamide

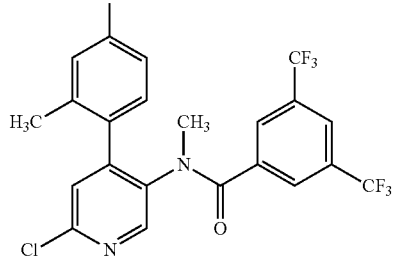

To a solution of N-(6-chloro-4-iodo-pyridin-3-yl)-N-methyl-3,5-bis-trifluoromethyl-benzamide (200 mg, 393 µmol) in DME (4 mL) under argon atmosphere was added 4-fluoro-2-methylphenylboronic acid (66.6 mg, 433 µmol, CAS RN 39911-29-8) and 2M aqueous Na$_2$CO$_3$ solution (1 mL) The reaction mixture was stirred for 15 minutes. Pd(II)acetate (4.41 mg, 19.7 µmol) and triphenylphosphine (10.3 mg, 39.3 µmol) were added and the reaction was stirred at 90° C. for 18 hours. The reaction mixture was poured on 10% aqueous NaHCO$_3$ solution (30 mL) and 30 mL EtOAc. The layers were separated and the aqueous layer was extracted a second time with 30 mL EtOAc. The combined organic layers were washed with 30 mL brine, dried over MgSO$_4$, filtered and concentrated under vacuum. The compound was purified by silica gel chromatography using a MPLC system (CombiFlash Companion, Isco Inc.) eluting with a gradient of n-heptane:EtOAc (100:0 to 50:50). Colorless solid (157 mg, 81.3%). MS (TurboSpray): m/z=491.075 [M+H]$^+$.

Intermediate

N-(6-Chloro-4-iodo-pyridin-3-yl)-N-methyl-3,5-bis-trifluoromethyl-benzamide

To a solution of (6-chloro-4-iodo-pyridin-3-yl)-methyl-amine (300 mg, 1.12 mmol, prepared according to WO2006013050) in THF (3 mL) was added dropwise at −78° C. lithium bis(trimethylsilyl)amide (1M solution in THF, 1.17 mL, 1.17 mmol). The reaction mixture was stirred at −78° C. for 30 minutes. Then, 3,5-bis(trifluoromethyl) benzoyl chloride (340 mg, 1.23 mmol, CAS RN 1271-19-8) was added at −78° C. and the reaction was stirred for 30 minutes at this temperature. The reaction mixture was allowed to warm to room temperature, stirred for another 1 hour and then poured on 30 mL H$_2$O and 30 mL EtOAc. The layers were separated and the aqueous layer was extracted a second time with 30 mL EtOAc. The combined organic layers were washed with 30 mL brine, dried over MgSO$_4$, filtered and concentrated under vacuum. The residue was purified by silica gel chromatography using a MPLC system (CombiFlash Companion, Isco Inc.) eluting with a gradient of n-heptane:EtOAc (100:0 to 70:30). Colorless solid (328 mg, 57.7%). MS (Turbo Spray): m/z=508.0 [M+H]$^+$.

Example 73

N-(3,6'-Dichloro-[2,4']bipyridinyl-3'-yl)-N-methyl-3,5-bis-trifluoromethyl-benzamide

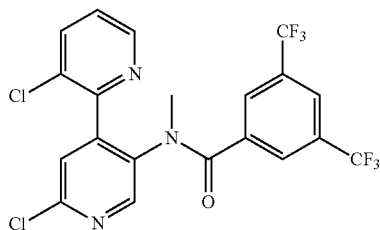 [SMILES: CN(C(=O)c1cc(C(F)(F)F)cc(C(F)(F)F)c1)c1cnc(Cl)cc1-c1ncccc1Cl]

To a solution of 3-chloro-2-iodopyridine (94.2 mg, 393 µmol, CAS RN 77332-89-9) in THF (3 mL) was added isopropylmagnesium chloride (2M solution in THF, 197 µl, 393 µmol) at −40° C. and the reaction mixture stirred for 20 minutes at this temperature. Freshly prepared ZnCl$_2$ solution (1M in THF, 1.57 mL, 1.57 mmol) was added at −40° C. The reaction mixture was allowed to warm to room temperature and was stirred for 90 minutes. A solution of N-(6-chloro-4-iodo-pyridin-3-yl)-N-methyl-3,5-bis-trifluoromethyl-benzamide (200 mg, 393 µmol, Ex. 72, intermediate) in THF (3 mL) and tetrakis(triphenylphosphine)palladium(0) (22.7 mg, 19.7 µmol) was added. The reaction mixture was stirred for 1 hour at reflux. The reaction mixture was poured on 30 mL 10% aqueous NaHCO$_3$ solution and 30 mL EtOAc. The layers were separated and the aqueous layer was extracted a second time with 30 mL EtOAc. The combined organic layers were washed with 30 mL brine, dried over MgSO$_4$, filtered and concentrated under vacuum. The compound was purified by silica gel chromatography using a MPLC system (CombiFlash Companion, Isco Inc.) eluting with a gradient of n-heptane:EtOAc (100:0 to 50:50). The product was further purified by preparative HPLC (phenomenex gemini column) with a gradient of acetonitrile:water (50:50 to 95:5). Colorless foam (85 mg, 44%). MS (ESI): m/z=494.025 [M+H]$^+$.

Example 74

3-Bromo-N-[4-(2-chloro-phenyl)-pyridin-3-yl]-N-methyl-5-trifluoromethyl-benzamide

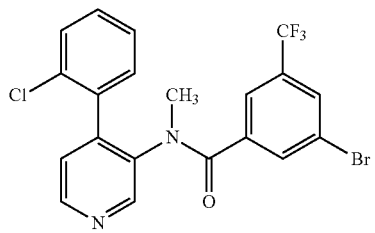 [SMILES: CN(C(=O)c1cc(Br)cc(C(F)(F)F)c1)c1cnccc1-c1ccccc1Cl]

To a solution of [4-(2-chloro-phenyl)-pyridin-3-yl]-methyl-amine (300 mg, 1.37 mmol, prepared according to DE10008042) in THF (3 mL) was added dropwise lithium bis(trimethylsilyl)amide (1M solution in THF, 1.44 mL, 1.44 mmol) at −78° C. The reaction mixture was stirred for 10 minutes at −78° C. A solution of 3-bromo-5-trifluoromethyl-benzoyl chloride (prepared by stirring 3-bromo-5-(trifluoromethyl)benzoic acid (406 mg, 1.51 mmol, CAS RN 328-67-6) in thionylchloride (3 mL) at 100° C. for 1 hour. The reaction mixture was evaporated and the residue was dissolved in 5 mL toluene and concentrated under vacuum. This procedure was repeated three times to completely remove remainder of thionylchloride) in THF (3 mL) was added at −78° C. The reaction mixture was stirred for 1 hour at this temperature and then poured on 30 mL H$_2$O and 30 mL EtOAc. The layers were separated and the aqueous layer extracted a second time with 30 mL EtOAc. The combined organic layers were washed with 30 mL brine, dried over MgSO$_4$, filtered and concentrated under vacuum. The residue was purified by silica gel chromatography using a MPLC system (CombiFlash Companion, Isco Inc.) eluting with a gradient of n-heptane:EtOAc (100:0 to 0:100). Yellow solid (265 mg, 41%). MS (TurboSpray): m/z=470.991 [M+H]$^+$.

Example 75

N-[4-(2-Chloro-phenyl)-pyridin-3-yl]-N-methyl-5-trifluoromethyl-isophthalamic acid methyl ester

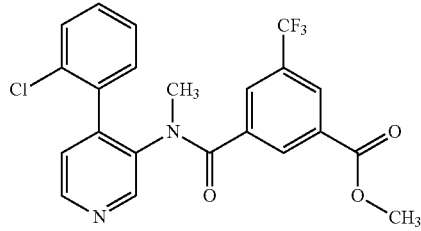 [SMILES: COC(=O)c1cc(C(=O)N(C)c2cnccc2-c2ccccc2Cl)cc(C(F)(F)F)c1]

To a solution of 3-bromo-N-[4-(2-chloro-phenyl)-pyridin-3-yl]-N-methyl-5-trifluoromethyl-benzamide (100 mg, 213 µmol, example 74) in MeOH (1.5 mL) and EtOAc (1.5 mL) was added PdCl$_2$(dppf)-CH$_2$Cl$_2$ complex (20.0 mg, 24.5 µmol, CAS RN 851232-71-8) and NEt$_3$ (32.3 mg, 44.5 µl, 319 µmol). The reaction mixture was stirred at 100° C. at 80 bar under CO atmosphere for 18 hours. The reaction mixture was poured on 30 mL 10% aqueous NaHCO$_3$ solution and 30 mL EtOAc and the layers were separated. The aqueous layer was extracted a second time with 30 mL EtOAc. The combined organic layers were washed with 30 mL brine, dried over MgSO$_4$, filtered and concentrated under vacuum. The compound was purified by silica gel chromatography using a MPLC system (CombiFlash Companion, Isco Inc.) eluting with a gradient of n-heptane:EtOAc (100:0 to 0:100). Colorless solid (93 mg, 97%). MS (TurboSpray): m/z=449.088 [M+H]$^+$.

Example 76

N-[4-(2-Chloro-phenyl)-pyridin-3-yl]-3-hydroxymethyl-N-methyl-5-trifluoromethyl-benzamide

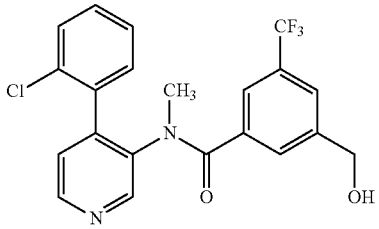 [SMILES: CN(C(=O)c1cc(CO)cc(C(F)(F)F)c1)c1cnccc1-c1ccccc1Cl]

To a solution of N-[4-(2-chloro-phenyl)-pyridin-3-yl]-N-methyl-5-trifluoromethyl-isophthalamic acid methyl ester (300 mg, 668 µmol, example 75) in THF (5 mL) was added LiAlH$_4$ (26.6 mg, 702 µmol) at 0° C. The reaction mixture was stirred at this temperature for 1 hour. The reaction mixture was poured on 30 mL aqueous 10% potassium-sodium-tartrate solution and 30 mL EtOAc and the layers were separated. The aqueous layer was extracted a second time with 30 mL EtOAc. The combined organic layers were washed with 30 mL brine, dried over MgSO$_4$, filtered and concentrated under vacuum. The compound was purified by silica gel chromatography using a MPLC system (Combi-Flash Companion, Isco Inc.) eluting with a gradient of n-heptane:EtOAc (100:0 to 0:100). Colorless solid (102 mg, 36%). MS (ESI): m/z=421.092 [M+H]$^+$.

Example 77

N-[4-(2-Chloro-phenyl)-pyridin-3-yl]-3-(1-hydroxy-1-methyl-ethyl)-N-methyl-5-trifluoromethyl-benzamide

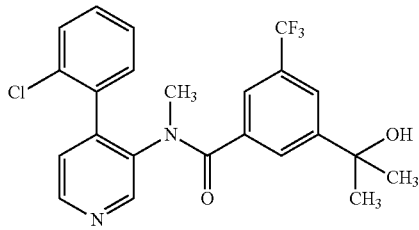 [SMILES: CN(C(=O)c1cc(C(C)(C)O)cc(C(F)(F)F)c1)c1cnccc1-c1ccccc1Cl]

To a solution of N-[4-(2-chloro-phenyl)-pyridin-3-yl]-N-methyl-5-trifluoromethyl-isophthalamic acid methyl ester (200 mg, 446 µM, example 75) in THF (3.3 mL) were added methyl magnesium bromide (1M solution in butyl ether, 1.6 mL, 1.56 mmol) within 2 min. The reaction was poured on EtOAc (20 mL) and aqueous sodium potassium tartrate solution (20 mL) and the phases were separated. The aqueous phase was extracted with EtOAc (20 mL) and the combined organic phases were washed with brine, dried over magnesium sulfate, filtered and evaporated. The compound was purified by silica gel chromatography using a MPLC system (CombiFlash Companion, Isco Inc.) eluting with a gradient of n-heptane:EtOAc (100:0 to 0:100). Colorless solid (115 mg, 57%). MS (ESI): m/z=449.123 [M+H]$^+$.

Example 78

N-[4-(2-Chloro-phenyl)-pyridin-3-yl]-N-methyl-3,5-bis-trifluoromethyl-benzamide

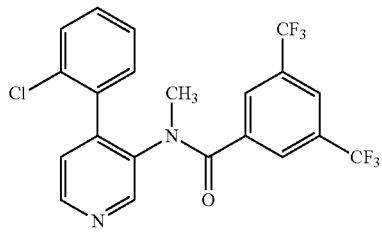 [SMILES: CN(C(=O)c1cc(C(F)(F)F)cc(C(F)(F)F)c1)c1cnccc1-c1ccccc1Cl]

The title compound was prepared in analogy to example 72, intermediate, from 4-(2-chloro-phenyl)-pyridin-3-yl]-methyl-amine (prepared according DE10008042) and 3,5-bis(trifluoromethyl)benzoyl chloride (CAS RN 1271-19-8) and using a gradient of n-heptane: EtOAc (100:0 to 0:100) for the chromatographic purification. Light yellow solid (52%). MS (ESI): m/z=459.068 [M+H]$^+$.

Example 79

N-[4-(2-Chloro-phenyl)-pyridin-3-yl]-3-hydroxy-N-methyl-5-trifluoromethyl-benzamide

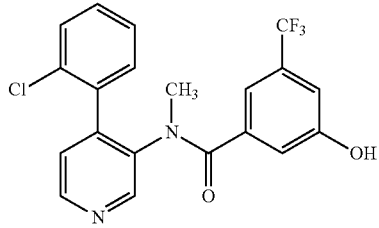 [SMILES: CN(C(=O)c1cc(O)cc(C(F)(F)F)c1)c1cnccc1-c1ccccc1Cl]

To a solution of 3-bromo-N-[4-(2-chloro-phenyl)-pyridin-3-yl]-N-methyl-5-trifluoromethyl-benzamide (332 mg, 707 µmol, example 74) in dry THF (5 ml) was added triisopropyl borate (257 mg, 317 µl, 1.36 mmol, CAS RN 5419-55-6). n-BuLi (552 µl, 884 µmol, 1.6 M solution in n-hexane) was added dropwise at −78° C. The reaction mixture was stirred at −78° C. for 1.5 hours. A solution of AcOH (180 mg, 172 µl, 3.0 mmol) in water (0.2 ml) and hydrogen peroxide (103 mg, 92.8 µl, 1.06 mmol) was added at 0° C. The reaction mixture was stirred at room temperature for 18 hours and then poured on 30 ml 10% aqueous NaHCO$_3$ solution and 30 ml EtOAc. The layers were separated and the aqueous layer was extracted a second time with 30 ml EtOAc. The combined organic layers were washed with 30 ml brine, dried over MgSO$_4$, filtered and concentrated under vacuum. The compound was purified by silica gel chromatography using a MPLC system (CombiFlash Companion, Isco Inc.) eluting with a gradient of n-heptane: EtOAc (100:0 to 0:100). Light yellow solid (77 mg, 27%). MS (ESI): m/z=407.077 [M+H]$^+$.

Example 80

4-Bromo-N-[4-(2-chloro-phenyl)-pyridin-3-yl]-N-methyl-3-trifluoromethyl-benzamide

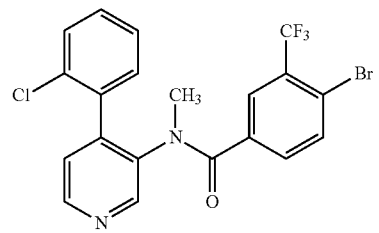 [SMILES: CN(C(=O)c1ccc(Br)c(C(F)(F)F)c1)c1cnccc1-c1ccccc1Cl]

To a solution of 4-(2-chloro-phenyl)-pyridin-3-yl]-methyl-amine (1.0 g, 4.57 mmol, prepared according to DE10008042) in THF (10 mL) was added dropwise lithium bis(trimethylsilyl)amide (1M solution in THF, 4.8 mL, 4.8 mmol) at −78° C. After 10 min a solution of 4-bromo-3-trifluoromethyl-benzoyl chloride (prepared by stirring a solution of 4-bromo-3-(trifluoromethyl)benzoic acid (1.23 g, 4.57 mmol, CAS RN 161622-14-6) in thionylchloride (10 mL) at 100° C. for 1 hour. The reaction mixture was evaporated and the residue was dissolved in 5 mL toluene and concentrated under vacuum. This was repeated for 3 times to completely remove remains of thionylchloride) in THF (10 mL) was added at −78° C. The reaction mixture was stirred at −78° C. for 1 hour and then poured on 30 mL $H_2O$ and 30 mL EtOAc. The layers were separated and the aqueous layer was extracted a second time with 30 ml EtOAc. The combined organic layers were washed with 30 mL brine, dried over $MgSO_4$, filtered and concentrated under vacuum. The residue was purified by silica gel chromatography using a MPLC system (CombiFlash Companion, Isco Inc.) eluting with a gradient of n-heptane:EtOAc (100:0 to 0:100). Colorless solid (741 mg, 34%). MS (ESI): m/z=470.990 $[M+H]^+$.

Example 81

N-[4-(2-Chloro-phenyl)-pyridin-3-yl]-3-methoxy-N-methyl-5-trifluoromethyl-benzamide

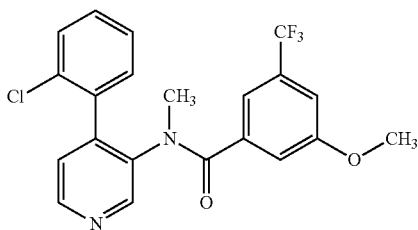 [SMILES: COc1cc(C(=O)N(C)c2cnccc2-c2ccccc2Cl)cc(C(F)(F)F)c1]

The title compound was prepared in analogy to example 74, from 4-(2-chloro-phenyl)-pyridin-3-yl]-methyl-amine (prepared according to DE10008042) and 3-methoxy-5-trifluoromethyl-benzoyl chloride (prepared in analogy to example 74 from 3-methoxy-5-trifluoromethyl-benzoic acid (CAS RN 53985-48-1) and thionyl chloride). Yellow oil (45%). MS (GC_MS (EI)): m/z=420.0 [M].

Example 82

N-[4-(5-Chloro-2-methyl-phenyl)-pyridin-3-yl]-N-methyl-3,5-bis-trifluoromethyl-benzamide

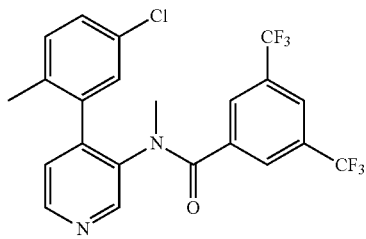 [SMILES: Cc1ccc(Cl)cc1-c1ccncc1N(C)C(=O)c1cc(C(F)(F)F)cc(C(F)(F)F)c1]

The title compound was prepared in analogy to example 72, intermediate, from [4-(5-chloro-2-methyl-phenyl)-pyridin-3-yl]-methyl-amine and 3,5-bis(trifluoromethyl)benzoyl chloride (CAS RN 1271-19-8) and using a gradient of n-heptane:EtOAc (100:0 to 70:30) for the chromatographic purification. Colorless solid (35%). MS (ESI): m/z=473.084 $[M+H]^+$.

Intermediates a) [4-(5-Chloro-2-methyl-phenyl)-pyridin-3-yl]-methyl-amine

To a solution of 4-(5-chloro-2-methyl-phenyl)-pyridin-3-ylamine (500 mg, 2.29 mmol) in trimethyl orthoformate (1.94 g, 2.00 mL, 18.3 mmol, CAS RN 149-73-5) was added 2-3 drops of TFA. The reaction mixture was stirred at reflux for 2 hours and then concentrated under vacuum. The residue was dissolved in 5 ml toluene and evaporated (repeated 3 times). The residue was dissolved in THF (10 mL) and $LiAlH_4$ (260 mg, 6.86 mmol) was added in portions at 0° C. The cooling bath was removed, the reaction mixture stirred at room temperature for 1 hour and then poured on 30 mL 10% aqueous $NH_4Cl$ solution and 30 mL EtOAc. The layers were separated and the aqueous layer extracted a second time with 30 mL EtOAc. The combined organic layers were washed with 30 mL brine, dried over $MgSO_4$, filtered and concentrated under vacuum. The compound was purified by silica gel chromatography using a MPLC system (CombiFlash Companion, Isco Inc.) eluting with a gradient of n-heptane:EtOAc (100:0 to 0:100). Light yellow solid (331 mg, 62%). MS (ESI): m/z=233.084 $[M+H]^+$.

b) 4-(5-Chloro-2-methyl-phenyl)-pyridin-3-ylamine

A solution of N-[4-(5-chloro-2-methyl-phenyl)-pyridin-3-yl]-2,2-dimethyl-propionamide (1 g, 3.3 mmol) in 3M aqueous HCl (50 mL) was stirred at 90° C. for 18 hours. The reaction mixture was poured on 200 mL 1M aqueous NaOH solution and 150 mL EtOAc. The layers were separated and the aqueous layer was extracted a second time with 150 mL EtOAc. The combined organic layers were washed with 150 mL brine, dried over $MgSO_4$, filtered and concentrated under vacuum. Light brown viscous oil (720 mg, 99%). MS (ESI): m/z=219.068 $[M+H]^+$.

c) N-[4-(5-Chloro-2-methyl-phenyl)-pyridin-3-yl]-2,2-dimethyl-propionamide

The title compound was prepared in analogy to example 72, from N-(4-iodo-pyridin-3-yl)-2,2-dimethyl-propionamide (CAS RN 113975-32-9) and 5-chloro-2-methylphenyl-boronic acid (CAS RN 148839-33-2) and using a gradient of n-heptane: EtOAc (100:0 to 0:100). Light yellow solid (99%). MS (ESI): m/z=303.126 $[M+H]^+$.

Example 83

3-{3-[(3,5-Bis-trifluoromethyl-benzoyl)-methyl-amino]-pyridin-4-yl}-4-methyl-benzoic acid methyl ester

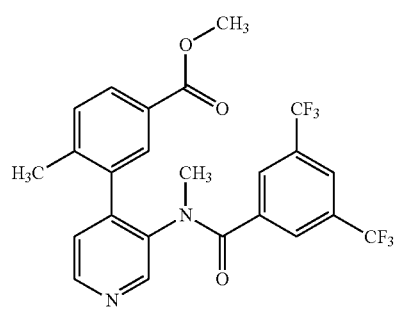 [SMILES: COC(=O)c1ccc(C)c(-c2ccncc2N(C)C(=O)c2cc(C(F)(F)F)cc(C(F)(F)F)c2)c1]

To a solution of N-[4-(5-chloro-2-methyl-phenyl)-pyridin-3-yl]-N-methyl-3,5-bis-trifluoromethyl-benzamide (160 mg, 338 µmol, example 82) in MeOH (1.2 mL) and EtOAc (1.2 mL) was added PdCl$_2$(dppf)-CH$_2$Cl$_2$ complex (31.8 mg, 38.9 µmol, CAS RN 851232-71-8) and NEt$_3$ (51.4 mg, 70.7 µL, 508 µmol). The reaction mixture was stirred at 150° C. at 70 bar under CO atmosphere for 24 hours. The reaction mixture was treated with silica gel and directly purified by silica gel chromatography using a MPLC system (CombiFlash Companion, Isco Inc.) eluting with a gradient of n-heptane:EtOAc (100:0 to 0:100). Light yellow oil (39 mg, 23%). MS (ESI): m/z=497.129 [M+H]$^+$.

Example 84

3-{ 3-[(3,5-Bis-trifluoromethyl-benzoyl)-methyl-amino]-pyridin-4-yl}-4-methyl-benzoic acid

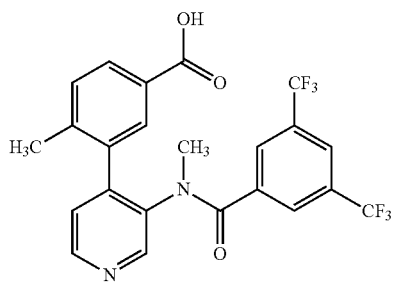 [SMILES: Cc1ccc(C(=O)O)cc1-c1ccncc1N(C)C(=O)c1cc(C(F)(F)F)cc(C(F)(F)F)c1]

To a solution of 3-{3-[(3,5-bis-trifluoromethyl-benzoyl)-methyl-amino]-pyridin-4-yl}-4-methyl-benzoic acid methyl ester (33 mg, 66.5 µmol, example 83) in dioxane (1 mL) was added water (2 mL) and LiOH.H$_2$O (3.49 mg, 83.1 µmol). The reaction mixture was stirred at room temperature for 2 hours and then poured on 20 mL 1M aqueous HCl and 20 mL EtOAc. The layers were separated and the aqueous layer extracted a second time with 20 mL EtOAc. The combined organic layers were washed with 20 ml brine, dried over MgSO$_4$, filtered and concentrated under vacuum. Colorless solid (32 mg, 99%). MS (ESI): m/z=483.113 [M+H]$^+$.

Example 85

N-[4-(2-Chloro-phenyl)-pyridin-3-yl]-N-(2,2,2-trifluoro-ethyl)-3,5-bis-trifluoromethyl-benzamide

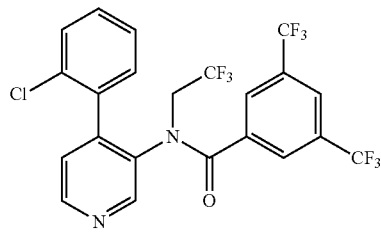 [SMILES: O=C(c1cc(C(F)(F)F)cc(C(F)(F)F)c1)N(CC(F)(F)F)c1cnccc1-c1ccccc1Cl]

The title compound was prepared in analogy to example 72, intermediate, from [4-(2-chloro-phenyl)-pyridin-3-yl]-(2,2,2-trifluoro-ethyl)-amine and 3,5-bis(trifluoromethyl) benzoyl chloride (CAS RN 1271-19-8) and using a gradient of n-heptane: EtOAc (100:0 to 40:60) for the chromatographic purification. Light yellow solid (138 mg, 63%). MS (ESI): m/z=527.057 [M+H]$^+$.

Intermediates a) [4-(2-Chloro-phenyl)-pyridin-3-yl]-(2,2,2-trifluoro-ethyl)-amine To a solution of [4-(2-chloro-phenyl)-pyridin-3-yl]-(2,2,2-trifluoro-ethyl)-carbamic acid tert-butyl ester (120 mg, 310 µmol) in CH$_2$Cl$_2$ (2 mL) at 0° C. was added TFA (2 mL) The reaction mixture was stirred at room temperature for 2 hours and then concentrated under vacuum. The residue was extracted with 30 mL 10% aqueous NaHCO$_3$ solution and 30 mL EtOAc. The layers were separated and the aqueous layer was extracted a second time with 30 mL EtOAc. The combined organic layers were washed with 30 mL brine, dried over MgSO$_4$, filtered and concentrated under vacuum. Light yellow solid (79 mg, 89%). MS (ESI): m/z=287.055 [M+H]$^+$.

b) [4-(2-Chloro-phenyl)-pyridin-3-yl]-(2,2,2-trifluoro-ethyl)-carbamic acid tert-butyl ester The title compound was prepared in analogy to example 72, from (4-iodo-pyridin-3-yl)-(2,2,2-trifluoro-ethyl)-carbamic acid tert-butyl ester and 2-chlorophenylboronic acid (CAS RN 1679-18-1) and using a gradient of n-heptane: EtOAc (100:0 to 30:70) for the chromatographic purification. Colorless oil (69%). MS (ESI): m/z=403.012 [M+H]$^+$.

c) (4-Iodo-pyridin-3-yl)-(2,2,2-trifluoro-ethyl)-carbamic acid tert-butyl ester

To a solution of (4-iodo-pyridin-3-yl)-carbamic acid tert-butyl ester (280 mg, 875 µmol) in DMF (4 mL) was added NaH (42.0 mg, 962 µmol, 60% dispersion in mineral oil) at 0° C. The reaction mixture was stirred at room temperature for 30 minutes. 2,2,2-Trifluoroethyl trifluoromethanesulphonate (203 mg, 126 µL, 875 µmol, CAS RN 6226-25-1) was added and the reaction stirred at room temperature for 2 hours. The reaction mixture was poured on 30 mL 10% aqueous NaHCO$_3$ solution and 30 mL EtOAc and the layers were separated. The aqueous layer was extracted a second time with 30 mL EtOAc and the combined organic layers were washed with 30 mL brine, dried over MgSO4, filtered and concentrated under vacuum. The compound was purified by silica gel chromatography using a MPLC system (CombiFlash Companion, Isco Inc.) eluting with a gradient of n-heptane:EtOAc (100:0 to 30:70). Colorless solid (207 mg, 59%). MS (ESI): m/z=403.012 [M+H]$^+$.

d) (4-Iodo-pyridin-3-yl)-carbamic acid tert-butyl ester

In heat-dried argon purged 4-neck flask was placed a solution of pyridin-3-yl-carbamic acid tert-butyl ester (10 g, 51.5 mmol, CAS RN 56700-70-0) in THF (100 mL) After cooling down to −75° C., tert-butyllithium (1.7M solution in n-pentane, 66.6 mL, 113 mmol) was added dropwise over 15 min keeping the temperature below −60° C. The resulting light brown suspension was stirred at −75° C. for 3.75 h. A solution of iodine (28.7 g, 113 mmol) in THF (50 mL) was added dropwise over 20 min. below −63° C. The reaction mixture was stirred at −75° C. for 1.5 h and then poured on saturated aqueous NH$_4$Cl solution (1000 mL) and EtOAc (500 mL) The layers were separated. The organic layer was washed once with 10% aqueous Na₂S₂O₃ solution (300 mL) and once with brine (250 mL), dried over MgSO₄, filtered, treated with silica gel and evaporated. The compound was purified by silica gel chromatography on a 120 g column using a MPLC system eluting with a gradient of n-heptane: EtOAc (100:0 to 0:100). Yellow solid (11.7 g; 71%). MS (ESI): m/z=321.1 [M+H]⁺.

Example 86

N-[4-(2-Chloro-phenyl)-pyridin-3-yl]-N-cyclopropylmethyl-3,5-bis-trifluoromethyl-benzamide

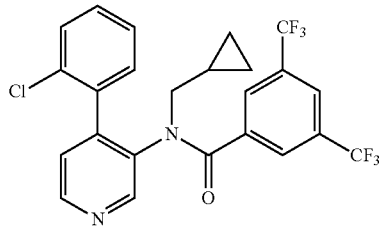 [SMILES: O=C(c1cc(C(F)(F)F)cc(C(F)(F)F)c1)N(CC1CC1)c1cnccc1-c1ccccc1Cl]

The title compound was prepared in analogy to example 72, intermediate, from [4-(2-chloro-phenyl)-pyridin-3-yl]-cyclopropylmethyl-amine and 3,5-bis(trifluoromethyl)benzoyl chloride (CAS RN 1271-19-8) and using a gradient of n-heptane: EtOAc (100:0 to 40:60) for the chromatographic purification. Light yellow oil (27%). MS (ESI): m/z=499.1005 [M+H]⁺.

Intermediates a) [4-(2-Chloro-phenyl)-pyridin-3-yl]-cyclopropylmethyl-amine

The title compound was prepared in analogy to example 85, intermediate a, from [4-(2-chloro-phenyl)-pyridin-3-yl]-cyclopropylmethyl-carbamic acid tert-butyl ester. Colorless solid (99%). MS (ESI): m/z=259.100 [M+H]⁺.

b) [4-(2-Chloro-phenyl)-pyridin-3-yl]-cyclopropylmethyl-carbamic acid tert-butyl ester The title compound was prepared in analogy to example 72, from cyclopropylmethyl-(4-iodo-pyridin-3-yl)-carbamic acid tert-butyl ester and 2-chlorophenylboronic acid (CAS RN 1679-18-1) and using a gradient of n-heptane:EtOAc (100:0 to 30:70) for the chromatographic purification. Light yellow oil (85%). MS (ESI): m/z=359.152 [M+H]⁺.

c) Cyclopropylmethyl-(4-iodo-pyridin-3-yl)-carbamic acid tert-butyl ester

The title compound was prepared in analogy to example 85, intermediate c, from (4-iodo-pyridin-3-yl)-carbamic acid tert-butyl ester (example 85, intermediate d) and (bromomethyl)cyclopropane (CAS RN 7051-34-5) and using a gradient of n-heptane: EtOAc (100:0 to 30:70) for the chromatographic purification. Colorless solid (76%). MS (ESI): m/z=375.056 [M+H]⁺.

Example 87

N-(6,5'-Dichloro-T-fluoro-[4,4']bipyridinyl-3-yl)-N-methyl-3,5-bis-trifluoromethyl-benzamide

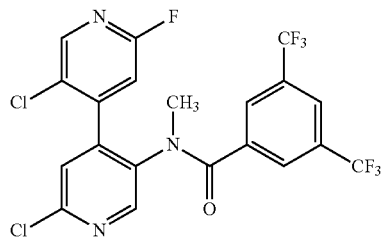 [SMILES: CN(C(=O)c1cc(C(F)(F)F)cc(C(F)(F)F)c1)c1cnc(Cl)cc1-c1cc(F)ncc1Cl]

The title compound was prepared in analogy to example 73, from N-(6-chloro-4-iodo-pyridin-3-yl)-N-methyl-3,5-bis-trifluoromethyl-benzamide (example 72, intermediate) and 5-chloro-2-fluoro-4-iodopyridine (CAS RN 659731-48-3) and using a gradient of n-heptane:EtOAc (100:0 to 30:70) for the chromatographic separation. Colorless oil (89%). MS (ESI): m/z=511.009 [M+H]⁺.

Example 88

{(3,5-Bis-trifluoromethyl-benzoyl)-[4-(2-chloro-phenyl)-pyridin-3-yl]-amino}-acetic acid methyl ester

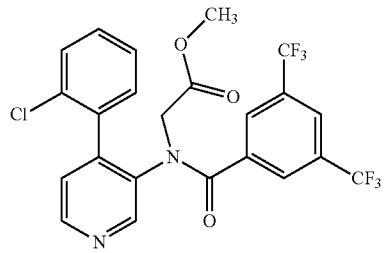 [SMILES: COC(=O)CN(C(=O)c1cc(C(F)(F)F)cc(C(F)(F)F)c1)c1cnccc1-c1ccccc1Cl]

The title compound was prepared in analogy to example 72, intermediate, from [4-(2-chloro-phenyl)-pyridin-3-ylamino]-acetic acid methyl ester and 3,5-bis(trifluoromethyl)benzoyl chloride (CAS RN 1271-19-8) and using a gradient of n-heptane: EtOAc (100:0 to 30:70) for the chromatographic purification. Yellow solid (26%). MS (ESI): m/z=517.075 [M+H]⁺.

a) [4-(2-Chloro-phenyl)-pyridin-3-ylamino]-acetic acid methyl ester

The title compound was prepared in analogy to example 85, intermediate a, from {tert-butoxycarbonyl-[4-(2-chloro-phenyl)-pyridin-3-yl]-amino}-acetic acid methyl ester. Off-white solid (95%). MS (ESI): m/z=277.074 [M+H]⁺.

b) {tert-Butoxycarbonyl-[4-(2-chloro-phenyl)-pyridin-3-yl]-amino}-acetic acid methyl ester The title compound was prepared in analogy to example 72, from [tert-butoxycarbonyl-(4-iodo-pyridin-3-yl)-amino]-acetic acid methyl ester and 2-chlorophenylboronic acid (CAS RN 1679-18-1) and using a gradient of n-heptane:EtOAc (100:0 to 60:40) for the chromatographic purification. Colorless oil (49%). MS (ESI): m/z=377.126 [M+H]+.

c) [tert-Butoxycarbonyl-(4-iodo-pyridin-3-yl)-amino]acetic acid methyl ester

The title compound was prepared in analogy to example 85, intermediate c, from (4-iodo-pyridin-3-yl)-carbamic acid tert-butyl ester (example 14, intermediate d) and methyl bromoacetate (CAS RN 96-32-2) and using a gradient of n-heptane:EtOAc (100:0 to 55:45) for the chromatographic purification. Yellow oil (77%). MS (ESI): m/z=393.031 [M+H]+.

Example 89

N-[4-(2-Chloro-phenyl)-pyridin-3-yl]-N-(2-methoxy-ethyl)-3,5-bis-trifluoromethyl-benzamide

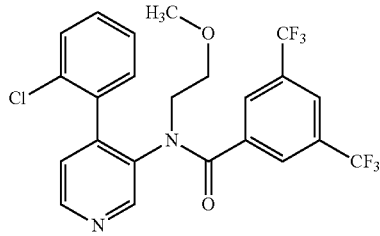 [SMILES: COCCN(C(=O)c1cc(C(F)(F)F)cc(C(F)(F)F)c1)c1cnccc1-c1ccccc1Cl]

The title compound was prepared in analogy to example 72, intermediate, from [4-(2-chloro-phenyl)-pyridin-3-yl]-(2-methoxy-ethyl)-amine and 3,5-bis(trifluoromethyl)benzoyl chloride (CAS RN 1271-19-8) and using a gradient of n-heptane: EtOAc (100:0 to 50:50) for the chromatographic purification. Yellow solid (53%). MS (ESI): m/z=503.095 [M+H]+.

Intermediates a) [4-(2-Chloro-phenyl)-pyridin-3-yl]-(2-methoxy-ethyl)-amine

The title compound was prepared in analogy to example 85, intermediate a, from [4-(2-chloro-phenyl)-pyridin-3-yl]-(2-methoxy-ethyl)-carbamic acid tert-butyl ester and using a gradient of n-heptane:EtOAc (100:0 to 0:100) for the chromatographic purification. Colorless oil (72%). MS (ESI): m/z=263.094 [M+H]+.

b) [4-(2-Chloro-phenyl)-pyridin-3-yl]-(2-methoxy-ethyl)-carbamic acid tert-butyl ester The title compound was prepared in analogy to example 72, from (4-iodo-pyridin-3-yl)-(2-methoxy-ethyl)-carbamic acid tert-butyl ester and 2-chlorophenylboronic acid (CAS RN 1679-18-1) and using a gradient of n-heptane:EtOAc (100:0 to 50:50) for the chromatographic purification. Colorless oil (70%). MS (ESI): m/z=363.147 [M+H]+.

c) (4-Iodo-pyridin-3-yl)-(2-methoxy-ethyl)-carbamic acid tert-butyl ester

The title compound was prepared in analogy to example 85, intermediate c, from (4-iodo-pyridin-3-yl)-carbamic acid tert-butyl ester (example 85, intermediate d) and 1-bromo-2-methoxyethane and using a gradient of n-heptane:EtOAc (100:0 to 20:80) for the chromatographic purification. Light yellow oil (65%). MS (ESI): m/z=379.051 [M+H]+.

Example 90

N-Methyl-N-(4-o-tolyl-pyridin-3-yl)-4-trifluoromethyl-benzamide

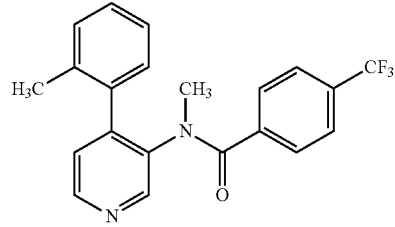 [SMILES: Cc1ccccc1-c1ccncc1N(C)C(=O)c1ccc(C(F)(F)F)cc1]

To a solution of 4-(trifluoromethyl)benzoic acid (115 mg, 605 µmol, CAS RN 328-90-5) in $CH_2Cl_2$ (2 mL) were added N-methyl-4-o-tolylpyridin-3-amine (0.1 g, 504 µmol, example 1, intermediate a), 2-bromo-1-ethylpyridinium tetrafluoroborate (166 mg, 605 µmol, CAS RN 878-23-9) and DIPEA (130 mg, 176 µL, 1.01 mmol). The reaction mixture was stirred at room temperature for 66 h. The red solution was poured on 10% aqueous citric acid and dichloromethane and the layers were separated. The aqueous layer was extracted twice with dichloromethane. The combined organic layers were washed with 10% aqueous citric acid solution and brine, dried over $MgSO_4$, filtered, treated with silica gel and evaporated. The compound was purified by silica gel chromatography on a 20 g column using a MPLC system eluting with EtOAc (isocratic). The compound-containing fractions were evaporated and the residue was dissolved in dichloromethane and the solution washed twice with 2M aqueous $Na_2CO_3$ solution, twice with 1M aqueous HCl and once with brine, dried over $MgSO_4$, filtered and evaporated. Brown solid (16%). MS (ESI): m/z=371.14 [M+H]+.

Example 91

4,N-Dimethyl-N-(4-o-tolyl-pyridin-3-yl)-3-trifluoromethyl-benzamide

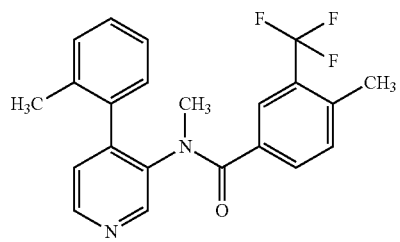

The title compound was prepared in analogy to example 90, from N-methyl-4-o-tolylpyridin-3-amine (example 1, intermediate a) and 4-methyl-3-trifluoromethyl-benzoic acid (CAS RN 261952-01-6) after a reaction time of 90 hours. Grey solid (32%). MS (ESI): m/z=385.15 [M+H]+.

Example 92

4-Methoxy-N-methyl-N-(4-o-tolyl-pyridin-3-yl)-3-trifluoromethyl-benzamide

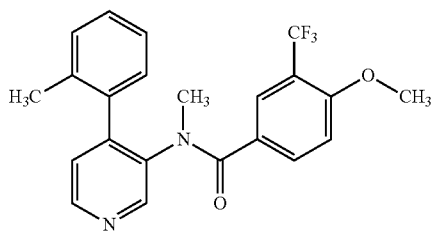

The title compound was prepared in analogy to example 90, from N-methyl-4-o-tolylpyridin-3-amine (example 1, intermediate a) and 4-methoxy-3-(trifluoromethyl)benzoic acid (CAS RN 213598-09-5) after a reaction time of 88 hours. Brown solid (4%). MS (ESI): m/z=401.15 [M+H]$^+$.

Example 93

N-{4-[2-(2-Hydroxy-ethyl)-phenyl]-pyridin-3-yl}-N-methyl-3,5-bis-trifluoromethyl-benzamide

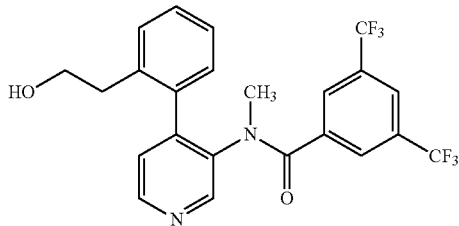 [SMILES: CN(C(=O)c1cc(C(F)(F)F)cc(C(F)(F)F)c1)c1cnccc1-c1ccccc1CCO]

To the solution of N-(4-iodo-pyridin-3-yl)-N-methyl-3,5-bis-trifluoromethyl-benzamide (150 mg, 316 µmol, example 36, intermediate a) in DME (3 mL) was added 2-(2-(tert-butyldimethylsilyloxy)ethyl)phenylboronic acid (88.7 mg, 316 µmol, CAS RN 913835-62-8) and 2M aqueous Na$_2$CO$_3$ solution (1 mL). The reaction mixture was stirred under argon atmosphere for 15 minutes. Pd(II)acetate (3.55 mg, 15.8 µmol) and triphenylphosphine (8.3 mg, 31.6 µmol) were added. The reaction mixture stirred at 90° C. for 18 hours and then poured on 30 mL 1M aqueous HCl and 30 mL EtOAc. The layers were separated and the aqueous layer was extracted a second time with 30 mL EtOAc. The organic layers were washed with 30 mL brine, dried over MgSO$_4$, filtered and concentrated under vacuum. The compound was purified by silica gel chromatography using a MPLC system (CombiFlash Companion, Isco Inc.) eluting with a gradient of n-heptane:EtOAc (100:0 to 60:40). Colorless solid (95 mg, 52%). MS (ESI): m/z=469.134 [M+H]$^+$.

Example 94

3-Fluoro-N-methyl-N-(4-o-tolyl-pyridin-3-yl)-4-trifluoromethyl-benzamide

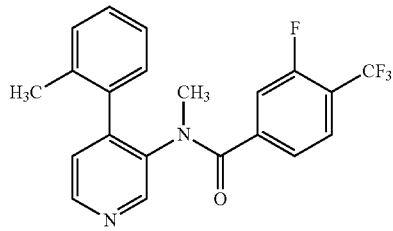 [SMILES: Cc1ccccc1-c1ccncc1N(C)C(=O)c1ccc(C(F)(F)F)c(F)c1]

The title compound was prepared in analogy to example 90, from N-methyl-4-o-tolylpyridin-3-amine (example 1, intermediate a) and 3-fluoro-4-(trifluoromethyl)benzoic acid (CAS RN 115754-21-7) and using a gradient of n-heptane:EtOAc (100:0 to 0:100) for the chromatographic purification. Light brown solid (20%). MS (ESI): m/z=389.13 [M+H]$^+$.

Example 95

4-Chloro-N-methyl-N-(4-o-tolyl-pyridin-3-yl)-3-trifluoromethyl-benzamide

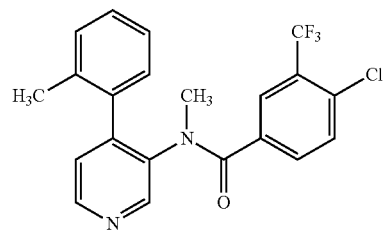 [SMILES: Cc1ccccc1-c1ccncc1N(C)C(=O)c1ccc(Cl)c(C(F)(F)F)c1]

The title compound was prepared in analogy to example 90, from N-methyl-4-o-tolylpyridin-3-amine (example 1, intermediate a) and 4-chloro-3-(trifluoromethyl)benzoic acid (CAS RN 1737-36-6) and using a gradient of n-heptane:EtOAc (100:0 to 0:100) for the chromatographic purification. Light brown solid (30%). MS (ESI): m/z=405.10 [M+H]$^+$.

Example 96

3,5,N-Trimethyl-N-(4-o-tolyl-pyridin-3-yl)-benzamide

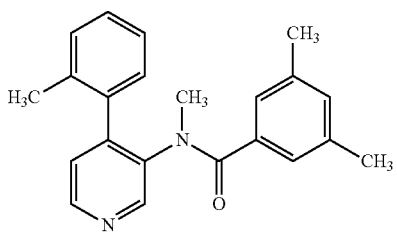

The title compound was prepared in analogy to example 90, from N-methyl-4-o-tolylpyridin-3-amine (example 1, intermediate a) and 3,5-dimethylbenzoic acid (CAS RN 499-06-9) and using a gradient of n-heptane:EtOAc (100:0 to 0:100) for the chromatographic purification. Brown oil (3%). MS (ESI): m/z=331.18 [M+H]$^+$.

Example 97

3-Chloro-N-methyl-N-(4-o-tolyl-pyridin-3-yl)-4-trifluoromethyl-benzamide

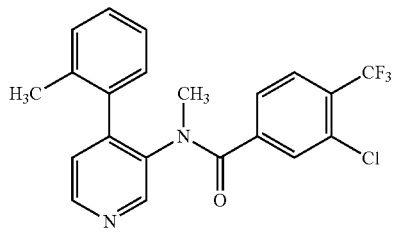 [SMILES: Cc1ccccc1-c1ccncc1N(C)C(=O)c1ccc(C(F)(F)F)c(Cl)c1]

The title compound was prepared in analogy to example 90, from N-methyl-4-o-tolylpyridin-3-amine (example 1, intermediate a) and 3-chloro-4-(trifluoromethyl)benzoic acid (CAS RN 115754-20-6) and using a gradient of n-heptane:EtOAc (100:0 to 0:100) for the chromatographic purification. Light brown solid (37%). MS (ESI): m/z=405.10 [M+H]$^+$.

Example 98

N-(6-Methoxy-[2,4']bipyridinyl-3'-yl)-N-methyl-3,5-bis-trifluoromethyl-benzamide

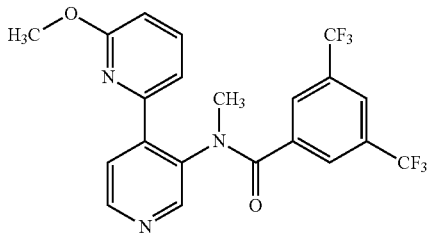 [SMILES: COc1cccc(-c2ccncc2N(C)C(=O)c2cc(C(F)(F)F)cc(C(F)(F)F)c2)n1]

The title compound was prepared in analogy to example 72, from N-(4-iodo-pyridin-3-yl)-N-methyl-3,5-bis-trifluoromethyl-benzamide and 6-methoxypyridine-2-ylboronic acid (CAS RN 372963-51-4) and using a gradient of n-heptane:EtOAc (100:0 to 60:40) for the chromatographic purification. The product was purified a second time by preparative HPLC (Phenomenex Gemini® column) eluting with a gradient of acetonitrile:water (50:50 to 95:5). Colorless oil (17%). MS (ESI): m/z=456.114 [M+H]$^+$.

Intermediate a) N-(4-Iodo-pyridin-3-yl)-N-methyl-3,5-bis-trifluoromethyl-benzamide The title compound was prepared in analogy to example 72, intermediate, from (4-iodo-pyridin-3-yl)-methyl-amine and 3,5-bis(trifluoromethyl)benzoyl chloride (CAS RN 1271-19-8) and using a gradient of n-heptane:EtOAc (100:0 to 40:60) for the chromatographic purification. Light yellow solid (18%). MS (ESI): m/z=474.9738 [M+H]$^+$.

b) (4-Iodo-pyridin-3-yl)-methyl-amine

The title compound was prepared in analogy to example 85, intermediate a, from (4-iodo-pyridin-3-yl)-methyl-carbamic acid tert-butyl ester. Brown oil (99%). MS (ESI): m/z=234.973 [M+H]$^+$.

c) (4-Iodo-pyridin-3-yl)-methyl-carbamic acid tert-butyl ester

The title compound was prepared in analogy to example 85, intermediate c, from (4-iodo-pyridin-3-yl)-carbamic acid tert-butyl ester (example 14, intermediate d), sodium hydride and iodomethane (CAS RN 74-88-4). The compound was purified by silica gel chromatography eluting with n-heptane:EtOAc (2:1). Colorless solid (58%). MS (ESI): m/z=355.025 [M+H]$^+$.

Example 99

N-(6-Methoxy-[3,4']bipyridinyl-3'-yl)-N-methyl-3,5-bis-trifluoromethyl-benzamide

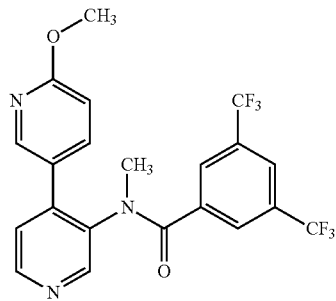 [SMILES: COc1ccc(-c2ccncc2N(C)C(=O)c2cc(C(F)(F)F)cc(C(F)(F)F)c2)cn1]

The title compound was prepared in analogy to example 72, from N-(4-iodo-pyridin-3-yl)-N-methyl-3,5-bis-trifluoromethyl-benzamide (example 98, intermediate a) and 6-methoxypyridin-3-ylboronic acid (CAS RN 163105-89-3) and using a gradient of n-heptane: EtOAc (100:0 to 60:40) for the chromatographic separation. Colorless solid (74%). MS (ESI): m/z=456.113 [M+H]$^+$.

Example 100

3-Chloro-N-methyl-N-(4-o-tolyl-pyridin-3-yl)-5-trifluoromethoxy-benzamide

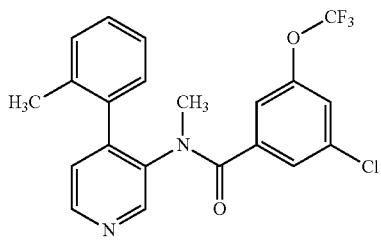 [SMILES: Cc1ccccc1-c1ccncc1N(C)C(=O)c1cc(Cl)cc(OC(F)(F)F)c1]

The title compound was prepared in analogy to example 90, from N-methyl-4-o-tolylpyridin-3-amine (example 1, intermediate a) and 3-chloro-5-(trifluoromethoxy)benzoic acid (CAS RN 158580-93-9) and using a gradient of n-heptane: EtOAc (100:0 to 50:50) for the chromatographic purification. Yellow solid (31%). MS (ESI): m/z=421.09 [M+H]$^+$.

Example 101

N-Methyl-N-(4-o-tolyl-pyridin-3-yl)-3,4-bis-trifluoromethyl-benzamide

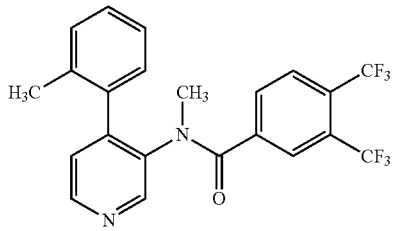 [SMILES: Cc1ccccc1-c1ccncc1N(C)C(=O)c1ccc(C(F)(F)F)c(C(F)(F)F)c1]

The title compound was prepared in analogy to example 90, from N-methyl-4-o-tolylpyridin-3-amine (example 1, intermediate a) and 3,4-bis(trifluoromethyl)benzoic acid (CAS RN 133804-66-7) and using a gradient of n-heptane: EtOAc (100:0 to 0:100) for the chromatographic purification. Yellow solid (43%). MS (ESI): m/z=439.12 [M+H]$^+$.

Example 102

N-[4-(2-Chloro-phenyl)-pyridin-3-yl]-N-methylcarbamoylmethyl-3,5-bis-trifluoromethyl-benzamide

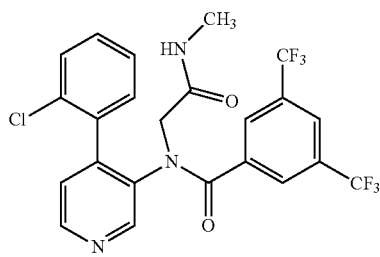 [SMILES: CNC(=O)CN(C(=O)c1cc(C(F)(F)F)cc(C(F)(F)F)c1)c1cnccc1-c1ccccc1Cl]

To a solution of {(3,5-bis-trifluoromethyl-benzoyl)-[4-(2-chloro-phenyl)-pyridin-3-yl]-amino}-acetic acid (100 mg, 199 μmol) in DMF (2 mL) was added DIPEA (129 mg, 169 μL, 994 μmol), HATU (91.5 mg, 239 μmol) and methylamine hydrochloride (16.1 mg, 239 μmol). The reaction mixture was stirred at room temperature for 2 hours and then poured on 30 mL 10% aqueous NaHCO$_3$ solution and 30 mL EtOAc. The layers were separated and the aqueous layer was extracted a second time with 30 mL EtOAc. The organic layers were washed with 30 mL brine, dried over MgSO4, filtered and concentrated under vacuum. The compound was purified by silica gel chromatography using a MPLC system (CombiFlash Companion, Isco Inc.) eluting with a gradient of n-heptane: EtOAc (100:0 to 0:100). Colorless solid (67 mg, 65%). MS (ESI): m/z=516.091 [M+H]$^+$.

Intermediate

{(3,5-Bis-trifluoromethyl-benzoyl)-[4-(2-chlorophenyl)-pyridin-3-yl]-amino}-acetic acid To a solution of {(3,5-bis-trifluoromethyl-benzoyl)-[4-(2-chloro-phenyl)-pyridin-3-yl]-amino}-acetic acid methyl ester (109 mg, 211 μmol, example 88) in dioxane (2 mL) was added water (2 mL) and lithium hydroxide hydrate (11.1 mg, 264 μmol). The reaction mixture was stirred at room temperature for 2 hours and then poured on 30 mL 1M aqueous HCl and 30 mL EtOAc. The layers were separated and the aqueous layer was extracted a second time with 30 mL EtOAc. The organic layers were washed with 30 mL brine, dried over MgSO$_4$, filtered and evaporated to give a yellow solid which was pure enough for the next step (119 mg, 112%). MS (ESI): m/z=503.060 [M+H]$^+$.

Example 103

3-Chloro-5-fluoro-N-methyl-N-(4-o-tolyl-pyridin-3-yl)-benzamide

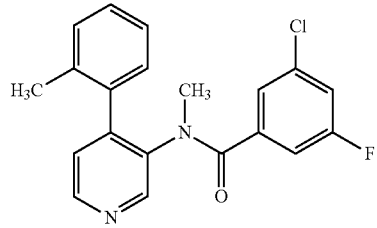 [SMILES: Cc1ccccc1-c1ccncc1N(C)C(=O)c1cc(F)cc(Cl)c1]

The title compound was prepared in analogy to example 90, from N-methyl-4-o-tolylpyridin-3-amine (example 1, intermediate a) and 3-chloro-5-fluorobenzoic acid (CAS RN 25026-64-6) and using a gradient of n-heptane:EtOAc (100:0 to 30:70) for the chromatographic purification. Yellow solid (17%). MS (ESI): m/z=355.10 [M+H]$^+$.

Example 104

3,4,5-Trifluoro-N-methyl-N-(4-o-tolyl-pyridin-3-yl)-benzamide

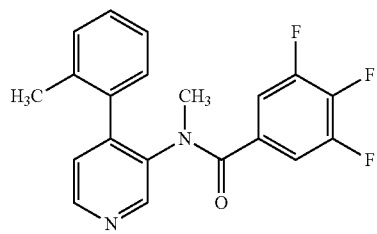 [SMILES: Cc1ccccc1-c1ccncc1N(C)C(=O)c1cc(F)c(F)c(F)c1]

The title compound was prepared in analogy to example 90, from N-methyl-4-o-tolylpyridin-3-amine (example 1, intermediate a) and 3,4,5-trifluorobenzoic acid (CAS RN 121602-93-5) after a reaction time of 64 hours. The compound was purified by silica gel chromatography on a 10 g column using a MPLC system eluting with a gradient of n-heptane: EtOAc (100:0 to 50:50). The product-containing fractions were pooled and evaporated. The resulting brown solid was chromatographed a second time by silica gel chromatography on a 10 g column using a MPLC system eluting with a gradient of n-heptane: EtOAc (100:0 to 50:50). Light brown solid (22%). MS (ESI): m/z=357.12 [M+H]+.

Example 105

N-[4-(2,3-Dimethyl-phenyl)-pyridin-3-yl]-N-methyl-3,5-bis-trifluoromethyl-benzamide

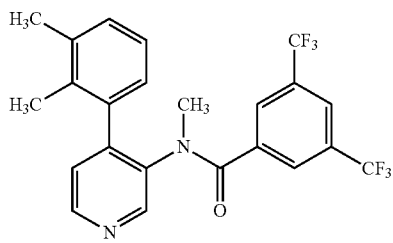 [SMILES: Cc1cccc(-c2ccncc2N(C)C(=O)c2cc(C(F)(F)F)cc(C(F)(F)F)c2)c1C]

The title compound was prepared in analogy to example 72, from N-(4-iodo-pyridin-3-yl)-N-methyl-3,5-bis-trifluoromethyl-benzamide (example 98, intermediate a) and 2,3-dimethylphenylboronic acid (CAS RN 183158-34-1) and using gradient of n-heptane: EtOAc (100:0 to 30:70) for the chromatographic purification. Colorless solid (81%). MS (ESI): m/z=453.140 [M+H]+.

Example 106

N-Methyl-N-[2-(2,2,2-trifluoro-ethoxy)-[3,4']bipyridinyl-3'-yl]-3,5-bis-trifluoromethyl-benzamide

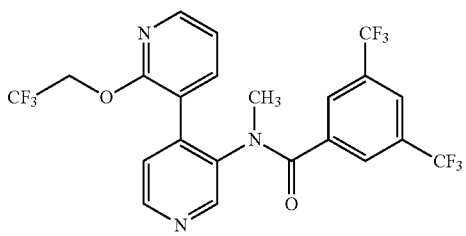 [SMILES: CN(C(=O)c1cc(C(F)(F)F)cc(C(F)(F)F)c1)c1cnccc1-c1cccnc1OCC(F)(F)F]

The title compound was prepared in analogy to example 72, from N-(4-iodo-pyridin-3-yl)-N-methyl-3,5-bis-trifluoromethyl-benzamide (example 98, intermediate a) and 2-(2,2,2-trifluoroethoxy)pyridin-3-ylboronic acid (Combi-Blocks Inc.) and using a gradient of n-heptane:EtOAc (100:0 to 30:70) for the chromatographic purification. Colorless solid (58%). MS (ESI): m/z=524.103 [M+H]+.

Example 107

N-(2-Cyclopropylmethoxy-[3,4']bipyridinyl-3'-yl)-N-methyl-3,5-bis-trifluoromethyl-benzamide

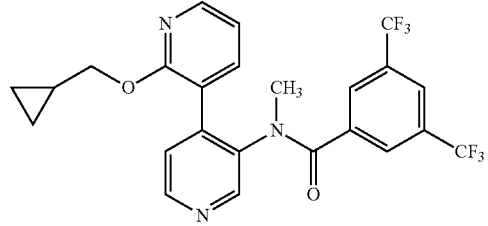 [SMILES: CN(C(=O)c1cc(C(F)(F)F)cc(C(F)(F)F)c1)c1cnccc1-c1cccnc1OCC1CC1]

The title compound was prepared in analogy to example 72, from N-(4-iodo-pyridin-3-yl)-N-methyl-3,5-bis-trifluoromethyl-benzamide (example 98, intermediate a) and 2-(cyclopropylmethoxy)-3-(4,4,5,5-tetramethyl-1,3,2-dioxaborolan-2-yl)pyridine (CAS RN 848243-26-5) and using a gradient of n-heptane:EtOAc (100:0 to 30:70) for the chromatographic purification. Light yellow oil (63%). MS (ESI): m/z=498.146 [M+H]+.

Example 108

3,N-Dimethyl-N-(4-o-tolyl-pyridin-3-yl)-5-trifluoromethyl-benzamide

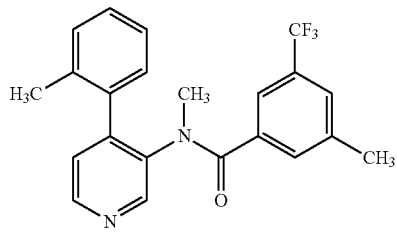

The title compound was prepared in analogy to example 90, from N-methyl-4-o-tolylpyridin-3-amine (example 1, intermediate a) and 3-methyl-5-(trifluoromethyl)benzoic acid (CAS RN 117186-02-4) after a reaction time of 67 hours. The compound was purified by silica gel chromatography on a 10 g column using a MPLC system eluting with a gradient of n-heptane:EtOAc (100:0 to 30:70). Light brown oil (9%). MS (ESI): m/z=385.15[M+H]+.

Example 109

3-Chloro-N-methyl-N-(4-o-tolyl-pyridin-3-yl)-5-trifluoromethyl-benzamide

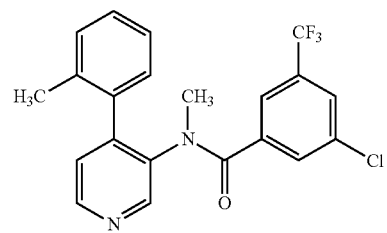 [SMILES: Cc1ccccc1-c1ccncc1N(C)C(=O)c1cc(Cl)cc(C(F)(F)F)c1]

The title compound was prepared in analogy to example 90, from N-methyl-4-o-tolylpyridin-3-amine (example 1, intermediate a) and 3-chloro-5-(trifluoromethyl)benzoic acid (CAS RN 39226-97-6) after a reaction time of 68 hours. The compound was purified by silica gel chromatography on a 10 g column using a MPLC system eluting with a gradient of n-heptane:EtOAc (100:0 to 30:70). The product-containing fractions were pooled and evaporated. The product was dissolved in EtOAc and extracted three time with 1M aqueous HCl. The organic layers were washed with brine, dried over MgSO$_4$, filtered, treated with silica gel and evaporated. The compound was purified a second time by silica gel chromatography on a 10 g column using a MPLC system eluting with a gradient of n-heptane:EtOAc (100:0 to 30:70). Light brown solid (47%). MS (ESI): m/z=405.10 [M+H]$^+$.

Example 110

N-[4-(2-Chloro-phenyl)-pyridin-3-yl]-N-(2-fluoro-ethyl)-3,5-bis-trifluoromethyl-benzamide

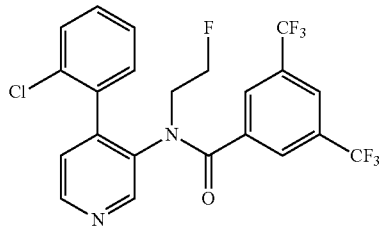 [SMILES: O=C(c1cc(C(F)(F)F)cc(C(F)(F)F)c1)N(CCF)c1cnccc1-c1ccccc1Cl]

The title compound was prepared in analogy to example 72, intermediate, from [4-(2-chloro-phenyl)-pyridin-3-yl]-(2-fluoro-ethyl)-amine and 3,5-bis(trifluoromethyl)benzoyl chloride (CAS RN 1271-19-8) and using a gradient of n-heptane:EtOAc (100:0 to 50:50) for the chromatographic purification to give a first batch of compound (light yellow solid). A second chromatographic purification of the remaining impure fractions and mother liquor gave a second batch of compound. Yellow solid (25% overall). MS (ESI): m/z=491.08 [M+H]$^+$.

Intermediates a) [4-(2-Chloro-phenyl)-pyridin-3-yl]-(2-fluoro-ethyl)-amine

The title compound was prepared in analogy to example 85, intermediate a, from [4-(2-chloro-phenyl)-pyridin-3-yl]-(2-fluoro-ethyl)-carbamic acid tert-butyl ester. Light brown solid (98%). MS (ESI): m/z=251.07 [M+H]$^+$.

b) [4-(2-Chloro-phenyl)-pyridin-3-yl]-(2-fluoro-ethyl)-carbamic acid tert-butyl ester The title compound was prepared in analogy to example 72, from (2-fluoro-ethyl)-(4-iodo-pyridin-3-yl)-carbamic acid tert-butyl ester and 2-chlorophenylboronic acid (CAS RN 1679-18-1). Yellow oil (86%). MS (ESI): m/z=351.13 [M+H]$^+$.

c) (2-Fluoro-ethyl)-(4-iodo-pyridin-3-yl)-carbamic acid tert-butyl ester

The title compound was prepared in analogy to example 85, intermediate c, from (4-iodo-pyridin-3-yl)-carbamic acid tert-butyl ester (example 85, intermediate d) and 1-bromo-2-fluoroethane (CAS RN 762-49-2) and using a gradient of n-heptane:EtOAc (100:0 to 30:70) for the chromatographic purification. Light brown solid (71%). MS (ESI): m/z=367.03 [M+H]$^+$.

Example 111

N-[4-(3-Chloro-2-fluoro-phenyl)-pyridin-3-yl]-N-methyl-3,5-bis-trifluoromethyl-benzamide

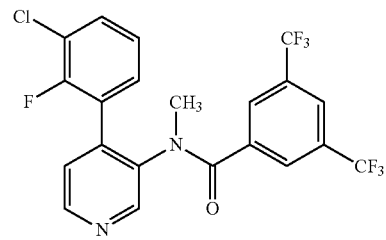

The title compound was prepared in analogy to example 72, from N-(4-iodo-pyridin-3-yl)-N-methyl-3,5-bis-trifluoromethyl-benzamide (example 98, intermediate a) and 3-chloro-2-fluorophenylboronic acid (CAS RN 352535-82-1) and using a gradient of n-heptane: EtOAc (100:0 to 30:70) for the chromatographic purification. Light yellow oil (64%). MS (ESI): m/z=477.061 [M+H]$^+$.

Example 112

N-[4-(2-Chloro-phenyl)-pyridin-3-yl]-N-(2-methane-sulfonyl-ethyl)-3,5-bis-trifluoromethyl-benzamide

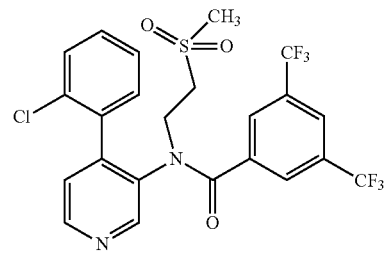 [SMILES: CS(=O)(=O)CCN(C(=O)c1cc(C(F)(F)F)cc(C(F)(F)F)c1)c1cnccc1-c1ccccc1Cl]

The title compound was prepared in analogy to example 72, intermediate, from [4-(2-chloro-phenyl)-pyridin-3-yl]-(2-methanesulfonyl-ethyl)-amine and 3,5-bis(trifluoromethyl) benzoyl chloride (CAS RN 1271-19-8) and using a gradient of n-heptane: EtOAc (100:0 to 0:100) for the chromatographic purification. Light yellow foam (36%). MS (ESI): m/z=551.06 [M+H]$^+$.

Intermediates a) [4-(2-Chloro-phenyl)-pyridin-3-yl]-(2-methane-sulfonyl-ethyl)-amine The title compound was prepared in analogy to example 85, intermediate a, from [4-(2-chloro-phenyl)-pyridin-3-yl]-(2-methanesulfonyl-ethyl)-carbamic acid tert-butyl ester. Colorless foam (84%). MS (ESI): m/z=311.02 [M+H]$^+$.

b) [4-(2-Chloro-phenyl)-pyridin-3-yl]-(2-methane-sulfonyl-ethyl)-carbamic acid tert-butyl ester The title compound was prepared in analogy to example 72, from (4-iodo-pyridin-3-yl)-(2-methanesulfonyl-ethyl)-carbamic acid Cert-butyl ester and 2-chlorophenylboronic acid (CAS RN 1679-18-1). The product was purified by preparative HPLC (phenomenex gemini column) with a gradient of acetonitrile:water (containing 0.05% formic acid) (10:90 to 98:2). Light brown foam (67%). MS (ESI): m/z=411.11 [M+H]+.

c) (4-Iodo-pyridin-3-yl)-(2-methanesulfonyl-ethyl)-carbamic acid tert-butyl ester The title compound was prepared in analogy to example 85, intermediate c, from (4-iodo-pyridin-3-yl)-carbamic acid tert-butyl ester (example 14, intermediate d) and 1-bromo-2-methanesulfonyl-ethane (CAS RN 16523-02-7) and using a gradient of n-heptane: EtOAc (100:0 to 0:100) for the chromatographic purification. Light brown solid (11%). MS (ESI): m/z=427.02 [M+H]+.

Example 113

N-Methyl-N-[6-(1H-pyrrol-2-yl)-4-o-tolyl-pyridin-3-yl]-3,5-bis-trifluoromethyl-benzamide

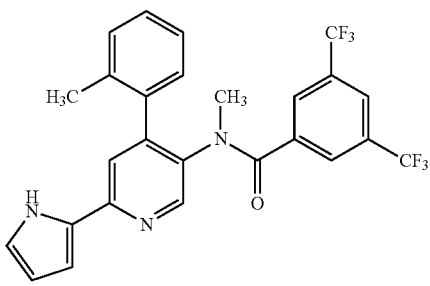 [SMILES: Cc1ccccc1-c1cc(-c2ccc[nH]2)ncc1N(C)C(=O)c1cc(C(F)(F)F)cc(C(F)(F)F)c1]

To a solution of 2-{5-[(3,5-bis-trifluoromethyl-benzoyl)-methyl-amino]-4-o-tolyl-pyridin-2-yl}-pyrrole-1-carbox-ylic acid tert-butyl ester (39 mg, 64.6 µmol) in CH2Cl2 (2 mL) was added TFA (2 mL) at 0° C. The reaction mixture was stirred for at room temperature for 1 hour and then concentrated under vacuum. The residue was poured on 30 mL aqueous NaHCO3 solution and 30 mL EtOAc and the layers were separated. The aqueous layer was extracted a second time with 30 mL EtOAc. The organic layers were washed with 30 mL brine, dried over MgSO4, filtered and concentrated under vacuum. Light yellow solid (32 mg, 98%). MS (ESI): m/z=504.151 [M+H]+.

Intermediate

2-{5-[(3,5-Bis-trifluoromethyl-benzoyl)-methyl-amino]-4-o-tolyl-pyridin-2-yl}-pyrrole-1-carboxylic acid tell-butyl ester The title compound was prepared in analogy to example 72, from N-(6-chloro-4-o-tolyl-pyridin-3-yl)-N-methyl-3,5-bis-trifluoromethyl-benzamide (example 12) and 1-(tert-butoxycarbonyl)pyrrole-2-boronic acid (CAS RN 135884-31-0) and using a gradient of n-heptane:EtOAc (100:0 to 50:50) for the chromatographic purification. Light yellow oil (18%). MS (ESI): m/z=604.202 [M+H]+.

Example 114

3-Methanesulfonyl-N-methyl-N-(4-o-tolyl-pyridin-3-yl)-5-trifluoromethyl-benzamide

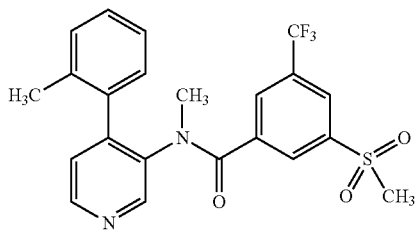

The title compound was prepared in analogy to example 90, from N-methyl-4-o-tolylpyridin-3-amine (example 1, intermediate a) and 3-methanesulfonyl-5-trifluoromethyl-benzoic acid (example 114, intermediate a) after a reaction time of 64 hours. The compound was purified by two silica gel chromatographies on a 10 g column using a MPLC system eluting with a gradient of n-heptane:EtOAc (100:0 to 0:100). Light brown foam (30%). MS (ESI): m/z=449.11 [M+H]+.

a) 3-Methanesulfonyl-5-trifluoromethyl-benzoic acid

To a solution of 3-methanesulfonyl-5-trifluoromethyl-benzoic acid methyl ester (1.0 g, 3.54 mmol) in dioxane (15 mL) was added water (15 mL) and lithium hydroxide monohydrate (186 mg, 4.43 mmol). The reaction mixture was stirred at room temperature for 2 hours and then poured on 100 ml 1M aqueous HCl and 100 mL EtOAc. The layers were separated and the aqueous layer was extracted a second time with 100 mL EtOAc. The organic layers were washed with 100 mL brine, dried over MgSO4, filtered and concentrated under vacuum. Colorless solid (930 mg, 98%). MS (ESI): m/z=266.995 [M–H]−.

b) 3-Methanesulfonyl-5-trifluoromethyl-benzoic acid methyl ester

The mixture consisting of 1-bromo-3-(methylsulfonyl)-5-(trifluoromethyl)benzene (0.20 g, 0.66 mmol, Combi-Blocks, Inc.), 1,1'-bis(diphenylphosphino)ferrocene-palladium(II)dichloride dichloromethane complex (20.4 mg, 0.025 mmol, CAS RN 72287-26-4) and NEt3 (0.134 g, 0.184 mL, 1.32 mmol) in EtOAc (2 mL) and methanol (2 mL) was stirred at 110° C. under a 70 bar carbon monoxide atmosphere for 20 h. After cooling to room temperature silica gel was added and the brown suspension evaporated. The compound was purified by silica gel chromatography on a 20 g column using a MPLC system eluting with a gradient of n-heptane:EtOAc (100:0 to 50:50). Light brown oil (0.156 g; 83%). MS (GC_MS (EI)): m/z=282.0 [M].

Example 115

N-[4-(2-Chloro-phenyl)-pyridin-3-yl]-N-(2-hydroxy-ethyl)-3,5-bis-trifluoromethyl-benzamide

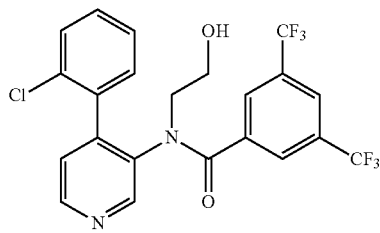 [SMILES: O=C(c1cc(C(F)(F)F)cc(C(F)(F)F)c1)N(CCO)c1cnccc1-c1ccccc1Cl]

The solution of methyl 2-(N-(4-(2-chlorophenyl)pyridin-3-yl)-3,5-bis(trifluoromethyl) benzamido)acetate (0.15 g, 0.29 mmol, example 88) in methanol (2.00 mL) was cooled down to 0° C. To the light yellow suspension was added NaBH$_4$ (22.0 mg, 0.58 mmol) and the reaction was stirred for 2 h at room temperature. The reaction mixture was poured on saturated aqueous NH$_4$Cl solution and EtOAc and the layers were separated. The aqueous layer was extracted twice with EtOAc. The organic layers were washed with brine, dried over MgSO$_4$, filtered, treated with silica gel and evaporated. The compound was purified by silica gel chromatography on a 10 g column using a MPLC system eluting with a gradient of n-heptane:EtOAc (100:0 to 30:70). The product containing fractions were combined and partially evaporated upon which crystallisation started. The supernatant light brown solution was pipetted off and the remaining solid dried under high vacuum. Colorless crystals (0.024 g; 16%). MS (ESI): m/z=489.08 [M+H]$^+$.

Example 116

N-[4-(2-Chloro-phenyl)-pyridin-3-yl]-N-(2,2-difluoro-ethyl)-3,5-bis-trifluoromethyl-benzamide

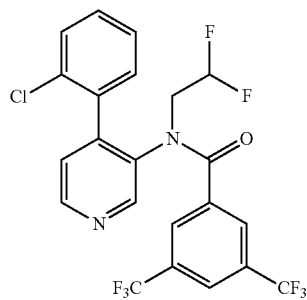 [SMILES: O=C(c1cc(C(F)(F)F)cc(C(F)(F)F)c1)N(CC(F)F)c1cnccc1-c1ccccc1Cl]

The title compound was prepared in analogy to example 72, intermediate, from [4-(2-chloro-phenyl)-pyridin-3-yl]-(2,2-difluoro-ethyl)-amine and 3,5-bis(trifluoromethyl)benzoyl chloride (CAS RN 1271-19-8) and using a gradient of n-heptane: EtOAc (100:0 to 70:30) for the chromatographic purification. Light brown solid (0.053 g; 11%). MS (ESI): m/z=509.07 [M+H]$^+$.

Intermediates a) [4-(2-Chloro-phenyl)-pyridin-3-yl]-(2,2-difluoro-ethyl)-amine

The title compound was prepared in analogy to example 85, intermediate a, from [4-(2-chloro-phenyl)-pyridin-3-yl]-(2,2-difluoro-ethyl)-carbamic acid tert-butyl ester. Light brown solid (94%). MS (ESI): m/z=269.07 [M+H]$^+$.

b) [4-(2-Chloro-phenyl)-pyridin-3-yl]-(2,2-difluoro-ethyl)-carbamic acid tert-butyl ester The title compound was prepared in analogy to example 72, from (2,2-difluoro-ethyl)-(4-iodo-pyridin-3-yl)-carbamic acid tert-butyl ester and 2-chlorophenylboronic acid (CAS RN 1679-18-1) and using a gradient of n-heptane: EtOAc (100:0 to 50:50) for the chromatographic purification. Light brown oil (0.726 g; 89%). MS (ESI): m/z=369.12 [M+H]$^+$.

c) (2,2-Difluoro-ethyl)-(4-iodo-pyridin-3-yl)-carbamic acid tert-butyl ester

The title compound was prepared in analogy to example 85, intermediate c, from (4-iodo-pyridin-3-yl)-carbamic acid tert-butyl ester (example 85, intermediate d) and 2-bromo-1,1-difluoroethane (CAS RN 359-07-9). Light brown solid (0.85 g; 77%). MS (ESI): m/z=385.02 [M+H]$^+$.

Example 117

N-Carbamoylmethyl-N-[4-(2-chloro-phenyl)-pyridin-3-yl]-3,5-bis-trifluoromethyl-benzamide

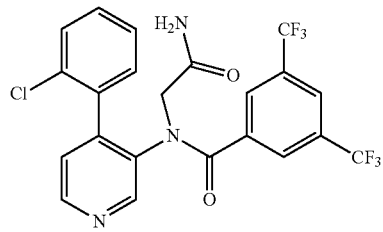 [SMILES: NC(=O)CN(C(=O)c1cc(C(F)(F)F)cc(C(F)(F)F)c1)c1cnccc1-c1ccccc1Cl]

A suspension of {(3,5-bis-trifluoromethyl-benzoyl)-[4-(2-chloro-phenyl)-pyridin-3-yl]-amino}-acetic acid (0.15 g, 298 µmol, example 102, intermediate) and EDC (172 mg, 895 µmol) in DMF (2 mL) was treated with 1-hydroxy-7-azabenzotriazole (122 mg, 895 µmol, CAS RN 39968-33-7) and stirred at room temperature for 20 min. to give a yellow solution. Ammonium chloride (160 mg, 2.98 mmol) and DIPEA (386 mg, 521 µL, 2.98 mmol) were added and the reaction was stirred for another 3.75 h. The reaction mixture was poured on saturated aqueous NH$_4$Cl solution and EtOAc and the layers were separated. The aqueous layer was extracted twice with EtOAc. The organic layers were washed twice with water and once with brine, dried over MgSO$_4$, filtered, treated with silica gel and evaporated. The compound was purified by silica gel chromatography on a 10 g column using a MPLC system eluting with a gradient of n-heptane:EtOAc (100:0 to 0:100). Light yellow solid (0.099 g; 66%). MS (ESI): m/z=502.07 [M+H]$^+$.

Example 118

N-[4-(2-Chloro-phenyl)-pyridin-3-yl]-N-dimethyl-carbamoylmethyl-3,5-bis-trifluoromethyl-benzamide

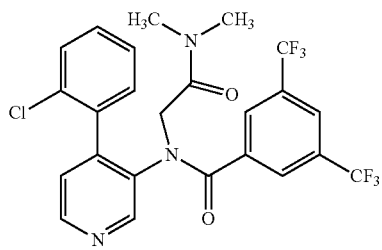 [SMILES: CN(C)C(=O)CN(C(=O)c1cc(C(F)(F)F)cc(C(F)(F)F)c1)c1cnccc1-c1ccccc1Cl]

A solution of {(3,5-bis-trifluoromethyl-benzoyl)-[4-(2-chloro-phenyl)-pyridin-3-yl]-amino}-acetic acid (0.15 g, 298 µmol, example 102, intermediate), HATU (136 mg, 358 µmol) and diethylamin hydrochloride (29.2 mg, 358 µmol) in DMF (2 mL) was treated with DIPEA (116 mg, 156 µL, 895 µmol) and stirred at room temperature for 1.75 h. The reaction mixture was poured on saturated aqueous NH$_4$Cl solution and EtOAc and the layers were separated. The aqueous layer was extracted twice with EtOAc. The organic layers were washed twice with water and once with brine, dried over MgSO$_4$, filtered, treated with silica gel and evaporated. The compound was purified by silica gel chromatography on a 10 g column using a MPLC system eluting with a gradient of n-heptane: EtOAc (100:0 to 0:100). Light yellow foam (0.127 g; 80%). MS (ESI): m/z=530.12 [M+H]$^+$.

Example 119

2-Chloro-6,N-dimethyl-N-(4-o-tolyl-pyridin-3-yl)-isonicotinamide

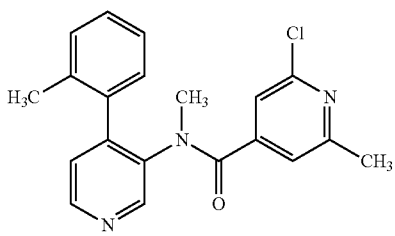

The title compound was prepared in analogy to example 90, from N-methyl-4-o-tolylpyridin-3-amine (example 1, intermediate a) and 2-chloro-6-methylisonicotinic acid (CAS RN 25462-85-5) after a reaction time of 64 hours. The compound was purified by silica gel chromatography on a 10 g column using a MPLC system eluting with a gradient of n-heptane:EtOAc (100:0 to 0:100). Light brown foam (7%). MS (ESI): m/z=352.12 [M+H]$^+$.

Example 120

2,6-Dichloro-N-methyl-N-(4-o-tolyl-pyridin-3-yl)-isonicotinamide

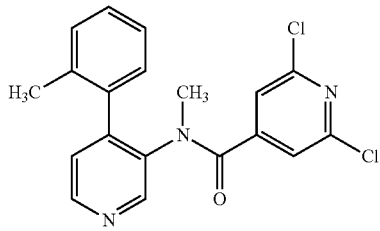 [SMILES: Cc1ccccc1-c1ccncc1N(C)C(=O)c1cc(Cl)nc(Cl)c1]

The title compound was prepared in analogy to example 90, from N-methyl-4-o-tolylpyridin-3-amine (example 1, intermediate a) and 2,6-dichloro-isonicotinic acid (CAS RN 5398-44-7) after a reaction time of 18 hours. The compound was purified by silica gel chromatography on a 50 g column using a MPLC system eluting with EtOAc (isocratic). The product-containing fractions were pooled and evaporated to give a colorless foam. The foam was dissolved in EtOAc and washed three times with 2M aqueous Na$_2$CO$_3$ solution and brine, dried over MgSO$_4$, filtered and evaporated. Colorless foam (13%). MS (ESI): m/z=372.07 [M+H]$^+$.

Example 121

4,6-Dimethyl-pyridine-2-carboxylic acid methyl-(4-o-tolyl-pyridin-3-yl)-amide

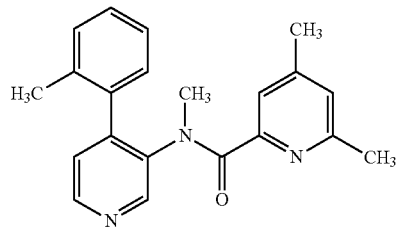

The title compound was prepared in analogy to example 90, from N-methyl-4-o-tolylpyridin-3-amine (example 1, intermediate a) and 4,6-dimethylpyridine-2-carboxylic acid (CAS RN 18088-10-3) after a reaction time of 64 hours. The compound was purified by silica gel chromatography on a 10 g column using a MPLC system eluting with a gradient of n-heptane:EtOAc (100:0 to 0:100). Light brown oil (37%). MS (ESI): m/z=332.18 [M+H]$^+$.

Example 122

4-Chloro-6-methyl-pyridine-2-carboxylic acid methyl-(4-o-tolyl-pyridin-3-yl)-amide

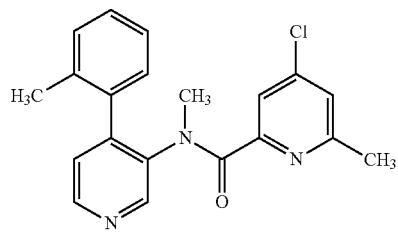

The title compound was prepared in analogy to example 90, from N-methyl-4-o-tolylpyridin-3-amine (example 1, intermediate a) and 4-chloro-6-methylpyridine-2-carboxylic acid (CAS RN 30235-19-9). Colorless solid (35%). MS (ESI): m/z=352.12 [M+H]+.

Example 123

4,6-Dichloro-pyridine-2-carboxylic acid methyl-(4-o-tolyl-pyridin-3-yl)-amide

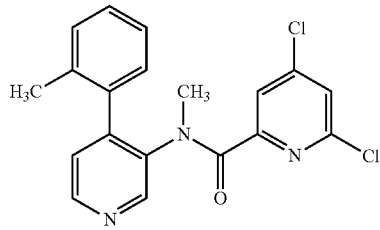 [SMILES: Cc1ccccc1-c1ccncc1N(C)C(=O)c1cc(Cl)cc(Cl)n1]

The title compound was prepared in analogy to example 90, from N-methyl-4-o-tolylpyridin-3-amine (example 1, intermediate a) and 4,6-dichloro-pyridine-2-carboxylic acid (CAS RN 88912-25-8) and using a gradient of n-heptane:EtOAc (100:0 to 0:100) for the chromatographic purification. Colorless solid (7%). MS (ESI): m/z=372.07 [M+H]+.

Example 124

N-[4-(2-Chloro-phenyl)-pyridin-3-yl]-N-cyclopropyl-3,5-bis-trifluoromethyl-benzamide

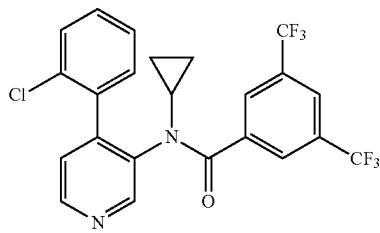 [SMILES: O=C(c1cc(C(F)(F)F)cc(C(F)(F)F)c1)N(c1cnccc1-c1ccccc1Cl)C1CC1]

The title compound was prepared in analogy to example 72, intermediate, from [4-(2-chloro-phenyl)-pyridin-3-yl]-cyclopropyl-amine and 3,5-bis(trifluoromethyl)benzoyl chloride (CAS RN 1271-19-8). The compound was purified by two subsequent silical gel chromatographies using a MPLC system (10 g column, gradient of n-heptane:EtOAc (100:0 to 50:50) and n-heptane:EtOAc (100:0 to 60:40)) and by preparative HPLC (phenomenex gemini column) with a gradient of acetonitrile:water (containing 0.05% formic acid) (10:90 to 98:2). Colorless solid (24%). MS (ESI): m/z=485.08 [M+H]+.

Intermediates a) [4-(2-Chloro-phenyl)-pyridin-3-yl]-cyclopropyl-amine

An ice-cold solution [4-(2-chloro-phenyl)-pyridin-3-yl]-(1-methoxy-cyclopropyl)-amine (0.105 g, 0.382 mmol) in THF (2 mL) was treated with LiAlH$_4$ (14.5 mg, 0.382 mmol) and stirred at 0° C. for 1 h. The reaction was allowed to warm to room temperature and stirring was continued for 2.25 h. The reaction mixture was poured on saturated aqueous potassium sodium tartrate solution and EtOAc and the layers were separated. The aqueous layer was extracted twice with EtOAc and the organic layers were washed with water and brine, dried over MgSO$_4$, filtered, treated with silica gel and evaporated. The compound was purified by silica gel chromatography on a 10 g column using a MPLC system eluting with a gradient of n-heptane:EtOAc (100:0 to 50:50). Colorless solid (0.074 g; 79%). MS (ESI): m/z=245.08 [M+H]+.

b) [4-(2-Chloro-phenyl)-pyridin-3-yl]-(1-methoxy-cyclopropyl)-amine

Step a: A solution of 4-(2-chlorophenyl)pyridin-3-amine (0.3 g, 1.47 mmol) in MeOH (1.5 mL) and AcOH (352 mg, 0.336 mL, 5.86 mmol) was treated dropwise with (1-ethoxy-cyclopropoxy)trimethylsilane (294 mg, 0.338 ml, 1.69 mmol, CAS RN 27374-25-0) at room temperature. After stirring for 1 h, the reaction mixture was heated to reflux, stirred for 22.5 hours and then evaporated. The crude product was used without further purification.

Step b: To an ice-cold suspension of NaBH$_4$ (111 mg, 2.93 mmol) in THF (2 mL) was added dropwise boron trifluoride dimethyl ether complex (416 mg, 0.372 ml, 2.93 mmol, CAS RN 353-42-4) and the white suspension was stirred at 0° C. for 1 h. To this reaction mixture a solution of crude product from step a in THF (4 mL) was added dropwise over 45 min. After stirring at 0° C. for 15 min., the cooling bath was removed and stirring was continued at room temperature for 21 hours. The reaction mixture was refluxed overnight and after cooling down to room temperature 2M aqueous NaOH solution and EtOAc were added. After stirring for 15 min. the layers were separated and the aqueous layer was extracted twice with EtOAc. The organic layers were washed with brine, dried over MgSO$_4$, filtered, treated with silica gel and evaporated. The compound was purified by silica gel chromatography on a 10 g column using a MPLC system eluting with a gradient of n-heptane:EtOAc (100:0 to 0:100), followed by three additional silica gel chromatographics eluting with a gradient of n-heptane:EtOAc (100:0 to 50:50). Colorless solid (0.044 g). MS (ESI): m/z=275.10 [M+H]+.

c) 4-(2-Chloro-phenyl)-pyridin-3-ylamine

An ice-cold solution of [4-(2-chloro-phenyl)-pyridin-3-yl]-carbamic acid tert-butyl ester (1.08 g, 3.54 mmol) in CH$_2$Cl$_2$ (11 mL) was treated with TFA (4.04 g, 2.73 mL) and stirred at room temperature for 3.5 hours. The volatiles were removed at a rotary evaporator and the residue taken up in CH$_2$Cl$_2$ and saturated aqueous NaHCO$_3$ solution and the layers were separated. The aqueous layer was extracted twice with CH$_2$Cl$_2$ and the organic layers were washed with brine, dried over MgSO$_4$, filtered, treated with silica gel and evaporated. The compound was purified by silica gel chromatography on a 10 g column using a MPLC system eluting with a gradient of n-heptane:EtOAc (100:0 to 0:100). Colorless solid (0.658 g, 90%). MS (ESI): m/z=205.05 [M+H]+.

d) [4-(2-Chloro-phenyl)-pyridin-3-yl]-carbamic acid tert-butyl ester

The title compound was prepared in analogy to example 72, from (4-iodo-pyridin-3-yl)-carbamic acid tert-butyl ester (example 85, intermediate d) and 2-chlorophenylboronic acid (672 mg, 4.3 mmol, CAS RN 1679-18-1) and using a gradient of n-heptane:EtOAc (100:0 to 50:50) for the chromatographic purification. Light yellow foam (1.08 g, 90%). MS (ESI): m/z=305.11 [M+H]+.

Example 125

(2-{(3,5-Bis-trifluoromethyl-benzoyl)-[4-(2-chloro-phenyl)-pyridin-3-yl]-amino}-ethyl)-carbamic acid benzyl ester

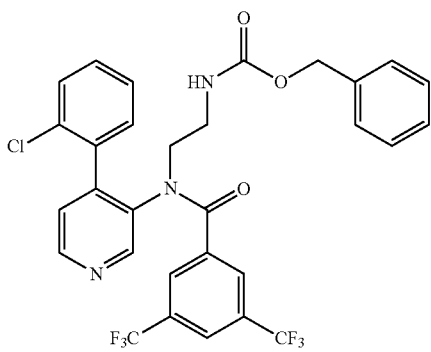 [SMILES: O=C(NCCN(C(=O)c1cc(C(F)(F)F)cc(C(F)(F)F)c1)c1cnccc1-c1ccccc1Cl)OCc1ccccc1]

The title compound was prepared in analogy to example 72, intermediate, from {2-[4-(2-chloro-phenyl)-pyridin-3-ylamino]-ethyl}-carbamic acid benzyl ester and 3,5-bis(trifluoromethyl) benzoyl chloride (CAS RN 1271-19-8) and using a gradient of n-heptane: EtOAc (100:0 to 0:100) for the chromatogrpahic purification. Light brown solid (36%). MS (ESI): m/z=622.13 [M+H]+.

Intermediates a) {2-[4-(2-Chloro-phenyl)-pyridin-3-ylamino]-ethyl}-carbamic acid benzyl ester The title compound was prepared in analogy to example 85, intermediate a, from (2-benzyloxycarbonylamino-ethyl)-[4-(2-chloro-phenyl)-pyridin-3-yl]-carbamic acid tert-butyl ester. Light brown foam (97%). MS (ESI): m/z=382.13 [M+H]+.

b) (2-Benzyloxycarbonylamino-ethyl)-[4-(2-chloro-phenyl)-pyridin-3-yl]-carbamic acid tert-butyl ester The title compound was prepared in analogy to example 85, intermediate c, from [4-(2-chloro-phenyl)-pyridin-3-yl]-carbamic acid tert-butyl ester (example 124, intermediate d) and (2-bromo-ethyl)-carbamic acid benzyl ester (CAS RN 53844-02-3) and using a gradient of n-heptane:tert-butyl methyl ether (100:0 to 30:70) for the chromatographic separation. Colorless foam (53%). MS (ESI): m/z=482.18 [M+H]+.

Example 126

N-[4-(2-Chloro-phenyl)-pyridin-3-yl]-N-isopropyl-3,5-bis-trifluoromethyl-benzamide

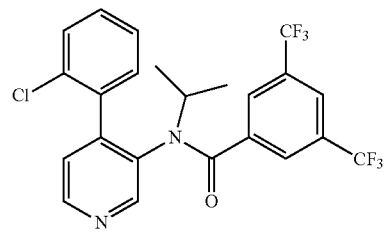 [SMILES: CC(C)N(C(=O)c1cc(C(F)(F)F)cc(C(F)(F)F)c1)c1cnccc1-c1ccccc1Cl]

The title compound was prepared in analogy to example 72, intermediate, from [4-(2-chloro-phenyl)-pyridin-3-yl]-isopropyl-amine and 3,5-bis(trifluoromethyl)benzoyl chloride (CAS RN 1271-19-8) and using a gradient of n-heptane: EtOAc (100:0 to 50:50) for the chromatographic purification. Yellow solid (19%). MS (ESI): m/z=487.10 [M+H]+.

Intermediates a) [4-(2-Chloro-phenyl)-pyridin-3-yl]-isopropyl-amine

The title compound was prepared in analogy to example 85, intermediate a, from [4-(2-chloro-phenyl)-pyridin-3-yl]-isopropyl-carbamic acid tert-butyl ester. The compound was purified by silica gel chromatography on a 10 g column using a MPLC system eluting with a gradient of n-heptane: EtOAc (100:0 to 50:50). Colorless oil (88%). MS (ESI): m/z=247.1 [M+H]+.

b) [4-(2-Chloro-phenyl)-pyridin-3-yl]-isopropyl-carbamic acid tert-butyl ester

The title compound was prepared in analogy to example 72, from (4-iodo-pyridin-3-yl)-isopropyl-carbamic acid tert-butyl ester and 2-chlorophenylboronic acid (CAS RN 1679-18-1) and using a gradient of n-heptane:EtOAc (100:0 to 50:50) for the chromatographic purification. Colorless oil (85%). MS (ESI): m/z=347.15 [M+H]+.

c) (4-Iodo-pyridin-3-yl)-isopropyl-carbamic acid tert-butyl ester

The title compound was prepared in analogy to example 85, intermediate c, from (4-iodo-pyridin-3-yl)-carbamic acid tert-butyl ester (example 85, intermediate d) and 2-bromo-propane (CAS RN 75-26-3) and using a gradient of n-heptane:EtOAc (100:0 to 50:50) for the chromatographic purification. Colorless solid (53%). MS (EST): m/z=363.06 [M+H]+.

Example 127

N-Methyl-N-(6-methyl-4-o-tolyl-pyridin-3-yl)-3,5-bis-trifluoromethyl-benzamide

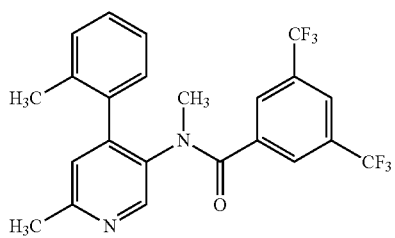 [SMILES: Cc1cc(-c2ccccc2C)c(N(C)C(=O)c2cc(C(F)(F)F)cc(C(F)(F)F)c2)cn1]

To a solution of N-(6-chloro-4-o-tolyl-pyridin-3-yl)-N-methyl-3,5-bis-trifluoromethyl-benzamide (0.15 g, 0.317 mmol, example 12) in THF (2 mL) were added methylzinc chloride (0.238 mL, 0.476 mmol, 2M solution in THF), 1,3-dimethyl-2-imidazolidinone (0.4 mL, CAS RN 80-73-9) and (1,3-bis(2,6-diisopropylphenyl)imidazolidene) (3-chloropyridyl) palladium(II) dichloride (4.31 mg, 0.00635 mmol, Sigma-Aldrich) and the reaction was stirred at 50° C. (oil bath temperature) for 1 h. The reaction mixture was poured on 10% aqueous citric acid solution and EtOAc and the layers were separated. The aqueous layer was extracted twice with EtOAc and the organic layers were washed with brine, dried over MgSO$_4$, filtered, treated with silica gel and evaporated. The compound was purified by silica gel chromatography on a 10 g column using a MPLC system eluting with a gradient of n-heptane:EtOAc (100:0 to 50:50). Colorless oil (0.122 g; 85%). MS (ESI): m/z=453.14 [M+H]$^+$.

Example 128

3-Dimethylsulfamoyl-N-methyl-N-(4-o-tolyl-pyridin-3-yl)-5-trifluoromethyl-benzamide

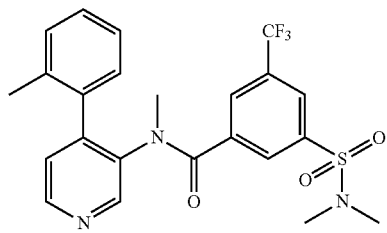

The title compound was prepared in analogy to example 90, from N-methyl-4-o-tolylpyridin-3-amine (example 1, intermediate a) and 3-[(dimethylamino)sulfonyl]-5-(trifluoromethyl)benzoic acid (Butt Park Ltd.). The product was purified a second time using preparative HPLC (Phenomenex Gemini® column) and a gradient of acetonitrile: water (containing 0.05% formic acid) (10:90 to 98:2). Light brown foam (20%). MS (ESI): m/z=478.1 [M+H]$^+$.

Example 129

3-Fluoro-N-[4-(4-fluoro-2-methoxy-phenyl)-pyridin-3-yl]-N-methyl-5-trifluoromethyl-benzamide

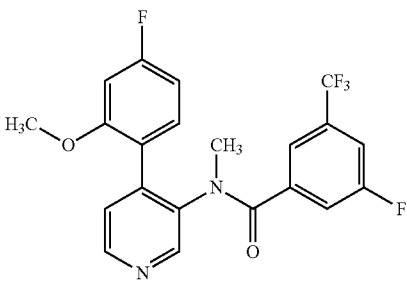 [SMILES: COc1cc(F)ccc1-c1ccncc1N(C)C(=O)c1cc(F)cc(C(F)(F)F)c1]

The title compound was prepared in analogy to example 72, intermediate, from [4-(4-fluoro-2-methoxy-phenyl)-pyridin-3-yl]-methyl-amine and 3-fluoro-5-(trifluoromethyl)benzoic acid chloride (CAS RN 171243-30-4). The compound was purified by silica gel chromatography using a MPLC system (CombiFlash Companion, Isco Inc.) eluting with a gradient of n-heptane:EtOAc (100:0 to 0:100). The product-containing fractions were pooled and evaporated. The yellow solid was further purified by preparative HPLC (Phenomenex Gemini® column) with a gradient of acetonitrile: water (containing 0.05% formic acid) (50:50 to 95:5). Light yellow solid (23%). MS (ESI): m/z=423.113 [M+H]$^+$.

Intermediate

[4-(4-Fluoro-2-methoxy-phenyl)-pyridin-3-yl]-methyl-amine

The title compound was prepared in analogy to example 72, from (4-iodo-pyridin-3-yl)-methyl-amine (example 98, intermediate b) and 4-fluoro-2-methoxyphenylboronic acid (CAS 179899-07-1) and using a gradient of n-heptane: EtOAc (100:0 to 20:80) for the chromatographic purification. Light yellow oil (85%). MS (ESI): m/z=233.108 [M+H]$^+$.

Example 130

N-[4-(4,5-Difluoro-2-methoxy-phenyl)-pyridin-3-yl]-3-fluoro-N-methyl-5-trifluoromethyl-benzamide

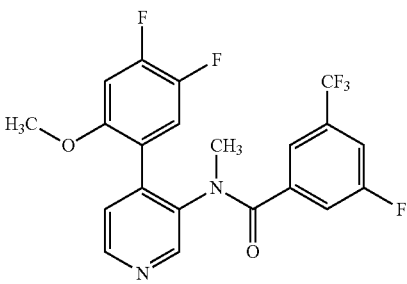 [SMILES: COc1cc(F)c(F)cc1-c1ccncc1N(C)C(=O)c1cc(F)cc(C(F)(F)F)c1]

The title compound was prepared in analogy to example 72, intermediate, from [4-(4,5-difluoro-2-methoxy-phenyl)-pyridin-3-yl]-methyl-amine and 3-fluoro-5-(trifluoromethyl)benzoic acid chloride (CAS RN 171243-30-4) and using a gradient of n-heptane: EtOAc (100:0 to 20:80) for the chromatographic purification. Yellow solid (33%). MS (ESI): m/z=441.103 [M+H]⁺.

Intermediate

[4-(4,5-Difluoro-2-methoxy-phenyl)-pyridin-3-yl]-methyl-amine

The title compound was prepared in analogy to example 72, from (4-iodo-pyridin-3-yl)-methyl-amine (example 98, intermediate b) and 4,5-difluoro-2-methoxyphenylboronic acid (CAS RN 870777-32-5) and using a gradient of n-heptane:EtOAc (100:0 to 50:50) for the chromatographic separation. Light brown solid (91%). MS (ESI): m/z=251.099 [M+H]⁺.

Example 131

N-Methyl-N-(4-o-tolyl-pyridin-3-yl)-2,6-bis-trifluoromethyl-isonicotinamide

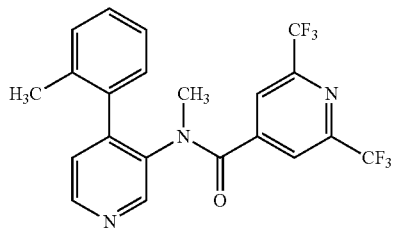

The title compound was prepared in analogy to example 90, from N-methyl-4-o-tolylpyridin-3-amine (example 1, intermediate a) and 2,6-bis(trifluoromethyl)isonicotinic acid (Key Organics Ltd.). The compound was purified by silica gel chromatography using a MPLC system (CombiFlash Companion, Isco Inc.) eluting with a gradient of CH₂Cl₂: EtOAc (100:0 to 70:30). Light yellow foam (61%). MS (ESI): m/z=440.118 [M+H]⁺.

Example 132

N-[4-(4,5-Difluoro-2-methoxy-phenyl)-pyridin-3-yl]-3-fluoro-N-(2,2,2-trifluoro-ethyl)-5-trifluoromethyl-benzamide

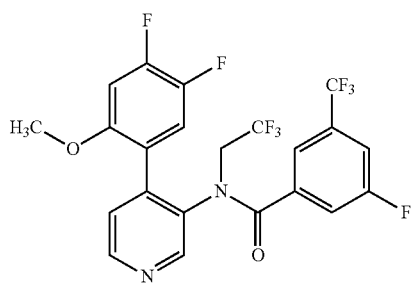 [SMILES: COc1cc(F)c(F)cc1-c1ccncc1N(CC(F)(F)F)C(=O)c1cc(F)cc(C(F)(F)F)c1]

The title compound was prepared in analogy to example 72, intermediate, from [4-(4,5-difluoro-2-methoxy-phenyl)-pyridin-3-yl]-(2,2,2-trifluoro-ethyl)-amine and 3-fluoro-5-(trifluoromethyl)benzoic acid chloride (CAS RN 171243-30-4) and using a gradient of n-heptane: EtOAc (100:0 to 50:50) for the chromatographic purification. Light yellow foam (39%). MS (ESI): m/z=509.091 [M+H]⁺.

Intermediates a) [4-(4,5-Difluoro-2-methoxy-phenyl)-pyridin-3-yl]-(2,2,2-trifluoro-ethyl)-amine The title compound was prepared in analogy to example 85, intermediate a, from [4-(4,5-difluoro-2-methoxy-phenyl)-pyridin-3-yl]-(2,2,2-trifluoro-ethyl)-carbamic acid tert-butyl ester. Colorless solid (99%). MS (ESI): m/z=319.087 [M+H]⁺.

b) [4-(4,5-Difluoro-2-methoxy-phenyl)-pyridin-3-yl]-(2,2,2-trifluoro-ethyl)-carbamic acid tert-butyl ester The title compound was prepared in analogy to example 72, from (4-iodo-pyridin-3-yl)-(2,2,2-trifluoro-ethyl)-carbamic acid tert-butyl ester and (example 85, intermediate c) and 4,5-difluoro-2-methoxyphenylboronic acid (CAS RN 870777-32-5) and using a gradient of n-heptane:EtOAc (100:0 to 50:50) for the chromatographic purification. Colorless solid (79%). MS (ESI): m/z=419.139 [M+H].

Example 133

3-Dimethylsulfamoyl-N-[4-(4-fluoro-2-methoxy-phenyl)-pyridin-3-yl]-N-(2,2,2-trifluoro-ethyl)-5-trifluoromethyl-benzamide

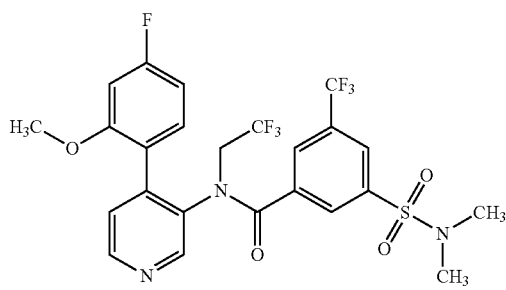

The title compound was prepared in analogy to example 90, from [4-(4-fluoro-2-methoxy-phenyl)-pyridin-3-yl]-(2,2,2-trifluoro-ethyl)-amine and 3-dimethylsulfamoyl-5-trifluoromethyl-benzoic acid (Buttpark Ltd.) and using a gradient of CH₂Cl₂:EtOAc (100:0 to 90:10) for the chromatographic purification. Light yellow foam (42%). MS (ESI): m/z=580.112 [M+H]⁺.

Intermediates a) [4-(4-Fluoro-2-methoxy-phenyl)-pyridin-3-yl]-(2,2,2-trifluoro-ethyl)-amine The title compound was prepared in analogy to example 85, intermediate a, from [4-(4-fluoro-2-methoxy-phenyl)-pyridin-3-yl]-(2,2,2-trifluoro-ethyl)-carbamic acid tert-butyl ester. Colorless solid (94%). MS (ESI): m/z=301.096 [M+H]⁺.

b) [4-(4-Fluoro-2-methoxy-phenyl)-pyridin-3-yl]-(2,2,2-trifluoro-ethyl)-carbamic acid tert-butyl ester The title compound was prepared in analogy to example 72, from (4-iodo-pyridin-3-yl)-(2,2,2-trifluoro-ethyl)-carbamic acid tert-butyl ester (example 85, intermediate c) and 4-fluoro-2-methoxyphenylboronic acid (CAS RN 179899-07-1) and using a gradient of n-heptane: EtOAc (100:0 to 50:50) for the chromatographic purification. Colorless solid (74%). MS (ESI): m/z=401.148 [M+H]⁺.

Example 134

3-Fluoro-N-[4-(4-fluoro-2-methoxy-phenyl)-pyridin-3-yl]-N-(2,2,2-trifluoro-ethyl)-5-trifluoromethyl-benzamide

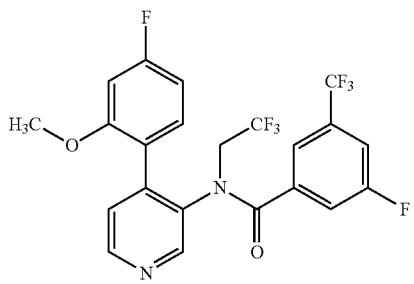

The title compound was prepared in analogy to example 72, intermediate, from [4-(4-fluoro-2-methoxy-phenyl)-pyridin-3-yl]-(2,2,2-trifluoro-ethyl)-amine (example 133, intermediate a) and 3-fluoro-5-(trifluoromethyl)benzoic acid chloride (CAS RN 171243-30-4). The compound was purified by silica gel chromatography using a MPLC system (CombiFlash Companion, Isco Inc.) eluting with a gradient of n-heptane:EtOAc (100:0 to 50:50), followed by preparative HPLC using a gradient of methanol:water (10:50 to 95:5). Colorless solid (22%). MS (ESI): m/z=491.099 [M+H]⁺.

Example 135

N-(2-Methoxy-[3,4']bipyridinyl-3'-yl)-N-(2,2,2-trifluoro-ethyl)-3,5-bis-trifluoromethyl-benzamide

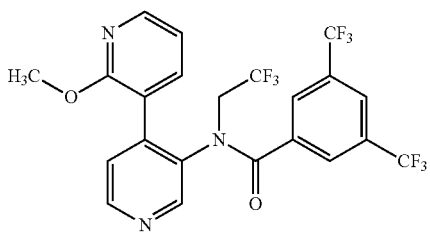 [SMILES: COc1ncccc1-c1ccncc1N(CC(F)(F)F)C(=O)c1cc(C(F)(F)F)cc(C(F)(F)F)c1]

The title compound was prepared in analogy to example 72, intermediate, from (2-methoxy-[3,4']bipyridinyl-3'-yl)-(2,2,2-trifluoro-ethyl)-amine and 3,5-bis(trifluoromethyl)benzoyl chloride (CAS RN 1271-19-8) and using a gradient of n-heptane: EtOAc (100:0 to 50:50) for the chromatographic purification. Light yellow foam (21%). MS (ESI): m/z=524.100 [M+H]⁺.

Intermediates a) (2-Methoxy-[3,4']bipyridinyl-3'-yl)-(2,2,2-trifluoro-ethyl)-amine The title compound was prepared in analogy to example 85, intermediate a, from (2-methoxy-[3,4']bipyridinyl-3'-yl)-(2,2,2-trifluoro-ethyl)-carbamic acid tert-butyl ester. Light yellow solid (92%). MS (EI): m/z=283 [M].

b) (2-Methoxy-[3,4']bipyridinyl-3'-yl)-(2,2,2-trifluoro-ethyl)-carbamic acid tert-butyl ester The title compound was prepared in analogy to example 72, from (4-iodo-pyridin-3-yl)-(2,2,2-trifluoro-ethyl)-carbamic acid tert-butyl ester (example 85, intermediate c) and 2-methoxypyridine-3-boronic acid (CAS RN 163105-90-6) and using a gradient of n-heptane: EtOAc (100:0 to 50:50) for the chromatographic purification. Light yellow oil (87%). MS (ESI): m/z=384.154 [M+H]⁺.

Example 136

N-[4-(4-Fluoro-2-methoxy-phenyl)-pyridin-3-yl]-3-methanesulfonyl-N-(2,2,2-trifluoro-ethyl)-5-trifluoromethyl-benzamide

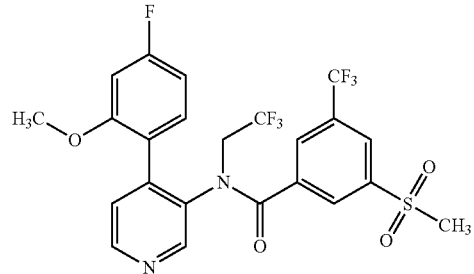

The title compound was prepared in analogy to example 90, from [4-(4-fluoro-2-methoxy-phenyl)-pyridin-3-yl]-(2,2,2-trifluoro-ethyl)-amine (example 133, intermediate a) and 3-methanesulfonyl-5-trifluoromethyl-benzoic acid (example 114, intermediate a) after a reaction time of 72 hours. The compound was purified by silica gel chromatography using a MPLC system (CombiFlash Companion, Isco Inc.) eluting with a gradient of CH₂Cl₂:EtOAc (100:0 to 85:15). Light yellow foam (43%). MS (ESI): m/z=551.087 [M+H]⁺.

Example 137

N-[4-(4,5-Difluoro-2-methoxy-phenyl)-pyridin-3-yl]-3-methanesulfonyl-N-methyl-5-trifluoromethyl-benzamide

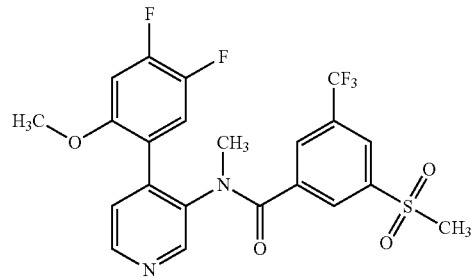

The title compound was prepared in analogy to example 90, from [4-(4,5-difluoro-2-methoxy-phenyl)-pyridin-3-yl]-methyl-amine (example 114, intermediate) and 3-methanesulfonyl-5-trifluoromethyl-benzoic acid (example 43, intermediate a) after a reaction time of 5 days. The compound was purified by silica gel chromatography using a MPLC system (CombiFlash Companion, Isco Inc.) eluting with a gradient of n-heptane: EtOAc (100:0 to 50:50), followed by preparative HPLC using a gradient of methanol: water (10:90 to 95:5). Colorless foam (46%). MS (ESI): m/z=501.091 [M+H]$^+$.

Example 138

N-[4-(4-Fluoro-2-methoxy-phenyl)-pyridin-3-yl]-3-methanesulfonyl-N-methyl-5-trifluoromethyl-benzamide

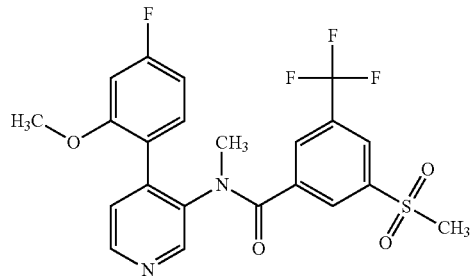

The title compound was prepared in analogy to example 90, from [4-(4-fluoro-2-methoxy-phenyl)-pyridin-3-yl]-methyl-amine (example 129, intermediate a) and 3-methanesulfonyl-5-trifluoromethyl-benzoic acid (example 114, intermediate a) after a reaction time of 72 hours. The compound was purified by silica gel chromatography using a MPLC system (CombiFlash Companion, Isco Inc.) eluting with a gradient of n-heptane: EtOAc (100:0 to 50:50), followed by preparative HPLC using a gradient of methanol: water (10:90 to 95:5). Colorless foam (44%). MS (ESI): m/z=483.099 [M+H]$^+$.

Example 139

N-[4-(4,5-Difluoro-2-methoxy-phenyl)-pyridin-3-yl]-3-methanesulfonyl-N-(2,2,2-trifluoro-ethyl)-5-trifluoromethyl-benzamide

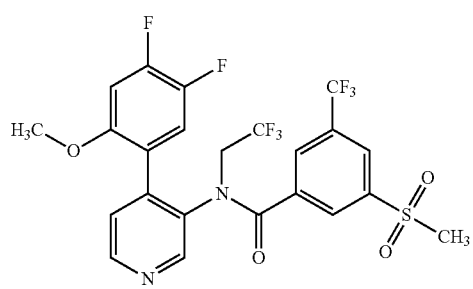

The title compound was prepared in analogy to example 90, from [4-(4,5-difluoro-2-methoxy-phenyl)-pyridin-3-yl]-(2,2,2-trifluoro-ethyl)-amine (example 132, intermediate a) and 3-methanesulfonyl-5-trifluoromethyl-benzoic acid (example 114, intermediate a) after a reaction time of 72 hours. The compound was purified by silica gel chromatography using a MPLC system (CombiFlash Companion, Isco Inc.) eluting with a gradient of CH$_2$Cl$_2$:EtOAc (100:0 to 85:15). Light brown foam (21%). MS (ESI): m/z=569.077 [M+H]$^+$.

Example 140

N-[4-(4,5-Difluoro-2-methoxy-phenyl)-pyridin-3-yl]-3-dimethylsulfamoyl-N-(2,2,2-trifluoro-ethyl)-5-trifluoromethyl-benzamide

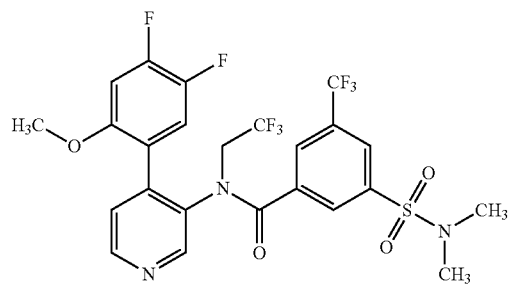

The title compound was prepared in analogy to example 90, from [4-(4,5-difluoro-2-methoxy-phenyl)-pyridin-3-yl]-(2,2,2-trifluoro-ethyl)-amine (example 132, intermediate a) and 3-dimethylsulfamoyl-5-trifluoromethyl-benzoic acid (Buttpark Ltd.). The compound was purified by silica gel chromatography using a MPLC system (CombiFlash Companion, Isco Inc.) eluting with a gradient of CH$_2$Cl$_2$:EtOAc (100:0 to 90:10), followed by preparative HPLC using a gradient of methanol:water (10:50 to 95:5). Light brown foam (13%). MS (ESI): m/z=598.104 [M+H]$^+$.

Example 141

3-Fluoro-N-(2-methoxy-[3,4']bipyridinyl-3'-yl)-N-(2,2,2-trifluoro-ethyl)-5-trifluoromethyl-benzamide

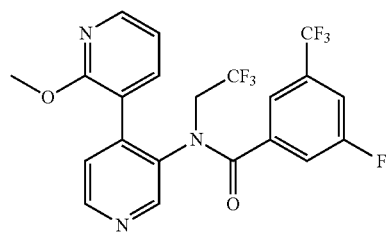 [SMILES: COc1ncccc1-c1ccncc1N(CC(F)(F)F)C(=O)c1cc(F)cc(C(F)(F)F)c1]

The title compound was prepared in analogy to example 72, intermediate, from (2-methoxy-[3,4']bipyridinyl-3'-yl)-(2,2,2-trifluoro-ethyl)-amine (example 135, intermediate a) and 3-fluoro-5-(trifluoromethyl)benzoic acid (CAS RN 161622-05-5) and using a gradient of n-heptane:EtOAc (100:0 to 50:50) for the chromatographic purification. Light yellow solid (16%). MS (ESI): m/z=474.104 [M+H]$^+$.

Example 142

3-Methanesulfonyl-N-(2-methoxy-[3,4']bipyridinyl-3'-yl)-N-(2,2,2-trifluoro-ethyl)-5-trifluoromethyl-benzamide

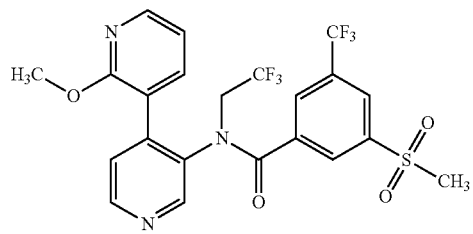

The title compound was prepared in analogy to example 90, from (2-methoxy-[3,4']bipyridinyl-3'-yl)-(2,2,2-trifluoro-ethyl)-amine (example 135, intermediate a) and 3-methanesulfonyl-5-trifluoromethyl-benzoic acid (example 114, intermediate a) after a reaction time of 72 hours. The compound was purified by silica gel chromatography using a MPLC system (CombiFlash Companion, Isco Inc.) eluting with a gradient of CH$_2$Cl$_2$:EtOAc (100:0 to 85:15), followed by preparative HPLC using a gradient of methanol:water (10:50 to 95:5). Light yellow foam (28%). MS (ESI): m/z=534.090 [M+H]$^+$.

Example 143

3-Dimethylsulfamoyl-N-[4-(4-fluoro-2-methoxy-phenyl)-pyridin-3-yl]-N-methyl-5-trifluoromethyl-benzamide

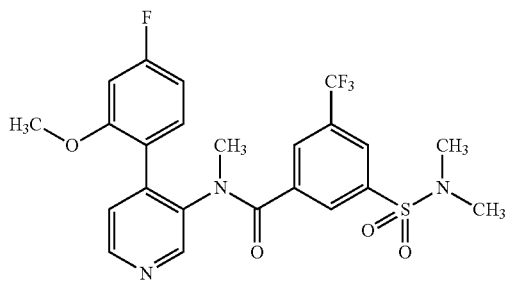

The title compound was prepared in analogy to example 90, from [4-(4-fluoro-2-methoxy-phenyl)-pyridin-3-yl]-methyl-amine (example 129, intermediate) and 3-dimethylsulfamoyl-5-trifluoromethyl-benzoic acid (Buttpark Ltd.) after a reaction time of 65 hours. The compound was purified by silica gel chromatography on a 50 g column using a MPLC system eluting with EtOAc. Light brown foam (19%). MS (ESI): m/z=512.13 [M+H]$^+$.

Example 144

N-[4-(4,5-Difluoro-2-methoxy-phenyl)-pyridin-3-yl]-N-methyl-2,6-bis-trifluoromethyl-isonicotinamide

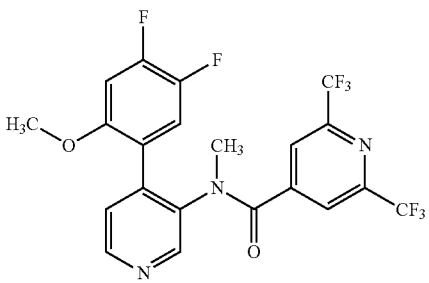 [SMILES: COc1cc(F)c(F)cc1-c1ccncc1N(C)C(=O)c1cc(C(F)(F)F)nc(C(F)(F)F)c1]

The title compound was prepared in analogy to example 90, from [4-(4,5-difluoro-2-methoxy-phenyl)-pyridin-3-yl]-methyl-amine (example 130, intermediate) and 2,6-bis(trifluoromethyl)isonicotinic acid (Key Organics Ltd.) after a reaction time of 23 hours. The compound was purified by silica gel chromatography on a 20 g column using a MPLC system eluting with a gradient of n-heptane:EtOAc (100:0 to 0:100). Light brown solid (38%). MS (ESI): m/z=492.10 [M+H]$^+$.

Example 145

N-(2-Methoxy-[3,4']bipyridinyl-3'-yl)-N-(2,2,2-trifluoro-ethyl)-2,6-bis-trifluoromethyl-isonicotinamide

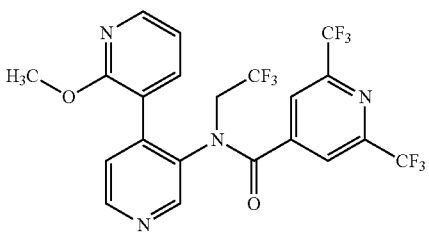 [SMILES: COc1ncccc1-c1ccncc1N(CC(F)(F)F)C(=O)c1cc(C(F)(F)F)nc(C(F)(F)F)c1]

The title compound was prepared in analogy to example 90, from (2-methoxy-[3,4']bipyridinyl-3'-yl)-(2,2,2-trifluoro-ethyl)-amine (example 135, intermediate a) and 2,6-bis(trifluoromethyl)isonicotinic acid (Key Organics Ltd.) after a reaction time of 96 hours. The compound was purified by silica gel chromatography on a 20 g column using a MPLC system eluting with a gradient of n-heptane:EtOAc (100:0 to 50:50). Light yellow solid (41%). MS (ESI): m/z=525.10 [M+H]$^+$.

Example 146

N-[4-(4,5-Difluoro-2-methoxy-phenyl)-pyridin-3-yl]-N-(2,2,2-trifluoro-ethyl)-2,6-bis-trifluoromethyl-isonicotinamide

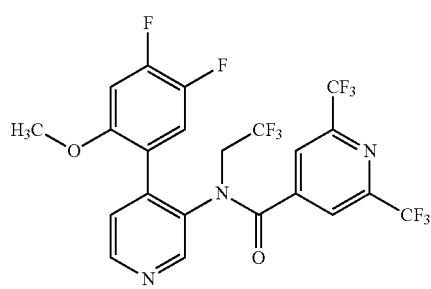 [SMILES: COc1cc(F)c(F)cc1-c1ccncc1N(CC(F)(F)F)C(=O)c1cc(C(F)(F)F)nc(C(F)(F)F)c1]

The title compound was prepared in analogy to example 90, from [4-(4,5-difluoro-2-methoxy-phenyl)-pyridin-3-yl]-(2,2,2-trifluoro-ethyl)-amine (example 132, intermediate a) and 2,6-bis(trifluoromethyl)isonicotinic acid (Key Organics Ltd.) after a reaction time of 96 hours. The compound was purified by silica gel chromatography on a 20 g column using a MPLC system eluting with a gradient of n-heptane:EtOAc (100:0 to 50:50). Light brown solid (31%). MS (ESI): m/z=560.08 [M+H]+.

Example 147

N-[4-(4-Fluoro-2-methoxy-phenyl)-pyridin-3-yl]-N-(2,2,2-trifluoro-ethyl)-2,6-bis-trifluoromethyl-isonicotinamide

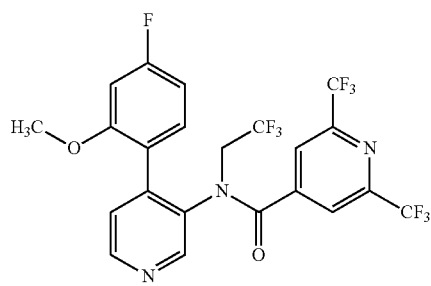 [SMILES: COc1cc(F)ccc1-c1ccncc1N(CC(F)(F)F)C(=O)c1cc(C(F)(F)F)nc(C(F)(F)F)c1]

The title compound was prepared in analogy to example 90, from [4-(4-fluoro-2-methoxy-phenyl)-pyridin-3-yl]-(2,2,2-trifluoro-ethyl)-amine (example 133, intermediate a) and 2,6-bis(trifluoromethyl)isonicotinic acid (Key Organics Ltd.) after a reaction time of 96 hours. The compound was purified by silica gel chromatography on a 20 g column using a MPLC system eluting with a gradient of n-heptane:EtOAc (100:0 to 50:50). Light brown solid (44%). MS (ESI): m/z=542.09 [M+H]+.

Example 148

N-[4-(4-Fluoro-2-methoxy-phenyl)-pyridin-3-yl]-N-methyl-2,6-bis-trifluoro methyl-isonicotinamide

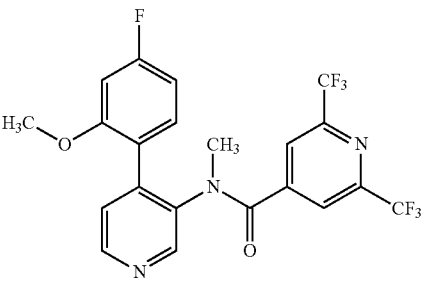 [SMILES: COc1cc(F)ccc1-c1ccncc1N(C)C(=O)c1cc(C(F)(F)F)nc(C(F)(F)F)c1]

The title compound was prepared in analogy to example 90, from [4-(4-fluoro-2-methoxy-phenyl)-pyridin-3-yl]-methyl-amine (example 129, intermediate) and 2,6-bis(trifluoromethyl) isonicotinic acid (Key Organics Ltd.) after a reaction time of 22 hours. The compound was purified by silica gel chromatography on a 20 g column using a MPLC system eluting with a gradient of n-heptane:EtOAc (100:0 to 0:100). Light brown solid (73%). MS (ESI): m/z=474.11 [M+H]+.

Example 149

3-Cyano-N-methyl-N-(4-o-tolyl-pyridin-3-yl)-5-trifluoromethyl-benzamide

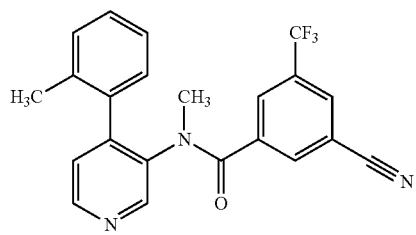 [SMILES: Cc1ccccc1-c1ccncc1N(C)C(=O)c1cc(C#N)cc(C(F)(F)F)c1]

The title compound was prepared in analogy to example 90, from N-methyl-4-o-tolylpyridin-3-amine (example 1, intermediate a) and 3-cyano-5-trifluoromethyl-benzoic acid after a reaction time of 94 hours. The product was purified by silica gel chromatography using a 10 g column eluting with EtOAc followed by a second chromatography on a 5 g column eluting with a gradient of n-heptane:EtOAc (100:0 to 50:50). Colorless solid (2%). MS (ESI): m/z=396.13 [M+H]+.

Intermediates a) 3-Cyano-5-trifluoromethyl-benzoic acid

To a solution of 3-cyano-5-trifluoromethyl-benzoic acid methyl ester (0.084 g, 0.367 mmol) in dioxane (0.5 mL) was added water (0.5 mL) and lithium hydroxide monohydrate (19.2 mg, 0.458 mmol) and the resulting mixture was stirred at room temperature for 1 h. The reaction mixture was evaporated, the residue was taken up in dioxane and 10% aqueous citric acid solution and the layers were separated.

The aqueous layer was extracted twice with EtOAc and the organic layers were washed with brine, dried over MgSO$_4$, filtered and evaporated. Light brown solid (0.09 g; 98%). MS (ESI): m/z=214.01 [M−H]⁻.

b) 3-Cyano-5-trifluoromethyl-benzoic acid methyl ester

The title compound was prepared in analogy to example 114, intermediate b, from 3-bromo-5-trifluoromethyl-benzonitrile (CAS RN 691877-03-9). The compound was purified by silica gel chromatography on a 20 g column using a MPLC system eluting with a gradient of n-heptane:EtOAc (100:0 to 50:50). Light brown solid (51%). MS (GC-MS (EI)): m/z=229 [M].

Example 150

N-(4-o-Tolyl-pyridin-3-yl)-N-(2,2,2-trifluoro-ethyl)-2,6-bis-trifluoromethyl-isonicotinamide

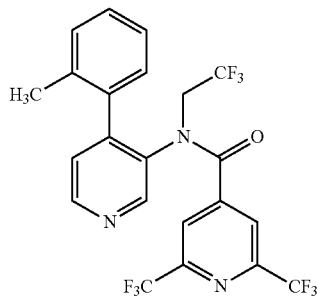 [SMILES: Cc1ccccc1-c1ccncc1N(CC(F)(F)F)C(=O)c1cc(C(F)(F)F)nc(C(F)(F)F)c1]

The title compound was prepared in analogy to example 90, from (4-o-tolyl-pyridin-3-yl)-(2,2,2-trifluoro-ethyl)-amine and 2,6-bis(trifluoromethyl)isonicotinic acid (Key Organics Ltd.) after a reaction time of 23 hours. The compound was purified by silica gel chromatography on a 10 g column using a MPLC system eluting with a gradient of n-heptane: EtOAc (100:0 to 50:50). Light brown solid (26%). MS (ESI): m/z=508.11 [M+H]⁺.

Intermediates a) (4-o-Tolyl-pyridin-3-yl)-(2,2,2-trifluoro-ethyl)-amine

The title compound was prepared in analogy to example 72, from (4-iodo-pyridin-3-yl)-(2,2,2-trifluoro-ethyl)-amine and 2-methylphenylboronic acid (CAS RN 16419-60-6) and using a gradient of n-heptane:EtOAc (100:0 to 50:50) for the chromatographic purification. Light brown solid (91%). MS (ESI): m/z=267.11 [M+H]⁺.

b) (4-Indo-pyridin-3-yl)-(2,2,2-trifluoro-ethyl)-amine

The title compound was prepared in analogy to example 85, intermediate a, from (4-iodo-pyridin-3-yl)-(2,2,2-trifluoro-ethyl)-carbamic acid tert-butyl ester (example 85, intermediate c). Colorless solid (98%). MS (ESI): m/z=302.96 [M+H]⁺.

Example 151

N-[4-(2-Fluoro-phenyl)-pyridin-3-yl]-N-(2,2,2-trifluoro-ethyl)-2,6-bis-trifluoromethyl-isonicotinamide

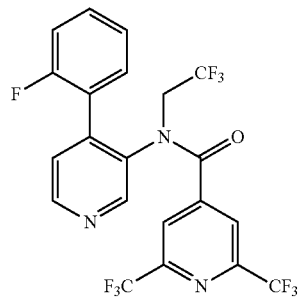 [SMILES: O=C(c1cc(C(F)(F)F)nc(C(F)(F)F)c1)N(CC(F)(F)F)c1cnccc1-c1ccccc1F]

The title compound was prepared in analogy to example 90, from [4-(2-fluoro-phenyl)-pyridin-3-yl]-(2,2,2-trifluoro-ethyl)-amine and 2,6-bis(trifluoromethyl)isonicotinic acid (Key Organics Ltd.) after a reaction time of 25 hours. The compound was purified by silica gel chromatography on a 10 g column using a MPLC system eluting with a gradient of n-heptane:EtOAc (100:0 to 50:50). Light brown solid (38%). MS (ESI): m/z=512.08 [M+H]⁺.

Intermediate

[4-(2-Fluoro-phenyl)-pyridin-3-yl]-(2,2,2-trifluoro-ethyl)-amine

The title compound was prepared from (4-iodo-pyridin-3-yl)-(2,2,2-trifluoro-ethyl)-amine (example 150, intermediate b) and 2-fluorophenylboronic acid (CAS RN 1193-03-9) and using a gradient of n-heptane:EtOAc (100:0 to 50:50) for the chromatographic purification. Light brown solid (85%). MS (ESI): m/z=271.09 [M+H]⁺.

Example 152

N-Methyl-3-morpholin-4-yl-N-(4-o-tolyl-pyridin-3-yl)-5-trifluoromethyl-benzamide

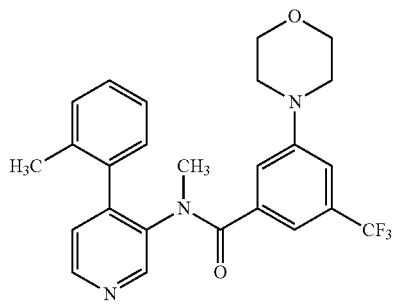 [SMILES: Cc1ccccc1-c1ccncc1N(C)C(=O)c1cc(N2CCOCC2)cc(C(F)(F)F)c1]

The title compound was prepared in analogy to example 90, from N-methyl-4-o-tolylpyridin-3-amine (example 1, intermediate a) and 3-morpholin-4-yl-5-trifluoromethyl-benzoic acid (CAS RN 250682-08-7) after a reaction time of 5 days. The compound was purified by silica gel chromatography using a MPLC system (CombiFlash Companion, Isco Inc.) eluting with a gradient of n-heptane:EtOAc (100:0 to 20:80). Colorless solid (12%). MS (ESI): m/z=456.188 [M+H]$^+$.

Example 153

N-(2,2-Difluoro-ethyl)-N-[4-(4-fluoro-2-methoxy-phenyl)-pyridin-3-yl]-2,6-bis-trifluoromethyl-isonicotinamide

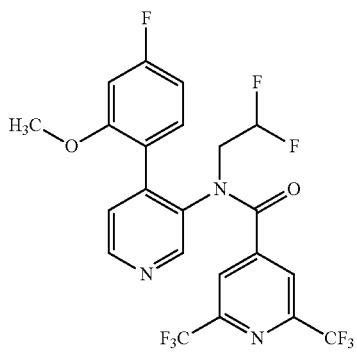 [SMILES: COc1cc(F)ccc1-c1ccncc1N(CC(F)F)C(=O)c1cc(C(F)(F)F)nc(C(F)(F)F)c1]

The title compound was prepared in analogy to example 90, from (2,2-difluoro-ethyl)-[4-(4-fluoro-2-methoxy-phenyl)-pyridin-3-yl]-amine and 2,6-bis(trifluoromethyl)isonicotinic acid (Key Organics Ltd.) after a reaction time of 68 hours. The compound was purified by silica gel chromatography on a 10 g column using a MPLC system eluting with a gradient of n-heptane:EtOAc (100:0 to 50:50). Light brown solid (57%). MS (ESI): m/z=524.10 [M+H]$^+$.

Intermediates a) (2,2-Difluoro-ethyl)-[4-(4-fluoro-2-methoxy-phenyl)-pyridin-3-yl]-amine The title compound was prepared in analogy to example 72, from (2,2-difluoro-ethyl)-(4-iodo-pyridin-3-yl)-amine and 4-fluoro-2-methoxyphenylboronic acid (CAS RN 179899-07-1) and using a gradient of n-heptane:EtOAc (100:0 to 50:50) for the chromatographic purification. Light brown solid (78%). MS (ESI): m/z=283.18 [M+H]$^+$.

b) (2,2-Difluoro-ethyl)-(4-iodo-pyridin-3-yl)-amine

The title compound was prepared in analogy to example 85, intermediate a, from (2,2-difluoro-ethyl)-(4-iodo-pyridin-3-yl)-carbamic acid tert-butyl ester (example 116, intermediate c). Off-white solid (98%). MS (ESI): m/z=284.97 [M+H]$^+$.

Example 154

N-(2,2-Difluoro-ethyl)-N-[4-(4,5-difluoro-2-methoxy-phenyl)-pyridin-3-yl]-2,6-bis-trifluoromethyl-isonicotinamide

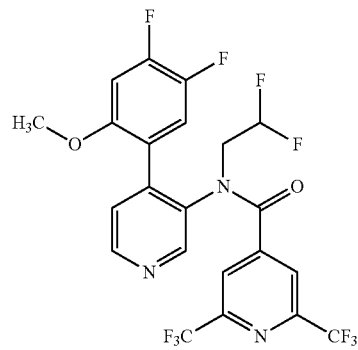 [SMILES: COc1cc(F)c(F)cc1-c1ccncc1N(CC(F)F)C(=O)c1cc(C(F)(F)F)nc(C(F)(F)F)c1]

The title compound was prepared in analogy to example 90, from (2,2-difluoro-ethyl)-[4-(4,5-difluoro-2-methoxy-phenyl)-pyridin-3-yl]-amine and 2,6-bis(trifluoromethyl)isonicotinic acid (Key Organics Ltd.) after a reaction time of 66 hours. The compound was purified by silica gel chromatography on a 20 g column using a MPLC system eluting with a gradient of n-heptane:EtOAc (100:0 to 50:50). Light brown solid (66%). MS (ESI): m/z=542.09 [M+H]$^+$.

Intermediate (2,2-Difluoro-ethyl)-[4-(4,5-difluoro-2-methoxy-phenyl)-pyridin-3-yl]-amine The title compound was prepared in analogy to example 72, from (2,2-difluoro-ethyl)-(4-iodo-pyridin-3-yl)-amine (example 153, intermediate b) and 4,5-difluoro-2-methoxyphenylboronic acid (CAS RN 870777-32-5) and using a gradient of n-heptane: EtOAc (100:0 to 50:50) for the chromatographic purification. Light brown solid (73%). MS (ESI): m/z=301.10 [M+H]$^+$.

Example 155

N-(2,2-Difluoro-ethyl)-N-[4-(2-fluoro-phenyl)-pyridin-3-yl]-2,6-bis-trifluoromethyl-isonicotinamide

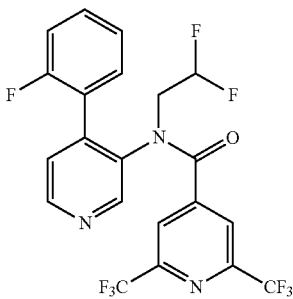 [SMILES: O=C(c1cc(C(F)(F)F)nc(C(F)(F)F)c1)N(CC(F)F)c1cnccc1-c1ccccc1F]

The title compound was prepared in analogy to example 90, from (2,2-difluoro-ethyl)-[4-(2-fluoro-phenyl)-pyridin-3-yl]-amine and 2,6-bis(trifluoromethyl)isonicotinic acid (Key Organics Ltd.) after a reaction time of 68 hours. The compound was purified by silica gel chromatography on a 10 g column using a MPLC system eluting with a gradient of n-heptane: EtOAc (100:0 to 50:50). Light brown solid (44%). MS (ESI): m/z=494.09 [M+H]+.

Intermediate (2,2-Difluoro-ethyl)-[4-(2-fluoro-phenyl)-pyridin-3-yl]-amine

The title compound was prepared in analogy to example 72, from (2,2-difluoro-ethyl)-(4-iodo-pyridin-3-yl)-amine (example 153, intermediate b) and 2-fluorophenylboronic acid (CAS RN 1193-03-9) and using a gradient of n-heptane: EtOAc (100:0 to 50:50) for the chromatographic purification. Colorless solid (87%). MS (ESI): m/z=252.1 [M+H]+.

Example 156

N-(2,2-Difluoro-ethyl)-N-(2-methoxy-[3,4']bipyridinyl-3'-yl)-2,6-bis-trifluoromethyl-isonicotinamide The title compound was prepared in analogy to example 90, from (2,2-difluoro-ethyl)-(2-methoxy-[3,4']bipyridinyl-3'-yl)-amine and 2,6-bis(trifluoromethyl)isonicotinic acid (Key Organics Ltd.) after a reaction time of 67 hours. The compound was purified by silica gel chromatography on a 10 g column using a MPLC system eluting with a gradient of n-heptane: EtOAc (100:0 to 50:50). Light brown solid (64%). MS (ESI): m/z=507.11 [M+H]+.

Intermediate (2,2-Difluoro-ethyl)-(2-methoxy-[3,4']bipyridinyl-3'-yl)-amine

The title compound was prepared in analogy to example 72, from (2,2-difluoro-ethyl)-(4-iodo-pyridin-3-yl)-amine (example 153, intermediate b) and 2-methoxypyridine-3-boronic acid (CAS RN 163105-90-6) and using a gradient of n-heptane:EtOAc (100:0 to 50:50) for the chromatographic purification. Colorless solid (83%). MS (ESI): m/z=266.11 [M+H]+.

Example 157

N-(2,2-Difluoro-ethyl)-N-(4-o-tolyl-pyridin-3-yl)-2,6-bis-trifluoromethyl-isonicotinamide The title compound was prepared in analogy to example 90, from (2,2-difluoro-ethyl)-(4-o-tolyl-pyridin-3-yl)-amine and 2,6-bis(trifluoromethyl)isonicotinic acid (Key Organics Ltd.) after a reaction time of 68 hours. The compound was purified by silica gel chromatography on a 10 g column using a MPLC system eluting with a gradient of n-heptane: EtOAc (100:0 to 50:50). Light brown solid (34%). MS (ESI): m/z=490.11 [M+H]+.

Intermediate (2,2-Difluoro-ethyl)-(4-o-tolyl-pyridin-3-yl)-amine

The title compound was prepared in analogy to example 72, from (2,2-difluoro-ethyl)-(4-iodo-pyridin-3-yl)-amine (example 153, intermediate b) and 2-methylphenylboronic acid (CAS RN 16419-60-6) and using a gradient of n-heptane:EtOAc (100:0 to 50:50) for the chromatographic purification. Colorless solid (93%). MS (ESI): m/z=248.1 [M+H]+.

Example 158

N-[4-(4,5-Difluoro-2-methoxy-phenyl)-pyridin-3-yl]-N-(2-methanesulfonyl-ethyl)-2,6-bis-trifluoromethyl-isonicotinamide

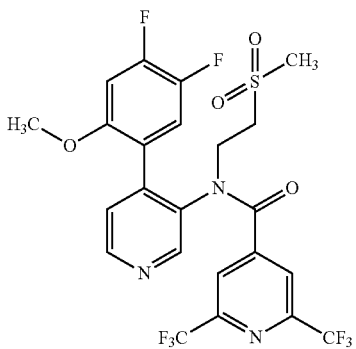 [SMILES: COc1cc(F)c(F)cc1-c1ccncc1N(CCS(C)(=O)=O)C(=O)c1cc(C(F)(F)F)nc(C(F)(F)F)c1]

The title compound was prepared in analogy to example 90, from [4-(4,5-difluoro-2-methoxy-phenyl)-pyridin-3-yl]-(2-methanesulfonyl-ethyl)-amine and 2,6-bis(trifluoromethyl) isonicotinic acid (Key Organics Ltd.) after a reaction time of 15 hours. The compound was purified by silica gel chromatography on a 10 g column using a MPLC system eluting with a gradient of n-heptane:EtOAc (100:0 to 0:100). Brown solid (42%). MS (ESI): m/z=584.09 [M+H]+.

Intermediates a) [4-(4,5-Difluoro-2-methoxy-phenyl)-pyridin-3-yl]-(2-methanesulfonyl-ethyl)-amine The title compound was prepared in analogy to example 72, from (4-iodo-pyridin-3-yl)-(2-methanesulfonyl-ethyl)-amine and 4,5-difluoro-2-methoxyphenylboronic acid (CAS RN 870777-32-5) and using a gradient of $CH_2Cl_2$:methanol (100:0 to 85:15) for the chromatographic purification. Light brown foam (76%). MS (ESI): m/z=343.09 [M+H]+.

b) (4-Iodo-pyridin-3-yl)-(2-methanesulfonyl-ethyl)-amine

The title compound was prepared in analogy to example 85, intermediate a, from (4-iodo-pyridin-3-yl)-(2-methanesulfonyl-ethyl)-carbamic acid tert-butyl ester (example 112, intermediate c). Off-white solid (98%). MS (ESI): m/z=326.97 [M+H]+.

Example 159

N-[4-(2-Fluoro-phenyl)-pyridin-3-yl]-N-(2-methanesulfonyl-ethyl)-2,6-bis-trifluoromethyl-isonicotinamide

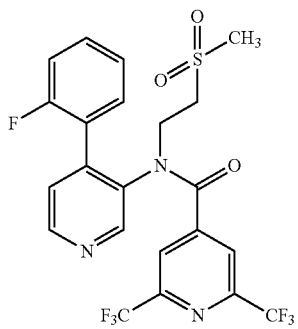 [SMILES: CS(=O)(=O)CCN(C(=O)c1cc(C(F)(F)F)nc(C(F)(F)F)c1)c1cnccc1-c1ccccc1F]

The title compound was prepared in analogy to example 90, from [4-(2-fluoro-phenyl)-pyridin-3-yl]-(2-methanesulfonyl-ethyl)-amine and 2,6-bis(trifluoromethyl)isonicotinic acid (Key Organics Ltd.) after a reaction time of 15 hours. The compound was purified by silica gel chromatography on a 10 g column using a MPLC system eluting with a gradient of n-heptane:EtOAc (100:0 to 0:100). Off-white solid (38%). MS (ESI): m/z=536.09 [M+H]+.

Intermediate

[4-(2-Fluoro-phenyl)-pyridin-3-yl]-(2-methanesulfonyl-ethyl)-amine

The title compound was prepared in analogy to example 72, from (4-iodo-pyridin-3-yl)-(2-methanesulfonyl-ethyl)-amine (example 158, intermediate b) and 2-fluorophenylboronic acid (CAS RN 1193-03-9) and using a gradient of $CH_2Cl_2$:methanol (100:0 to 70:30) for the chromatographic purification. Light brown solid (85%). MS (ESI): m/z=295.09 [M+H]+.

Example 160

N-(2-Methanesulfonyl-ethyl)-N-(2-methoxy-[3,4']bipyridinyl-3'-yl)-2,6-bis-trifluoromethyl-isonicotinamide

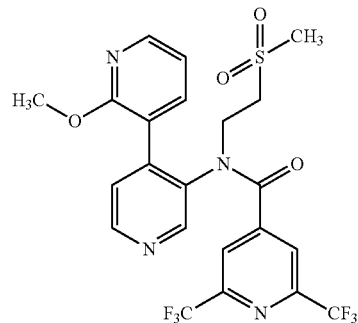 [SMILES: COc1ncccc1-c1ccncc1N(CCS(C)(=O)=O)C(=O)c1cc(C(F)(F)F)nc(C(F)(F)F)c1]

The title compound was prepared in analogy to example 90, from (2-methanesulfonyl-ethyl)-(2-methoxy-[3,4']bipyridinyl-3'-yl)-amine and 2,6-bis(trifluoromethyl) isonicotinic acid (Key Organics Ltd.) after a reaction time of 15 hours. The compound was purified by silica gel chromatography on a 10 g column using a MPLC system eluting with a gradient of n-heptane:EtOAc (100:0 to 0:100). Light brown solid (14%). MS (ESI): m/z=549.10 [M+H]+.

Intermediate (2-Methanesulfonyl-ethyl)-(2-methoxy-[3,4']bipyridinyl-3'-yl)-amine The title compound was prepared in analogy to example 72, from (4-iodo-pyridin-3-yl)-(2-methanesulfonyl-ethyl)-amine (example 158, intermediate b) and 2-methoxypyridine-3-boronic acid (CAS RN 163105-90-6) and using a gradient of $CH_2Cl_2$:methanol (100:0 to 85:15) for the chromatographic purification. Brown solid (89%). MS (ESI): m/z=308.11 [M+H]+.

Example 161

N-Cyanomethyl-N-(4-o-tolyl-pyridin-3-yl)-3,5-bis-trifluoromethyl-benzamide

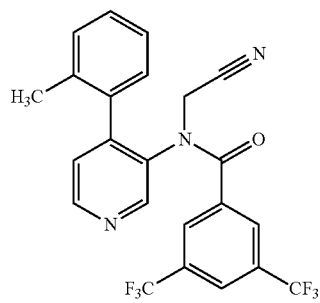 [SMILES: Cc1ccccc1-c1ccncc1N(CC#N)C(=O)c1cc(C(F)(F)F)cc(C(F)(F)F)c1]

The title compound was prepared in analogy to example 90, from (4-o-tolyl-pyridin-3-ylamino)-acetonitrile and 3,5-bis-trifluoromethyl-benzoic acid (CAS RN 725-89-3) after a reaction time of 18 hours. The compound was purified by silica gel chromatography on a 20 g column using a MPLC system eluting with a gradient of n-heptane:EtOAc (100:0 to 0:100). The product-containing fractions were pooled and evaporated until a suspension formed. The colorless solid was filtered off and washed with a small amount of a mixture of EtOAc:n-heptane (1:6). Colorless solid (37%). MS (ESI): m/z=464.12 [M+H]+.

Intermediates a) (4-o-Tolyl-pyridin-3-ylamino)-acetonitrile

The title compound was prepared in analogy to example 72, from (4-iodo-pyridin-3-ylamino)-acetonitrile and 2-methylphenylboronic acid (CAS RN 16419-60-6) and using a gradient of n-heptane:EtOAc (100:0 to 0:100) for the chromatographic purification. Light brown solid (48%). MS (ESI): m/z=224.12 [M+H]+.

b) (4-Indo-pyridin-3-ylamino)-acetonitrile

The title compound was prepared in analogy to example 85, intermediate a, from cyanomethyl-(4-iodo-pyridin-3-yl)-carbamic acid tert-butyl ester. The compound was purified by silica gel chromatography on a 20 g column using a MPLC system eluting with a gradient of n-heptane:EtOAc (100:0 to 20:80). Light brown oil (62%). MS (ESI): m/z=259.97 [M+H]+.

c) Cyanomethyl-(4-iodo-pyridin-3-yl)-carbamic acid tert-butyl ester

The title compound was prepared in analogy to example 85, intermediate c, from (4-iodo-pyridin-3-yl)-carbamic acid tert-butyl ester (example 85, intermediate d) and bromoacetonitrile (CAS RN 590-17-0) and using a gradient of n-heptane:EtOAc (100:0 to 50:50) for the chromatographic purification. Light yellow oil (95%). MS (ESI): m/z=360.02 [M+H]+.

Example 162

N-[4-(4-Fluoro-2-methoxy-phenyl)-pyridin-3-yl]-N-(2-methanesulfonyl-ethyl)-2,6-bis-trifluoromethyl-isonicotinamide

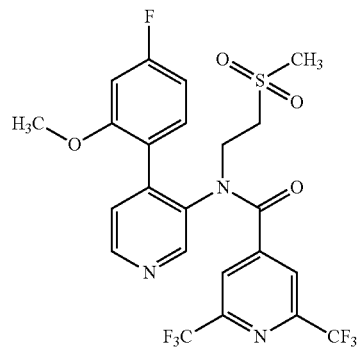 [SMILES: COc1cc(F)ccc1-c1ccncc1N(CCS(C)(=O)=O)C(=O)c1cc(C(F)(F)F)nc(C(F)(F)F)c1]

The title compound was prepared in analogy to example 90, from [4-(4-fluoro-2-methoxy-phenyl)-pyridin-3-yl]-(2-methanesulfonyl-ethyl)-amine and 2,6-bis(trifluoromethyl)isonicotinic acid (Key Organics Ltd.) after a reaction time of 17 hours. The compound was purified by silica gel chromatography on a 10 g column using a MPLC system eluting with a gradient of n-heptane:EtOAc (100:0 to 0:100). A second chromatography (preparative HPLC (Phenomenex Gemini® column), gradient of acetonitrile:water (containing 0.05% formic acid) (10:90 to 98:2)) gave the desired product as an off-white foam (10%). MS (ESI): m/z=566.10 [M+H]+.

Intermediate

[4-(4-Fluoro-2-methoxy-phenyl)-pyridin-3-yl]-(2-methanesulfonyl-ethyl)-amine

The title compound was prepared in analogy to example 72, from (4-iodo-pyridin-3-yl)-(2-methanesulfonyl-ethyl)-amine (example 158, intermediate b) and 4-fluoro-2-methoxyphenyl-boronic acid (CAS RN 179899-07-1) and using a gradient of CH$_2$Cl$_2$:methanol (100:0 to 85:15) for the chromatographic purification. Colorless foam (55%). MS (ESI): m/z=325.10 [M+H]+.

Example 163

N-(2-Methanesulfonyl-ethyl)-N-(4-o-tolyl-pyridin-3-yl)-2,6-bis-trifluoromethyl-isonicotinamide

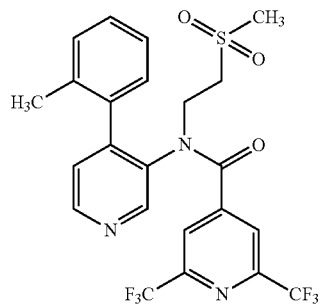 [SMILES: Cc1ccccc1-c1ccncc1N(CCS(C)(=O)=O)C(=O)c1cc(C(F)(F)F)nc(C(F)(F)F)c1]

The title compound was prepared in analogy to example 90, from (2-methanesulfonyl-ethyl)-(4-o-tolyl-pyridin-3-yl)-amine and 2,6-bis(trifluoromethyl)isonicotinic acid (Key Organics Ltd.) after a reaction time of 17 hours. The compound was purified by silica gel chromatography on a 10 g column using a MPLC system eluting with a gradient of n-heptane: EtOAc (100:0 to 0:100). A second chromatography (preparative HPLC (phenomenex gemini column), gradient of acetonitrile:water (containing 0.05% formic acid) (10:90 to 98:2)) yielded the desired product as an off-white solid (10%). MS (ESI): m/z=532.11 [M+H]+.

Intermediate (2-Methanesulfonyl-ethyl)-(4-o-tolyl-pyridin-3-yl)-amine

The title compound was prepared in analogy to example 72, from (4-iodo-pyridin-3-yl)-(2-methanesulfonyl-ethyl)-amine (example 158, intermediate b) and 2-methylphenyl-boronic acid (CAS RN 16419-60-6) and using a gradient of CH$_2$Cl$_2$:methanol (100:0 to 85:15) for the chromatographic purification. Brown oil (85%). MS (ESI): m/z=291.12 [M+H]$^+$.

Example 164

3-Amino-N-methyl-N-(4-o-tolyl-pyridin-3-yl)-5-trifluoromethyl-benzamide

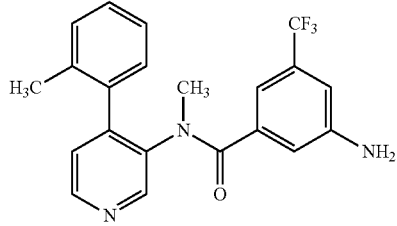 [SMILES: Cc1ccccc1-c1ccncc1N(C)C(=O)c1cc(N)cc(C(F)(F)F)c1]

The title compound was prepared in analogy to example 85, intermediate a, from {3-[methyl-(4-o-tolyl-pyridin-3-yl)-carbamoyl]-5-trifluoromethyl-phenyl}-carbamic acid tert-butyl ester and using a gradient of n-heptane:EtOAc (100:0 to 0:100) for the chromatographic purification. Colorless solid (94%). MS (ESI): m/z=386.147 [M+H]$^+$.

Intermediates a) {3-[Methyl-(4-o-tolyl-pyridin-3-yl)-carbamoyl]-5-trifluoromethyl-phenyl}-carbamic acid tert-butyl ester The title compound was prepared in analogy to example 90, from N-methyl-4-o-tolylpyridin-3-amine (example 1, intermediate a) and 3-tert-butoxycarbonylamino-5-trifluoromethyl-benzoic acid and using a gradient of n-heptane:EtOAc (100:0 to 0:60) for the chromatographic purification. Light brown solid (4%). MS (ESI): m/z=486.20 [M+H]$^+$.

b) 3-tert-Butoxycarbonylamino-5-trifluoromethyl-benzoic acid

The title compound was prepared in analogy to example 84, from 3-tert-butoxycarbonylamino-5-trifluoromethyl-benzoic acid methyl ester. MS (ESI): m/z=304.0809 [M−H]$^-$.

c) 3-tert-Butoxycarbonylamino-5-trifluoromethyl-benzoic acid methyl ester

To a solution of 3-amino-5-trifluoromethyl-benzoic acid methyl ester (2 g, 9.13 mmol, CAS RN 22235-25-2) in CH$_2$Cl$_2$ (30 mL) was added di-tert-butyl dicarbonate (1.99 g, 9.13 mmol, CAS RN 24424-99-5) and DMAP (1.11 g, 9.13 mmol). The reaction mixture was stirred at room temperature for 2 hours. The reaction mixture was treated with silica gel and concentrated under vacuum and purified by silica gel chromatography using a MPLC system (CombiFlash Companion, Isco Inc.) eluting with a gradient of n-heptane:EtOAc (100:0 to 70:30). Colorless solid (76%). MS (GC_MS (EI)): 319.1 (M$^+$).

Example 165

N-(2-Cyano-ethyl)-N-(4-o-tolyl-pyridin-3-yl)-3,5-bis-trifluoromethyl-benzamide

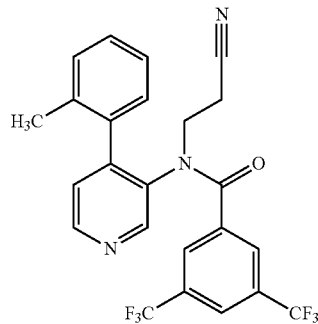 [SMILES: Cc1ccccc1-c1ccncc1N(CCC#N)C(=O)c1cc(C(F)(F)F)cc(C(F)(F)F)c1]

The title compound was prepared in analogy to example 90, from 3-(4-o-tolyl-pyridin-3-ylamino)-propionitrile and 3,5-bis(trifluoromethyl)benzoic acid (CAS RN 725-89-3) after a reaction time of 19 hours. The compound was purified by two silica gel chromatographies (10 g and 5 g column, respectively) using a MPLC system eluting with a gradient of n-heptane:EtOAc (100:0 to 50:50). Colorless solid (2%). MS (ESI): m/z=478.13 [M+H]$^+$.

Intermediates a) 3-(4-o-Tolyl-pyridin-3-ylamino)-propionitrile

The title compound was prepared in analogy to example 72, from 3-(4-iodo-pyridin-3-ylamino)-propionitrile and 2-methylphenylboronic acid (CAS RN 16419-60-6) and using a gradient of heptane:EtOAc (100:0 to 0:100) for the chromatographic purification. Light brown solid (81%). MS (ESI): m/z=238.13 [M+H]$^+$.

b) 3-(4-Iodo-pyridin-3-ylamino)-propionitrile

The title compound was prepared in analogy to example 85, intermediate a, from (2-cyano-ethyl)-(4-iodo-pyridin-3-yl)-carbamic acid tert-butyl ester. The compound was purified by silica gel chromatography on a 20 g column using a MPLC system eluting with a gradient of n-heptane:EtOAc (100:0 to 20:80). Light brown solid (75%). MS (ESI): m/z=273.98 [M+H]$^+$.

c) (2-Cyano-ethyl)-(4-iodo-pyridin-3-yl)-carbamic acid tert-butyl ester

The title compound was prepared in analogy to example 85, intermediate c, from (4-iodo-pyridin-3-yl)-carbamic acid tert-butyl ester (example 85, intermediate d) and 3-bromo-propionitrile (CAS RN 2417-90-5) and using a gradient of n-heptane:EtOAc (100:0 to 50:50) for the chromatographic purification. Light yellow oil (92%). MS (ESI): m/z=374.1 [M+H]$^+$.

Example 166

N-[4-(3,6-Dihydro-2H-pyran-4-yl)-pyridin-3-yl]-N-methyl-3,5-bis-trifluoromethyl-benzamide

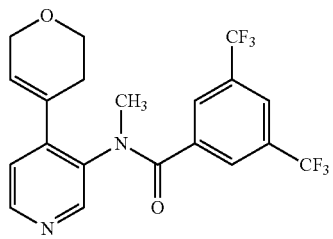 [SMILES: CN(C(=O)c1cc(C(F)(F)F)cc(C(F)(F)F)c1)c1cnccc1C1=CCOCC1]

The title compound was prepared in analogy to example 73, from N-(4-iodo-pyridin-3-yl)-N-methyl-3,5-bis-trifluoromethyl-benzamide (example 98, intermediate a) and trifluoro-methanesulfonic acid 3,6-dihydro-2H-pyran-4-yl ester (CAS RN 188975-30-6). The compound was purified by silica gel chromatography using a MPLC system (CombiFlash Companion, Isco Inc.) eluting with a gradient of n-heptane:EtOAc (100:0 to 40:60). Colorless solid (56%). MS (ESI): m/z=431.177 [M+H]$^+$.

Example 167

N-[4-(2,3-Dimethoxy-phenyl)-pyridin-3-yl]-N-methyl-3,5-bis-trifluoromethyl-benzamide

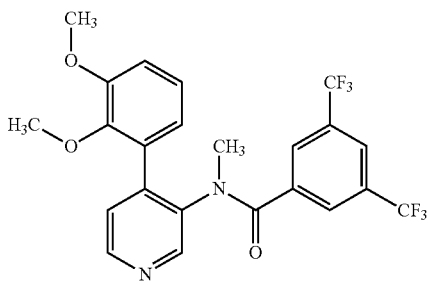 [SMILES: COc1cccc(-c2ccncc2N(C)C(=O)c2cc(C(F)(F)F)cc(C(F)(F)F)c2)c1OC]

The title compound was prepared in analogy to example 72, intermediate, from [4-(2,3-dimethoxy-phenyl)-pyridin-3-yl]-methyl-amine and 3,5-bis(trifluoromethyl)benzoyl chloride (CAS RN 1271-19-8) and using a gradient of n-heptane:EtOAc (100:0 to 40:60) for the chromatographic purification. Light yellow solid (72%). MS (ESI): m/z=485.127 [M+H]$^+$.

Intermediate

[4-(2,3-Dimethoxy-phenyl)-pyridin-3-yl]-methyl-amine

The title compound was prepared in analogy to example 72, from (4-iodo-pyridin-3-yl)-methyl-amine (example 98, intermediate b) and 2,3-dimethoxyphenylboronic acid (CAS RN 28611-39-4) and using a gradient of n-heptane:EtOAc (100:0 to 30:70) for the chromatographic purification. Light yellow solid (79%). MS (ESI): m/z=245.128 [M+H]$^+$.

Example 168

N-[4-(2-Ethyl-phenyl)-pyridin-3-yl]-N-methyl-3,5-bis-trifluoromethyl-benzamide

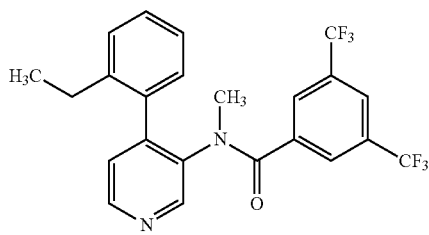 [SMILES: CCc1ccccc1-c1ccncc1N(C)C(=O)c1cc(C(F)(F)F)cc(C(F)(F)F)c1]

The title compound was prepared in analogy to example 72, intermediate, from [4-(2-ethyl-phenyl)-pyridin-3-yl]-methyl-amine and 3,5-bis(trifluoromethyl)benzoyl chloride (CAS RN 1271-19-8) and a gradient of n-heptane:EtOAc (100:0 to 40:60) for the chromatographic purification. Light yellow solid (54%). MS (ESI): m/z=453.139 [M+H]$^+$.

Intermediate

[4-(2-Ethyl-phenyl)-pyridin-3-yl]-methyl-amine

The title compound was prepared in analogy to example 72, from (4-iodo-pyridin-3-yl)-methyl-amine (example 36, intermediate b) and 2-ethylphenylboronic acid (CAS RN 90002-36-1) and using a gradient of n-heptane:EtOAc (100:0 to 40:60) for the chromatographic purification. Light yellow solid (87%). MS (ESI): m/z=213.138 [M+H]$^+$.

Example 169

2-Chloro-N-[4-(4-fluoro-2-methoxy-phenyl)-pyridin-3-yl]-N-methyl-6-trifluoromethyl-isonicotinamide

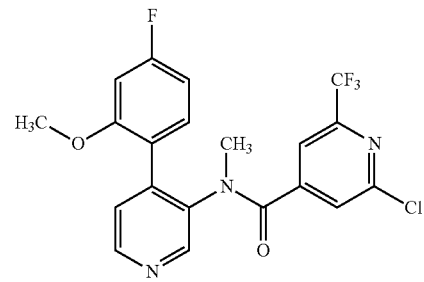 [SMILES: COc1cc(F)ccc1-c1ccncc1N(C)C(=O)c1cc(Cl)nc(C(F)(F)F)c1]

The title compound was prepared in analogy to example 90, from [4-(4-fluoro-2-methoxy-phenyl)-pyridin-3-yl]-methyl-amine (example 129, intermediate) and 2-chloro-6-trifluoromethyl-isonicotinic acid (prepared in analogy to F. Cottet, M. Schlosser, *Eur. J. Org. Chem.* 2004, 18, 3793-3798) after a reaction time of 18 hours. The compound was purified by two silica gel chromatographies on a 10 g column using a MPLC system eluting with a gradient of n-heptane:EtOAc (100:0 to 50:50). Colorless solid (26%). MS (ESI): m/z=440.08 [M+H]$^+$.

Example 170

3-Dimethylsulfamoyl-N-(2-methoxy-[3,4']bipyridinyl-3'-yl)-N-(2,2,2-trifluoro-ethyl)-5-trifluoromethyl-benzamide

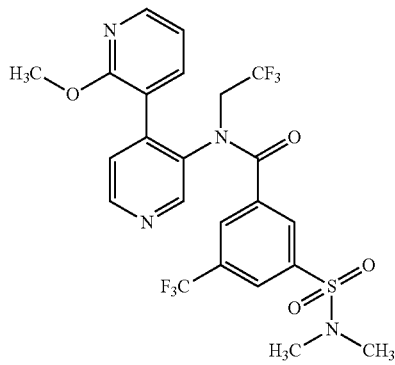

The title compound was prepared in analogy to example 72, intermediate from (2-methoxy-[3,4']bipyridinyl-3'-yl)-(2,2,2-trifluoro-ethyl)-amine (example 135, intermediate a) and 3-dimethylsulfamoyl-5-trifluoromethyl-benzoyl chloride (prepared in analogy to example 74 from 3-dimethylsulfamoyl-5-trifluoromethyl-benzoic acid, Buttpark Ltd.). The compound was purified twice by silica gel chromatography on a 10 g column using a MPLC system eluting with a gradient of n-heptane:EtOAc (100:0 to 0:100). A final chromatography using preparative HPLC (phenomenex gemini column) and a gradient of acetonitrile:water (containing 0.05% formic acid) (10:90 to 98:2) gave the title product as a colorless solid (24%). MS (ESI): m/z=563.12 [M+H]+.

Example 171

2-Chloro-N-methyl-N-(4-o-tolyl-pyridin-3-yl)-6-trifluoromethyl-isonicotinamide

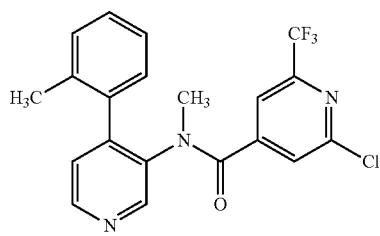 [SMILES: Cc1ccccc1-c1ccncc1N(C)C(=O)c1cc(Cl)nc(C(F)(F)F)c1]

The title compound was prepared in analogy to example 90, from N-methyl-4-o-tolylpyridin-3-amine (example 1, intermediate a) and 2-chloro-6-trifluoromethyl-isonicotinic acid (prepared in analogy to F. Cottet, M. Schlosser, Eur. J. Org. Chem. 2004, 18, 3793-3798) after a reaction time of 66 hours. The compound was purified by two silica gel chromatographies (10 g column each, gradient of n-heptane: EtOAc (100:0 to 50:50) for the first and EtOAc for the second chromatography), followed by preparative HPLC (phenomenex gemini column, gradient of acetonitrile:water (containing 0.05% formic acid) (10:90 to 98:2)). Colorless foam (49%). MS (ESI): m/z=406.09 [M+H]+.

Example 172

[[4-(4,5-Difluoro-2-methoxy-phenyl)-pyridin-3-yl]-(3-methanesulfonyl-5-trifluoromethyl-benzoyl)-amino]-acetic acid methyl ester

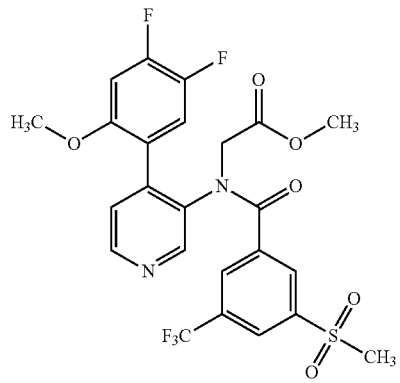

The title compound was prepared in analogy to example 90, from [4-(4,5-difluoro-2-methoxy-phenyl)-pyridin-3-ylamino]-acetic acid methyl ester and 3-methanesulfonyl-5-trifluoromethyl-benzoic acid (example 114, intermediate a) and using a gradient of n-heptane: EtOAc (100:0 to 0:80) for the chromatographic purification. Colorless solid (30%). MS (ESI): m/z=559.096 [M+H]+.

Intermediates a) [4-(4,5-Difluoro-2-methoxy-phenyl)-pyridin-3-ylamino]-acetic acid methyl ester The title compound was prepared in analogy to example 72, from (4-iodo-pyridin-3-ylamino)-acetic acid methyl ester and 4,5-difluoro-2-methoxyphenylboronic acid (CAS RN 870777-32-5) and using a gradient of n-heptane:EtOAc (100:0 to 0:100) for the chromatographic purification. Light yellow oil (82%). MS (ESI): m/z=309.104 [M+H]+.

b) (4-Indo-pyridin-3-ylamino)-acetic acid methyl ester

The title compound was prepared in analogy to example 85, intermediate a, from [ten-butoxycarbonyl-(4-iodo-pyridin-3-yl)-amino]-acetic acid methyl ester. The compound was purified by silica gel chromatography using a MPLC system (CombiFlash Companion, Isco Inc.) eluting with a gradient of n-heptane:EtOAc (100:0 to 0:100). Light yellow solid (91%). MS (ESI): m/z=292.980 [M+H]+.

c) [tert-Butoxycarbonyl-(4-iodo-pyridin-3-yl)-amino]acetic acid methyl ester

The title compound was prepared in analogy to example 85, intermediate c, from (4-iodo-pyridin-3-yl)-carbamic acid tert-butyl ester (example 85, intermediate d) and bromoacetic acid methyl ester (CAS RN 96-32-2) and using a gradient of n-heptane:EtOAc (100:0 to 50:50) for the chromatographic purification. Light brown oil (96%). MS (ESI): m/z=393.030 [M+H]+.

Example 173

{(2,6-Bis-trifluoromethyl-pyridine-4-carbonyl)-[4-(4,5-difluoro-2-methoxy-phenyl)-pyridin-3-yl]-amino}-acetic acid methyl ester

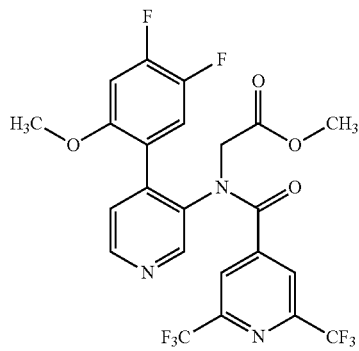

The title compound was prepared in analogy to example 90, from [4-(4,5-difluoro-2-methoxy-phenyl)-pyridin-3-ylamino]-acetic acid methyl ester (example 172, intermediate a) and 2,6-bis(trifluoromethyl)isonicotinic acid (Key Organics Ltd.) after a reaction time of 72 hours. The compound was purified by silica gel chromatography using a MPLC system (CombiFlash Companion, Isco Inc.) eluting with a gradient of n-heptane:EtOAc (100:0 to 0:80). Colorless solid (48%). MS (ESI): m/z=550.102 [M+H]$^+$.

Example 174

N-(2-Amino-2-oxoethyl)-N-(4-(4,5-difluoro-2-methoxyphenyl)pyridin-3-yl)-2,6-bis(trifluoromethyl)isonicotinamide

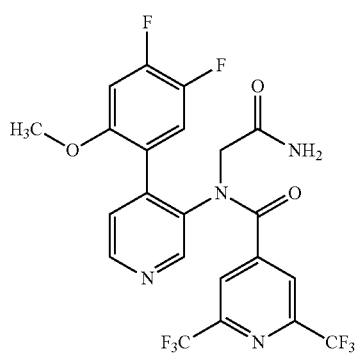 [SMILES: COc1cc(F)c(F)cc1-c1ccncc1N(CC(N)=O)C(=O)c1cc(C(F)(F)F)nc(C(F)(F)F)c1]

The title compound was prepared in analogy to example 117, from {(2,6-bis-trifluoromethyl-pyridine-4-carbonyl)-[4-(4,5-difluoro-2-methoxy-phenyl)-pyridin-3-yl]-amino}-acetic acid and using a gradient of n-heptane:EtOAc:methanol (100:0:0 to 0:100:0 to 0:50:50) for the chromatographic purification. Light yellow foam (63%). MS (ESI): m/z=535.100 [M+H]$^+$.

Intermediate

{(2,6-Bis-trifluoromethyl-pyridine-4-carbonyl)-[4-(4,5-difluoro-2-methoxy-phenyl)-pyridin-3-yl]-amino}-acetic acid The title compound was prepared in analogy to example 84, from {(2,6-bis-trifluoromethyl-pyridine-4-carbonyl)-[4-(4,5-difluoro-2-methoxy-phenyl)-pyridin-3-yl]-amino}-acetic acid methyl ester (example 173). Light yellow solid (99%). MS (ESI): m/z=536.085 [M+H]$^+$.

Example 175

N-[4-(2-Cyanomethyl-phenyl)-pyridin-3-yl]-N-methyl-3,5-bis-trifluoromethyl-benzamide

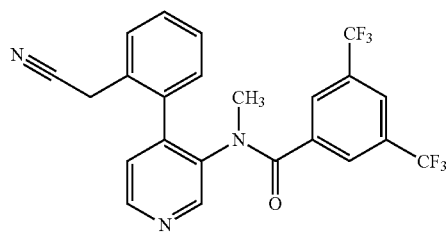 [SMILES: CN(C(=O)c1cc(C(F)(F)F)cc(C(F)(F)F)c1)c1cnccc1-c1ccccc1CC#N]

The title compound was prepared in analogy to example 90, from [2-(3-methylamino-pyridin-4-yl)-phenyl]-acetonitrile and 3,5-bis(trifluoromethyl)benzoic acid (CAS RN 725-89-3) after a reaction time of 5 days. The compound was purified by silica gel chromatography using a MPLC system (CombiFlash Companion, Isco Inc.) eluting with a gradient of n-heptane:EtOAc (100:0 to 50:50) followed by a second chromatography, using preparative HPLC (Phenomenex Gemini® column, gradient of methanol:water (10:90 to 95:5)). Colorless solid (3%). MS (ESI): m/z=464.118 [M+H]$^+$.

Intermediate

[2-(3-Methylamino-pyridin-4-yl)-phenyl]-acetonitrile

The title compound was prepared in analogy to example 72, from (4-iodo-pyridin-3-yl)-methyl-amine (example 98, intermediate b) and [2-(4,4,5,5-tetramethyl-[1,3,2]dioxaborolan-2-yl)-phenyl]acetonitrile (CAS RN 325141-71-7) after a reaction time of 6 days and using a gradient of n-heptane:EtOAc (100:0 to 20:80) for the chromatographic purification. Light yellow solid (69%). MS (ESI): m/z=224.118 [M+H]$^+$.

Example 176

{(2,6-Bis-trifluoromethyl-pyridine-4-carbonyl)-[4-(4-fluoro-2-methoxy-phenyl)-pyridin-3-yl]-amino}-acetic acid methyl ester

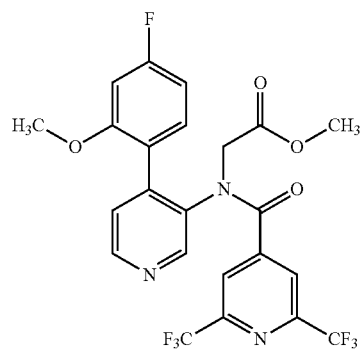 [SMILES: COC(=O)CN(C(=O)c1cc(C(F)(F)F)nc(C(F)(F)F)c1)c1cnccc1-c1ccc(F)cc1OC]

The title compound was prepared in analogy to example 90, from [4-(4-fluoro-2-methoxy-phenyl)-pyridin-3-ylamino]-acetic acid methyl ester and 2,6-bis(trifluoromethyl)isonicotinic acid (Key Organics Ltd.) after a reaction time of 72 hours. The compound was purified by silica gel chromatography using a MPLC system (CombiFlash Companion, Isco Inc.) eluting with a gradient of n-heptane:EtOAc (100:0 to 20:80). Colorless solid (46%). MS (ESI): m/z=532.109 [M+H]$^+$.

Intermediates a) [4-(4-Fluoro-2-methoxy-phenyl)-pyridin-3-ylamino]-acetic acid methyl ester The title compound was prepared in analogy to example 72, from (4-iodo-pyridin-3-ylamino)-acetic acid methyl ester and 4-fluoro-2-methoxyphenylboronic acid (CAS RN 179899-07-1) and using a gradient of n-heptane:EtOAc (100:0 to 0:100) for the chromatographic purification. Light yellow oil (73%). MS (ESI): m/z=291.113 [M+H]$^+$.

b) (4-Indo-pyridin-3-ylamino)-acetic acid methyl ester

The title compound was prepared in analogy to example 85, intermediate a, from [tert-butoxycarbonyl-(4-iodo-pyridin-3-yl)-amino]-acetic acid methyl ester. The compound was purified by silica gel chromatography using a MPLC system (CombiFlash Companion, Isco Inc.) eluting with a gradient of n-heptane:EtOAc (100:0 to 0:100). Light yellow solid (91%). MS (ESI): m/z=292.980 [M+H]$^+$.

c) [tert-Butoxycarbonyl-(4-iodo-pyridin-3-yl)-amino]acetic acid methyl ester

The title compound was prepared in analogy to example 85, intermediate c, from (4-iodo-pyridin-3-yl)-carbamic acid tert-butyl ester (example 85, intermediate d) and bromoacetic acid methyl ester (CAS RN 96-32-2) and using a gradient of n-heptane:EtOAc (100:0 to 50:50) for the chromatographic purification. Light brown oil (96%). MS (ESI): m/z=393.030 [M+H]$^+$.

Example 177

N-Carbamoylmethyl-N-[4-(4-fluoro-2-methoxy-phenyl)-pyridin-3-yl]-2,6-bis-trifluoromethyl-isonicotinamide

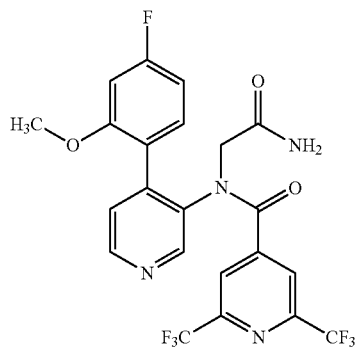

The title compound was prepared in analogy to example 117, from {(2,6-bis-trifluoromethyl-pyridine-4-carbonyl)-[4-(4-fluoro-2-methoxy-phenyl)-pyridin-3-yl]-amino}-acetic acid and using a gradient of n-heptane:EtOAc:methanol (100:0:0 to 0:100:0 to 0:50:50) for the chromatographic separation. Colorless solid (79%). MS (ESI): m/z=517.110 [M+H]$^+$.

Intermediate

{(2,6-Bis-trifluoromethyl-pyridine-4-carbonyl)-[4-(4-fluoro-2-methoxy-phenyl)-pyridin-3-yl]-amino}-acetic acid The title compound was prepared in analogy to example 84, from {(2,6-bis-trifluoromethyl-pyridine-4-carbonyl)-[4-(4-fluoro-2-methoxy-phenyl)-pyridin-3-yl]-amino}-acetic acid methyl ester (example 176). Light yellow solid (99%). MS (ESI): m/z=518.094 [M+H]$^+$.

Example 178

Methyl 2-(3-(N,N-dimethylsulfamoyl)-N-(2-methoxy-3,4'-bipyridin-3'-yl)-5-(trifluoromethyl)benzamido)acetate

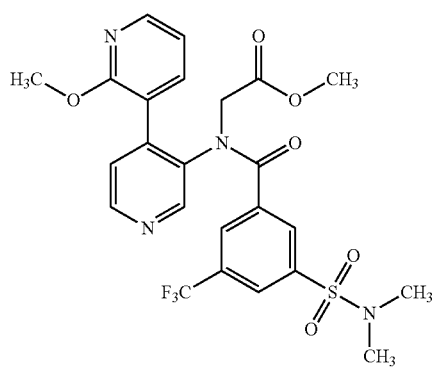

The title compound was prepared in analogy to example 90, from (2-methoxy-[3,4']bipyridinyl-3'-ylamino)-acetic acid methyl ester and 3-dimethylsulfamoyl-5-trifluoromethyl-benzoic acid (Buttpark Ltd.) after a reaction time of 72 hours. The compound was purified by silica gel chromatography using a MPLC system (CombiFlash Companion, Isco Inc.) eluting with a gradient of n-heptane:EtOAc (100:0 to 20:80). The product-containing fractions were pooled and evaporated and the residue poured on 30 mL 1M aqueous HCl and 30 mL EtOAc. The layers were separated and the aqueous layer was extracted a second time with 30 mL EtOAc. The organic layers were washed twice with 30 mL 1M aqueous HCl followed by 30 mL brine, dried over MgSO$_4$, filtered and concentrated under vacuum. Light yellow solid (30%). MS (ESI): m/z=553.135 [M+H]$^+$.

Intermediates (2-Methoxy-[3,4']bipyridinyl-3'-ylamino)-acetic acid methyl ester

The title compound was prepared in analogy to example 72, from (4-iodo-pyridin-3-ylamino)-acetic acid methyl ester (example 176, intermediate b) and 2-methoxypyridine-3-boronic acid (CAS RN 163105-90-6) and using a gradient of n-heptane:EtOAc (100: 0 to 0:100) for the chromatographic purification. Light yellow oil (73%). MS (ESI): m/z=274.119 [M+H]$^+$.

Example 179

N-Carbamoylmethyl-3-dimethylsulfamoyl-N-(2-methoxy-[3,4']bipyridinyl-3'-yl)-5-trifluoromethyl-benzamide

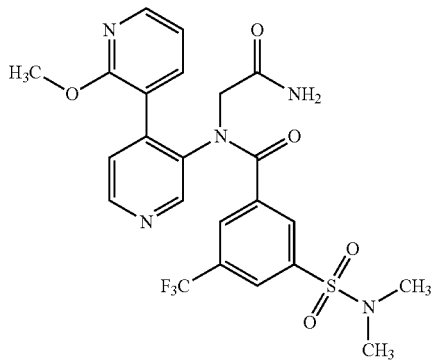

The title compound was prepared in analogy to example 117, from [(3-dimethylsulfamoyl-5-trifluoromethyl-benzoyl)-(2-methoxy-[3,4']bipyridinyl-3'-yl)-amino]-acetic acid (0.35 mol % NEt$_3$) and using a gradient of n-heptane: EtOAc: methanol (100:0:0 to 0:100:0 to 0:50:50) for the chromatographic purification. Colorless solid (81%). MS (ESI): m/z=537.107 [M−H]$^−$.

Intermediate

[(3-Dimethylsulfamoyl-5-trifluoromethyl-benzoyl)-(2-methoxy-[3,4']bipyridinyl-3'-yl)-amino]-acetic acid, triethylamine salt (1:0.35)

The title compound was prepared in analogy to example 84, from methyl 2-(3-(N,N-dimethylsulfamoyl)-N-(2-methoxy-3,4'-bipyridin-3'-yl)-5-(trifluoromethyl)benzamido)acetate. The compound was purified by preparative HPLC (Gemini NX column) with a gradient of methanol:water containing 0.1% NEt$_3$ (80:20 to 98:2). Colorless solid (75%). MS (ESI): m/z=537.107 [M−H]$^−$.

Example 180

[(3-Methanesulfonyl-5-trifluoromethyl-benzoyl)-(2-methoxy-[3,4']bipyridinyl-3'-yl)-amino]-acetic acid methyl ester

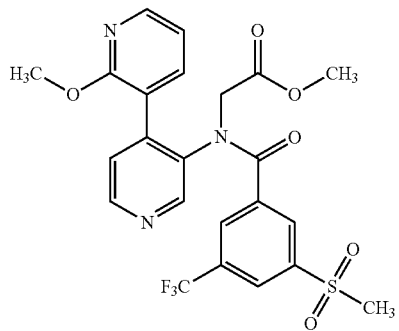

The title compound was prepared in analogy to example 90, from (2-methoxy-[3,4']bipyridinyl-3'-ylamino)-acetic acid methyl ester (example 178, intermediate) and 3-methanesulfonyl-5-trifluoromethyl-benzoic acid (example 114, intermediate a) after a reaction time of 72 hours. The compound was purified by silica gel chromatography using a MPLC system (CombiFlash Companion, Isco Inc.) eluting with a gradient of n-heptane: EtOAc (100:0 to 20:80). The product-containing fractions were pooled and evaporated. The remaining solid was purified by preparative HPLC (Gemini NX column) with a gradient of methanol:water (containing 0.05% formic acid) (80:20 to 98:2). Light yellow foam (32%). MS (ESI): m/z=524.108 [M+H]$^+$.

Example 181

N-Carbamoylmethyl-3-methanesulfonyl-N-(2-methoxy-[3,4']bipyridinyl-3'-yl)-5-trifluoromethyl-benzamide

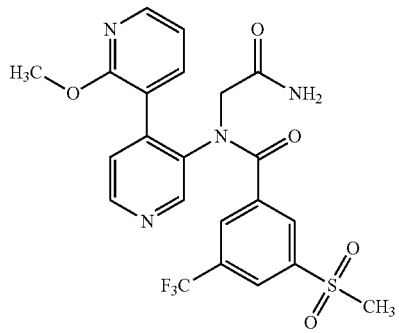

The title compound was prepared in analogy to example 117, from [(3-methanesulfonyl-5-trifluoromethyl-benzoyl)-(2-methoxy-[3,4']bipyridinyl-3'-yl)-amino]-acetic acid and using a gradient of n-heptane:EtOAc:methanol (100:0:0 to 0:100:0 to 0:50:50) for the chromatographic purification. Colorless solid (72%). MS (ESI): m/z=509.109 [M+H]+.

Intermediate

[(3-Methanesulfonyl-5-trifluoromethyl-benzoyl)-(2-methoxy-[3,4']bipyridinyl-3'-yl)-amino]-acetic acid The title compound was prepared in analogy to example 84, from [(3-methanesulfonyl-5-trifluoromethyl-benzoyl)-(2-methoxy-[3,4']bipyridinyl-3'-yl)-amino]-acetic acid methyl ester. Colorless solid (76%). MS (ESI): m/z=510.092 [M+H]+.

Example 182

Methyl 2-(N-(2-methoxy-3,4'-bipyridin-3'-yl)-2,6-bis(trifluoromethyl)isonicotinamido)acetate

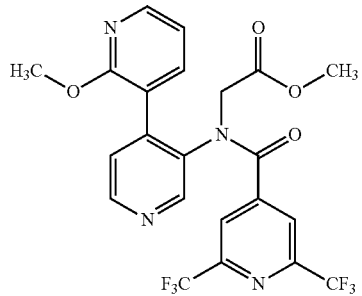 [SMILES: COC(=O)CN(C(=O)c1cc(C(F)(F)F)nc(C(F)(F)F)c1)c1cnccc1-c1cccnc1OC]

The title compound was prepared in analogy to example 90, from (2-methoxy-[3,4']bipyridinyl-3'-ylamino)-acetic acid methyl ester (example 178, intermediate) and 2,6-bis(trifluoromethyl)isonicotinic acid (Key Organics Ltd.) after a reaction time of 48 hours. The compound was purified by silica gel chromatography using a MPLC system (CombiFlash Companion, Isco Inc.) eluting with a gradient of n-heptane:EtOAc (100:0 to 20:80). Light yellow solid (55%). MS (ESI): m/z=515.114 [M+H]+.

Example 183

N-(2-Amino-2-oxoethyl)-N-(2-methoxy-3,4'-bipyridin-3'-yl)-2,6-bis(trifluoromethyl)-isonicotinamide

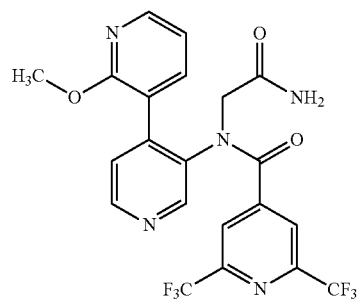 [SMILES: COc1ncccc1-c1ccncc1N(CC(N)=O)C(=O)c1cc(C(F)(F)F)nc(C(F)(F)F)c1]

The title compound was prepared in analogy to example 117, from [(2,6-bis-tri fluoro methyl-pyridine-4-carbonyl)-(2-methoxy-[3,4']bipyridinyl-3'-yl)-amino]-acetic acid and using a gradient of n-heptane:EtOAc:methanol (100:0:0 to 0:100:0 to 0:50:50) for the chromatographic purification. Light yellow foam (80%). MS (ESI): m/z=500.114 [M+H]+.

Intermediate

[(2,6-Bis-trifluoromethyl-pyridine-4-carbonyl)-(2-methoxy-[3,4']bipyridinyl-3'-yl)-amino]-acetic acid The title compound was prepared in analogy to example 84, from methyl 2-(N-(2-methoxy-3,4'-bipyridin-3'-yl)-2,6-bis(trifluoromethyl)isonicotinamido)acetate (example 182). Light yellow foam (99%). MS (ESI): m/z=501.099 [M+H]+.

Example 184

N-Methyl-3-nitro-N-(4-o-tolylpyridin-3-yl)-5-(trifluoromethyl)benzamide

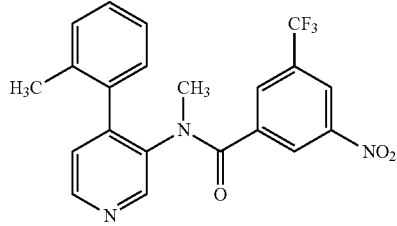

The title compound was prepared in analogy to example 90, from N-methyl-4-o-tolylpyridin-3-amine (example 1, intermediate a) and 3-nitro-5-trifluoromethyl-benzoic acid (CAS RN 328-80-3) after a reaction time of 48 hours. The compound was purified by silica gel chromatography using a MPLC system (CombiFlash Companion, Isco Inc.) eluting with a gradient of n-heptane:EtOAc (100:0 to 0:80). The product-containing fractions were pooled and concentrated under vacuum. The residue was dissolved in 30 mL 1M aqueous HCl and 30 mL EtOAc and the layers were separated. The aqueous layer was extracted a second time with 30 mL EtOAc. The organic layers were washed twice with 30 mL 1M aqueous HCl and with 30 mL brine, dried over MgSO4, filtered and concentrated under vacuum. Light yellow solid (66%). MS (ESI): m/z=416.121 [M+H]+.

Example 185

N-Methyl-3-(2-oxo-pyrrolidin-1-yl)-N-(4-o-tolyl-pyridin-3-yl)-5-trifluoromethyl-benzamide

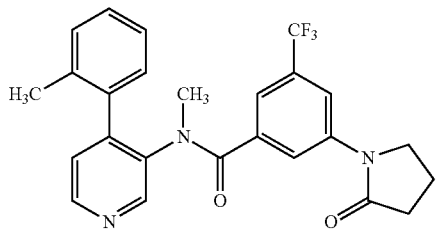 [SMILES: Cc1ccccc1-c1ccncc1N(C)C(=O)c1cc(N2CCCC2=O)cc(C(F)(F)F)c1]

The title compound was prepared in analogy to example 90, from N-methyl-4-o-tolylpyridin-3-amine (example 1, intermediate a) and 3-(2-oxo-pyrrolidin-1-yl)-5-trifluoromethyl-benzoic acid (Selena Chemicals Inc.) after a reaction time of 120 hours. The product was purified by preparative HPLC (Phenomenex Gemini® column) with a gradient of acetonitrile:water (containing 0.05% formic acid) (10:90 to 98:2). Light brown solid (2%). MS (ESI): m/z=454.17 [M+H]⁺.

Example 186

[[4-(4-Fluoro-2-methoxy-phenyl)-pyridin-3-yl]-(3-methanesulfonyl-5-trifluoromethyl-benzoyl)-amino]-acetic acid methyl ester

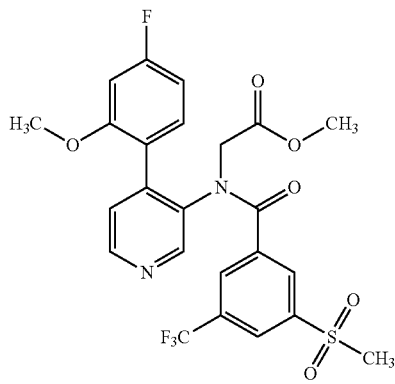

The title compound was prepared in analogy to example 90, from [4-(4-fluoro-2-methoxy-phenyl)-pyridin-3-ylamino]-acetic acid methyl ester (example 176, intermediate a) and 3-methanesulfonyl-5-trifluoromethyl-benzoic acid (example 114, intermediate a).

The compound was purified by silica gel chromatography using a MPLC system (CombiFlash Companion, Isco Inc.) eluting with a gradient of n-heptane:EtOAc (100:0 to 0:100). The product-containing fractions were pooled and evaporated. The residue was dissolved in 30 mL 1M aqueous HCl and 30 mL EtOAc and the layers were separated. The aqueous layer was extracted a second time with 30 mL EtOAc. The organic layers were washed twice with 30 mL 1M aqueous HCl and with 30 mL brine, dried over MgSO₄, filtered and concentrated under vacuum. The remaining light yellow solid was purified by preparative HPLC (Gemini NX column) with a gradient of methanol:water with 0.05% formic acid (80:20 to 98:2). Colorless solid (20%). MS (ESI): m/z=504.104 [M+H]⁺.

Example 187

N-Carbamoylmethyl-N-[4-(4-fluoro-2-methoxy-phenyl)-pyridin-3-yl]-3-methanesulfonyl-5-trifluoromethyl-benzamide

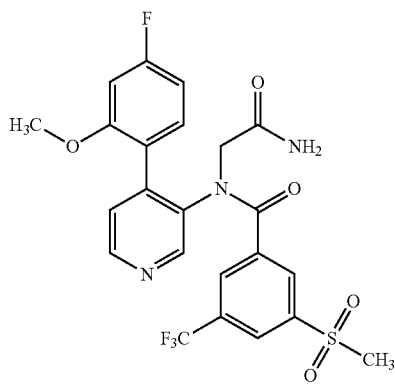

The title compound was prepared in analogy to example 117, from [[4-(4-fluoro-2-methoxy-phenyl)-pyridin-3-yl]-(3-methanesulfonyl-5-trifluoromethyl-benzoyl)-amino]-acetic acid and using a gradient of n-heptane:EtOAc:methanol (100:0:0 to 0:100:0 to 0:50:50) for the chromatographic purification. Colorless solid (77%). MS (ESI): m/z=526.104 [M+H]⁺.

Intermediate

[[4-(4-Fluoro-2-methoxy-phenyl)-pyridin-3-yl]-(3-methanesulfonyl-5-trifluoromethyl-benzoyl)-amino]-acetic acid The title compound was prepared in analogy to example 84, from [[4-(4-fluoro-2-methoxy-phenyl)-pyridin-3-yl]-(3-methanesulfonyl-5-trifluoromethyl-benzoyl)-amino]-acetic acid methyl ester (example 186). Colorless solid (100%). MS (ESI): m/z=527.089 [M+H]⁺.

Example 188

{(3,5-Bis-trifluoromethyl-benzoyl)-[4-(4,5-difluoro-2-methoxy-phenyl)-pyridin-3-yl]-amino}-acetic acid methyl ester

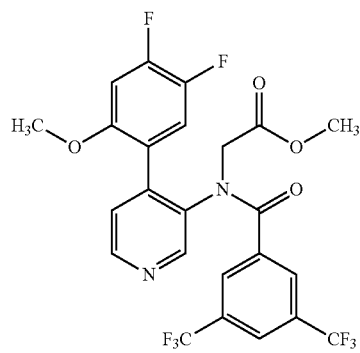 [SMILES: COC(=O)CN(C(=O)c1cc(C(F)(F)F)cc(C(F)(F)F)c1)c1cnccc1-c1cc(F)c(F)cc1OC]

The title compound was prepared in analogy to example 90, from [4-(4,5-difluoro-2-methoxy-phenyl)-pyridin-3-ylamino]-acetic acid methyl ester (example 172, intermediate a) and 3,5-bis(trifluoromethyl)benzoic acid (CAS RN 725-89-3) after a reaction time of 72 hours. The compound was purified by silica gel chromatography using a MPLC system (CombiFlash Companion, Isco Inc.) eluting with a gradient of n-heptane:EtOAc (100:0 to 0:100). The product-containing fractions were pooled and evaporated and the residue purified by preparative HPLC (Gemini NX column) using a gradient of methanol: water with 0.05% formic acid (80:20 to 98:2). Colorless solid (10%). MS (ESI): m/z=549.105 [M+H]⁺.

Example 189

N-Carbamoylmethyl-N-[4-(4,5-difluoro-2-methoxy-phenyl)-pyridin-3-yl]-3,5-bis-trifluoromethyl-benzamide

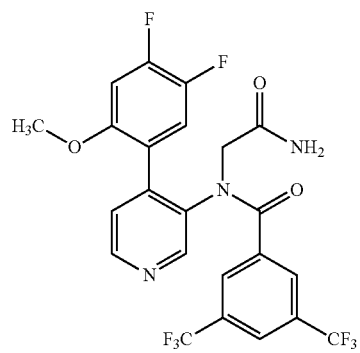 [SMILES: COc1cc(F)c(F)cc1-c1ccncc1N(CC(N)=O)C(=O)c1cc(C(F)(F)F)cc(C(F)(F)F)c1]

The title compound was prepared in analogy to example 117, from {(3,5-bis-trifluoromethyl-benzoyl)-[4-(4,5-difluoro-2-methoxy-phenyl)-pyridin-3-yl]-amino}-acetic acid and using a gradient of n-heptane:EtOAc:methanol (100:0:0 to 0:100:0 to 0:50:50) for the chromatographic purification. Colorless solid (100%). MS (ESI): m/z=534.105 [M+H]$^+$.

Intermediate

{(3,5-Bis-trifluoromethyl-benzoyl)-[4-(4,5-difluoro-2-methoxy-phenyl)-pyridin-3-yl]-amino}-acetic acid The title compound was prepared in analogy to example 84, from {(3,5-bis-trifluoromethyl-benzoyl)-[4-(4,5-difluoro-2-methoxy-phenyl)-pyridin-3-yl]-amino}-acetic acid methyl ester (example 188). Light yellow solid (98%). MS (ESI): m/z=535.089 [M+H]$^+$.

Example 190

4,6-Bis-trifluoromethyl-pyridine-2-carboxylic acid methyl-(4-o-tolyl-pyridin-3-yl)-amide

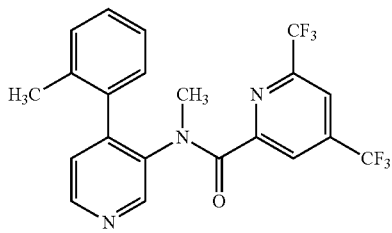

The title compound was prepared in analogy to example 90, from N-methyl-4-o-tolylpyridin-3-amine (example 1, intermediate a) and 4,6-bis(trifluoromethyl)-2-pyridinecarboxylic acid (Bionet Research) and using a gradient of n-heptane:EtOAc (100:0 to 0:100) for the chromatographic purification. Light brown oil (66%). MS (ESI): m/z=440.12 [M+H]$^+$.

Example 191

N-[4-(2-Fluoro-phenyl)-pyridin-3-yl]-N-(2-methanesulfonyl-ethyl)-3,5-bis-trifluoromethyl-benzamide

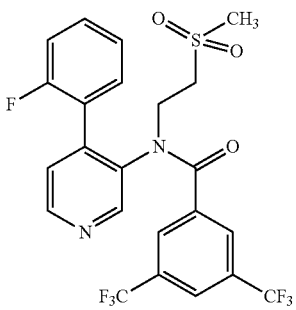 [SMILES: CS(=O)(=O)CCN(C(=O)c1cc(C(F)(F)F)cc(C(F)(F)F)c1)c1cnccc1-c1ccccc1F]

The title compound was prepared in analogy to example 90, from [4-(2-fluoro-phenyl)-pyridin-3-yl]-(2-methanesulfonyl-ethyl)-amine (example 159, intermediate) and 3,5-bis(trifluoromethyl)benzoic acid (CAS RN 725-89-3) after a reaction time of 40 hours. The compound was purified by two silica gel chromatographies using a 10 g column and 5 g column, respectively, on a MPLC system (CombiFlash Companion, Isco Inc.) eluting with a gradient of n-heptane:EtOAc (100:0 to 0:100). The resulting brown solid was suspended in tert-butyl methyl ether, filtered and washed with tert-butyl methyl ether to give the title compound as an off-white solid (8%). MS (ESI): m/z=535.09 [M+H]$^+$.

Example 192

N-[4-(4-Fluoro-2-methoxy-phenyl)-pyridin-3-yl]-N-(2-methanesulfonyl-ethyl)-3,5-bis-tri fluoro methyl-benzamide

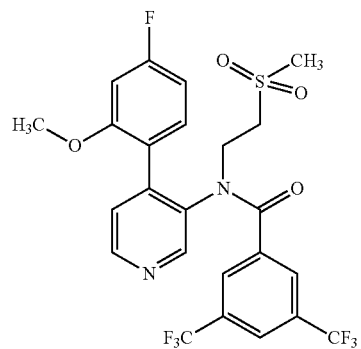

The title compound was prepared in analogy to example 90, from [4-(4-fluoro-2-methoxy-phenyl)-pyridin-3-yl]-(2-methanesulfonyl-ethyl)-amine (example 162, intermediate) and 3,5-bis(trifluoromethyl)benzoic acid (CAS RN 725-89-3) after a reaction time of 40 hours. The compound was purified by silica gel chromatography using a MPLC system (ISCO) and a 10 g and 5 g column, respectively, eluting with a gradient of n-heptane:EtOAc (100:0 to 0:100). A third chromatography, using preparative HPLC (Gemini NX column) eluting with a gradient of methanol:water (containing 0.05% formic acid) (20:80 to 98:2), yielded the product as a colorless solid (4%). MS (ESI): m/z=565.10 [M+H]$^+$.

Example 193

N-(2-Amino-2-oxoethyl)-N-(4-(4,5-difluoro-2-methoxyphenyl)pyridin-3-yl)-3-(methylsulfonyl)-5-(trifluoromethyl)benzamide

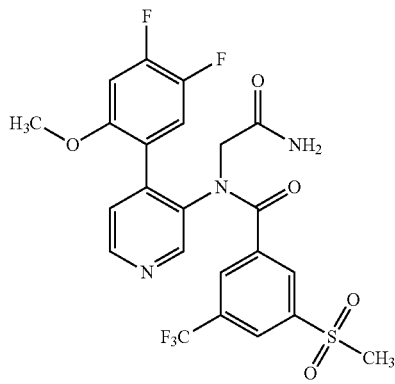

The title compound was prepared in analogy to example 117, from [[4-(4,5-difluoro-2-methoxy-phenyl)-pyridin-3-yl]-(3-methanesulfonyl-5-trifluoromethyl-benzoyl)-amino]-acetic acid and using a gradient of n-heptane:EtOAc:methanol (100:0:0 to 0:100:0 to 0:50:50) for the chromatographic purification. Colorless solid (78%). MS (ESI): m/z=588.0868 [M+HCOO]⁻.

Intermediate

[[4-(4,5-Difluoro-2-methoxy-phenyl)-pyridin-3-yl]-(3-methanesulfonyl-5-trifluoromethyl-benzoyl)-amino]-acetic acid, triethylamine salt (1:0.4)

The title compound was prepared in analogy to example 84, from [[4-(4,5-difluoro-2-methoxy-phenyl)-pyridin-3-yl]-(3-methanesulfonyl-5-trifluoromethyl-benzoyl)-amino]-acetic acid methyl ester (example 172). The compound was purified by preparative HPLC (Gemini NX column) using a gradient of methanol:water with 0.1% NEt₃ (80:20 to 98:2). Colorless solid (53%). MS (ESI): m/z=545.079 [M+H]⁺.

Example 194

2-Methanesulfonyl-N-methyl-N-(4-o-tolyl-pyridin-3-yl)-6-trifluoromethyl-isonicotinamide

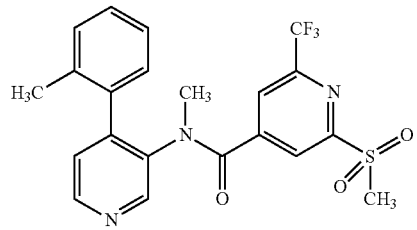 [SMILES: Cc1ccccc1-c1ccncc1N(C)C(=O)c1cc(C(F)(F)F)nc(S(C)(=O)=O)c1]

The title compound was prepared in analogy to example 90, from N-methyl-4-o-tolylpyridin-3-amine (example 1, intermediate a) and 2-methanesulfonyl-6-trifluoromethyl-isonicotinic acid after a reaction time of 22 hours. The compound was purified by silica gel chromatography on a 50 g column using a MPLC (ISCO) system eluting with EtOAc as an eluant. The product-containing fractions were pooled, evaporated and the remaining light brown foam purified by preparative HPLC (Gemini NX column) using a gradient of methanole:water (containing 0.1% formic acid) (20:80 to 98:2). Colorless solid (40%). MS (ESI): m/z=450.11 [M+H]⁺.

Intermediates a) 2-Methanesulfonyl-6-trifluoromethyl-isonicotinic acid

To an ice-cold suspension of Oxone® (525 mg, 854 μmol, CAS RN 10058-23-8) in methanol (0.6 mL) and water (0.6 mL) was added dropwise a solution of 2-methylsulfanyl-6-trifluoromethyl-isonicotinic acid (0.09 g, 341 μmol) in methanol (1.2 mL) and the reaction mixture was stirred in an ice-bath for 2 hours. After stirring at room temperature for another 4.5 hours the reaction mixture was poured on 10% aqueous citric acid solution and EtOAc and the layers were separated. The aqueous layer was extracted twice with EtOAc and the organic layers were washed with water, 10% aqueous Na₂S₂O₃ solution and brine, dried over MgSO₄, filtered, and evaporated. Colorless solid (0.106 g; 98%). MS (ESI): m/z=267.99 [M−H]⁻. This material was used in the next step without further purification.

b) 2-Methylsulfanyl-6-trifluoromethyl-isonicotinic acid

To a suspension of 2-chloro-6-(trifluoromethyl)isonicotinic acid (0.1 g, 443 μmol, prepared according to F. Cottet, M. Schlosser, Eur. J. Org. Chem. 2004, 18, 3793-3798) in THF (5 mL) was added sodium thiomethoxide (155 mg, 2.22 mmol, CAS RN 50615-16-2) and the reaction mixture was heated to 70° C. (oil bath temperature) for 15 hours. After cooling down to room temperature, EtOAc (5 mL) and 1M aqueous HCl (2 mL) were added and the reaction mixture was stirred at room temperature for 30 min. The layers were separated and the aqueous layer was extracted with EtOAc. The organic layers were washed with brine, dried over MgSO₄, filtered and evaporated to give the desired compound as an off-white solid (0.105 g; 99%) which was used in the next step without further purification. MS (ESI): m/z=236.01 [M−H]⁻.

Example 195

Methyl 2-(N-(4-(2-fluoro-6-methoxyphenyl)pyridin-3-yl)-2,6-bis(trifluoromethyl) isonicotinamido)acetate

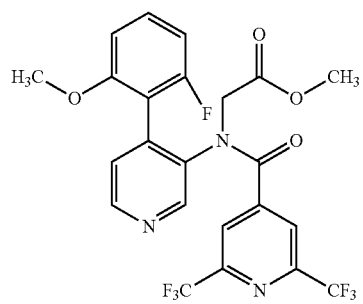 [SMILES: COC(=O)CN(C(=O)c1cc(C(F)(F)F)nc(C(F)(F)F)c1)c1cnccc1-c1c(F)cccc1OC]

The title compound was prepared in analogy to example 90, from [4-(2-fluoro-6-methoxy-phenyl)-pyridin-3-ylamino]-acetic acid methyl ester and 2,6-bis(trifluoromethyl)isonicotinic acid (Key Organics Ltd.) after a reaction time of 72 hours. The compound was purified by silica gel chromatography using a MPLC system (CombiFlash Companion, Isco Inc.) eluting with a gradient of n-heptane:EtOAc (100:0 to 20:80). Light yellow solid (48%). MS (ESI): m/z=532.109 [M+H]+.

Intermediate

[4-(2-Fluoro-6-methoxy-phenyl)-pyridin-3-ylamino]-acetic acid methyl ester

The title compound was prepared in analogy to example 72, from 4-iodo-pyridin-3-ylamino)-acetic acid methyl ester (example 176, intermediate b) and 2-fluoro-6-methoxyphenylboronic acid (CAS RN 78495-63-3) and using a gradient of n-heptane: EtOAc (100:0 to 0:100) for the chromatographic purification. Light yellow oil (34%). MS (GC_MS (TIC): m/z=290.1 [M+].].

Example 196

Methyl 2-(N-(4-(2-fluorophenyl)pyridin-3-yl)-2,6-bis(trifluoromethyl)isonicotinamido)acetate

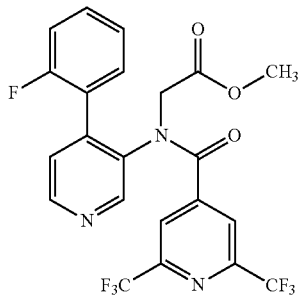 [SMILES: COC(=O)CN(C(=O)c1cc(C(F)(F)F)nc(C(F)(F)F)c1)c1cnccc1-c1ccccc1F]

The title compound was prepared in analogy to example 90, from [4-(2-fluoro-phenyl)-pyridin-3-ylamino]-acetic acid methyl ester and 2,6-bis(trifluoromethyl)isonicotinic acid (Key Organics Ltd.) after a reaction time of 72 hours. The compound was purified by silica gel chromatography using a MPLC system (CombiFlash Companion, Isco Inc.) eluting with a gradient of n-heptane:EtOAc (100:0 to 20:80). Light yellow solid (39%). MS (ESI): m/z=502.099 [M+H]+.

Intermediate

[4-(2-Fluoro-phenyl)-pyridin-3-ylamino]-acetic acid methyl ester

The title compound was prepared in analogy to example 72, from (4-iodo-pyridin-3-ylamino)-acetic acid methyl ester (example 176, intermediate b) and 2-fluorophenylboronic acid (CAS RN 1193-03-9) and using a gradient of n-heptane: EtOAc (100:0 to 0:100) for the chromatographic purification. Off-white solid (37%). MS (ESI): m/z=261.104 [M+H]+.

Example 197

N-Carbamoylmethyl-N-[4-(2-fluoro-phenyl)-pyridin-3-yl]-2,6-bis-trifluoromethyl-isonicotinamide

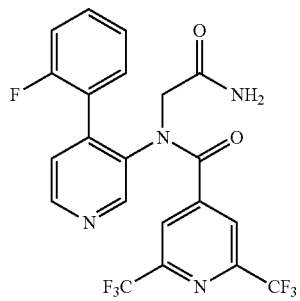 [SMILES: NC(=O)CN(C(=O)c1cc(C(F)(F)F)nc(C(F)(F)F)c1)c1cnccc1-c1ccccc1F]

The title compound was prepared in analogy to example 117, from {(2,6-bis-trifluoromethyl-pyridine-4-carbonyl)-[4-(2-fluoro-phenyl)-pyridin-3-yl]-amino}-acetic acid. The compound was purified by silica gel chromatography using an MPLC (Flashmaster) system eluting with a gradient of n-heptane:EtOAc:methanol (100:0:0 to 0:100:0 to 0:50:50). Light yellow solid (74%). MS (ESI): m/z=487.099 [M+H]+.

Intermediate

{(2,6-Bis-trifluoromethyl-pyridine-4-carbonyl)-[4-(2-fluoro-phenyl)-pyridin-3-yl]-amino}-acetic acid The title compound was prepared in analogy to example 72, from {(2,6-bis-trifluoromethyl-pyridine-4-carbonyl)-[4-(2-fluoro-phenyl)-pyridin-3-yl]-amino}-acetic acid methyl ester (example 196). White solid (89%). MS (ESI): m/z=488.083 [M+H]+.

Example 198

2-Chloro-N-[4-(4-fluoro-2-methoxy-phenyl)-pyridin-3-yl]-6-methoxy-N-methyl-isonicotinamide

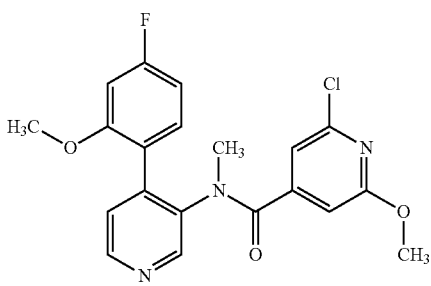

The title compound was prepared in analogy to example 90, from [4-(4-fluoro-2-methoxy-phenyl)-pyridin-3-yl]-methyl-amine (example 129, intermediate) and 2-chloro-6-methoxy-isonicotinic acid (CAS RN 15855-06-8). Colorless solid (21%). MS (ESI): m/z=402.10 [M+H]+.

Example 199

N-Carbamoylmethyl-N-[4-(2-fluoro-6-methoxy-phenyl)-pyridin-3-yl]-2,6-bis-trifluoromethyl-isonicotinamide

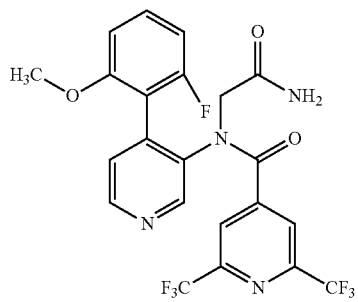

The title compound was prepared in analogy to example 117, from {(2,6-bis-trifluoromethyl-pyridine-4-carbonyl)-[4-(2-fluoro-6-methoxy-phenyl)-pyridin-3-yl]-amino}-acetic acid. The compound was purified by silica gel chromatography using an MPLC system (Flashmaster) eluting with a gradient of n-heptane:EtOAc:methanol (100:0:0 to 0:100:0 to 0:50:50). Light yellow solid (78%). MS (ESI): m/z=517.109 [M+H]$^+$.

Intermediate

{(2,6-Bis-trifluoromethyl-pyridine-4-carbonyl)-[4-(2-fluoro-6-methoxy-phenyl)-pyridin-3-yl]-amino}-acetic acid The title compound was prepared in analogy to example 84, from {(2,6-bis-trifluoromethyl-pyridine-4-carbonyl)-[4-(2-fluoro-6-methoxy-phenyl)-pyridin-3-yl]-amino}-acetic acid methyl ester (example 195). White solid (99%). MS (ESI): m/z=518.094 [M+H]$^+$.

Example 200

N-Oxetan-3-yl-N-(4-o-tolyl-pyridin-3-yl)-3,5-bis-trifluoromethyl-benzamide

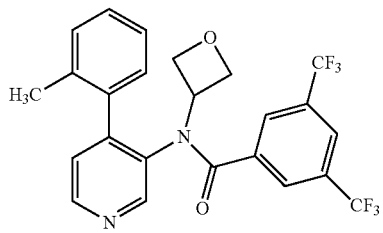 [SMILES: Cc1ccccc1-c1ccncc1N(C(=O)c1cc(C(F)(F)F)cc(C(F)(F)F)c1)C1COC1]

The title compound was prepared in analogy to example 72, intermediate, from oxetan-3-yl-(4-o-tolyl-pyridin-3-yl)-amine and 3,5-bis(trifluoromethyl)benzoyl chloride (CAS RN 1271-19-8) and using a gradient of gradient of n-heptane:EtOAc (100:0 to 30:70) for the chromatographic purification. Light yellow solid (34%). MS (ESI): m/z=481.13 [M+H]$^+$.

Intermediates a) Oxetan-3-yl-(4-o-tolyl-pyridin-3-yl)-amine

A solution of 4-o-tolylpyridin-3-amine (0.125 g, 678 μmol) and oxetan-3-one (147 mg, 2.04 mmol, CAS RN 6704-31-0) in methanol (2 mL) was treated with zinc chloride (370 mg, 2.71 mmol). The reaction mixture got slightly warm and a solution formed. Then, molecular sieves 4 Å (100 mg, 678 μmol) were added and the reaction mixture refluxed for 19 hours. After cooling to room temperature another batch of oxetan-3-one (147 mg, 2.04 mmol) was added and the reaction mixture was heated again to reflux for another 24 hours before zinc chloride (185 mg, 1.36 mmol) was added. After stirring for another 2 hours sodium cyanoborohydride (128 mg, 2.04 mmol, CAS RN 25895-60-7) was added and the reaction mixture was stirred at reflux for 2 hours. After stirring at room temperature overnight, the reaction mixture was poured on saturated aqueous NH$_4$Cl solution and EtOAc and the mixture was filtered over dicalite. The layers were separated and the aqueous layer was extracted twice with EtOAc. The organic layers were washed with brine, dried over MgSO$_4$, filtered, treated with silica gel and evaporated. The compound was purified twice by silica gel chromatography on a 10 g column using a MPLC system eluting with a gradient of n-heptane:EtOAc (100:0 to 0:100). Off-white foam (0.072 g; 42%). MS (ESI): m/z=241.13 [M+H]$^+$.

b) 4-o-Tolylpyridin-3-amine

The title compound was prepared in analogy to example 85, intermediate a, from (4-o-tolyl-pyridin-3-yl)-carbamic acid tert-butyl ester. Brown solid (100%). MS (ESI): m/z=185.1 [M+H]$^+$.

a) (4-o-Tolyl-pyridin-3-yl)-carbamic acid tert-butyl ester

The title compound was prepared in analogy to example 72, from (4-iodo-pyridin-3-yl)-carbamic acid tert-butyl ester (example 85, intermediate d) and 2-methylphenylboronic acid (CAS RN 16419-60-6) and using a gradient of n-heptane:EtOAc (100:0 to 50:50) for the chromatographic purification. Light brown solid (94%). MS (ESI): m/z=285.16 [M+M]$^+$.

Example 201

N-[6-Chloro-4-(4-fluoro-2-methoxy-phenyl)-pyridin-3-yl]-3-methanesulfonyl-N-methyl-5-trifluoromethyl-benzamide

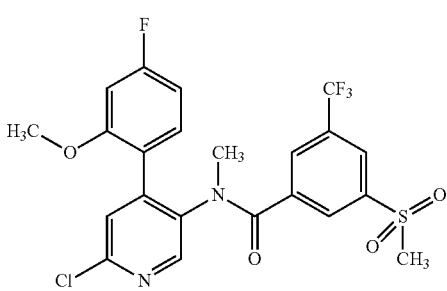 [SMILES: COc1cc(F)ccc1-c1cc(Cl)ncc1N(C)C(=O)c1cc(C(F)(F)F)cc(S(C)(=O)=O)c1]

The title compound was prepared in analogy to Example 90, from [6-chloro-4-(4-fluoro-2-methoxy-phenyl)-pyridin-3-yl]-methyl-amine and 3-methanesulfonyl-5-trifluoromethyl-benzoic acid (example 114, intermediate a) after a reaction time of 17 hours. The compound was purified by silica gel chromatography using an MPLC (ISCO) system eluting with a gradient of n-heptane:EtOAc (100:0 to 50:50). The volatiles were evaporated until a precipitate formed. The suspension was filtered and the filter cake was washed three times with a small amount of a mixture of EtOAc:n-heptane (1:4) to give the title compound as a colorless solid (61%). MS (ESI): m/z=517.06 [M+H]$^+$.

Intermediates a) [6-Chloro-4-(4-fluoro-2-methoxy-phenyl)-pyridin-3-yl]-methyl-amine The title compound was prepared in analogy to example 72, from (6-chloro-4-iodo-pyridin-3-yl)-methyl-amine (prepared according to WO2006013050) and 4-fluoro-2-methoxyphenylboronic acid (CAS RN 179899-07-1) and using a gradient of n-heptane: EtOAc (100:0 to 50:50) for the chromatographic purification. Off-white solid (81%). MS (ESI): m/z=267.07 [M+H]$^+$.

Example 202

N-[4-(4-Fluoro-2-methoxy-phenyl)-6-methyl-pyridin-3-yl]-3-methanesulfonyl-N-methyl-5-trifluoromethyl-benzamide

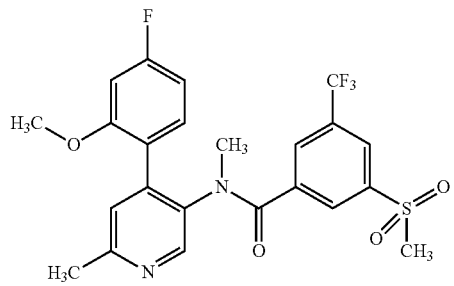 [SMILES: COc1cc(F)ccc1-c1cc(C)ncc1N(C)C(=O)c1cc(C(F)(F)F)cc(S(C)(=O)=O)c1]

To a solution of N-(6-chloro-4-(4-fluoro-2-methoxyphenyl)pyridin-3-yl)-N-methyl-3-(methylsulfonyl)-5-(trifluoromethyl)benzamide (0.1 g, 0.193 mmol, example 201) in THF (2 mL) were added methylzinc chloride (0.145 mL, 0.29 mmol, 2M solution in THF, CAS RN 5158-46-3), 1,3-dimethyl-2-imidazolidinone (0.4 mL, CAS RN 80-73-9) and (1,3-bis(2,6-diisopropyl-phenyl)imidazolidene) (3-chloropyridyl) palladium(II) dichloride (PEPPSI-IPr, 2.63 mg, 3.87 µmol, Aldrich). The reaction mixture was stirred at 50° C. for 30 min. and then poured on 10% aqueous citric acid solution and EtOAc and the layers were separated. The aqueous layer was extracted twice with EtOAc. The organic layers were washed with brine, dried over MgSO$_4$, filtered, treated with silica gel and evaporated. The compound was purified by silica gel chromatography on a 10 g column using a MPLC system eluting with a gradient of n-heptane:EtOAc (100:0 to 0:100), followed by a second chromatography, using preparative HPLC (Gemini NX column) eluting with a gradient of methanol:water (containing 0.1% formic acid) (20:80 to 98:2). Colorless solid (0.073 g; 76%). MS (ESI): m/z=497.11 [M+H]$^+$.

Example 203

N-[4-(4-Fluoro-2-methoxy-phenyl)-pyridin-3-yl]-N-(2-oxo-butyl)-2,6-bis-trifluoromethyl-isonicotinamide

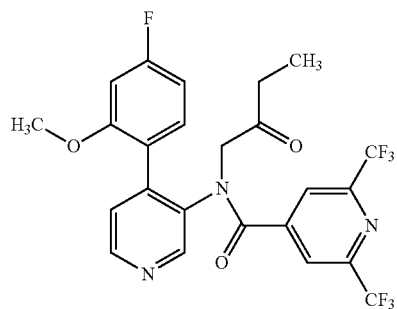 [SMILES: CCC(=O)CN(C(=O)c1cc(C(F)(F)F)nc(C(F)(F)F)c1)c1cnccc1-c1ccc(F)cc1OC]

The title compound was prepared in analogy to example 90, from 1-[4-(4-fluoro-2-methoxy-phenyl)-pyridin-3-ylamino]-butan-2-one and 2,6-bis(trifluoromethyl)isonicotinic acid (Key Organics Ltd.) after a reaction time of 24 hours. The compound was purified by silica gel chromatography on a 5 g column using a MPLC system (CombiFlash Companion, Isco Inc.) eluting with a gradient of n-heptane:EtOAc (100:0 to 0:100), followed by a second chromatography using preparative HPLC (Gemini NX column) and a gradient of methanol:water (with 0.05% formic acid) (80:20 to 98:2). Colorless solid (10%). MS (ESI): m/z=530.130 [M+H]$^+$.

Intermediates a) 1-[4-(4-Fluoro-2-methoxy-phenyl)-pyridin-3-ylamino]-butan-2-one The title compound was prepared in analogy to Example 72, from 1-(4-iodo-pyridin-3-ylamino)-butan-2-one and 4-fluoro-2-methoxyphenylboronic acid (CAS RN 179899-07-1) and using a gradient of n-heptane:EtOAc (100:0 to 0:100) for the chromatographic purification. Yellow oil (43%). MS (ESI): m/z=289.134 [M+H]$^+$.

b) 1-(4-Iodo-pyridin-3-ylamino)-butan-2-one

The title compound was prepared in analogy to Example 85, intermediate a, from (4-iodo-pyridin-3-yl)-(2-oxo-butyl)-carbamic acid tert-butyl ester. The compound was purified by silica gel chromatography on a 50 g column using an MPLC (Flashmaster) system eluting with a gradient of n-heptane:EtOAc (100:0 to 0:100). Light yellow solid (95%). MS (ESI): m/z=290.999 [M+H]$^+$.

c) (4-Iodo-pyridin-3-yl)-(2-oxo-butyl)-carbamic acid tert-butyl ester

The title compound was prepared in analogy to Example 85, intermediate c, from (4-iodo-pyridin-3-yl)-carbamic acid tert-butyl ester (example 85, intermediate d) and 1-bromo-butan-2-one (CAS RN 816-40-0) and using a gradient of n-heptane:EtOAc (100:0 to 40:60) for the chromatographic purification. Light brown solid (85%). MS (ESI): m/z=391.051 [M+H]$^+$.

Example 204

N-[4-(4-Fluoro-2-methoxy-phenyl)-pyridin-3-yl]-3-methanesulfonyl-N-(2-oxo-butyl)-5-trifluoromethyl-benzamide

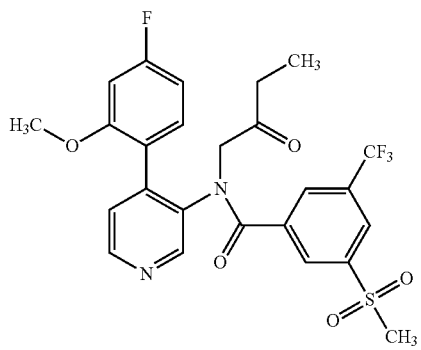 [SMILES: CCC(=O)CN(C(=O)c1cc(C(F)(F)F)cc(S(C)(=O)=O)c1)c1cnccc1-c1ccc(F)cc1OC]

The title compound was prepared in analogy to Example 90, from 1-[4-(4-fluoro-2-methoxy-phenyl)-pyridin-3-ylamino]-butan-2-one (example 203, intermediate a) and 3-methanesulfonyl-5-trifluoromethyl-benzoic acid (example 114, intermediate a) after a reaction time of 24 hours. The compound was purified by silica gel chromatography on a 20 g column using a MPLC system (CombiFlash Companion, Isco Inc.) eluting with a gradient of n-heptane:EtOAc (100:0 to 0:100), followed by a second chromatography using preparative HPLC (Gemini NX column) and a gradient of methanol:water (with 0.05% formic acid) (80:20 to 98:2). Light red foam (13%). MS (ESI): m/z=539.126 [M+H]$^+$.

Example 205

N-[4-(2-Fluoro-6-methoxy-phenyl)-pyridin-3-yl]-3-methanesulfonyl-N-methyl-5-trifluoromethyl-benzamide

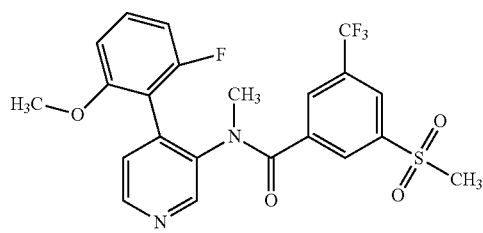

The title compound was prepared in analogy to Example 90, from [4-(2-fluoro-6-methoxy-phenyl)-pyridin-3-yl]-methyl-amine and 3-methanesulfonyl-5-trifluoromethyl-benzoic acid (example 114, intermediate a) after a reaction time of 18 hours. The residue was purified by silica gel chromatography on a 20 g column using a MPLC system (CombiFlash Companion, Isco Inc.) eluting with a gradient of n-heptane:EtOAc (100:0 to 0:100). White solid (58%). MS (ESI): m/z=483.100 [M+H]$^+$.

Intermediate

[4-(2-Fluoro-6-methoxy-phenyl)-pyridin-3-yl]-methyl-amine

The title compound was prepared in analogy to Example 72, from (4-iodo-pyridin-3-yl)-methyl-amine (example 36, intermediate b) and 2-fluoro-6-methoxyphenylboronic acid (CAS RN 78495-63-3) and using a gradient of n-heptane:EtOAc (100:0 to 0:100) for the chromatographic purification. Light yellow oil (65%). MS (ESI): m/z=233.109 [M+H]$^+$.

Example 206

N-[4-(4-Fluoro-2-methoxy-phenyl)-pyridin-3-yl]-2-methoxy-N-methyl-6-trifluoromethyl-isonicotinamide

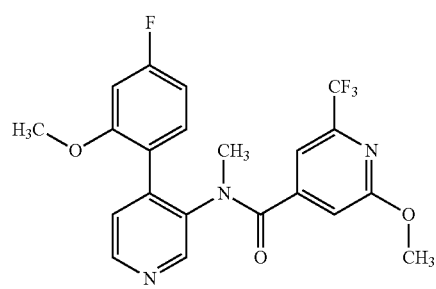

The title compound was prepared in analogy to example 90, from [4-(4-fluoro-2-methoxy-phenyl)-pyridin-3-yl]-methyl-amine (example 129, intermediate) and 2-methoxy-6-trifluoromethyl-isonicotinic acid after a reaction time of 64 hours. The compound was purified by silica gel chromatography on a 10 g column using a MPLC system eluting with a gradient of n-heptane:EtOAc (100:0 to 0:100), followed by a second chromatography using preparative HPLC (Gemini NX column) and a gradient of methanol:water (containing 0.1% formic acid) (20:80 to 98:2) as eluant. Colorless solid (33%). MS (ESI): m/z=436.13 [M+H]$^+$.

Intermediate

2-Methoxy-6-trifluoromethyl-isonicotinic acid

To a solution of 2-chloro-6-(trifluoromethyl)isonicotinic acid (0.15 g, 665 µmol, prepared according to F. Cottet, M. Schlosser, Eur. J. Org. Chem. 2004, 18, 3793-3798) in methanol (2 mL) sodium methoxide (79.0 mg, 1.46 mmol) was added and the reaction refluxed for 5 hours. Another 287 mg (5.32 mmol) sodium methoxide was added and the white suspension was stirred at reflux temperature overnight. After 23 hours the suspension was allowed to cool to room temperature and was poured on saturated 1M HCl solution and EtOAc and the layers were separated. The aqueous layer was extracted twice with EtOAc. The organic layers were washed once with brine, dried over MgSO$_4$, filtered and evaporated to give the desired compound as a colorless solid (0.133 g; 90%). MS (ESI): m/z=220.02 [M−H]$^−$.

Example 207

N-[4-(4-Fluoro-2-methoxy-phenyl)-pyridin-3-yl]-N-(3-methyl-oxctan-3-ylmethyl)-2,6-bis-trifluoromethyl-isonicotinamide

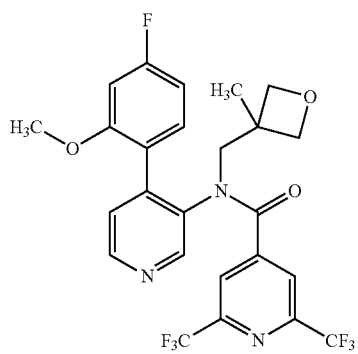 [SMILES: COc1cc(F)ccc1-c1ccncc1N(CC1(C)COC1)C(=O)c1cc(C(F)(F)F)nc(C(F)(F)F)c1]

The title compound was prepared in analogy to example 90, from [4-(4-fluoro-2-methoxy-phenyl)-pyridin-3-yl]-(3-methyl-oxetan-3-ylmethyl)-amine and 2,6-bis(trifluoromethyl) isonicotinic acid (Key Organics Ltd.) after a reaction time of 16 hours. The compound was purified by silica gel chromatography on a 10 g column using a MPLC system eluting with a gradient of n-heptane:EtOAc (100:0 to 0:100) followed by a second chromatography using preparative HPLC (Gemini NX column) and a gradient of methanol: water (containing 0.1% formic acid) (20:80 to 98:2) as eluant. Colorless solid (12%). MS (ESI): m/z=544.15 [M+H]$^+$.

Intermediates a) [4-(4-Fluoro-2-methoxy-phenyl)-pyridin-3-yl]-(3-methyl-oxetan-3-ylmethyl)-amine A solution of tert-butyl 4-(4-fluoro-2-methoxyphenyl) pyridin-3-yl((3-methyloxetan-3-yl)methyl)carbamate (0.3 g, 745 µmol) in 2,2,2-trifluorethanol (3.0 mL) was stirred in a microwave oven at 150° C. for 2 hours. The compound was purified by silica gel chromatography on a 10 g column using an MPLC (ISCO) system eluting with a gradient of n-heptane:EtOAc (100:0 to 0:100) to give the desired compound as a light brown oil (0.111 g; 49%). MS (ESI): m/z=303.1 [M+H]$^+$.

b) tert-Butyl 4-(4-fluoro-2-methoxyphenyl)pyridin-3-yl((3-methyloxetan-3-yl)methyl)carbamate To a solution of (4-iodo-pyridin-3-yl)-(3-methyl-oxetan-3-ylmethyl)-carbamic acid tert-butyl ester (0.878 g, 2.17 mmol) in DME (10 mL) under argon 4-fluoro-2-methoxyphenylboronic acid (424 mg, 2.5 mmol, CAS RN 179899-07-1) and 2M aqueous Na$_2$CO$_3$ solution (2.77 mL, 5.54 mmol) were added. After stirring for 30 min. at room temperature, palladium(II) acetate (24.4 mg, 0.109 mmol, CAS RN 3375-31-3) and triphenylphosphine polymer bound (73.0 mg, 0.217 mmol, CAS RN 39319-11-4) were added and the reaction was stirred at reflux (90° C. oil bath temperature) for 22 hours. Another 4-fluoro-2-methoxyphenylboronic acid (111 mg, 0.652 mmol) was added and reaction mixture was refluxed for another 4 hours before another 4-fluoro-2-methoxyphenylboronic acid (111 mg, 0.652 mmol) was added. After stirring at reflux temperature for 18 hours the reaction mixture was poured on saturated aqueous NH$_4$Cl solution and EtOAc and the layers were separated. The aqueous layer was extracted twice with EtOAc. The organic layers were washed with brine, dried over MgSO$_4$, filtered, treated with silica gel and evaporated. The compound was purified by silica gel chromatography on a 20 g column using a MPLC system eluting with a gradient of n-heptane: EtOAc (100:0 to 0:100) to give the title compounds as a light brown oil (0.784 g; 89%). MS (ESI): m/z=403.20 [M+H]$^+$.

(4-Iodo-pyridin-3-yl)-(3-methyl-oxetan-3-ylmethyl)-carbamic acid tert-butyl ester The title compound was prepared in analogy to example 85, intermediate c, from (4-iodo-pyridin-3-yl)-carbamic acid tert-butyl ester (example 85, intermediate d) and 3-chloromethyl-3-methyl-oxetane (CAS RN8 22-48-0). After stirring at room temperature for 18 hours another NaH (75.0 mg, 1.72 mmol) and 3-(chloromethyl)-3-methyloxetane (207 mg, 1.72 mmol) were added and stirring was continued at 60° C. for 64 hours. The reaction mixture was poured on saturated aqueous NH$_4$Cl solution and EtOAc and the layers were separated. The aqueous layer was extracted twice with EtOAc. The organic layers were washed twice with water and once with brine, dried over MgSO$_4$, filtered, treated with silica gel and evaporated. The compound was purified by silica gel chromatography on a 20 g column using a MPLC system eluting with a gradient of n-heptane: EtOAc (100:0 to 50:50) to furnish the desired compound as an off-white solid (0.888 g; 70%). MS (ESI): m/z=405.07 [M+H]$^+$.

Example 208

N-Methyl-3,5-bis-trifluoromethyl-N-[4-(1,3,5-trimethyl-1H-pyrazol-4-yl)-pyridin-3-yl]-benzamide

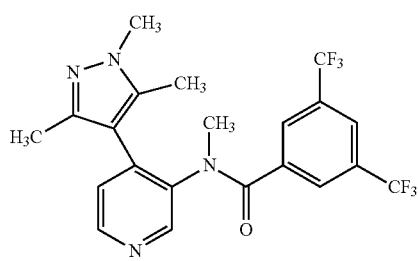 [SMILES: Cc1nn(C)c(C)c1-c1ccncc1N(C)C(=O)c1cc(C(F)(F)F)cc(C(F)(F)F)c1]

The title compound was prepared in analogy to example 25, from N-(4-bromo-pyridin-3-yl)-N-methyl-3,5-bis-trifluoromethyl-benzamide (example 25, intermediate a) and 1,3,5-trimethyl-4-(4,4,5,5-tetramethyl-[1,3,2]dioxaborolan-2-yl)-1H-pyrazole (CAS RN 844891-04-9) and using DMF as reaction solvent. Pale yellow sticky liquid (11%). MS (ESI): m/z=457.6 [M+H]$^+$.

Example 209

N-[4-(2,4-Dimethyl-thiazol-5-yl)-pyridin-3-yl]-N-methyl-3,5-bis-trifluoromethyl-benzamide

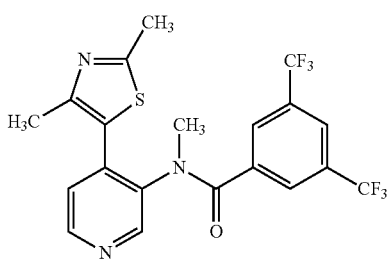 [SMILES: Cc1nc(C)c(-c2ccncc2N(C)C(=O)c2cc(C(F)(F)F)cc(C(F)(F)F)c2)s1]

A mixture of N-(4-bromo-pyridin-3-yl)-N-methyl-3,5-bis-trifluoromethyl-benzamide (200 mg, 0.468 mmol, example 25, intermediate a), 2,4-dimethyl-5-(4,4,5,5-tetramethyl-1,3,2-dioxaborolan-2-yl)-1,3-thiazole (107.4 mg, 0.7 mmol, CAS RN 859833-13-9) and $K_2CO_3$ (193.75 mg, 1.4 mmol) in DMF (6 mL), taken in a sealed tube, was degassed well for 30 min with argon. To this mixture was added S-PHOS (50.1 mg, 0.25 mmol, CAS RN 657408-07-6) and $Pd(PPh_3)_4$ (54 mg, 0.05 mmol), and degassed again for 15 min. The reaction mixture was heated to 80° C. for 30 min irradiated with microwave. After the completion of reaction, it was cooled to room temperature, filtered through a bed of celite and the residue washed with EtOAc (50 mL) Volatilities were removed in vacuo and the resultant residue was diluted with water (30 mL) and extracted with EtOAc (2×50 mL). The combined organic layers were washed with brine (30 mL), dried over anhydrous $Na_2SO_4$, filtered, and evaporated. The crude residue was purified by column chromatography over silica gel (30-40% EtOAc in n-hexane) to afford the title compound as a pale yellow solid (15 mg, 7%). MS (ESI): m/z=460.1 $[M+H]^+$.

Example 210

N-[4-(3,5-Dimethyl-isoxazol-4-yl)-pyridin-3-yl]-N-methyl-3,5-bis-trifluoromethyl-benzamide

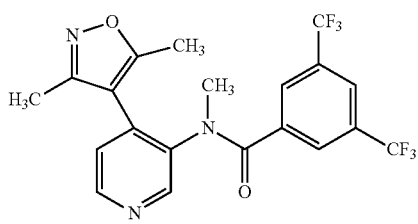 [SMILES: Cc1noc(C)c1-c1ccncc1N(C)C(=O)c1cc(C(F)(F)F)cc(C(F)(F)F)c1]

The title compound was prepared in analogy to example 25, from N-(4-bromo-pyridin-3-yl)-N-methyl-3,5-bis-trifluoromethyl-benzamide (example 25, intermediate a) and 3,5-dimethylisoxazole-4-boronic acid (CAS RN 16114-47-9) and using DMF as reaction solvent. Light brown solid (20%). MS (ESI): m/z=444.0 $[M+H]^+$.

Example 211

N-Methyl-N-[4-(4-methyl-2H-pyrazol-3-yl)-pyridin-3-yl]-3,5-bis-trifluoromethyl-benzamide

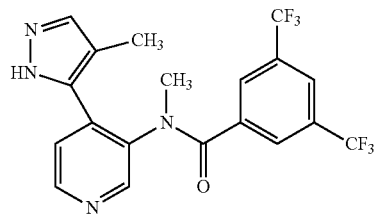 [SMILES: Cc1cn[nH]c1-c1ccncc1N(C)C(=O)c1cc(C(F)(F)F)cc(C(F)(F)F)c1]

To a solution of N-[4-(2-benzyloxymethyl-4-methyl-2H-pyrazol-3-yl)-pyridin-3-yl]-N-methyl-3,5-bis-trifluoromethyl-benzamide (70 mg, 128 µmol) in TFA (3 mL) was added $CH_2Cl_2$ (300 µL). The reaction mixture was stirred at 80° C. for 2 hours and then concentrated in vacuum. The reaction mixture was poured on 30 mL 10% aqueous $NaHCO_3$ solution and 30 mL EtOAc and the layers were separated. The aqueous layer was extracted a second time with 30 mL EtOAc. The organic layers were washed with 30 mL brine, dried over $MgSO_4$, filtered and concentrated under vacuum. The compound was purified by silica gel chromatography on a 20 g column using a MPLC system (CombiFlash Companion, Isco Inc.) eluting with a gradient of n-heptane:EtOAc (100:0 to 0:100). Colorless foam (20 mg, 37%). MS (ESI): m/z=429.114 $[M+H]^+$.

Intermediates a) N-[4-(2-Benzyloxymethyl-4-methyl-2H-pyrazol-3-yl)-pyridin-3-yl]-N-methyl-3,5-bis-trifluoromethyl-benzamide To a solution of N-(4-iodo-pyridin-3-yl)-N-methyl-3,5-bis-trifluoromethyl-benzamide (138 mg, 422 µmol, example 98, intermediate a) in THF (4 mL) was added isopropylmagnesium chloride (2M solution in THF, 211 µL, 422 µmol) dropwise at −40° C. The reaction mixture was stirred at −40° C. for 20 minutes. Freshly prepared $ZnCl_2$ (1M solution in THF, 1.69 mL, 1.69 mmol) was added dropwise at −40° C. The cooling bath was removed and the reaction mixture was stirred at room temperature for 90 minutes. A solution of 1-benzyloxymethyl-5-iodo-4-methyl-1H-pyrazole (200 mg, 422 µmol) in THF (4 mL) and tetrakis(triphenylphosphine)palladium(0) (24.4 mg, 21.1 µmol) was added. The reaction mixture was stirred at reflux for 18 hours and then was poured on 30 mL 10% aqueous $NaHCO_3$ solution and 30 mL EtOAc and the layers were separated. The aqueous layer was extracted a second time with 30 mL EtOAc. The organic layers were washed with 30 mL brine, dried over $MgSO_4$, filtered and concentrated under vacuum. The compound was purified by silica gel chromatography on a 20 g column using an MPLC (Flashmaster) system eluting with a gradient of n-heptane: EtOAc (100:0 to 50:50). Light yellow foam (79 mg, 34%). MS (ESI): m/z=549.170 $[M+H]^+$. 1M $ZnCl_2$ solution in THF was prepared by melting solid $ZnCl_2$ under high vacuum by heating with a heatgun. The flask was allowed to cool down to room temperature and then ventilated with argon. The dry $ZnCl_2$ was then dissolved under argon with the required amount of THF.

b) 1-Benzyloxymethyl-5-iodo-4-methyl-1H-pyrazole

To a solution of 5-iodo-4-methyl-1H-pyrazole (0.5 g, 2.4 mmol, CAS RN 24086-18-8) in $CH_2Cl_2$ (5 mL) was added N,N-diisopropylethylamine (342 mg, 450 μL, 2.64 mmol) and benzyl chloromethyl ether (460 mg, 407 μL, 2.64 mmol, CAS RN 3587-60-8) at 0° C. The reaction mixture was stirred at room temperature for 30 minutes and then poured on 30 mL 10% aqueous $NaHCO_3$ solution and 30 mL $CH_2Cl_2$. The layers were separated and the aqueous layer was extracted a second time with 30 mL $CH_2Cl_2$. The organic layers were washed with 30 mL brine, dried with $MgSO_4$, filtered and concentrated under vacuum. The compound was purified by silica gel chromatography using a MPLC system (CombiFlash Companion, Isco Inc.) eluting with a gradient of n-heptane:EtOAc (100:0 to 70:30). Colorless oil (610 mg, 77%). MS (ESI): m/z=329.014 [M+H]$^+$.

Example 212

N-[2-Chloro-4-(4-fluoro-2-methoxy-phenyl)-pyridin-3-yl]-3-methanesulfonyl-N-methyl-5-trifluoromethyl-benzamide

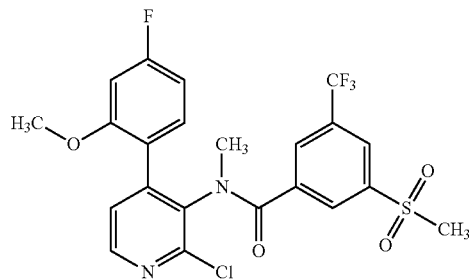

The title compound was prepared in analogy to example 90, from [2-chloro-4-(4-fluoro-2-methoxy-phenyl)-pyridin-3-yl]-methyl-amine and 3-methanesulfonyl-5-trifluoromethyl-benzoic acid (example 114, intermediate a) after a reaction time of 66 hours. The compound was purified by silica gel chromatography on a 20 g column using an MPLC (ISCO) system eluting with a gradient of n-heptane:EtOAc (100:0 to 50:50), followed by a second chromatography using preparative HPLC (Gemini NX column) eluting with a gradient of methanol:water (containing 0.1% formic acid) (20:80 to 98:2). Colorless solid (30%). MS (ESI): m/z=517.06 [M+H]$^+$.

Intermediates a) [2-Chloro-4-(4-fluoro-2-methoxy-phenyl)-pyridin-3-yl]-methyl-amine The title compound was prepared in analogy to example 72, from (2-chloro-4-iodo-pyridin-3-yl)-methyl-amine and 4-fluoro-2-methoxyphenylboronic acid (CAS RN 179899-07-1). The compound was purified by silica gel chromatography on a 20 g column using a MPLC system eluting with a gradient of n-heptane:EtOAc (100:0 to 60:40). Light yellow solid (78%). MS (ESI): m/z=267.07 [M+H]$^+$.

b) (2-Chloro-4-iodo-pyridin-3-yl)-methyl-amine

To an ice-cold solution of (2-chloro-4-iodo-pyridin-3-yl)-methyl-carbamic acid tert-butyl ester (0.97 g, 2.63 mmol) in $CH_2Cl_2$ (5 mL) was added TFA (6.00 g, 4.05 mL, 52.6 mmol) and the solution was stirred at room temperature for 1.5 hours before another TFA (6.00 g, 4.05 mL, 52.6 mmol) was added. After stirring at room temperature for 3 hours the clear solution was evaporated. The residue was taken up in saturated aqueous $NaHCO_3$ solution (50 mL) and $CH_2Cl_2$ (30 mL) and the layers were separated. The aqueous layer was extracted twice with $CH_2Cl_2$ (30 mL each) and the organic layers were washed with brine, dried over $MgSO_4$, filtered and evaporated. Colorless oil (0.61 g; 86%). MS (ESI): m/z=268.93 [M+H]$^+$.

c) (2-Chloro-4-iodo-pyridin-3-yl)-methyl-carbamic acid tert-butyl ester

The title compound was prepared in analogy to example 85, intermediate c, from (2-chloro-4-iodo-pyridin-3-yl)-carbamic acid tert-butyl ester (CAS RN 855784-39-3) and methyl iodide and using a gradient of n-heptane:EtOAc (100:0 to 50:50) for the chromatographic purification. Colorless solid (88%). MS (ESI): m/z=368.99 [M+H]$^+$.

Example 213

[[4-(2-Fluoro-phenyl)-pyridin-3-yl]-(3-methanesulfonyl-5-trifluoromethyl-benzoyl)-amino]-acetic acid methyl ester

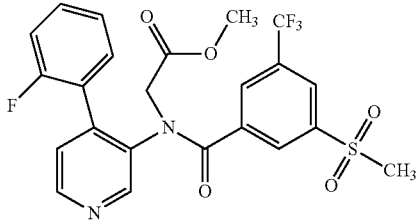 [SMILES: COC(=O)CN(C(=O)c1cc(C(F)(F)F)cc(S(C)(=O)=O)c1)c1cnccc1-c1ccccc1F]

To a solution of methyl 2-(4-(2-fluorophenyl)pyridin-3-ylamino)acetate (272 mg, 1.05 mmol; example 196, intermediate) in $CH_2Cl_2$ (3 mL) was added 3-(methylsulfonyl)-5-(trifluoromethyl)benzoic acid (280 mg, 1.05 mmol, example 114, intermediate a) and 2-bromo-1-ethylpyridinium tetrafluoroborate (343 mg, 1.25 mmol) and N,N-diisopropylethylamine (270 mg, 365 μL, 2.09 mmol). The reaction mixture was stirred at room temperature for 22 hours and then concentrated under vacuum. The residue was dissolved in 30 mL 1M aqueous HCl and 30 mL EtOAc and the layers were separated. The aqueous layer was extracted a second time with 30 mL EtOAc. The organic layers were washed with 30 mL 1M aqueous HCl and 30 mL 10% aqueous $NaHCO_3$ and 30 mL brine, dried over $MgSO_4$, filtered and concentrated under vacuum. The residue was purified by silica gel chromatography on a 20 g column using an MPLC (Flashmaster) system eluting with a gradient of n-heptane:EtOAc (100:0 to 0:100). Light brown foam (323 mg, 61%). MS (ESI): m/z=511.094 [M+H]$^+$.

Example 214

N-[4-(2-Fluoro-phenyl)-pyridin-3-yl]-3-methanesulfonyl-N-(2,2,2-trifluoro-ethyl)-5-trifluoromethyl-benzamide

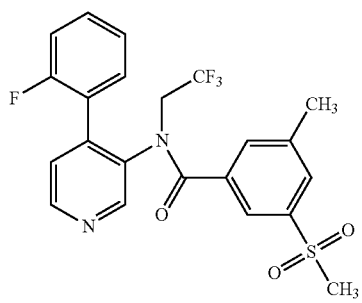 [SMILES: Cc1cc(C(=O)N(CC(F)(F)F)c2cnccc2-c2ccccc2F)cc(S(C)(=O)=O)c1]

To a solution of 4-(2-fluorophenyl)-N-(2,2,2-trifluoroethyl)pyridin-3-amine (79 mg, 292 µmol, example 151, intermediate) in CH$_2$Cl$_2$ (2 mL) was added 3-(methylsulfonyl)-5-(trifluoromethyl)benzoic acid (78.4 mg, 292 µmol, example 114, intermediate) and 2-bromo-1-ethylpyridinium tetrafluoroborate (96.1 mg, 351 µmol) and N,N-diisopropylethylamine (75.6 mg, 102 µL, 585 µmol). The reaction mixture was stirred at room temperature for 23 hours. The reaction mixture was concentrated under vacuum. The residue was dissolved in 30 mL 1N aqueous HCl and 30 mL EtOAc and the layers were separated. The aqueous layer was extracted a second time with 30 mL EtOAc. The organic layers were washed with 30 mL 1M aqueous HCl and 30 mL 10% aqueous NaHCO$_3$ and 30 mL brine, dried over MgSO$_4$, filtered and concentrated under vacuum. The residue was purified by silica gel chromatography on a 10 g column using an MPLC (Flashmaster) system eluting with a gradient of n-heptane:EtOAc (100:0 to 0:100). Light yellow solid (37 mg, 24%). MS (ESI): m/z=521.076 [M+H]$^+$.

Example 215

Error! Not a valid link. N-(2,2-Difluoro-ethyl)-N-[4-(2-fluoro-phenyl)-pyridin-3-yl]-3-methanesulfonyl-5-trifluoromethyl-benzamide

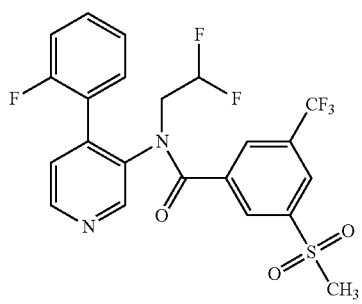 [SMILES: CS(=O)(=O)c1cc(C(=O)N(CC(F)F)c2cnccc2-c2ccccc2F)cc(C(F)(F)F)c1]

To a solution of N-(2,2-difluoroethyl)-4-(2-fluorophenyl)pyridin-3-amine (112 mg, 444 µmol) in CH$_2$Cl$_2$ (3 mL) was added 3-(methylsulfonyl)-5-(trifluoromethyl)benzoic acid (119 mg, 444 µmol, example 114, intermediate) and 2-bromo-1-ethylpyridinium tetrafluoroborate (146 mg, 533 µmol) and N,N-diisopropylethylamine (115 mg, 155 µL, 888 µmol). The reaction mixture was stirred at room temperature for 24 hours and then concentrated under vacuum. The residue was dissolved in 30 mL 1M aqueous HCl and 30 mL EtOAc and the layers were separated. The aqueous layer was extracted a second time with 30 mL EtOAc. The organic layers were washed with 30 mL 1M aqueous HCl and 30 mL 10% aqueous NaHCO$_3$ solution and 30 mL brine, dried over MgSO$_4$, filtered and concentrated under vacuum. Yellow solid (84 mg, 38%). MS (ESI): m/z=503.085 [M+H]$^+$.

Example 216

N-[4-(4-Fluoro-2-methoxy-phenyl)-pyridin-3-yl]-3-(2-hydroxy-ethylsulfanyl)-N-methyl-5-trifluoromethyl-benzamide

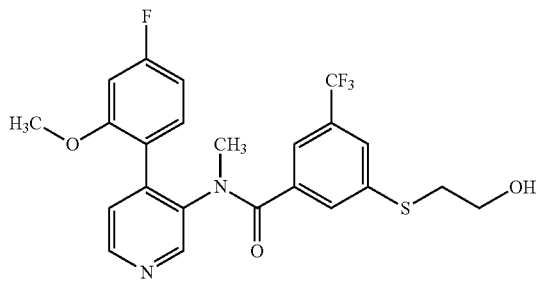

A solution of N-[4-(4-fluoro-2-methoxy-phenyl)-pyridin-3-yl]-3-mercapto-5,N-dimethyl-benzamide (0.15 g, 344 µmol) in acetonitrile (4 mL) was treated with 2-bromoethanol (51.5 mg, 29.2 µL, 412 µmol) and DIPEA (88.8 mg, 120 µL, 687 µmol) and the clear solution was stirred at room temperature for 6 hours. The reaction mixture was poured on saturated aqueous NH$_4$Cl solution and EtOAc and the layers were separated. The aqueous layer was extracted twice with EtOAc. The organic layers were dried over MgSO$_4$, filtered, treated with silica gel and evaporated. The compound was purified by silica gel chromatography on a 10 g column using an MPLC system eluting with a gradient of n-heptane:EtOAc (100:0 to 0:100). Colorless foam (0.14 g; 84%). MS (ESI): m/z=481.12 [M+H]$^+$.

Intermediates a) N-[4-(4-Fluoro-2-methoxy-phenyl)-pyridin-3-yl]-3-mercapto-5,N-dimethyl-benzamide To a solution of N-(4-(4-fluoro-2-methoxyphenyl)pyridin-3-yl)-N-methyl-3-(trifluoromethyl)-5-(2-(trimethylsilyl)ethylthio)benzamide (0.711 g, 1.32 mmol) in THF (12.6 mL) was added tetrabutylammonium fluoride (1M solution in THF, 6.96 mL, 6.96 mmol) and the clear light yellow solution was stirred at room temperature for 90 minutes. The reaction mixture was poured on 10% aqueous citric acid solution and EtOAc and the layers were separated. The aqueous layer was extracted twice with EtOAc. The organic layers were washed with brine, dried over MgSO$_4$, filtered, treated with silica gel and evaporated. The compound was purified by silica gel chromatography on a 20 g column using an MPLC system eluting with a gradient of CH$_2$Cl$_2$:MeOH (100:0 to 90:10). Colorless solid (0.41 g; 63%). MS (ESI): m/z=437.09 [M+H]$^+$.

b) N-(4-(4-Fluoro-2-methoxyphenyl)pyridin-3-yl)-N-methyl-3-(trifluoromethyl)-5-(2-(trimethylsilyl)ethylthio)benzamide A solution of 3-bromo-N-(4-(4-fluoro-2-methoxyphenyl)pyridin-3-yl)-N-methyl-5-(trifluoromethyl)benzamide (0.135 g, 279 µmol) and 2-(trimethylsilyl)ethanethiol (37.5 mg, 44.1 µL, 279 µmol) in dioxane (2 mL) was stirred under argon for 5 minutes in a sealed tube. To the clear light yellow solution were added tris(dibenzylideneacetone)dipalladium (0) (6.4 mg, 6.98 µmol, CAS RN 52409-22-0) and 4,5-bis(diphenylphosphino)-9,9-dimethylxanthene (8.08 mg, 14.0 µmol, CAS RN 161265-03-8) and DIPEA (72.2 mg, 97.6 µL, 559 µmol) and the reaction mixture was stirred at 120° C. After stirring for 4 hours in a sealed tube, heating was stopped. The reaction mixture was poured on saturated aqueous NH$_4$Cl solution and EtOAc and the layers were separated. The aqueous layer was extracted twice with EtOAc. The organic layers were dried over MgSO$_4$, filtered, treated with silica gel and evaporated. The compound was purified by silica gel chromatography on a 20 g column using an MPLC system eluting with a gradient of n-heptane:EtOAc (100:0 to 0:100). Colorless solid (0.116 g; 77%). MS (ESI): m/z=537.17 [M+H]$^+$.

c) 3-Bromo-N-(4-(4-fluoro-2-methoxyphenyl)pyridin-3-yl)-N-methyl-5-(trifluoromethyl)-benzamide The title compound was prepared in analogy to example 90, from 4-(4-fluoro-2-methoxyphenyl)-N-methylpyridin-3-amine (example 129, intermediate) and 3-bromo-5-(trifluoromethyl)benzoic acid after a reaction time of 22 hours. The compound was purified by silica gel chromatography on a 20 g column using an MPLC (ISCO) system eluting with a gradient of n-heptane:EtOAc (100:0 to 20:80). Off-white solid (68%). MS (ESI): m/z=483.03 [M+H]$^1$.

Example 217

N-[4-(4-Fluoro-2-methoxy-phenyl)-pyridin-3-yl]-3-(2-methoxy-ethanesulfonyl)-N-methyl-5-trifluoromethyl-benzamide

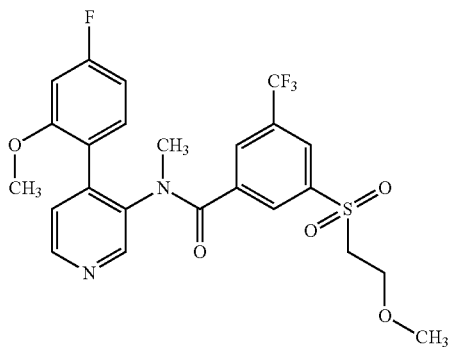 [SMILES: COCCS(=O)(=O)c1cc(C(=O)N(C)c2cnccc2-c2ccc(F)cc2OC)cc(C(F)(F)F)c1]

To an ice-cold solution of N-(4-(4-fluoro-2-methoxyphenyl)pyridin-3-yl)-3-(2-methoxyethylthio)-N-methyl-5-(trifluoromethyl)benzamide (0.032 g, 64.7 µmol) in MeOH (4 mL) and water (0.5 mL) was added Oxone® (99.5 mg, 162 µmol) and the reaction mixture was stirred at room temperature for 4.5 hours. The white suspension was poured on saturated aqueous NH$_4$Cl solution and EtOAc. The two layers were separated. The aqueous layer was extracted twice with EtOAc. The organic layers were washed once with aqueous sodium thiosulfate 10% solution and once with brine, dried over MgSO$_4$, filtered, treated with silica gel and evaporated. The compound was purified by silica gel chromatography on a 5 g column using an MPLC (ISCO) system eluting with a gradient of n-heptane:EtOAc (100:0 to 0:100). Colorless solid (0.027 g; 79%). MS (ESI): m/z=527.13 [M+H]$^+$.

Intermediate a) N-(4-(4-fluoro-2-methoxyphenyl)pyridin-3-yl)-3-(2-methoxyethylthio)-N-methyl-5-(trifluoromethyl)benzamide A solution of N-(4-(4-fluoro-2-methoxyphenyl)pyridin-3-yl)-3-mercapto-N-methyl-5-(trifluoromethyl)benzamide (0.065 g, 149 µmol, example 216, intermediate a) in acetonitrile (2 mL) was treated with 1-bromo-2-methoxyethane (24.8 mg, 16.8 µL, 179 µmol) and DIPEA (38.5 mg, 52.0 µL, 298 gimp and stirred at room temperature for 5 hours. The reaction mixture was poured on saturated aqueous NH$_4$Cl solution and EtOAc and the layers were separated. The aqueous layer was extracted twice with EtOAc. The organic layers were dried over MgSO$_4$, filtered, treated with silica gel and evaporated. The compound was purified by silica gel chromatography on a 10 g column using an MPLC system eluting with a gradient of n-heptane:EtOAc (100:0 to 0:100). Colorless solid (0.04 g; 54%). MS (ESI): m/z=495.14 [M+H]$^+$.

Example 218

N-[4-(4-Fluoro-2-methoxy-phenyl)-pyridin-3-yl]-3-(2-hydroxy-ethanesulfonyl)-N-methyl-5-trifluoromethyl-benzamide

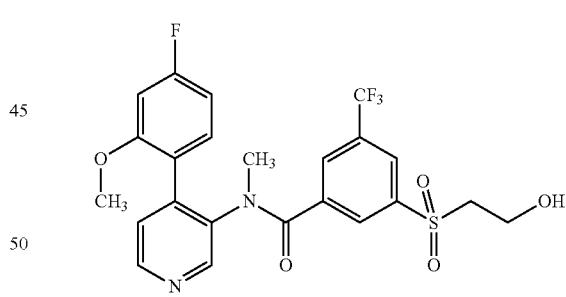

To an ice-cold solution of N-[4-(4-fluoro-2-methoxyphenyl)-pyridin-3-yl]-3-(2-hydroxy-ethylsulfanyl)-N-methyl-5-trifluoromethyl-benzamide (0.1 g, 208 µmol, example 216) in MeOH (4 mL) and water (0.5 mL) was added Oxone® (320 mg, 520 µmol) and the white suspension was stirred at room temperature for 3.25 hours. The white suspension was poured on saturated aqueous NH$_4$Cl solution and EtOAc. The two layers were separated and the aqueous layer was extracted twice with EtOAc. The organic layers were washed once with aqueous sodium thiosulfate 10% solution and once with brine, dried over MgSO$_4$, filtered, treated with silica gel and evaporated. The compound was purified by silica gel chromatography on a 5 g column using an MPLC (ISCO) system eluting with a gradient of n-heptane:EtOAc (100:0 to 0:100). Colorless foam (0.069 g; 64%). MS (ESI): m/z=513.11 [M+H]⁺.

Example 219

N-Carbamoylmethyl-N-[4-(2-fluoro-phenyl)-pyridin-3-yl]-3-methanesulfonyl-5-trifluoromethyl-benzamide

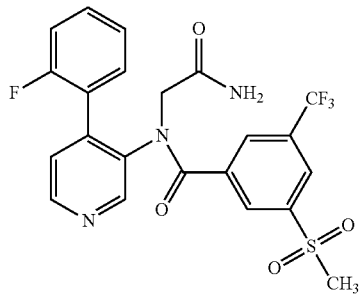 [SMILES: CS(=O)(=O)c1cc(C(=O)N(CC(N)=O)c2cnccc2-c2ccccc2F)cc(C(F)(F)F)c1]

The title compound was prepared in analogy to example 117, from 2-(N-(4-(2-fluorophenyl)pyridin-3-yl)-3-(methylsulfonyl)-5-(trifluoromethyl)benzamido)acetic acid after a reaction time of 4 hours. The compound was purified by silica gel chromatography on a 20 g column using an MPLC (Flashmaster) system eluting with a gradient of n-heptane:EtOAc:MeOH (100:0:0 to 0:100:0 to 0:50:50). Further purification by preparative HPLC (Gemini NX) with a gradient of MeOH:water (containing 0.05% formic acid) (80:20 to 98:2) furnished the desired compound a a colorless solid (67.5%). MS (ESI): m/z=496.095 [M+H]⁺.

Intermediates a) 2-(N-(4-(2-fluorophenyl)pyridin-3-yl)-3-(methylsulfonyl)-5-(trifluoromethyl)benzamido)-acetic acid The title compound was prepared in analogy to example 84 from [[4-(2-fluoro-phenyl)-pyridin-3-yl]-(3-methanesulfonyl-5-trifluoromethyl-benzoyl)-amino]-acetic acid methyl ester. Yellow foam (103%). MS (EST): m/z=497.079 [M+H]⁺.

b) [[4-(2-Fluoro-phenyl)-pyridin-3-yl]-(3-methanesulfonyl-5-trifluoromethyl-benzoyl)-amino]-acetic acid methyl ester The title compound was prepared in analogy to example 90, from [4-(2-fluoro-phenyl)-pyridin-3-ylamino]-acetic acid methyl ester (example 196, intermediate) and 3-methanesulfonyl-5-trifluoromethyl-benzoic acid (280 mg, 1.05 mmol, example 114, intermediate a) after a reaction time of 22 hours. The compound was purified by silica gel chromatography on a 20 g column using an MPLC (Flashmaster) system eluting with a gradient of n-heptane:EtOAc (100:0 to 0:100). Light brown foam (323 mg, 61%). MS (ESI): m/z=511.094 [M+H]⁺.

Example 220

N-(6-Ethyl-4-o-tolyl-pyridin-3-yl)-N-methyl-3,5-bis-trifluoromethyl-benzamide

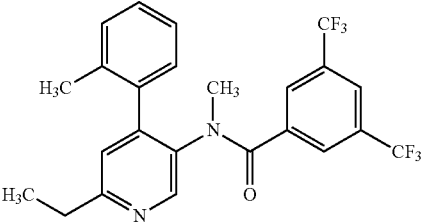 [SMILES: CCc1cc(-c2ccccc2C)c(N(C)C(=O)c2cc(C(F)(F)F)cc(C(F)(F)F)c2)cn1]

To a solution of N-(6-chloro-4-o-tolylpyridin-3-yl)-N-methyl-3,5-bis(trifluoromethyl)-benzamide (0.1 g, 212 µmol, example 12) in THF (1 mL) were added tetrakis(triphenyl-phosphine)palladium(0) (12.2 mg, 10.6 µmol) and diethylzinc (1M solution in n-hexane, 137 µL, 137 µmol) and the brown solution was stirred at reflux for 16 hours. The solvent was evaporated and the brown gum was diluted with 1M aqueous HCl and EtOAc and the layers were separated. The aqueous layer was extracted twice with EtOAc. The organic layers were washed with brine, dried over MgSO₄, filtered, treated with silica gel and evaporated. The compound was purified by silica gel chromatography on a 10 g column using an MPLC system eluting with a gradient of n-heptane:EtOAc (100:0 to 30:70). Light yellow solid (0.051 g; 51%). MS (ESI): m/z=467.16 [M+H]⁺.

Example 221

N-[4-(4-Fluoro-2-methoxy-phenyl)-pyridin-3-yl]-2-methanesulfonyl-N-methyl-6-trifluoro-methyl-isonicotinamide

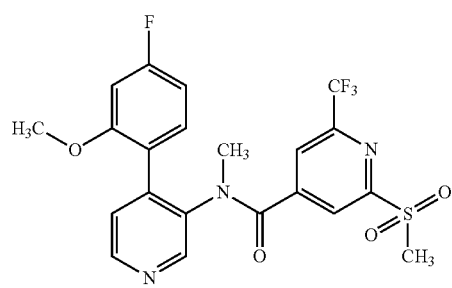 [SMILES: COc1cc(F)ccc1-c1ccncc1N(C)C(=O)c1cc(C(F)(F)F)nc(S(C)(=O)=O)c1]

A suspension of L-proline (15.7 mg, 136 µmol) in DMSO (2 mL) was treated with sodium hydride (5.46 mg, 136 µmol, 60% dispersion in mineral oil) and stirred at room temperature for 30 minutes. The suspension was added to a flask containing 2-chloro-N-(4-(4-fluoro-2-methoxyphenyl)pyridin-3-yl)-N-methyl-6-(trifluoromethyl)isonicotinamide (0.075 g, 171 µmol, example 169). Then sodium methanesulfinate (139 mg, 1.36 mmol) and copper (I) iodide (26.0 mg, 136 µmol) were added and the mixture was heated to 120° C. After 1.5 hours the light blue and turbid solution was cooled down to room temperature and poured on saturated aqueous NH₄Cl solution and EtOAc and the layers were separated. The aqueous layer was extracted twice with EtOAc. The organic layers were washed once with brine, dried over MgSO₄, filtered, treated with silica gel and evaporated. The compound was purified by silica gel chromatography on a 10 g column using an MPLC system eluting with a gradient of n-heptane: EtOAc (100:0 to 25:75). Colorless solid (0.045 g; 54%). MS (ESI): m/z=484.09 [M+H]⁺.

Example 222

N-[4-(2-Amino-phenyl)-pyridin-3-yl]-N-methyl-3,5-bis-trifluoromethyl-benzamide

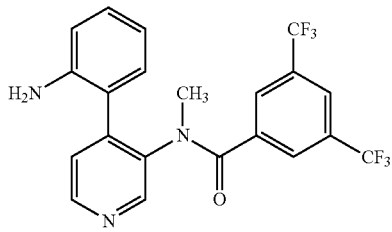

The title compound was prepared in analogy to example 72, from N-(4-iodopyridin-3-yl)-N-methyl-3,5-bis(trifluoromethyl)benzamide (example 98, intermediate a) and 2-amino-phenylboronic acid after a reaction time of 4 hours. The compound was purified by silica gel chromatography on a 50 g column using an MPLC system (CombiFlash Companion, Isco Inc.) eluting with a gradient of n-heptane: EtOAc (100:0 to 0:100). Further purification by preparative HPLC (Gemini NX) with a gradient of MeOH:water (containing 0.05% formic acid) (80:20 to 98:2). Colorless solid (19%). MS (ESI): m/z=440.119 [M+H]⁺.

Example 223

N-[4-(2-Fluoro-6-methoxy-phenyl)-pyridin-3-yl]-3-methanesulfonyl-N-(2,2,2-trifluoro-ethyl)-5-trifluoromethyl-benzamide

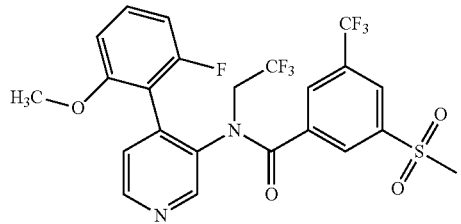

The title compound was prepared in analogy to example 72, intermediate, from [4-(2-fluoro-6-methoxy-phenyl)-pyridin-3-yl]-(2,2,2-trifluoro-ethyl)-amine and 3-methanesulfonyl-5-trifluoromethyl-benzoyl chloride after a reaction time of 12 hours. The compound was purified by preparative HPLC (ammonium acetate/acetonitril e). Off-white solid (27%). MS (ESI): m/z=551.1 [M+H]⁺.

Intermediates a) [4-(2-Fluoro-6-methoxy-phenyl)-pyridin-3-yl]-(2,2,2-trifluoro-ethyl)-amine The title compound was prepared in analogy to example 72, from (4-iodo-pyridin-3-yl)-(2,2,2-trifluoro-ethyl-amine and 2-fluoro-6-methoxyphenylboronic acid after a reaction time of 18 hours. The compound was purified by silica gel column chromatography eluting with a gradient of n-hexane: EtOAc (20:80 to 0:100). Yellow liquid (62%). LC-MS (ESI): m/z=301.6 [M+H]⁺.

b) (4-Indo-pyridin-3-yl)-(2,2,2-trifluoro-ethyl)-amine

The title compound was prepared in analogy to example 85, intermediate a, from 4-iodo-pyridin-3-yl)-(2,2,2-trifluoro-ethyl)-carbamic acid tert-butyl ester. Yellow solid (95%). LC-MS (ESI): m/z=303.0 [M+H]⁺.

c) (4-Iodo-pyridin-3-yl)-(2,2,2-trifluoro-ethyl)-carbamic acid tert-butyl ester

The title compound was prepared in analogy to example 85, intermediate c, from (4-iodo-pyridin-3-yl)-carbamic acid tert-butyl ester (example 85, intermediate d) and 2,2,2-trifluoroethyl trifluoromethanesulfonate after a reaction time of 24 hours. The compound was purified by silica gel column chromatography eluting with a gradient of n-hexane: EtOAc (70:30 to 60:40). Light yellow oil (67%). LC-MS (ESI): m/z=403.0 [M+H]⁺.

d) 3-Methanesulfonyl-5-trifluoromethyl-benzoyl chloride

To a solution of 3-methanesulfonyl-5-trifluoromethyl-benzoic acid (70 mg, 0.26 mmol) in toluene (5 mL) were added catalytic amount of DMF and SOCl₂ (0.2 mL, 2.61 mmol) and the reaction mixture was heated to reflux for 6 hours. The solvent was evaporated and the resulting 3-methanesulfonyl-5-trifluoromethyl-benzoyl chloride (70 mg, crude) was used in the next step without further purification.

Example 224

3-(3-{[4-(4-Fluoro-2-methoxy-phenyl)-pyridin-3-yl]-methyl-carbamoyl}-5-trifluoromethyl-benzenesulfonyl)-propionic acid methyl ester

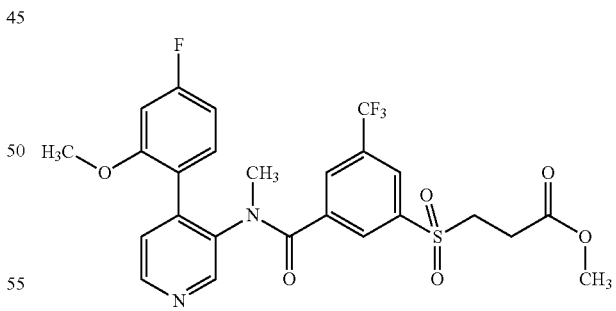

To a suspension of methyl 3-(3-((4-(4-fluoro-2-methoxyphenyl)pyridin-3-yl)(methyl)-carbamoyl)-5-(trifluoromethyl)phenylthio)propanoate (0.2 g, 383 μmol, Example 225) in McOH (6 mL) and water (0.5 mL) at 0° C. was added Oxone® (588 mg, 957 μmol) and the colorless mixture was stirred at room temperature for 1.75 hours. The white suspension was poured on saturated aqueous NH₄Cl solution and EtOAc. The two layers were separated. The aqueous layer was extracted twice with EtOAc. The organic layers were washed with 10% aqueous sodium thiosulfate solution and once with brine, dried over MgSO₄, filtered, treated with silica gel and evaporated. The compound was purified by silica gel chromatography on a 10 g column using an MPLC (ISCO) system eluting with a gradient of n-heptane:EtOAc (100:0 to 0:100). Colorless foam (0.165 g; 77%). MS (ESI): m/z=555.12 [M+H]⁺.

Example 225

3-(3-{[4-(4-Fluoro-2-methoxy-phenyl)-pyridin-3-yl]-methyl-carbamoyl}-5-trifluoromethyl-phenylsulfanyl)-propionic acid methyl ester

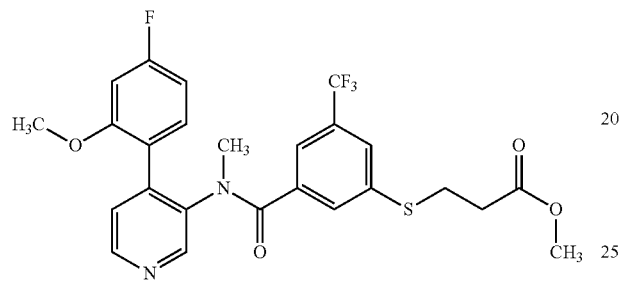

To a suspension of N-(4-(4-fluoro-2-methoxyphenyl)pyridin-3-yl)-3-mercapto-N-methyl-5-(trifluoromethyl)benzamide (0.2 g, 458 µmol, example 216, intermediate a) in acetonitrile (4 mL) were added DIPEA (118 mg, 160 µL, 917 µmol) and methyl 3-bromopropanoate (91.8 mg, 60.0 µL, 550 µmol) and the clear and colorless solution was stirred at room temperature for 2.25 hours. The reaction mixture was poured on saturated aqueous NH₄Cl solution and EtOAc and the layers were separated. The aqueous layer was extracted twice with EtOAc. The organic layers were filtered, treated with silica gel and evaporated. The compound was purified by silica gel chromatography on a 10 g column using an MPLC system eluting with a gradient of n-heptane:EtOAc (100:0 to 0:100). Colorless solid (0.178 g; 74%). MS (ESI): m/z=523.13 [M+H]⁺.

Example 226

N-[4-(4-Fluoro-2-methoxy-phenyl)-pyridin-3-yl]-3-hydroxy-N-methyl-5-trifluoromethyl-benzamide

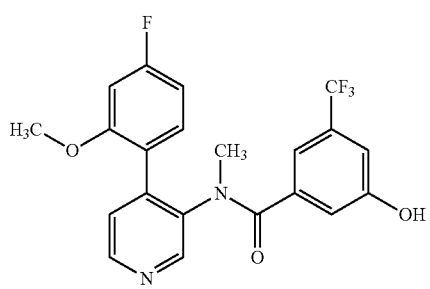

To a solution of 3-bromo-N-(4-(4-fluoro-2-methoxyphenyl)pyridin-3-yl)-N-methyl-5-(trifluoromethyl)benzamide (0.1 g, 207 µmol, example 216, intermediate c) in THF (1 mL) was added triisopropyl borate (75.1 mg, 92.7 µL, 399 µmol) and a cooling bath was installed. At −75° C. n-butyllithium in (1.6 M solution in n-hexane, 136 µL, 217 µmol) was added dropwise and the brown mixture was stirred at −75° C. for 2 hours. To this mixture at 0° C., a solution of acetic acid (52.7 mg, 50.2 µL, 877 µmol in water (0.05 mL) was added, followed by addition of hydrogen peroxide (35% solution in water, 30.2 mg, 27.2 µL, 310 µmol). The reaction mixture was stirred at 0° C. for 1.25 hours, then poured on saturated aqueous NH₄Cl solution and EtOAc and the layers were separated. The aqueous layer was extracted twice with EtOAc. The organic layers were washed with brine, dried over MgSO₄, filtered and evaporated. The product was purified by preparative HPLC (Gemini NX column) using a gradient of MeOH:water (containing 0.1% formic acid) (20:80 to 98:2). Colorless solid (0.020 g; 23%). MS (ESI): m/z=421.12 [M+H]⁺.

Example 227

3-Chloro-N-[4-(4-fluoro-2-methoxy-phenyl)-pyridin-3-yl]-N-methyl-5-trifluoromethoxy-benzamide

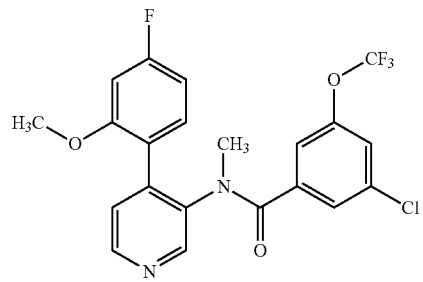 [SMILES: COc1cc(F)ccc1-c1ccncc1N(C)C(=O)c1cc(Cl)cc(OC(F)(F)F)c1]

The title compound was prepared in analogy to example 90, from 4-(4-fluoro-2-methoxyphenyl)-N-methylpyridin-3-amine (example 129, intermediate) and 3-chloro-5-(trifluoromethoxy)benzoic acid (228 mg, 947 µmol, CAS RN 433926-46-6) after a reaction time of 19.5 hours. The compound was purified by silica gel chromatography on a 10 g column using an MPLC (ISCO) system eluting with a gradient of n-heptane: EtOAc (100:0 to 0:100). Colorless solid (47%). MS (ESI): m/z=455.08 [M+H]⁺.

Example 228

N-Cyanomethyl-N-[4-(4-fluoro-2-methoxy-phenyl)-pyridin-3-yl]-3-methanesulfonyl-5-trifluoromethyl-benzamide

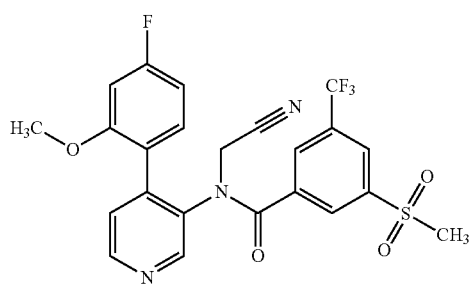

The title compound was prepared in analogy to example 90, from 2-(4-(4-fluoro-2-methoxyphenyl)pyridin-3- ylamino)acetonitrile and 3-(methylsulfonyl)-5-(trifluoromethyl)benzoic acid (example 114, intermediate a) after a reaction time of 18 hours. The compound was purified by silica gel chromatography on a 20 g column using an MPLC (Flashmaster) system eluting with a gradient of n-heptane:EtOAc (100:0 to 0:100). Light brown solid (51%). MS (ESI): m/z=508.096 [M+H]$^+$.

Intermediate a) 2-(4-(4-Fluoro-2-methoxyphenyl)pyridin-3-ylamino)acetonitrile

The title compound was prepared in analogy to example 85, intermediate a, from tert-butyl cyanomethyl(4-(4-fluoro-2-methoxyphenyl)pyridin-3-yl)carbamate (example 161, intermediate c) after a reaction time of 4 hours at room temperature. The compound was purified by silica gel chromatography on a 10 g column using an MPLC (Flashmaster) system eluting with a gradient of n-heptane:EtOAc (100:0 to 0:100). Light yellow solid (37%). MS (ESI): m/z=258.105 [M+H]$^+$.

Example 229

N-[4-(2-Fluoro-6-methoxy-phenyl)-pyridin-3-yl]-3-methanesulfonyl-N-(2-methoxy-ethyl)-5-trifluoromethyl-benzamide

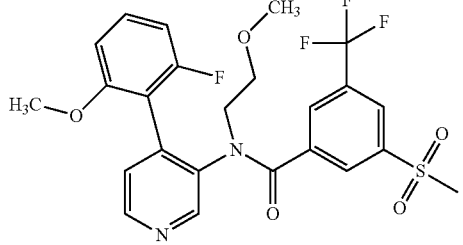

The title compound was prepared in analogy to example 223, from [4-(2-fluoro-6-methoxy-phenyl)-pyridin-3-yl]-(2-methoxy-ethyl)-amine and 3-methanesulfonyl-5-trifluoromethyl-benzoyl chloride (example 223, intermediate d) and using preparative HPLC (ammonium acetate/acetonitrile) for purification. Yellow solid (17%). MS (ESI): m/z=527.2 [M+H]$^+$.

Intermediates a)[4-(2-Fluoro-6-methoxy-phenyl)-pyridin-3-yl]-(2-methoxy-ethyl)-amine The title compound was prepared in analogy to example 85, intermediate a, from [4-(2-fluoro-6-methoxy-phenyl)-pyridin-3-yl]-(2-methoxy-ethyl)-carbamic acid tert-butyl ester after a reaction time of 2 hours. Colourless sticky liquid (82%). MS (ESI): m/z=277.0 [M+H]$^+$.

b) [4-(2-Fluoro-6-methoxy-phenyl)-pyridin-3-yl]-(2-methoxy-ethyl)-carbamic acid tert-butyl ester The title compound was prepared in analogy to example 72, from (4-iodo-pyridin-3-yl)-(2-methoxy-ethyl)-carbamic acid tert-butyl ester and 2-fluoro-6-methoxyphenylboronic after a reaction time of 18 hours at 100° C. The compound was purified by column chromatography eluting with a gradient of n-hexane:EtOAc (50:50 to 0:100). Yellow liquid (52%). MS (ESI): m/z=377.0 [M+H]$^+$.

c) (4-Iodo-pyridin-3-yl)-(2-methoxy-ethyl)-carbamic acid tert-butyl ester

The title compound was prepared in analogy to example 85, intermediate d from (4-iodo-pyridin-3-yl)-carbamic acid tert-butyl ester (example 85, intermediate d) and 1-bromo-2-methoxyethane and using a gradient of n-hexane:EtOAc (70:30 to 60:40) for the chromatographic purification. Light yellow oil (63%). MS (ESI): m/z=379.2 [M+H]$^+$.

Example 230

N-[4-(4-Fluoro-2-methoxy-phenyl)-2-methyl-pyridin-3-yl]-3-methanesulfonyl-N-methyl-5-trifluoromethyl-benzamide

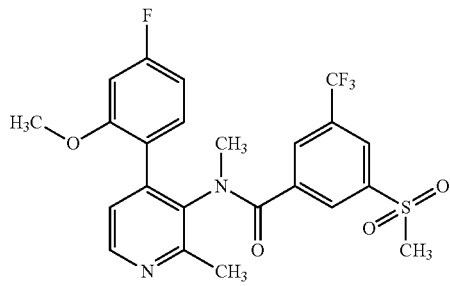 [SMILES: COc1cc(F)ccc1-c1ccnc(C)c1N(C)C(=O)c1cc(C(F)(F)F)cc(S(C)(=O)=O)c1]

To a solution of N-(2-chloro-4-(4-fluoro-2-methoxyphenyl)pyridin-3-yl)-N-methyl-3-(methylsulfonyl)-5-(trifluoromethyl)benzamide (0.1 g, 193 µmol, Example 212) in THF (3 mL) were added methylzinc(II)chloride (193 µL, 387 µmol), 1,3-dimethyl-2-imidazolidinone (DMI) (0.6 mL) and PEPPSI-IPr (CAS 905459-27-0) (2.7 mg, 3.87 µmol) and the reaction mixture was heated at 50° C. for 3 hours. The reaction mixture was poured on 10% aqueous citric acid solution and EtOAc and the layers were separated. The aqueous layer was extracted twice with EtOAc. The organic layers were washed with brine, dried over MgSO$_4$, filtered and evaporated. The compound was purified by silica gel chromatography on a 10 g column using an MPLC (ISCO) system eluting with a gradient of n-heptane:EtOAc (100:0 to 0:100). The product was purified by preparative HPLC (Gemini NX column) using a gradient of MeOH:water (containing 0.1% formic acid) (20:80 to 98:2). The product was purified by preparative HPLC (Gemini NX column) using a gradient of MeOH:water (containing 0.05% triethylamine) (20:80 to 60:40). Colorless solid (0.035 g; 36%). MS (ESI): m/z=497.12 [M+H]$^+$.

Example 231

N-[4-(4-Fluoro-2-methoxy-phenyl)-pyridin-3-yl]-3-methanesulfonyl-N-(5-methyl-isoxazol-3-ylmethyl)-5-trifluoromethyl-benzamide

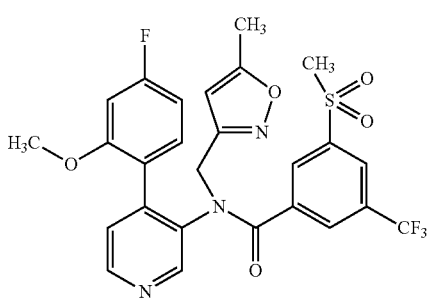 [SMILES: COc1cc(F)ccc1-c1ccncc1N(Cc1cc(C)on1)C(=O)c1cc(C(F)(F)F)cc(S(C)(=O)=O)c1]

The title compound was prepared in analogy to example 90, from [4-(4-fluoro-2-methoxy-phenyl)-pyridin-3-yl]-(5-methyl-isoxazol-3-ylmethyl)-amine and 3-(methylsulfonyl)-5-(trifluoromethyl)benzoic acid (example 114, intermediate a) after a reaction time of 18 hours at room temperature. The compound was purified by silica gel chromatography on a 20 g column using an MPLC (Flashmaster) system eluting with a gradient of n-heptane:EtOAc (100:0 to 0:100). Light brown solid (53%). MS (ESI): m/z=564.121 [M+H]$^+$.

Intermediates a) [4-(4-Fluoro-2-methoxy-phenyl)-pyridin-3-yl]-(5-methyl-isoxazol-3-ylmethyl)-amine The title compound was prepared in analogy to example 85, intermediate a, from tert-butyl 4-(4-fluoro-2-methoxy-phenyl)pyridin-3-yl((5-methylisoxazol-3-yl)methyl)carbamate after a reaction time of 2 hours at room temperature. The compound was purified by silica gel chromatography on a 20 g column using an MPLC (Flashmaster) system eluting with a gradient of n-heptane:EtOAc (100:0 to 0:100). Colorless solid (82%). MS (EST): m/z=314.130 [M+H]$^+$.

b) tert-Butyl 4-(4-fluoro-2-methoxyphenyl)pyridin-3-yl ((5-methylisoxazol-3-yl)methyl)-carbamate The title compound was prepared in analogy to example 72, from tert-butyl 4-iodopyridin-3-yl((5-methylisoxazol-3-yl)methyl)carbamate and 4-fluoro-2-methoxyphenylboronic acid after a reaction time of 18 hours at 90° C. The compound was purified by silica gel chromatography on a 20 g column using an MPLC (Flashmaster) system eluting with a gradient of n-heptane:EtOAc (100:0 to 0:100). Colorless foam (88%). MS (ESI): m/z=414.182 [M+H]$^+$.

c) tert-Butyl 4-iodopyridin-3-yl((5-methylisoxazol-3-yl)methyl)carbamate

The title compound was prepared in analogy to example 85, intermediate c, from tert-butyl 4-iodopyridin-3-ylcarbamate (example 85, intermediate d) and 3-(bromomethyl)-5-methylisoxazole (CAS RN 130628-75-0) after a reaction time of 18 hours at room temperature. The compound was purified by silica gel chromatography on a 20 g column using an MPLC system (CombiFlash Companion, Isco Inc.) eluting with a gradient of n-heptane: EtOAc (100:0 to 20:80). Light yellow solid (66%). MS (EI): m/z=415 [M]

Example 232 and Example 233

(+)-N-[4-(4-Fluoro-2-methoxy-phenyl)-pyridin-3-yl]-3-methanesulfonyl-N-[1-(tetrahydro-furan-2-yl)methyl]-5-trifluoromethyl-benzamide and (−)-N-[4-(4-Fluoro-2-methoxy-phenyl)-pyridin-3-yl]-3-methanesulfonyl-N-[1-(tetrahydro-furan-2-yl)methyl]-5-trifluoromethyl-benzamide

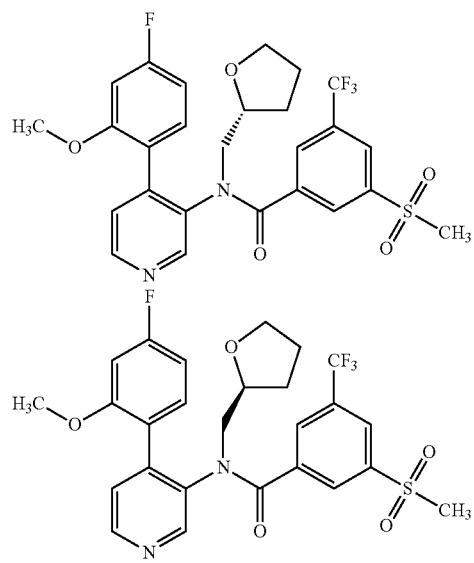

The title compounds were prepared in analogy to example 90, from [4-(4-fluoro-2-methoxy-phenyl)-pyridin-3-yl]-[1-(tetrahydro-furan-2-yl)methyl]-amine and 3-(methylsulfonyl)-5-(trifluoromethyl)benzoic acid (example 114, intermediate a) after a reaction time of 18 hours at room temperature. The enantiomeric mixture was purified by silica gel chromatography on a 20 g column using an MPLC (Flashmaster) system eluting with a gradient of n-heptane:EtOAc (100:0 to 0:100). Chiral chromatography on a Chiralpak AD column with a gradient of 2-propanol:n-heptane (30:70) furnished the two enantiomers with the (+)-enantiomer eluting first. (+)-N-[4-(4-Fluoro-2-methoxy-phenyl)-pyridin-3-yl]-3-methanesulfonyl-N-[1-(tetrahydro-furan-2-yl)methyl]-5-trifluoromethyl-benzamide: Light yellow oil (28 mg, 43%). MS (ESI): m/z=553.142 [M+H]$^+$ and (−)-N-[4-(4-Fluoro-2-methoxy-phenyl)-pyridin-3-yl]-3-methanesulfonyl-N-[(5)-1-(tetrahydro-furan-2-yl)methyl]-5-trifluoromethyl-benzamide: Light yellow oil (49%). MS (ESI): m/z=553.142 [M+H]$^+$.

Intermediates a) [4-(4-Fluoro-2-methoxy-phenyl)-pyridin-3-yl]-[1-(tetrahydro-furan-2-yl)methyl]-amine The title compound was prepared in analogy to example 85, intermediate a, from tert-butyl 4-(4-fluoro-2-methoxy-phenyl)pyridin-3-yl((tetrahydrofuran-2-yl)methyl)carbamate after a reaction time of 2 hours at room temperature. The compound was purified by silica gel chromatography on a 20 g column using an MPLC (Flashmaster) system eluting with a gradient of n-heptane:EtOAc (100:0 to 0:100). Colorless oil (208 mg, 84.2%). MS (ESI): m/z=303.150 [M+H]+.

b) tert-Butyl 4-(4-fluoro-2-methoxyphenyl)pyridin-3-yl((tetrahydrofuran-2-yl)methyl)carbamate The title compound was prepared in analogy to example 85, intermediate c, from tert-butyl 4-(4-fluoro-2-methoxyphenyl)pyridin-3-ylcarbamate and tetrahydrofurfurylchloride after a reaction time of 72 hours at 70° C. The compound was purified by silica gel chromatography on a 20 g column using an MPLC system (CombiFlash Companion, Isco Inc.) eluting with a gradient of n-heptane:EtOAc (100:0 to 0:100). Light yellow solid (38%). MS (ESI): m/z=403.205 [M+H]+.

c) tert-Butyl 4-(4-fluoro-2-methoxyphenyl)pyridin-3-ylcarbamate

The title compound was prepared in analogy to example 72, from tert-butyl 4-iodopyridin-3-ylcarbamate (example 85, intermediate d) and 4-fluoro-2-methoxyphenylboronic acid after a reaction time of 18 hours at 90° C. The residue was purified by silica gel chromatography on a 120 g column using an MPLC system (CombiFlash Companion XL, Isco Inc.) eluting with a gradient of n-heptane:EtOAc (100:0 to 20:80). Colorless solid (67%). MS (ESI): m/z=319.146 [M+H]+.

Example 234

[2-(3-{[4-(4-Fluoro-2-methoxy-phenyl)-pyridin-3-yl]-methyl-carbamoyl}-5-trifluoromethyl-phenylsulfanyl)-ethyl]-carbamic acid tert-butyl ester

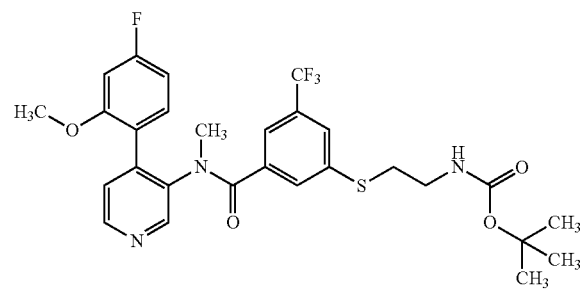 [SMILES: COc1cc(F)ccc1-c1ccncc1N(C)C(=O)c1cc(SCCNC(=O)OC(C)(C)C)cc(C(F)(F)F)c1]

To a suspension of N-(4-(4-fluoro-2-methoxyphenyl)pyridin-3-yl)-3-mercapto-N-methyl-5-(trifluoromethyl)benzamide (0.1 g, 229 μmol, example 216, intermediate a) in acetonitrile (2 mL) were added tert-butyl 2-bromoethylcarbamate (56.5 mg, 252 μmol) and DIPEA (59.2 mg, 80.0 μL, 458 μmol). After the addition of DIPEA the white suspension turned to a yellow solution, which was stirred a troom temperature for 3 hours. The reaction mixture was poured on saturated aqueous NH4Cl solution and EtOAc and the layers were separated. The aqueous layer was extracted twice with EtOAc. The organic layers were dried over MgSO4, filtered, treated with silica gel and evaporated. The compound was purified by silica gel chromatography on a 10 g column using an MPLC system eluting with a gradient of n-heptane:EtOAc (100:0 to 0:100). Colorless foam (0.111 g; 83%). MS (ESI): m/z=580.19 [M+H]+.

Example 235

N-[4-(4-Fluoro-2-methoxy-phenyl)-pyridin-3-yl]-N-methyl-3-oxetan-3-yl-5-trifluoromethyl-benzamide

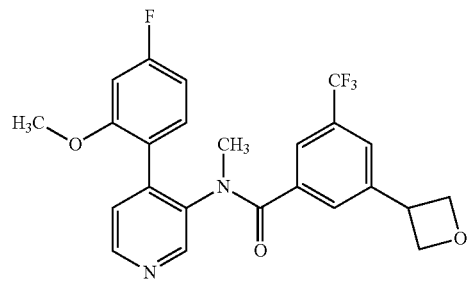 [SMILES: COc1cc(F)ccc1-c1ccncc1N(C)C(=O)c1cc(C2COC2)cc(C(F)(F)F)c1]

To a suspension of 3-((4-(4-fluoro-2-methoxyphenyl)pyridin-3-yl)(methyl)carbamoyl)-5-(trifluoromethyl)phenylboronic acid (0.1 g, 223 μmol) in 2-propanol (1 mL) were added 3-iodooxetane (41.0 mg, 223 μmol), (1R,2R)-2-aminocyclohexanol hydrochloride (2.03 mg, 13.4 μmol), nickel(II) iodide (4.18 mg, 13.4 μmol) and sodium hexamethyldisilazan (40.9 mg, 223 μmol) and the suspension was heated in a microwave oven at 80° C. for 20 minutes. The reaction mixture was poured on saturated aqueous NH4Cl solution and EtOAc and the layers were separated. The aqueous layer was extracted twice with EtOAc. The organic layers were dried over MgSO4, filtered, treated with silica gel and evaporated. The compound was purified by silica gel chromatography on a 10 g column using an MPLC system eluting with a gradient of n-heptane:EtOAc (100:0 to 0:100). The mixture was purified by preparative HPLC (Gemini NX column) using a gradient of MeOH:water (containing 0.1% formic acid) (20:80 to 98:2). Colorless solid (0.004 g; 3%). MS (ESI): m/z=461.15 [M+H]+.

Intermediates a) 3-((4-(4-Fluoro-2-methoxyphenyl)pyridin-3-yl)(methyl)carbamoyl)-5-(trifluoromethyl)-phenylboronic acid To a solution of 3-bromo-N-(4-(4-fluoro-2-methoxyphenyl)pyridin-3-yl)-N-methyl-5-(trifluoromethyl)benzamide (1 g, 2.07 mmol, example 216, intermediate c) in THF (10.0 mL) was added triisopropyl borate (751 mg, 927 μL, 3.99 mmol) and a cooling bath was installed. At −75° C. n-butyllithium (1.6 M solution in hexane, 1.36 mL, 2.17 mmol) was added dropwise and the brown mixture was stirred at −75° C. for 2 hours. To this mixture at 0° C., a solution of acetic acid (527 mg, 502 μL, 8.77 mmol) in water (0.50 mL) was added, followed by addition of hydrogen peroxide (35% in water, 302 mg, 272 μL, 3.1 mmol). The reaction mixture was stirred at 0° C. for 2.25 hours, then poured on saturated aqueous NH4Cl solution and EtOAc and the layers were separated. The aqueous layer was extracted twice with EtOAc. The organic layers were washed twice with 10% aqueous sodium thioslufate solution and once with brine, dried over MgSO4, filtered and evaporated. The product was purified by preparative SFC (Waters Viridis SFC 2-Ethylpyridine column) using an isocratic mixture of MeOH:carbondioxide (40:60). Light brown solid (0.363 g; 31%). MS (ESI): m/z=493.12 [M+HCOO]−.

Example 236

N-[4-(4-Fluoro-2-methoxy-phenyl)-pyridin-3-yl]-3-(2-methoxy-ethoxy)-N-methyl-5-trifluoromethyl-benzamide

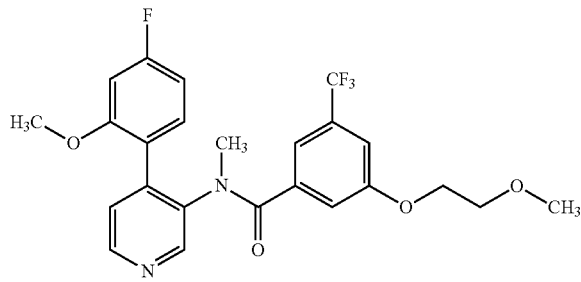

To a suspension of N-[4-(4-fluoro-2-methoxy-phenyl)-pyridin-3-yl]-3-hydroxy-N-methyl-5-trifluoromethyl-benzamide (0.06 g, 143 µmol) in acetonitrile (1 mL) were added 1-bromo-2-methoxyethane (19.8 mg, 143 µmol) and DIPEA (22.1 mg, 29.9 µL, 171 µmol) and the light yellow suspension was stirred at room temperature for 45 minutes. To the reaction mixture was added potassium carbonate (23.7 mg, 171 µmol) and stirring was continued for 2.75 hours at room temperature. Then the reaction mixture was stirred at reflux temperature for 16 hours. The reaction mixture was poured on saturated aqueous NH$_4$Cl solution and EtOAc and the layers were separated. The aqueous layer was extracted twice with EtOAc. The organic layers were dried over MgSO$_4$, filtered, treated with silica gel and evaporated. The product was purified by preparative HPLC (Gemini NX column) using a gradient of MeOH:water (containing 0.1% formic acid) (20:80 to 98:2). Light brown solid (0.048 g; 70%). MS (ESI): m/z=479.16 [M+H]$^+$.

Intermediates a) N-[4-(4-Fluoro-2-methoxy-phenyl)-pyridin-3-yl]-3-hydroxy-N-methyl-5-trifluoromethyl-benzamide To a solution of 3-bromo-N-(4-(4-fluoro-2-methoxyphenyl)pyridin-3-yl)-N-methyl-5-(trifluoromethyl)benzamide (1 g, 2.07 mmol, example 216, intermediate c) in THF (10.0 mL) was added triisopropyl borate (751 mg, 927 µL, 3.99 mmol) and a cooling bath was installed. At −75° C. n-butyllithium (1.6M solution in hexane, 1.36 mL, 2.17 mmol) was added dropwise and the brown mixture was stirred at −75° C. for 2 hours. To this mixture, at 0° C., a solution of acetic acid (527 mg, 502 µL, 8.77 mmol) in water (0.50 mL) was added, followed by addition of hydrogen peroxide (35% in water, 302 mg, 272 µL, 3.1 mmol). The reaction mixture was stirred at 0° C. for 2.25 hours, then poured on saturated aqueous NH$_4$Cl solution and EtOAc and the layers were separated. The aqueous layer was extracted twice with EtOAc. The organic layers were washed twice with 10% aqueous sodium thioslufate solution and once with brine, dried over MgSO$_4$, filtered and evaporated. The product was purified by preparative SFC (Waters Viridis SFC 2-Ethylpyridine column) using an isocratic mixture of MeOH:carbondioxide (40:60). Light brown solid (0.195 g; 22%). MS (ESI): m/z=421.12 [M+H]$^+$.

Example 237

3-(2-Amino-ethylsulfanyl)-N-[4-(4-fluoro-2-methoxy-phenyl)-pyridin-3-yl]-N-methyl-5-trifluoromethyl-benzamide

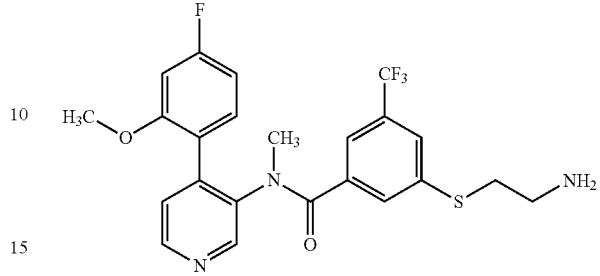

The title compound was prepared in analogy to example 85, intermediate a, from tert-butyl 2-(3-((4-(4-fluoro-2-methoxyphenyl)pyridin-3-yl)(methyl)carbamoyl)-5-(trifluoromethyl)-phenylthio)ethylcarbamate after a reaction time of 2 hours. The compound was purified by silica gel chromatography on a 10 g column using an MPLC system eluting with a gradient of CH$_2$Cl$_2$:MeOHe (100:0 to 70:30). Colorless foam (85%). MS (ESI): m/z=480.14 [M+H]$^+$.

Intermediates a) tert-Butyl 2-(3-((4-(4-fluoro-2-methoxyphenyl)pyridin-3-yl)(methyl)carbamoyl)-5-(trifluoromethyl)phenylthio)ethylcarbamate To a suspension of N-(4-(4-fluoro-2-methoxyphenyl)pyridin-3-yl)-3-mercapto-N-methyl-5-(trifluoromethyl)benzamide (0.1 g, 229 µmol, example 216, intermediate a) in acetonitrile (2 mL) were added tert-butyl 2-bromoethylcarbamate (56.5 mg, 252 µmol) and DIPEA (59.2 mg, 80.0 µL, 458 µmol). After the addition of DIPEA the white suspension turned to a yellow solution, which was stirred at room temperature for 3 hours. The reaction mixture was poured on saturated aqueous NH$_4$Cl solution and EtOAc and the layers were separated. The aqueous layer was extracted twice with EtOAc. The organic layers were dried over MgSO$_4$, filtered, treated with silica gel and evaporated. The compound was purified by silica gel chromatography on a 10 g column using an MPLC system eluting with a gradient of n-heptane:EtOAc (100:0 to 0:100). Colorless foam (0.111 g; 83%). MS (ESI): m/z=580.19 [M+H]$^+$.

Example 238

3-Chloro-5-cyclopropyl-N-[4-(4-fluoro-2-methoxy-phenyl)-pyridin-3-yl]-N-methyl-benzamide

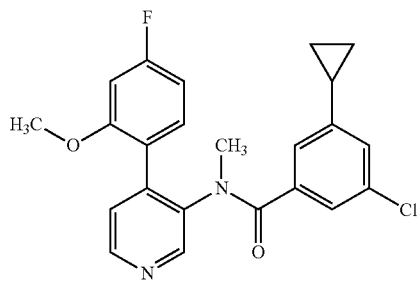 [SMILES: COc1cc(F)ccc1-c1ccncc1N(C)C(=O)c1cc(Cl)cc(C2CC2)c1]

The title compound was prepared in analogy to example 90, from 3-chloro-5-cyclopropylbenzoic acid and 4-(4-fluoro-2-methoxyphenyl)-N-methylpyridin-3-amine (0.18 g, 775 μmol, example 129, intermediate) after a reaction time of 41 hours at room temperature. The compound was purified by silica gel chromatography on a 10 g column using an MPLC system eluting with a gradient of n-heptane:EtOAc (100:0 to 0:100). The product was purified by preparative HPLC (Gemini NX column) using a gradient of MeOH:water (containing 0.1% formic acid) (20:80 to 98:2). The product was purified by preparative HPLC (Gemini NX column) using a gradient of MeOH:water (containing 0.1% formic acid) (20:80 to 98:2). Colorless solid (0.012 g; 3%). MS (ESI): m/z=411.13 [M+H]$^+$.

Intermediates a) 3-Chloro-5-cyclopropylbenzoic acid

The title compound was prepared in analogy to example 84, from methyl 3-chloro-5-cyclopropylbenzoate. Silica gel chromatography on a 10 g column using an MPLC system eluting with a gradient of n-heptane:EtOAc (100:0 to 0:100) gave the desired compound as a 2:1 mixture with 3,5-dicyclopropyl-benzoic acid. Colorless solid (76%).

b) Methyl 3-chloro-5-cyclopropylbenzoate

To a solution of methyl 3-chloro-5-iodobenzoate (0.5 g, 1.69 mmol) in THF (5 mL) were added cyclopropylzine(11) bromide (3.71 mL, 1.86 mmol), PEPPSI-IPr (22.9 mg, 33.7 μmol, CAS RN 905459-27-0) and 1,3-dimethyl-2-imidazolidinone (DMI) (1 mL) and the turbid light brown solution was stirred at 50° C. for 2.25 hours. The reaction mixture was poured on 10% aqueous citric acid solution and EtOAc and the layers were separated. The aqueous layer was extracted twice with EtOAc. The organic layers were washed with brine, dried over MgSO$_4$, filtered, treated with silica gel and evaporated. The compound was purified by silica gel chromatography on a 50 g column using an MPLC (Flasmaster) system eluting with a gradient of n-heptane:EtOAc (100:0 to 70:30). The obtained fraction (light yellow oil, 315 mg) was dissolved in THF (5 mL), to the clear solution were added cyclopropylzine(II) bromide (3.71 mL, 1.86 mmol), PEPPSI-IPr (22.9 mg, 33.7 μmol, CAS RN 905459-27-0) and 1,3-dimethyl-2-imidazolidinone (DMI) (1 mL) and the reaction mixture was heated at 50° C. for 2.25 hours. The reaction mixture was poured on 10% aqueous citric acid solution and EtOAc and the layers were separated. The aqueous layer was extracted twice with EtOAc. The organic layers were dried over MgSO$_4$, filtered, treated with silica gel and evaporated. The compound was purified by silica gel chromatography on a 10 g column using an MPLC (ISCO) system eluting with a gradient of n-heptane:EtOAc (100:0 to 40:60) to give the title compound as a light brown oil (0.225 g; 63%) containing 3,5-dicyclopropyl-benzoic acid methyl ester.

Example 239

4-(3-{[4-(4-Fluoro-2-methoxy-phenyl)-pyridin-3-yl]-methyl-carbamoyl}-5-trifluoromethyl-phenylsulfanyl)-butyric acid

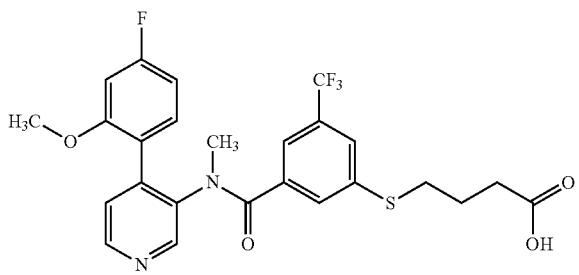 [SMILES: COc1cc(F)ccc1-c1ccncc1N(C)C(=O)c1cc(SCCCC(=O)O)cc(C(F)(F)F)c1]

To a suspension of N-(4-(4-fluoro-2-methoxyphenyl)pyridin-3-yl)-3-mercapto-N-methyl-5-(trifluoromethyl)benzamide (0.05 g, 115 μmol, Example 216, intermediate a) in acetonitrile (1 mL) were added 4-bromobutanoic acid (36.4 mg, 218 μmol) and DIPEA (29.6 mg, 40.0 μL, 229 μmol). After the addition of DIPEA the white suspension turned to a light yellow solution, which was stirred at room temperature for 24 hours before another batch of DIPEA (29.6 mg, 40.0 μL, 229 μmol) was added (white suspension turned into light yellow solution). The reaction mixture was stirred at room temperature for another 20 hours and then poured on saturated aqueous NH$_4$Cl solution and EtOAc and the layers were separated. The aqueous layer was extracted twice with EtOAc. The organic layers were dried over MgSO$_4$, filtered and evaporated. The product was purified by preparative HPLC (Gemini NX column) using a gradient of MeOH:water (containing 0.1% formic acid) (20:80 to 98:2). Colorless solid (0.01 g; 16%). MS (ESI): m/z=523.13 [M+H]$^+$.

Example 240

N-[4-(4-Fluoro-2-methoxy-phenyl)-pyridin-3-yl]-3-(2-hydroxy-ethoxy)-N-methyl-5-trifluoromethyl-benzamide

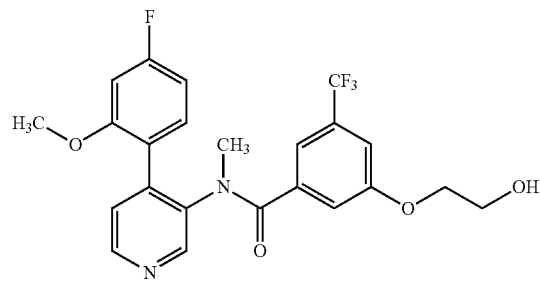 [SMILES: COc1cc(F)ccc1-c1ccncc1N(C)C(=O)c1cc(OCCO)cc(C(F)(F)F)c1]

To a suspension of N-(4-(4-fluoro-2-methoxyphenyl)pyridin-3-yl)-3-hydroxy-N-methyl-5-(trifluoromethyl)benzamide (0.06 g, 143 μmol, Example 236, intermediate) in acetonitrile (2 mL) were added 2-bromoethanol (21.4 mg, 12.1 μL, 171 μmol) and potassium carbonate (23.7 mg, 171 μmol) and the light brown suspension was heated to reflux for 24 hours before another batch of 2-bromoethanol (21.4 mg, 12.1 μL, 171 μmol) and potassium carbonate (29.6 mg, 214 µmol) were added. After heating at reflux for another 20 hours the reaction mixture was poured on saturated aqueous NH₄Cl solution and EtOAc and the layers were separated. The aqueous layer was extracted twice with EtOAc. The organic layers were dried over MgSO₄, filtered and evaporated. The product was purified by preparative HPLC (Gemini NX column) using a gradient of MeOH: water (containing 0.1% formic acid) (20:80 to 98:2). Colorless foam (0.021 g; 31%). MS (ESI): m/z=465.14 [M+H]⁺.

Example 241

3-(2-Amino-ethanesulfonyl)-N-[4-(4-fluoro-2-methoxy-phenyl)-pyridin-3-yl]-N-methyl-5-trifluoromethyl-benzamide

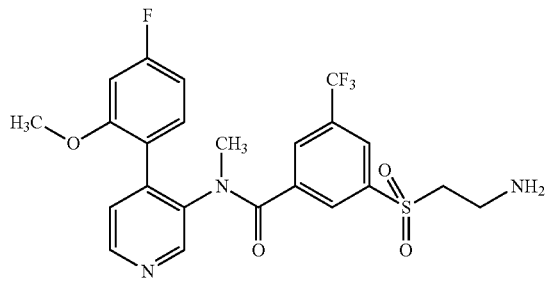 [SMILES: COc1cc(F)ccc1-c1ccncc1N(C)C(=O)c1cc(C(F)(F)F)cc(S(=O)(=O)CCN)c1]

To an ice-cold solution of 3-(2-aminoethylthio)-N-(4-(4-fluoro-2-methoxyphenyl)pyridin-3-yl)-N-methyl-5-(trifluoromethyl)benzamide (0.064 g, 133 µmol, example 237) in MeOH (2 mL) and water (0.5 mL) was added oxone (205 mg, 334 µmol) and the white suspension was stirred at room temperature for 4.5 hours. The reaction mixture was poured on 10% aqueous Na₂S₂O₃ solution and EtOAc and the layers were separated. The aqueous layer was extracted twice with EtOAc. The organic layers were washed once with brine, dried over MgSO₄, filtered, treated with silica gel and evaporated. The compound was purified by silica gel chromatography on a 10 g column using an MPLC (Flasmaster) system eluting with a gradient of CH₂Cl₂:MeOH (100:0 to 85:15). Colorless solid (0.016 g; 23%). MS (ESI): m/z=512.13 [M+H]⁺.

Example 242

N-[4-(2-Cyclopropoxy-phenyl)-pyridin-3-yl]-3-methanesulfonyl-N-methyl-5-trifluoromethyl-benzamide

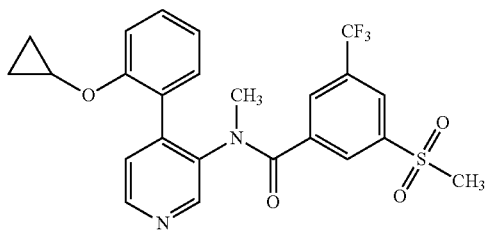 [SMILES: CN(C(=O)c1cc(C(F)(F)F)cc(S(C)(=O)=O)c1)c1cnccc1-c1ccccc1OC1CC1]

The title compound was prepared in analogy to example 90, from [4-(2-cyclopropoxy-phenyl)-pyridin-3-yl]-methyl-amine and 3-(methylsulfonyl)-5-(trifluoromethyl)benzoic acid (example 114, intermediate a) after a reaction time of 18 hours at room temperature. The compound was purified by silica gel chromatography on a 20 g column using an MPLC (Flashmaster) system eluting with a gradient of n-heptane: EtOAc (100:0 to 0:100). Light yellow foam (65%). MS (ESI): m/z=491.125 [M+H]⁺.

Intermediate

[4-(2-Cyclopropoxy-phenyl)-pyridin-3-yl]-methyl-amine

The title compound was prepared in analogy to example 72, from (4-iodo-pyridin-3-yl)-methyl-amine (example 36, intermediate b) and 2-cyclopropoxyphenylboronic acid after stirring at 90° C. for 18 hours. The compound was purified by silica gel chromatography on a 20 g column using a MPLC system (CombiFlash Companion, Isco Inc.) eluting with a gradient of n-heptane:EtOAc (100:0 to 0:100). Light yellow oil (94%). MS (ESI): m/z=241.134 [M+H]⁺.

Example 243

5-(3-{[4-(4-Fluoro-2-methoxy-phenyl)-pyridin-3-yl]-methyl-carbamoyl}-5-trifluoromethyl-phenylsulfanyl)-pentanoic acid

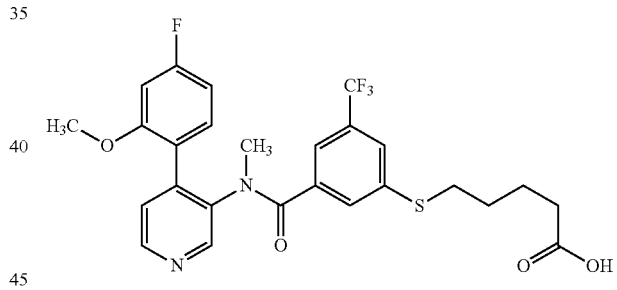

To a suspension of N-(4-(4-fluoro-2-methoxyphenyl)pyridin-3-yl)-3-mercapto-N-methyl-5-(trifluoromethyl)benzamide (0.115 g, 264 µmol, Example 216, intermediate a) in acetonitrile (2 mL) were added 5-bromopentanoic acid (59.6 mg, 329 µmol) and DIPEA (85.1 mg, 115 µL, 659 µmol). After the addition of DIPEA the white suspension turned to a light yellow solution, which was stirred at room temperature for 18 hours. The reaction mixture was poured on saturated aqueous NH₄Cl solution and EtOAc and the layers were separated. The aqueous layer was extracted twice with EtOAc. The organic layers were dried over MgSO₄, filtered, treated with silica gel and evaporated. The compound was purified by silica gel chromatography on a 10 g column using an MPLC (Flashmaster) system eluting with a gradient of CH₂Cl₂:MeOH (100:0 to 0:0). The product was further purified by preparative HPLC (Gemini NX column) using a gradient of MeOH:water (containing 0.1% formic acid) (20:80 to 98:2). Colorless solid (0.10 g; 70%). MS (ESI): m/z=537.15 [M+H]⁺.

Example 244

N-[4-(2-Fluoro-phenyl)-pyridin-3-yl]-N-(2-hydroxy-ethyl)-3-methanesulfonyl-5-trifluoromethyl-benzamide

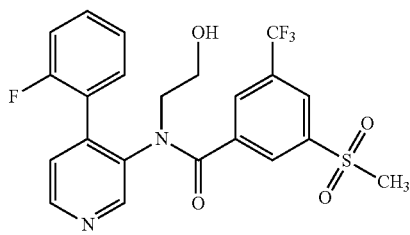 [SMILES: CS(=O)(=O)c1cc(C(=O)N(CCO)c2cnccc2-c2ccccc2F)cc(C(F)(F)F)c1]

To a solution of [[4-(2-fluoro-phenyl)-pyridin-3-yl]-(3-methanesulfonyl-5-trifluoromethyl-benzoyl)-amino]-acetic acid methyl ester (80 mg, 157 example 186) in MeOH (2 mL) was added NaBH$_4$ (11.9 mg, 313 µmol) at 0° C. The reaction mixture was stirred at room temperature for 18 hours. The reaction mixture was poured on 30 mL 10% aqueous NaHCO$_3$ solution and 30 mL EtOAc and the layers were separated. The aqueous layer was extracted a second time with 30 mL EtOAc. The organic layers were washed with 30 mL brine, dried over MgSO$_4$, filtered and concentrated under vacuum. The compound was purified by silica gel chromatography on a 10 g column using an MPLC (Flashmaster) system eluting with a gradient of n-heptane:EtOAc (100:0 to 0:100). Colorless solid (9 mg, 12%). MS (ESI): m/z=483.100 [M+H]$^+$.

Example 245

3-(3-{[4-(4-Fluoro-2-methoxy-phenyl)-pyridin-3-yl]-methyl-carbamoyl}-5-trifluoromethyl-phenyl)-azetidine-1-carboxylic acid tert-butyl ester

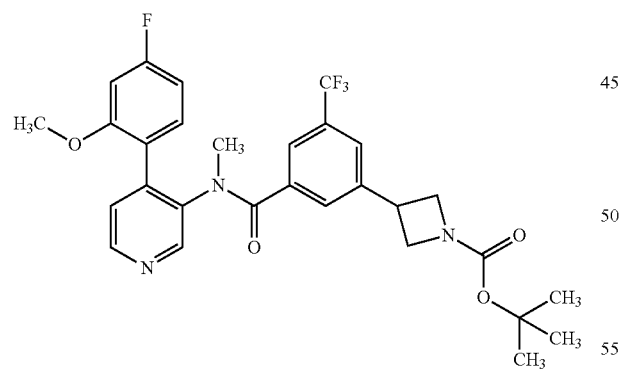

To a suspension of 3-((4-(4-fluoro-2-methoxyphenyl)pyridin-3-yl)(methyl)carbamoyl)-5-(trifluoromethyl)phenylboronic acid (0.1 g, 223 µmol, example 235, intermediate) in 2-propanol (1.0 mL) were added tert-butyl 3-iodoazetidine-1-carboxylate (63.2 mg, 223 µmol), (1R,2R)-2-aminocyclohexanol hydrochloride (2.03 mg, 13.4 µmol, CAS RN 13374-31-7), nickel(II) iodide (4.18 mg, 13.4 µmol) and sodium hexamethyldisilazan (40.9 mg, 223 µmol) and the suspension was heated in a microwave oven at 80° C. for 50 minutes. The reaction mixture was poured on saturated aqueous NH$_4$Cl solution and EtOAc and the layers were separated. The aqueous layer was extracted twice with EtOAc. The organic layers were dried over MgSO$_4$, filtered, treated with silica gel and evaporated. The compound was purified by silica gel chromatography on a 10 g column using an MPLC system eluting with a gradient of n-heptane:EtOAc (100:0 to 0:100). The product (light brown solid, 0.048 g) was purified by preparative HPLC (Gemini NX column) using a gradient of MeOH:water (containing 0.1% formic acid) (20:80 to 98:2). Colorless solid (0.008 g; 6%). MS (ESI): m/z=560.22 [M+H]$^+$.

Example 246

3-Bromo-N-[4-(4-fluoro-2-methoxy-phenyl)-pyridin-3-yl]-N-methyl-5-trifluoromethoxy-benzamide

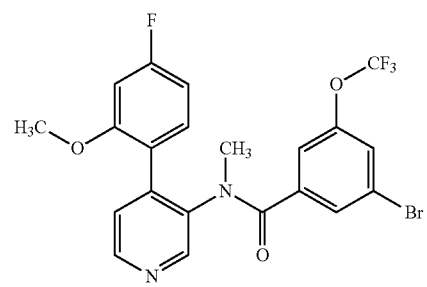

The title compound was prepared in analogy to example 90, from 4-(4-fluoro-2-methoxyphenyl)-N-methylpyridin-3-amine (example 129, intermediate) and 3-bromo-5-(trifluoromethoxy)benzoic acid (CAS RN 453565-90-7) after a reaction time of 16 hours. The compound was purified by silica gel chromatography on a 10 g column using an MPLC (ISCO) system eluting with a gradient of n-heptane:EtOAc (100:0 to 0:100). Colorless solid (60%). MS (ESI): m/z=501.03 [M+H]$^+$.

Example 247

4-(3-{[4-(4-Fluoro-2-methoxy-phenyl)-pyridin-3-yl]-methyl-carbamoyl}-5-trifluoromethyl-benzenesulfonyl)-butyric acid

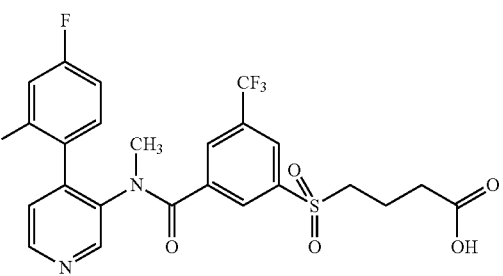

To an ice-cold suspension of 4-(3-((4-(4-fluoro-2-methoxyphenyl)pyridin-3-yl)(methyl)carbamoyl)-5-(trifluoromethyl)phenylthio)butanoic acid (0.027 g, 51.7 µmol, example 239) in MeOH (2 mL) and water (0.5 mL) was added Oxone® (79.4 mg, 129 µmol) and the reaction mixture was stirred at room temperature for 4.5 hours. The reaction mixture was poured on 10% aqueous Na₂S₂O₃ solution and EtOAc and the layers were separated. The aqueous layer was extracted twice with EtOAc. The organic layers were washed once with brine, dried over MgSO₄, filtered, and evaporated. The crude product was purified by preparative HPLC (Gemini NX column) using a gradient of MeOH:water (containing 0.1% formic acid) (20:80 to 98:2). Colorless foam (0.012 g; 41%). MS (ESI): m/z=555.12 [M+H]⁺.

Example 248

5-(3-{[4-(4-Fluoro-2-methoxy-phenyl)-pyridin-3-yl]-methyl-carbamoyl}-5-trifluoromethyl-benzene-sulfonyl)-pentanoic acid

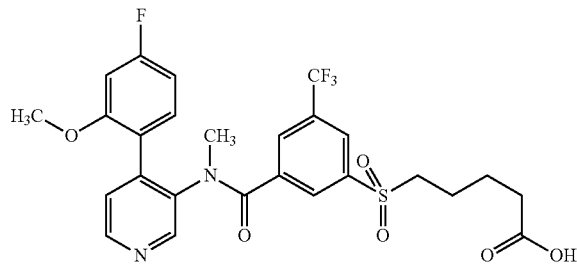 [SMILES: COc1cc(F)ccc1-c1ccncc1N(C)C(=O)c1cc(C(F)(F)F)cc(S(=O)(=O)CCCCC(=O)O)c1]

To an ice-cold suspension of 5-(3-44-(4-fluoro-2-methoxyphenyl)pyridin-3-yl)(methyl)-carbamoyl)-5-(trifluoromethyl)phenylthio)pentanoic acid (0.086 g, 160 µmol, example 243) in MeOH (4 mL) and water (0.5 mL) was added Oxone® (246 mg, 401 µmol) and the reaction mixture was stirred at room temperature for 4.5 hours. The reaction mixture was poured on 10% aqueous Na₂S₂O₃ solution and EtOAc and the layers were separated. The aqueous layer was extracted twice with EtOAc. The organic layers were washed once with brine, dried over MgSO₄, filtered, and evaporated. The crude product (0.11 g) was purified by preparative HPLC (Gemini NX column) using a gradient of MeOH: water (containing 0.1% formic acid) (20:80 to 98:2). Colorless foam (0.05 g; 54%). MS (ESI): m/z=569.13 [M+H]⁺.

Example 249

3-(Azetidine-1-sulfonyl)-N-[4-(4-fluoro-2-methoxy-phenyl)-pyridin-3-yl]-N-methyl-5-trifluoromethyl-benzamide

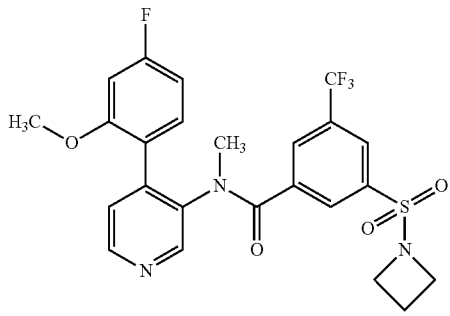 [SMILES: COc1cc(F)ccc1-c1ccncc1N(C)C(=O)c1cc(C(F)(F)F)cc(S(=O)(=O)N2CCC2)c1]

The title compound was prepared in analogy to example 90, from 4-(4-fluoro-2-methoxyphenyl)-N-methylpyridin-3-amine (example 129, intermediate) and 3-(azetidine-1-sulfonyl)-5-trifluoromethyl-benzoic acid after a reaction time of 16.5 hours. The compound was purified by silica gel chromatography on a 20 g column using an MPLC (ISCO) system eluting with EtOAc (isocratic). Colorless foam (43%). MS (ESI): m/z=524.13 [M+H]⁺.

Intermediates a) 3-(Azetidine-1-sulfonyl)-5-trifluoromethyl-benzoic acid

The title compound was prepared in analogy to example 84, from methyl 3-(azetidin-1-ylsulfonyl)-5-(trifluoromethyl)benzoate after a reaction time of 2.25 hours. The clear, light yellow solution was evaporated until dioxane was removed. The residue was adjusted to pH 1 using 1M aqueous HCl. The resulting suspension was filtered and the filter cake was washed with water. Colorless solid (76%). MS (ESI): m/z=308.02 [M−H]⁻.

b) Methyl 3-(azetidin-1-ylsulfonyl)-5-(trifluoromethyl)benzoate

To a solution of methyl 3-(chlorosulfonyl)-5-(trifluoromethyl)benzoate (0.3 g, 991 µmol; Buttpark Ltd.) in CH₂Cl₂ (1 mL) were added DIPEA (192 mg, 260 µL, 1.49 mmol) and azetidine (62.3 mg, 73.5 µL, 1.09 mmol). The clear, light yellow solution was stirred at room temperature for 4 hours and then poured on saturated aqueous NH₄Cl solution and EtOAc and the layers were separated. The aqueous layer was extracted twice with EtOAc. The organic layers were dried over MgSO₄, filtered, and evaporated. Light brown solid (0.316 g; 98%). MS (EI): m/z=323 [M].

Example 250

N-[4-(4-Fluoro-2-methoxy-phenyl)-pyridin-3-yl]-3-methanesulfonyl-N-(1-methyl-1H-imidazol-2-ylmethyl)-5-trifluoromethyl-benzamide

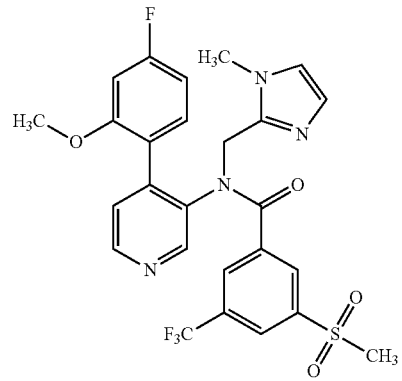

The title compound was prepared in analogy to example 90, from [4-(4-fluoro-2-methoxy-phenyl)-pyridin-3-yl]-(1-methyl-1H-imidazol-2-ylmethyl)-amine and 3-(methylsulfonyl)-5-(trifluoromethyl)benzoic acid (example 114, intermediate a) after a reaction time of 18 hours at room temperature. The compound was purified by silica gel chromatography on a 20 g column using an MPLC (Flashmaster) system eluting with a gradient of CH$_2$Cl$_2$:MeOH (100:0 to 80:15). Further purification by preparative HPLC (Gemini NX) with a gradient of MeOH:water (containing 0.05% formic acid) (80:20 to 98:2). Light yellow foam (54%). MS (ESI): m/z=563.135 [M+H]$^+$.

Intermediate a) [4-(4-Fluoro-2-methoxy-phenyl)-pyridin-3-yl]-(1-methyl-1H-imidazol-2-ylmethyl)-amine The title compound was prepared in analogy to example 72, from 4-iodo-N-((l-methyl-1H-imidazol-2-yl)methyl)pyridin-3-amine and 4-fluoro-2-methoxyphenylboronic acid after a reaction time of 18 hours at 90° C. The compound was purified by silica gel chromatography on a 20 g column using an MPLC (Flashmaster) system eluting with a gradient of CH$_2$Cl$_2$:MeOH (100:0 to 85:15). Light yellow solid (95%). MS (ESI): m/z=313.145 [M+H]$^+$.

b) 4-Iodo-N-((1-methyl-1H-imidazol-2-yl)methyl)pyridin-3-amine

The title compound was prepared in analogy to example 85, intermediate a, from tert-butyl 4-iodopyridin-3-yl((l-methyl-1H-imidazol-2-yl)methyl)carbamate after a reaction time of 2 hours at room temperature. Light yellow solid (83%). MS (ESI): m/z=315.010 [M+H]$^+$.

c) tert-Butyl 4-iodopyridin-3-yl((1-methyl-1H-imidazol-2-yl)methyl)carbamate

The title compound was prepared in analogy to example 85, intermediate c, from tert-butyl 4-iodopyridin-3-ylcarbamate (example 85, intermediate d) and 2-(chloromethyl)-1-methyl-1H-imidazole hydrochloride after a reaction time of 18 hours at room temperature. The residue was purified by silica gel chromatography on a 50 g column using an MPLC system (CombiFlash Companion, Isco Inc.) eluting with a gradient of n-heptane:EtOAc: MeOH (100:0:0 to 0:100:0 to 0:50:50). Colorless solid (90%). MS (ESI): m/z=437.046 [M+H]$^+$.

Example 251

N-[4-(4-Fluoro-2-methoxy-phenyl)-pyridin-3-yl]-N-methyl-3-(oxetan-3-ylsulfanyl)-5-trifluoromethyl-benzamide

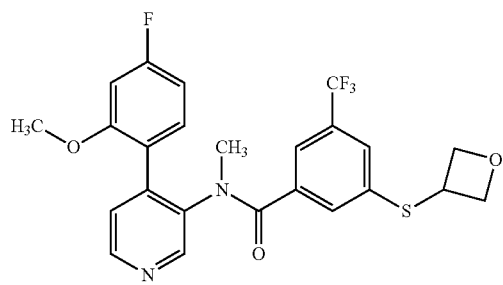 [SMILES: COc1cc(F)ccc1-c1ccncc1N(C)C(=O)c1cc(SC2COC2)cc(C(F)(F)F)c1]

To a solution of N-(4-(4-fluoro-2-methoxyphenyl)pyridin-3-yl)-3-mercapto-N-methyl-5-(trifluoromethyl)benzamide (0.1 g, 229 µmol, example 129, intermediate) in acetonitrile (2 mL) were added 3-iodooxetane (52.7 mg, 286 µmol, CAS RN 26272-85-5) and DIPEA (74.0 mg, 100 µL, 573 µmol) and the yellow solution was stirred at room temperature for 1.5 hours. Then heating was installed and the yellow solution was stirred at reflux for 2.5 hours. The colorless solution was poured on saturated aqueous NH$_4$Cl solution and EtOAc and the layers were separated. The aqueous layer was extracted twice with EtOAc. The organic layers were dried over MgSO$_4$, filtered, and evaporated. The compound was purified by silica gel chromatography on a 10 g column using an MPLC system eluting with a gradient of n-heptane:EtOAc (100:0 to 0:100). Light brown foam (0.052 g; 46%). MS (ESI): m/z=493.12 [M+H]$^+$.

Example 252

N-[4-(4-Fluoro-2-methoxy-phenyl)-pyridin-3-yl]-3-methanesulfonyl-N-methyl-5-trifluoromethoxy-benzamide

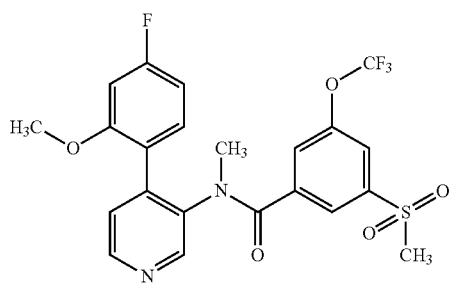

To a solution of L-proline (18.4 mg, 160 µmol) in DMSO (2 mL) was added sodium hydroxide (6.41 mg, 160 µmol) and the turbid mixture was stirred at room temperature for 30 minutes. This mixture was added to 3-bromo-N-[4-(4-fluoro-2-methoxy-phenyl)-pyridin-3-yl]-N-methyl-5-trifluoromethoxy-benzamide (0.1 g, 200 µmol) and the resulting suspension was treated with copper(I)iodide (30.5 mg, 160 µmol) and sodium methanesulfinate (164 mg, 1.6 mmol). The reaction mixture was heated to 120° C. for 19 hours. After cooling down to room temperature the reaction mixture was poured on saturated aqueous NH$_4$Cl solution and EtOAc and the layers were separated. The aqueous layer was extracted twice with EtOAc. The organic layers were washed with brine, dried over MgSO$_4$, filtered, treated with silica gel and evaporated. The compound was purified by silica gel chromatography on a 10 g column using an MPLC system eluting with a gradient of n-heptane:EtOAc (100:0 to 0:100). Colorless foam (0.065 g; 65%). MS (ESI): m/z=499.09 [M+H]$^+$.

Intermediate a) 3-Bromo-N-[4-(4-fluoro-2-methoxy-phenyl)-pyridin-3-yl]-N-methyl-5-trifluoromethoxy-benzamide The title compound was prepared in analogy to example 90, from 4-(4-fluoro-2-methoxyphenyl)-N-methylpyridin-3-amine (example 129, intermediate) and 3-bromo-5-(trifluoromethoxy)benzoic acid (CAS RN 453565-90-7) after a reaction time of 16 hours. The compound was purified by silica gel chromatography on a 10 g column using an MPLC (ISCO) system eluting with a gradient of n-heptane:EtOAc (100:0 to 0:100). Colorless solid (60%). MS (ESI): m/z=501.03 [M+H]+.

Example 253

N-[6-Chloro-4-(5-fluoro-2-methyl-phenyl)-pyridin-3-yl]-3-methanesulfonyl-N-methyl-5-trifluoromethyl-benzamide

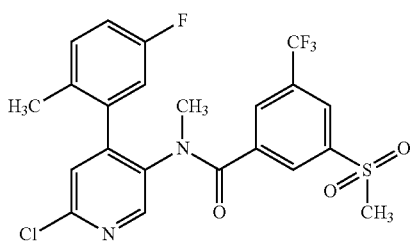 [SMILES: Cc1ccc(F)cc1-c1cc(Cl)ncc1N(C)C(=O)c1cc(C(F)(F)F)cc(S(C)(=O)=O)c1]

The title compound was prepared in analogy to example 90, from [6-chloro-4-(5-fluoro-2-methyl-phenyl)-pyridin-3-yl]-methyl-amine and 3-(methylsulfonyl)-5-(trifluoromethyl)benzoic acid (example 114, intermediate a) after a reaction time of 64 hours. The compound was purified by silica gel chromatography on a 20 g column using an MPLC (ISCO) system eluting with a gradient of n-heptane:EtOAc (100:0 to 20:80). The product was further purified by preparative HPLC (Gemini NX column) using a gradient of MeOH:water (containing 0.1% formic acid) (20:80 to 98:2). Colorless foam (5%). MS (ESI): m/z=501.07 [M+H]+.

Intermediates a) [6-Chloro-4-(5-fluoro-2-methyl-phenyl)-pyridin-3-yl]-methyl-amine The title compound was prepared in analogy to example 72, from 6-chloro-4-iodo-N-methylpyridin-3-amine (prepared according to WO2006013050) and 5-fluoro-2-methylphenylboronic acid after heating at reflux for 21 hours. The compound was purified by silica gel chromatography on a 50 g column using an MPLC system eluting with a gradient of n-heptane:EtOAc (100:0 to 50:50). Light brown solid (85%). MS (ESI): m/z=251.08 [M+H]+.

Example 254

3-(4-Carbamoyl-butane-1-sulfonyl)-N-[4-(4-fluoro-2-methoxy-phenyl)-pyridin-3-yl]-N-methyl-5-trifluoromethyl-benzamide

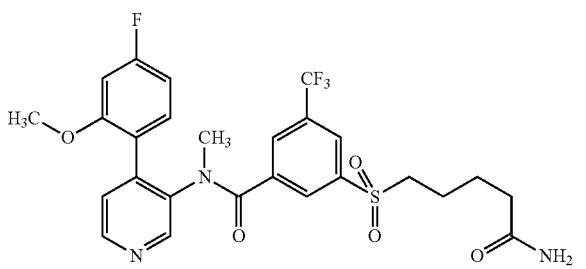 [SMILES: COc1cc(F)ccc1-c1ccncc1N(C)C(=O)c1cc(C(F)(F)F)cc(S(=O)(=O)CCCCC(N)=O)c1]

The title compound was prepared in analogy to example 117, from 5-(3-((4-(4-fluoro-2-methoxyphenyl)pyridin-3-yl)(methyl)carbamoyl)-5-(trifluoromethyl)phenylsulfonyl)pentanoic acid (example 243) after a reaction time of 68 hours. The compound was purified by silica gel chromatography on a 10 g column using an MPLC (Flasmaster) system eluting with a gradient of CH$_2$Cl$_2$:MeOH (100:0 to 40:60). Colorless foam (84%). MS (ESI): m/z=568.15 [M+H]+.

Example 255

N-[4-(4-Fluoro-2-methoxy-phenyl)-pyridin-3-yl]-N-methyl-3-(oxetane-3-sulfonyl)-5-trifluoromethyl-benzamide

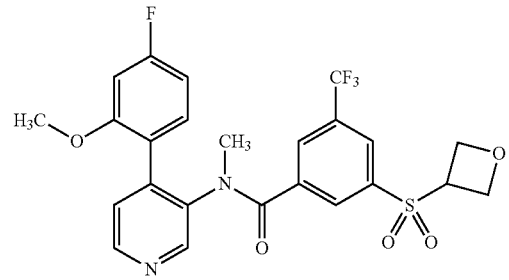 [SMILES: COc1cc(F)ccc1-c1ccncc1N(C)C(=O)c1cc(C(F)(F)F)cc(S(=O)(=O)C2COC2)c1]

To an ice-cold solution of N-(4-(4-fluoro-2-methoxyphenyl)pyridin-3-yl)-N-methyl-3-(oxetan-3-ylthio)-5-(trifluoromethyl)benzamide (0.042 g, 85.3 μmol, example 251) in MeOH (2 mL) and water (0.5 mL) was added Oxone® (131 mg, 213 μmol) and the reaction mixture was stirred at room temperature for 2.75 hours. The reaction mixture was poured on 10% aqueous Na$_2$S$_2$O$_3$ solution and EtOAc and the layers were separated. The aqueous layer was extracted twice with EtOAc. The organic layers were washed once with brine, dried over MgSO4, filtered, treated with silica gel and evaporated. The compound was purified by silica gel chromatography on a 5 g column using an MPLC (ISCO) system eluting with a gradient of n-heptane:EtOAc (100:0 to 0:100). Colorless gum (0.021 g; 46%). MS (ESI): m/z=525.11 [M+H]+.

Example 256

N-[4-(4-Fluoro-2-methoxy-phenyl)-pyridin-3-yl]-N-methyl-3-(morpholine-4-sulfonyl)-5-trifluoromethyl-benzamide

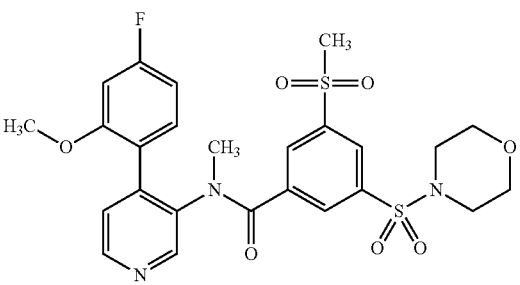 [SMILES: COc1cc(F)ccc1-c1ccncc1N(C)C(=O)c1cc(S(C)(=O)=O)cc(S(=O)(=O)N2CCOCC2)c1]

The title compound was prepared in analogy to example 90, from 4-(4-fluoro-2-methoxyphenyl)-N-methylpyridin-3- amine (example 129, intermediate) and 3-(morpholine-4-sulfonyl)-5-trifluoromethyl-benzoic acid after a reaction time of 64 hours. The compound was purified by silica gel chromatography on a 20 g column using an MPLC (ISCO) system eluting with EtOAc (isocratic). Light yellow solid (34%). MS (ESI): m/z=554.14 [M+H]⁺.

Intermediates a) 3-(Morpholine-4-sulfonyl)-5-trifluoromethyl-benzoic acid

The title compound was prepared in analogy to example 84, from methyl 3-(morpholinosulfonyl)-5-(trifluoromethyl) benzoate after a reaction time of 2.5 hours. Dioxane was evaporated and the residue was diluted with water and the pH was adjusted to 1 using concentrated HCl. The resulting off-white suspension was filtered and washed with water. Colorless solid (75%). MS (ESI): m/z=338.03 [M−H]⁻.

b) Methyl 3-(morpholinosulfonyl)-5-(trifluoromethyl)benzoate

To a solution of methyl 3-(chlorosulfonyl)-5-(trifluoromethyl)benzoate (0.3 g, 991 µmol, Buttpark Ltd.) in CH₂Cl₂ (1.0 mL) were added DIPEA (192 mg, 260 µL, 1.49 mmol) and morpholine (86.4 mg, 86.4 µL, 991 µmol). The clear light yellow solution was stirred at room temperature for 1.3 hours and then poured on saturated aqueous NH₄Cl solution and CH₂Cl₂. The layers were separated and the aqueous layer was extracted twice with CH₂Cl₂. The organic layers were dried over MgSO₄, filtered, treated with silica gel and evaporated. Light brown solid (0.357 g; 91%). MS (EI): m/z=353 [M].

Example 257

3-Chloro-N-[4-(4-fluoro-2-methoxy-phenyl)-pyridin-3-yl]-5-methanesulfonyl-N-methyl-benzamide

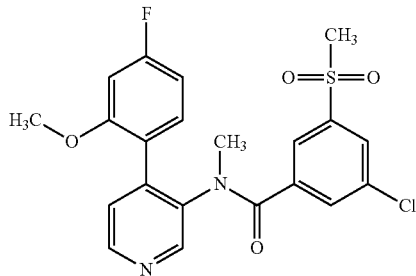 [SMILES: COc1cc(F)ccc1-c1ccncc1N(C)C(=O)c1cc(Cl)cc(S(C)(=O)=O)c1]

To a solution of L-proline (27.8 mg, 242 µmol) in DMSO (3 ml) was added sodium hydride (9.66 mg, 242 µmol, 60% dispersion in mineral oil). The mixture was stirred at room temperature for 30 minutes then copper(I)iodide (46.0 mg, 242 µmol) and N-[4-(4-fluoro-2-methoxy-phenyl)-pyridin-3-yl]-3-iodo-5-methanesulfonyl-N-methyl-benzamide (150 mg, 302 µmol) and sodium methanesulfonate (247 mg, 2.42 mmol) were added. The reaction mixture was stirred for 4 hours at 120° C. The reaction mixture was poured on 30 mL 10% aqueous NH₄Cl solution and 30 mL EtOAc and the layers were separated. The aqueous layer was extracted a second time with 30 mL EtOAc. The organic layers were washed with 30 mL brine, dried over MgSO₄, filtered and concentrated under vacuum. The residue was purified by silica gel chromatography on a 20 g column using an MPLC (Flashmaster) system eluting with a gradient of n-heptane:EtOAc (100:0 to 0:100). Light yellow solid (121 mg, 89.3%). MS (ESI): m/z=449.071 [M+H]⁺.

Intermediates a) N-[4-(4-Fluoro-2-methoxy-phenyl)-pyridin-3-yl]-3-iodo-5-methanesulfonyl-N-methyl-benzamide The title compound was prepared in analogy to example 90, from [4-(4-fluoro-2-methoxy-phenyl)-pyridin-3-yl]-methyl-amine (example 239, intermediate a) and 3-chloro-5-iodobenzoic acid after a reaction time of 18 hours at room temperature. The compound was purified by silica gel chromatography on a 20 g column using an MPLC (Flashmaster) system eluting with a gradient of CH₂Cl₂:MeOH (100:0 to 80:15). Light yellow solid (77%). MS (ESI): m/z=496.991 [M+H]⁺.

b) 3-Chloro-5-iodobenzoic acid

The title compound was prepared in analogy to example 84, from methyl 3-chloro-5-iodobenzoate after a reaction time of 3 hours. Colorless solid (100%). MS (ESI): m/z=280.888 [M−H]⁻.

Example 258

N-[4-(2-Benzyloxy-phenyl)-pyridin-3-yl]-3-methanesulfonyl-N-methyl-5-trifluoromethyl-benzamide

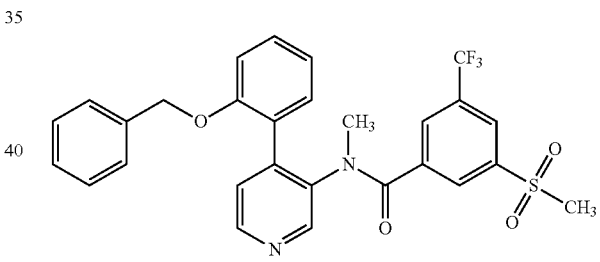

The title compound was prepared in analogy to example 90, from 4-(2-(benzyloxy)phenyl)-N-methylpyridin-3-amine and 3-(methylsulfonyl)-5-(trifluoromethyl)benzoic acid (example 114, intermediate a) after a reaction time of 18 hours at room temperature. The compound was purified by silica gel chromatography on a 50 g column using an MPLC system (CombiFlash Companion, Isco Inc.) eluting with a gradient of n-heptane:EtOAc (100:0 to 0:100). Light yellow foam (83%). MS (ESI): m/z=541.140 [M+H]⁺.

Intermediate 4-(2-(Benzyloxy)phenyl)-N-methylpyridin-3-amine

The title compound was prepared in analogy to example 72, from (4-iodo-pyridin-3-yl)-methyl-amine (example 36, intermediate b) and 2-(benzyloxy)phenylboronic acid after a reaction time of 18 hours at 90° C. The compound was purified by silica gel chromatography on a 20 g column using an MPLC system (CombiFlash Companion, Isco Inc.) eluting with a gradient of n-heptane:EtOAc (100:0 to 0:100). Light yellow oil (81%). MS (ESI): m/z=291.149 [M+H]⁺.

Example 259

3-(2-Azetidin-1-yl-ethylsulfanyl)-N-[4-(4-fluoro-2-methoxy-phenyl)-pyridin-3-yl]-N-methyl-5-trifluoromethyl-benzamide

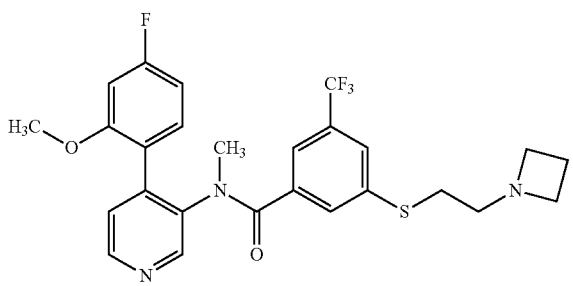 [SMILES: COc1cc(F)ccc1-c1ccncc1N(C)C(=O)c1cc(SCCN2CCC2)cc(C(F)(F)F)c1]

To an ice-cold solution of N-(4-(4-fluoro-2-methoxyphenyl)pyridin-3-yl)-3-(2-hydroxyethylthio)-N-methyl-5-(trifluoromethyl)benzamide (0.16 g, 333 µmol, example 216) in CH$_2$Cl$_2$ (2 mL) were added triethylamine (50.5 mg, 69.6 µL, 500 µmol) and methanesulfonyl chloride (38.1 mg, 25.8 µl-, 333 µmol) and the clear colorless solution was stirred at 0° C. for 3.75 hours. The reaction mixture was poured on saturated aqueous NaHCO$_3$ solution and CH$_2$Cl$_2$ and the layers were separated. The aqueous layer was extracted twice with CH$_2$Cl$_2$. The organic layers were washed once with brine, dried over MgSO$_4$, filtered, and evaporated. The intermediate mesylate was dissolved in isopropylacetate (2.0 mL), treated with azetidine (41.8 mg, 49.4 µL, 733 µmol) and heated to reflux (oil bath 95° C.) for 16 hours. The reaction mixture was poured on saturated aqueous NH$_4$Cl solution and EtOAc and the layers were separated. The aqueous layer was extracted twice with EtOAc. The organic layers were dried over MgSO4, filtered and evaporated. The product was purified by preparative HPLC (Gemini NX column) using a gradient of MeOH:water (containing 0.1% formic acid) (20:80 to 98:2). Colorless solid (0.055 g; 31%). MS (ESI): m/z=520.17 [M+H]$^+$.

Example 260

3-Cyclopropyl-N-[4-(4-fluoro-2-methoxy-phenyl)-pyridin-3-yl]-5-methanesulfonyl-N-methyl-benzamide

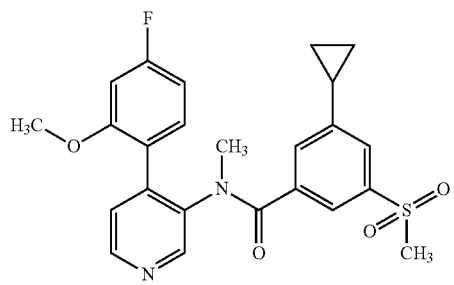 [SMILES: COc1cc(F)ccc1-c1ccncc1N(C)C(=O)c1cc(C2CC2)cc(S(C)(=O)=O)c1]

The title compound was prepared in analogy to example 90, from 3-cyclopropyl-5-methanesulfonyl-benzoic acid (119 mg, 495 µmol) and 4-(4-fluoro-2-methoxyphenyl)-N-methylpyridin-3-amine (example 129, intermediate) after a reaction time of 19.5 hours. The compound was purified by preparative HPLC (Gemini NX column) using a gradient of MeOH:water (containing 0.1% formic acid) (20:80 to 98:2). Off-white solid (0.082 g; 36%). MS (ESI): m/z=455.14 [M+H]$^+$.

Intermediates a) 3-Cyclopropyl-5-methanesulfonyl-benzoic acid

To a solution of methyl 3-chloro-5-(methylsulfonyl)benzoate (1.32 g, 5.31 mmol) in THF (15 mL) were added PEPPSI-IPr (72.1 mg, 106 µmol, CAS RN 905459-27-0), cyclopropylzine(II) bromide (0.5 M solution in THF, 25.5 mL, 12.7 mmol) and 1,3-dimethyl-2-imidazolidinone (3 mL) and the reaction mixture was heated to reflux for 22 hours before another batch of cyclopropylzine(II) bromide (0.5 M solution in THF, 12.7 mL, 6.37 mmol) was added. Stirring at reflux was continued for 22 hours. The reaction mixture was poured on saturated aqueous NH$_4$Cl solution and EtOAc and the layers were separated. The aqueous layer was extracted twice with EtOAc. The organic layers were washed once with saturated aqueous NaHCO$_3$ solution. The pH of the aqueous phase was adjusted to 1, saturated with solid sodium chloride and extracted three times with EtOAc. The organic layers were dried over MgSO$_4$, filtered and evaporated. The product was purified by preparative SFC (Waters Viridis SFC 2-Ethylpyridine column) using an isocratic mixture of MeOH:carbondioxide (40:60). Light brown solid (0.119 g; 9%). MS (ESI): m/z=239.0 [M+H]$^+$.

b) Methyl 3-chloro-5-(methylsulfonyl)benzoate

To a solution of L-proline (77.7 mg, 675 µmol) in DMSO (4 mL) was added sodium hydride (27.0 mg, 675 µmol, 60% dispersion in mineral oil) and the mixture was stirred at room temperature for 30 minutes before copper(I)iodide (128 mg, 675 µmol), methyl 3-chloro-5-iodobenzoate (0.25 g, 843 µmol) and sodium methanesulfinate (689 mg, 6.75 mmol) were added. The reaction mixture was heated to 120° C. in a sealed tube to give a turbid blue solution. After 2 hours the reaction mixture was allowed to cool down and was poured on saturated aqueous NaHCO$_3$ solution and EtOAc and filtered. The filtrate layers were separated and the aqueous layer was extracted twice with EtOAc. The organic layers were washed once with brine, dried over MgSO$_4$, filtered and evaporated. Light brown solid (0.135 g; 64%). MS (EI): m/z=248 [M].

Example 261

N-[4-(4-fluoro-2-methoxyphenyl)pyridin-3-yl]-N-methyl-3-{[2-(sulfamoylamino)ethyl]-sulfanyl}-5-(trifluoromethyl)benzamide

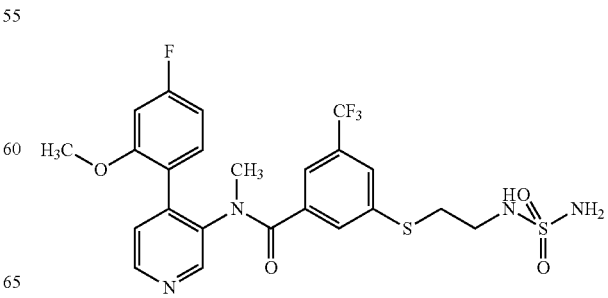

To a solution of 3-(2-aminoethylthio)-N-(4-(4-fluoro-2-methoxyphenyl)pyridin-3-yl)-N-methyl-5-(trifluoromethyl)benzamide (0.1 g, 209 µmol, example 237) in isopropylacetate (2 mL) was added sulfamide (80.2 mg, 834 µmol) and the mixture was heated at reflux for 23 hours while the solvent was vaporized. The product was purified by preparative HPLC (Gemini NX column) using a gradient of MeOH:water (containing 0.1% formic acid) (20:80 to 98:2). Colorless foam (0.067 g; 57%). MS (ESI): m/z=559.11 [M+H]+.

Example 262

N-[4-(4-Fluoro-2-methoxy-phenyl)-pyridin-3-yl]-3-(2-methanesulfonylamino-ethylsulfanyl)-N-methyl-5-trifluoromethyl-benzamide

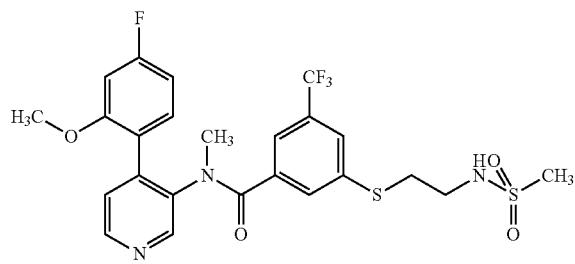

To an ice-cold solution of 3-(2-aminoethylthio)-N-(4-(4-fluoro-2-methoxyphenyl)pyridin-3-yl)-N-methyl-5-(trifluoromethyl)benzamide (0.12 g, 250 µmol, example 237) and DIPEA (64.7 mg, 87.4 µL, 501 µmol) in CH$_2$Cl$_2$ (2 mL) was added methanesulfonyl chloride (35.8 mg, 24.4 µL, 313 µmol) and the clear colorless solution was stirred at 0° C. for 2.5 hours. The reaction mixture was poured on saturated aqueous NH$_4$Cl solution and CH$_2$Cl$_2$ and the layers were separated. The aqueous layer was extracted three times with CH$_2$Cl$_2$. The organic layers were dried over MgSO$_4$, filtered, treated with silica gel and evaporated. The compound was purified by silica gel chromatography on a 5 g column using an MPLC system eluting with a gradient of n-heptane:EtOAc (100:0 to 0:100). Colorless foam (0.121 g; 86%). MS (ESI): m/z=558.11 [M+H]+.

Example 263

3-Methanesulfonyl-N-[4-(2-methoxy-phenyl)-pyridin-3-yl]-N-methyl-5-trifluoromethyl-benzamide

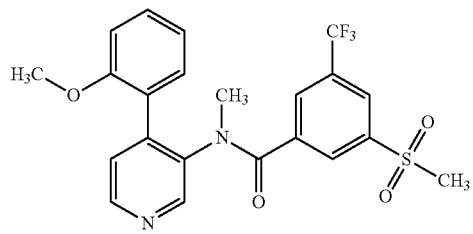

To a solution of N-[4-(2-hydroxy-phenyl)-pyridin-3-yl]-3-methanesulfonyl-N-methyl-5-trifluoromethyl-benzamide (40 mg, 88.8 µmol) in DMF (1 ml) was added K$_2$CO$_3$ (24.5 mg, 178 µmol) and methyliodide (13.9 mg, 6.09 µl, 97.7 µmol). The reaction mixture was stirred at room temperature for 2 hours. The reaction mixture was poured on 30 mL 10% aqueous NaHCO$_3$ solution and 30 mL EtOAc and the layers were separated. The aqueous layer was extracted a second time with 30 mL EtOAc. The organic layers were washed with 30 mL brine, dried over MgSO$_4$, filtered and concentrated under vacuum. The residue was purified by silica gel chromatography on a 5 g column using an MPLC (Flashmaster) system eluting with a gradient of n-heptane:EtOAc (100:0 to 0:100). Colorless foam (28 mg, 68%). MS (ESI): m/z=465.108 [M+H]+.

Intermediate a) N-[4-(2-Hydroxy-phenyl)-pyridin-3-yl]-3-methanesulfonyl-N-methyl-5-trifluoromethyl-benzamide To a solution of N-[4-(2-benzyloxy-phenyl)-pyridin-3-yl]-3-methanesulfonyl-N-methyl-5-trifluoromethyl-benzamide (200 mg, 370 µmol, example 258) in MeOH (2 mL) and EtOAc (2.00 mL) was added 10% palladium on charcoal (30 mg, 370 µmol) under argon atmosphere. The reaction was evacuated and purged with hydrogen gas. The reaction was stirred for 5 hours at 1.7 bar under H$_2$ atmosphere. The reaction mixture was filtered over dicalite and the filtrate was concentrated under vacuum. The residue was purified by silica gel chromatography on a 20 g column using an MPLC (Flashmaster) system eluting with a gradient of n-heptane:EtOAc (100:0 to 0:100). Colorless foam (150 mg, 90%). MS (ESI): m/z=451.094 [M+H]+.

Example 264

N-[4-(5-Fluoro-2-methyl-phenyl)-6-methyl-pyridin-3-yl]-3-methanesulfonyl-N-methyl-5-trifluoromethyl-benzamide

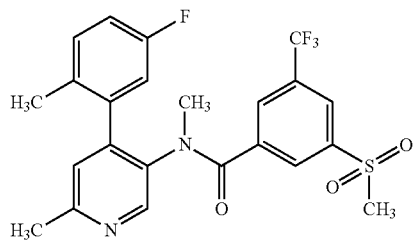 [SMILES: Cc1cc(-c2cc(F)ccc2C)c(N(C)C(=O)c2cc(C(F)(F)F)cc(S(C)(=O)=O)c2)cn1]

To a solution of N-(6-chloro-4-(5-fluoro-2-methylphenyl)pyridin-3-yl)-N-methyl-3-(methylsulfonyl)-5-(trifluoromethyl)benzamide (0.055 g, 110 µmol, example 253) in THF (1.5 mL) were added methylzinc(II) chloride (82.4 µL, 165 µmol), 1,3-dimethyl-2-imidazolidinone (DMI) (0.3 mL) and PEPPSI-IPr (1.49 mg, 2.2 µmol, CAS RN 905459-27-0) and the clear solution was stirred at 50° C. for 2 hours. The reaction mixture was poured on 10% aqueous citric acid solution and EtOAc and the layers were separated. The aqueous layer was extracted twice with EtOAc. The organic layers were washed once with brine, dried over MgSO$_4$, filtered, treated with silica gel and evaporated. The compound was purified by silica gel chromatography on a 5 g column using an MPLC system eluting with a gradient of n-heptane:EtOAc (100:0 to 100:100). The product was purified by preparative HPLC (Gemini NX column) using a gradient of MeOH: water (containing 0.05% triethylamine) (20:80 to 98:2). Colorless foam (0.022 g; 41%). MS (ESI): m/z=481.12 [M+H]⁺.

Example 265

3-(2-Azetidin-1-yl-ethanesulfonyl)-N-[4-(4-fluoro-2-methoxy-phenyl)-pyridin-3-yl]-N-methyl-5-trifluoromethyl-benzamide

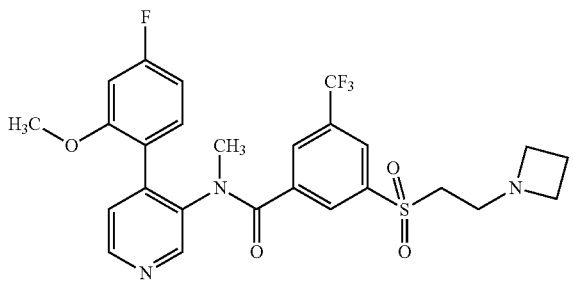 [SMILES: COc1cc(F)ccc1-c1ccncc1N(C)C(=O)c1cc(C(F)(F)F)cc(S(=O)(=O)CCN2CCC2)c1]

To an ice-cold solution of 3-(2-(azetidin-1-yl)ethylthio)-N-(4-(4-fluoro-2-methoxyphenyl)-pyridin-3-yl)-N-methyl-5-(trifluoromethyl)benzamide (0.05 g, 96.2 μmol, example 259) in MeOH (2 mL) and water (0.5 mL) was added Oxone® (148 mg, 241 μmol) and the white suspension was stirred at room temperature for 3 hours. The reaction mixture was poured on 10% aqueous $Na_2S_2O_3$ solution and EtOAc and the layers were separated. The aqueous layer was extracted twice with EtOAc. The organic layers were washed once with brine, dried over $MgSO_4$, filtered, treated with silica gel and evaporated. The crude product was purified by preparative HPLC (Gemini NX column) using a gradient of MeOH:water (containing 0.05% triethylamine) (20:80 to 98:2). Colorless solid (0.017 g; 32%). MS (ESI): m/z=552.16 [M+H]⁺.

Example 266

3-(3-{[4-(4-Fluoro-2-methoxy-phenyl)-pyridin-3-yl]-methyl-carbamoyl}-5-trifluoromethyl-phenyl)-propionic acid ethyl ester

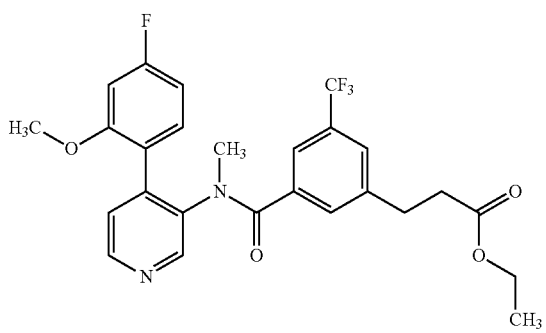 [SMILES: CCOC(=O)CCc1cc(C(=O)N(C)c2cnccc2-c2ccc(F)cc2OC)cc(C(F)(F)F)c1]

To a solution of 3-bromo-N-(4-(4-fluoro-2-methoxyphenyl)pyridin-3-yl)-N-methyl-5-(trifluoromethyl)benzamide (0.1 g, 207 example 216, intermediate c) in DMF (1 mL) were added 3,3-diethoxyprop-1-ene (80.8 mg, 95.1 μL, n-tributylamine (76.7 mg, 98.7 μL, 414 μmol), tetrabutylammonium chloride (57.5 mg, 207 μmol) and palladium (II) acetate (1.39 mg, 6.21 μmol) and the light brown solution was stirred at 90° C. for 25 hours. The reaction mixture was poured on aqueous 1M HCl solution and EtOAc and the layers were separated. The aqueous layer was extracted twice with EtOAc. The organic layers were washed once with brine, dried over $MgSO_4$, filtered, treated with silica gel and evaporated. The compound was purified by silica gel chromatography on a 20 g column using an MPLC system eluting with a gradient of n-heptane:EtOAc (100:0 to 0:100). The product was purified by preparative HPLC (Gemini NX column) using a gradient of MeOH:water (containing 0.05% triethylamine) (20:80 to 98:2). Colorless gum (0.015 g; 12%). MS (ESI): m/z=[M+H]⁺.

Example 267

N-[4-(2-Benzyloxy-4-fluoro-phenyl)-pyridin-3-yl]-3-methanesulfonyl-N-methyl-5-trifluoromethyl-benzamide

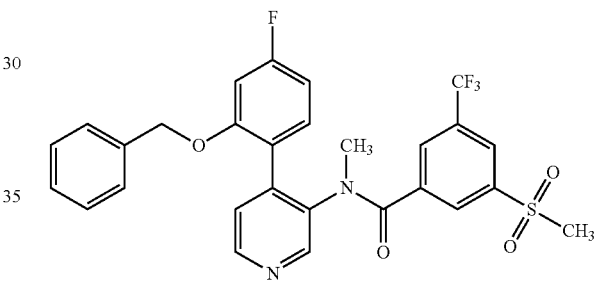

The title compound was prepared in analogy to example 90, from 4-(2-(benzyloxy)-4-fluorophenyl)-N-methylpyridin-3-amine and 3-(methylsulfonyl)-5-(trifluoromethyl)benzoic acid (example 114, intermediate a) after a reaction time of 18 hours at room temperature. The compound was purified by silica gel chromatography on a 50 g column using an MPLC system (CombiFlash Companion, Isco Inc.) eluting with a gradient of n-heptane:EtOAc (100:0 to 0:100). Light brown foam (637 mg, 69%). MS (ESI): m/z=559.131 [M+H]⁺.

Intermediate a) 4-(2-(Benzyloxy)-4-fluorophenyl)-N-methylpyridin-3-amine

The title compound was prepared in analogy to example 72, from (4-iodo-pyridin-3-yl)-methyl-amine (example 36, intermediate b) and 2-(benzyloxy)-4-fluorophenylboronic acid after a reaction time of 72 hours at 90° C. The compound was purified by silica gel chromatography on a 50 g column using an MPLC system (CombiFlash Companion, Isco Inc.) eluting with a gradient of n-heptane:EtOAc (100:0 to 0:100). Light yellow solid (79%). MS (ESI): m/z=309.140 [M+H]⁺.

Example 268

3-(3-{[4-(4-Fluoro-2-methoxy-phenyl)-pyridin-3-yl]-methyl-carbamoyl}-5-trifluoromethyl-phenylsulfanyl)-azetidine-1-carboxylic acid tert-butyl ester

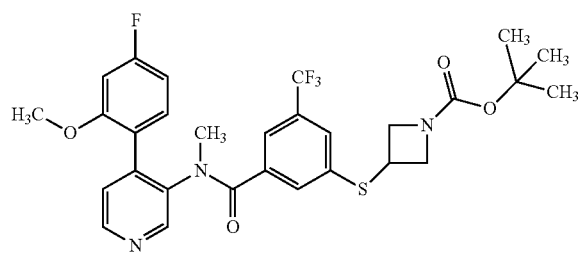 [SMILES: COc1cc(F)ccc1-c1ccncc1N(C)C(=O)c1cc(SC2CN(C(=O)OC(C)(C)C)C2)cc(C(F)(F)F)c1]

To a suspension of N-(4-(4-fluoro-2-methoxyphenyl)pyridin-3-yl)-3-mercapto-N-methyl-5-(trifluoromethyl)benzamide (0.35 g, 802 µmol, example 216, intermediate a) in acetonitrile (4 mL) was added DIPEA (259 mg, 350 µL, 2.00 mmol). The instantly formed yellow solution was treated with tert-butyl 3-iodoazetidine-1-carboxylate (284 mg, 1.0 mmol) and heated to reflux for 75 minutes. The reaction mixture was poured on saturated aqueous NH$_4$Cl solution and EtOAc and the layers were separated. The aqueous layer was extracted twice with EtOAc. The organic layers were dried over MgSO$_4$, filtered, treated with silica gel and evaporated. The compound was purified by silica gel chromatography on a 10 g column using an MPLC system eluting with a gradient of n-heptane: EtOAc (100:0 to 0:100). Colorless foam (0.405 g; 85%). MS (ESI): m/z=592.19 [M+H]$^+$.

Example 269

N-[4-(4-fluoro-2-methoxyphenyl)pyridin-3-yl]-N-methyl-3-{[2-(sulfamoylamino)ethyl]-sulfonyl}-5-(trifluoromethyl)benzamide

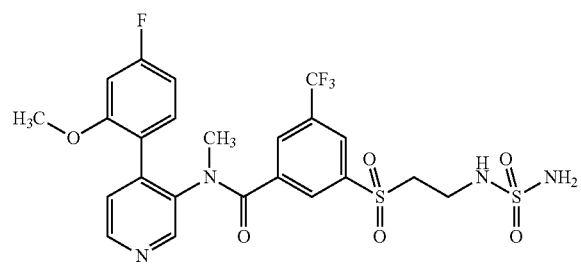 [SMILES: COc1cc(F)ccc1-c1ccncc1N(C)C(=O)c1cc(C(F)(F)F)cc(S(=O)(=O)CCNS(N)(=O)=O)c1]

To an ice-cold solution of N-(4-(4-fluoro-2-methoxyphenyl)pyridin-3-yl)-N-methyl-3-(2-(sulfamoylamino)ethylthio)-5-(trifluoromethyl)benzamide (0.058 g, 104 µmol, example 261) in MeOH (2 mL) and water (0.5 mL) was added oxone (160 mg, 260 µmol) and the white suspension was stirred at room temperature for 3.5 hours. The reaction mixture was poured on 10% aqueous Na$_2$S$_2$O$_3$ solution and EtOAc and the layers were separated. The aqueous layer was extracted twice with EtOAc. The organic layers were washed once with brine, dried over MgSO$_4$, filtered, treated with silica gel and evaporated. The crude product was purified by preparative HPLC (Gemini NX column) using a gradient of MeOH:water (containing 0.1% formic acid) (20:80 to 98:2). Colorless solid (0.047 g; 76%). MS (ESI): m/z=591.10 [M+H]$^+$.

Example 270

N-[4-(4-Fluoro-2-methoxy-phenyl)-pyridin-3-yl]-3-(2-methanesulfonylamino-ethanesulfonyl)-N-methyl-5-trifluoromethyl-benzamide

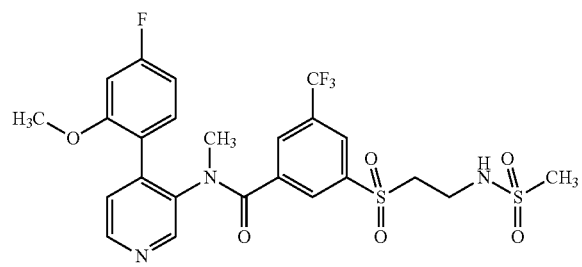

To an ice-cold solution of N-(4-(4-fluoro-2-methoxyphenyl)pyridin-3-yl)-N-methyl-3-(2-(methylsulfonamido)ethylthio)-5-(trifluoromethyl)benzamide (0.105 g, 188 µmol, example 262) in MeOH (3 mL) and water (0.6 mL) was added Oxone® (289 mg, 471 µmol) and the white suspension was stirred at room temperature for 4 hours. The reaction mixture was poured on 10% aqueous Na$_2$S$_2$O$_3$ solution and EtOAc and the layers were separated. The aqueous layer was extracted twice with EtOAc. The organic layers were washed once with brine, dried over MgSO4, filtered, treated with silica gel and evaporated. The crude product was purified by preparative HPLC (Gemini NX column) using a gradient of MeOH:water (containing 0.1% formic acid) (20:80 to 98:2). Colorless foam (0.094 g; 84%). MS (ESI): m/z=590.10 [M+H]$^+$.

Example 271

3-(2-Hydroxy-ethylamino)-N-methyl-N-(4-o-tolyl-pyridin-3-yl)-5-trifluoromethyl-benzamide

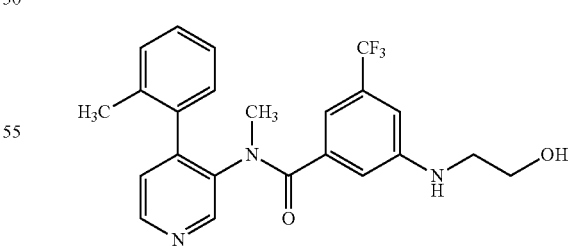

The title compound was prepared in analogy to example 85, intermediate c, from 3-amino-N-methyl-N-(4-o-tolylpyridin-3-yl)-5-(trifluoromethyl)benzamide (example 164) and 2-bromoethanol after a reaction time of 48 hours at 80° C. Light yellow oil (11%). MS (ESI): m/z=430.175 [M+H]$^+$.

Example 272

3-Methanesulfonyl-N-methyl-N-{4-[2-(oxetan-3-yloxy)-phenyl]-pyridin-3-yl}-5-trifluoromethyl-benzamide

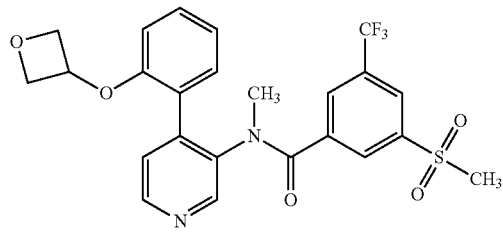 [SMILES: CN(C(=O)c1cc(C(F)(F)F)cc(S(C)(=O)=O)c1)c1cnccc1-c1ccccc1OC1COC1]

To a solution N-(4-(2-hydroxyphenyl)pyridin-3-yl)-N-methyl-3-(methylsulfonyl)-5-(trifluoromethyl)benzamide (100 mg, 222 µmol, example 263, intermediate a) in DMF (2 ml) was added K$_2$CO$_3$ (61.4 mg, 444 µmol) and 3-iodooxetane (44.9 mg, 244 µmol). The reaction mixture was stirred for 18 hours at 80° C. The reaction mixture was poured on 30 mL 10% aqueous NaHCO$_3$ solution and 30 mL EtOAc and the layers were separated. The aqueous layer was extracted a second time with 30 mL EtOAc. The organic layers were washed with 30 mL brine, dried over MgSO$_4$, filtered and concentrated under vacuum. The compound was purified by silica gel chromatography on a 20 g column using an MPLC (Flashmaster) system eluting with a gradient of n-heptane:EtOAc (100:0 to 0:100). Colorless foam (52 mg, 46%). MS (ESI): m/z=507.120 [M+H]$^+$.

Example 273

N-[4-(4-Fluoro-2-methoxy-phenyl)-pyridin-3-yl]-3-methanesulfonyl-N-(tetrahydro-furan-3-ylmethyl)-5-trifluoromethyl-benzamide

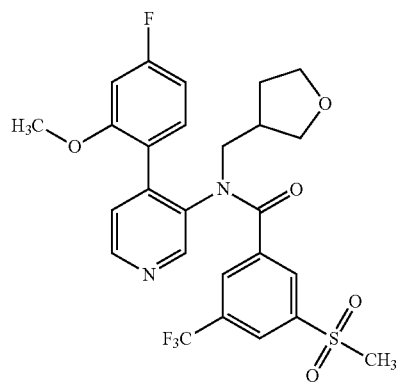

The title compound was prepared in analogy to example 90, from [4-(4-fluoro-2-methoxy-phenyl)-pyridin-3-yl]-(tetrahydro-furan-3-ylmethyl)-amine and 3-(methylsulfonyl)-5-(trifluoromethyl)benzoic acid (example 114, intermediate a) after a reaction time of 72 hours at room temperature. The compound was purified by silica gel chromatography on a 20 g column using an MPLC (Flashmaster) system eluting with a gradient of n-heptane:EtOAc (100:0 to 0:100). The resulting brown oil was further purification by preparative HPLC (Gemini NX) with a gradient of MeOH:water (containing 0.05% formic acid) (80:20 to 98:2). Colorless foam (11%). MS (ESI): m/z=553.141 [M+H]$^+$.

Intermediate a) [4-(4-Fluoro-2-methoxy-phenyl)-pyridin-3-yl]-(tetrahydro-furan-3-ylmethyl)-amine The title compound was prepared in analogy to example 85, intermediate a, from tert-butyl 4-(4-fluoro-2-methoxyphenyl)pyridin-3-yl((tetrahydrofuran-3-yl)methyl)carbamate after a reaction time of 2 hours at room temperature. Light yellow foam (99%). MS (ESI): m/z=303.150 [M+H]$^+$.

b) tert-Butyl 4-(4-fluoro-2-methoxyphenyl)pyridin-3-yl((tetrahydrofuran-3-yl)methyl)carbamate The title compound was prepared in analogy to example 72, from tert-butyl 4-iodopyridin-3-yl((tetrahydrofuran-3-yl)methyl)carbamate and 4-fluoro-2-methoxyphenylboronic acid after a reaction time of 18 hours at 90° C. The compound was purified by silica gel chromatography on a 20 g column using an MPLC system (CombiFlash Companion, Isco Inc.) eluting with a gradient of n-heptane:EtOAc (100:0 to 0:100). Light yellow oil (79%). MS (ESI): m/z=403.203 [M+H]$^+$.

c) tert-Butyl 4-iodopyridin-3-yl((tetrahydrofuran-3-yl)methyl)carbamate

The title compound was prepared in analogy to example 85, intermediate c, from tert-butyl 4-iodopyridin-3-ylcarbamate (example 85, intermediate d) and 3-(bromomethyl)tetrahydrofuran (567 mg, 3.44 mmol) after a reaction time of 18 hours at 60° C. The compound was purified by silica gel chromatography on a 50 g column using an MPLC (Flashmaster) system eluting with a gradient of n-heptane:EtOAc (100:0 to 0:100). Light yellow solid (883 mg, 69.9%). MS (ESI): m/z=405.064 [M+H]$^+$.

Example 274

3-Methanesulfonyl-N-methyl-N-[4-(2-trifluoromethoxy-phenyl)-pyridin-3-yl]-5-trifluoromethyl-benzamide

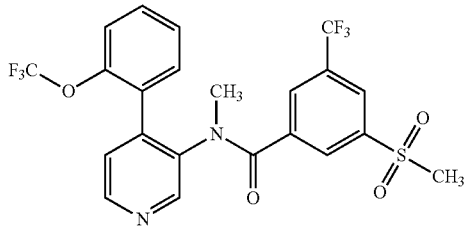 [SMILES: CN(C(=O)c1cc(C(F)(F)F)cc(S(C)(=O)=O)c1)c1cnccc1-c1ccccc1OC(F)(F)F]

The title compound was prepared in analogy to example 90, from methyl-[4-(2-trifluoromethoxy-phenyl)-pyridin-3-yl]-amine and 3-(methylsulfonyl)-5-(trifluoromethyl)-benzoic acid (example 114, intermediate a) after a reaction time of 18 hours at room temperature. The compound was purified by silica gel chromatography on a 20 g column using an MPLC system (CombiFlash Companion, Isco Inc.)

eluting with a gradient of n-heptane:EtOAc (100:0 to 0:100). Light red foam (39%). MS (ESI): m/z=519.081 [M+H]⁺.

Intermediate

Methyl-[4-(2-trifluoromethoxy-phenyl)-pyridin-3-yl]-amine

The title compound was prepared in analogy to example 72, from (4-iodo-pyridin-3-yl)-methyl-amine (example 36, intermediate b) and 2-(trifluoromethoxy)phenylboronic acid after a reaction time of 7 hours at 90° C. The compound was purified by silica gel chromatography on a 50 g column using an MPLC system (CombiFlash Companion, Isco Inc.) eluting with a gradient of n-heptane:EtOAc (100:0 to 0:100). Light brown solid (91%). MS (ESI): m/z=269.090 [M+H]⁺.

Example 275

3-(Azetidin-3-ylsulfanyl)-N-[4-(4-fluoro-2-methoxy-phenyl)-pyridin-3-yl]-N-methyl-5-trifluoromethyl-benzamide

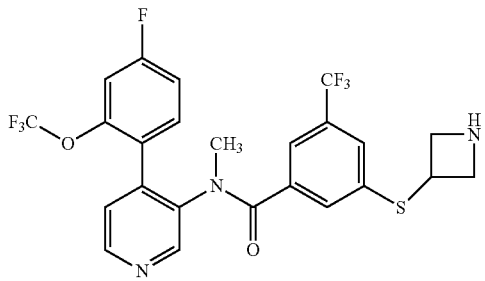 [SMILES: CN(C(=O)c1cc(SC2CNC2)cc(C(F)(F)F)c1)c1cnccc1-c1ccc(F)cc1OC(F)(F)F]

The title compound was prepared in analogy to example 85, intermediate a, from tert-butyl 3-(3-44-(4-fluoro-2-methoxyphenyl)pyridin-3-yl)(methyl)carbamoyl)-5-(trifluoromethyl)-phenylthio)azetidine-1-carboxylate (example 268) after a reaction time of 1.25 hours. The compound was purified by preparative HPLC (Gemini NX column) using a gradient of MeOH:water (containing 0.1% formic acid) (20:80 to 98:2). Colorless foam (81%). MS (ESI): m/z=492.14 [M+H]⁺.

Example 276

N-[4-(5-Fluoro-2-methyl-phenyl)-pyridin-3-yl]-3-methanesulfonyl-N-methyl-5-trifluoromethyl-benzamide

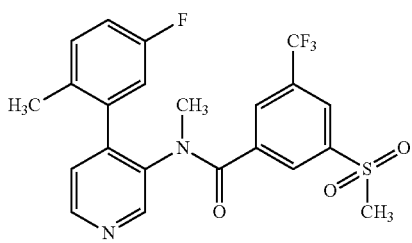 [SMILES: Cc1ccc(F)cc1-c1ccncc1N(C)C(=O)c1cc(C(F)(F)F)cc(S(C)(=O)=O)c1]

The title compound was prepared in analogy to example 90, from [4-(5-fluoro-2-methyl-phenyl)-pyridin-3-yl]-methyl-amine and 3-(methylsulfonyl)-5-(trifluoromethyl) benzoic acid (example 114, intermediate a) after a reaction time of 20.5 hours. The compound was purified by preparative HPLC (Gemini NX column) using a gradient of MeOH: water (containing 0.1% formic acid) (20:80 to 98:2). Colorless foam (20%). MS (ESI): m/z=467.10 [M+H]⁺.

Intermediate

[4-(5-Fluoro-2-methyl-phenyl)-pyridin-3-yl]-methyl-amine

A solution of 6-chloro-4-(5-fluoro-2-methylphenyl)-N-methylpyridin-3-amine (0.2 g, 798 µmol, example 253, intermediate a) in EtOAc (1 mL) and MeOH (1.0 mL) under argon was treated with palladium on carbon (21.2 mg, 19.9 µmol) and stirred under an hydrogen atmosphere (0.5 bar overpressure) for 4 hours. Stirring was continued overnight at room temperature. The reaction mixture was filtered over Dicalite and evaporated. The residue was taken up in CH₂Cl₂ and saturated aqueous NaHCO₃ solution and the layers were separated. The aqueous layer was extracted three times with CH₂Cl₂. The organic layers were dried over MgSO₄, filtered and evaporated. Light brown solid (0.16 g; 92%). MS (ESI): m/z=217.11 [M+H]⁺.

Example 277

N-[4-(2-Cyclobutoxy-phenyl)-pyridin-3-yl]-3-methanesulfonyl-N-methyl-5-trifluoromethyl-benzamide

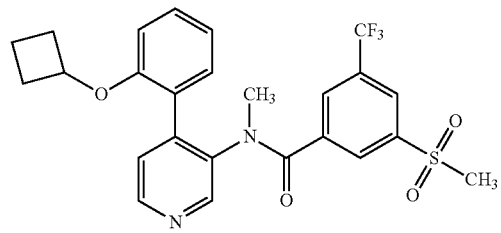 [SMILES: CN(C(=O)c1cc(C(F)(F)F)cc(S(C)(=O)=O)c1)c1cnccc1-c1ccccc1OC1CCC1]

To a solution N-(4-(2-hydroxyphenyl)pyridin-3-yl)-N-methyl-3-(methylsulfonyl)-5-(trifluoromethyl)benzamide (100 mg, 222 µmol, example 263, intermediate a) in DMF (2 mL) was added K₂CO₃ (61.4 mg, 444 µmol) and cyclobutylbromide (33.0 mg, 244 µmol). The reaction mixture was stirred for 2 hours at room temperature. The reaction mixture was stirred for 18 hours at 80° C. The reaction mixture was poured on 30 mL 10% aqueous NaHCO₃ solution and 30 mL EtOAc and the layers were separated. The aqueous layer was extracted a second time with 30 mL EtOAc. The organic layers were washed with 30 mL brine, dried over MgSO₄, filtered and concentrated under vacuum. The compound was purified by silica gel chromatography on a 20 g column using an MPLC (Flashmaster) system eluting with a gradient of n-heptane:EtOAc (100:0 to 0:100). A second purification step using preparative HPLC (Gemini NX column) with a gradient of MeOH:water (containing 0.05% formic acid) (80:20 to 98:2) furnished the desired compound as a colorless foam (39 mg, 35%). MS (ESI): m/z=505.141 [M+H]⁺.

Example 278

N-[4-(2-Chloro-phenyl)-pyridin-3-yl]-3-methanesulfonyl-N-methyl-5-trifluoromethyl-benzamide

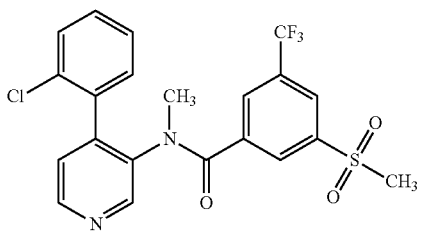 [SMILES: CN(C(=O)c1cc(C(F)(F)F)cc(S(C)(=O)=O)c1)c1cnccc1-c1ccccc1Cl]

The title compound was prepared in analogy to example 90, from [4-(2-chloro-phenyl)-pyridin-3-yl]-methyl-amine (prepared according to DE10008042) and 3-(methylsulfonyl)-5-(trifluoromethyl)benzoic acid (example 114, intermediate a) after a reaction time of 18 hours at room temperature. The compound was purified by silica gel chromatography on a 20 g column using an MPLC system (CombiFlash Companion, Isco Inc.) eluting with a gradient of n-heptane:EtOAc (100:0 to 0:100). Another purification step using preparative HPLC (Gemini NX column) with a gradient of MeOH: water (containing 0.05% formic acid) (80:20 to 98:2) gave the desired compound as a colorless foam (26%). MS (ESI): m/z=469.060 [M+H]$^+$.

Example 279

3-Methanesulfonyl-N-methyl-N-[2-(2,2,2-trifluoro-ethoxy)-[3,4']bipyridinyl-3'-yl]-5-trifluoromethyl-benzamide

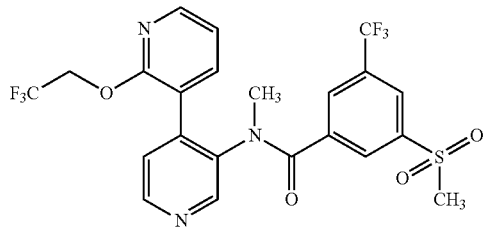 [SMILES: CN(C(=O)c1cc(C(F)(F)F)cc(S(C)(=O)=O)c1)c1cnccc1-c1cccnc1OCC(F)(F)F]

The title compound was prepared in analogy to example 90, from methyl-[2-(2,2,2-trifluoro-ethoxy)-[3,4']bipyridinyl-3'-yl]-amine and 3-(methylsulfonyl)-5-(trifluoromethyl)-benzoic acid (example 114, intermediate a) after a reaction time of 18 hours. The reaction mixture was poured on saturated aqueous NH$_4$Cl solution and CH$_2$Cl$_2$ and the layers were separated. The aqueous layer was extracted three times with CH$_2$Cl$_2$. The organic layers were dried over MgSO$_4$, filtered, treated with silica gel and evaporated. The compound was purified by silica gel chromatography on a 20 g column using an MPLC (ISCO) system eluting with EtOAc (isocratic). Further purification by preparative HPLC (Gemini NX column) using a gradient of MeOH:water (containing 0.1% formic acid) (20:80 to 98:2). Colorless foam (41%). MS (ESI): m/z=534.09 [M+H]$^+$.

Intermediate

Methyl-[2-(2,2,2-trifluoro-ethoxy)-[3,4']bipyridinyl-3'-yl]-amine

The title compound was prepared in analogy to example 72, from 4-iodo-N-methylpyridin-3-amine (example 98, intermediate b) and 2-(2,2,2-trifluoroethoxy)pyridin-3-yl-boronic acid after a reaction time of 5 hours at 90° C. The compound was purified by silica gel chromatography on a 10 g column using a MPLC system eluting with a gradient of n-heptane:EtOAc (100:0 to 0:100). Colorless oil (76%). MS (ESI): m/z=284.10 [M+H]$^+$.

Example 280

3-(Azetidine-3-sulfonyl)-N-[4-(4-fluoro-2-methoxy-phenyl)-pyridin-3-yl]-N-methyl-5-trifluoromethyl-benzamide

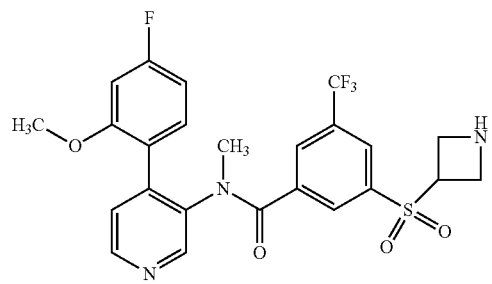 [SMILES: COc1cc(F)ccc1-c1ccncc1N(C)C(=O)c1cc(C(F)(F)F)cc(S(=O)(=O)C2CNC2)c1]

To an ice-cold solution of 3-(azetidin-3-ylthio)-N-(4-(4-fluoro-2-methoxyphenyl)pyridin-3-yl)-N-methyl-5-(trifluoromethyl)benzamide (0.257 g, 523 µmol, example 275) in MeOH (6 mL) and water was added Oxone® (804 mg, 1.31 mmol) and stirring was continued at room temperature for 3.5 hours. The reaction mixture was poured on 10% aqueous Na$_2$S$_2$O$_3$ solution and EtOAc and the layers were separated. The aqueous layer was saturated with sodium chloride, extracted eight times with EtOAc. The organic layers were washed once with brine, dried over MgSO4, filtered and evaporated. The product (43 mg) was purified by preparative HPLC (Gemini NX column) using a gradient of MeOH: water (containing 0.05% triethylamine) (20:80 to 98:2). Colorless solid (0.135 g; 49%). MS (ESI): m/z=524.13 [M+H]$^+$.

Example 281

3-(2-Carbamoyl-ethyl)-N-[4-(4-fluoro-2-methoxy-phenyl)-pyridin-3-yl]-N-methyl-5-trifluoromethyl-benzamide

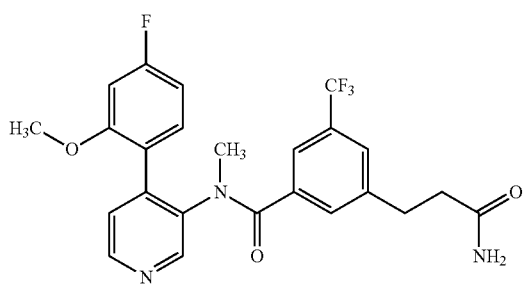 [SMILES: COc1cc(F)ccc1-c1ccncc1N(C)C(=O)c1cc(CCC(N)=O)cc(C(F)(F)F)c1]

The title compound was prepared in analogy to example 117, from 3-(3-((4-(4-fluoro-2-methoxyphenyl)pyridin-3-yl)(methyl)carbamoyl)-5-(trifluoromethyl)phenyl)propanoic after a reaction time of 18 hours. The compound was purified by silica gel chromatography on a 10 g column using an MPLC system eluting with a gradient of CH₂Cl₂:MeOH (100:0 to 90:10). Colorless foam (38%). MS (ESI): m/z=476.16 [M+H]⁺.

Intermediate 3-(3-{[4-(4-Fluoro-2-methoxy-phenyl)-pyridin-3-yl]-methyl-carbamoyl}-5-trifluoromethyl-phenyl)-propionic acid To a solution of 3-bromo-N-(4-(4-fluoro-2-methoxyphenyl)pyridin-3-yl)-N-methyl-5-(trifluoromethyl)benzamide (0.4 g, 828 µmol, example 216, intermediate c) in DMF (4.0 mL) were added 3,3-diethoxyprop-1-ene (323 mg, 380 µL, 2.48 mmol), n-tributylamine (921 mg, 1.18 mL, 4.97 mmol), tetrabutylammonium chloride (230 mg, 828 µmol) and palladium (II) acetate (13.9 mg, 62.1 µmol) and the light brown solution was stirred at 90° C. for 72 hours. The reaction mixture was poured on aqueous 1M HCl solution and EtOAc and the layers were separated. The aqueous layer was extracted twice with EtOAc. The organic layers were washed once with brine, dried over MgSO₄, filtered, treated with silica gel and evaporated. The compound was purified by silica gel chromatography on a 10 g column using an MPLC system eluting with a gradient of n-heptane:EtOAc (100:0 to 0:100). The crude product was dissolved in dioxane (4.0 mL) and water (4.0 mL) and lithium hydroxide monohydrate (34.7 mg, 828 µmol) was added. The product was purified by preparative HPLC (Gemini NX column) using a gradient of MeOH:water (containing 0.1% formic acid) (20:80 to 98:2), followed by a second chromatography on a 10 g silica gel column using an MPLC (Flasmaster) system eluting with a gradient of CH₂Cl₂:MeOH (100:0 to 90:10). Colorless foam (0.139 g; 35%). MS (ESI): m/z=477.14 [M+H]⁺.

Example 282

N-[4-(4-Fluoro-2-methoxy-phenyl)-pyridin-3-yl]-3-(1-methanesulfonyl-azetidine-3-sulfonyl)-N-methyl-5-trifluoromethyl-benzamide

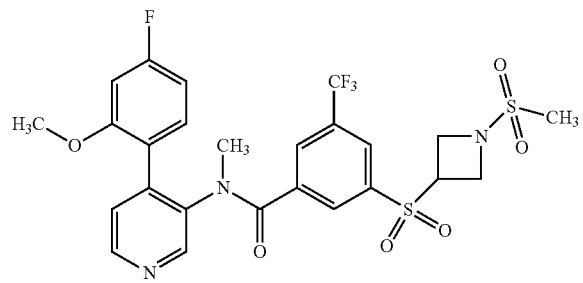

To an ice-cold solution of 3-(azetidin-3-ylsulfonyl)-N-(4-(4-fluoro-2-methoxyphenyl)-pyridin-3-yl)-N-methyl-5-(trifluoromethyl)benzamide (0.05 g, 95.5 µmol, example 280) and DIPEA (24.7 mg, 33.4 µL, 191 µmol) in CH₂Cl₂ (1 mL) was added methanesulfonyl chloride (16.4 mg, 11.2 µL, 143 µmol) and stirring was continued in an ice-bath for 1.75 hours. The reaction mixture was poured on saturated aqueous NH₄Cl solution and CH₂Cl₂ and the layers were separated. The aqueous layer was extracted twice with CH₂Cl₂. The organic layers were dried over MgSO₄, filtered, treated with silica gel and evaporated. The compound was purified by silica gel chromatography on a 5 g column using an MPLC system eluting with a gradient of n-heptane:EtOAc (100:0 to 0:100). Colorless solid (0.044 g; 76%). MS (ESI): m/z=602.10 [M+H]⁺.

Example 283

N-[4-(4-Fluoro-2-methoxy-phenyl)-pyridin-3-yl]-3-methanesulfonyl-N-(5-methyl-oxazol-2-ylmethyl)-5-trifluoromethyl-benzamide

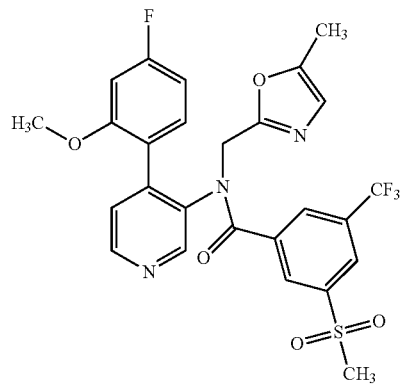 [SMILES: COc1cc(F)ccc1-c1ccncc1N(Cc1ncc(C)o1)C(=O)c1cc(C(F)(F)F)cc(S(C)(=O)=O)c1]

The title compound was prepared in analogy to example 90, from 4-(4-fluoro-2-methoxyphenyl)-N-((5-methyloxazol-2-yl)methyl)pyridin-3-amine (example 231, intermediate) and 3-(methylsulfonyl)-5-(trifluoromethyl)benzoic acid (example 114, intermediate a) after a reaction time of 23 hours at room temperature. The compound was purified by silica gel chromatography on a 20 g column using an MPLC (Flashmaster) system eluting with a gradient of n-heptane:EtOAc:MeOH (100:0:0 to 0:100:0 to 0:90:10). Further purification by preparative HPLC (Gemini NX) with a gradient of MeOH:water (containing 0.05% formic acid) (80:20 to 98:2). Colorless solid (8%). MS (ESI): m/z=564.120 [M+H]⁺.

Example 284

N-[4-(2,4-Difluoro-5-methoxy-phenyl)-pyridin-3-yl]-3-methanesulfonyl-N-methyl-5-trifluoromethyl-benzamide

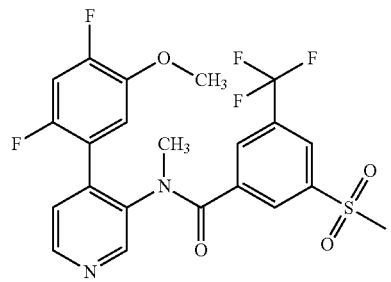 [SMILES: COc1cc(-c2ccncc2N(C)C(=O)c2cc(C(F)(F)F)cc(S(C)(=O)=O)c2)c(F)cc1F]

To a solution of [4-(2,4-difluoro-5-methoxy-phenyl)-pyridin-3-yl]-methyl-amine (70 mg, 0.28 mmol) in 2.5 mL pyridine were added 3-(methylsulfonyl)-5-(trifluoromethyl)benzoic acid (example 114, intermediate a) (90 mg, 0.34 mmol) and POCl₃ (2.3 mL) dropwise at 25° C. and the reaction mixture was stirred for 12 hours at 25° C. The solvent was evaporated, the residue was dissolved in EtOAc (15 ml) and washed with 2M aqueous HCl solution (5 mL) followed by saturated NaHCO₃ solution (10 mL). The organic layer was dried over anhydrous Na₂SO₄ and evaporated. The crude product was purified by preparative HPLC (ammonium acetate/acetonitrile) to furnish the title compound as a light yellow solid (40 mg, 29%). MS (ESI): m/z=501.2 [M+H]⁺.

Intermediate

[4-(2,4-Difluoro-5-methoxy-phenyl)-pyridin-3-yl]-methyl-amine

To a solution of (4-iodo-pyridin-3-yl)-methyl-amine (100 mg, 0.43 mmol, example 98, intermediate b) in THF (3 mL) and water (1.5 mL) were added 2,4-difluoro-5-methoxyphenyl-boronic acid (231 mg, 0.85 mmol) and potassium fluoride (50 mg, 0.85 mmol) and the reaction mixture was purged with argon for 15 min. Then Pd₂(dba)₃ (78 mg, 0.09 mmol) and triphenyl phosphine (22 mg, 0.09 mmol) were added to the reaction mixture and the reaction mixture was stirred at 120° C. for 45 min in a microwave oven. The solvent was evaporated under reduced pressure and the residue was purified by column chromatography eluting with a gradient of n-hexane:EtOAc (80:20 to 50:50) to give the desired compound as a yellow liquid (75 mg, 70%). MS (ESI): m/z=251.4 [M+H]⁺.

Example 285

N-[4-(2,6-Difluoro-3-methoxy-phenyl)-pyridin-3-yl]-3-methanesulfonyl-N-methyl-5-trifluoromethyl-benzamide

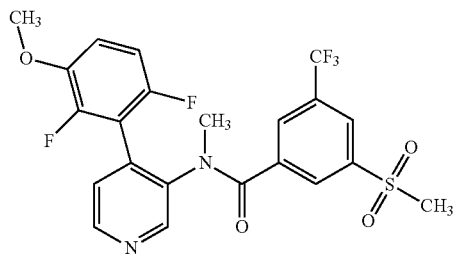

The title compound was prepared in analogy to example 284, from [4-(2,6-difluoro-3-methoxy-phenyl)-pyridin-3-yl]-methyl-amine and 3-methanesulfonyl-5-trifluoromethyl-benzoyl chloride (example 223, intermediate d) and using preparative HPLC (ammonium acetate/acetonitrile) for the purification. Off-white solid (25%). MS (ESI): m/z=501.2 [M+H]⁺.

Intermediate

[4-(2,6-Difluoro-3-methoxy-phenyl)-pyridin-3-yl]-methyl-amine

The title compound was prepared in analogy to compound 284, intermediate, from (4-iodo-pyridin-3-yl)-methyl-amine (example 98, intermediate) and 2,6-difluoro-3-methoxyphenylboronic acid and using a gradient of n-hexane:EtOAc (70:30 to 60:40) for the chromatographic purification. Brown solid (75%). MS (ESI): m/z=251.2 [M+H]⁺.

Example 286

N-[4-(2-Chloro-phenyl)-pyridin-3-yl]-N-cyanomethyl-3-methanesulfonyl-5-trifluoromethyl-benzamide

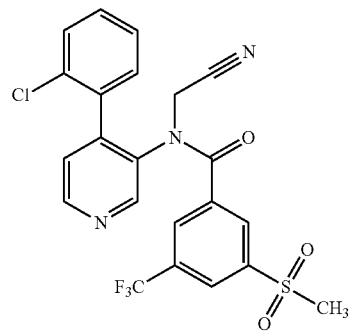 [SMILES: CS(=O)(=O)c1cc(C(=O)N(CC#N)c2cnccc2-c2ccccc2Cl)cc(C(F)(F)F)c1]

The title compound was prepared in analogy to example 90, from [4-(2-chloro-phenyl)-pyridin-3-ylamino]-acetonitrile and 3-(methylsulfonyl)-5-(trifluoromethyl)benzoic acid (example 114, intermediate a) after a reaction time of 6 hours at room temperature. The compound was purified by silica gel chromatography on a 20 g column using an MPLC (Flashmaster) system eluting with a gradient of n-heptane:EtOAc (100:0 to 0:100). Another purification step using preparative HPLC (Gemini NX column) with a gradient of MeOH:water (containing 0.05% formic acid) (80:20 to 98:2) yielded the title compound as colorless solid (25%). MS (ESI): m/z=494.055 [M+H]⁺.

Intermediates a) [4-(2-Chloro-phenyl)-pyridin-3-ylamino]-acetonitrile

The title compound was prepared in analogy to example 85, intermediate a, from tert-butyl 4-(2-chlorophenyl)pyridin-3-yl(cyanomethyl)carbamate after a reaction time of 4 hours at room temperature. The compound was purified by silica gel chromatography on a 20 g column using an MPLC (Flashmaster) system eluting with a gradient of n-heptane:EtOAc (100:0 to 0:100). Colorless solid (51%). MS (ESI): m/z=244.064 [M+H]⁺.

b) tert-butyl 4-(2-chlorophenyl)pyridin-3-yl(cyanomethyl)carbamate

The title compound was prepared in analogy to example 72, from tert-butyl cyanomethyl(4-iodopyridin-3-yl)carbamate (example 161, intermediate c) and 2-chlorophenylboronic acid after a reaction time of 18 hours at 90° C. The compound was purified by silica gel chromatography on a 20 g column using an MPLC system (CombiFlash Compan-

Example 287

N-[4-(2-Chloro-phenyl)-pyridin-3-yl]-3-methanesulfonyl-N-(2,2,2-trifluoro-ethyl)-5-trifluoromethyl-benzamide

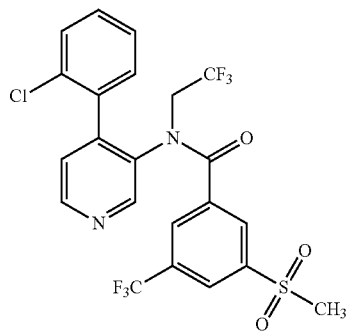 [SMILES: CS(=O)(=O)c1cc(C(=O)N(CC(F)(F)F)c2cnccc2-c2ccccc2Cl)cc(C(F)(F)F)c1]

The title compound was prepared in analogy to example 90, from 4-(2-chlorophenyl)-N-(2,2,2-trifluoro ethyl)pyridin-3-amine and 3-(methylsulfonyl)-5-(trifluoromethyl)benzoic acid (example 114, intermediate a) after a reaction time of 18 hours at room temperature. The compound was purified by silica gel chromatography on a 20 g column using an MPLC (Flashmaster) system eluting with a gradient of n-heptane:EtOAc (100:0 to 0:100). Further purification by preparative HPLC (Gemini NX) with a gradient of MeOH: water (containing 0.05% formic acid) (80:20 to 98:2). Colorless solid (31%). MS (ESI): m/z=537.045 [M+H]$^+$.

Intermediate

[4-(2-Chloro-phenyl)-pyridin-3-yl]-(2,2,2-trifluoroethyl)-amine

The title compound was prepared in analogy to example 85, intermediate a, from tert-butyl 4-(2-chlorophenyl)pyridin-3-yl(2,2,2-trifluoroethyl)carbamate after a reaction time of 4 hours at room temperature. Light yellow solid (33%). MS (ESI): m/z=287.057 [M+H]$^+$. tert-Butyl 4-(2-chlorophenyl)pyridin-3-yl(2,2,2-trifluoroethyl)carbamate The title compound was prepared in analogy to example 72, from tert-butyl 4-iodopyridin-3-yl(2,2,2-trifluoroethyl)carbamate (example 85, intermediate c) and 2-chlorophenylboronic acid after a reaction time of 18 hours at 90° C. The compound was purified by silica gel chromatography on a 20 g column using an MPLC system (CombiFlash Companion, Isco Inc.) eluting with a gradient of n-heptane:EtOAc (100:0 to 0:100). Yellow oil (90%). MS (ESI): m/z=387.109 [M+H]$^+$.

Example 288

N-[4-(2-Chloro-phenyl)-pyridin-3-yl]-3-methanesulfonyl-N-(2-methanesulfonyl-ethyl)-5-trifluoromethyl-benzamide

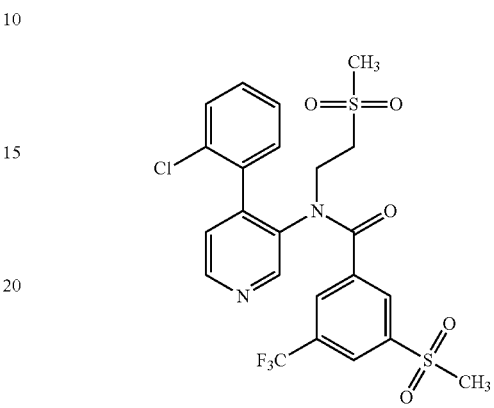

The title compound was prepared in analogy to example 90, from [4-(2-chloro-phenyl)-pyridin-3-yl]-(2-methanesulfonyl-ethyl)-amine and 3-(methylsulfonyl)-5-(trifluoromethyl)-benzoic acid (example 114, intermediate a) after a reaction time of 18 hours at room temperature. The compound was purified by silica gel chromatography on a 20 g column using an MPLC (Flashmaster) system eluting with a gradient of n-heptane: EtOAc (100:0 to 0:100). A further purification step using preparative HPLC (Gemini NX) with a gradient of MeOH:water (containing 0.05% formic acid) (80:20 to 98:2) gave the desired compound as a colorless oil (13%). MS (ESI): m/z=561.052 [M+H]$^+$.

a) [4-(2-Chloro-phenyl)-pyridin-3-yl]-(2-methanesulfonyl-ethyl)-amine

The title compound was prepared in analogy to example 85, intermediate a, from tert-butyl 4-(2-chlorophenyl)pyridin-3-yl(2-(methylsulfonyl)ethyl)carbamate after a reaction time of 4 hours at room temperature. The compound was purified by silica gel chromatography on a 20 g column using an MPLC (Flashmaster) system eluting with a gradient of n-heptane:EtOAc:MeOH (100:0:0 to 0:100:0 to 0:75:25). Colorless foam (91%). MS (ESI): m/z=331.062 [M+H]$^+$.

b) tert-Butyl 4-(2-chlorophenyl)pyridin-3-yl(2-(methylsulfonyl)ethyl)carbamate The title compound was prepared in analogy to example 72, from tert-butyl 4-iodopyridin-3-yl(2-(methylsulfonyl)ethyl)carbamate (example 112, intermediate c) and 2-chlorophenyl-boronic acid after a reaction time of 18 hours at 90° C. The compound was purified by silica gel chromatography on a 20 g column using an MPLC system (CombiFlash Companion, Isco Inc.) eluting with a gradient of n-heptane:EtOAc (100:0 to 0:100). Colorless foam (87%). MS (ESI): m/z=411.115 [M+H]$^+$.

(ion, Isco Inc.) eluting with a gradient of n-heptane:EtOAc (100:0 to 0:100). Light yellow oil (83%). MS (ESI): m/z=344.116 [M+H]$^+$.

Example 289

[[4-(2-Chloro-phenyl)-pyridin-3-yl]-(3-methanesulfonyl-5-trifluoromethyl-benzoyl)-amino]-acetic acid methyl ester

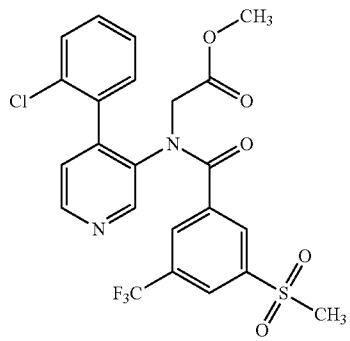 [SMILES: COC(=O)CN(C(=O)c1cc(C(F)(F)F)cc(S(C)(=O)=O)c1)c1cnccc1-c1ccccc1Cl]

The title compound was prepared in analogy to example 90, from [4-(2-chloro-phenyl)-pyridin-3-ylamino]-acetic acid methyl ester and 3-(methylsulfonyl)-5-(trifluoromethyl)benzoic acid (example 114, intermediate a) after a reaction time of 6 hours at room temperature. The compound was purified by silica gel chromatography on a 20 g column using an MPLC (Flashmaster) system eluting with a gradient of n-heptane: EtOAc (100:0 to 0:100). Light red foam (25%). MS (ESI): m/z=527.066 [M+H]$^+$.

Intermediates a) [4-(2-Chloro-phenyl)-pyridin-3-ylamino]-acetic acid methyl ester The title compound was prepared in analogy to example 85, intermediate a, from methyl 2-(tert-butoxycarbonyl(4-(2-chlorophenyl)pyridin-3-yl)amino)acetate after a reaction time of 4 hours at room temperature. Colorless solid (99%). MS (ESI): m/z=277.074 [M+H]$^+$.

b) Methyl 2-(tert-butoxycarbonyl(4-(2-chlorophenyl)pyridin-3-yl)amino)acetate

The title compound was prepared in analogy to example 72, from methyl 2-(tert-butoxycarbonyl(4-iodopyridin-3-yl)amino)acetate (example 165, intermediate c) and 2-chlorophenylboronic acid after a reaction time of 18 hours at 90° C. The compound was purified by silica gel chromatography on a 20 g column using a MPLC system (CombiFlash Companion, Isco Inc.) eluting with a gradient of n-heptane: EtOAc (100:0 to 0:100). Light yellow oil (33%). MS (ESI): m/z=377.127 [M+H]$^+$.

Examples 290 and 291

(−)-N-[4-(4-Fluoro-2-methoxy-phenyl)-pyridin-3-yl]-3-methanesulfonyl-N-[1-(tetrahydro-pyran-2-yl)methyl]-5-trifluoromethyl-benzamide and (+)-N-[4-(4-Fluoro-2-methoxy-phenyl)-pyridin-3-yl]-3-methanesulfonyl-N-[1-(tetrahydro-pyran-2-yl)methyl]-5-trifluoromethyl-benzamide

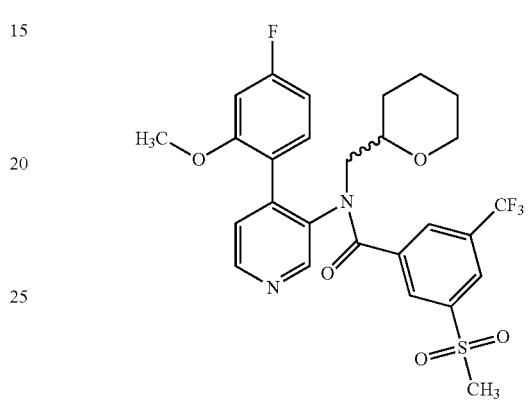

The title compounds were prepared in analogy to example 90, from [4-(4-fluoro-2-methoxy-phenyl)-pyridin-3-yl]-[1-(tetrahydro-pyran-2-yl)methyl]-amine and 3-(methylsulfonyl)-5-(trifluoromethyl)benzoic acid (example 114, intermediate a) after a reaction time of 68 hours at room temperature. The residue obtained after work-up was purified by silica gel chromatography on a 20 g column using an MPLC (Flashmaster) system eluting with a gradient of n-heptane:EtOAc (100:0 to 0:100). The product-containing fractions were pooled, evaporated and the mixture was dissolved in 50 mL 1M aqueous HCl and 50 mL EtOAc and the layers were separated. The organic layer was separated, dried over Mg$_2$SO$_4$, filtered and evaporated. The product was purified by preparative HPLC (Gemini NX column) with a gradient of MeOH:water (containing 0.05% formic acid) (80:20 to 98:2). Chiral chromatography on a Chiralpak AD column with a gradient of ethanol (containing 0.05% formic acid):n-heptane (30:70) furnished the two enantiomers with the (−)-enantiomer eluting first. (−)-N-[4-(4-Fluoro-2-methoxy-phenyl)-pyridin-3-yl]-3-methanesulfonyl-N-[1-(tetrahydro-pyran-2-yl)methyl]-5-trifluoromethyl-benzamide. Off-white solid (43%). MS (ESI): m/z=567.156 [M+H]$^+$ and (+)-N-[4-(4-Fluoro-2-methoxy-phenyl)-pyridin-3-yl]-3-methanesulfonyl-N-[1-(tetrahydro-pyran-2-yl)methyl]-5-trifluoromethyl-benzamide. Light red solid (43%). MS (ESI): m/z=567.157 [M+H]$^+$.

Intermediates a) [4-(4-Fluoro-2-methoxy-phenyl)-pyridin-3-yl]-[1-(tetrahydro-pyran-2-yl)methyl]-amine The title compound was prepared in analogy to example 72, from 4-iodo-N-((tetrahydro-2H-pyran-2-yl)methyl)pyridin-3-amine and 4-fluoro-2-methoxyphenylboronic acid after a reaction time of 3.5 hours at reflux. The compound was purified by silica gel chromatography on a 20 g column using an MPLC system (CombiFlash Companion, Isco Inc.) eluting with a gradient of n-heptane:EtOAc (100:0 to 0:100) followed by EtOAc:MeOH (100:0 to 90:10). Brown oil (103%). MS (ESI): m/z=317.167 [M+H]⁺.

b) 4-Iodo-N-((tetrahydro-2H-pyran-2-yl)methyl) pyridin-3-amine

The title compound was prepared in analogy to example 85, intermediate a, from tert-butyl 4-iodopyridin-3-yl((tetrahydro-2H-pyran-2-yl)methyl)carbamate after a reaction time of 2 hours at room temperature. Light brown solid (97%). MS (ESI): m/z=319.032 [M+H]⁺.

c) tert-Butyl 4-iodopyridin-3-yl((tetrahydro-2H-pyran-2-yl)methyl)carbamate

The title compound was prepared in analogy to example 85, intermediate c, from tert-butyl 4-iodopyridin-3-ylcarbamate (example 85, intermediate d) and 2-(bromomethyptetrahydro-2H-pyran after a reaction time of 22 hours at 60° C. The compound was purified by silica gel chromatography on a 50 g column using an MPLC system (CombiFlash Companion, Isco Inc.) eluting with a gradient of n-heptane:EtOAc (100:0 to 50:50). Light yellow viscous oil (56%). MS (ESI): m/z=419.084 [M+H]⁺.

Example 292

N-[4-(4-Fluoro-2-methoxy-phenyl)-pyridin-3-yl]-N-methyl-3-(1-sulfamoyl-azetidine-3-sulfonyl)-5-trifluoromethyl-benzamide

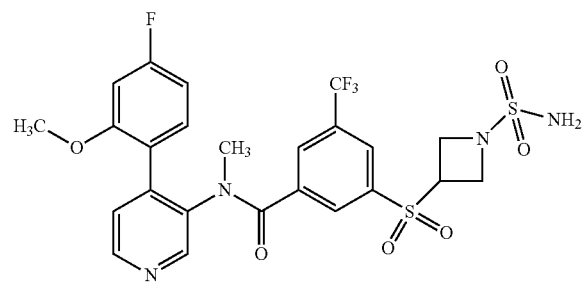 [SMILES: COc1cc(F)ccc1-c1ccncc1N(C)C(=O)c1cc(C(F)(F)F)cc(S(=O)(=O)C2CN(S(N)(=O)=O)C2)c1]

A suspension of 3-(azetidin-3-ylsulfonyl)-N-(4-(4-fluoro-2-methoxyphenyl)pyridin-3-yl)-N-methyl-5-(trifluoromethyl)benzamide (0.05 g, 95.5 µmol, example 280) and sulfuric diamide (36.7 mg, 382 µmol) in isopropylacetate (1 mL) was heated at reflux for 19 hours. The reaction mixture was evaporated and the product purified by preparative HPLC (Gemini NX column) using a gradient of MeOH:water (containing 0.1% formic acid) (20:80 to 98:2). Light brown solid (0.035 g; 60%). MS (ESI): m/z=603.10 [M+1-1]⁺.

Example 293

N-[4-(4-Fluoro-2-methoxy-phenyl)-pyridin-3-yl]-3-methanesulfonyl-N-(4-methyl-oxazol-2-ylmethyl)-5-trifluoromethyl-benzamide

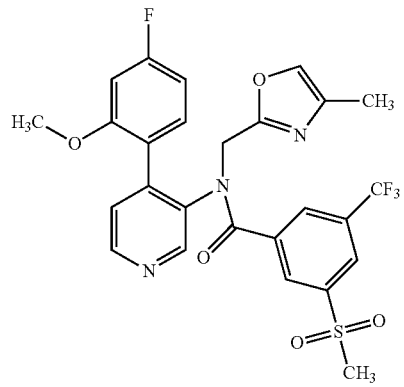 [SMILES: COc1cc(F)ccc1-c1ccncc1N(Cc1nc(C)co1)C(=O)c1cc(C(F)(F)F)cc(S(C)(=O)=O)c1]

The title compound was prepared in analogy to example 90, from [4-(4-fluoro-2-methoxy-phenyl)-pyridin-3-yl]-(4-methyl-oxazol-2-ylmethyl)-amine and 3-(methylsulfonyl)-5-(trifluoromethyl)benzoic acid (example 114, intermediate a) after a reaction time of 90 hours at room temperature. The product was purified by preparative HPLC (Gemini NX) with a gradient of MeOH:water (containing 0.05% formic acid) (80:20 to 98:2). Colorless solid (34%). MS (ESI): m/z=564.121 [M+H]⁺.

Intermediate a) [4-(4-Fluoro-2-methoxy-phenyl)-pyridin-3-yl]-(4-methyl-oxazol-2-ylmethyl)-amine The title compound was prepared in analogy to example 72, from 4-iodo-N-((4-methyloxazol-2-yl)methyl)pyridin-3-amine and 4-fluoro-2-methoxyphenylboronic acid after a reaction time of 23 hours at reflux. The compound was purified by silica gel chromatography on a 20 g column using an MPLC system (CombiFlash Companion, Isco Inc.) eluting with a gradient of n-heptane:EtOAc (100:0 to 0:100), then EtOAc: MeOH (100:0 to 90:10). Off-white solid (88%). MS (ESI): m/z=314.130 [M+H]⁺. b) 4-Iodo-N((4-methyloxazol-2-yl)methyl)pyridin-3-amine The title compound was prepared in analogy to example 85, intermediate a, from tert-butyl 4-iodopyridin-3-yl((4-methyloxazol-2-yl)methyl)carbamate after a reaction time of 2 hours at room temperature. Off-white solid (97%). MS (ESI): m/z=315.995 [M+H]⁺.

c) tert-Butyl 4-iodopyridin-3-yl((4-methyloxazol-2-yl)methyl)carbamate

The title compound was prepared in analogy to example 85, intermediate c, from tert-butyl 4-iodopyridin-3-ylcarbamate (example 85, intermediate d) and 2-(chloromethyl)-4-methyloxazole after a reaction time of 23 hours. The compound was purified by silica gel chromatography on a 50 g column using an MPLC system (CombiFlash Companion, Isco Inc.) eluting with a gradient of n-heptane:EtOAc (100:0 to 0:100). Yellow oil (48%). MS (ESI): m/z=416.046 [M+H]⁺.

Example 294

N-[4-(2-Chloro-phenyl)-pyridin-3-yl]-3-methanesulfonyl-N-oxazol-2-ylmethyl-5-trifluoromethyl-benzamide

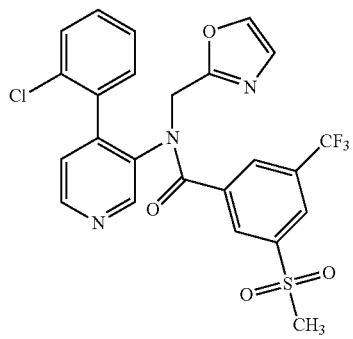 [SMILES: CS(=O)(=O)c1cc(C(=O)N(Cc2ncco2)c2cnccc2-c2ccccc2Cl)cc(C(F)(F)F)c1]

The title compound was prepared in analogy to example 90, from [4-(2-chloro-phenyl)-pyridin-3-yl]-oxazol-2-ylmethyl-amine and 3-(methylsulfonyl)-5-(trifluoromethyl)benzoic acid (example 114, intermediate a) after a reaction time of 21 hours at room temperature. The compound was purified by silica gel chromatography on a 20 g column using an MPLC system (CombiFlash Companion, Isco Inc.) eluting with a gradient of n-heptane:EtOAc (100:0 to 0:100). The product was purified by preparative HPLC (Gemini NX column) with a gradient of MeOH:water (containing 0.05% formic acid) (80:20 to 98:2). Colorless solid (157 mg, 42%). MS (ESI): m/z=536.065 [M+H]$^+$.

Intermediates a) [4-(2-Chloro-phenyl)-pyridin-3-yl]-oxazol-2-ylmethyl-amine

The title compound was prepared in analogy to example 72, from 4-iodo-N-(oxazol-2-ylmethyl)pyridin-3-amine and 2-chlorophenylboronic acid after a reaction time of 5 hours at reflux. The compound was purified by silica gel chromatography on a 20 g column using an MPLC system (CombiFlash Companion, Isco Inc.) eluting with a gradient of n-heptane: EtOAc (100:0 to 0:100), then EtOAc:MeOH (100:0 to 90:10). Light yellow solid (93%). MS (ESI): m/z=286.074 [M+H]$^+$.

b) 4-Iodo-N-(oxazol-2-ylmethyl)pyridin-3-amine

The title compound was prepared in analogy to example 85, intermediate a, from tert-butyl 4-iodopyridin-3-yl(oxazol-2-ylmethyl)carbamate after a reaction time of 2 hours at room temperature. Off-white solid (98%). MS (ESI): m/z=301.979 [M+H]$^+$.

c) tert-Butyl4-iodopyridin-3-yl(oxazol-2-ylmethyl)carbamate

The title compound was prepared in analogy to example 85, intermediate c, from tert-butyl 4-iodopyridin-3-ylcarbamate (example 85, intermediate d) and 2-(chloromethyl)oxazole after a reaction time of 3 hours at room temperature. The residue was purified by silica gel chromatography on a 20 g column using a MPLC system (CombiFlash Companion, Isco Inc.) eluting with a gradient of n-heptane:EtOAc (100:0 to 0:100). Light yellow oil (92%). MS (ESI): m/z=402.031 [M+H]$^+$.

Example 295

N-[4-(3-Fluoro-2-methyl-phenyl)-pyridin-3-yl]-3-methanesulfonyl-N-methyl-5-trifluoromethyl-benzamide

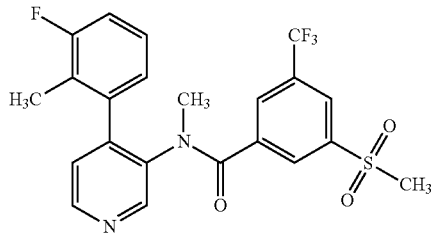

The title compound was prepared in analogy to example 90, from [4-(3-fluoro-2-methyl-phenyl)-pyridin-3-yl]-methyl-amine and 3-(methylsulfonyl)-5-(trifluoromethyl)benzoic acid (example 114, intermediate a) after a reaction time of 23 hours at room temperature. The compound was purified by silica gel chromatography on a 20 g column using an MPLC (Flashmaster) system eluting with a gradient of n-heptane:EtOAc (100:0 to 0:100). The Product was purified by preparative HPLC (Gemini NX column) with a gradient of MeOH:water (containing 0.05% formic acid) (80:20 to 98:2). Colorless solid (42%). MS (ESI): m/z=467.104 [M+H]$^+$.

Intermediate

[4-(3-Fluoro-2-methyl-phenyl)-pyridin-3-yl]-methyl-amine

The title compound was prepared in analogy to example 72, from (4-iodo-pyridin-3-yl)-methyl-amine (example 36, intermediate b) and 3-fluoro-2-methylphenylboronic after a reaction time of 24 hours at reflux. The compound was purified by silica gel chromatography on a 20 g column using an MPLC system (CombiFlash Companion, Isco Inc.) eluting with a gradient of n-heptane:EtOAc (100:0 to 0:100). Light yellow solid (96%). MS (ESI): m/z=217.114 [M+H]$^+$.

Example 296

N-Carbamoylmethyl-N-[4-(2-chloro-phenyl)-pyridin-3-yl]-3-methanesulfonyl-5-trifluoromethyl-benzamide

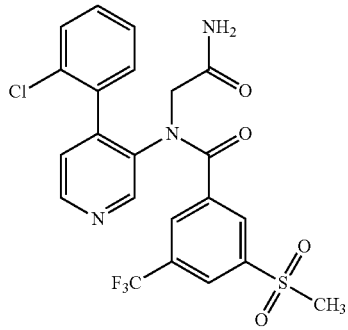 [SMILES: CS(=O)(=O)c1cc(C(=O)N(CC(N)=O)c2cnccc2-c2ccccc2Cl)cc(C(F)(F)F)c1]

The title compound was prepared in analogy to example 117, from 2-[[4-(2-chloro-phenyl)-pyridin-3-yl]-(3-methanesulfonyl-5-trifluoromethyl-benzoyl)-amino]-acetic acid after a reaction time of 4 hours. The compound was purified by silica gel chromatography on a 20 g column using an MPLC (Flashmaster) system eluting with a gradient of n-heptane: EtOAc:MeOH (100:0:0 to 0:100:0 to 0:80:20). Colorless solid (66%). MS (ESI): m/z=512.065 [M+H]+.

Intermediates a) [[4-(2-Chloro-phenyl)-pyridin-3-yl]-(3-methane sulfonyl-5-trifluoromethyl-benzoyl)-amino]-acetic acid The title compound was prepared in analogy to example 84, from methyl 2-(N-(4-(2-chlorophenyl)pyridin-3-yl)-3-(methylsulfonyl)-5-(trifluoromethyl)benzamido)acetate (example 289) after a reaction time of 2 hours at room temperature. Off-white solid (101%). MS (ESI): m/z=513.049 [M+H]+.

Example 297

[[4-(5-Fluoro-2-methoxy-phenyl)-pyridin-3-yl]-(3-methanesulfonyl-5-trifluoromethyl-benzoyl)-amino]-acetic acid methyl ester

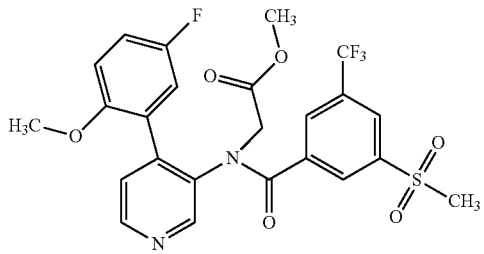

To a solution of N-[4-(5-fluoro-2-methoxy-phenyl)-pyridin-3-yl]-3-methanesulfonyl-5-trifluoromethyl-benzamide (50 mg, 0.11 mmol) in THF (5 mL) were added potassium tert-butoxide (24 mg, 0.21 mmol) and methyl bromoacetate (22 mg, 0.14 mmol) at 0° C. and the reaction mixture was stirred for 12 hours at 25° C. The reaction mixture was quenched with water (5 mL) and extracted by EtOAc (2×20 mL) The combined EtOAc layers were dried over Na2SO4 and evaporated. The crude product was purified by preparative HPLC (ammonium acetate/acetonitrile) to get the desired compound as an off-white solid (8 mg, 14%). MS (ESI): m/z=541.0 [M+H]+.

Intermediates a) N-[4-(5-Fluoro-2-methoxy-phenyl)-pyridin-3-yl]-3-methanesulfonyl-5-trifluoromethyl-benzamide The title compound was prepared in analogy to example 90, from 4-(5-fluoro-2-methoxy-phenyl)-pyridin-3-ylamine and 3-methanesulfonyl-5-trifluoromethyl-benzoic acid (example 114, intermediate a) after a reaction time of 18 hours. The residue was purified by column chromatography eluting with a gradient of n-hexane:EtOAc (40:60 to 20:80. Brown liquid (68%). MS (ESI): m/z=469.2 [M+H]+.

b) 4-(5-Fluoro-2-methoxy-phenyl)-pyridin-3-ylamine

The title compound was prepared in analogy to example 72, from 4-iodo-pyridin-3-ylamine (CAS RN 105752-11-2) and 3-fluoro-6-methoxy-phenylboronic acid (CAS RN 179897-94-0) after a reaction time of 18 hours at reflux. The compound was purified by column chromatography eluting with a gradient of n-hexane:EtOAc (40:60 to 20:80). Yellow solid (84%). MS (ESI): m/z=219.6 [M+H]+.

Example 298

3-Methanesulfonyl-N-(2,2,2-trifluoro-ethyl)-N-[4-(2-trifluoromethoxy-phenyl)-pyridin-3-yl]-5-trifluoromethyl-benzamide

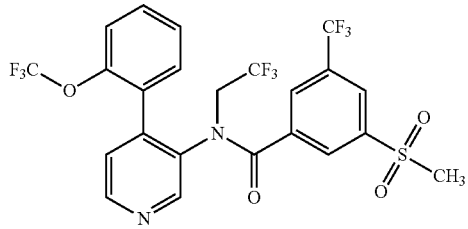

The title compound was prepared in analogy to example 72, intermediate, from (2,2,2-trifluoro-ethyl)-[4-(2-trifluoromethoxy-phenyl)-pyridin-3-yl]-amine (37) and 3-methanesulfonyl-5-trifluoromethyl-benzoyl chloride (example 223, intermediate d) after a reaction time of 12 hours at 25° C. The crude product was purified by preparative HPLC (ammonium acetate/acetonitrile) to give the desired compound as an off-white solid (12 mg, 20%). MS (ESI): m/z=587.2 [M+H]+.

Intermediates a) (2,2,2-Trifluoro-ethyl)-[4-(2-trifluoromethoxy-phenyl)-pyridin-3-yl]-amine The title compound was prepared in analogy to example 85, intermediate a, from (2,2,2-trifluoro-ethyl)-[4-(2-trifluoromethoxy-phenyl)-pyridin-3-yl]-carbamic acid tert-butyl ester after a reaction time of 2 hours. Yellow solid (95%). MS (ESI): m/z=337.6 [M+H]+.

b) (2,2,2-Trifluoro-ethyl)-[4-(2-trifluoromethoxy-phenyl)-pyridin-3-yl]-carbamic acid tert-butyl ester The title compound was prepared in analogy to example 85, intermediate c, from [4-(2-trifluoromethoxy-phenyl)-pyridin-3-yl]-carbamic acid tert-butylester and 2,2,2-trifluoroethyl trifluoromethanesulfonate after a reaction time of 12 hours. The resulting crude was purified by column chromatography eluting with a gradient of n-hexane: EtOAc (90:10 to 85:15). Light brown sticky liquid (66%). MS (ESI): m/z=437.4 [M+H]+.

c) [4-(2-Trifluoromethoxy-phenyl)-pyridin-3-yl]-carbamic acid tert-butylester

The title compound was prepared in analogy to example 72, from (4-iodo-pyridin-3-yl)-carbamic acid tert-butyl ester and 2-trifluoromethoxyphenylboronic acid after a reaction time of 16 hours at reflux. The crude product was purified by column chromatography eluting with a gradient of n-hexane:EtOAc (80:20 to 70:30). Light yellow sticky liquid (80%). MS (EST): m/z=355.2 [M+H]⁺.

Example 299

(+)-N-[4-(4-Fluoro-2-methoxy-phenyl)-pyridin-3-yl]-3-methanesulfonyl-N-[1-(tetrahydro-pyran-3-yl)methyl]-5-trifluoromethyl-benzamide

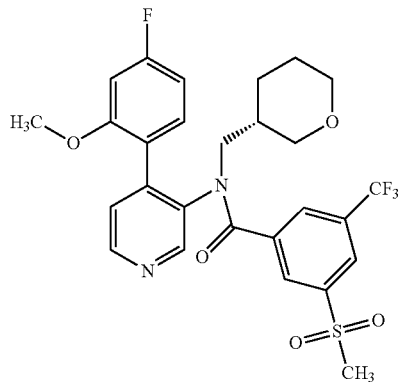 [SMILES: COc1cc(F)ccc1-c1ccncc1N(C[C@@H]1CCCOC1)C(=O)c1cc(C(F)(F)F)cc(S(C)(=O)=O)c1]

The title compound was prepared in analogy to example 90, from 4-(4-fluoro-2-methoxyphenyl)-N-((tetrahydro-2H-pyran-3-yl)methyl)pyridin-3-amine and 3-(methylsulfonyl)-5-(trifluoromethyl)benzoic acid (example 114, intermediate a) after a reaction time of 90 hours at room temperature. The compound was purified by silica gel chromatography on a 20 g column using an MPLC system (CombiFlash Companion, Isco Inc.) eluting with a gradient of n-heptane:EtOAc (100:0 to 0:100). Chiral chromatography on a Ciralpak AD column with a gradient of ethanol (containing 0.05% formic acid): n-heptane (40:60) furnished both enantiomers, with the desired enantiomer eluting second. Colorless solid (19%). MS (ESI): m/z=567.158 [M+H]⁺.

Intermediates a) 4-(4-Fluoro-2-methoxyphenyl)-N-((tetrahydro-2H-pyran-3-yl)methyl)pyridin-3-amine The title compound was prepared in analogy to example 72, from 4-iodo-N-((tetrahydro-2H-pyran-3-yl)methyl)pyridin-3-amine and 4-fluoro-2-methoxyphenylboronic acid after a reaction time of 5 hours at reflux. The compound was purified by silica gel chromatography on a 20 g column using an MPLC system (CombiFlash Companion, Isco Inc.) eluting with a gradient of n-heptane:EtOAc (100:0 to 0:100) followed by EtOAc:MeOH (100:0 to 90:10). Yellow oil (106%). MS (ESI): m/z=317.166 [M+H]⁺.

b) 4-Iodo-N-((tetrahydro-2H-pyran-3-yl)methyl)pyridin-3-amine

The title compound was prepared in analogy to example 85, intermediate a, from tert-butyl 4-iodopyridin-3-yl((tetrahydro-2H-pyran-3-yl)methyl)carbamate after a reaction time of 2 hours at room temperature (96%). MS (ESI): m/z=319.030 [M+H]⁺.

c) tert-Butyl 4-iodopyridin-3-yl((tetrahydro-2H-pyran-3-yl)methyl)carbamate

The title compound was prepared in analogy to example 85, intermediate c, from (4-iodo-pyridin-3-yl)-carbamic acid tert-butyl ester (example 85, intermediate d) and 3-(bromomethyl)tetrahydro-2H-pyran after a reaction time of 24 hours. The compound was purified by silica gel chromatography on a 20 g column using an MPLC system (CombiFlash Companion, Isco Inc.) eluting with a gradient of n-heptane:EtOAc (100:0 to 30:70). Colorless oil (74%). MS (ESI): m/z=419.083 [M+H]⁺.

Example 300

N-[4-(2-Chloro-phenyl)-6-methyl-pyridin-3-yl]-3-methanesulfonyl-N-(2,2,2-trifluoro-ethyl)-5-trifluoromethyl-benzamide

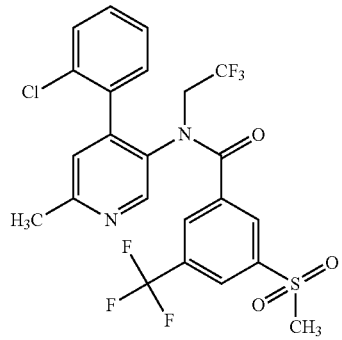 [SMILES: Cc1cc(-c2ccccc2Cl)c(N(CC(F)(F)F)C(=O)c2cc(C(F)(F)F)cc(S(C)(=O)=O)c2)cn1]

To a solution of 4-(2-chlorophenyl)-6-methyl-N-(2,2,2-trifluoroethyl)pyridin-3-amine (0.066 g, 219 µmol) and 3-(methylsulfonyl)-5-(trifluoromethyl)benzoyl chloride (66.1 mg, 230 µmol, example 223, intermediate d) in CH₂Cl₂ (1 mL) was added DIPEA (56.7 mg, 76.7 µL, 439 µmol) and the clear yellow solution was stirred at room temperature for 4 hours. Another batch of 3-(methylsulfonyl)-5-(trifluoromethyl)benzoyl chloride (66.1 mg, 230 µmol, example 223, intermediate d) and DIPEA (56.7 mg, 76.7 µL, 439 µmol) were added and stirring was continued for another 48 hours. The compound was purified by silica gel chromatography on a 20 g column using an MPLC (ISCO) system eluting with EtOAc (isocratic). The product was further purified by preparative HPLC (Gemini NX column) using a gradient of MeOH:water (containing 0.1% formic acid) (20:80 to 98:2). Light brown solid (5%). MS (ESI): m/z=551.06 [M+H]⁺.

Intermediates a) 4-(2-chlorophenyl)-6-methyl-N-(2,2,2-trifluoroethyl)pyridin-3-amine The title compound was prepared in analogy to example 72, from 4-iodo-6-methyl-N-(2,2,2-trifluoroethyl)pyridin-3-amine and 2-chlorophenylboronic acid after a reaction time of 15.5 hours. The compound was purified by silica gel chromatography on a 10 g column using a MPLC system eluting with a gradient of n-heptane:EtOAc (100:0 to 50:50). Light brown solid (71%). MS (ESI): m/z=301.07 [M+H]⁺.

b) 4-Iodo-6-methyl-N-(2,2,2-trifluoroethyl)pyridin-3-amine

The title compound was prepared in analogy to example 85, intermediate a, from tert-butyl 4-iodo-6-methylpyridin-3-yl-(2,2,2-trifluoroethyl)carbamate after a reaction time of 2.5 hours. Colorless solid (58%). MS (ESI): m/z=316.98 [M+H]$^+$.

c) tert-Butyl 4-iodo-6-methylpyridin-3-yl-(2,2,2-trifluoroethyl)carbamate

The title compound was prepared in analogy to example 85, intermediate c, from tert-butyl 4-iodo-6-methylpyridin-3-ylcarbamate and 2,2,2-trifluoroethyl trifluoromethanesulfonate after a reaction time of 4 hours. The compound was purified by silica gel chromatography on a 20 g column using a MPLC system eluting with a gradient of n-heptane:EtOAc (100:0 to 50:50). Colorless solid (76%). MS (ESI): m/z=417.03 [M+H]$^+$.

d) tert-Butyl 4-iodo-6-methylpyridin-3-ylcarbamate

To a solution of tert-butyl 6-methylpyridin-3-ylcarbamate (9 g, 43.2 mmol) in diethyl ether (150 mL) was added TMEDA (5.27 g, 6.85 mL, 45.4 mmol) and the solution was cooled down to −75° C. n-Butyl lithium (1.6 M solution in hexane, 72.1 mL, 115 mmol) was added dropwise over 20 minutes. The orange suspension was stirred for 1.25 hours at temperatures between −14 to −25° C. After cooling down to −75° C. a solution of iodine (16.8 g, 66.1 mmol) in diethyl ether (150 mL) was added dropwisw over 45 minutes below −68° C. The resulting mixture was stirred at −75° C. for 30 minutes before stirring in an ice bath for 1.75 hours. The reaction mixture was poured on 10% aqueous Na$_2$S$_2$O$_3$ solution (300 mL) and EtOAc (200 mL) and the layers were separated. The aqueous layer was extracted twice with EtOAc (100 mL) The organic layers were washed with 10% aqueous Na$_2$S$_2$O$_3$ solution (100 mL) and brine (100 mL), dried over MgSO$_4$, filtered, treated with silica gel (30 g) and evaporated. The compound was purified by silica gel chromatography on a 330 g column using a MPLC system eluting with a gradient of n-heptane: EtOAc (100:0 to 50:50). The impure fractions were combined, purified by silica gel chromatography on a 120 g column using an MPLC (Flasmaster) system eluting with a gradient of n-heptane:EtOAc (100:0 to 50:50). The product containing fractions were combined and evaporated until a suspension formed, which was filtered and washed with n-heptane. Colorless solid (2.84 g; 19%). MS (ESI): m/z=335.1 [M+H]$^+$.

e) tert-Butyl 6-methylpyridin-3-ylcarbamate

To a suspension of 6-methylnicotinic acid (4.5 g, 32.8 mmol) in toluene (45.0 mL) were added DIPEA (4.67 g, 6.3 mL, 36.1 mmol) and diphenyl phosphorazidate (9.93 g, 7.78 mL, 36.1 mmol) and the suspension was stirred at room temperature for 15 minutes before tert-butanol (24.3 g, 30.8 mL, 328 mmol) was added and the reaction mixture was heated to 80° C. overnight. The reaction mixture was poured on saturated aqueous NH$_4$Cl solution and EtOAc and the layers were separated. The aqueous layer was extracted six times with EtOAc. The organic layers were dried over MgSO$_4$, filtered, treated with silica gel and evaporated. The compound was purified by silica gel chromatography on a 120 g column using a MPLC system eluting with a gradient of n-heptane:EtOAc (100:0 to 0:100). Colorless solid (5.05 g; 73%). MS (ESI): m/z=209.1 [M+H]$^+$.

Example 301

3-Chloro-N-[4-(4-fluoro-2-methoxy-phenyl)-6-methyl-pyridin-3-yl]-5-methanesulfonyl-N-methyl-benzamide

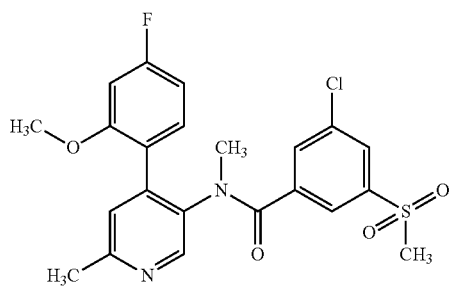

The title compound was prepared in analogy to example 90, from 4-(4-fluoro-2-methoxyphenyl)-N,6-dimethylpyridin-3-amine and 3-chloro-5-(methylsulfonyl)benzoic acid (example 114, intermediate a) after a reaction time of 15.5 hours. The product was purified by preparative HPLC (Gemini NX column) using a gradient of MeOH:water (containing 0.1% formic acid) (20:80 to 98:2). Colorless oil (41%). MS (ESI): m/z=463.09 [M+H]$^+$.

Intermediates a) 4-(4-fluoro-2-methoxyphenyl)-N,6-dimethylpyridin-3-amine

The title compound was prepared in analogy to example 72, from (4-iodo-6-methyl-pyridin-3-yl)-methyl-amine and 4-fluoro-2-methoxyphenylboronic acid after a reaction time of 14.5 hours at reflux. The compound was purified by silica gel chromatography on a 10 g column using a MPLC system eluting with a gradient of n-heptane:EtOAc (100:0 to 0:100). Light brown solid (84%). MS (ESI): m/z=247.12 [M+H]$^+$.

b) (4-Iodo-6-methyl-pyridin-3-yl)-methyl-amine

The title compound was prepared in analogy to example 85, intermediate a, from (4-iodo-6-methyl-pyridin-3-yl)-methyl-carbamic acid tert-butyl ester after a reaction time of 1.25 hours. Colorless solid (99%). MS (ESI): m/z=248.99 [M+H]$^+$.

c) (4-Iodo-6-methyl-pyridin-3-yl)-methyl-carbamic acid tert-butyl ester

The title compound was prepared in analogy to example 85, intermediate c, from tert-butyl 4-iodo-6-methylpyridin-3-ylcarbamate (example 300, intermediate d) and iodomethane after a reaction time of 4 hours. The compound was purified by silica gel chromatography on a 10 g column using a MPLC system eluting with a gradient of n-heptane:EtOAc (100:0 to 50:50). Light brown solid (0.846 g; 81%). MS (ESI): m/z=369.04 [M+H]$^+$.

Example 302

N-[4-(4-Fluoro-2-methoxy-phenyl)-6-methyl-pyridin-3-yl]-N-methyl-3-(morpholine-4-sulfonyl)-5-trifluoromethyl-benzamide

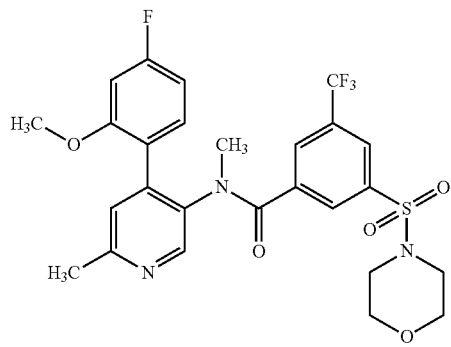 [SMILES: COc1cc(F)ccc1-c1cc(C)ncc1N(C)C(=O)c1cc(C(F)(F)F)cc(S(=O)(=O)N2CCOCC2)c1]

The title compound was prepared in analogy to example 90, from 4-(4-fluoro-2-methoxyphenyl)-N,6-dimethylpyridin-3-amine (example 301, intermediate a) and 3-(morpholinosulfonyl)-5-(trifluoromethyl)benzoic acid (example 256, intermediate) after a reaction time of 15.5 hours. The compound was purified by silica gel chromatography on a 20 g column using an MPLC system eluting with EtOAc (isocratic). The product was purified by preparative HPLC (Gemini NX column) using a gradient of MeOH:water (containing 0.1% formic acid) (20:80 to 98:2). Colorless oil (67%). MS (ESI): m/z=568.15 [M+H]$^+$.

Example 303

3-Bromo-N-[4-(4-fluoro-2-methoxy-phenyl)-6-methyl-pyridin-3-yl]-N-methyl-5-trifluoromethyl-benzamide

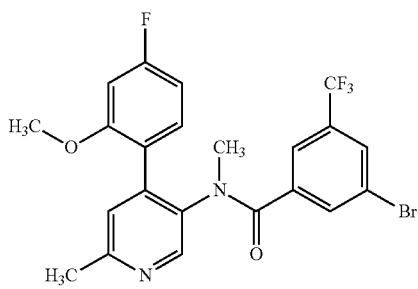 [SMILES: COc1cc(F)ccc1-c1cc(C)ncc1N(C)C(=O)c1cc(Br)cc(C(F)(F)F)c1]

The title compound was prepared in analogy to example 90, from 4-(4-fluoro-2-methoxyphenyl)-N,6-dimethylpyridin-3-amine (example 301, intermediate a) and 3-bromo-5-(trifluoromethyl)benzoic acid after a reaction time of 20 hours. The compound was purified by silica gel chromatography on a 10 g column using an MPLC system eluting with a gradient of n-heptane:EtOAc (100:0 to 0:100). Colorless solid (88%). MS (ESI): m/z=497.05 [M+H]$^+$.

Example 304

3-(1,1-Dioxo-thiomorpholine-4-sulfonyl)-N-[4-(4-fluoro-2-methoxy-phenyl)-pyridin-3-yl]-N-methyl-5-trifluoromethyl-benzamide

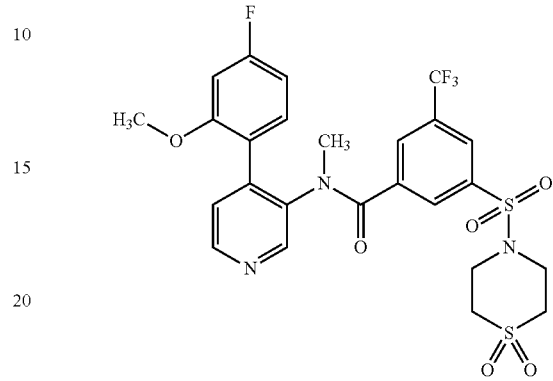

The title compound was prepared in analogy to example 90, from 4-(4-fluoro-2-methoxyphenyl)-N-methylpyridin-3-amine (example 129, intermediate) and 3-(1,1-dioxo-thiomorpholine-4-sulfonyl)-5-trifluoromethyl-benzoic acid after a reaction time of 46 hours. The product was purified by preparative HPLC (Gemini NX column) using a gradient of MeOH:water (containing 0.1% formic acid) (20:80 to 98:2). The product-containing fractions were pooled, evaporated and dissolved in EtOAc. The organic layer was extracted three times with aqueous 1M NaOH solution and once with brine, dried over MgSO$_4$, filtered and evaporated. Light brown solid (3%). MS (ESI): m/z=602.10 [M+H]$^+$.

IntermediateS a) 3-(1,1-Dioxo-thiomorpholine-4-sulfonyl)-5-trifluoromethyl-benzoic acid The title compound was prepared in analogy to example 84, from 3-(1,1-dioxo-thiomorpholine-4-sulfonyl)-5-trifluoromethyl-benzoic acid methyl after a reaction time of 3 hours. Colorless solid (95%). MS (ESI): m/z=386.00 [M–H]$^-$.

b) 3-(1,1-Dioxo-thiomorpholine-4-sulfonyl)-5-trifluoromethyl-benzoic acid methyl ester To a solution of methyl 3-(chlorosulfonyl)-5-(trifluoromethyl)benzoate (1 g, 3.3 mmol, Buttpark Ltd.) and DIPEA (641 mg, 866 μL, 4.96 mmol) in CH$_2$Cl$_2$ (4 mL) was added dropwise a solution of thiomorpholine 1,1-dioxide (447 mg, 3.3 mmol, CAS RN 39093-93-1) in CH$_2$Cl$_2$ (4.00 mL). After 90 min tes the suspension was poured on saturated aqueous NH$_4$Cl solution and CH$_2$Cl$_2$ and the layers were separated. The aqueous layer was extracted twice with CH$_2$Cl$_2$. The organic layers were dried over MgSO$_4$, filtered and evaporated. The compound was purified by silica gel chromatography on a 50 g column using an MPLC (Flasmaster) system eluting with a gradient of n-heptane:EtOAc (100:0 to 80:20). Light brown solid (0.99 g; 74%). MS (ESI): m/z=419.05 [M+NH4]$^+$.

Example 305

N-[4-(4-Fluoro-2-methoxy-phenyl)-pyridin-3-yl]-N-methyl-3-(2-oxa-6-aza-spiro[3.3]heptane-6-sulfonyl)-5-trifluoromethyl-benzamide

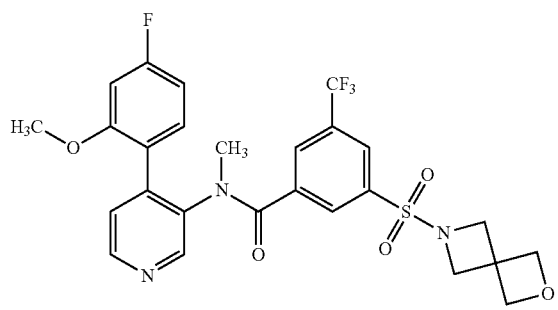 [SMILES: COc1cc(F)ccc1-c1ccncc1N(C)C(=O)c1cc(C(F)(F)F)cc(S(=O)(=O)N2CC3(COC3)C2)c1]

The title compound was prepared in analogy to example 90, from [4-(4-fluoro-2-methoxy-phenyl)-pyridin-3-yl]-methyl-amine (example 129, intermediate) and 3-(2-oxa-6-azaspiro[3.3]heptan-6-ylsulfonyl)-5-(trifluoromethyl)benzoic acid after a reaction time of 90 hours at room temperature. The compound was purified by silica gel chromatography on a 20 g column using an MPLC system (CombiFlash Companion, Isco Inc.) eluting with a gradient of n-heptane:EtOAc (100:0 to 0:100). Colorless solid (61%). MS (ESI): m/z=566.136 [M+H]$^+$.

Intermediates a) 3-(2-Oxa-6-azaspiro[3.3]heptan-6-ylsulfonyl)-5-(trifluoromethyl)benzoic acid The title compound was prepared in analogy to example 84, from methyl 3-(2-oxa-6-azaspiro[3.3]heptan-6-ylsulfonyl)-5-(trifluoromethyl)benzoate after a reaction time of 3 hours. Colorless solid (99%). MS (ESI): m/z=350.033 [M−H]$^−$.

b) Methyl 3-(2-oxa-6-azaspiro[3.3]heptan-6-ylsulfonyl)-5-(trifluoromethyl)benzoate To an ice-cooled solution of methyl 3-(chlorosulfonyl)-5-(trifluoromethyl)benzoate (1 g, 1.33 mmol, Buttpark Ltd.) in CH$_2$Cl$_2$ (10 mL) was added N,N-ethyldiisopropylamine (1.28 g, 1.73 mL, 9.91 mmol, Eq: 3) and 2-oxa-6-aza-spiro[3.3]heptane oxalate (524 mg, 1.82 mmol). The reaction mixture was stirred for 2 hours at room temperature. The reaction mixture was poured on 30 mL 10% aqueous NaHCO$_3$ solution and 30 mL CH$_2$Cl$_2$ and the layers were separated. The aqueous layer was extracted a second time with 30 mL CH$_2$Cl$_2$. The organic layers were washed with 30 mL brine, dried over MgSO$_4$, filtered and concentrated under vacuum. The compound was purified by silica gel chromatography on a 20 g column using an MPLC (Flashmaster) system eluting with a gradient of n-heptane:EtOAc (100:0 to 30:70). Colorless solid (460 mg, 38.1%). MS (ESI): m/z=365 [M+H]$^+$.

Example 306

N-[4-(4-Fluoro-2-methoxy-phenyl)-pyridin-3-yl]-3-methanesulfonyl-N-(2-methanesulfonyl-ethyl)-5-trifluoromethyl-benzamide

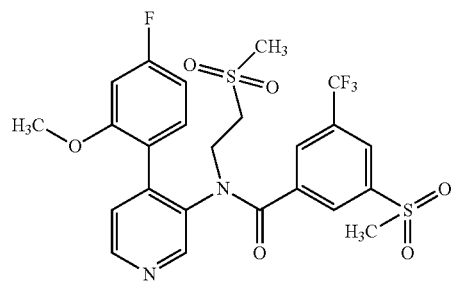 [SMILES: COc1cc(F)ccc1-c1ccncc1N(CCS(C)(=O)=O)C(=O)c1cc(C(F)(F)F)cc(S(C)(=O)=O)c1]

To a solution of 4-(4-fluoro-2-methoxyphenyl)-N-(2-(methylsulfonyl)ethyl)pyridin-3-amine (0.08 g, 247 µmol, example192, intermediate a) and 3-(methylsulfonyl)-5-(trifluoromethyl)benzoyl chloride (177 mg, 617 µmol, example 223, intermediate d) in CH$_2$Cl$_2$ (2 mL) was added DIPEA (128 mg, 172 µL, 987 gimp and the clear solution was stirred at room temperature for 19 hours. The reaction mixture was poured on saturated aqueous NH$_4$Cl solution and CH$_2$Cl$_2$ and the layers were separated. The aqueous layer was extracted twice with CH$_2$Cl$_2$. The organic layers were dried over MgSO$_4$, filtered, treated with silica gel and evaporated. The compound was purified by silica gel chromatography on a 20 g column using a MPLC system eluting with a gradient of n-heptane:EtOAc (100:0 to 0:100). Light brown foam (0.075 g; 52%). MS (ESI): m/z=575.09 [M+H]$^+$.

Example 307

N-[4-(4-Fluoro-2-methoxy-phenyl)-6-methyl-pyridin-3-yl]-3-methanesulfonyl-N-(2,2,2-trifluoro-ethyl)-5-trifluoromethyl-benzamide

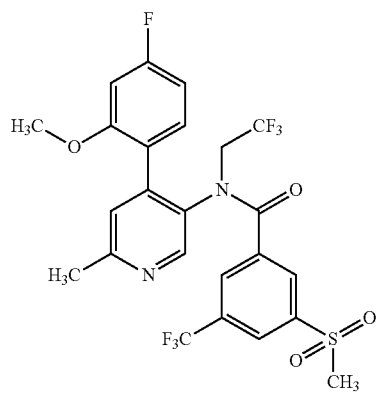 [SMILES: COc1cc(F)ccc1-c1cc(C)ncc1N(CC(F)(F)F)C(=O)c1cc(C(F)(F)F)cc(S(C)(=O)=O)c1]

The title compound was prepared in analogy to example 72, intermediate, from 4-(4-fluoro-2-methoxyphenyl)-6-methyl-N-(2,2,2-trifluoroethyl)pyridin-3-amine and 3-(methylsulfonyl)-5-(trifluoromethyl)benzoyl chloride (example 223, intermediate d) after a reaction time of 42 hours. The product was purified by preparative HPLC (Gemini NX column) using a gradient of MeOH:water (containing 0.1% formic acid) (20:80 to 98:2). Colorless solid (32%). MS (ESI): m/z=565.10 [M+H]$^+$.

Intermediates a) 4-(4-Fluoro-2-methoxyphenyl)-6-methyl-N-(2,2,2-trifluoroethyl)pyridin-3-amine The title compound was prepared in analogy to example 72, from 4-iodo-6-methyl-N-(2,2,2-trifluoroethyl)pyridin-3-amine (example 300, intermediate b) and 4-fluoro-2-methoxyphenylboronic acid after a reaction time of 16.5 hours. The compound was purified by silica gel chromatography on a 10 g column using a MPLC system eluting with a gradient of n-heptane:EtOAc (100:0 to 0:100). Colorless solid (83%). MS (ESI): m/z=315.11 [M+H]$^+$.

Example 308

3-Methanesulfonyl-N-(2-methanesulfonyl-ethyl)-N-[4-(2-trifluoromethoxy-phenyl)-pyridin-3-yl]-5-trifluoromethyl-benzamide

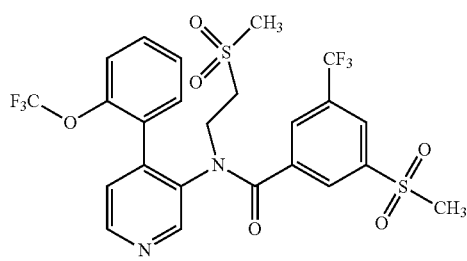 [SMILES: CS(=O)(=O)CCN(C(=O)c1cc(C(F)(F)F)cc(S(C)(=O)=O)c1)c1cnccc1-c1ccccc1OC(F)(F)F]

The title compound was prepared in analogy to example 72, intermediate, from (2-methanesulfonyl-ethyl)-[4-(2-trifluoromethoxy-phenyl)-pyridin-3-yl]-amine, DIPEA and 3-methanesulfonyl-5-trifluoromethyl-benzoyl chloride (example 223, intermediate d) in CH$_2$Cl$_2$ after a reaction time of 12 hours at 25° C. The crude thus obtained was purified by preparative HPLC (ammonium acetate/acetonitrile) to furnish the title compound as an off-white solid (15 mg, 13%). MS (ESI): m/z=611.2 [M+H]$^+$.

Intermediates a) (2-Methanesulfonyl-ethyl)-[4-(2-trifluoromethoxy-phenyl)-pyridin-3-yl]-amine (41)

The title compound was prepared in analogy to example 298, intermediate a, from (2-methanesulfonyl-ethyl)-[4-(2-trifluoromethoxy-phenyl)-pyridin-3-yl]-carbamic acid tert-butyl ester. Brown solid (97%). MS (ESI): m/z=361.0 [M+H]$^+$.

b) (2-Methanesulfonyl-ethyl)-[4-(2-trifluoromethoxy-phenyl)-pyridin-3-yl]-carbamic acid tert-butyl ester The title compound was prepared in analogy to example 298, intermediate b, from [4-(2-trifluoromethoxy-phenyl)-pyridin-3-yl]-carbamic acid tert-butyl ester and 1-chloro-2-(methylsulfonyl)ethane and using a gradient of n-hexane: EtOAc (50:50 to 40:60) for the chromatographic purification. Colourless sticky solid (96%). MS (ESI): m/z=461.4 [M+H]$^+$.

Example 309

N-Carbamoylmethyl-N-[4-(5-fluoro-2-methoxy-phenyl)-pyridin-3-yl]-3-methanesulfonyl-5-trifluoromethyl-benzamide

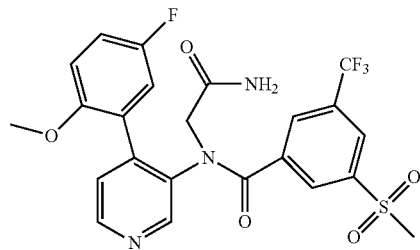 [SMILES: COc1ccc(F)cc1-c1ccncc1N(CC(N)=O)C(=O)c1cc(C(F)(F)F)cc(S(C)(=O)=O)c1]

The title compound was prepared in analogy to example 117, from [[4-(5-fluoro-2-methoxy-phenyl)-pyridin-3-yl]-(3-methanesulfonyl-5-trifluoromethyl-benzoyl)-amino]-acetic acid after a reaction time of 4 hours. The crude product was purified by preparative HPLC (ammonium acetate/acetonitrile) to get the desired product as a colourless sticky solid (35%). MS (ESI): m/z=526.4 [M+H]$^+$.

Intermediate

[[4-(5-Fluoro-2-methoxy-phenyl)-pyridin-3-yl]-(3-methanesulfonyl-5-trifluoromethyl-benzoyl)-amino]-acetic acid The title compound was prepared in analogy to example 84, from [[4-(5-fluoro-2-methoxy-phenyl)-pyridin-3-yl]-(3-methanesulfonyl-5-trifluoromethyl-benzoyl)-amino]-acetic acid methyl ester (example 297) after a reaction time of 3 hours at 25° C. The product was purified by preparative HPLC (ammonium acetate/acetonitrile) to yield the title compound as an off-white solid (40%). MS (ESI): m/z=527.2 [M+H]$^+$.

Example 310

N-[4-(4-Fluoro-2-methoxy-phenyl)-6-methyl-pyridin-3-yl]-N-methyl-3-(oxetan-3-ylsulfanyl)-5-trifluoromethyl-benzamide

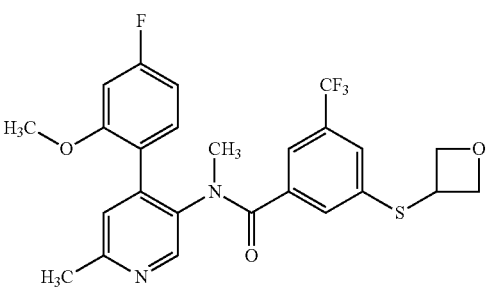 [SMILES: COc1cc(F)ccc1-c1cc(C)ncc1N(C)C(=O)c1cc(SC2COC2)cc(C(F)(F)F)c1]

To a solution of N-(4-(4-fluoro-2-methoxyphenyl)-6-methylpyridin-3-yl)-3-mercapto-N-methyl-5-(trifluoromethyl)benzamide (0.093 g, 206 µmol) in acetonitrile (2 mL) were added 3-iodooxetane (57.0 mg, 310 µmol) and DIPEA (66.7 mg, 90.1 µL, 516 µmol) and the clear, light yellow solution was heated under reflux for 2.5 hours. The reaction mixture was poured on saturated aqueous NH$_4$Cl solution and EtOAc and the layers were separated. The aqueous layer was extracted twice with EtOAc. The organic layers were dried over MgSO$_4$, filtered, treated with silica gel and evaporated. The compound was purified by silica gel chromatography on a 10 g column using an MPLC system eluting with a gradient of n-heptane:EtOAc (100:0 to 0:100). Colorless foam (0.05 g; 47%). MS (ESI): m/z=507.14 [M+H]$^+$.

Intermediates a) N-(4-(4-fluoro-2-methoxyphenyl)-6-methylpyridin-3-yl)-3-mercapto-N-methyl-5-(trifluoromethyl)benzamide To a solution of N-(4-(4-fluoro-2-methoxyphenyl)-6-methylpyridin-3-yl)-N-methyl-3-(trifluoromethyl)-5-(2-(trimethylsilyl)ethylthio)benzamide (0.477 g, 866 µmol) in THF (10 mL) was added tetrabutylammonium fluoride (1M solution in THF, 4.55 mL, 4.55 mmol) and the the clear, light yellow solution was stirred at room temperature for 75 minutes. The reaction mixture was poured on 10% aqueous citric acid solution and EtOAc and the layers were separated. The aqueous layer was extracted twice with EtOAc. The organic layers were washed with brine, dried over MgSO$_4$, filtered, treated with silica gel and evaporated. The compound was purified by silica gel chromatography on a 20 g column using a MPLC system eluting with a gradient of CH$_2$Cl$_2$:MeOH (100:0 to 90:10). Light brown solid (93%). MS (ESI): m/z=449.10 [M+H]$^+$.

b) N-(4-(4-fluoro-2-methoxyphenyl)-6-methylpyridin-3-yl)-N-methyl-3-(trifluoromethyl)-5-(2-(trimethylsilyl)ethylthio)benzamide A solution of 3-bromo-N-(4-(4-fluoro-2-methoxyphenyl)-6-methylpyridin-3-yl)-N-methyl-5-(trifluoromethyl)benzamide (0.59 g, 1.19 mmol) and 2-(trimethylsilyl)ethanethiol (159 mg, 187 µL, 1.19 mmol) in dioxane (5.9 mL) was stirred under argon for 5 minutes in a sealed tube. To the clear, light yellow solution were added tris(dibenzylideneacetone)dipalladium (0) (27.2 mg, 29.7 µmol, CAS RN 52409-22-0), 4,5-bis(diphenylphosphino)-9,9-dimethylxanthene (34.3 mg, 59.3 µmol, CAS RN 161265-03-8) and DIPEA (307 mg, 414 µL, 2.37 mmol) and the reaction mixture was stirred at 120° C. for 5.5 hours, followed by stirring at room temperature overnight. The reaction mixture was poured on saturated aqueous NH$_4$Cl solution and EtOAc and the layers were separated. The aqueos layer was extracted twice with EtOAc. The organic layers were dried over MgSO$_4$, filtered, treated with silica gel and evaporated. The compound was purified twice by silica gel chromatography on a 20 g column using a MPLC system eluting with a gradient of n-heptane:EtOAc (100:0 to 50:50). Off-white solid (0.483 g; 73%). MS (ESI): m/z=551.18 [M+H]$^+$.

c) 3-Bromo-N-(4-(4-fluoro-2-mahoxyphenyl)-6-methylpyridin-3-yl)-N-methyl-5-(trifluoromethyl)benzamide The title compound was prepared in analogy to example 90, from 4-(4-fluoro-2-methoxyphenyl)-N,6-dimethylpyridin-3-amine and 3-bromo-5-(trifluoromethyl)benzoic acid after a reaction time of 20 hours. The compound was purified by silica gel chromatography on a 10 g column using a MPLC system eluting with a gradient of n-heptane: EtOAc (100:0 to 0:100). Colorless solid (88%). MS (ESI): m/z=497.05 [M+H]$^+$.

Example 311

N-Cyanomethyl-3-methanesulfonyl-N-[4-(2-trifluoromethoxy-phenyl)-pyridin-3-yl]-5-trifluoromethyl-benzamide

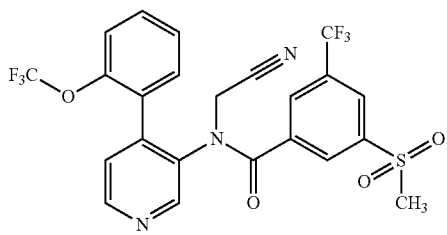 [SMILES: CS(=O)(=O)c1cc(C(=O)N(CC#N)c2cnccc2-c2ccccc2OC(F)(F)F)cc(C(F)(F)F)c1]

To a solution of 2-(4-(2-(trifluoromethoxy)phenyl)pyridin-3-ylamino)acetonitrile (0.07 g, 239 µmol) in CH$_2$Cl$_2$ (2 mL) were added 3-(methylsulfonyl)-5-(trifluoromethyl)benzoyl chloride (137 mg, 477 µmol, example 223, intermediate d) and DIPEA (123 mg, 167 µL, 955 µmol) and the clear, yellow solution was stirred at room temperature for 18 hours. The reaction mixture was poured on saturated aqueous NH$_4$Cl solution and CH$_2$Cl$_2$ and the layers were separated. The aqueous layer was extracted three times with CH$_2$Cl$_2$. The organic layers were dried over MgSO$_4$, filtered, treated with silica gel and evaporated. The compound was purified by silica gel chromatography on a 20 g column using a MPLC system eluting with a gradient of n-heptane: EtOAc (100:0 to 0:100). The product was purified by preparative HPLC (Gemini NX column) using a gradient of MeOH:water (containing 0.1% formic acid) (20:80 to 98:2). Colorless solid (0.085 g; 65%). MS (ESI): m/z=544.08 [M+H]$^+$.

Intermediates a) 2-(4-(2-(Trifluoromethoxy)phenyl)pyridin-3-ylamino)acetonitrile To a solution of cyanomethyl-[4-(2-trifluoromethoxy-phenyl)-pyridin-3-yl]-carbamic acid tert-butyl ester (185 mg, 0.47 mmol) in CH$_2$Cl$_2$ (5 mL) was added trifluoroacetic acid (1 mL) at 0° C. The reaction mixture was stirred at 25° C. for 2 hours and then concentrated under vacuum. The residue was dissolved in 10 mL aqueous sodium bicarbonate solution and 20 mL CH$_2$Cl$_2$ and the layers were separated. The aqueous layer was extracted again with 10 mL CH$_2$Cl$_2$. The combined organic layer was washed with 20 mL brine, dried over Na$_2$SO$_4$, filtered and concentrated under vacuum. The resulting light yellow solid was pure enough to be used in the next step without further opurification (115 mg, 83%). LC-MS (ESI): m/z=294.0 (M+H).

b) Cyanomethyl-[4-(2-trifluoromethoxy-phenyl)-pyridin-3-yl]-carbamic acid tert-butyl ester To a solution of [4-(2-trifluoromethoxy-phenyl)-pyridin-3-yl]-carbamic acid tert-butyl ester (190 mg, 0.54 mmol) in DMF (5 mL) was added sodium hydride (24 mg, 0.59 mmol, 60% dispersion in mineral oil) at 0° C. The reaction mixture was stirred at 25° C. for 30 minutes. Then bromoacetonitrile (71 mg, 0.59 mmol) was added to the reaction mixture and it was stirred at 25° C. for 24 hours. The reaction mixture was quenched with 10 mL saturated NH₄Cl solution and extracted with EtOAc (2×40 mL) The combined EtOAc part was dried over Na₂SO₄ and evaporated. The residue crude was purified by silica gel column chromatography eluting with a gradient of n-hexane:EtOAc (85:15 to 70:30) to get the desired compound as a light yellow sticky liquid (185 mg, 88%). LC-MS (ESI): m/z=394.4 [M+H]⁺.

c) [4-(2-Trifluoromethoxy-phenyl)-pyridin-3-yl]-carbamic acid tert-butylester

To a solution of (4-iodo-pyridin-3-yl)-carbamic acid tert-butyl ester (500 mg, 1.56 mmol, example 85, intermediate d) in 6 mL DME were added 2-trifluoromethoxyphenylboronic acid (643 mg, 3.12 mmol) and 2M aqueous Na₂CO₃ solution (2.0 mL) and the reaction mixture was purged with nitrogen for 15 min. Then Pd(OAc)₂ (36 mg, 0.16 mmol) and triphenylphosphine (82 mg, 0.31 mmol) were added and the reaction mixture was stirred at 100° C. for 16 hours. The reaction mixture was poured on 30 mL 10% aqueous NaHCO₃ solution and 30 mL EtOAc and the layers were separated. The aqueous layer was extracted with 30 mL EtOAc. The combined organic layer was washed with 30 mL brine, dried over Na₂SO₄ and evaporated. The residue was purified by column chromatography eluting with a gradient of n-hexane:EtOAc (80:20 to 70:30) to yield the desried compound as a light yellow sticky liquid (440 mg, 80%). LC-MS: m/z=355.0 [M+H]⁺.

Example 312

5-(3-{[4-(4-Fluoro-2-methoxy-phenyl)-6-methyl-pyridin-3-yl]-methyl-carbamoyl}-5-trifluoromethyl-phenylsulfanyl)-pentanoic acid

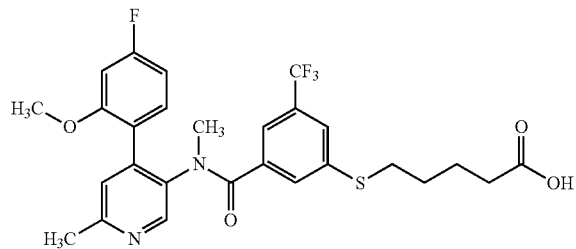 [SMILES: COc1cc(F)ccc1-c1cc(C)ncc1N(C)C(=O)c1cc(SCCCCC(=O)O)cc(C(F)(F)F)c1]

To a solution of N-(4-(4-fluoro-2-methoxyphenyl)-6-methylpyridin-3-yl)-3-mercapto-N-methyl-5-(trifluoromethyl)benzamide (0.263 g, 584 μmol, example 310, intermediate a) in acetonitrile (4 mL) were added 5-bromopentanoic acid (132 mg, 730 μmol) and DIPEA (189 mg, 255 μL, 1.46 mmol) and the clear, light yellow solution was stirred at room temperature for 2.25 hours. The reaction mixture was poured on saturated aqueous NH₄Cl solution and EtOAc and the layers were separated. The aqueous layer was extracted twice with EtOAc. The organic layers were dried over MgSO₄, filtered, treated with silica gel and evaporated. The compound was purified by silica gel chromatography on a 20 g column using an MPLC system eluting with a gradient of CH₂Cl₂:MeOH (100:0 to 50:50). The product was purified by preparative HPLC (Gemini NX column) using a gradient of MeOH:water (containing 0.1% formic acid) (20:80 to 98:2). Colorless solid (0.119 g, 74%). MS (ESI): m/z=551.16 [M+H]⁺.

Example 313

N-(2-Chloro-[3,4']bipyridinyl-3'-yl)-3-methanesulfonyl-N-methyl-5-trifluoromethyl-benzamide

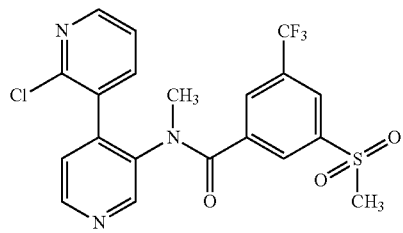 [SMILES: CN(C(=O)c1cc(C(F)(F)F)cc(S(C)(=O)=O)c1)c1cnccc1-c1cccnc1Cl]

The title compound was prepared in analogy to example 90, from 2-chloro-N-methyl-3,4'-bipyridin-3'-amine and 3-(methylsulfonyl)-5-(trifluoromethyl)benzoic acid (example 114, intermediate a) after a reaction time of 18 hours. The compound was purified by silica gel chromatography on a 20 g column using an MPLC system (CombiFlash Companion, Isco Inc.) eluting with a gradient of n-heptane: EtOAc (100:0 to 0:100). Light brown foam (12%). MS (ESI): m/z=470.055 [M+H]⁺.

Intermediate

2-Chloro-N-methyl-3,4'-bipyridin-3'-amine

The title compound was prepared in analogy to example 72, from (4-iodo-pyridin-3-yl)-methyl-amine and 2-chloro-pyridin-3-ylboronic acid after a reaction time of 5 hours at 90° C. The compound was purified by silica gel chromatography on a 50 g column using an MPLC system (CombiFlash Companion, Isco Inc.) eluting with a gradient of n-heptane: EtOAc (100:0 to 0:100). Light yellow solid (82%). MS (EI): m/z=219 [M]

Example 314

N-[4-(4-Fluoro-2-methoxy-phenyl)-6-methyl-pyridin-3-yl]-N-methyl-3-(oxctane-3-sulfonyl)-5-trifluoromethyl-benzamide

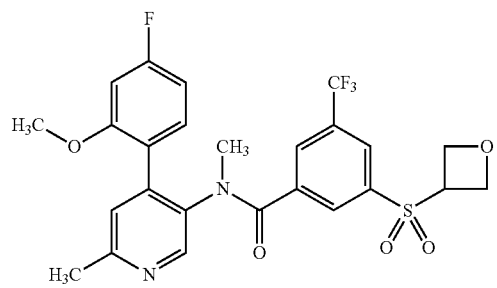 [SMILES: COc1cc(F)ccc1-c1cc(C)ncc1N(C)C(=O)c1cc(C(F)(F)F)cc(S(=O)(=O)C2COC2)c1]

To an ice-cold solution of N-(4-(4-fluoro-2-methoxyphenyl)-6-methylpyridin-3-yl)-N-methyl-3-(oxetan-3-ylthio)-

5-(trifluoromethyl)benzamide (0.045 g, 88.8 µmol, example 310) in MeOH (2 mL) and water (0.5 mL) was added Oxone® (137 mg, 222 µmol) and stirring was continued at room temperature for 2.5 hours. The reaction mixture was poured on 10% aqueous Na₂S₂O₃ solution and EtOAc and the layers were separated. The aqueous layer was saturated with sodium chloride, extracted three times with EtOAc. The organic layers were washed once with brine, dried over MgSO₄, filtered and evaporated. The compound was purified by silica gel chromatography on a 10 g column using an MPLC (ISCO) system eluting with a gradient of n-heptane:EtOAc (100:0 to 0:100). The product was purified by preparative HPLC (Gemini NX column) using a gradient of MeOH:water (containing 0.1% formic acid) (20:80 to 98:2). Light brown foam (0.038 g; 79%). MS (ESI): m/z=539.13 [M+H]⁺.

Example 315

[5-(3-{[4-(4-Fluoro-2-methoxy-phenyl)-6-methyl-pyridin-3-yl]-methyl-carbamoyl}-5-trifluoromethyl-phenylsulfanyl)-pentanoylamino]-acetic acid

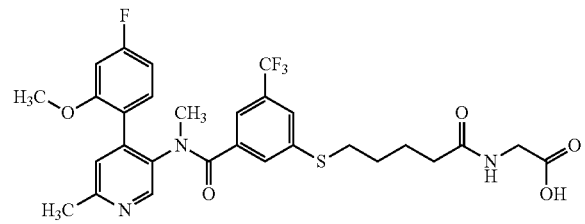 [SMILES: COc1cc(F)ccc1-c1cc(C)ncc1N(C)C(=O)c1cc(SCCCCC(=O)NCC(=O)O)cc(C(F)(F)F)c1]

The title compound was prepared in analogy to example 84, from methyl 2-(5-(3-((4-(4-fluoro-2-methoxyphenyl)-6-methylpyridin-3-yl)(methyl)carbamoyl)-5-(trifluoromethyl)phenyl-thio)pentanamido)acetate after a reaction time of 1.5 hours. The product was purified by preparative HPLC (Gemini NX column) using a gradient of MeOH:water (containing 0.1% formic acid) (20:80 to 98:2). Colorless foam (65%). MS (ESI): m/z=608.18 [M+H]⁺.

Intermediates a) Methyl 2-(5-(3-44-(4-fluoro-2-methoxyphenyl)-6-methylpyridin-3-yl)(methyl)carbamoyl)-5-(trifluoromethyl)phenylthio)pentanamido)acetate To a solution of 5-(3-((4-(4-fluoro-2-methoxyphenyl)-6-methylpyridin-3-yl)(methyl)carbamoyl)-5-(trifluoromethyl)phenylthio)pentanoic acid (0.15 g, 272 µmol, example 312) in DMF (1 mL) was added 1,1'-carbonyldiimidazole (66.3 mg, 409 µmol) and the clear solution was stirred at room temperature for 45 minutes before glycin methyl ester hydrochloride (37.6 mg, 300 µmol) was added. Reaction mixture was stirred at room temperature for 20.5 hours before DIPEA (35.2 mg, 47.6 µL, 272 µmol) and glycin methyl ester hydrochloride (37.6 mg, 300 µmol) was added. After 23 hours the reaction mixture was poured on saturated aqueous NH₄Cl solution and EtOAc and the layers were separated. The aqueous layer was extracted twice with EtOAc. The organic layers were washed twice with water and once with brine, dried over MgSO₄, filtered, treated with silica gel and evaporated. The compound was purified by silica gel chromatography on a 20 g column using a MPLC system eluting with a gradient of CH₂Cl₂:MeOHe (100:0 to 90:10). Colorless foam (0.142 g; 79%). MS (ESI): m/z=622.20 [M+H]⁺.

Example 316

5-(3-{[4-(5-Chloro-4-fluoro-2-methoxy-phenyl)-6-methyl-pyridin-3-yl]-methyl-carbamoyl}-5-trifluoromethyl-benzenesulfonyl)-pentanoic acid

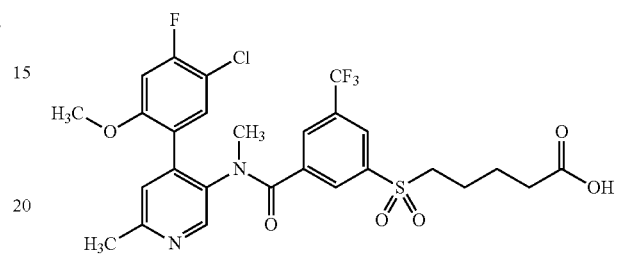

To an ice-cold, turbid solution of 5-(3-((4-(4-fluoro-2-methoxyphenyl)-6-methylpyridin-3-yl)(methyl)carbamoyl)-5-(trifluoromethyl)phenylthio)pentanoic acid (0.115 g, 209 µmol, example 312) in MeOH (7 mL) and water (0.5 mL) was added Oxone® (321 mg, 522 µmol) and the reaction mixture was stirred at room temperature for 2.5 hours. The reaction mixture was poured on 10% aqueous citric acid solution and EtOAc and the layers were separated. The aqueous layer was saturated with sodium chloride, extracted three times with EtOAc. The organic layers were washed once with 10% aqueous Na₂S₂O₃ solution and once with brine, dried over MgSO₄, filtered and evaporated. The compound was purified by silica gel chromatography on a 20 g column using an MPLC (Flashmaster) system eluting with a gradient of CH₂Cl₂:MeOH (100:0 to 90:10). The product was purified by preparative HPLC (Gemini NX column) using a gradient of MeOH:water (containing 0.1% formic acid) (20:80 to 98:2). Colorless solid (0.065 g; 50%). MS (ESI): m/z=617.11 [M+H]⁺.

Example 317

[5-(3-{[4-(4-Fluoro-2-methoxy-phenyl)-6-methyl-pyridin-3-yl]-methyl-carbamoyl}-5-trifluoromethyl-benzenesulfonyl)-pentanoylamino]-acetic acid

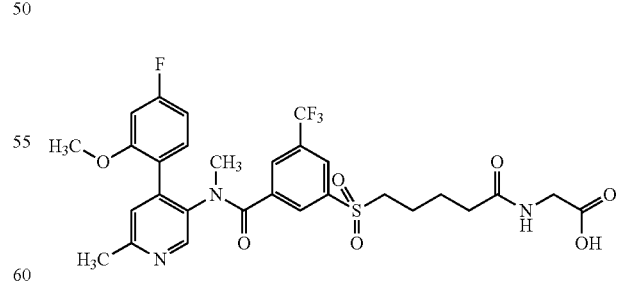

To an ice-cold solution of 2-(5-(3-44-(4-fluoro-2-methoxyphenyl)-6-methylpyridin-3-yl)(methypcarbamoyl)-5-(trifluoromethyl)phenylthio)pentanamido)acetic acid (0.08 g, 132 µmol, example 315) in MeOH (2 mL) and water (0.5 ml) was added Oxone® (202 mg, 329 µmol) and the white suspension was stirred at room temperature for 3.5 hours. The reaction mixture was poured on 10% aqueous Na$_2$S$_2$O$_3$ solution and EtOAc and the layers were separated. The aqueous layer was extracted twice with EtOAc. The organic layers were washed once with brine, dried over MgSO$_4$, filtered, and evaporated. The crude product (0.11 g) was purified by preparative HPLC (Gemini NX column) using a gradient of MeOH:water (containing 0.1% formic acid) (20:80 to 98:2). Colorless solid (0.068 g; 80%). MS (ESI): m/z=640.17 [M+H]$^+$.

Example 318

3-Methanesulfonyl-N-methyl-N-{6-methyl-4-[2-(oxetan-3-yloxy)-phenyl]-pyridin-3-yl}-5-trifluoromethyl-benzamide

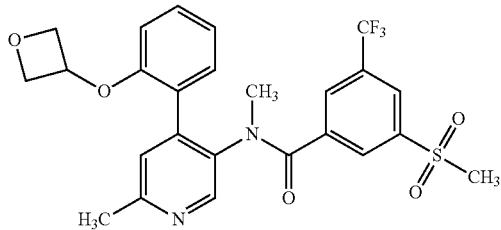 [SMILES: Cc1cc(-c2ccccc2OC2COC2)c(N(C)C(=O)c2cc(C(F)(F)F)cc(S(C)(=O)=O)c2)cn1]

To a solution of N-(4-(2-hydroxyphenyl)-6-methylpyridin-3-yl)-N-methyl-3-(methylsulfonyl)-5-(trifluoromethyl)benzamide (100 mg, 215 µmol) in DMF (2 mL) was added K$_2$CO$_3$ (59.5 mg, 431 µmol) and 3-iodooxetane (43.6 mg, 237 µmol). The reaction mixture was stirred for 2 hours at room temperature followed by stirring for 18 hours at 80° C. The reaction mixture was poured on 30 mL 10% aqueous NaHCO$_3$ solution and 30 mL EtOAc and the layers were separated. The aqueous layer was extracted a second time with 30 mL EtOAc. The organic layers were washed with 30 mL brine, dried over MgSO$_4$, filtered and concentrated under vacuum. The compound was purified by silica gel chromatography on a 10 g column using an MPLC system (CombiFlash Companion, Isco Inc.) eluting with a gradient of n-heptane:EtOAc (100:0 to 0:100). Colorless solid (30 mg, 27%). MS (ESI): m/z=521.134 [M+H]$^+$.

Intermediates a) N-(4-(2-hydroxyphenyl)-6-methylpyridin-3-yl)-N-methyl-3-(methylsulfonyl)-5-(trifluoromethyl)benzamide To a solution of N-(4-(2-(benzyloxy)phenyl)-6-methylpyridin-3-yl)-N-methyl-3-(methylsulfonyl)-5-(trifluoromethyl)benzamide (1.63 g, 2.94 mmol) in MeOH (16 mL) and EtOAc (16 mL) was added Pd on carbon (10%, 200 mg, 2.94 mmol) under argon atmosphere. The reaction was evacuated and purged with hydrogen. The reaction was stirred for 5 hours at 1.7 bar under hydrogen atmosphere. The reaction mixture was filtered over dicalite. The filtrate was concentrated under vacuum and the compound was purified by silica gel chromatography on a 50 g column using an MPLC system (CornbiFlash Companion, Isco Inc.) eluting with a gradient of n-heptane:EtOAc (100:0 to 0:100). Colorless solid (1.367 g, 100%). MS (ESI): m/z=465.109 [M+H]$^+$.

b) N-(4-(2-(benzyloxy)phenyl)-6-methylpyridin-3-yl)-N-methyl-3-(methylsulfonyl)-5-(trifluoromethyl)benzamide The title compound was prepared in analogy to example 90, from 4-(2-(benzyloxy)phenyl)-N,6-dimethylpyridin-3-amine and 3-(methylsulfonyl)-5-(trifluoromethyl)benzoic acid (1.49 g, 5.55 mmol, example 114, intermediate a) after a reaction time of 3.5 days at room temperature. The compound was purified by silica gel chromatography on a 50 g column using an MPLC system (CombiFlash Companion, Isco Inc.) eluting with a gradient of n-heptane:EtOAc (100:0 to 10:90). Off-white solid (53%). MS (ESI): m/z=555.156 [M+H]$^+$.

c) 4-(2-(Benzyloxy)phenyl)-N,6-dimethylpyridin-3-amine

The title compound was prepared in analogy to example 72, intermediate a, from (4-iodo-6-methyl-pyridin-3-yl)-methyl-amine (example 301, intermediate b) and 2-(benzyloxy)phenylboronic acid after a reaction time of 5 hours at 90° C. The compound was purified by silica gel chromatography on a 50 g column using an MPLC system (CombiFlash Companion, Isco Inc.) eluting with a gradient of n-heptane:EtOAc (100:0 to 20:80). Yellow solid (93%). MS (ESI): m/z=305.165 [M+H]$^+$.

Example 319

N-Carbamoylmethyl-3-methanesulfonyl-N-[4-(2-trifluoromethoxy-phenyl)-pyridin-3-yl]-5-trifluoromethyl-benzamide

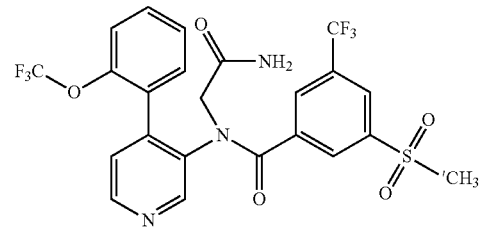

To a solution of {(3-methanesulfonyl-5-trifluoromethyl-benzoyl)-[4-(2-trifluoromethoxy-phenyl)-pyridin-3-yl]-amino}-acetic acid (190 mg, crude, 0.34 mmol) in DMF (2 mL) were added EDC (130 mg, 0.68 mmol), HOBt-NH$_3$ complex (103 mg, 0.68 mmol) and N,N diisopropyl ethylamine (0.57 mL, 3.37 mmol) and the reaction mixture was stirred at room temperature for 4 hours. The solvent was evaporated and the resulting residue was dissolved in EtOAc (15 mL) and washed with water (2×10 mL) and brine (10 mL) The organic layer was dried (Na$_2$SO$_4$) and evaporated under reduced pressure. The residue was purified by preparative HPLC (ammonium acetate/acetonitrile) to yield the desired compound as a brown solid (23 mg, 4% from intermediate c). MS (ESI): m/z=562.0 [M+H]$^+$.

Intermediates a) {(3-Methanesulfonyl-5-trifluoromethyl-benzoyl)-[4-(2-trifluoromethoxy-phenyl)-pyridin-3-yl]-amino}-acetic acid The title compound was prepared in analogy to example 84, from [{(3-methanesulfonyl-5-trifluoromethyl-benzoyl)-

[4-(2-trifluoromethoxy-phenyl)-pyridin-3-yl]-amino}-acetic acid methyl ester and was used in the next step without further purification. Brown solid. MS (ESI): m/z=563.2 [M+H]⁺.

b) {(3-Methanesulfonyl-5-trifluoromethyl-benzoyl)-[4-(2-trifluoromethoxy-phenyl)-pyridin-3-yl]-amino}-acetic acid methyl ester The title compound was prepared in analogy to example 284, from [4-(2-trifluoromethoxy-phenyl)-pyridin-3-ylamino]-acetic acid methyl ester and 3-methanesulfonyl-5-trifluoromethyl-benzoyl chloride (example 223, intermediate d). The crude product was used in the next step without further purification. Brown sticky liquid. MS (ESI): m/z=577.2 [M+H]⁺.

c) [4-(2-Trifluoromethoxy-phenyl)-pyridin-3-ylamino]-acetic acid methyl ester

The title compound was prepared in analogy to example 298, intermediate c, from (4-iodo-pyridin-3-ylamino)-acetic acid methyl ester (example 176, intermediate b) and 2-trifluoromethoxyphenyl boronic acid (CAS RN 175676-65-0). Yellow liquid (87%). MS (ESI): m/z=328.4 [M+H]⁺.

Example 320

3-{3'-[(3-Methanesulfonyl-5-trifluoromethyl-benzoyl)-methyl-amino]-[3,4']bipyridinyl-2-yloxy}-azetidine-1-carboxylic acid tert-butyl ester

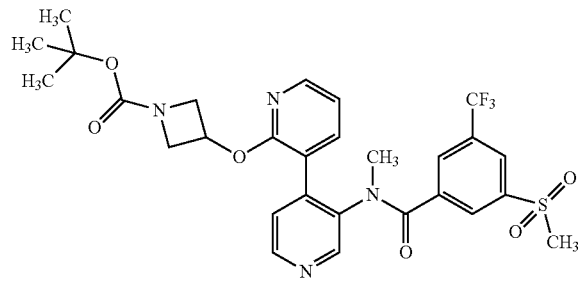 [SMILES: CN(C(=O)c1cc(C(F)(F)F)cc(S(C)(=O)=O)c1)c1cnccc1-c1cccnc1OC1CN(C(=O)OC(C)(C)C)C1]

To a solution of tert-butyl 3-(3'-(methylamino)-3,4'-bipyridin-2-yloxy)azetidine-1-carboxylate (0.149 g, 418 µmol) in CH₂Cl₂ (4 mL) were added 3-(methylsulfonyl)-5-(trifluoromethyl)benzoyl chloride (240 mg, 836 µmol, example 223, intermediate d) and DIPEA (216 mg, 292 µL, 1.67 mmol) and the light yellow solution was stirred a troom temperature for 24 hours. Another batch of 3-(methylsulfonyl)-5-(trifluoromethyl)benzoyl chloride (164 mg, 573 µmol) and DIPEA (162 mg, 219 µL, 1.25 mmol) was added and stirring was continued at room temperature for 24 hours. The reaction mixture was poured on saturated aqueous NH₄Cl solution and CH₂Cl₂ and the layers were separated. The aqueous layer was extracted three times with CH₂Cl₂. The organic layers were dried over MgSO₄, filtered, treated with silica gel and evaporated. The compound was twice purified by silica gel chromatography on a 20 g column using an MPLC system eluting with EtOAc. Light yellow gum (0.105 g; 41%). MS (ESI): m/z=607.18 [M+H]⁺.

Intermediates a) tert-Butyl 3-(3'-(methylamino)-3,4'-bipyridin-2-yloxy)azetidine-1-carboxylate To a solution of tert-butyl 3-hydroxyazetidine-1-carboxylate (81.1 mg, 468 µmol, Fluorochem) in DMF (1 mL) was added sodium hydride (approx. 55% in mineral oil) (18.6 mg, 426 µmol) and the resulting suspension was stirred at room temperature for 30 minutes until gas evolution ceased. To the turbid solution was added N-(2-chloro-3,4'-bipyridin-3'-yl)-N-methyl-3-(methylsulfonyl)-5-(trifluoromethyl)benzamide (0.1 g, 213 µmol) in one portion. The light brown reaction mixture was stirred at room temperature for 3 hours. The reaction mixture was poured on saturated aqueous NH₄Cl solution and EtOAc and the layers were separated. The aqueous layer was extracted twice with EtOAc. The organic layers were washed twice with water and once with brine, dried over MgSO₄, filtered and evaporated. The product was purified by preparative HPLC (Gemini NX column) using a gradient of MeOH:water (containing 0.1% formic acid) (20:80 to 98:2). Colorless oil (0.027 g; 35%). MS (ESI): m/z=357.19 [M+H]⁺.

b) N-(2-chloro-3,4'-bipyridin-3'-yl)-N-methyl-3-(methylsulfonyl)-5-(trifluoromethyl)benzamide To a solution of 2-chloro-N-methyl-3,4'-bipyridin-3'-amine (0.2 g, 910 µmol, example 313, intermediate a) in CH₂Cl₂ (5 mL) were added 3-(methylsulfonyl)-5-(trifluoromethyl)benzoyl chloride (522 mg, 1.82 mmol, example 223, intermediate d) and DIPEA (471 mg, 636 µL, 3.64 mmol) and the light yellow solution was stirred at room temperature for 16 hours. The reaction mixture was poured on saturated aqueous NH₄Cl solution and CH₂Cl₂ and the layers were separated. The aqueous layer was extracted four times with CH₂Cl₂. The organic layers dried over MgSO₄, filtered, treated with silica gel and evaporated. The compound was purified by silica gel chromatography on a 10 g column using a MPLC system eluting with a gradient of n-heptane:EtOAc (100:0 to 0:100). Light brown foam (0.393 g; 91%). MS (ESI): m/z=470.06 [M+H]⁺.

Example 321

3-Methanesulfonyl-N-methyl-N-{6-methyl-4-[2-(oxetan-3-ylmethoxy)-phenyl]-pyridin-3-yl}-5-trifluoromethyl-benzamide

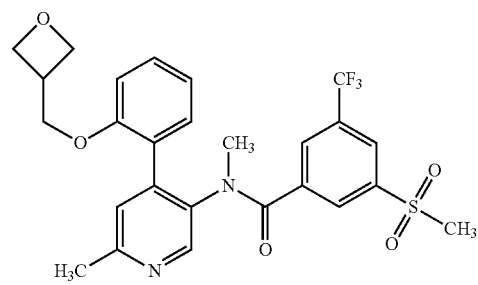 [SMILES: Cc1cc(-c2ccccc2OCC2COC2)c(N(C)C(=O)c2cc(C(F)(F)F)cc(S(C)(=O)=O)c2)cn1]

To a solution N-(4-(2-hydroxyphenyl)-6-methylpyridin-3-yl)-N-methyl-3-(methylsulfonyl)-5-(trifluoromethyfibenzamide (100 mg, 215 µmol, example 318, intermediate a) in DMF (2 ml) was added K₂CO₃ (59.5 mg, 431 µmol) and oxetan-3-ylmethyl 4-methylbenzenesulfonate (57.4 mg, 237 µmol). The reaction mixture was stirred for 2 hours at room temperature and for 18 hours at 80° C. The reaction mixture was poured on 30 mL 10% aqueous NaHCO₃ solution and 30 mL EtOAc and the layers were separated. The aqueous layer was extracted a second time with 30 mL EtOAc. The organic layers were washed with 30 mL brine, dried over MgSO₄, filtered and concentrated under vacuum. The compound was purified by silica gel chromatography on a 10 g column using an MPLC system (CombiFlash Companion, Isco Inc.) eluting with a gradient of n-heptane:EtOAc (100:0 to 0:100). Colorless solid (87 mg, 76%). MS (ESI): m/z=535.150 [M+H]⁺.

Intermediate

Oxetan-3-ylmethyl 4-methylbenzenesulfonate

To a solution of oxetan-3-yl-methanol (300 mg, 3.41 mmol, CAS RN 6246-06-6) in CH₂Cl₂ (3 mL) was added triethylamine (517 mg, 712 µl, 5.11 mmol), DMAP (41.6 mg, 341 µmol) and p-toluenesulfonyl chloride (779 mg, 4.09 mmol) at 0° C. The reaction mixture was stirred for 3 hours at room temperature. The reaction mixture was poured on 30 mL 1M aqueous HCl and 30 mL CH₂Cl₂ and the layers were separated. The aqueous layer was extracted a second time with 30 mL CH₂Cl₂. The organic layers were washed with 30 mL brine, dried over MgSO₄, filtered and concentrated under vacuum. The compound was purified by silica gel chromatography on a 20 g column using a MPLC system (CombiFlash Companion, Isco Inc.) eluting with a gradient of n-heptane:EtOAc (100:0 to 50:50). Colorless liquid (595 mg, 72%).

Example 322

N-Methyl-N-(4-phenyl-pyridin-3-yl)-3,5-bis-trifluoromethyl-benzamide

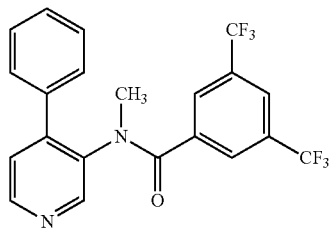 [SMILES: CN(C(=O)c1cc(C(F)(F)F)cc(C(F)(F)F)c1)c1cnccc1-c1ccccc1]

To a solution of methyl-(4-phenyl-pyridin-3-yl)-amine (160 mg, 0.87 mmol) in THF (4 mL) under nitrogen was added LiHMDS (1.3 mL, 1.3 mmol, 1M solution in THF) at −78° C. and the resulting reaction mixture was stirred for 30 min at −78° C. Then 3,5-bis(trifluoromethyl)-benzoyl chloride (480 mg, 1.74 mmol, CAS RN 1271-19-8) in THF (1 mL) was added to the reaction mixture at −78° C. and the reaction mixture was stirred for another 12 hours at 25° C. The reaction mixture was quenched with 10 mL saturated NH₄Cl solution and extracted with EtOAc (2×20 mL) The combined organic layers were dried and evaporated. The crude product was purified by preparative HPLC (ammonium acetate/acetonitrile) to furnish the desired compound as off-white solid (125 mg, 34%). MS (ESI): m/z=425.2 [M+H]⁺.

Intermediate

Methyl-(4-phenyl-pyridin-3-yl)-amine

To a solution of (4-iodo-pyridin-3-yl)-methyl-amine (225 mg, 0.96 mmol, example 36, intermediate b) in DME (5 mL) were added phenyl boronic acid (234 mg, 1.92 mmol) and 2M aqueous Na₂CO₃ solution (2 mL) and the reaction mixture was purged with nitrogen for 15 min. Then Pd(OAc)₂ (22 mg, 0.1 mmol) and triphenylphosphine (50 mg, 0.19 mmol) were added and the reaction mixture was stirred at 100° C. for 5 hours. The reaction mixture was poured on 30 mL 10% aqueous NaHCO₃ solution and 30 mL EtOAc and the layers were separated. The aqueous layer was extracted with 30 mL EtOAc. The combined organic layer was washed with brine (30 mL), dried over Na₂SO₄ and evaporated. The residue was purified by column chromatography eluting with a gradient of n-hexane:EtOAc (80:20 to 70:30) to yield the desired compound as a yellow solid (160 mg, 90%) MS (ESI): m/z=185.0 [M+H]⁺.

Example 323

3-Methanesulfonyl-N-methyl-N-(4-phenyl-pyridin-3-yl)-5-trifluoromethyl-benzamide

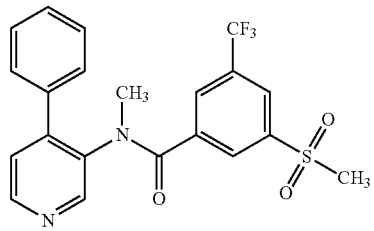 [SMILES: CN(C(=O)c1cc(C(F)(F)F)cc(S(C)(=O)=O)c1)c1cnccc1-c1ccccc1]

The title compound was prepared in analogy to example 284, from methyl-(4-phenyl-pyridin-3-yl)-amine (example 322, intermediate) and 3-methanesulfonyl-5-trifluoromethyl-benzoic acid (example 114, intermediate a). Off-white solid (34%). MS (ESI): m/z=435.2 [M+H]⁺.

Example A

Film coated tablets containing the following ingredients can be manufactured in a conventional manner:

| Ingredients | Per tablet | |
|---|---|---|
| Kernel: | | |
| Compound of formula I | 10.0 mg | 200.0 mg |
| Microcrystalline cellulose | 23.5 mg | 43.5 mg |
| Lactose hydrous | 60.0 mg | 70.0 mg |
| Polyvinylpyrrolidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |

305
-continued

| Ingredients | Per tablet | |
|---|---|---|
| Iron oxyde (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg, respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| Compound of formula I | 3.0 mg |
|---|---|
| Polyethylene Glycol 400 | 150.0 mg |
| Acetic acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula I | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85 % | 32.0 mg |
| Karion 83 | 8.0 mg (dry matter) |
| Titan dioxide | 0.4 mg |
| Iron oxide yellow | 1.1 mg |

306

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| Compound of formula I | 50.0 mg |
|---|---|
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidone in water. The granulate is mixed with magnesium stearate and the flavouring additives and filled into sachets.

The invention claimed is:
1. A compound according to formula (I),

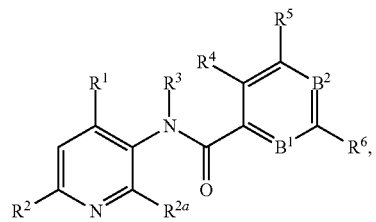

wherein:
$B^1$ is $CR^7$;
$B^2$ is N;
$R^1$ is selected from the group consisting of
phenyl, said phenyl being unsubstituted or substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy, cycloalkyl-oxy, cycloalky-$C_{1-7}$-alkoxy, cyano, cyano-$C_{1-7}$-alkoxy, carboxyl, carboxyl-$C_{1-7}$-alkyl, $C_{1-7}$-alkoxycarbonyl, hydroxy-$C_{1-7}$-alkyl, hydroxy-$C_{1-7}$-alkoxy, $C_{1-7}$-alkoxy-$C_{1-7}$-alkyl, carboxyl-$C_{1-7}$-alkoxy, $C_{1-7}$-alkoxycarbonyl-$C_{1-7}$-alkoxy, amino, $C_{1-7}$-alkylamino, di-$C_{1-7}$-alkylamino, phenyl-$C_{1-7}$-alkoxy, heterocyclyl-oxy and heterocyclyl-$C_{1-7}$-alkoxy, wherein heterocyclyl is unsubstituted or substituted by $C_{1-7}$-alkoxycarbonyl;
heteroaryl, said heteroaryl being unsubstituted or substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy, cycloalkyl-oxy, cycloalky-$C_{1-7}$-alkoxy, heterocyclyl-oxy and heterocyclyl-$C_{1-7}$-alkoxy, wherein heterocyclyl is unsubstituted or substituted by $C_{1-7}$-alkoxycarbonyl;
3,6-dihydro-2H-pyran-4-yl; and
piperidinyl, said piperidinyl being substituted with one to four $C_{1-7}$-alkyl groups;

R² is selected from the group consisting of hydrogen, $C_{1-7}$-alkyl, halogen, halogen-$C_{1-7}$-alkyl, halogen-$C_{1-7}$-alkoxy, cyano, $C_{1-7}$-alkoxy, amino, $C_{1-7}$-alkylamino, di-$C_{1-7}$-alkylamino, aminocarbonyl, $C_{1-7}$-alkylaminocarbonyl, di-$C_{1-7}$-alkylaminocarbonyl, hydroxy-$C_{1-7}$-alkyl-($C_{1-7}$-alkyl)amino, $C_{1-7}$-alkoxy-$C_{1-7}$-alkyl-($C_{1-7}$-alkyl)amino, and heteroaryl;

$R^{2a}$ is selected from the group consisting of hydrogen, methyl and halogen;

R³ is selected from the group consisting of $C_{1-7}$-alkyl, halogen-$C_{1-7}$-alkyl, hydroxy-$C_{1-7}$-alkyl, $C_{1-7}$-alkoxy-$C_{1-7}$-alkyl, $C_{1-7}$-alkylcarbonyl-$C_{1-7}$-alkyl, carboxyl-$C_{1-7}$-alkyl, $C_{1-7}$-alkoxycarbonyl-$C_{1-7}$-alkyl, cyano-$C_{1-7}$-alkyl, aminocarbonyl-$C_{1-7}$-alkyl, $C_{1-7}$-alkylaminocarbonyl-$C_{1-7}$-alkyl, di-$C_{1-7}$-alkylaminocarbonyl-$C_{1-7}$-alkyl, $C_{1-7}$-alkylsulfonyl-$C_{1-7}$-alkyl, $C_{3-7}$-cycloalkyl, $C_{3-7}$-cycloalkyl-$C_{1-7}$-alkyl, unsubstituted heterocyclyl or heterocyclyl substituted with one or two groups selected from halogen, oxo, hydroxy and $C_{1-7}$-alkyl, heterocyclyl-$C_{1-7}$-alkyl, wherein heterocyclyl is unsuhstituted or substituted with one or two groups selected from halogen, oxo and $C_{1-7}$-alkyl, heteroaryl-$C_{1-7}$-alkyl, wherein heteroaryl is unsubstituted or substituted with one or two groups selected from halogen, oxo and $C_{1-7}$-alkyl and phenyl-$C_{1-7}$-alkoxycarbonylamino-$C_{1-7}$-alkyl;

R⁴ is selected from the group consisting of hydrogen, halogen, $C_{1-7}$-alkyl and $C_{1-7}$-alkoxy;

R⁵ and R⁶ are independently from each other selected from the group consisting of hydrogen, $C_{1-7}$-alkyl, $C_{1-7}$-cycloalkyl, halogen, halogen-$C_{1-7}$-alkyl, halogen-$C_{1-7}$-alkoxy, hydroxy, hydroxy-$C_{1-7}$-alkyl, $C_{1-7}$-alkoxy, cyano, carboxyl, $C_{1-7}$-alkoxycarbonyl, $C_{1-7}$-alkoxycarbonyl-$C_{1-7}$-alkyl, hydroxy-$C_{1-7}$-alkoxy, $C_{1-7}$-alkoxy-$C_{1-7}$-alkoxy, $C_{1-7}$-alkylsulfanyl, hydroxy-$C_{1-7}$-alkylsulfanyl, $C_{1-7}$-alkoxy-$C_{1-7}$-alkylsulfanyl, $C_{1-7}$-alkylsulfonyl, hydroxy-$C_{1-7}$-alkylsulfonyl, $C_{1-7}$-alkoxy-$C_{1-7}$-alkylsulfonyl, carboxyl-$C_{1-7}$-alkylsulfanyl, carboxyl-$C_{1-7}$-alkylsulfonyl, $C_{1-7}$-alkoxycarbonyl-$C_{1-7}$-alkylsulfanyl, $C_{1-7}$-alkoxycarbonyl-$C_{1-7}$-alkylsulfonyl, $C_{1-7}$-alkoxycarbonylamino-$C_{1-7}$-alkylsulfanyl, carboxyl-$C_{1-7}$-alkyl-aminocarbonyl-$C_{1-7}$-alkysulfanyl, carboxyl-$C_{1-7}$-alkyl-aminocarbonyl-$C_{1-7}$-alkylsulfonyl, heterocyclylsulfanyl, wherein heterocyclyl is unsubstituted or substituted by $C_{1-7}$-alkoxycarbonyl, oxo, $C_{1-7}$-alkylsulfonyl or aminosulfonyl, heterocyclylsulfonyl, wherein heterocyclyl is unsubstituted or substituted by $C_{1-7}$-alkoxycarbonyl, oxo, $C_{1-7}$-alkylsulfornyl or aminosulfonyl, heterocyclyl-$C_{1-7}$-alkylsulfanyl, heterocyelyl-$C_{1-7}$-alkylsulfonyl, aminosulfonyl, $C_{1-7}$-alkylaminosulfonyl, di-($C_{1-7}$-aklyl)-aminosulfonyl, $C_{1-7}$-alkylsulfonylamino-$C_{1-7}$-alkylsulfanyl, $C_{1-7}$-alkylsulfonylamino-$C_{1-7}$-alkyisulfonyl, aminosulfonylamino-$C_{1-7}$-alkylsulfanyl, aminosulfonylamino-$C_{1-7}$-alkylsulfonyl, amino-$C_{1-7}$-alkylsulfanyl, amino-$C_{1-7}$-alkylsulfonyl, aminocarbonyl-$C_{1-7}$-alkyl, aminocarbonyl-$C_{1-7}$-alkylsulfonyl amino, $C_{1-7}$-alkylamino, di-($C_{1-7}$-alkyl)-amino, hydroxy-$C_{1-7}$-alkylamno, nitro, and unsubstituted heterocyclyl or heterocyclyl substituted with one or two groups selected from the group consisting of halogen, oxo, $C_{1-7}$-alkyl and $C_{1-7}$-alkoxycarbonyl; and R⁷ is hydrogen or halogen; or a pharmaceutically acceptable salt thereof.

2. A compound according to claim 1, wherein R¹ is phenyl, said phenyl being substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy, cycloalkyl-oxy, cycloalkyl-$C_{1-7}$-alkoxy, cyano, cyano-$C_{1-7}$-alkoxy, carboxyl, carboxyl-$C_{1-7}$-alkyl, $C_{1-7}$-alkoxycarbonyl, hydroxy-$C_{1-7}$-alkyl, hydroxy-$C_{1-7}$-alkoxy, $C_{1-7}$-alkoxy- $C_{1-7}$-alkyl, carboxyl-$C_{1-7}$-alkoxy, $C_{1-7}$-alkoxycarbonyl-$C_{1-7}$-alkoxy, amino, $C_{1-7}$-alkylamino, di-$C_{1-7}$-alkylamino, phenyl-$C_{1-7}$-alkoxy, heterocyclyl-oxy and heterocyclyl-$C_{1-7}$-alkoxy, wherein heterocyclyl is unsubstituted or substituted by $C_{1-7}$-alkoxycarbonyl.

3. A compound according to claim 1, wherein R¹ is phenyl, said phenyl being substituted with one, two or three groups selected from the group consisting of $C_{1-7}$-alkyl, halogen and $C_{1-7}$-alkoxy.

4. A compound according to claim 1, wherein R¹ is selected from the group consisting of
heteroaryl, said heteroaryl being substituted with one, two or three groups selected from the group consisting of $C_{1-7}$-alkyl, $C_{1-7}$cycloalkyl, halogen, hydroxy, $C_{1-7}$-alkoxy, halogen-$C_{1-7}$-alkyl, halogen-$C_{1-7}$-alkoxy, cycloalkyl-oxy, cycloalkyl-$C_{1-7}$-alkoxy,
heterocyclyl-oxy and heterocyclyl-$C_{1-7}$-alkoxy, wherein heterocyclyl is unsubstituted or substituted by $C_{1-7}$-alkoxycarborl,
3,6-dihydro-2H-pyran-4-yl, and
piperidinyl, said piperidinyl being substituted with one to four $C_{1-7}$-alkyl groups.

5. A compound according to claim 1, wherein R¹ is pyridyl, said pyridyl being substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy, cycloalkyl-oxy, cycloalkyl-$C_{1-7}$-alkoxy, heterocyclyl-oxy and heterocyclyl-$C_{1-7}$-alkoxy, wherein heterocyclyl is unsubstituted or substituted by $Ci_{1-7}$-alkoxycarbonyl.

6. A compound according to claim 1, wherein R² is hydrogen or halogen.

7. A compound according to claim 1, wherein $R^{2a}$ is hydrogen.

8. A compound according to claim 1, wherein R³ is selected from the group consisting of $C_{1-7}$-alkyl, halogen-$C_{1-7}$-alkyl, aminocarbonyl-$C_{1-7}$-alkyl and $C_{1-7}$-alkylsulfonyl-$C_{1-7}$alkyl.

9. A compound according to claim 1, wherein R⁴ is hydrogen or halogen.

10. A compound according to claim 1, wherein R⁵ and R⁶ are independently from each other selected from the group consisting of hydrogen, $C_{1-7}$-alkyl, halogen, halogen-$C_{1-7}$-alkyl, halogen-$C_{1-7}$-alkoxy, hydroxy, hydroxy-$C_{1-7}$-alkyl, $C_{1-7}$-alkoxy, cyano, $C_{1-7}$-alkoxycarbonyl, $C_{1-7}$-alkylsulfonyl, di-($C_{1-7}$-alkyl)-aminosulfonyl, amino, nitro, heterocyclyl selected from morpholinyl or 2-oxo-pyrrolidinyl, and heterocyclylsulfonyl, wherein heterocyclyl is oxetanyl or morpholinyl.

11. A compound according to claim 1, wherein R⁵ and R⁶ are independently from each other selected from the group consisting of halogen, halogen-$C_{1-7}$-alkyl, $C_{1-7}$-alkyl and $C_{1-7}$-alkylsulfonyl.

12. A compound according to claim 1, wherein R⁷ is hydrogen or halogen.

13. A pharmaceutical composition, comprising a compound according to claim 1, or a pharmaceutically acceptable salt thereof, and a pharmaceutically acceptable carrier and/or adjuvant.

14. A compound, selected from the group consisting of:
2-chloro-6-N-dimethyl-N(4-o-tolyl-pyridin-3-yl)-isonicotinamide, 2,6-dichloro-N-methyl-N-(4-o-tolyl-pyridin-3-yl)-isonicotinamide,
N-methyl-N-(4-o-tolyl-pyridin-3-yl)-2,6-bis-trifluoromethyl-isonicotinamide,
N-[4-(4,5difluoro-2-methoxy-phenyl)-pyridin-3-yl]-N-methyl-2,6-bis-trifluoromethyl-isonicotinamide,
N-(2-methoxy-[3,4']bipyridinyl-3'-yl)-N-(2,2,2-trifluoro-ethyl)-2,6-bis-trifluoromethyl-isonicotinamide,
N-[4-(4,5-difluoro-2-methoxy-phenyl)-pyridin-3- yl]-N-(2,2,2-trifluoro-ethyl)-2,6-bis-trifluoromethyl-isonicotinamide,
N-[4-(4-fluoro-2-methoxy-phenyl)-pyridin-3-yl]-N-(2,2,2-trifluoro-ethyl)-2,6-bis-trifluoromethyl-isonicotinamide,
N-[4-(4-fluoro-2-methoxy-phenyl)-pyridin-3-yl]-N-methyl-2,6-bis-trifluoromethyl-isonicotinamide,
N-(4-o-tolyl-pyridin-3-yl)-N-(2,2,2-trifluoro-ethyl)-2,6-bis-trifluoromethyl-isonicotinamide,
N-[4-(2-fluoro-phenyl)-pyridin-3-yl]-N-(2,2,2-trifluoro-ethyl)-2,6-bis-trifluoromethyl-isonicotinamide,
N-(2,2-difluoro-ethyl)-N-[4-(4-fluoro-2-methoxy-phenyl)-pyridin-3-yl]-2,6-bis-trifluoromethyl-isonicotinamide,
N-(2,2-difluoro-ethyl)-N-[4-(4,5-difluoro-2-methoxy-phenyl)-pyridin-3-yl]-2,6-bis-trifluoromethyl-isonicotinamide,
N-(2,2-difluoro-ethyl)-N-[4-(2-fluoro-phenyl)-pyridin-3-yl]-2,6-bis-trifluoromethyl-isorticotinamide,
N-(2,2-difluoro-ethyl)-N-(2-methoxy[3,4']bipyridinyl -3'-yl)-2,6-bis-trifluoromethy-isonicotinarnide,
N-(2,2-difluoro-ethyl)-N-(4-o-tolyl-pyridin-3yl)-2,6-bis-trifluoromethyl-isonieotinamide,
N-[4-(4,5-difluoro-2-methoxy-phenyl)-pyridin-3-yl]-N-(2-methanesulfonyl-ethyl)-2,6-bis-trifluoromethyl-isonicotinamide,
N-[4-(2-fluoro-phenyl)-pyridin-3-yl]-N-(2-methanesulfontyl-ethyl)-2,6-bis-trifluoromethyl-isonicotinamide,
N-(2-methanesulfonyl-ethyl)-N-(2-methoxy-[3,4']bipyridinyl-3'-yl)-2,6-bis-trifuloromethyl-insonicotinamide,
N-[4-(4-fluoro-2-methoxy-phenyl)-pridin-3-yl]-N-(2-methanesulfonyl-ethyl)-2,6-bis-trifuloromethyl-insonicotinamide,
N-(2-methariesulfonyl-ethyl)-N-(4-o-tolyl-pyridin-3-y)-2,6-bis-trifluoromethyl-isonicotinamide,
2-chloro-N-[4-(4-fluoro-2-methoxy-phenyl)-pyridin-3-yl]-N-methyl-6-trifluorometlayl-isonicotinamide,
2-chloro-N-methyl-N-(4-o-tolyl-pyridin-3-yl)-6-trifluoromethyl-isonicotinide, {(2,6-bis-trifluoromethyl-pyridine-4-carbonyl)[4-(4,5-difluoro-2-methoxy-phenyl)-pyridin-3-yl]-amino}-acetic acid methyl ester,
N-(2-amino-2-oxoethyl)-N-(4-(4,5-difluoro-2-methoxyphenyl)pyridin-3-yl)-2,6-bis(trifluoromethyl)isonicotinamide,
N-[4-(2-cyanomethyl-phenyl)-pyridin-3-yl]-N-methyl-3,5-bis-trifluoromethyl-benzamide,
methyl 2-(N-(4-(4-fluoro-2-methoxyphenyl)pyridin-3-yl)-2,6-bis(trifluoromethy pisonicotinamido)acetate,
N-carbamoylmethyl-N-[4-(4-fluoro-2-methoxy-phenyl)-pyridin-3-yl]-2,6-bis-trifluoromethyl-isonicofinamide,
methyl 2-(N-(2-methoxy-3,4'-bipyridin-3'-yl)-2,6-bis(trifluoromethy)isonicotinamido)acetate,
N-(2-amino-2-oxoethyl)-N-(2-methoxy-3,4'bipyridin-3'-yl)-2,6-bis(trifluoromethyl)isonicotinamide,
2-methanesulfonyl-N-methyl-N-(4-o-toly-pyridin-3-yl)-6-trifluoromethyl-isonicotinamide,
methyl 2-(N-(4-(2-fluoro-6-methoxyphenyl)pyridin-3-yl)-2,6-bis(trifiuoromethy)isonieotinamido)acetate,
methyl 2-(N-(4(2-fluoropheny)pyridin-3-yl)-2,6-bis(trifluoromethy)isonicotinamido)acetate,
N-carbamoylmethyl-N-[4-(2-fluoro-phenyl)-pyridin-3-yl]-2,6-bis-trifluoromethyl-isonicotinamide,
2-chloro-N-[4-(4-fluoro-2-methoxy-phenyl)-pyridin-3-yl]-6-methoxy-N-methyl-isonicotinamide,
N-carbaoylmethyl-N-[4-(2-fluoro-6-methoxy-phenyl)-pyridin-3-yl]-2,6-bis-trifluoromethyl-isonicotinamide,
N-[4-(4-fluoro-2-methoxy-phenyl)-pyridi-N-3-yl]-N-(2-oxo-butyl)-2,6-bis-trifluoromethyl-isonicotinamide,
N-[4-(4-fluoro-2-methoxy-phenyl)-pyridin-3-yl]-N-3-methyl-oxetan-3-ylmethyl)-2,6-bis-trifluoromethyl-isonicotinamide,
N-[4-(4-fluoro-2-rnethoxy-phenyl)-pyridin-3-yl]-2-methanesulforiyl-N-methyl-6-trifluoromethyl-isonicotinamide,
N-(2-amino-2-oxoethyl)-N-(4-(4,5-difluoro-2-methoxyphenyl)pyridin-3-yl)-2,6-bis(trifluoromethyl)isonicotinamid,
N-carbamoylmethyl-N-[4-(2-fluoro-6-methoxy-phenyl)-pyridin-3-yl]-2,6-bis-trifluoromethyl isonicotinamide, and
N-[4-(4-fluoro-2-methoxy-phenyl)-pyridin-3-yl]-2-methoxy-N-methyl-6-trifluoromethyl-isonicotinamide,
or a pharmaceutically acceptable salt thereof.

15. A pharmaceutical composition, comprising a compound according to claim 14, or a pharmaceutically acceptable salt thereof, and a pharmaceutically acceptable carrier and/or adjuvant.

\* \* \* \* \*

UNITED STATES PATENT AND TRADEMARK OFFICE
CERTIFICATE OF CORRECTION

PATENT NO.         : 10,385,022 B2
APPLICATION NO.    : 14/615609
DATED              : August 20, 2019
INVENTOR(S)        : Caterina Bissantz et al.

It is certified that error appears in the above-identified patent and that said Letters Patent is hereby corrected as shown below:

In the Claims

At Column 306, Lines 48 and 61, Claim 1 "cycloalky-C1-7" should be printed as "cycloalkyl- C1-7."
At Column 307, Line 21, Claim 1 "unsuhstituted" should be printed as "unsubstituted."
At Column 307, Line 43, Claim 1 "-C1-7-alkysulfanyl" should be printed as "-C1-7-alkylsulfanyl."
At Column 307, Line 49, Claim 1 "C1-7-alkylsulfornyl" should be printed as "C1-7-alkylsulfonyl."
At Column 307, Line 50, Claim 1 "heterocyelyl" should be printed as "heterocyclyl."
At Column 307, Line 52, Claim 1 "di-( C1-7-aklyl)" should be printed as "di-( C1-7-alkyl)."
At Column 307, Line 54, Claim 1 "-C1-7-alkyisulfonyl" should be printed as "-C1-7-alkylsulfonyl."
At Column 307, Line 59, Claim 1 "hydroxy-C1-7-alkylamno" should be printed as "hydroxy-C1-7-alkylamino."
At Column 308, Line 24, Claim 2 "alkoxycarborl" should be printed as "alkoxycarbonyl."
At Column 309, Line 8, Claim 14 "-triftuoromethyl-" should be printed as "-trifluoromethyl-"
At Column 309, Line 28, Claim 14 "-isorticotinamide" should be printed as "-isonticotinamide."
At Column 309, Line 30, Claim 14 "-isonicotinarnide" should be printed as "-isonicotinamide."
At Column 309, Line 32, Claim 14 "-isonieotinamide" should be printed as "-isonicotinamide."
At Column 309, Line 37, Claim 14 "fontyl-" should be printed as "fonyl-"
At Column 309, Line 39, Claim 14 "-insonicotina-" should be printed as "-isonicotina-"
At Column 309, Line 41, Claim 14 "-pridin-" should be printed as "-pyridin-"
At Column 309, Line 44, Claim 14 "N-(2-methariesulfonyl-ethyl)" should be printed as "N-(2-methanesulfonyl-ethyl)."
At Column 309, Line 44, Claim 14 "-pyridin-3-y)-" should be printed as "-pyridin-3-yl)-"
At Column 309, Line 47, Claim 14 "-trifluorometlayl-" should be printed as "-trifluoromethyl-"
At Column 309, Line 49, Claim 14 "-isonicotinide" should be printed as "-isonicotinamide."
At Column 310, Line 9, Claim 14 "-bis(trifluoromethy pisonicotinamido)" should be printed as "-bis(trifluoromethyl) isonicotinamido)."
At Column 310, Line 11, Claim 14 "-isonicofinamide" should be printed as "-isonicotinamide."
At Column 310, Line 16, Claim 14 "4-o-toly-pyridin-" should be printed as "4-o-tolyl-pyridin-"
At Column 310, Line 19, Claim 14 "isonieotinamido" should be printed as "isonicotinamido."

Signed and Sealed this
Nineteenth Day of November, 2019

Andrei Iancu
*Director of the United States Patent and Trademark Office*

CERTIFICATE OF CORRECTION (continued)
U.S. Pat. No. 10,385,022 B2

At Column 310, Line 26, Claim 14 "N-carbaoylmethyl" should be printed as "N-carbamoylmethyl."
At Column 310, Line 34, Claim 14 "anesulforiyl" should be printed as "anesulfonyl"